United States Patent
Olson et al.

(10) Patent No.: US 12,241,065 B2
(45) Date of Patent: Mar. 4, 2025

(54) ANTISENSE OLIGONUCLEOTIDES TARGETING ALPHA-SYNUCLEIN AND USES THEREOF

(71) Applicants: Bristol-Myers Squibb Company, Princeton, NJ (US); Roche Innovation Center Copenhagen A/S, Hørsholm (DK)

(72) Inventors: Richard E. Olson, Cambridge, MA (US); Angela M. Cacace, Haddam Neck, CT (US); Jere E. Meredith, Jr., Haddam, CT (US); Nino Devidze, Conshohocken, PA (US); James K. Loy, Gales Ferry, CT (US); Carl J. Baldick, Pennington, NJ (US); Annapurna Pendri, South Glastonbury, CT (US); Ivar M. McDonald, Woodstock, CT (US); Peter Hagedorn, Hørsholm (DK); Marianne Lerbech Jensen, Køge (DK)

(73) Assignees: Bristol-Myers Squibb Company, Princeton, NJ (US); Roche Innovation Center Copenhagen A/S, Hørsholm (DK)

( * ) Notice: Subject to any disclaimer, the term of this patent is extended or adjusted under 35 U.S.C. 154(b) by 1194 days.

(21) Appl. No.: 16/961,578

(22) PCT Filed: Jan. 11, 2019

(86) PCT No.: PCT/US2019/013255
§ 371 (c)(1),
(2) Date: Jul. 10, 2020

(87) PCT Pub. No.: WO2019/140236
PCT Pub. Date: Jul. 18, 2019

(65) Prior Publication Data
US 2020/0362347 A1    Nov. 19, 2020

Related U.S. Application Data

(60) Provisional application No. 62/616,994, filed on Jan. 12, 2018.

(51) Int. Cl.
| | |
|---|---|
| C12N 15/113 | (2010.01) |
| A61K 9/00 | (2006.01) |
| A61K 31/7088 | (2006.01) |
| A61K 39/395 | (2006.01) |

(52) U.S. Cl.
CPC .......... *C12N 15/113* (2013.01); *A61K 9/0085* (2013.01); *A61K 31/7088* (2013.01); *A61K 39/3955* (2013.01); *C12N 2310/31* (2013.01); *C12N 2310/3231* (2013.01); *C12N 2310/3341* (2013.01); *C12N 2310/341* (2013.01); *C12N 2310/351* (2013.01); *C12N 2320/31* (2013.01); *C12N 2320/32* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,845,205 A | 7/1989 | Dinh et al. |
| 5,102,785 A | 4/1992 | Livak et al. |
| 5,130,302 A | 7/1992 | Spielvogel et al. |
| 5,175,273 A | 12/1992 | Bischofberger et al. |
| 5,367,066 A | 11/1994 | Urdea et al. |
| 5,432,272 A | 7/1995 | Benner |
| 5,459,255 A | 10/1995 | Cook et al. |
| 5,484,908 A | 1/1996 | Froehler et al. |
| 5,502,177 A | 3/1996 | Matteucci et al. |
| 5,525,711 A | 6/1996 | Hawkins et al. |
| 5,587,469 A | 12/1996 | Cook et al. |
| 5,594,121 A | 1/1997 | Froehler et al. |
| 5,596,091 A | 1/1997 | Switzer |
| 5,681,941 A | 10/1997 | Cook et al. |
| 5,750,692 A | 5/1998 | Cook et al. |
| 5,840,708 A | 11/1998 | Weiss |
| 5,932,557 A | 8/1999 | Mustafa et al. |
| 5,981,279 A | 11/1999 | Weiss |
| 6,025,193 A | 2/2000 | Weiss |
| 6,268,490 B1 | 7/2001 | Imanishi et al. |
| 6,277,640 B1 | 8/2001 | Bennett et al. |
| 6,455,308 B1 | 9/2002 | Freier |

(Continued)

FOREIGN PATENT DOCUMENTS

| | | |
|---|---|---|
| CA | 2817960 C | 6/2020 |
| EP | 0673252 A1 | 9/1995 |

(Continued)

OTHER PUBLICATIONS

Abeliovich, A. et al., "Mice lacking α-synuclein display functional deficits in the nigrostriatal dopamine system," *Neuron*, 25: 239-252, Elsevier, Inc., Netherlands (2000).

(Continued)

*Primary Examiner* — Brian Whiteman
(74) *Attorney, Agent, or Firm* — Sterne, Kessler, Goldstein & Fox P.L.L.C.

(57) ABSTRACT

The present disclosure relates to antisense oligonucleotides, which target SNCA mRNA (e.g., at an intron exon junction) in a cell, leading to reduced expression of SNCA protein. Reduction of SNCA protein expression is beneficial for the treatment of certain medical disorders, e.g., a neurological disorder.

11 Claims, 129 Drawing Sheets
Specification includes a Sequence Listing.

(56) References Cited

U.S. PATENT DOCUMENTS

| | | |
|---|---|---|
| 6,525,191 B1 | 2/2003 | Ramasamy |
| 6,599,718 B1 | 7/2003 | Liu et al. |
| 6,670,461 B1 | 12/2003 | Wengel et al. |
| 6,770,748 B2 | 8/2004 | Imanishi et al. |
| 6,794,499 B2 | 9/2004 | Wengel et al. |
| 6,833,361 B2 | 12/2004 | Hong et al. |
| 6,890,535 B1 | 5/2005 | Schenk |
| 7,034,133 B2 | 4/2006 | Wengel et al. |
| 7,053,207 B2 | 5/2006 | Wengel |
| 7,101,993 B1 | 9/2006 | Cook et al. |
| 7,399,845 B2 | 7/2008 | Seth et al. |
| 7,414,034 B2 | 8/2008 | Schneider |
| 7,427,672 B2 | 9/2008 | Imanishi et al. |
| 7,595,306 B2 | 9/2009 | Bumcrot et al. |
| 7,691,563 B2 | 4/2010 | Michaelis et al. |
| 7,705,016 B2 | 4/2010 | Rossetti et al. |
| 7,727,957 B2 | 6/2010 | Schenk et al. |
| 7,750,141 B2 | 7/2010 | Crooke et al. |
| 7,763,747 B2 | 7/2010 | Snow et al. |
| 7,776,538 B2 | 8/2010 | Nitta et al. |
| 7,838,657 B2 | 11/2010 | Singh et al. |
| 8,012,116 B2 | 9/2011 | Del Bigio et al. |
| 8,022,045 B1 | 9/2011 | Bogdahan et al. |
| 8,110,560 B2 | 2/2012 | Singh et al. |
| 8,283,334 B2 | 10/2012 | Bogdahan et al. |
| 8,361,977 B2 | 1/2013 | Baker et al. |
| 8,580,756 B2 | 11/2013 | Hansen et al. |
| 8,703,728 B2 | 4/2014 | Swayze et al. |
| 8,980,853 B2 | 3/2015 | Bennett et al. |
| 9,193,969 B2 | 11/2015 | Montefeltro et al. |
| 9,271,992 B2 | 3/2016 | Michaelis et al. |
| 9,492,415 B2 | 11/2016 | Bankiewicz et al. |
| 9,605,263 B2 | 3/2017 | Rigo |
| 9,663,783 B2 | 5/2017 | Freier |
| 9,701,708 B2 | 7/2017 | Cedillo et al. |
| 9,717,750 B2 | 8/2017 | Bennett et al. |
| 9,803,200 B2 | 10/2017 | Henshall et al. |
| 9,872,900 B2 | 1/2018 | Ciaramella et al. |
| 9,925,277 B2 | 3/2018 | Almarsson et al. |
| 9,926,559 B2 | 3/2018 | Bennett et al. |
| 9,994,850 B2 | 6/2018 | Christensen et al. |
| 10,022,435 B2 | 7/2018 | Ciaramella et al. |
| 10,023,626 B2 | 7/2018 | Bolen et al. |
| 10,138,482 B2 | 11/2018 | Rigo |
| 10,221,414 B2 | 3/2019 | Freier et al. |
| 10,258,698 B2 | 4/2019 | Hog et al. |
| 10,266,822 B2 | 4/2019 | Singh et al. |
| 10,323,076 B2 | 6/2019 | Ellsworth et al. |
| 10,407,680 B2 | 9/2019 | Kordasiewicz |
| 10,436,802 B2 | 10/2019 | Rigo et al. |
| 10,479,995 B2 | 11/2019 | Vargeese et al. |
| 10,709,779 B2 | 7/2020 | Ciaramella et al. |
| 10,724,035 B2 | 7/2020 | Vargeese et al. |
| 10,815,480 B2 | 10/2020 | Freier |
| 11,359,197 B2 * | 6/2022 | Olson .................. A61K 31/712 |
| 11,447,775 B2 * | 9/2022 | Olson .................. C12N 15/113 |
| 2003/0032791 A1 | 2/2003 | Alan et al. |
| 2003/0060436 A1 | 3/2003 | Schneider |
| 2003/0060438 A1 | 3/2003 | Henry et al. |
| 2003/0143738 A1 | 7/2003 | Yokata |
| 2004/0171570 A1 | 9/2004 | Allerson et al. |
| 2004/0226056 A1 | 11/2004 | Roch et al. |
| 2004/0241651 A1 | 12/2004 | Olek et al. |
| 2005/0014689 A1 | 1/2005 | Sugaru et al. |
| 2005/0019320 A1 | 1/2005 | Sugaru et al. |
| 2005/0020530 A1 | 1/2005 | Schneider |
| 2005/0032695 A1 | 2/2005 | Michaelis et al. |
| 2005/0032744 A1 | 2/2005 | Michaelis et al. |
| 2005/0064548 A1 | 3/2005 | Lindquist et al. |
| 2005/0130923 A1 | 6/2005 | Bhat et al. |
| 2005/0186591 A1 | 8/2005 | Bumcrot et al. |
| 2007/0161595 A1 | 7/2007 | Bumcrot et al. |
| 2007/0213366 A1 | 9/2007 | Justman et al. |
| 2007/0225209 A1 | 9/2007 | Roch et al. |
| 2007/0287831 A1 | 12/2007 | Seth et al. |
| 2008/0003570 A1 | 1/2008 | Rogers et al. |
| 2008/0039418 A1 | 2/2008 | Freier |
| 2008/0039618 A1 | 2/2008 | Allerson et al. |
| 2008/0206253 A1 | 8/2008 | Hua et al. |
| 2008/0300204 A1 | 12/2008 | Federoff et al. |
| 2008/0306143 A1 | 12/2008 | Choi et al. |
| 2009/0012281 A1 | 1/2009 | Swayze et al. |
| 2009/0092981 A1 | 4/2009 | Swayze et al. |
| 2009/0123575 A1 | 5/2009 | Lake et al. |
| 2009/0155778 A1 | 6/2009 | Niita et al. |
| 2009/0176729 A1 | 7/2009 | Tan |
| 2009/0286745 A1 | 11/2009 | Zurdo et al. |
| 2009/0306190 A1 | 12/2009 | Stenzel-Poore et al. |
| 2010/0031377 A1 | 2/2010 | Schenk et al. |
| 2010/0036122 A1 | 2/2010 | Suh |
| 2010/0056622 A1 | 3/2010 | Lauterbach |
| 2010/0137257 A1 | 6/2010 | Michaelis et al. |
| 2010/0151520 A1 | 6/2010 | Rogers et al. |
| 2010/0179223 A1 | 7/2010 | Esposito et al. |
| 2010/0204306 A1 | 8/2010 | Tan |
| 2010/0261753 A1 | 10/2010 | Boyd et al. |
| 2010/0278814 A1 | 11/2010 | Schenk et al. |
| 2011/0009445 A1 | 1/2011 | Stenzel-Poore et al. |
| 2011/0105405 A1 | 5/2011 | Michaelis et al. |
| 2011/0130441 A1 | 6/2011 | Seth et al. |
| 2011/0263678 A1 | 10/2011 | Bogdahn et al. |
| 2011/0300077 A1 | 12/2011 | Weihofen et al. |
| 2012/0014964 A1 | 1/2012 | Baekelandt et al. |
| 2012/0322851 A1 | 12/2012 | Hardee et al. |
| 2014/0005252 A1 | 1/2014 | Bennett et al. |
| 2014/0235696 A1 | 8/2014 | Henshall et al. |
| 2014/0323552 A1 | 10/2014 | Burghes et al. |
| 2016/0002627 A1 | 1/2016 | Bennett et al. |
| 2016/0038612 A1 | 2/2016 | Hoge et al. |
| 2016/0083726 A1 | 3/2016 | Montefeltro et al. |
| 2016/0194368 A1 | 7/2016 | Hoge et al. |
| 2016/0194625 A1 | 7/2016 | Hoge et al. |
| 2016/0235856 A1 | 8/2016 | Montefeltro et al. |
| 2016/0237427 A1 | 8/2016 | Olson et al. |
| 2016/0243221 A1 | 8/2016 | Hoge et al. |
| 2016/0243259 A1 | 8/2016 | Almarsson et al. |
| 2016/0244501 A1 | 8/2016 | Ellsworth et al. |
| 2016/0244502 A1 | 8/2016 | Bolen et al. |
| 2016/0251655 A1 | 9/2016 | Freier et al. |
| 2016/0304871 A1 | 10/2016 | Frank |
| 2016/0317647 A1 | 11/2016 | Ciaramella et al. |
| 2016/0331828 A1 | 11/2016 | Ciaramella et al. |
| 2016/0369270 A1 | 12/2016 | Henshall et al. |
| 2017/0002060 A1 | 1/2017 | Bolen et al. |
| 2017/0173128 A1 | 6/2017 | Hoge et al. |
| 2017/0283496 A1 | 10/2017 | Pedersen et al. |
| 2017/0349897 A1 | 12/2017 | Frank |
| 2018/0073022 A1 | 3/2018 | Freier |
| 2018/0085391 A1 | 3/2018 | Bouchon et al. |
| 2018/0092992 A1 | 4/2018 | Harley et al. |
| 2018/0119145 A1 | 5/2018 | Kordasiewicz |
| 2018/0208925 A1 | 7/2018 | Henshall et al. |
| 2018/0214579 A1 | 8/2018 | Almarsson et al. |
| 2018/0216108 A1 | 8/2018 | Vargeese et al. |
| 2019/0000959 A1 | 1/2019 | Ciaramella et al. |
| 2019/0008886 A1 | 1/2019 | Nakamori et al. |
| 2019/0008948 A1 | 1/2019 | Ciaramella et al. |
| 2019/0015501 A1 | 1/2019 | Ciaramella et al. |
| 2019/0016781 A1 | 1/2019 | Bolen et al. |
| 2019/0142971 A1 | 5/2019 | Hoge et al. |
| 2019/0192653 A1 | 6/2019 | Hoge et al. |
| 2019/0211332 A1 | 7/2019 | Kordasiewicz |
| 2019/0224339 A1 | 7/2019 | Paul et al. |
| 2019/0248864 A1 | 8/2019 | Ellsworth et al. |
| 2019/0264204 A1 | 8/2019 | Rigo |
| 2019/0270990 A1 | 9/2019 | Kordasiewicz et al. |
| 2019/0367916 A1 | 12/2019 | Freier et al. |
| 2020/0056173 A1 | 2/2020 | Vargeese et al. |
| 2020/0056179 A1 | 2/2020 | Freier et al. |
| 2020/0080083 A1 | 3/2020 | Vargeese et al. |
| 2020/0172903 A1 | 6/2020 | Nakamori et al. |
| 2020/0199589 A1 | 6/2020 | Kordasiewicz |

(56) References Cited

U.S. PATENT DOCUMENTS

| | | |
|---|---|---|
| 2020/0354720 A1 | 11/2020 | Olson et al. |
| 2020/0392494 A1 | 12/2020 | Kordasiewicz et al. |
| 2023/0193260 A1 | 6/2023 | Olson et al. |

FOREIGN PATENT DOCUMENTS

| | | |
|---|---|---|
| EP | 1135113 A1 | 9/2001 |
| EP | 1152009 A1 | 11/2001 |
| EP | 1238069 A2 | 9/2002 |
| EP | 1468694 A1 | 10/2004 |
| EP | 1481680 A1 | 12/2004 |
| EP | 1481685 A1 | 12/2004 |
| EP | 1635859 A2 | 3/2006 |
| EP | 1641468 A2 | 4/2006 |
| EP | 1716235 A2 | 11/2006 |
| EP | 1940419 A2 | 7/2008 |
| EP | 1135113 B1 | 10/2008 |
| EP | 1635859 B1 | 4/2010 |
| EP | 2322178 A2 | 5/2011 |
| EP | 1641468 B1 | 11/2011 |
| EP | 1716235 B1 | 6/2012 |
| EP | 2761002 A1 | 8/2014 |
| EP | 1670896 B1 | 1/2015 |
| EP | 2906255 A2 | 8/2015 |
| EP | 3041938 A1 | 7/2016 |
| EP | 3055414 A2 | 8/2016 |
| EP | 3076994 A2 | 10/2016 |
| EP | 3283080 A2 | 2/2018 |
| EP | 3325017 A1 | 5/2018 |
| EP | 2640853 B1 | 12/2018 |
| EP | 3415524 A1 | 12/2018 |
| EP | 3452596 A1 | 3/2019 |
| EP | 3519572 A1 | 5/2019 |
| EP | 3521451 A1 | 8/2019 |
| EP | 3283080 B1 | 3/2020 |
| EP | 2971010 B1 | 6/2020 |
| JP | 6126009 B2 | 5/2017 |
| WO | WO 1992/02258 A1 | 2/1992 |
| WO | WO 1993/007883 A1 | 4/1993 |
| WO | WO 1993/010820 A1 | 6/1993 |
| WO | WO 1994/013303 A1 | 6/1994 |
| WO | WO 1997/033550 A2 | 9/1997 |
| WO | WO 1998/039352 A1 | 9/1998 |
| WO | WO 1999/014226 A2 | 3/1999 |
| WO | WO 1999/060855 A1 | 12/1999 |
| WO | WO 1999/061066 A2 | 12/1999 |
| WO | WO 2000/002919 A1 | 1/2000 |
| WO | WO 2000/025798 A1 | 5/2000 |
| WO | WO 2000/037483 A1 | 6/2000 |
| WO | WO 2000/047599 A1 | 8/2000 |
| WO | WO 2000/066604 A2 | 11/2000 |
| WO | WO 2000/066725 A1 | 11/2000 |
| WO | WO 2001/005963 A2 | 1/2001 |
| WO | WO 2001/023613 A1 | 4/2001 |
| WO | WO 2001/057277 A2 | 8/2001 |
| WO | WO 2001/077384 A2 | 10/2001 |
| WO | WO 2001/086003 A2 | 11/2001 |
| WO | WO 2002/013799 A2 | 2/2002 |
| WO | WO 2002/032286 A2 | 4/2002 |
| WO | WO 2002/033112 A2 | 4/2002 |
| WO | WO 2002/033113 A2 | 4/2002 |
| WO | WO 2002/033114 A2 | 4/2002 |
| WO | WO 2003/004602 A2 | 1/2003 |
| WO | WO 2003/055507 A1 | 7/2003 |
| WO | WO 2004/046160 A2 | 6/2004 |
| WO | WO 2004/093783 A2 | 11/2004 |
| WO | WO 2004/093790 A2 | 11/2004 |
| WO | WO 2004/105773 A2 | 12/2004 |
| WO | WO 2004/105785 A2 | 12/2004 |
| WO | WO 2004/106356 A1 | 12/2004 |
| WO | WO 2005/004794 A2 | 1/2005 |
| WO | WO 2005/021570 A1 | 3/2005 |
| WO | WO 2005/074981 A2 | 8/2005 |
| WO | WO 2005/097817 A2 | 10/2005 |
| WO | WO 2006/034348 A2 | 3/2006 |
| WO | WO 2006/039253 | 4/2006 |
| WO | WO 2006/093034 A1 | 9/2006 |
| WO | WO 2006/099495 A2 | 9/2006 |
| WO | WO 2007/030580 A2 | 3/2007 |
| WO | WO 2007/030581 A2 | 3/2007 |
| WO | WO-2007031081 A2 | 3/2007 |
| WO | WO-2007031091 A2 | 3/2007 |
| WO | WO 2007/089584 A2 | 8/2007 |
| WO | WO 2007/089611 A2 | 8/2007 |
| WO | WO-2007090071 A2 | 8/2007 |
| WO | WO 2007/135426 A2 | 11/2007 |
| WO | WO-2007134181 A2 | 11/2007 |
| WO | WO 2007/146511 A2 | 12/2007 |
| WO | WO 2008/101157 A1 | 8/2008 |
| WO | WO 2008/113832 A2 | 9/2008 |
| WO | WO-2008150729 A2 | 12/2008 |
| WO | WO-2008154401 A2 | 12/2008 |
| WO | WO-2009006478 A2 | 1/2009 |
| WO | WO 2009/023855 | 2/2009 |
| WO | WO-2009043354 A2 | 4/2009 |
| WO | WO-2009067647 A1 | 5/2009 |
| WO | WO 2009/079399 A2 | 6/2009 |
| WO | WO-2010036698 A1 | 4/2010 |
| WO | WO-2010077578 A1 | 7/2010 |
| WO | WO-2011017521 A2 | 2/2011 |
| WO | WO-2011156202 A1 | 12/2011 |
| WO | WO 2012/027558 | 3/2012 |
| WO | WO-2012027713 A2 | 3/2012 |
| WO | WO-2012068405 A2 | 5/2012 |
| WO | WO-2013033230 A1 | 3/2013 |
| WO | WO-2013036868 A1 | 3/2013 |
| WO | WO 2013/045652 A1 | 4/2013 |
| WO | WO-2013154798 A1 | 10/2013 |
| WO | WO 2014/056298 A1 | 4/2014 |
| WO | WO 2014/059341 A2 | 4/2014 |
| WO | WO-2014076196 A1 | 5/2014 |
| WO | WO 2014/110291 A1 | 7/2014 |
| WO | WO-2014179620 A1 | 11/2014 |
| WO | WO-2014207232 A1 | 12/2014 |
| WO | WO 2015/034925 A1 | 3/2015 |
| WO | WO 2015/054676 A2 | 4/2015 |
| WO | WO 2015/085318 A2 | 6/2015 |
| WO | WO 2016/040748 A1 | 3/2016 |
| WO | WO-2016079181 A1 | 5/2016 |
| WO | WO-2016127002 A1 | 8/2016 |
| WO | WO-2016/164977 A1 | 10/2016 |
| WO | WO 2016/168592 A2 | 10/2016 |
| WO | WO 2017/015555 A1 | 1/2017 |
| WO | WO 2017/053995 A1 | 3/2017 |
| WO | WO 2017/053999 A1 | 3/2017 |
| WO | WO 2017/192664 A1 | 11/2017 |
| WO | WO-2018/064593 A1 | 4/2018 |
| WO | WO 2019/009298 A1 | 1/2019 |
| WO | WO 2019/009299 A1 | 1/2019 |
| WO | WO 2019/138057 A1 | 7/2019 |
| WO | WO 2019/140231 A1 | 7/2019 |
| WO | WO 2019/140236 A1 | 7/2019 |
| WO | WO 2019/164562 A2 | 8/2019 |
| WO | WO 2019/195519 A1 | 10/2019 |
| WO | WO 2019/217708 A1 | 11/2019 |
| WO | WO 2019/241648 A1 | 12/2019 |
| WO | WO 2020/006267 A1 | 1/2020 |
| WO | WO 2020/023737 A1 | 1/2020 |
| WO | WO 2020/055917 A1 | 3/2020 |
| WO | WO 2020/061497 A1 | 3/2020 |
| WO | WO 2020/106996 A1 | 5/2020 |
| WO | WO 2020/132558 A1 | 6/2020 |
| WO | WO-2020160163 A1 | 8/2020 |

OTHER PUBLICATIONS

Akinc, A., et al., "A combinatorial library of lipid-like materials for delivery of RNAi therapeutics," *Nature Biotechnology*, 26(5):561-569, Springer Nature Limited, Germany (2008).

Alarcon-Aris D., et al., "Selective α-Synuclein Knockdown in Monoamine Neurons by Intranasal Oligonucleotide Delivery: Potential Therapy for Parkinson's Disease," Molecular Therapy, 26(2):550-567, Cell Press, Cambridge. (Feb. 2018).

(56) References Cited

OTHER PUBLICATIONS

Albaek, N. et al., "Analogues of a Locked Nucleic Acid with Three-Carbon 2',4'-Linkages: Synthesis by Ring-Closing Metathesis and Influence on Nucleic Acid Duplex Stability and Structure," J Org Chem., 71(20): 7731-7740, Supplemental Information, American Chemical Society, United States (2006).

Altmann, K.H. et al., "Second generation of antisense oligonucleotides: from nuclease resistance to biological efficacy in animals," Chimia, 50(4): 168-176, New Swiss Chemical Society, Switzerland (1996).

Altmann, K.H. et al., "Second-generation antisense oligonucleotides: structure-activity relationships and the design of improved signal-transduction inhibitors," Biochem Soc Trans., 24(3): 630-637, Portland Press, United Kingdom (1996).

Altmann, K.H. et al., "Second Generation Antisense Oligonucleotides—Inhibition of PKC-α and c-raf Kinase Expression by Chimeric Oligonucleotides Incorporating 6"-Substituted Carbocyclic Nucleosides and 2"-O-Ethylene Glycol Substituted Ribonucleosides," Nucleosides and Nucleotides, 16: 917-926, Informa UK Limited, England (1997).

Baker, B.F. et al., "2'-O-(2-Methoxy)ethyl-modified Anti-intercellular Adhesion Molecule 1 (ICAM-1) Oligonucleotides Selectively Increase the ICAM-1mRNA Level and Inhibit Formation of the ICAM-1 Translation Initiation Complex in Human Umbilical Vein Endothelial Cells," J Biol Chem., 272(18): 11994-12000, the American Society of Biochemistry and Molecular Biology, Inc., United States (1997).

Bergstrom, D.E., "Unnatural Nucleosides With Unusual Base Pairing Properties," Current Protocols in Nucleic Acid Chemistry 37(1):1.4.1-1.4.32, Wiley, United States (2009).

Bodles, A.M., et al., "Inhibition of fibril formation and toxicity of a fragment of α-synuclein by an N-methylated peptide analogue," Neuroscience Letters, 359 (1-2): 89-93, Elsevier, Netherlands (2004).

Braasch, D.A. and Corey, D.R., "Locked nucleic acid (LNA): fine-tuning the recognition of DNA and RNA," Chem. Biol., 8(1): 1-7, Elsevier, Netherlands (2001).

Braga, C.A., et al., "The Anti-Parkinsonian Drug Selegiline Delays the Nucleation Phase of α-Synuclein Aggregation Leading to the Formation of Nontoxic Species," Journal of Molecular Biology, 405(1): 254-273, Elsevier, Netherlands (2011).

Burre, J. et al., "α-Synuclein promotes Snare-complex assembly in vivo and in vitro," Science, 329(5999): 1663-1667, America Association for the Advancement of Science, United States (2010).

Cabin, D.E. et al., "Synaptic vesicle depletion correlates with attenuated synaptic responses to prolonged repetitive stimulation in mice lacking α-synuclein," J Neurosci., 22(20): 8797-8807, Society for Neuroscience, United States (2002).

Chan, J.H.P. et al., "Antisense oligonucleotides: from design to therapeutic application," Clinical and Experimental Pharmacology and Physiology, 33(5-6): 533-540, Blackwell Publishing Asia Pty Ltd., Australia (2006).

Chiasson, B.J. et al., "The application of antisense oligonucleotide technology to the brain: some pitfalls," Cell Mol Neurobiol., 14: 507-521, Springer Nature, United Kingdom (1994).

Chun, S., et al., "Effect of infusion of vasoactive intestinal peptide (VIP)-antisense oligodeoxynucleotide into the third cerebral ventricle above the hypothalamic suprachiasmatic nucleus on the hyperglycemia caused by intracranial injection of 2-deoxy-D-glucose in rats," Neuroscience Letters, 257:135-138, Elsevier, Netherlands (1998).

Clayton, D.F. and George, J.M., "Synucleins in synaptic plasticity and neurodegenerative disorders," J. Neurosci., 58: 120-129, John Wiley & Sons, Inc., United States (1999).

Cole, T., et al., "Alpha-synuclein antisense oligonucleotides as a disease-modifying therapy for Parkinson's disease," bioRxiv 830554, doi: https://doi.org/10.1101/830554, pp. 1-42, Supplementary Materials, Cold Spring Harbor Laboratory, United States (Nov. 4, 2019).

Conway, K.A. et al., "Kinetic stabilization of the α-synuclein protofibril by a dopamine-α-synuclein adduct," Science, 294(5545): 1346-1349, American Association for the Advancement of Science, United States (2001).

Dass, C.R., "Vehicles for Oligonucleotide Delivery to Tumours," The Journal of Pharmacy and Pharmacology 54(1):3-27, Wiley, England (2002).

Database Geneseq [Online]., "Human SCNA mRNA targeted modified antisense oligonucleotide, SEQ ID 11," XP002789807. retrieved from EBI accession No. GSN:AZW44940, Database accession No. AZW44940 sequence, Jul. 5, 2012.

Database Geneseq [Online]., "Human SCNA mRNA targeted modified antisense oligonucleotide, SEQ ID 86," XP002789806. retrieved from EBI accession No. GSN:AZW45015, Database Accession No. AZW45015 sequence, Jul. 5, 2012.

Davidson, W.S. et al., "Stabilization of α-synuclein secondary structure upon binding to synthetic membranes," J Biol Chem., 273: 9443-9449, the American Society for Biochemistry and Molecular Biology, Inc., United States (1998).

Deleavey, G.R. and Damha, M.J., "Designing Chemically Modified Oligonucleotides for Targeted Gene Silencing," Chemistry & Biology 19(8):937-954, Elsevier, United States (2012).

Dravid, S.M and Murray, T.F., "Spontaneous Synchronized Calcium Oscillations in Neocortical Neurons in the Presence of Physiological [Mg(2+)]: Involvement of Ampa/kainate and Metabotropic Glutamate Receptors," Brain Research 1006(1):8-17, Elsevier/North-Holland Biomedical Press, Netherlands (2004).

Dyllick-Brenzinger, M., et al., "Reciprocal Effects of α-Synuclein Overexpression and Proteasome Inhibition in Neuronal Cells and Tissue," Neurotoxicity Research, 17: 215-227, Springer Nature Switzerland AG, Switzerland (2010).

El-Agnaf, O.M.A. et al., "A strategy for designing inhibitors of α□synuclein aggregation and toxicity as a novel treatment for Parkinson's disease and related disorders," The FASEB Journal, 18(11): 1315-1317, John Wiley & Sons, Inc., United States (2004).

Elayadi, A.N. and Corey, D.R., "Application of PNA and LNA oligomers to chemotherapy," Current Opinion in Investigational Drugs, 2(4): 558-561, PharmaPress Ltd, London (2001).

Fairman, M., et al., "Physiologically Based Pharmacokinetic (PBPK) Modeling of RNAi Therapeutics: Opportunities and Challenges," Biochemical Pharmacology, https://doi.org/10.1016/j.bcp.2021.114468, pp. 1-39, Elsevier, Inc., Netherlands (Feb. 10, 2021).

Freier, S.M. and Altmann, K.H., "The Ups and Downs of Nucleic Acid Duplex Stability: Structure-stability Studies on Chemically-modified DNA: RNA Duplexes," Nucleic Acids Research 25(22):4429-4443, Oxford University Press, England (1997).

Frieden, M. et al., "Expanding the design horizon of antisense oligonucleotides with alpha-I-LNA," Nucleic Acids Research, 31(21): 6365-6372, Oxford University Press, England (2003).

Galvin J. E., et al., "Synucleinopathies: Clinical and Pathological Implications," Archives of Neurology, 58(2):186-190, American Medical Assn., Chicago. (2001).

Gautschi, O., et al., "Activity of a Novel bcl-2/bcl-xL-Bispecific Antisense Oligonucleotide Against Tumors of Diverse Histologic Origins," J Natl Cancer Inst., 93(6): 463-471, Oxford University Press, England (2001).

GenBank Accession No. BC013293.2, "Homa sapiens synuclein, alpha (non A4 component o amyloied precursor), mRNA (cDNA clone MGC:3484 Image:3604532), complete cds," available at (https://www.ncbi.nlm.nih.gov/nuccore/BC013293.2).

GenBank Accession No. BG701026.1, "602682033F1 NIH_MGC_95 Homo sapiens cDNA clone Image:4814505 5', mRNA dequence," available at (https://www.ncbi.nlm.nih.gov/nuccore/BG701026).

GenBank Accession No. BM069769.1, "ie89b06.y1 Melton Normalized Human Islet 4 N4-HIS 1 Homo sapiens cDNA clone Image:5673946 5' similar to SW:SYUA_Human P37840 Alpha-Synuclein, mRNA sequence," available at (https://www.ncbi.nlm.nih.gov/nuccore/BM069769).

GenBank Accession No. L36674.1, "Human (clone 2-5) synuclein (NACP) mRNA, complete cds," available at (https://www.ncbi.nlm.nih.gov/nuccore/L36674).

Gerard, M., et al., "Inhibition of FK506 Binding Proteins Reduces α-Synuclein Aggregation and Parkinson's Disease-Like Pathology," The Journal of Neuroscience, 30(7): 2454-2463, the Society for Neurosciences, United States (2010).

(56) References Cited

OTHER PUBLICATIONS

Glaser, C.B., et al., "Methionine oxidation, α-synuclein and Parkinson's disease," *Biochimica et Biophysica Acta*, 1703(2): 157-169, Elsevier, Netherlands (2005).

Goodchild, J., (ed), Methods in Molecular Biology, Therapeutic Oligonucleotides, Methods and Protocols, vol. 764, pp. 1-340, Humana Press, United States (2011).

Grunweller A., et al., "Locked Nucleic Acid Oligonucleotides: The Next Generation of Antisense Agents?," Bio Drugs, 21(4):235-243, Springer International, Adis. (2007).

Henry, S. et al., "Chemically modified oligonucleotides exhibit decreased immune stimulation in mice," *The Journal of Pharmacology and Experimental Therapeutics*, 292(2): 468-479, the American Society for Pharmacology and Experimental Therapeutics, United States (2000).

Herrera, F.E., et al., "Inhibition of α-Synuclein Fibrillization by Dopamine Is Mediated by Interactions with Five C-Terminal Residues and with E83 in the NAC Region," *PLoS One*, 3(10): e3394, (2008).

Hillmer, A.S., et al., "Converse modulation of toxic α-synuclein oligomers in living cells by N'-benzylidene-benzohydrazide derivates and ferric iron," *Biochem Biophys Res Commun.*, 391(1): 461-466, Elsevier, Netherlands (2010).

Hirao, I., et al., "Natural Versus Artificial Creation of Base Pairs in DNA: Origin of Nucleobases From the Perspectives of Unnatural Base Pair Studies," Accounts of Chemical Research 45(12):2055-2065, American Chemical Society, United States (2012).

Hughes, E., et al., "Inhibition of Toxicity in the β-Amyloid Peptide Fragment β-(25-35) Using N-Methylated Derivatives: A General Strategy to Prevent Amyloid Formation," *J. Biol. Chem.*, 275(33):25109-25112, the American Society for Biochemistry and Molecular Biology, Inc., United States (2000).

International Search Report and Written Opinion for International Application No. PCT/US2019/013255, European Patent Office, Netherlands, mailed Apr. 8, 2019.

International Search Report and Written Opinion for International Application No. PCT/US2019/013249, mailed on Apr. 2, 2019, 13 pages.

Ishido, M., "Melatonin inhibits maneb-induced aggregation of α-synuclein in rat pheochromocytoma cells," *Journal of Pineal Research*, 42(2): 125-130, Wiley-Blackwell, United States (2007).

Iwai, A. et al., "The precursor protein of non-Aβ component of Alzheimer's disease amyloid is a presynaptic protein of the central nervous system," *Neurol*, 14: 467-475, Cell Press, United States (1995).

Jafar-nejad, P., et al., "The atlas of RNase H antisense oligonucleotide distribution and activity in the CNS of rodents and non-human primates following central administration," *Nucleic Acids Research*, 49(2):657-673, Oxford University Press, England (Dec. 4, 2020).

Jiang, M., et al., "Baicalein reduces E46K α☐synuclein aggregation in vitro and protects cells against E46K α☐synuclein toxicity in cell models of familiar Parkinsonism," *Journal of Neurochemistry*, 114(2): 419-429, International Society for Neurochemistry, Switzerland (2010).

Kalivendi, S., et al., "α-Synuclein Up-regulation and Aggregation during MPP+-induced Apoptosis in Neuroblastoma Cells: Intermediacy of Transferrin Receptor Iron and Hydrogen Peroxide," *The Journal of Biological Chemistry*, 279(15):15240-15247, the American Society for Biochemistry and Molecular Biology, Inc., United State (2004).

Karimy, JK, et al., "Inflammation-dependent cerebrospinal fluid hypersecretion by the choroid plexus epithelium in posthemorrhagic hydrocephalus," *Nature Medicine*, 23:997-1003, Supplemental Information, Springer Nature Limited, Germany (2017).

Koshkin, A.A., et al., "LNA (Locked Nucleic Acids): Synthesis of the adenine, cytosine, guanine, 5-methylcytosine, thymine and uracil bicyclonucleoside monomers, oligomerisation, and unprecedented nucleic acid recognition," *Tetrahedron*, 54(14): 3607-3630, Elsevier, Netherlands (1998).

Kramer, M.L. and Schulz-Schaeffer, W.J., "Presynaptic α-synuclein aggregates, not Lewy bodies, cause neurodegeneration in dementia with Lewy bodies," *J. Neurosci.*, 27: 1405-1410, Society for Neuroscience, United States (2007).

Kumar, R. et al., "The first analogues of LNA (Locked Nucleic Acids) phosphorothioate-LNA and 2'-thio-LNA," *Bioorg Med Chem Lett.*, 8: 2219-2222, Elsevier, Netherlands (1998).

Kuo Y. M., et al., "Extensive Enteric Nervous System Abnormalities in Mice Transgenic for Artificial Chromosomes Containing Parkinson Disease-Associated Alpha-Synuclein Gene Mutations Precede Central Nervous System Changes," Human Molecular Genetics, 19(9):1633-1650, Oxford University Press, Oxford. (2010).

Lamberto, G.R., et al., "Structural and mechanistic basis behind the inhibitory interaction of PcTS on α-synuclein amyloid fibril formation," *Proc Natl Acad Sci USA*, 106(50): 21057-21062 (2009).

Ledochowitsch, P., et al., "Fabrication and testing of a large area, high density, parylene MEMS μECoG array," 2011 IEEE 24th International Conference on Micro Electro Mechanical Systems, Cancun, Mexico Jan. 23-27, 2011, pp. 1031-1034 (2011).

Lee, H.J. at al., "Membrane-bound α-synuclein has a high aggregation propensity and the ability to seed the aggregation of the cytosolic form," *J. Biol. Chem.*, 277(1): 671-678, Elsevier, Netherlands (2002).

Lendel, C., et al., "On the Mechanism of Nonspecific Inhibitors of Protein Aggregation: Dissecting the Interactions of α-Synuclein with Congo Red and Lacmoid," *Biochemistry*, 48(35): 8322-8334, Supplemental Information, American Chemical Society, United States (2009).

Leumann, C.J., "Dna analogues: from supramolecular principles to biological properties," *Bioorganic & Medicinal Chemistry*, 10:841-854, Elsevier Science Ltd., Netherlands (2002).

Li, J., et al., "Rifampicin Inhibits α-Synuclein Fibrillation and Disaggregates Fibrils," *Chem Biol.*, 11(11): 1513-1521, Elsevier Science Ltd., Netherlands (2004).

Liu, S., et al., "α-Synuclein produces a long-lasting increase in neurotransmitter release," *The EMBO Journal*, 23(2): 4506-4516, European Molecular Biology Organization, Germany (2004).

Lotharius, J. and Brundin, P., "Pathogenesis of parkinson's disease: dopamine, vesicles and α-synuclein," *Nature Reviews Neuroscience*, 3:932-942, Springer Nature Limited, Germany (2002).

Lu, Z.J., and D.H. Mathews, "Fundamental differences in the equilibrium considerations for siRNA and antisense oligodeoxynucleotide design," *Nucleic Acids Research*, 36(11): 3738-3745, Oxford University Press, England (2008).

Lucking, C.B. and Brice, A., "Alpha-synuclein and Parkinson's disease," *Cell. Mol. Life Sci. CMLS*, 57:1894-1908 (2000).

Maguire-Zeiss, K.A., "α-Synuclein: A therapeutic target for Parkinson's disease," *Pharmacol Res.*, 58: 271-280, Elsevier, Netherlands (2008).

Maher, L.J. and B.J. Dolnick, "Comparative hybrid arrest by tandem antisense oligodeoxyribonucleotides or oligodeoxyribonucleoside methylpbosphonates in a cell-free system," *Nucleic Acids Research*, 16(8): 3341-3358, IRL Press Limited, Oxford, England (1988).

Manoharan M., "Oligonucleotide Conjugates as Potential Antisense Drugs with Improved Uptake, Biodistribution, Targeted Delivery, and Mechanism of Action," Antisense and Nucleic Acid Drug Development, 12(2):103-128, Mary Ann Liebert, Inc., New York. (2002).

Marques O., et al., "Alpha-Synuclein: From Secretion to Dysfunction and Death," Cell Death & Disease, 3(7):e350, Nature Pub. Group, London. (2012).

Martin, P., Ein neuer Zugang zu 2'☐O☐Alkylribonucleosiden und Eigenschaften deren Oligonucleotide,: *Helv Chim Acta*, 78: 486-504, John Wiley & Sons, Switzerland (1995) (English Language Abstract).

Martinez, Z., et al., "GM1 Specifically Interacts with α-Synuclein and Inhibits Fibrillation," *Biochemistry*, 46(7): 1868-1877, American Chemical Society, United States (2007).

McCormack, A., et al., "α-Synuclein Suppression by Targeted Small Interfering RNA in the Primate Substantia Nigra," *PLoS ONE*, 5(8): e12122, pp. 1-8, Public Library of Sciene, United States (2010).

(56) References Cited

OTHER PUBLICATIONS

Meng, X., et al., "Molecular Mechanisms Underlying the Flavonoid-Induced Inhibition of α-Synuclein Fibrillation," *Biochemistry*, 48(43): 8206-8224, American Chemical Society, United States (2009).
Mitsuoka Y., et al., "A Bridged Nucleic Acid, 2',4'-BNA COC: Synthesis of Fully Modified Oligonucleotides Bearing Thymine, 5-Methylcytosine, Adenine and Guanine 2',4'-BNA COC Monomers and RNA-Selective Nucleic-Acid Recognition," Nucleic Acids Research, 37(4):1225-1238, Oxford University Press, Oxford. (2009).
Monti, B., et al., "Alpha-synuclein protects cerebellar granule neurons against 6-hydroxydopamine-induced death," *Journal of Neurochemistry*, 103(2): 518-530, International Society for Neurochemistry, Switzerland (2007).
Monti, B., et al., "Valproic Acid is Neuroprotective in the Rotenone Rat Model of Parkinson's Disease: Involvement of α-Synuclein," *Neurotoxicity Research*, 17: 130-141, Springer, Germany (2010).
Morita K., et al., "2'-O,4'-C-Ethylene-Bridged Nucleic Acids (ENA): Highly Nuclease-Resistant and Thermodynamically Stable Oligonucleotides for Antisense Drug," Bioorganic and Medicinal Chemistry Letters, 12(1):73-76, Elsevier Science Ltd, Oxford. (2002).
Murphy, D.D., et al., "Synucleins are Developmentally Expressed, and α-Synuclein Regulates the Size of the Presynaptic Vesicular Pool in Primary Hippocampal Neurons," *Journal of Neuroscience*, 20(9):3214-3220, Society for Neuroscience, United States (2000).
NCBI Accession No. NC_000004.12, "*Homo sapiens* chromosome 4, GRCh38.p13 Primary Assembly," available at (https://www.ncbi.nlm.nih.gov/nuccore/NC_000004.12/).
NCBI, "*Homo sapiens* Synuclein Alpha (Snca), RefSeqGene on Chromosome 4," Accession No. NG_011851.1, accessed at https://www.ncbi.nlm.nih.gov/nuccore/NG_011851.1.
NCBI Accession No. NM_000345.3, "NM_000345.3(SNCA):c.*2501C>A and Parkinson Disease, Dominant," available at (https://www.ncbi.nlm.nih.gov/clinvar/21945055/).
NCBI Accession No. NM_007308.1, "*Homo sapiens* synuclein, alpha (non A4 component of amyloid precursor) (SNCA), transcript variant NACP112, mRNA," available at (https://www.ncbi.nlm.nih.gov/nuccore/NM_007308.1).
NCBI Accession No. NM_001042451.1, "Mus musculus synuclein, alpha (Snca), transcript variant 1, mRNA," available at (https://www.ncbi.nlm.nih.gov/nuccore/NM_001042451.1).
NCBI Accession No. NT_016354.17, "*Homo sapiens* chromosome 4 genomic contig," available at (https://www.ncbi.nlm.nih.gov/nuccore/NT_016354.17).
Ono, K., et al., "α-Synuclein Assembly as a Therapeutic Target of Parkinson's Disease and Related Disorders," *Curr. Pharm. Des.*, 14(30): 3247-3266 (2008).
Orum, H. and J. Wengel, "Locked nucleic acids: a promising molecular family for gene-function analysis and antisense drug development," *Current Opinion in Molecular Therapeutics*, 3(3): 239-243 (2001).
Paleologou, K.E., et al., "α-Synuclein aggregation in neurodegenerative diseases and its inhibition as a potential therapeutic strategy," *Biochem Soc Trans.*, 33(5): 1106-1110, Biochemical Society, London (2005).
Pasti, L., et al., "Cytosolic Calcium Oscillations in Astrocytes May Regulate Exocytotic Release of Glutamate," The Journal of Neuroscience 21(2):477-484, Society for Neuroscience, United States (2001).
Putcha, P., et al., "Brain-Permeable Small-Molecule Inhibitors of Hsp90 Prevent α-Synuclein Oligomer Formation and Rescue α-Synuclein-Induced Toxicity," *J Pharmacol Exp Ther*, 332(3): 849-857, the American Society for Pharmacology and Experimental Therapeutics, United States (2010).
Qin, Z., et al., "Effect of 4-Hydroxy-2-nonenal Modification on α-Synuclein Aggregation," *J Biol Chem.*, 282: 5862-5870, the American Society for Biochemistry and Molecular Biology, Inc., United States (2007).
Rayburn, E.R. and Zhang, R., "Antisense, RNAi, and gene silencing strategies for therapy: Mission possible or impossible?," *Drug Discovery Today*, 13(11-12):513-521, Elsevier, Netherlands (2008).

Recchia A., et al., "Alpha-Synuclein and Parkinson's Disease," FASEB J, 18(6):617-626, Hoboken, NJ. (2004).
Rekas, A., et al., "PAMAM Dendrimers as Potential Agents against Fibrillation of α-Synuclein, a Parkinson's Disease-Related Protein," *Macromolecular Bioscience*, 9(3): 230-238, Wiley-VCH Verlag GmbH & Co. KGaA, Weinheim (2009).
Rockenstein, E. et al., "Differential neuropathological alterations in transgenic mice expressing α-synuclein from the platelet-derived growth factor and Thy-1 promoters," *J Neurosci Res.*, 68: 568-578, Wiley-Liss, Inc., United States (2002).
Rose, C.R. and Konnerth, A., "Exciting Glial Oscillations," Nature Neuroscience 4(8):773-774, Nature Publishing Group, United States (2001).
Sarkar, S., et al., "Trehalose, a Novel mTOR-independent Autophagy Enhancer, Accelerates the Clearance of Mutant Huntingtin and α-Synuclein," *J Biol Chem.*, 282: 5641-5652, the American Society for Biochemistry and Molecular Biology, Inc., United States (2007).
Segers-Nolten, I.M.J., "Tissue transglutaminase modulates α☐synuclein oligomerization," *Protein Science*, 17(8): 1395-1402, Cold Spring Harbor Laboratory Press, United States (2008).
Seth, P.P., et al., "Synthesis and Biophysical Evaluation of 2',4'-constrained 2'O-methoxyethyl and 2',4'-constrained 2'O-ethyl Nucleic Acid Analogues," Journal of Organic Chemistry 75(5):1569-1581, American Chemical Society, United States (2010).
Schulze-Schaeffer, W.J., "The synaptic pathology of α-synuclein aggregation in dementia with Lewy bodies, Parkinson's disease and Parkinson's disease dementia," *Acta Neuropathol.*, 120: 131-143, Springer, Germany (2010).
Singh, S.K. et al., "LNA (locked nucleic acids): synthesis and high-affinity nucleic acid recognition," *Chem Commun.*, 4: 455-456, Elsevier B.V., Netherlands (1998).
Singh, S.K. et al., "Synthesis of 2'-Amino-LNA: A Novel Conformationally Restricted High-Affinity Oligonucleotide Analogue with a Handle," J Org Chem., 63(26): 10035-10039, American Chemical Society, United States (1998).
Smith, L., et al., "Rational selection of antisense oligonucleotide sequences," European Journal of Pharmaceutical Sciences, 11:191-198, Elsevier Sciences B.V., Netherlands (2000).
Snyder, H., et al., "β-Synuclein Reduces Proteasomal Inhibition by α-Synuclein but Not γ-Synuclein," *Journal of Biological Chemistry*, 280(9): 7562-7569, Elsevier, Netherlands (2005).
Sohail, M. and Southern, E.M., "Selecting optimal antisense reagents," *Advanced Drug Delivery Reviews*, 44:23-34, Elsevier, Netherlands (2000).
Souza, J.M. et al., "Chaperone-like activity of synucleins," *FEBS Lett.*, 474: 116-119, Elsevier, Netherlands (2000).
Srivastava, P., et al., "Five- and Six-Membered Conformationally Locked 2',4'-Carbocyclic ribo-Thymidines: Synthesis, Structure, and Biochemical Studies," *J Am Chem Soc.*, 129 (26): 8362-8379, American Chemical Society, United States (2007).
Stowe, R.P., et al., "Detection and Quantification of Epstein-Barr Virus EBER1 in EBV-infected Cells by Fluorescent in situ Hybridization and Flow Cytometry," Journal of Virological Methods 75(1):83-91, Elsevier/North-Holland Biomedical Press, Netherlands (1998).
Touboul, M., et al., "Early Detection of Chemoresistance in Vivo through the use of a Radiolabeled Antisense Oligonucleotide," Anticancer Research 22(6A):3349-3356, International Institute of Anticancer Research, Greece (2002).
Uehara T., et al., "Anti Sense Oligonucleotides Containing Amido-Bridged Nucleic Acid Reduce SNCA Expression and Improve Motor Function in Parkinson's Disease Animal Models," A Journal of Neurological Sciences, vol. 381:1044-1045, Science Direct. (2017).
Uehara, T., "Amido-bridged nucleic acid (AmNA)-modified antisense oligonucleotides targeting α-synuclein as a novel therapy for Parkinson's disease," Scientific Reports, 9:7567, Springer Nature Limited, Germany (May 21, 2019).
Uhlmann, E., "Recent Advances in the Medicinal Chemistry of Antisense Oligonucleotides," Current Opinion in Drug Discovery and Development 3(2):203-213, Thomson Reuters Scientific Ltd., England (2000).

(56) References Cited

OTHER PUBLICATIONS

UniProtKB Primary Accession Number P37840; Secondary Accession Nos. A8K2A4, Q6IAU6, Q13701, Q4JHI3, Q6IAU6 available at (https://www.uniprot.org/uniprot/P37840).

Uversky, V.N., "Neuropathology, biochemistry, and biophysics of α□synuclein aggregation," *J. Neurochem.*, 103:17-37, International Society for Neurochemistry, Switzerland (2007).

Valera E., et al., "Therapeutic Approaches in Parkinson's Disease and Related Disorders," Journal of Neurochemistry, 139 Suppl 1(Suppl 1):346-352, Wiley on behalf of the International Society for Neurochemistry, Oxford. (2016).

Verjat et al., "Detection of 8-oxoG DNA glycosylase activity and OGG1 transcripts in the rat CNS," *Mutat. Res.*, 640: 127-38, Elsevier, Netherlands (2000).

Vickers, T.A. et al., "Effects of RNA secondary structure on cellular antisense activity," *Nucleic Acids Research*, 28(6): 1340-1347, Oxford University Press, England (2000).

Vickers, T.A. et al., "Efficient reduction of target RNAs by small interfering RNA and RNase H-dependent antisense agents—A comparative analysis," *The Journal of Biological Chemistry*, 278(9): 7108-7118, the American Society for Biochemistry and Molecular Biology, Inc., United States (2003).

Wahlestedt, C. et al., "Potent and nontoxic antisense oligonucleotides containing locked nucleic acids," *Proc Natl Acad Sci USA*, 97(10): 5633-5638 (2000).

Wan W. B., et al., "The Medicinal Chemistry of Therapeutic Oligonucleotides," Journal of Medicinal Chemistry, 59(21):9645-9667, American Chemical Society, Washington. (2016).

Woolf, T.M., et al., "Specificity of antisense oligonucleotides in vivo," *Proc Natl Acad Sci USA*, 89(16): 7305-7309 (1992).

Xu, J., "Rifampicin protects PC12 cells against MPP+-induced apoptosis and inhibits the expression of an α-Synuclein multimer," *Brain Research*, 1139: 220-225, Elsevier, Netherlands (2007).

Yoshida, M., "Multiple system atrophy: α□synuclein and neuronal degeneration," *Neuropathology*, 27: 484-493, Japanese Society of Neuropathology, Tokyo (2007).

Zhou, C., et al., "A human single-chain Fv intrabody blocks aberrant cellular effects of overexpressed α-synuclein," *Molecular Therapy*, 10(6): 1023-1031, the American Society of Gene Therapy, United States (2004).

Zhou, C. et al., "Fine Tuning of Electrostatics around the Internucleotidic Phosphate through Incorporation of Modified 2',4'-Carbocyclic-LNAs and -ENAs Leads to Significant Modulation of Antisense Properties," *J Org Chem*, 74(1): 118-134, Supplemental Information, American Chemical Society, United States (2009).

Zhou, W., et al., "At Low Concentrations, 3,4-Dihydroxyphenylacetic Acid (DOPAC) Binds Non-Covalently to α-Synuclein and Prevents Its Fibrillation," *Journal of Molecular Biology*, 388(3): 597-610, Elsevier, Netherlands (2009).

Zhu, M. and A.L. Fink, "Lipid Binding Inhibits a-Synuclein Fibril Formation," *J Biol Chem.*, 278: 16873-16877, the American Society for Biochemistry and Molecular Biology, Inc., United States (2003).

Zonta, M. and Carmignoto, G., "Calcium Oscillations Encoding Neuron-to-astrocyte Communication," Journal of Physiology 96(3-4):193-198, Editions Scientifiques Elsevier, France (2002).

Toth, Z.E., et al., "Bone Marrow-Derived Nonreactive Astrocytes in the Mouse Brain After Permanent Middle Cerebral Artery Occlusion," *Stem Cells and Development*, 20(3):539-546, Mary Ann Liebert, Inc., United States (2011).

Kole, R., et al., "RNA therapeutics: beyond RNA interference and antisense oligonucleotides," Nature Reviews, 11:125-140, Macmillan Publishers Limited, United States (2012).

Peng, B., et al., "Tissue Distribution and Physiologically Based Pharmacokinetics of Antisense Phosphorothioate Oligonucleotide ISIS 1082 in Rat," *Antisense & Nucleic Acid Drug Development*, 11:15-27, Mary Ann Liebert, Inc., United States (2001).

Beaucage, S.L. and R.P. Iyer, "Advances in the Synthesis of Oligonucleotides by the Phosphoramidite Approach," *Tetrahedron*, 48(12):2223-2311, Elsevier, Netherlands (1992).

U.S. Appl. No. 08/050,698, inventors Froehler, B., et al., filed Apr. 19, 1993 (Not Published).

U.S. Appl. No. 17/165,841, inventors Richard E. Olson, et al., filed Feb. 2, 2021 (Not Published).

Alterman, J.F., et al., "A divalent siRNA chemical scaffold for potent and sustained modulation of gene expression throughout the central nervous system," Nature Biotechnology 37:884-894, Nature Publishing Group, England (Aug. 2019).

Bennett, C.F., et al., "RNA Targeting Therapeutics: Molecular Mechanisms of Antisense Oligonucleotides as a Therapeutic Platform," Annu. Rev. Pharmacol. Toxicol 50:259-293, Annual Reviews, United States (2010).

Burel, S.A., et al., "Hepatotoxicity of high affinity gapmer antisense oligonucleotides is mediated by RNase H1 dependent promiscuous reduction of very long pre-mRNA transcripts," Nucleic Acids Research 44(5):2093-2109, Oxford University Press, England (2016).

Crooke, S.T., et al., "Antisense technology: A review," J. Biol. Chem 296: 1-39, Elsevier, Netherlands (Feb. 2021).

Crooke, S.T., et al., "Antisense drug discovery and development technology considered in a pharmacological context," Biochemical Pharmacology 189:114196, Elsevier, Netherlands (Aug. 2020).

Crooke, S.T., et al., "Antisense technology: an overview and prospectus," Nature Rev Drug Discov 20(6):427-453, Nature Publishing Group, England (Mar. 2021).

European Patent Register, "European Patent EP2640853 File History," retrieved from: <https://register.epo.org/application?number=EP11840796&lng-en&tab=doclist>, retrieved on Jan. 25, 2022, 3258 pages.

Jahns, H., et al., "Chirality matters: stereo-defined phosphorothioate linkages at the termini of small interfering RNAs improve pharmacology in vivo," Nucleic Acids Research: 1-20, Oxford University Press, England (Jul. 2021).

Kamola, P.J., et al., "In silico and in vitro evaluation of exonic and intronic off-target effects form a critical element of therapeutic ASO gapmer optimization," Nucleic Acids Research 43(18):8638-8650, Oxford University Press, England (2015).

Kurreck, J., et al., "Design of antisense oligonucleotides stabilized by locked nucleic acids," Nucleic Acids Res 30(9):1911-1918, Oxford University Press, England (May 2002).

Karaki, S., et al., "Antisense Oligonucleotides, a Novel Developing Targeting Therapy," Antisense Therapy:1-19, IntechOpen, France (Feb. 2019).

Khvorova, A., et al., "The chemical evolution of oligonucleotide therapies of clinical utility," Nature Biotechnology 35(3):238-248, Nature Publishing Group, England (Mar. 2017).

Lewis, J., et al., "In vivo silencing of alpha-synuclein using naked siRNA," Molecular Neurodegeneration 3(19):1-10, BioMed Central, United Kingdom (2008).

Martinez, J., et al., "Single-Stranded Antisense siRNAs Guide Target RNA Cleavage in RNAi," Cell 110:563-574, Cell Press, United States (2002).

Possin, K.L., et al., "Visual Spatial Cognition in Neurodegenerative disease," Neurocase 16(6):466-487, Taylor & Francis Online, United States (2010).

Rudin, C.M., et al., "Delivery of a Liposomal c-raf-1 Antisense Oligonucleotide by Weekly Bolus dosing in Patients with Advanced Solid Tumors: A Phase I Study," Clinical Cancer Research 10:7244-7251, American Association for Cancer Research, United States (2004).

Scoles, D.R., et al., "Antisense oligonucleotides," Neurology: Genetics 5(2):1-8, American Academy of Neurology, United States (Apr. 2019).

Seth, P.P., et al., "Short Antisense Oligonucleotides with Novel 2'-4' Conformationaly Restricted Nucleoside Analogues Show Improved Potency without Increased Toxicity in Animals," J. Med. Chem 52:10-13, American Chemical Society, United States (2008).

Seth, P.P., et al., "Design, Synthesis and Evaluation of Constrained Methoxyethyl (cMOE) and Constrained Ethyl (cEt) Nucleoside Analogs," Nucleic Acids Symposium Series 52:553-554, Oxford University Press, England (2008).

(56) References Cited

OTHER PUBLICATIONS

Swayze, E.C., et al., "Antisense oligonucleotides containing locked nucleic acid improve potency but cause significant hepatotoxicity in animals," Nucleic Acid Research 35(2): 687-700, Oxford University Press, England (2007).
Yu, R.Z., et al., "Cross-Species Pharmacokinetic Comparison from Mouse to Man of a Second-Generation Antisense Oligonucleotide, ISIS 301012, Targeting Human Apolipoprotein B-100," Drug Metabolism and Disposition 35(3):460-468, American Society for Pharmacology and Experimental Therapeutics, United States (2007).
Yu, R.Z., et al., "Comparison of Pharmacokinetics and Tissue Disposition of an Antisense Phosphorothioate Oligonucleotide Targeting Human Ha-ras mRNA in Mouse and Mickey," Journal of Pharmaceutical Sciences 90(2):182-193, Wiley-Liss, United States (2001).
Office Action mailed Jul. 13, 2021 in U.S. Appl. No. 17/165,841, inventor Olson; Richard E., filed Feb. 2, 2021, 7 pages.
Office Action mailed Mar. 31, 2021 in U.S. Appl. No. 17/165,841, inventor Olson; Richard E., filed Feb. 2, 2021, 9 pages.
Office Action mailed Sep. 21, 2021 in U.S. Appl. No. 16/961,624, inventor Olson; Richard E., filed Jan. 11, 2019, 8 pages.

\* cited by examiner

FIG. 1A.

```
6001 gagataggga cgaggagcac gctgcaggga aagcagcgag cgccgggaga ggggcgggca
6061 gaagcgctga caaatcagcg gtggggcgg agagccgagg agaaggagaa ggaggaggac
6121 taggaggagg aggacggcga cgaccagaag gggcccaaga gaggggggcga gcgaccgagc
6181 gccgcgacgc ggaagtgagg tgcgtgcggg ctgcagcgca gaccccggcc cggcccctcc
6241 gagagcgtcc tgggcgctcc ctcacgcctt gccttcaagc cttctgcctt tccaccctcg
6301 tgagcggaga actgggagtg gccattcgac gacaggttag cgggtttgcc tcccactccc
6361 ccagcctcgc gtcgccggct cacagcggcc tcctctgggg acagtcccc ccgggtgccg
6421 cctccgccct tcctgtgcgc tccttttcct tcttctttcc tattaaatat tatttgggaa
6481 ttgtttaaat ttttttttta aaaaagaga gaggcgggga ggagtcggag ttgtggagaa
6541 gcagagggac tcaggtaagt acctgtggat ctaaacgggc gtctttggaa atcctggaga
6601 acgccggatg ggagacgaat ggtcgtgggc accgggaggg ggtggtgctg ccatgaggac
6661 ccgctgggcc aggtctctgg gaggtgagta cttgtccctt tggggagcct aaggaaagag
6721 acttgacctg gctttcgtcc tgcttctgat attcccttct ccacaagggc tgagagatta
6781 ggctgcttct ccgggatccg cttttccccg ggaaacgcga ggatgctcca tggagcgtga
6841 gcatccaact tttctctcac ataaaatctg tctgcccgct ctcttggttt ttctctgtaa
6901 agtaagcaag ctgcgtttgg caaataatga aatggaagtg caaggaggcc aagtcaacag
6961 gtggtaacgg gttaacaagt gctggcgcgg ggtccgctag ggtggaggct gagaacgccc
7021 cctcgggtgg ctggcgcggg gttggagacg gcccgcgagt gtgagcggcg cctgctcagg
7081 gtagatagct gagggcgggg gtggatgttg gatggattag aaccatcaca cttgggcctg
7141 ctgtttgcct gagtttgaac cacacccga gtgagcagtt agttctgttg cctacgcctt
7201 tccaccatca acctgttagc cttcttctgg gattcatgtt aaggataccc ctgaccctaa
7261 gcctccagct tccatgcttc taactcatac tgttacccct tagaccccgg gaatttaaaa
7321 aaggggttaa tcttttcatg caactccact tctgaaatgc agtaataaca actcagagga
7381 ttcatcctaa tccgtggtta ggtggctaga cttttactag ccaagatgga tgggagatgc
7441 taaattttta atgccagagc taaaaatgtc tgctttgtcc aatggttaaa tgagtgtaca
7501 cttaaaagag tctcacactt tggagggttt ctcatgattt tcagtgttt tttgtttatt
7561 tttccccgaa agttctcatt caaagtgtat tttatgtttt ccagtgtggt gtaaaggaat
7621 tcattagcca tggatgtatt catgaaagga cttcaaagg ccaaggaggg agttgtggct
7681 gctgctgaga aaccaaaca gggtgtggca gaagcagcag gaaagacaaa agagggtgtt
7741 ctctatgtag gtaggtaaac cccaaatgtc agtttggtgc ttgttcatga gtgatgggtt
7801 aggataatca atactctaaa tgctggtagt tctctctctt gattcatttt tgcatcattg
7861 cttgtcaaaa aggtggactg agtcagaggt atgtgtaggt aggtgaatgt gaacgtgtgt
7921 atttgagcta atagtaaaaa atgcgactgt ttgcttttcc agatttttaa ttttgcccta
7981 atatttatga cttttaaaa atgaatgttt ctgtacctac ataattctat ttcagagaac
8041 agttttaaaa actcatagtc tttaaaaaa taatcaagaa tattcttaag aatcaaaatc
8101 attgatggat ctgtgatttc ttttaccatc atgaaaaatg tttgtcaatt ttaatccatt
8161 ctgatttta aaatatgact ttgatatgcc cctgtgatgt gtataaagag acctatttgt
8221 ggccctaaaa tggaaagaac agattagtct ttgatagagt tacttcatgt gatcatttgg
8281 tctctgtgaa cactgaggac agagaaaagt gcttgagggc tgctactaat ctctcagaaa
8341 catttgtata gttcatccat caaatgacac acatactaaa agaataaaga aattgatgct  8400
```

FIG. 1B.

```
   1 aggagaagga gaaggaggag gactaggagg aggaggacgg cgacgaccag aagggcccca
  61 agagaggggg cgagcgaccg agcgccgcga cgcggaagtg aggtgcgtgc gggctgcagc
 121 gcagacccg gcccggcccc tccgagagcg tcctgggcgc tccctcacgc cttgccttca
 181 agccttctgc ctttccaccc tcgtgagcgg agaactggga gtggccattc gacgacagtg
 241 tggtgtaaag gaattcatta gccatggatg tattcatgaa aggactttca aaggccaagg
 301 agggagttgt ggctgctgct gagaaaacca acagggtgt ggcagaagca gcaggaaaga
 361 caaaagaggg tgttctctat gtaggctcca aaaccaagga gggagtggtg catggtgtgg
 421 caacagtggc tgagaagacc aaagagcaag tgacaaatgt tggaggagca gtggtgacgg
 481 gtgtgacagc agtagcccag aagacagtgg agggagcagg gagcattgca gcagccactg
 541 gctttgtcaa aaaggaccag ttgggcaaga atgaagaagg agccccacag gaaggaattc
 601 tggaagatat gcctgtggat cctgacaatg aggcttatga aatgccttct gaggaagggt
 661 atcaagacta cgaacctgaa gcctaagaaa tatctttgct cccagtttct tgagatctgc
 721 tgacagatgt tccatcctgt acaagtgctc agttccaatg tgcccagtca tgacatttct
 781 caaagttttt acagtgtatc tcgaagtctt ccatcagcag tgattgaagt atctgtacct
 841 gcccccactc agcatttcgg tgcttccctt tcactgaagt gaatacatgg tagcagggtc
 901 tttgtgtgct gtggattttg tggcttcaat ctacgatgtt aaaacaaatt aaaaacacct
 961 aagtgactac cacttatttc taaatcctca ctatttttt gttgctgttg ttcagaagtt
1021 gttagtgatt tgctatcata tattataaga ttttaggtg tcttttaatg atactgtcta
1081 agaataatga cgtattgtga aatttgttaa tatatataat acttaaaaat atgtgagcat
1141 gaaactatgc acctataaat actaaatatg aaatttacc attttgcgat gtgttttatt
1201 cacttgtgtt tgtatataaa tggtgagaat taaaataaaa cgttatctca ttgcaaaaat
1261 atttattt tatcccatct cactttaata ataaaaatca tgcttataag caacatgaat
1321 taagaactga cacaaaggac aaaaatataa agttattaat agccatttga agaaggagga
1381 attttagaag aggtagagaa aatggaacat taacccctaca ctcggaattc cctgaagcaa
1441 cactgccaga agtgtgttt ggtatgcact ggttccttaa gtggctgtga ttaattattg
1501 aaagtggggt gttgaagacc ccaactacta ttgtagagtg gtctatttct cccttcaatc
1561 ctgtcaatgt ttgctttacg tatttgggg aactgttgtt tgatgtgtat gtgtttataa
1621 ttgttataca ttttaattg agccttttat taacatatat tgttattttt gtctcgaaat
1681 aatttttag ttaaaatcta ttttgtctga tattggtgtg aatgctgtac ctttctgaca
1741 ataaataata ttcgaccatg aataaaaaaa aaaaaaagt gggttcccgg gaactaagca
1801 gtgtagaaga tgattttgac tacaccctcc ttagagagcc ataagacaca ttagcacata
1861 ttagcacatt caaggctctg agagaatgtg gttaactttg tttaactcag cattcctcac
1921 tttttttt taatcatcag aaattctctc tctctctc tctttttctc tcgctctctt
1981 tttttttt ttttacagg aaatgccttt aaacatcgtt ggaactacca gagtcacctt
2041 aaaggagatc aattctctag actgataaaa atttcatggc ctcctttaaa tgttgccaaa
2101 tatatgaatt ctaggatttt tccttaggaa aggttttct ctttcaggga agatctatta
2161 actccccatg ggtgctgaaa ataaacttga tggtgaaaaa ctctgtataa attaatttaa
2221 aaattatttg gtttctcttt ttaattattc tggggcatag tcatttctaa aagtcactag
2281 tagaaagtat aatttcaaga cagaatattc tagacatgct agcagtttat atgtattcat
2341 gagtaatgtg atatatattg ggcgctggtg aggaaggaag gaggaatgag tgactataag
2401 gatggttacc atagaaactt cctttttac ctaattgaag agagactact acagagtgct
2461 aagctgcatg tgtcatctta cactagagag aaatggtaag tttcttgttt tatttaagtt
2521 atgtttaagc aaggaaagga tttgttattg aacagtatat ttcaggaagg ttagaaagtg
2581 gcggttagga tatattttaa atctacctaa agcagcatat tttaaaaatt taaagtatt
2641 ggtattaaat taagaaatag aggacagaac tagactgata gcagtgacct agaacaattt
2701 gagattagga aagttgtgac catgaattta aggatttatg tggatacaaa ttctccttta
2761 aagtgtttct tcccttaata tttatctgac ggtaattttt gagcagtgaa ttactttata
2821 tatcttaata gtttatttgg gaccaaacac ttaaacaaaa agttctttaa gtcatataag
2881 ccttttcagg aagcttgtct catattcact cccgagacat tcacctgcca agtggcctga
2941 ggatcaatcc agtcctaggt ttattttgca gacttacatt ctcccaagtt attcagcctc
3001 atatgactcc acggtcggct ttaccaaaac agttcagagt gcactttggc acacaattgg
3061 gaacagaaca atctaatgtg tggtttggta ttccaagtgg ggtcttttc agaatctctg
```

FIG. 1B. (cont.)

3121 cactagtgtg agatgcaaac atgtttcctc atctttctgg cttatccagt atgtagctat
    3181 ttgtgacata ataaatatat acatatatga aaata

FIG. 1C.

MDVFMKGLSKAKEGVVAAAEKTKQGVAEAAGKTKEGVLYVGSKTKEGVVHGVATVAEKTKEQVTNVGGAV
VTGVTAVAQKTVEGAGSIAAATGFVKKDQLGKNEEGAPQEGILEDMPVDPDNEAYEMPSEEGYQDYEPEA

FIG. 2.

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 4 | 7,602 | 7,617 | 236 | 251 | DES-001464 | CCtttacaccacTG | ASO-001464 | OxyMCs OxyMCs DNAts DNAts DNAts DNAas DNAcs DNAcs DNAcs DNAas DNAcs OxyTs OxyG |
| 4 | 7,602 | 7,617 | 236 | 251 | DES-001649 | CCTttacaccacTG | ASO-001649 | OxyMCs OxyMCs OxyTs DNAts DNAts DNAas DNAcs DNAcs DNAcs DNAas DNAcs OxyTs OxyG |
| 6 | 7,602 | 7,621 | 236 | 255 | DES-002030 | AATTCctttacaccaACTG | ASO-002030 | OxyAs OxyAs OxyTs OxyTs DNAcs DNAcs DNAts DNAts DNAas DNAcs DNAcs DNAas DNAcs OxyAs OxyMCs OxyTs OxyG |
| 5 | 7,602 | 7,619 | 236 | 253 | DES-002031 | TTccttacaccacCTG | ASO-002031 | OxyTs OxyTs DNAcs DNAcs DNAts DNAts DNAas DNAcs DNAcs DNAas DNAcs OxyMCs OxyTs OxyG |
| 5 | 7,602 | 7,619 | 236 | 253 | DES-002032 | TTCCtttacaccaCACTG | ASO-002032 | OxyTs OxyTs OxyMCs OxyMCs DNAcs DNAcs DNAts DNAts DNAas DNAcs OxyAs OxyMCs OxyTs OxyG |
| 6 | 7,602 | 7,621 | 236 | 255 | DES-002040 | AATTCctttacaccaCACTG | ASO-002040 | OxyAs OxyAs OxyTs OxyTs OxyMCs OxyMCs DNAcs DNAcs DNAts DNAts DNAas DNAcs DNAcs OxyMCs OxyAs OxyMCs OxyTs OxyG |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 5 | 7,602 | 7,619 | 236 | 253 | DES-002041 | TTCctttacaccacTG | ASO-002041 | OxyTs OxyTs OxyMCs DNAcs DNAts DNAts DNAts DNAts DNAas DNAcs DNAas DNAcs DNAas DNAcs OxyTs OxyG |
| 5 | 7,602 | 7,619 | 236 | 253 | DES-002042 | TTCCtttacaccacCTG | ASO-002042 | OxyTs OxyTs OxyMCs OxyMCs OxyTs DNAts DNAts DNAts DNAas DNAcs DNAas DNAcs DNAas DNAcs OxyMCs OxyTs OxyG |
| 6 | 7,602 | 7,621 | 236 | 255 | DES-002050 | AATtcctttacaccacACTG | ASO-002050 | OxyAs OxyAs OxyTs DNAts DNAcs DNAcs DNAts DNAts DNAas DNAcs DNAas DNAcs DNAas DNAcs OxyAs OxyMCs OxyTs OxyG |
| 5 | 7,602 | 7,619 | 236 | 253 | DES-002051 | TTCCtttacaccacTG | ASO-002051 | OxyTs OxyTs OxyMCs OxyMCs DNAts DNAts DNAts DNAts DNAas DNAcs DNAas DNAcs DNAas DNAcs OxyTs OxyG |
| 5 | 7,602 | 7,619 | 236 | 253 | DES-002052 | TTCCtttacaccaCACTG | ASO-002052 | OxyTs OxyTs OxyMCs OxyMCs DNAts DNAts DNAts DNAcs DNAas DNAcs DNAas DNAas OxyMCs OxyAs OxyMCs OxyTs OxyG |
| 6 | 7,602 | 7,621 | 236 | 255 | DES-002060 | AATTcctttacaccacCTG | ASO-002060 | OxyAs OxyAs OxyTs OxyTs DNAcs DNAcs DNAts DNAts DNAas DNAcs DNAas DNAcs DNAas DNAas OxyMCs OxyTs OxyG |
| 5 | 7,602 | 7,619 | 236 | 253 | DES-002061 | TTCctttacaccacCTG | ASO-002061 | OxyTs OxyTs OxyMCs DNAcs DNAts DNAts DNAts DNAts DNAas DNAcs DNAas DNAcs DNAas DNAcs OxyMCs OxyTs OxyG |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 6 | 7,602 | 7,621 | 236 | 255 | DES-002069 | AATtcctttacaccaCACTG | ASO-002069 | OxyAs OxyAs OxyTs DNAts DNAcs DNAts DNAts DNAts DNAas DNAcs DNAas DNAcs DNAcs OxyMCs OxyAs OxyMCs OxyTs OxyG |
| 5 | 7,602 | 7,619 | 236 | 253 | DES-002070 | TTCCtttacaccacaCTG | ASO-002070 | OxyTs OxyTs OxyMCs OxyMCs DNAts DNAts DNAts DNAas DNAcs DNAas DNAcs DNAas OxyMCs OxyTs OxyG |
| 6 | 7,602 | 7,621 | 236 | 255 | DES-002078 | AATTCctttacaccacaCT | ASO-002078 | OxyAs OxyAs OxyTs OxyTs OxyMCs DNAcs DNAts DNAts DNAas DNAcs DNAas DNAcs DNAcs DNAas OxyMCs OxyTs OxyG |
| 5 | 7,602 | 7,619 | 236 | 253 | DES-002079 | TTCCtttacaccacACTG | ASO-002079 | OxyTs OxyTs OxyMCs OxyMCs DNAcs DNAts DNAas DNAcs DNAas DNAcs DNAas OxyAs OxyMCs OxyTs OxyG |
| 6 | 7,602 | 7,621 | 236 | 255 | DES-002087 | AATTcctttacaccacaCACT | ASO-002087 | OxyAs OxyAs OxyTs OxyTs DNAcs DNAcs DNAts DNAas DNAcs DNAas DNAcs DNAcs OxyAs OxyMCs OxyTs OxyG |
| 5 | 7,602 | 7,619 | 236 | 253 | DES-002088 | TTCCtttacaccacACTG | ASO-002088 | OxyTs OxyTs OxyMCs OxyMCs DNAcs DNAts DNAts DNAas DNAcs DNAas DNAcs DNAcs OxyAs OxyMCs OxyTs OxyG |
| 6 | 7,602 | 7,621 | 236 | 255 | DES-002096 | AATTcctttacaccacaCT | ASO-002096 | OxyAs OxyAs OxyTs DNAts DNAcs DNAts DNAts DNAts DNAas DNAcs DNAas DNAcs DNAcs DNAas DNAas OxyMCs |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| | | | | | | | | OxyTs OxyG |
| 6 | 7,602 | 7,621 | 236 | 255 | DES-002097 | AATTCctttacaccacACTG | ASO-002097 | OxyAs OxyAs OxyTs OxyTs OxyMCs DNAcs DNAts DNAts DNAts DNAas DNAcs DNAas DNAcs DNAas DNAcs OxyAs OxyMCs OxyTs OxyG |
| 5 | 7,602 | 7,619 | 236 | 253 | DES-002098 | TTCCtttacaccacACTG | ASO-002098 | OxyTs OxyTs OxyMCs OxyMCs DNAts DNAts DNAts DNAas DNAcs DNAas DNAcs DNAas DNAcs OxyAs OxyMCs OxyTs OxyG |
| 4 | 7,602 | 7,617 | 236 | 251 | DES-002780 | CCtttacaccacCTG | ASO-002780 | OxyMCs OxyMCs DNAts DNAas DNAcs DNAas DNAcs DNAas DNAcs DNAas DNAcs OxyMCs OxyTs OxyG |
| 8 | 7,603 | 7,618 | 237 | 252 | DES-001435 | TCctttacaccacCT | ASO-001435 | OxyTs OxyMCs DNAcs DNAts DNAts DNAts DNAas DNAcs DNAas DNAcs DNAas DNAcs OxyMCs OxyT |
| 8 | 7,603 | 7,618 | 237 | 252 | DES-001490 | TCCtttacaccacCT | ASO-001490 | OxyTs OxyMCs DNAcs DNAts DNAts DNAts DNAas DNAcs DNAas DNAcs DNAas DNAcs OxyMCs OxyT |
| 7 | 7,603 | 7,620 | 237 | 254 | DES-002755 | ATtcctttacaccacACT | ASO-002755 | OxyAs OxyTs DNAts DNAcs DNAts DNAts DNAts DNAas DNAcs DNAas DNAcs DNAas DNAcs OxyAs OxyMCs OxyT |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 7 | 7,603 | 7,620 | 237 | 254 | DES-005559 | AttcCtttacaCCAcacACT | ASO-005559 | OxyAs DNAts DNAts OxyMCs DNAcs DNAts DNAts DNAts DNAas DNAts DNAas OxyMCs DNAcs DNAas OxyAs DNAas OxyMCs OxyT |
| 7 | 7,603 | 7,620 | 237 | 254 | DES-005560 | AttcCtttacaCCAcacACT | ASO-005560 | OxyAs DNAts DNAts OxyMCs DNAcs DNAts DNAts DNAts DNAas DNAts DNAas OxyMCs DNAcs DNAas OxyAs DNAas OxyMCs OxyT |
| 7 | 7,603 | 7,620 | 237 | 254 | DES-005561 | AttcCtttacaCcacACT | ASO-005561 | OxyAs DNAts DNAts OxyMCs DNAcs DNAts DNAts DNAts DNAas DNAts DNAas OxyMCs DNAcs OxyAs DNAas OxyMCs OxyT |
| 7 | 7,603 | 7,620 | 237 | 254 | DES-005562 | AttcCtttacaCcacACT | ASO-005562 | OxyAs DNAts DNAts OxyMCs DNAcs DNAts DNAts DNAts DNAas DNAts DNAcs OxyAs DNAas OxyMCs OxyT |
| 7 | 7,603 | 7,620 | 237 | 254 | DES-005563 | AttcCtttacaCcacACT | ASO-005563 | OxyAs DNAts DNAts OxyMCs DNAcs DNAts DNAts DNAts DNAas DNAts DNAas OxyMCs DNAcs DNAas OxyAs DNAas OxyMCs OxyT |
| 7 | 7,603 | 7,620 | 237 | 254 | DES-005564 | AttcCtttacaCcacACT | ASO-005564 | OxyAs DNAts DNAts OxyMCs DNAcs DNAts DNAts DNAts DNAas DNAts DNAas OxyMCs DNAcs DNAas OxyAs DNAas OxyMCs OxyT |
| 7 | 7,603 | 7,620 | 237 | 254 | DES-005565 | AttccttacacCAcacCT | ASO-005565 | OxyAs DNAts DNAts DNAcs DNAcs OxyMCs OxyAs DNAcs DNAts DNAts DNAas DNAcs DNAas OxyMCs OxyT |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 7 | 7,603 | 7,620 | 237 | 254 | DES-005566 | AttccTttacacCaCaCT | ASO-005566 | OxyAs DNAts DNAcs DNAcs OxyTs DNAts DNAcs DNAas DNAcs DNAcs OxyMCs DNAas OxyMCs DNAas OxyMCs OxyT |
| 7 | 7,603 | 7,620 | 237 | 254 | DES-005567 | AttccTttacacCaCaCT | ASO-005567 | OxyAs DNAts DNAcs DNAcs OxyMCs DNAts DNAcs DNAas DNAcs DNAcs OxyMCs DNAas OxyMCs DNAas OxyMCs OxyT |
| 7 | 7,603 | 7,620 | 237 | 254 | DES-005568 | AttCcTttacacCacACT | ASO-005568 | OxyAs DNAts DNAcs DNAcs OxyMCs DNAts DNAcs DNAas DNAcs DNAcs OxyMCs DNAas OxyAs OxyMCs OxyT |
| 7 | 7,603 | 7,620 | 237 | 254 | DES-005569 | AttCctttacacCacACT | ASO-005569 | OxyAs DNAts DNAcs DNAcs OxyMCs DNAts DNAcs DNAas DNAcs DNAcs OxyMCs DNAas OxyAs OxyMCs OxyT |
| 7 | 7,603 | 7,620 | 237 | 254 | DES-005570 | AttccTttacacCacACT | ASO-005570 | OxyAs DNAts DNAcs DNAcs OxyMCs DNAts DNAcs DNAas DNAcs DNAcs OxyMCs DNAas OxyAs OxyMCs OxyT |
| 7 | 7,603 | 7,620 | 237 | 254 | DES-005571 | AttccTttacacCacACT | ASO-005571 | OxyAs DNAts DNAcs DNAcs OxyTs DNAts DNAcs DNAas DNAcs DNAcs OxyMCs DNAas OxyAs OxyMCs OxyT |
| 7 | 7,603 | 7,620 | 237 | 254 | DES-005572 | AttCcTttacacCacACT | ASO-005572 | OxyAs DNAts DNAcs DNAcs OxyMCs DNAts DNAcs DNAas DNAcs DNAcs OxyMCs DNAas DNAcs OxyMCs OxyT |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 7 | 7,603 | 7,620 | 237 | 254 | DES-005573 | AttcCtttacacCacaCT | ASO-005573 | OxyAs DNAts DNAts OxyMCs DNAcs DNAts DNAts DNAts DNAas DNAcs DNAas OxyMCs DNAas DNAcs DNAas OxyMCs OxyT |
| 7 | 7,603 | 7,620 | 237 | 254 | DES-005574 | AttcCtttacacCacaCT | ASO-005574 | OxyAs DNAts DNAts OxyMCs DNAcs DNAts DNAts DNAts DNAas DNAcs DNAas OxyMCs DNAas DNAcs DNAas OxyMCs OxyT |
| 7 | 7,603 | 7,620 | 237 | 254 | DES-005575 | AttccTtttacacCacaCT | ASO-005575 | OxyAs DNAts DNAts DNAts OxyMCs DNAcs DNAts DNAts OxyTs DNAts DNAas DNAcs DNAas OxyMCs DNAas DNAcs DNAas OxyMCs OxyT |
| 7 | 7,603 | 7,620 | 237 | 254 | DES-005576 | AtTCctttacaccACaCT | ASO-005576 | OxyAs DNAts OxyTs OxyMCs DNAcs DNAts DNAts DNAas DNAcs DNAas OxyAs OxyMCs DNAas OxyMCs OxyT |
| 7 | 7,603 | 7,620 | 237 | 254 | DES-005577 | AttCcTtttacacCacaCT | ASO-005577 | OxyAs DNAts DNAts OxyMCs DNAcs DNAts DNAts DNAts OxyTs DNAas DNAcs DNAas OxyAs OxyMCs DNAas OxyMCs OxyT |
| 7 | 7,603 | 7,620 | 237 | 254 | DES-005578 | AttCctttacaccACaCT | ASO-005578 | OxyAs DNAts DNAts OxyMCs DNAcs DNAts DNAts DNAas DNAcs DNAas OxyAs OxyMCs DNAas OxyMCs OxyT |
| 7 | 7,603 | 7,620 | 237 | 254 | DES-005579 | AttcCtttacaccACaCT | ASO-005579 | OxyAs DNAts DNAts DNAts OxyMCs DNAcs DNAts DNAts DNAas DNAcs DNAas OxyAs OxyMCs DNAas OxyMCs OxyT |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 7 | 7,603 | 7,620 | 237 | 254 | DES-005580 | AttcctttacaccACaCT | ASO-005580 | OxyAs DNAts DNAcs DNAcs DNAts DNAts DNAts DNAas DNAcs DNAas DNAcs DNAcs OxyAs OxyMCs DNAas OxyMCs OxyT |
| 7 | 7,603 | 7,620 | 237 | 254 | DES-005581 | ATtcctttacaccAcACT | ASO-005581 | OxyAs OxyTs DNAts DNAcs DNAcs DNAts DNAts DNAas DNAcs DNAas DNAcs DNAcs OxyAs OxyMCs OxyAs OxyT |
| 7 | 7,603 | 7,620 | 237 | 254 | DES-005582 | AtTCctttacaccAcACT | ASO-005582 | OxyAs DNAts OxyTs OxyMCs DNAts DNAts DNAts DNAas DNAcs DNAas DNAcs DNAcs OxyAs OxyMCs OxyAs OxyT |
| 7 | 7,603 | 7,620 | 237 | 254 | DES-005583 | AttCcTttacaccAcACT | ASO-005583 | OxyAs DNAts DNAcs OxyMCs DNAts OxyTs DNAts DNAas DNAcs DNAas DNAcs DNAcs OxyAs OxyMCs OxyAs OxyT |
| 7 | 7,603 | 7,620 | 237 | 254 | DES-005584 | AttCctttacaccAcACT | ASO-005584 | OxyAs DNAts DNAcs OxyMCs DNAts DNAts DNAts DNAas DNAcs DNAas DNAcs DNAcs OxyAs OxyMCs OxyAs OxyT |
| 7 | 7,603 | 7,620 | 237 | 254 | DES-005585 | AttCctttacaccAcACT | ASO-005585 | OxyAs DNAts DNAcs DNAcs DNAts DNAts DNAts DNAas DNAcs DNAas DNAcs DNAcs OxyAs DNAts OxyMCs OxyT |
| 7 | 7,603 | 7,620 | 237 | 254 | DES-005586 | AttccttacaccAcACT | ASO-005586 | OxyAs DNAts DNAcs DNAcs DNAts DNAts DNAts DNAas DNAcs DNAas DNAcs DNAcs OxyAs OxyMCs DNAts OxyT |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 7 | 7,603 | 7,620 | 237 | 254 | DES-005587 | ATtCctttacaccAcaCT | ASO-005587 | OxyAs OxyTs DNAts OxyMCs DNAcs DNAts OxyMCs DNAts DNAts DNAas DNAas DNAcs DNAts OxyAs DNAas DNAcs OxyMCs OxyT |
| 7 | 7,603 | 7,620 | 237 | 254 | DES-005588 | ATtccttacaccAcaCT | ASO-005588 | OxyAs OxyTs DNAts DNAcs DNAcs DNAts DNAts DNAts DNAas DNAas DNAcs DNAts OxyAs DNAas DNAcs OxyMCs OxyT |
| 7 | 7,603 | 7,620 | 237 | 254 | DES-005589 | AtTCctttacaccAcaCT | ASO-005589 | OxyAs DNAts OxyTs OxyMCs DNAcs DNAts DNAts DNAts DNAas DNAas DNAcs DNAts OxyAs DNAas DNAcs OxyMCs OxyT |
| 7 | 7,603 | 7,620 | 237 | 254 | DES-005590 | AtTccttacaccAcaCT | ASO-005590 | OxyAs DNAts OxyTs DNAcs DNAcs DNAts DNAts DNAts DNAas DNAas DNAcs DNAts OxyAs DNAas DNAcs OxyMCs OxyT |
| 7 | 7,603 | 7,620 | 237 | 254 | DES-005591 | AttCcttacaccAcaCT | ASO-005591 | OxyAs DNAts DNAts OxyMCs DNAcs DNAts DNAts DNAts OxyTs DNAts DNAas DNAcs DNAts OxyAs DNAas DNAcs OxyMCs OxyT |
| 7 | 7,603 | 7,620 | 237 | 254 | DES-005592 | AttCctttacaccAcaCT | ASO-005592 | OxyAs DNAts DNAts OxyMCs DNAcs DNAts DNAts DNAts DNAas DNAcs DNAts OxyAs DNAas DNAcs OxyMCs OxyT |
| 7 | 7,603 | 7,620 | 237 | 254 | DES-005593 | AttcCTttacaccAcaCT | ASO-005593 | OxyAs DNAts DNAts DNAcs OxyMCs OxyTs DNAts DNAts DNAas DNAcs DNAts OxyAs DNAas DNAcs OxyMCs OxyT |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 7 | 7,603 | 7,620 | 237 | 254 | DES-005594 | AttcCtttacaccAcaCT | ASO-005594 | OxyAs DNAts DNAts DNAcs OxyMCs DNAts DNAts DNAts DNAas DNAcs DNAts DNAas DNAcs DNAcs DNAas OxyMCs OxyT |
| 7 | 7,603 | 7,620 | 237 | 254 | DES-005595 | AttccttacaccAcaCT | ASO-005595 | OxyAs DNAts DNAts DNAcs DNAcs DNAts DNAts DNAts DNAas DNAcs DNAts DNAas DNAcs DNAcs DNAas OxyMCs OxyT |
| 7 | 7,603 | 7,620 | 237 | 254 | DES-005596 | AtTccttacaccaCACT | ASO-005596 | OxyAs DNAts OxyTs DNAcs DNAcs DNAts DNAts DNAts DNAas DNAcs DNAts DNAas OxyMCs OxyAs OxyMCs OxyT |
| 7 | 7,603 | 7,620 | 237 | 254 | DES-005597 | AttCcttacaccaCACT | ASO-005597 | OxyAs DNAts DNAts OxyMCs DNAcs DNAts DNAts DNAts DNAas DNAcs DNAts DNAas OxyMCs OxyAs OxyMCs OxyT |
| 7 | 7,603 | 7,620 | 237 | 254 | DES-005598 | AttccttacaccaCACT | ASO-005598 | OxyAs DNAts DNAts DNAcs DNAcs DNAts DNAts DNAts DNAas DNAcs DNAts DNAas OxyMCs OxyAs OxyMCs OxyT |
| 7 | 7,603 | 7,620 | 237 | 254 | DES-005599 | AtTCcttacaccaCACT | ASO-005599 | OxyAs DNAts OxyTs OxyMCs DNAcs DNAts DNAts DNAts DNAas DNAcs DNAts DNAas OxyMCs OxyAs OxyMCs OxyT |
| 7 | 7,603 | 7,620 | 237 | 254 | DES-005600 | AttCcTttacaccaCaCT | ASO-005600 | OxyAs DNAts DNAts OxyMCs DNAcs OxyTs DNAts DNAts DNAas DNAcs DNAts DNAas DNAcs OxyMCs DNAas OxyT |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 7 | 7,603 | 7,620 | 237 | 254 | DES-005601 | AttCctTtacaccaCaCT | ASO-005601 | OxyAs DNAts DNAts OxyMCs DNAcs DNAts OxyTs DNAts DNAas DNAas DNAas DNAcs DNAcs OxyMCs DNAaas OxyMCs OxyT |
| 7 | 7,603 | 7,620 | 237 | 254 | DES-005602 | AttCctttacaccaCaCT | ASO-005602 | OxyAs DNAts DNAts OxyMCs DNAcs DNAts DNAts DNAas DNAas DNAas DNAcs DNAcs OxyMCs DNAaas OxyMCs OxyT |
| 7 | 7,603 | 7,620 | 237 | 254 | DES-005603 | AttCctTtacaccaCaCT | ASO-005603 | OxyAs DNAts DNAts DNAcs DNAcs DNAts OxyTs DNAts DNAas DNAas DNAas DNAcs DNAcs OxyMCs DNAaas OxyMCs OxyT |
| 7 | 7,603 | 7,620 | 237 | 254 | DES-005604 | AttcCtttacaccaCaCT | ASO-005604 | OxyAs DNAts DNAts DNAcs DNAcs DNAts DNAts DNAas DNAas DNAas DNAcs DNAcs OxyMCs DNAaas OxyMCs OxyT |
| 7 | 7,603 | 7,620 | 237 | 254 | DES-005605 | AttccttTacaccaCaCT | ASO-005605 | OxyAs DNAts DNAts DNAcs DNAcs DNAts DNAts DNAas DNAas DNAas DNAcs DNAcs OxyMCs DNAaas OxyMCs OxyT |
| 7 | 7,603 | 7,620 | 237 | 254 | DES-005606 | ATtCctttacaccaACT | ASO-005606 | OxyAs OxyTs OxyMCs DNAcs DNAcs DNAts DNAts DNAas DNAas DNAcs DNAcs OxyAs OxyMCs OxyT |
| 7 | 7,603 | 7,620 | 237 | 254 | DES-005607 | AtTCCtTtacaccacACT | ASO-005607 | OxyAs DNAts OxyTs OxyMCs OxyMCs DNAts DNAts DNAas DNAas DNAas DNAcs DNAcs DNAcs OxyAs OxyMCs OxyT |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 7 | 7,603 | 7,620 | 237 | 254 | DES-005608 | AtTCctttacaccacACT | ASO-005608 | OxyAs DNAts OxyTs OxyMCs DNAcs DNAts DNAts DNAas DNAcs DNAts DNAcs DNAas DNAcs OxyAs OxyMCs OxyT |
| 7 | 7,603 | 7,620 | 237 | 254 | DES-005609 | AttCcCTttacaccacACT | ASO-005609 | OxyAs DNAts DNAts OxyMCs DNAcs OxyTs DNAts DNAas DNAcs DNAts DNAcs DNAas DNAcs OxyAs OxyMCs OxyT |
| 7 | 7,603 | 7,620 | 237 | 254 | DES-005610 | AttCcCTttacaccacACT | ASO-005610 | OxyAs DNAts DNAts OxyMCs DNAcs DNAts DNAts OxyTs DNAas DNAcs DNAts DNAcs DNAas DNAcs OxyAs OxyMCs OxyT |
| 7 | 7,603 | 7,620 | 237 | 254 | DES-005611 | AttCcCtttacaccacACT | ASO-005611 | OxyAs DNAts DNAts OxyMCs DNAcs DNAts DNAts DNAas DNAcs DNAts DNAcs DNAas DNAcs OxyAs OxyMCs OxyT |
| 7 | 7,603 | 7,620 | 237 | 254 | DES-005612 | AttCcCTttacaccacACT | ASO-005612 | OxyAs DNAts DNAts DNAcs OxyMCs OxyTs DNAts DNAas DNAcs DNAts DNAcs DNAas DNAcs OxyAs OxyMCs OxyT |
| 7 | 7,603 | 7,620 | 237 | 254 | DES-005613 | AttCcCTttacaccacACT | ASO-005613 | OxyAs DNAts DNAts DNAcs OxyMCs DNAts DNAts OxyTs DNAas DNAcs DNAts DNAcs DNAas DNAcs OxyAs OxyMCs OxyT |
| 7 | 7,603 | 7,620 | 237 | 254 | DES-005614 | AttccTttacaccacACT | ASO-005614 | OxyAs DNAts DNAts DNAcs DNAcs DNAts DNAts DNAas DNAcs DNAts DNAcs DNAas DNAcs OxyAs OxyMCs OxyT |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 7 | 7,603 | 7,620 | 237 | 254 | DES-005615 | ATtCctttacaccacaCT | ASO-005615 | OxyAs OxyTs DNAts OxyMCs DNAcs DNAts DNAts DNAts DNAts DNAcs DNAas DNAcs DNAas DNAcs DNAas OxyMCs OxyT |
| 7 | 7,603 | 7,620 | 237 | 254 | DES-005616 | ATtcctttacaccacaCT | ASO-005616 | OxyAs OxyTs DNAts DNAcs DNAts DNAts DNAts DNAts DNAcs DNAas DNAcs DNAas DNAcs DNAas OxyMCs OxyT |
| 7 | 7,603 | 7,620 | 237 | 254 | DES-005617 | AtTCcTttacaccacaCT | ASO-005617 | OxyAs DNAts OxyTs OxyMCs DNAcs OxyTs DNAts DNAts DNAts DNAcs DNAas DNAcs DNAas DNAcs DNAas OxyMCs OxyT |
| 7 | 7,603 | 7,620 | 237 | 254 | DES-005618 | AtTCCcTttacaccacaCT | ASO-005618 | OxyAs DNAts OxyTs OxyMCs DNAcs DNAts OxyTs DNAts DNAts DNAcs DNAas DNAcs DNAas DNAcs DNAas OxyMCs OxyT |
| 7 | 7,603 | 7,620 | 237 | 254 | DES-005619 | AtTCcctttacaccacaCT | ASO-005619 | OxyAs DNAts OxyTs OxyMCs DNAcs DNAts DNAts DNAts DNAts DNAcs DNAas DNAcs DNAas DNAcs DNAas OxyMCs OxyT |
| 7 | 7,603 | 7,620 | 237 | 254 | DES-005620 | AttCcTTtacaccacaCT | ASO-005620 | OxyAs DNAts DNAts OxyMCs DNAcs OxyTs OxyTs DNAts DNAts DNAcs DNAas DNAcs DNAas DNAcs DNAas OxyMCs OxyT |
| 7 | 7,603 | 7,620 | 237 | 254 | DES-005621 | AttCcTttacaccacaCT | ASO-005621 | OxyAs DNAts DNAts OxyMCs DNAcs OxyTs DNAts DNAts DNAts DNAcs DNAas DNAcs DNAas DNAcs DNAas OxyMCs OxyT |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 7 | 7,603 | 7,620 | 237 | 254 | DES-005622 | AttCCtTtacaccacaCT | ASO-005622 | OxyAs DNAts DNAts OxyMCs DNAts DNAts OxyTs DNAts DNAas DNAcs DNAcs DNAas DNAcs DNAcs DNAas OxyMCs OxyT |
| 7 | 7,603 | 7,620 | 237 | 254 | DES-005623 | AttCcttacaccacaCT | ASO-005623 | OxyAs DNAts DNAts OxyMCs DNAcs DNAts OxyTs DNAts DNAas DNAcs DNAcs DNAas DNAcs DNAcs DNAas OxyMCs OxyT |
| 7 | 7,603 | 7,620 | 237 | 254 | DES-005624 | AttCCTttacaccacaCT | ASO-005624 | OxyAs DNAts DNAts DNAcs OxyMCs DNAts OxyTs DNAts DNAas DNAcs DNAcs DNAas DNAcs DNAcs DNAas OxyMCs OxyT |
| 7 | 7,603 | 7,620 | 237 | 254 | DES-005625 | AttcCtTtacaccacaCT | ASO-005625 | OxyAs DNAts DNAts DNAcs OxyMCs DNAts OxyTs DNAts DNAas DNAcs DNAcs DNAas DNAcs DNAcs DNAas OxyMCs OxyT |
| 11 | 7,603 | 7,619 | 237 | 253 | DES-005626 | TtCtttacAcCacaCT | ASO-005626 | OxyTs DNAts OxyTs DNAcs DNAts OxyAs DNAts DNAcs OxyMCs DNAcs DNAas DNAcs DNAas DNAcs DNAas OxyMCs OxyT |
| 11 | 7,603 | 7,619 | 237 | 253 | DES-005627 | TtCctttacacCacACT | ASO-005627 | OxyTs DNAts OxyTs DNAcs OxyMCs DNAts DNAts DNAas DNAcs DNAas DNAcs DNAcs OxyAs OxyMCs OxyT |
| 11 | 7,603 | 7,619 | 237 | 253 | DES-005628 | TtCctttaccACaCT | ASO-005628 | OxyTs DNAts OxyTs DNAcs OxyMCs DNAcs DNAts DNAas DNAcs DNAcs OxyAs OxyMCs DNAas OxyMCs OxyT |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 11 | 7,603 | 7,619 | 237 | 253 | DES-005629 | TtcctttacaccACaCT | ASO-005629 | OxyTs DNAts DNAcs DNAcs DNAts DNAts DNAts DNAts DNAas DNAcs DNAas DNAcs DNAcs DNAts DNAas OxyMCs DNAas OxyMCs OxyT |
| 11 | 7,603 | 7,619 | 237 | 253 | DES-005630 | TTCctttacaccAcACT | ASO-005630 | OxyTs OxyTs OxyMCs DNAcs DNAts DNAts DNAts DNAts DNAas DNAcs DNAas DNAcs DNAcs OxyAs DNAcs OxyAs OxyT |
| 11 | 7,603 | 7,619 | 237 | 253 | DES-005631 | TtCctttacaccAcACT | ASO-005631 | OxyTs DNAts OxyMCs DNAcs DNAts DNAts DNAts DNAts DNAas DNAcs DNAas DNAcs DNAcs OxyAs DNAcs OxyMCs OxyT |
| 11 | 7,603 | 7,619 | 237 | 253 | DES-005632 | TtCctttacaccAcACT | ASO-005632 | OxyTs DNAts DNAcs OxyMCs DNAts DNAts DNAts DNAts DNAas DNAcs DNAas DNAcs DNAcs OxyAs DNAcs OxyMCs OxyT |
| 11 | 7,603 | 7,619 | 237 | 253 | DES-005633 | TtcctttacaccAcACT | ASO-005633 | OxyTs DNAts DNAcs DNAcs DNAts DNAts DNAts DNAts DNAas DNAcs DNAas DNAcs DNAcs OxyAs DNAcs OxyMCs OxyT |
| 11 | 7,603 | 7,619 | 237 | 253 | DES-005634 | TTCctttacaccAcACT | ASO-005634 | OxyTs OxyTs OxyMCs DNAcs DNAts DNAts DNAts DNAts DNAas DNAcs DNAas DNAcs DNAcs OxyAs DNAcs OxyMCs OxyT |
| 11 | 7,603 | 7,619 | 237 | 253 | DES-005635 | TTcctttacaccAcACT | ASO-005635 | OxyTs OxyTs DNAcs DNAcs DNAts DNAts DNAts DNAts DNAas DNAcs DNAas DNAcs DNAcs OxyAs DNAcs OxyMCs OxyT |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 11 | 7,603 | 7,619 | 237 | 253 | DES-005636 | TtCctttacaccAcaCT | ASO-005636 | OxyTs DNAts OxyMCs DNAcs DNAts DNAts DNAts DNAts DNAcs DNAas DNAas DNAcs DNAas OxyMCs OxyAs OxyMCs OxyT |
| 11 | 7,603 | 7,619 | 237 | 253 | DES-005637 | TtCctttacaccaCACT | ASO-005637 | OxyTs DNAts OxyMCs DNAcs DNAts DNAts DNAts DNAts DNAcs DNAas DNAas DNAcs DNAas OxyMCs OxyAs OxyMCs OxyT |
| 11 | 7,603 | 7,619 | 237 | 253 | DES-005638 | TTCctttacaccaCaCT | ASO-005638 | OxyTs OxyTs OxyMCs DNAcs DNAts DNAts DNAts DNAts DNAcs DNAas DNAas DNAcs DNAas OxyMCs OxyAs OxyMCs OxyT |
| 11 | 7,603 | 7,619 | 237 | 253 | DES-005639 | TtCctttacaccaCaCT | ASO-005639 | OxyTs DNAts OxyMCs DNAcs DNAts DNAts DNAts DNAts DNAcs DNAas DNAas DNAcs DNAas OxyMCs OxyAs OxyMCs OxyT |
| 11 | 7,603 | 7,619 | 237 | 253 | DES-005640 | TTCctttacaccaCaCT | ASO-005640 | OxyTs OxyTs OxyMCs DNAcs DNAts DNAts DNAts DNAts DNAcs DNAas DNAas DNAcs DNAcs OxyAs OxyMCs OxyT |
| 11 | 7,603 | 7,619 | 237 | 253 | DES-005641 | TtCctTtacaccacACT | ASO-005641 | OxyTs DNAts OxyMCs DNAcs DNAts OxyTs DNAts DNAcs DNAas DNAas DNAcs DNAcs OxyAs OxyMCs OxyT |
| 11 | 7,603 | 7,619 | 237 | 253 | DES-005642 | TtCctttacaccacACT | ASO-005642 | OxyTs DNAts OxyMCs DNAcs DNAts DNAts DNAts DNAcs DNAas DNAas DNAcs DNAcs OxyAs OxyMCs OxyT |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 11 | 7,603 | 7,619 | 237 | 253 | DES-005643 | TTCctttacaccacaCT | ASO-005643 | OxyTs OxyTs OxyMCs DNAcs DNAts DNAts DNAts DNAts DNAts DNAcs DNAas DNAas DNAcs DNAcs DNAas OxyMCs OxyT |
| 11 | 7,603 | 7,619 | 237 | 253 | DES-005644 | TtCctttacaccacaCT | ASO-005644 | OxyTs DNAts OxyMCs DNAcs DNAts DNAts DNAts DNAts DNAts DNAcs DNAas DNAas DNAcs DNAcs DNAas OxyMCs OxyT |
| 9 | 7,603 | 7,621 | 237 | 255 | DES-005655 | AAttcctttaCacCacaCT | ASO-005655 | OxyAs OxyAs DNAts DNAts DNAcs DNAts DNAts DNAcs DNAas DNAas DNAcs OxyMCs DNAas DNAcs OxyMCs DNAas OxyMCs OxyT |
| 9 | 7,603 | 7,621 | 237 | 255 | DES-005656 | AAttCctttaCaccacaCT | ASO-005656 | OxyAs OxyAs DNAts DNAts DNAcs DNAts DNAts OxyMCs DNAas DNAas DNAcs DNAas DNAcs DNAas DNAcs OxyMCs OxyT |
| 9 | 7,603 | 7,621 | 237 | 255 | DES-005657 | AAttCctttaCaccacaCT | ASO-005657 | OxyAs OxyAs DNAts DNAts DNAcs DNAts DNAts OxyMCs DNAas DNAas DNAcs OxyMCs DNAas DNAcs DNAas OxyMCs OxyT |
| 9 | 7,603 | 7,621 | 237 | 255 | DES-005658 | AAttCctttacAcCacaCT | ASO-005658 | OxyAs OxyAs DNAts DNAts DNAcs OxyAs DNAts DNAcs DNAas DNAas OxyAs DNAcs DNAcs DNAas OxyMCs OxyT |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 9 | 7,603 | 7,621 | 237 | 255 | DES-005659 | AAttccttacAcCacacT | ASO-005659 | OxyAs OxyAs DNAts DNAcs DNAts DNAts DNAts DNAas DNAcs OxyAs DNAcs OxyMCs DNAas DNAcs DNAts OxyMCs OxyT |
| 9 | 7,603 | 7,621 | 237 | 255 | DES-005660 | AAttCcttacAccAcacT | ASO-005660 | OxyAs OxyAs DNAts DNAcs OxyMCs DNAts DNAts DNAas DNAcs OxyAs DNAcs OxyAs DNAcs DNAts OxyMCs OxyT |
| 9 | 7,603 | 7,621 | 237 | 255 | DES-005661 | AattCctttacAccAcacT | ASO-005661 | OxyAs DNAas DNAts DNAcs OxyMCs DNAts DNAts DNAas DNAcs OxyAs DNAcs OxyAs DNAcs DNAts OxyMCs OxyT |
| 9 | 7,603 | 7,621 | 237 | 255 | DES-005662 | AAttCcttacAccaCaCT | ASO-005662 | OxyAs OxyAs DNAts DNAcs OxyMCs DNAts DNAts DNAas DNAcs OxyAs DNAcs DNAts OxyMCs DNAts OxyAs OxyMCs OxyT |
| 9 | 7,603 | 7,621 | 237 | 255 | DES-005663 | AAttCctttacAccacACT | ASO-005663 | OxyAs OxyAs DNAts DNAcs OxyMCs DNAts DNAts DNAas DNAcs OxyAs DNAcs DNAts DNAts DNAaas OxyAs OxyMCs OxyT |
| 9 | 7,603 | 7,621 | 237 | 255 | DES-005664 | AAttCctttacAccacaCT | ASO-005664 | OxyAs OxyAs DNAts DNAcs OxyMCs DNAts DNAts DNAas DNAcs OxyAs DNAcs DNAts DNAts DNAas DNAcs OxyMCs OxyT |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 9 | 7,603 | 7,621 | 237 | 255 | DES-005665 | AAttCctttacaCcAcaCT | ASO-005665 | OxyAs OxyAs DNAts DNAts OxyMCs DNAcs DNAts DNAts DNAas DNAcs DNAas OxyMCs DNAcs OxyAs DNAcs DNAas OxyMCs OxyT |
| 9 | 7,603 | 7,621 | 237 | 255 | DES-005666 | AAttcCtttacaCcAcaCT | ASO-005666 | OxyAs OxyAs DNAts DNAts OxyMCs DNAcs DNAts DNAts DNAas DNAcs DNAaas OxyMCs DNAcs OxyAs DNAcs DNAas OxyMCs OxyT |
| 9 | 7,603 | 7,621 | 237 | 255 | DES-005667 | AAttCctttacaCcacaCT | ASO-005667 | OxyAs OxyAs DNAts DNAts OxyMCs DNAcs DNAts DNAts DNAas DNAcs DNAas OxyMCs DNAcs DNAcs DNAas OxyMCs OxyT |
| 9 | 7,603 | 7,621 | 237 | 255 | DES-005668 | AAttccCtttacaCcacaCT | ASO-005668 | OxyAs OxyAs DNAts DNAts DNAcs OxyMCs DNAcs DNAts DNAts DNAas DNAcs DNAas OxyMCs DNAcs DNAcs DNAas OxyMCs OxyT |
| 9 | 7,603 | 7,621 | 237 | 255 | DES-005669 | AAttccctttacacCaCaCT | ASO-005669 | OxyAs OxyAs DNAts DNAts DNAcs OxyMCs DNAcs DNAts DNAts DNAas DNAcs DNAas DNAcs DNAas OxyMCs DNAas OxyMCs OxyT |
| 9 | 7,603 | 7,621 | 237 | 255 | DES-005670 | AAttccTttacacCacACT | ASO-005670 | OxyAs OxyAs DNAts DNAts DNAcs DNAcs DNAts DNAts OxyTs DNAts DNAas DNAcs DNAas DNAcs DNAcs OxyMCs DNAas OxyAs OxyMCs OxyT |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 9 | 7,603 | 7,621 | 237 | 255 | DES-005671 | AattCctttacacCacACT | ASO-005671 | OxyAs DNAas DNAts DNAts OxyMCs OxyMCs DNAcs DNAts DNAts DNAas DNAcs DNAcs DNAas OxyMCs DNAcs OxyAs OxyMCs OxyT |
| 9 | 7,603 | 7,621 | 237 | 255 | DES-005672 | AattcCtttacacCacaCT | ASO-005672 | OxyAs DNAas DNAts DNAts DNAcs OxyMCs DNAts DNAts DNAas DNAas DNAcs OxyMCs DNAcs DNAas OxyAs OxyMCs OxyT |
| 9 | 7,603 | 7,621 | 237 | 255 | DES-005673 | AAttCctttacacCacaCT | ASO-005673 | OxyAs DNAas DNAts DNAts OxyMCs DNAcs DNAts DNAts DNAas DNAas DNAcs OxyMCs DNAcs DNAas DNAcs OxyMCs OxyT |
| 9 | 7,603 | 7,621 | 237 | 255 | DES-005674 | AAttcCtttacacCacaCT | ASO-005674 | OxyAs OxyAs DNAts DNAts DNAcs OxyMCs DNAts DNAts DNAas DNAas DNAcs DNAcs DNAcs DNAas DNAcs OxyMCs OxyT |
| 9 | 7,603 | 7,621 | 237 | 255 | DES-005675 | AAttccTttacacCacaCT | ASO-005675 | OxyAs OxyAs DNAts DNAts DNAcs DNAcs OxyTs DNAts DNAas DNAas DNAcs DNAcs DNAcs DNAas DNAcs OxyMCs OxyT |
| 9 | 7,603 | 7,621 | 237 | 255 | DES-005676 | AAtTCctttacaccACaCT | ASO-005676 | OxyAs OxyAs DNAts OxyTs OxyMCs DNAcs DNAts DNAts DNAas DNAcs DNAas DNAcs DNAcs OxyAs OxyMCs DNAas OxyT |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 9 | 7,603 | 7,621 | 237 | 255 | DES-005677 | AattCctttacaccACaCT | ASO-005677 | OxyAs OxyAs DNAts DNAts OxyMCs DNAcs DNAts DNAts DNAas DNAcs DNAcs DNAts DNAcs OxyAs OxyMCs DNAas OxyMCs OxyT |
| 9 | 7,603 | 7,621 | 237 | 255 | DES-005678 | AattcctttacaccACaCT | ASO-005678 | OxyAs OxyAs DNAts DNAts OxyMCs DNAcs DNAts DNAts DNAas DNAcs DNAcs DNAts DNAcs OxyAs OxyMCs DNAas OxyMCs OxyT |
| 9 | 7,603 | 7,621 | 237 | 255 | DES-005679 | AattCctttacaccAcACT | ASO-005679 | OxyAs OxyAs DNAts DNAts OxyMCs DNAcs DNAts DNAts DNAas DNAcs DNAcs DNAts DNAcs OxyAs OxyMCs DNAas OxyMCs OxyT |
| 9 | 7,603 | 7,621 | 237 | 255 | DES-005680 | AattcctttacaccAcACT | ASO-005680 | OxyAs DNAas DNAts DNAts OxyMCs DNAcs DNAts DNAts DNAas DNAcs DNAcs DNAts DNAcs OxyAs OxyMCs DNAas OxyMCs OxyT |
| 9 | 7,603 | 7,621 | 237 | 255 | DES-005681 | AAtTCctttacaccAcACT | ASO-005681 | OxyAs OxyAs DNAts OxyTs OxyMCs DNAcs DNAts DNAts DNAas DNAcs DNAcs DNAts DNAcs OxyAs DNAcs OxyAs OxyMCs OxyT |
| 9 | 7,603 | 7,621 | 237 | 255 | DES-005682 | AAttCctttacaccAcACT | ASO-005682 | OxyAs OxyAs DNAts DNAts OxyMCs DNAcs DNAts DNAts DNAas DNAcs DNAcs DNAts DNAcs OxyAs DNAcs OxyAs OxyMCs OxyT |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 9 | 7,603 | 7,621 | 237 | 255 | DES-005683 | AAttcCtttacaccAcACT | ASO-005683 | OxyAs OxyAs DNAts DNAcs DNAts DNAcs OxyMCs DNAts DNAts DNAas DNAcs DNAcs DNAas DNAcs OxyAs DNAcs OxyAs OxyMCs OxyT |
| 9 | 7,603 | 7,621 | 237 | 255 | DES-005684 | AAttccttttacaccAcACT | ASO-005684 | OxyAs OxyAs DNAts DNAcs DNAts DNAts DNAas DNAcs DNAcs DNAas DNAcs OxyAs DNAcs OxyAs OxyMCs OxyT |
| 9 | 7,603 | 7,621 | 237 | 255 | DES-005685 | AaTtCcttttacaccAcACT | ASO-005685 | OxyAs DNAas OxyTs DNAts OxyMCs DNAts DNAts DNAas DNAcs DNAcs DNAas DNAcs OxyAs DNAcs OxyAs OxyMCs OxyT |
| 9 | 7,603 | 7,621 | 237 | 255 | DES-005686 | AaTtccttttacaccAcACT | ASO-005686 | OxyAs DNAas OxyTs DNAts DNAts DNAts DNAas DNAcs DNAcs DNAas DNAcs OxyAs DNAcs OxyAs OxyMCs OxyT |
| 9 | 7,603 | 7,621 | 237 | 255 | DES-005687 | AattCcttttacaccAcACT | ASO-005687 | OxyAs DNAas DNAts DNAts OxyMCs DNAts DNAts DNAas DNAcs DNAcs DNAas DNAcs OxyAs DNAcs OxyAs OxyMCs OxyT |
| 9 | 7,603 | 7,621 | 237 | 255 | DES-005688 | AattccttttacaccAcACT | ASO-005688 | OxyAs DNAas DNAts DNAts DNAts DNAts DNAas DNAcs DNAcs DNAas DNAcs OxyAs DNAcs OxyAs OxyMCs OxyT |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 9 | 7,603 | 7,621 | 237 | 255 | DES-005689 | AAtTCctttacaccAcaCT | ASO-005689 | OxyAs OxyAs DNAts OxyTs OxyMCs DNAcs DNAts DNAts DNAas DNAcs DNAas DNAcs OxyAs DNAcs DNAas OxyMCs OxyT |
| 9 | 7,603 | 7,621 | 237 | 255 | DES-005690 | AAtTCcttacaccAcaCT | ASO-005690 | OxyAs OxyAs DNAts OxyTs DNAcs DNAts DNAts DNAts DNAaas DNAcs DNAas DNAcs OxyAs DNAcs DNAas OxyMCs OxyT |
| 9 | 7,603 | 7,621 | 237 | 255 | DES-005691 | AAttCcTttacaccAcaCT | ASO-005691 | OxyAs OxyAs DNAts DNAcs OxyMCs DNAcs DNAts DNAts OxyTs DNAts DNAaas DNAcs DNAas DNAcs OxyAs DNAcs DNAas OxyMCs OxyT |
| 9 | 7,603 | 7,621 | 237 | 255 | DES-005692 | AAttCcttacaccAcaCT | ASO-005692 | OxyAs OxyAs DNAts DNAcs OxyMCs DNAts DNAts DNAts DNAaas DNAcs DNAas DNAcs OxyAs DNAcs DNAas OxyMCs OxyT |
| 9 | 7,603 | 7,621 | 237 | 255 | DES-005693 | AAttcCtttacaccAcaCT | ASO-005693 | OxyAs OxyAs DNAts DNAcs DNAts OxyMCs DNAcs DNAts DNAts DNAaas DNAcs DNAas DNAcs OxyAs DNAcs DNAas OxyMCs OxyT |
| 9 | 7,603 | 7,621 | 237 | 255 | DES-005694 | AAttccttacaccAcaCT | ASO-005694 | OxyAs OxyAs DNAts DNAcs DNAts DNAcs DNAts DNAts DNAaas DNAcs DNAas DNAcs OxyAs DNAcs DNAas OxyMCs OxyT |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 9 | 7,603 | 7,621 | 237 | 255 | DES-005695 | AaTtCctttacaccAcaCT | ASO-005695 | OxyAs DNAaas OxyTs DNAts OxyMCs DNAcs DNAts DNAts DNAas DNAcs DNAcs DNAts DNAas OxyAs DNAcs DNAas OxyMCs OxyT |
| 9 | 7,603 | 7,621 | 237 | 255 | DES-005696 | AaTtcctttacaccAcaCT | ASO-005696 | OxyAs DNAaas OxyTs DNAts OxyMCs DNAcs DNAts DNAts DNAas DNAcs DNAcs DNAts DNAas OxyAs DNAcs DNAas OxyMCs OxyT |
| 9 | 7,603 | 7,621 | 237 | 255 | DES-005697 | AatTCctttacaccAcaCT | ASO-005697 | OxyAs DNAaas OxyTs DNAts OxyMCs DNAcs DNAts DNAts DNAas DNAcs DNAcs DNAts DNAas OxyAs DNAcs DNAas OxyMCs OxyT |
| 9 | 7,603 | 7,621 | 237 | 255 | DES-005698 | AatTcctttacaccAcaCT | ASO-005698 | OxyAs DNAaas OxyTs DNAts OxyMCs DNAcs DNAts DNAts DNAas DNAcs DNAcs DNAts DNAas OxyAs DNAcs DNAas OxyMCs OxyT |
| 9 | 7,603 | 7,621 | 237 | 255 | DES-005699 | AattCcttTacaccAcaCT | ASO-005699 | OxyAs DNAas DNAts DNAts OxyMCs DNAcs DNAts DNAts DNAas DNAcs DNAcs DNAts DNAas OxyAs DNAcs DNAas OxyMCs OxyT |
| 9 | 7,603 | 7,621 | 237 | 255 | DES-005700 | AAttCcttTacaccaCACT | ASO-005700 | OxyAs OxyAs DNAts DNAts OxyMCs DNAcs DNAts DNAts DNAas DNAcs DNAcs DNAts DNAas OxyAs OxyMCs OxyT |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 9 | 7,603 | 7,621 | 237 | 255 | DES-005701 | AAttccttacaccaCACT | ASO-005701 | OxyAs OxyAs DNAts DNAts DNAcs DNAts DNAts DNAts DNAts DNAas DNAcs DNAts DNAcs DNAts DNAts OxyMCs OxyAs OxyMCs OxyT |
| 9 | 7,603 | 7,621 | 237 | 255 | DES-005702 | AAtTCctttacaccaCaCT | ASO-005702 | OxyAs OxyAs DNAts OxyTs OxyMCs DNAts DNAts DNAts DNAts DNAas DNAcs DNAts DNAcs DNAts DNAas OxyMCs OxyT |
| 9 | 7,603 | 7,621 | 237 | 255 | DES-005703 | AAttCctttacaccaCaCT | ASO-005703 | OxyAs OxyAs DNAts DNAts OxyMCs DNAts DNAts DNAts DNAts DNAas DNAcs DNAts DNAcs DNAts DNAas OxyMCs OxyT |
| 9 | 7,603 | 7,621 | 237 | 255 | DES-005704 | AAttcCtttacaccaCaCT | ASO-005704 | OxyAs OxyAs DNAts DNAts DNAcs OxyMCs DNAts DNAts DNAts DNAas DNAcs DNAts DNAcs DNAts DNAas OxyMCs OxyT |
| 9 | 7,603 | 7,621 | 237 | 255 | DES-005705 | AAttccttacaccaCaCT | ASO-005705 | OxyAs DNAas DNAts DNAts DNAcs DNAts DNAts DNAts DNAts DNAas DNAcs DNAts DNAcs DNAts DNAas OxyMCs OxyT |
| 9 | 7,603 | 7,621 | 237 | 255 | DES-005706 | AaTtCctttacaccaCaCT | ASO-005706 | OxyAs DNAas OxyTs DNAts OxyMCs DNAts DNAts DNAts DNAts DNAas DNAcs DNAts DNAcs DNAts DNAas OxyMCs OxyT |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 9 | 7,603 | 7,621 | 237 | 255 | DES-005707 | AattCctttacaccaCaCT | ASO-005707 | OxyAs DNAas DNAts DNAts OxyMCs DNAcs DNAts DNAts DNAas DNAts DNAcs DNAts DNAas DNAcs DNAcs OxyMCs DNAas OxyMCs OxyT |
| 9 | 7,603 | 7,621 | 237 | 255 | DES-005708 | AattcctttacaccaCaCT | ASO-005708 | OxyAs DNAas DNAts DNAts DNAcs DNAcs DNAts DNAts DNAas DNAts DNAcs DNAts DNAas DNAcs DNAcs OxyMCs DNAas OxyMCs OxyT |
| 9 | 7,603 | 7,621 | 237 | 255 | DES-005709 | AAttCctttacaccaACT | ASO-005709 | OxyAs OxyAs DNAts OxyTs OxyMCs DNAcs DNAts DNAts DNAas DNAts DNAcs DNAts DNAas DNAcs DNAcs OxyAs OxyMCs OxyT |
| 9 | 7,603 | 7,621 | 237 | 255 | DES-005710 | AAttCctTtacaccacACT | ASO-005710 | OxyAs OxyAs DNAts DNAts OxyMCs DNAcs DNAts DNAts OxyTs DNAts DNAcs DNAcs DNAas DNAcs DNAcs OxyAs OxyMCs DNAts OxyT |
| 9 | 7,603 | 7,621 | 237 | 255 | DES-005711 | AAttCctttacaccacACT | ASO-005711 | OxyAs OxyAs DNAts DNAts OxyMCs DNAcs DNAts DNAts DNAas DNAts DNAcs DNAcs DNAas DNAcs DNAcs OxyAs OxyMCs DNAts OxyT |
| 9 | 7,603 | 7,621 | 237 | 255 | DES-005712 | AAttcCtTtacaccacACT | ASO-005712 | OxyAs OxyAs DNAts DNAts DNAcs OxyMCs DNAts DNAts OxyTs DNAts DNAcs DNAcs DNAas DNAcs DNAcs OxyAs OxyMCs DNAts OxyT |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 9 | 7,603 | 7,621 | 237 | 255 | DES-005713 | AAttcCtttacaccacACT | ASO-005713 | OxyAs OxyAs DNAts DNAts DNAcs OxyMCs DNAts DNAts DNAas DNAcs DNAas DNAcs DNAas DNAcs OxyAs OxyMCs OxyT |
| 9 | 7,603 | 7,621 | 237 | 255 | DES-005714 | AAttccCtttacaccacACT | ASO-005714 | OxyAs OxyAs DNAts DNAts DNAcs DNAcs OxyMCs DNAts DNAts DNAas DNAcs DNAas DNAcs DNAas DNAcs OxyAs OxyMCs OxyT |
| 9 | 7,603 | 7,621 | 237 | 255 | DES-005715 | AaTtCctttacaccacACT | ASO-005715 | OxyAs DNAas OxyTs DNAts OxyMCs DNAts DNAts DNAas DNAcs DNAas DNAcs DNAas DNAcs OxyAs OxyMCs OxyT |
| 9 | 7,603 | 7,621 | 237 | 255 | DES-005716 | AaTtccttacaccacACT | ASO-005716 | OxyAs DNAas OxyTs DNAts DNAcs DNAcs DNAts DNAts DNAas DNAcs DNAas DNAcs DNAas DNAcs OxyAs OxyMCs OxyT |
| 9 | 7,603 | 7,621 | 237 | 255 | DES-005717 | AatTCctttacaccacACT | ASO-005717 | OxyAs DNAaas DNAts OxyTs OxyMCs DNAts DNAts DNAas DNAcs DNAas DNAcs DNAas DNAcs OxyAs OxyMCs OxyT |
| 9 | 7,603 | 7,621 | 237 | 255 | DES-005718 | AattCctttacaccacACT | ASO-005718 | OxyAs DNAas DNAts DNAts OxyMCs DNAts DNAts DNAas DNAcs DNAas DNAcs DNAas DNAcs OxyAs OxyMCs OxyT |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 9 | 7,603 | 7,621 | 237 | 255 | DES-005719 | AattcCtTtacaccacACT | ASO-005719 | OxyAs DNAas DNAts DNAts DNAcs OxyMCs DNAts OxyTs DNAts DNAas DNAcs DNAas DNAcs DNAcs DNAas DNAcs OxyAs OxyMCs OxyT |
| 9 | 7,603 | 7,621 | 237 | 255 | DES-005720 | AAtTCcttacaccacaCT | ASO-005720 | OxyAs OxyAs DNAas OxyTs OxyMCs DNAcs DNAts DNAts DNAas DNAcs DNAas DNAcs DNAcs DNAas DNAcs OxyMCs OxyT |
| 9 | 7,603 | 7,621 | 237 | 255 | DES-005721 | AAttCcTtacaccacaCT | ASO-005721 | OxyAs OxyAs DNAts DNAts DNAcs OxyMCs DNAts DNAts DNAas DNAcs DNAas DNAcs DNAcs DNAaa DNAcs OxyMCs OxyT |
| 9 | 7,603 | 7,621 | 237 | 255 | DES-005722 | AAttCcTTtacaccacaCT | ASO-005722 | OxyAs OxyAs DNAts DNAts DNAcs OxyMCs DNAts DNAts DNAas DNAcs DNAaa DNAcs DNAcs DNAaa DNAcs OxyMCs OxyT |
| 9 | 7,603 | 7,621 | 237 | 255 | DES-005723 | AAttCcttttacaccacaCT | ASO-005723 | OxyAs OxyAs DNAts DNAts DNAcs DNAts DNAts DNAas DNAcs DNAaa DNAcs DNAcs DNAaa DNAcs OxyMCs OxyT |
| 9 | 7,603 | 7,621 | 237 | 255 | DES-005724 | AAttcCtTtacaccacaCT | ASO-005724 | OxyAs OxyAs DNAas DNAts DNAts DNAcs OxyMCs DNAts OxyTs DNAts DNAas DNAcs DNAaa DNAcs DNAcs DNAaa DNAcs OxyMCs OxyT |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 9 | 7,603 | 7,621 | 237 | 255 | DES-005725 | AAttcctttaccacacaCT | ASO-005725 | OxyAs OxyAs DNAts DNAcs DNAcs DNAts DNAts DNAts DNAts DNAas DNAcs DNAas DNAts DNAcs DNAas OxyMCs OxyT |
| 9 | 7,603 | 7,621 | 237 | 255 | DES-005726 | AaTtCctttaccacacaCT | ASO-005726 | OxyAs DNAas OxyTs DNAts OxyMCs DNAcs DNAts DNAts DNAas DNAcs DNAas DNAts DNAcs DNAas OxyMCs OxyT |
| 9 | 7,603 | 7,621 | 237 | 255 | DES-005727 | AaTtCctttaccacacaCT | ASO-005727 | OxyAs DNAas DNAts OxyTs OxyMCs DNAcs DNAts DNAts DNAas DNAcs DNAas DNAts DNAcs DNAas OxyMCs OxyT |
| 9 | 7,603 | 7,621 | 237 | 255 | DES-005728 | AattCctttaccacacaCT | ASO-005728 | OxyAs DNAas DNAts DNAts OxyMCs DNAcs DNAts DNAts DNAas DNAcs DNAas DNAts DNAcs DNAas OxyMCs OxyT |
| 9 | 7,603 | 7,621 | 237 | 255 | DES-005729 | AaTTCctttacaccACaCT | ASO-005729 | OxyAs DNAas OxyTs OxyTs DNAts DNAcs DNAts DNAts DNAas DNAcs OxyAs OxyMCs DNAas OxyMCs OxyT |
| 9 | 7,603 | 7,621 | 237 | 255 | DES-005730 | AATtCctttacacCaCaCT | ASO-005730 | OxyAs OxyAs OxyTs DNAts OxyMCs DNAcs DNAts DNAts DNAas DNAcs DNAcs DNAas OxyMCs DNAas OxyMCs OxyT |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 7 | 7,603 | 7,620 | 237 | 254 | DES-005731 | AttcctttaCacCacacT | ASO-005731 | OxyAs DNAts DNAcs DNAcs DNAts DNAts DNAts DNAas OxyMCs DNAaas DNAcs OxyMCs DNAaas DNAcs OxyMCs OxyT |
| 7 | 7,603 | 7,620 | 237 | 254 | DES-005732 | AttCcCtttaCaccacacT | ASO-005732 | OxyAs DNAts DNAcs OxyMCs DNAcs OxyMCs DNAaas DNAcs OxyTs DNAts DNAas OxyMCs DNAaas DNAcs OxyMCs OxyT |
| 7 | 7,603 | 7,620 | 237 | 254 | DES-005733 | AttCcfTtaCaccacacT | ASO-005733 | OxyAs DNAts DNAcs OxyMCs DNAcs DNAaas DNAcs OxyTs DNAas OxyMCs DNAaas DNAcs OxyMCs OxyT |
| 7 | 7,603 | 7,620 | 237 | 254 | DES-005734 | AttCcttttaCaccacacT | ASO-005734 | OxyAs DNAts DNAcs OxyMCs DNAcs OxyMCs DNAaas DNAcs DNAts DNAas OxyMCs DNAaas DNAcs OxyMCs OxyT |
| 7 | 7,603 | 7,620 | 237 | 254 | DES-005735 | AttCctTtaCaccacacT | ASO-005735 | OxyAs DNAts DNAcs DNAcs DNAcs OxyMCs DNAaas DNAcs OxyTs DNAts DNAas OxyMCs DNAaas DNAcs OxyMCs OxyT |
| 7 | 7,603 | 7,620 | 237 | 254 | DES-005736 | AttCcttttaCaccacacT | ASO-005736 | OxyAs DNAts DNAcs OxyMCs DNAcs OxyMCs DNAaas DNAcs DNAts DNAas OxyMCs DNAaas DNAcs OxyMCs OxyT |
| 7 | 7,603 | 7,620 | 237 | 254 | DES-005737 | AttCctttacACCaCacT | ASO-005737 | OxyAs DNAts DNAcs OxyMCs DNAcs DNAts DNAts DNAas OxyAs OxyMCs DNAcs OxyAs DNAas DNAcs OxyMCs OxyT |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 7 | 7,603 | 7,620 | 237 | 254 | DES-005738 | AttCctttacACcacaCT | ASO-005738 | OxyAs DNAts DNAts OxyMCs DNAcs DNAts DNAts DNAts DNAas DNAcs OxyAs DNAcs OxyMCs DNAas DNAcs DNAas OxyMCs OxyT |
| 7 | 7,603 | 7,620 | 237 | 254 | DES-005739 | AttccttacAcCAcaCT | ASO-005739 | OxyAs DNAts DNAts OxyMCs DNAcs DNAts DNAts DNAts DNAas DNAcs OxyAs DNAcs OxyMCs OxyAs DNAcs DNAas OxyMCs OxyT |
| 7 | 7,603 | 7,620 | 237 | 254 | DES-005740 | AttCctttacAcCcacACT | ASO-005740 | OxyAs DNAts DNAts OxyMCs DNAcs DNAts DNAts DNAts DNAas DNAcs OxyAs DNAcs OxyMCs DNAcs OxyAs DNAas OxyMCs OxyT |
| 7 | 7,603 | 7,620 | 237 | 254 | DES-005741 | AttCctttacAcCacaCT | ASO-005741 | OxyAs DNAts DNAts OxyMCs DNAcs DNAts DNAts DNAts DNAas DNAcs OxyAs DNAcs OxyMCs OxyAs DNAcs DNAas OxyMCs OxyT |
| 7 | 7,603 | 7,620 | 237 | 254 | DES-005742 | AttCctttacAccaCaCT | ASO-005742 | OxyAs DNAts DNAts OxyMCs DNAcs DNAts DNAts DNAts DNAas DNAcs OxyAs DNAcs DNAcs OxyAs DNAcs DNAas OxyMCs OxyT |
| 7 | 7,603 | 7,620 | 237 | 254 | DES-005743 | AttCctttacAccaCaCT | ASO-005743 | OxyAs DNAts DNAts OxyMCs DNAcs DNAts DNAts DNAts DNAas DNAcs OxyAs DNAcs DNAcs OxyAs DNAcs OxyMCs DNAas OxyMCs OxyT |
| 7 | 7,603 | 7,620 | 237 | 254 | DES-005744 | AttCctttacAccacACT | ASO-005744 | OxyAs DNAts DNAts OxyMCs DNAcs DNAts DNAts DNAts DNAas DNAcs OxyAs DNAcs DNAcs DNAas DNAcs OxyAs OxyAs OxyMCs OxyT |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 7 | 7,603 | 7,620 | 237 | 254 | DES-005745 | AtTccttacAccacaCT | ASO-005745 | OxyAs DNAts OxyTs OxyMCs DNAcs DNAts DNAts DNAts DNAts DNAcs OxyAs DNAt DNAcs DNAas DNAcs DNAas OxyMCs OxyT |
| 7 | 7,603 | 7,620 | 237 | 254 | DES-005746 | AttCcttacAccacaCT | ASO-005746 | OxyAs DNAts DNAts OxyMCs DNAcs DNAts DNAts DNAts DNAts DNAcs OxyAs DNAt DNAcs DNAas DNAcs DNAas OxyMCs OxyT |
| 7 | 7,603 | 7,620 | 237 | 254 | DES-005747 | AttCcttacaCcAcaCT | ASO-005747 | OxyAs DNAts DNAts OxyMCs DNAcs DNAts DNAts DNAcs OxyAs DNAcs DNAts DNAts DNAcs OxyAs OxyMCs OxyT |
| 7 | 7,603 | 7,620 | 237 | 254 | DES-005748 | AttcCtttacaCcAcACT | ASO-005748 | OxyAs DNAts DNAts OxyMCs DNAcs OxyAs DNAts DNAts DNAcs OxyAs DNAcs DNAts DNAts DNAcs OxyAs OxyMCs OxyT |
| 10 | 7,603 | 7,622 | 237 | 256 | DES-005796 | GaAttccttacCacCacaCT | ASO-005796 | OxyGs DNAas OxyAs DNAts DNAts OxyMCs DNAcs DNAts DNAts DNAcs OxyMCs DNAas DNAcs OxyAs DNAcs DNAts DNAts OxyMCs OxyT |
| 10 | 7,603 | 7,622 | 237 | 256 | DES-005797 | GaAttccttacAcCacaCT | ASO-005797 | OxyGs DNAas OxyAs DNAts DNAts OxyMCs DNAcs DNAts DNAas DNAcs OxyMCs DNAas DNAcs OxyAs DNAcs DNAts DNAts OxyMCs OxyT |
| 10 | 7,603 | 7,622 | 237 | 256 | DES-005798 | GaAttCcttacAccAcaCT | ASO-005798 | OxyGs DNAas OxyAs DNAts DNAts OxyMCs DNAcs DNAts DNAts OxyMCs DNAcs DNAas DNAcs OxyAs DNAcs DNAts DNAas OxyMCs OxyT |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 10 | 7,603 | 7,622 | 237 | 256 | DES-005799 | GaAttCctttacAccacAC T | ASO-005799 | OxyGs DNAas OxyAs DNAts DNAts OxyMCs DNAcs DNAts DNAts DNAts DNAas OxyAs DNAcs DNAts DNAas DNAcs DNAcs OxyAs OxyMCs OxyT |
| 10 | 7,603 | 7,622 | 237 | 256 | DES-005800 | GaAttCctttacAccacaC T | ASO-005800 | OxyGs DNAas OxyAs DNAts DNAts OxyMCs DNAcs DNAts DNAts DNAts DNAas OxyAs DNAcs DNAts DNAas DNAcs DNAas OxyMCs OxyT |
| 10 | 7,603 | 7,622 | 237 | 256 | DES-005801 | GaAttccttacAccacaCT | ASO-005801 | OxyGs DNAas OxyAs DNAts DNAts DNAts DNAts DNAts DNAts DNAts DNAas OxyAs DNAcs DNAts DNAas DNAcs DNAas OxyMCs OxyT |
| 10 | 7,603 | 7,622 | 237 | 256 | DES-005802 | GaAttccttacaCcAcaC T | ASO-005802 | OxyGs DNAas OxyAs DNAts DNAts DNAts DNAcs DNAts DNAts OxyAs DNAcs DNAas DNAcs DNAas OxyMCs OxyT |
| 10 | 7,603 | 7,622 | 237 | 256 | DES-005803 | GaAttcctttacaCcacaCT | ASO-005803 | OxyGs DNAas OxyAs DNAts DNAts DNAts DNAts DNAcs DNAts DNAas OxyMCs DNAas DNAcs DNAas OxyMCs OxyT |
| 10 | 7,603 | 7,622 | 237 | 256 | DES-005804 | GAAtTccttacacCaCaC T | ASO-005804 | OxyGs OxyAs OxyAs DNAts OxyTs DNAcs DNAts DNAts DNAts DNAas DNAcs DNAas OxyMCs DNAcs OxyMCs DNAas OxyMCs OxyT |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 10 | 7,603 | 7,622 | 237 | 256 | DES-005805 | GaAttccTttacacCaCaCT | ASO-005805 | OxyGs DNAaas OxyAs DNAts DNAts DNAcs DNAts DNAts DNAts DNAts DNAcs DNAaas OxyMCs DNAaas OxyMCs OxyT |
| 10 | 7,603 | 7,622 | 237 | 256 | DES-005806 | GaAttCcTttacacCacaCT | ASO-005806 | OxyGs DNAaas OxyAs DNAts DNAts DNAts OxyMCs DNAts DNAts DNAts DNAcs DNAaas OxyMCs DNAaas OxyMCs OxyT |
| 10 | 7,603 | 7,622 | 237 | 256 | DES-005807 | GaAttccTttacacCacaC T | ASO-005807 | OxyGs DNAaas OxyAs DNAts DNAts DNAcs DNAts OxyMCs DNAts DNAts DNAcs DNAaas OxyTs DNAts DNAaas OxyMCs OxyT |
| 10 | 7,603 | 7,622 | 237 | 256 | DES-005808 | GaAttcctTtacacCacaCT | ASO-005808 | OxyGs DNAaas OxyAs DNAts DNAts DNAcs DNAts OxyMCs DNAts DNAts DNAcs DNAaas DNAts DNAaas OxyMCs OxyT |
| 10 | 7,603 | 7,622 | 237 | 256 | DES-005809 | GaATTccttTtacaccACaC T | ASO-005809 | OxyGs DNAaas OxyAs DNAts OxyTs OxyTs DNAcs DNAcs DNAts DNAts DNAcs DNAaas OxyAs OxyMCs DNAaas OxyMCs OxyT |
| 10 | 7,603 | 7,622 | 237 | 256 | DES-005810 | GaAttCcttTtacaccACAC T | ASO-005810 | OxyGs DNAaas OxyAs DNAts DNAts DNAts OxyMCs DNAts DNAts DNAcs DNAaas OxyAs DNAts DNAcs OxyAs DNAcs OxyAs OxyMCs OxyT |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 10 | 7,603 | 7,622 | 237 | 256 | DES-005811 | GaAttccTttacaccAcaCT | ASO-005811 | OxyGs DNAas OxyAs DNAts DNAcs DNAts DNAcs OxyTs DNAts DNAts DNAts DNAas DNAts DNAcs DNAts DNAcs OxyAs DNAcs OxyAs OxyMCs OxyT |
| 10 | 7,603 | 7,622 | 237 | 256 | DES-005812 | GaAttCcTttacaccAcaCT | ASO-005812 | OxyGs DNAas OxyAs DNAts DNAcs DNAts OxyMCs OxyTs DNAts DNAts DNAts DNAas DNAts DNAcs DNAts DNAcs OxyAs DNAcs DNAas OxyMCs OxyT |
| 10 | 7,603 | 7,622 | 237 | 256 | DES-005813 | GaAttCctttacaccAcaCT | ASO-005813 | OxyGs DNAas OxyAs DNAts DNAcs DNAts OxyMCs DNAts DNAts DNAts DNAts DNAas DNAts DNAcs DNAts DNAcs OxyAs DNAcs DNAas OxyMCs OxyT |
| 10 | 7,603 | 7,622 | 237 | 256 | DES-005814 | GaAttccTttacaccAcaCT | ASO-005814 | OxyGs DNAas OxyAs DNAts DNAcs DNAts DNAcs OxyMCs DNAts DNAts DNAts DNAas DNAts DNAcs DNAts DNAcs OxyAs DNAcs DNAas OxyMCs OxyT |
| 10 | 7,603 | 7,622 | 237 | 256 | DES-005815 | GaAttccTttacaccAcaCT | ASO-005815 | OxyGs DNAas OxyAs DNAts DNAcs DNAts DNAcs OxyTs DNAts DNAts DNAts DNAas DNAts DNAcs DNAts DNAcs OxyAs DNAcs DNAas OxyMCs OxyT |
| 10 | 7,603 | 7,622 | 237 | 256 | DES-005816 | GaAttcctttacaccAcaCT | ASO-005816 | OxyGs DNAas OxyAs DNAts DNAcs DNAts DNAcs DNAts DNAts DNAts DNAts DNAas DNAts DNAcs DNAts DNAcs OxyAs DNAcs DNAas OxyMCs OxyT |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 10 | 7,603 | 7,622 | 237 | 256 | DES-005817 | GAATtcctttacaccaCACT | ASO-005817 | OxyGs OxyAs OxyAs OxyTs DNAts DNAcs DNAcs DNAts DNAts DNAts DNAas DNAcs DNAcs DNAts DNAcs DNAas OxyMCs OxyAs OxyMCs OxyT |
| 10 | 7,603 | 7,622 | 237 | 256 | DES-005818 | GAAttcctttacaccaCACT | ASO-005818 | OxyGs OxyAs OxyAs DNAts DNAcs DNAcs DNAts DNAts DNAts DNAas DNAcs DNAcs DNAts DNAcs DNAas OxyMCs OxyAs OxyMCs OxyT |
| 10 | 7,603 | 7,622 | 237 | 256 | DES-005819 | GAattcctttacaccaCACT | ASO-005819 | OxyGs OxyAs DNAas DNAts DNAcs DNAcs DNAts DNAts DNAts DNAas DNAcs DNAcs DNAts DNAcs DNAas OxyMCs OxyAs OxyMCs OxyT |
| 10 | 7,603 | 7,622 | 237 | 256 | DES-005820 | GAATtcctttacaccacAC T | ASO-005820 | OxyGs OxyAs OxyAs OxyTs DNAts DNAcs DNAcs DNAts DNAts DNAts DNAas DNAcs DNAcs DNAts DNAcs DNAcs OxyMCs OxyT |
| 10 | 7,603 | 7,622 | 237 | 256 | DES-005821 | GAAttcctttacaccacACT | ASO-005821 | OxyGs OxyAs OxyAs DNAts DNAcs DNAcs DNAts DNAts DNAts DNAas DNAcs DNAcs DNAts DNAcs DNAcs OxyMCs OxyT |
| 10 | 7,603 | 7,622 | 237 | 256 | DES-005822 | GAattcctttacaccacACT | ASO-005822 | OxyGs OxyAs DNAas DNAts DNAcs DNAcs DNAts DNAts DNAts DNAas DNAcs DNAcs DNAts DNAcs DNAcs OxyMCs OxyT |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 10 | 7,603 | 7,622 | 237 | 256 | DES-005823 | GaAttcCtttacaccacACT | ASO-005823 | OxyGs DNAaas OxyAs DNAts DNAts DNAcs OxyMCs DNAts DNAts DNAts DNAas DNAts DNAcs DNAas DNAcs OxyAs OxyMCs OxyT |
| 10 | 7,603 | 7,622 | 237 | 256 | DES-005824 | GaAttccTttacaccacACT | ASO-005824 | OxyGs DNAaas OxyAs DNAts DNAts DNAcs OxyTs DNAts DNAts DNAts DNAas DNAts DNAcs DNAas DNAcs OxyAs OxyMCs OxyT |
| 10 | 7,603 | 7,622 | 237 | 256 | DES-005825 | GaAttcctTtacaccacACT | ASO-005825 | OxyGs DNAaas OxyAs DNAts DNAts DNAcs DNAts OxyTs DNAts DNAas DNAts DNAcs DNAas DNAcs OxyAs OxyMCs OxyT |
| 10 | 7,603 | 7,622 | 237 | 256 | DES-005826 | GAATtcctttacaccacaC T | ASO-005826 | OxyGs OxyAs OxyAs OxyTs DNAts DNAcs DNAcs DNAts DNAts DNAts DNAas DNAcs DNAas DNAcs DNAas OxyMCs OxyT |
| 10 | 7,603 | 7,622 | 237 | 256 | DES-005827 | GAAttcctttacaccacaCT | ASO-005827 | OxyGs OxyAs OxyAs DNAts DNAts DNAcs DNAcs DNAts DNAts DNAts DNAas DNAcs DNAas DNAcs DNAas OxyMCs OxyT |
| 10 | 7,603 | 7,622 | 237 | 256 | DES-005828 | GAattcctttacaccacaCT | ASO-005828 | OxyGs OxyAs DNAas DNAts DNAts DNAcs DNAcs DNAts DNAts DNAts DNAas DNAcs DNAas DNAcs DNAas OxyMCs OxyT |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 10 | 7,603 | 7,622 | 237 | 256 | DES-005829 | GaAttCcTtacaccacaCT | ASO-005829 | OxyGs DNAaas OxyAs DNAts DNAts DNAcs OxyMCs DNAts OxyTs DNAts DNAts DNAaas DNAts DNAcs DNAas DNAts DNAcs DNAaas OxyMCs OxyT |
| 10 | 7,603 | 7,622 | 237 | 256 | DES-005830 | GaAttCctTtacaccacaCT | ASO-005830 | OxyGs DNAaas OxyAs DNAts DNAts DNAcs OxyMCs DNAts DNAts OxyTs DNAts DNAaas DNAts DNAcs DNAas DNAts DNAcs DNAaas OxyMCs OxyT |
| 10 | 7,603 | 7,622 | 237 | 256 | DES-005831 | GaAttCctttacaccacaCT | ASO-005831 | OxyGs DNAaas OxyAs DNAts DNAts DNAcs OxyMCs DNAts DNAts DNAts OxyTs DNAaas DNAts DNAcs DNAas DNAts DNAcs DNAaas OxyMCs OxyT |
| 10 | 7,603 | 7,622 | 237 | 256 | DES-005832 | GaAttccCtTtacaccacaCT | ASO-005832 | OxyGs DNAaas OxyAs DNAts DNAts DNAcs DNAcs OxyMCs DNAts DNAts OxyTs DNAaas DNAts DNAcs DNAas DNAts DNAcs DNAaas OxyMCs OxyT |
| 10 | 7,603 | 7,622 | 237 | 256 | DES-005833 | GaAttccCtttacaccacaCT | ASO-005833 | OxyGs DNAaas OxyAs DNAts DNAts DNAcs DNAcs OxyMCs DNAts DNAts DNAts OxyTs DNAaas DNAts DNAcs DNAas DNAts DNAcs DNAaas OxyMCs OxyT |
| 10 | 7,603 | 7,622 | 237 | 256 | DES-005834 | GaAttccTttacaccacaCT | ASO-005834 | OxyGs DNAaas OxyAs DNAts DNAts DNAcs DNAcs DNAts OxyTs DNAts DNAts OxyTs DNAaas DNAts DNAcs DNAas DNAts DNAcs DNAaas OxyMCs OxyT |

FIG. 2 (cont.)

| Sequence ID No. | NG_011 851.1 Start | NG_011 851.1 End | NM_0 00345 .3 Start | NM_0 00345 .3 End | DES No. | ASO with Design | ASO No. | ASO with Chemical Structure |
|---|---|---|---|---|---|---|---|---|
| 10 | 7,603 | 7,622 | 237 | 256 | DES-005835 | GaAttccTttacaccacaCt | ASO-005835 | OxyGs DNAaas OxyAs DNAts DNAcs DNAts DNAcs DNAts OxyTs DNAts DNAts DNAas DNAts DNAts DNAas DNAcs DNAas DNAts OxyMCs OxyT |
| 10 | 7,603 | 7,622 | 237 | 256 | DES-005836 | GaAttcctTtacaccacaCt | ASO-005836 | OxyGs DNAaas OxyAs DNAts DNAcs DNAts DNAcs DNAts OxyTs DNAts DNAts DNAas DNAts DNAts DNAas DNAcs DNAas DNAts OxyMCs OxyT |
| 7 | 7,603 | 7,620 | 237 | 254 | DES-316392 | attCctttacaccACact | ASO-316392 | OMeas OMets OMets OxyMCs DNAcs DNAts DNAts DNAts DNAts DNAcs DNAas DNAts DNAcs OxyAs OxyMCs OMeas OMecs OMet |
| 7 | 7,603 | 7,620 | 237 | 254 | DES-316393 | attCcttttacaccAcActt | ASO-316393 | OMeas OMets OMets OxyMCs DNAcs DNAts DNAts DNAts DNAts DNAcs DNAas DNAts DNAcs OxyAs OxyMCs OMeas OMecs OMet |
| 7 | 7,603 | 7,620 | 237 | 254 | DES-316394 | AttCctttacaccAcActt | ASO-316394 | OxyAs OMets OMets OxyMCs DNAcs DNAts DNAts DNAts DNAts DNAcs DNAas DNAts DNAcs OxyAs OxyMCs OMeas OMecs OMet |
| 7 | 7,603 | 7,620 | 237 | 254 | DES-316395 | AttCctttacaccACactt | ASO-316395 | OxyAs OMets OMets OxyMCs DNAcs DNAts DNAts DNAts DNAts DNAcs DNAas DNAts DNAcs OxyAs OxyMCs OMeas OMecs OMet |
| 12 | 7,604 | 7,619 | 238 | 253 | DES-001263 | TTCcttttacaccaCAC | ASO-001263 | OxyTs OxyTs OxyMCs DNAcs DNAts DNAts DNAts DNAts DNAts DNAcs DNAas DNAcs DNAcs OxyAs OxyMCs OxyMC |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 12 | 7,604 | 7,619 | 238 | 253 | DES-001421 | TTCctttacaccaCAC | ASO-001421 | OxyTs OxyTs OxyMCs DNAcs DNAts DNAts DNAts DNAts DNAas DNAts DNAas DNAcs DNAcs DNAas OxyAs OxyMC |
| 12 | 7,604 | 7,619 | 238 | 253 | DES-002816 | TTCctttacaccACAC | ASO-002816 | OxyTs OxyTs OxyMCs DNAcs DNAts DNAts DNAts DNAts DNAas DNAcs DNAcs OxyAs OxyAs OxyMCs OxyMC |
| 14 | 7,604 | 7,621 | 238 | 255 | DES-005367 | AAttCctttacaccaCAC | ASO-005367 | OxyAs OxyAs DNAts DNAts DNAcs DNAts DNAts OxyTs DNAts DNAas OxyMCs DNAcs DNAcs DNAas OxyMCs OxyAs OxyMC |
| 14 | 7,604 | 7,621 | 238 | 255 | DES-005368 | AAttcCTttacaccaCAC | ASO-005368 | OxyAs OxyAs DNAts DNAts DNAcs DNAts DNAcs DNAts OxyTs DNAts DNAas OxyMCs DNAcs DNAcs DNAas OxyMCs OxyAs OxyMC |
| 14 | 7,604 | 7,621 | 238 | 255 | DES-005369 | AAttcCtTtacaccaCAC | ASO-005369 | OxyAs OxyAs DNAts DNAts DNAcs DNAts DNAcs OxyMCs DNAts OxyTs DNAts DNAas OxyMCs DNAcs DNAcs DNAas OxyMCs OxyAs OxyMC |
| 14 | 7,604 | 7,621 | 238 | 255 | DES-005370 | AAttcCtttacaccaCAC | ASO-005370 | OxyAs OxyAs DNAts DNAts DNAcs DNAts DNAcs DNAts DNAts DNAts DNAas OxyMCs DNAcs DNAcs DNAas OxyMCs OxyAs OxyMC |
| 14 | 7,604 | 7,621 | 238 | 255 | DES-005371 | AAttccTTtacaccaCAC | ASO-005371 | OxyAs OxyAs DNAts DNAts DNAcs DNAcs OxyTs OxyTs DNAts DNAas DNAcs DNAcs DNAas OxyMCs OxyAs OxyMC |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 14 | 7,604 | 7,621 | 238 | 255 | DES-005372 | AAttcctttacaccaCAC | ASO-005372 | OxyAs OxyAs DNAts DNAts DNAcs DNAcs DNAts DNAts DNAts DNAas DNAcs DNAts DNAas OxyMCs OxyAs OxyMC |
| 14 | 7,604 | 7,621 | 238 | 255 | DES-005373 | AaTTCctttacaccaCAC | ASO-005373 | OxyAs DNAas OxyTs OxyTs OxyMCs DNAcs DNAts DNAts DNAas DNAcs DNAts DNAas OxyMCs OxyAs OxyMC |
| 14 | 7,604 | 7,621 | 238 | 255 | DES-005374 | AaTTccttacaccaCAC | ASO-005374 | OxyAs DNAas OxyTs OxyTs DNAcs OxyMCs DNAts DNAts DNAas DNAcs DNAts DNAas OxyMCs OxyAs OxyMC |
| 14 | 7,604 | 7,621 | 238 | 255 | DES-005375 | AaTtCctTtacaccaCAC | ASO-005375 | OxyAs DNAas OxyTs DNAts OxyMCs DNAcs DNAts OxyTs DNAas DNAcs DNAts DNAas OxyMCs OxyAs OxyMC |
| 14 | 7,604 | 7,621 | 238 | 255 | DES-005376 | AaTtCctttacaccaCAC | ASO-005376 | OxyAs DNAas OxyTs DNAts OxyMCs DNAcs DNAts DNAts DNAas DNAcs DNAts DNAas OxyMCs OxyAs OxyMC |
| 14 | 7,604 | 7,621 | 238 | 255 | DES-005377 | AaTtCcTTtacaccaCAC | ASO-005377 | OxyAs DNAas OxyTs DNAts OxyMCs DNAcs OxyTs OxyTs DNAas DNAcs DNAts DNAas OxyMCs OxyAs OxyMC |
| 14 | 7,604 | 7,621 | 238 | 255 | DES-005378 | AaTtCcttTtacaccaCAC | ASO-005378 | OxyAs DNAas OxyTs DNAts OxyMCs DNAcs DNAts OxyMCs DNAts DNAas DNAcs DNAts DNAas OxyMCs OxyAs OxyMC |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 14 | 7,604 | 7,621 | 238 | 255 | DES-005379 | AaTtcctttacaccaCAC | ASO-005379 | OxyAs DNAas OxyTs DNAts DNAcs DNAts DNAcs DNAts DNAts DNAts DNAas DNAas DNAcs DNAts DNAas DNAcs OxyMCs OxyAs OxyMC |
| 14 | 7,604 | 7,621 | 238 | 255 | DES-005380 | AatTCctTtacaccaCAC | ASO-005380 | OxyAs DNAas DNAts OxyTs OxyMCs DNAts DNAcs DNAts OxyTs DNAts DNAas DNAas DNAcs DNAts DNAas DNAcs OxyMCs OxyAs OxyMC |
| 14 | 7,604 | 7,621 | 238 | 255 | DES-005381 | AatTCctTtacaccaCAC | ASO-005381 | OxyAs DNAas DNAts OxyTs OxyMCs DNAts DNAcs DNAts OxyTs DNAts DNAas DNAas DNAcs DNAts DNAas DNAcs OxyMCs OxyAs OxyMC |
| 14 | 7,604 | 7,621 | 238 | 255 | DES-005382 | AatTcCtTtacaccaCAC | ASO-005382 | OxyAs DNAas DNAts OxyTs DNAcs OxyMCs DNAts DNAcs DNAts DNAas DNAas DNAcs DNAts DNAas DNAcs OxyMCs OxyAs OxyMC |
| 14 | 7,604 | 7,621 | 238 | 255 | DES-005383 | AatTccttTacaccaCAC | ASO-005383 | OxyAs DNAas DNAts OxyTs DNAcs DNAts OxyTs DNAts OxyTs DNAts DNAas DNAas DNAcs DNAts DNAas DNAcs OxyMCs OxyAs OxyMC |
| 14 | 7,604 | 7,621 | 238 | 255 | DES-005384 | AattCctttacaccaCAC | ASO-005384 | OxyAs DNAas OxyTs DNAts DNAcs OxyMCs DNAts DNAcs DNAts DNAts DNAas DNAas DNAcs DNAts DNAas DNAcs OxyMCs OxyAs OxyMC |
| 14 | 7,604 | 7,621 | 238 | 255 | DES-005385 | AATtCCtttacaccacAC | ASO-005385 | OxyAs OxyAs OxyTs DNAts DNAcs OxyMCs OxyMCs DNAts DNAts DNAts DNAas DNAas DNAcs DNAts DNAas DNAcs DNAas DNAcs OxyAs OxyMC |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 14 | 7,604 | 7,621 | 238 | 255 | DES-005386 | AAtTCcTtacaccacAC | ASO-005386 | OxyAs OxyAs DNAts OxyTs OxyMCs OxyMCs DNAts OxyTs DNAts DNAas DNAcs DNAas DNAcs DNAcs OxyAas OxyAs OxyMC |
| 14 | 7,604 | 7,621 | 238 | 255 | DES-005387 | AAtTCCtttacaccacAC | ASO-005387 | OxyAs OxyAs DNAts OxyTs OxyMCs OxyMCs DNAts OxyTs DNAts DNAas DNAcs DNAas DNAcs DNAcs OxyAas OxyAs OxyMC |
| 14 | 7,604 | 7,621 | 238 | 255 | DES-005388 | AAtTCcTttacaccacAC | ASO-005388 | OxyAs OxyAs DNAts OxyTs DNAts OxyMCs DNAcs OxyTs DNAts DNAas DNAcs DNAas DNAcs DNAcs OxyAas OxyAs OxyMC |
| 14 | 7,604 | 7,621 | 238 | 255 | DES-005389 | AAtTCcTtTacaccacAC | ASO-005389 | OxyAs OxyAs DNAts OxyTs DNAts OxyMCs DNAcs OxyTs DNAts OxyTs DNAas DNAcs DNAas DNAcs DNAcs OxyAas OxyAs OxyMC |
| 14 | 7,604 | 7,621 | 238 | 255 | DES-005390 | AAtTCcttacaccacAC | ASO-005390 | OxyAs OxyAs DNAts OxyTs DNAts OxyMCs DNAcs OxyTs DNAts DNAts DNAas DNAcs DNAas DNAcs DNAcs OxyAas OxyAs OxyMC |
| 14 | 7,604 | 7,621 | 238 | 255 | DES-005391 | AAttCCTttacaccacAC | ASO-005391 | OxyAs OxyAs DNAts DNAts OxyMCs OxyMCs OxyTs DNAts DNAts DNAas DNAcs DNAas DNAcs DNAcs OxyAas OxyAs OxyMC |
| 14 | 7,604 | 7,621 | 238 | 255 | DES-005392 | AAttCCtTtacaccacAC | ASO-005392 | OxyAs OxyAs DNAts DNAts OxyMCs OxyMCs DNAts OxyTs DNAts DNAas DNAcs DNAas DNAcs DNAcs OxyAas OxyAs OxyMC |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 14 | 7,604 | 7,621 | 238 | 255 | DES-005393 | AAttcCTTtacacacAC | ASO-005393 | OxyAs OxyAs DNAts DNAcs OxyMCs OxyTs OxyTs DNAts DNAas DNAcs DNAas DNAcs DNAas OxyAs OxyMC |
| 14 | 7,604 | 7,621 | 238 | 255 | DES-005394 | AaTTCcTTtacacacAC | ASO-005394 | OxyAs DNAas OxyTs OxyTs OxyMCs DNAcs OxyTs DNAts DNAas DNAcs DNAas DNAcs DNAas OxyAs OxyMC |
| 14 | 7,604 | 7,621 | 238 | 255 | DES-005395 | AaTTCctttacaccacAC | ASO-005395 | OxyAs DNAas OxyTs OxyTs OxyMCs DNAcs DNAts DNAts DNAas DNAcs DNAas DNAcs DNAas OxyAs OxyMC |
| 14 | 7,604 | 7,621 | 238 | 255 | DES-005396 | AaTtCCtttacaccacAC | ASO-005396 | OxyAs DNAas OxyTs DNAts OxyMCs OxyMCs DNAts DNAts DNAas DNAcs DNAas DNAcs DNAas OxyAs OxyMC |
| 14 | 7,604 | 7,621 | 238 | 255 | DES-005397 | AaTtCCCTtacaccacAC | ASO-005397 | OxyAs DNAas OxyTs DNAts OxyMCs OxyMCs OxyTs DNAts DNAas DNAcs DNAas DNAcs DNAas OxyAs OxyMC |
| 14 | 7,604 | 7,621 | 238 | 255 | DES-005398 | AaTtCCttttacaccacAC | ASO-005398 | OxyAs DNAas DNAts DNAts OxyMCs OxyMCs DNAts DNAts DNAas DNAcs DNAas DNAcs DNAas OxyAs OxyMC |
| 14 | 7,604 | 7,621 | 238 | 255 | DES-005399 | AattCCTttacaccacAC | ASO-005399 | OxyAs DNAas DNAts DNAts OxyMCs OxyMCs OxyTs DNAts DNAas DNAcs DNAas DNAcs DNAas OxyAs OxyMC |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 14 | 7,604 | 7,621 | 238 | 255 | DES-005400 | AattCCtTtacaccacAC | ASO-005400 | OxyAs DNAts DNAts DNAts OxyMCs OxyMCs DNAts OxyTs DNAts DNAas DNAcs DNAas DNAcs DNAas DNAcs OxyAs OxyMC |
| 15 | 7,604 | 7,620 | 238 | 254 | DES-005401 | ATtcctttaCACcacAC | ASO-005401 | OxyAs OxyTs DNAts DNAcs DNAcs DNAts DNAts DNAts DNAas OxyMCs OxyAs OxyMCs DNAas DNAcs DNAas OxyAs OxyMC |
| 15 | 7,604 | 7,620 | 238 | 254 | DES-005402 | AttcctttaCAcCacAC | ASO-005402 | OxyAs DNAts DNAts DNAcs DNAcs DNAts DNAts DNAts DNAas OxyMCs DNAas OxyMCs OxyAs DNAcs OxyAs OxyMC |
| 15 | 7,604 | 7,620 | 238 | 254 | DES-005403 | AttCctttacACCacAC | ASO-005403 | OxyAs DNAts DNAts DNAcs OxyMCs DNAts DNAts DNAts DNAas OxyMCs OxyAs OxyMCs DNAas DNAcs OxyAs OxyMC |
| 15 | 7,604 | 7,620 | 238 | 254 | DES-005404 | AttCctttacACcaCAC | ASO-005404 | OxyAs DNAts DNAts DNAcs OxyMCs DNAts DNAts DNAts DNAas OxyMCs OxyAs DNAcs DNAas OxyAs OxyAs OxyMC |
| 15 | 7,604 | 7,620 | 238 | 254 | DES-005405 | ATtCctttacACCacAC | ASO-005405 | OxyAs OxyTs DNAts DNAcs OxyMCs DNAts DNAts DNAts DNAas OxyMCs OxyAs OxyMCs DNAas DNAcs OxyAs OxyMC |
| 15 | 7,604 | 7,620 | 238 | 254 | DES-005406 | AttCctttacACcaCAC | ASO-005406 | OxyAs DNAts DNAts DNAcs OxyMCs DNAts DNAts DNAts DNAas OxyMCs OxyAs DNAcs DNAas OxyMCs OxyAs OxyMC |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 15 | 7,604 | 7,620 | 238 | 254 | DES-005407 | ATTCctttacACcacAC | ASO-005407 | OxyAs OxyTs OxyTs OxyMCs DNAcs DNAts DNAts DNAas DNAcs OxyAs OxyMCs OxyMCs DNAcs DNAas DNAcs OxyAs OxyMC |
| 15 | 7,604 | 7,620 | 238 | 254 | DES-005408 | ATtCcttacAcCAcAC | ASO-005408 | OxyAs OxyTs DNAts OxyMCs DNAcs DNAts DNAts DNAas DNAcs OxyAs DNAcs OxyMCs OxyAs OxyMCs OxyAs OxyMC |
| 15 | 7,604 | 7,620 | 238 | 254 | DES-005409 | ATtCcttacAccACAC | ASO-005409 | OxyAs OxyTs DNAts OxyMCs DNAcs DNAts DNAts DNAas DNAcs OxyAs DNAcs DNAcs OxyAs OxyMCs OxyAs OxyMC |
| 15 | 7,604 | 7,620 | 238 | 254 | DES-005410 | ATtCcttacAccaCAC | ASO-005410 | OxyAs OxyTs DNAts OxyMCs DNAcs DNAts DNAts DNAas DNAcs OxyAs DNAcs DNAcs DNAas OxyMCs OxyAs OxyMC |
| 15 | 7,604 | 7,620 | 238 | 254 | DES-005411 | AtTCcttacAccaCAC | ASO-005411 | OxyAs DNAts OxyMCs DNAcs DNAts DNAts DNAas DNAcs OxyAs DNAcs DNAcs DNAas OxyMCs OxyAs OxyMC |
| 15 | 7,604 | 7,620 | 238 | 254 | DES-005412 | AttccttacaCCAcAC | ASO-005412 | OxyAs DNAts DNAts OxyMCs DNAcs DNAts DNAts DNAas DNAcs DNAcs DNAcs OxyMCs OxyAs DNAcs OxyAs OxyMC |
| 15 | 7,604 | 7,620 | 238 | 254 | DES-005413 | ATtCcttacaCCacAC | ASO-005413 | OxyAs OxyTs DNAts OxyMCs DNAcs DNAts DNAts DNAas DNAcs DNAcs DNAcs OxyMCs OxyMCs DNAcs OxyAs OxyMC |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 15 | 7,604 | 7,620 | 238 | 254 | DES-005414 | ATtcCtttacaCCacAC | ASO-005414 | OxyAs OxyTs DNAts DNAcs OxyMCs DNAts DNAcs OxyMCs DNAts DNAts DNAas DNAcs DNAas OxyMCs OxyMCs DNAas DNAcs OxyAs OxyMC |
| 15 | 7,604 | 7,620 | 238 | 254 | DES-005415 | AttcCtttacaCCacAC | ASO-005415 | OxyAs DNAts DNAts DNAcs OxyMCs DNAts DNAcs OxyMCs DNAts DNAts DNAas DNAcs DNAas OxyMCs OxyMCs DNAas DNAcs OxyAs OxyMC |
| 15 | 7,604 | 7,620 | 238 | 254 | DES-005416 | AttcCtttacaCCacAC | ASO-005416 | OxyAs DNAts DNAts DNAcs OxyMCs DNAts DNAcs OxyMCs DNAts DNAts DNAas DNAcs DNAas OxyMCs OxyMCs DNAas DNAcs OxyAs OxyMC |
| 15 | 7,604 | 7,620 | 238 | 254 | DES-005417 | ATtcCtttacaCcACAC | ASO-005417 | OxyAs OxyTs DNAts DNAcs OxyMCs DNAts DNAcs OxyMCs DNAts DNAts DNAas DNAcs DNAcs OxyAs OxyMCs DNAas DNAcs OxyAs OxyMC |
| 15 | 7,604 | 7,620 | 238 | 254 | DES-005418 | AttcCtttacaCcACAC | ASO-005418 | OxyAs DNAts DNAts DNAcs OxyMCs DNAts DNAcs OxyMCs DNAts DNAts DNAas DNAcs DNAcs OxyAs OxyMCs DNAas DNAcs OxyAs OxyMC |
| 15 | 7,604 | 7,620 | 238 | 254 | DES-005419 | AttcCtttacaCcACAC | ASO-005419 | OxyAs DNAts DNAts DNAcs OxyMCs DNAts DNAcs OxyMCs DNAts DNAts DNAas DNAcs DNAcs OxyAs OxyMCs DNAas DNAcs OxyAs OxyMC |
| 15 | 7,604 | 7,620 | 238 | 254 | DES-005420 | ATTCctttacaCcACAC | ASO-005420 | OxyAs OxyTs OxyTs OxyMCs DNAts DNAcs OxyMCs DNAts DNAts DNAas DNAcs DNAcs OxyAs OxyMCs DNAas DNAcs OxyAs OxyMC |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 15 | 7,604 | 7,620 | 238 | 254 | DES-005421 | ATTcCtttacaCcAcAC | ASO-005421 | OxyAs OxyTs DNAcs OxyMCs DNAts DNAts DNAas DNAcs DNAts OxyMCs DNAts DNAas OxyAs DNAcs DNAas OxyAs OxyMC |
| 15 | 7,604 | 7,620 | 238 | 254 | DES-005422 | AttCCtttacaCcAcAC | ASO-005422 | OxyAs DNAts DNAts OxyMCs OxyMCs DNAts DNAts DNAas DNAcs DNAts OxyMCs DNAts DNAas OxyAs DNAcs DNAas OxyAs OxyMC |
| 15 | 7,604 | 7,620 | 238 | 254 | DES-005423 | ATtcCtttacaCcaCAC | ASO-005423 | OxyAs OxyTs DNAts DNAcs DNAts DNAts DNAas DNAcs DNAts OxyMCs DNAts DNAas OxyAs DNAcs DNAas OxyAs OxyMC |
| 15 | 7,604 | 7,620 | 238 | 254 | DES-005424 | AttcCtttacaCcaCAC | ASO-005424 | OxyAs DNAts DNAts OxyMCs DNAts DNAts DNAas DNAcs DNAts OxyMCs DNAts DNAas OxyAs DNAcs DNAas OxyAs OxyMC |
| 15 | 7,604 | 7,620 | 238 | 254 | DES-005425 | AttcCtttacaCcaCAC | ASO-005425 | OxyAs DNAts DNAts DNAcs OxyMCs DNAts DNAts DNAas DNAcs DNAts OxyMCs DNAts DNAas OxyAs DNAcs DNAas OxyAs OxyMC |
| 15 | 7,604 | 7,620 | 238 | 254 | DES-005426 | ATTCctttacaCcacAC | ASO-005426 | OxyAs OxyTs OxyTs DNAcs DNAts DNAts DNAas DNAcs DNAts OxyMCs DNAts DNAas OxyAs DNAcs DNAas OxyAs OxyMC |
| 15 | 7,604 | 7,620 | 238 | 254 | DES-005427 | ATTcCtttacaCcacAC | ASO-005427 | OxyAs OxyTs OxyTs DNAcs OxyMCs DNAts DNAts DNAas DNAcs DNAts OxyMCs DNAts DNAas OxyAs DNAcs DNAas OxyAs OxyMC |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 15 | 7,604 | 7,620 | 238 | 254 | DES-005428 | AttCCtttacaCcacAC | ASO-005428 | OxyAs DNAts DNAts OxyMCs OxyMCs DNAts DNAts DNAts DNAas DNAcs DNAas OxyMCs DNAas DNAcs DNAas OxyAs OxyMC |
| 15 | 7,604 | 7,620 | 238 | 254 | DES-005429 | ATTcCtttacacCAcAC | ASO-005429 | OxyAs OxyTs OxyTs DNAcs OxyMCs DNAts DNAts DNAts DNAas DNAcs DNAas OxyMCs OxyAs DNAcs OxyAs OxyMC |
| 15 | 7,604 | 7,620 | 238 | 254 | DES-005430 | ATTccTttacacCAcAC | ASO-005430 | OxyAs OxyTs OxyTs DNAcs OxyTs DNAts DNAts DNAts DNAas DNAcs DNAas OxyMCs OxyAs DNAcs OxyAs OxyMC |
| 15 | 7,604 | 7,620 | 238 | 254 | DES-005431 | ATtCcTttacacCAcAC | ASO-005431 | OxyAs OxyTs DNAts OxyMCs DNAcs OxyTs DNAts DNAts DNAas DNAcs DNAas OxyMCs OxyAs DNAcs OxyAs OxyMC |
| 15 | 7,604 | 7,620 | 238 | 254 | DES-005432 | ATtCctttacacCAcAC | ASO-005432 | OxyAs OxyTs DNAts OxyMCs DNAcs DNAts DNAts DNAts DNAas DNAcs DNAas OxyMCs OxyAs DNAcs OxyAs OxyMC |
| 15 | 7,604 | 7,620 | 238 | 254 | DES-005433 | ATtCctttacacCAcAC | ASO-005433 | OxyAs OxyTs DNAts OxyMCs DNAcs DNAts DNAts DNAts DNAas DNAcs DNAas OxyMCs OxyAs DNAcs OxyAs OxyMC |
| 15 | 7,604 | 7,620 | 238 | 254 | DES-005434 | ATtccTttacacCAcAC | ASO-005434 | OxyAs OxyTs DNAts DNAcs DNAcs OxyTs DNAts DNAts DNAas DNAcs DNAas OxyMCs OxyAs DNAcs OxyAs OxyMC |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 15 | 7,604 | 7,620 | 238 | 254 | DES-005435 | AtTCctttacacCAcCAC | ASO-005435 | OxyAs DNAts OxyTs OxyMCs DNAcs DNAts DNAts DNAas DNAcs DNAts DNAcs OxyMCs OxyMCs DNAcs OxyAs DNAcs OxyMC |
| 15 | 7,604 | 7,620 | 238 | 254 | DES-005436 | AtTcCTttacacCAcCAC | ASO-005436 | OxyAs DNAts OxyTs DNAcs OxyMCs OxyTs DNAts DNAas DNAcs DNAts DNAcs OxyMCs OxyAs DNAcs OxyAs OxyMC |
| 15 | 7,604 | 7,620 | 238 | 254 | DES-005437 | AttcCTttacacCaCAC | ASO-005437 | OxyAs DNAts DNAcs OxyMCs OxyTs DNAts DNAas DNAcs DNAts DNAcs OxyMCs DNAcs OxyAs DNAcs OxyAs OxyMC |
| 15 | 7,604 | 7,620 | 238 | 254 | DES-005438 | ATtCctttacacCaCAC | ASO-005438 | OxyAs OxyTs DNAts OxyMCs DNAcs DNAts DNAts DNAas DNAcs DNAts DNAcs OxyMCs DNAcs OxyAs DNAcs OxyMC |
| 15 | 7,604 | 7,620 | 238 | 254 | DES-005439 | ATtcCtttacacCaCAC | ASO-005439 | OxyAs OxyTs DNAts DNAcs OxyMCs DNAts DNAts DNAas DNAcs DNAts DNAcs OxyMCs DNAcs OxyAs DNAcs OxyMC |
| 15 | 7,604 | 7,620 | 238 | 254 | DES-005440 | ATtccTttacacCaCAC | ASO-005440 | OxyAs OxyTs DNAts DNAcs DNAcs OxyTs DNAts DNAas DNAcs DNAts DNAcs OxyMCs DNAcs OxyAs OxyMCs OxyMC |
| 15 | 7,604 | 7,620 | 238 | 254 | DES-005441 | ATtcctttacacCaCAC | ASO-005441 | OxyAs OxyTs DNAcs DNAcs DNAts DNAts DNAts DNAas DNAcs DNAts DNAcs OxyMCs DNAas OxyMCs OxyAs OxyMC |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 15 | 7,604 | 7,620 | 238 | 254 | DES-005442 | AttCcTttacacCaCAC | ASO-005442 | OxyAs DNAts DNAts OxyMCs DNAcs OxyTs DNAts DNAts DNAas DNAcs DNAas OxyMCs DNAas OxyMCs OxyAs OxyMC |
| 15 | 7,604 | 7,620 | 238 | 254 | DES-005443 | AttcCTttacacCaCAC | ASO-005443 | OxyAs DNAts DNAts OxyMCs DNAcs OxyTs DNAts DNAts DNAas DNAcs DNAas OxyMCs DNAas OxyMCs OxyAs OxyMC |
| 15 | 7,604 | 7,620 | 238 | 254 | DES-005444 | ATTCcTttacacCacAC | ASO-005444 | OxyAs OxyTs OxyTs OxyMCs DNAcs OxyTs DNAts DNAts DNAas DNAcs DNAas OxyMCs DNAas DNAcs OxyAs OxyMC |
| 15 | 7,604 | 7,620 | 238 | 254 | DES-005445 | ATTCctttacacCacAC | ASO-005445 | OxyAs OxyTs OxyTs DNAcs DNAcs OxyTs DNAts DNAts DNAas DNAcs DNAas OxyMCs DNAas DNAcs OxyAs OxyMC |
| 15 | 7,604 | 7,620 | 238 | 254 | DES-005446 | ATTcCtttacacCacAC | ASO-005446 | OxyAs OxyTs OxyTs DNAcs OxyMCs OxyTs DNAts DNAts DNAas DNAcs DNAas OxyMCs DNAas DNAcs OxyAs OxyMC |
| 15 | 7,604 | 7,620 | 238 | 254 | DES-005447 | ATtCCtttacacCacAC | ASO-005447 | OxyAs OxyTs DNAts OxyMCs OxyMCs OxyTs DNAts DNAts DNAas DNAcs DNAas OxyMCs DNAas DNAcs OxyAs OxyMC |
| 15 | 7,604 | 7,620 | 238 | 254 | DES-005448 | ATtcCTttacacCacAC | ASO-005448 | OxyAs OxyTs DNAts DNAcs OxyMCs OxyTs DNAts DNAts DNAas DNAcs DNAas OxyMCs DNAas DNAcs OxyAs OxyMC |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 15 | 7,604 | 7,620 | 238 | 254 | DES-005449 | AttCCTttacacCacAC | ASO-005449 | OxyAs DNAts DNAts OxyMCs OxyMCs OxyTs DNAts DNAts DNAas DNAcs DNAas OxyMCs OxyMCs DNAas DNAcs OxyAs OxyMC |
| 15 | 7,604 | 7,620 | 238 | 254 | DES-005450 | AttCCtttacaCCacAC | ASO-005450 | OxyAs DNAts DNAts OxyMCs OxyMCs DNAts DNAts DNAas DNAcs DNAas OxyMCs OxyMCs DNAas DNAcs OxyAs OxyMC |
| 15 | 7,604 | 7,620 | 238 | 254 | DES-005451 | ATTCctttacaccACAC | ASO-005451 | OxyAs OxyTs OxyTs OxyMCs OxyMCs DNAcs DNAas DNAcs DNAas DNAcs OxyAs OxyMCs OxyAs OxyMC |
| 15 | 7,604 | 7,620 | 238 | 254 | DES-005452 | ATTccttacaccACAC | ASO-005452 | OxyAs OxyTs DNAts OxyMCs OxyMCs DNAcs DNAts DNAas DNAcs DNAas DNAcs OxyAs OxyMCs OxyAs OxyMC |
| 15 | 7,604 | 7,620 | 238 | 254 | DES-005453 | AtTCctttacaccACAC | ASO-005453 | OxyAs OxyTs DNAts OxyMCs OxyMCs OxyTs DNAts DNAts DNAas DNAcs DNAas DNAcs OxyAs OxyMCs OxyAs OxyMC |
| 15 | 7,604 | 7,620 | 238 | 254 | DES-005454 | ATtCctttacaccACAC | ASO-005454 | OxyAs OxyTs DNAts OxyMCs DNAts DNAcs DNAas DNAcs DNAas DNAcs OxyAs OxyMCs OxyAs OxyMC |
| 15 | 7,604 | 7,620 | 238 | 254 | DES-005455 | ATtCctttacaccACAC | ASO-005455 | OxyAs OxyTs DNAts DNAts OxyMCs DNAcs DNAcs DNAas DNAcs DNAas DNAcs OxyAs OxyMCs OxyAs OxyMC |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 15 | 7,604 | 7,620 | 238 | 254 | DES-005456 | ATtccttacaccACAC | ASO-005456 | OxyAs OxyTs DNAts DNAcs DNAcs DNAts DNAcs DNAts DNAts DNAas DNAcs DNAcs DNAcs OxyAs OxyMCs OxyAs OxyMC |
| 15 | 7,604 | 7,620 | 238 | 254 | DES-005457 | AtTCcTttacaccACAC | ASO-005457 | OxyAs DNAts OxyTs OxyMCs DNAcs OxyTs DNAts DNAts DNAas DNAcs DNAcs DNAcs OxyAs OxyMCs OxyAs OxyMC |
| 15 | 7,604 | 7,620 | 238 | 254 | DES-005458 | AtTCcttacaccACAC | ASO-005458 | OxyAs DNAts OxyTs OxyMCs DNAcs DNAts DNAts DNAts DNAas DNAcs DNAcs DNAcs OxyAs OxyMCs OxyAs OxyMC |
| 15 | 7,604 | 7,620 | 238 | 254 | DES-005459 | AtTcctttacaccACAC | ASO-005459 | OxyAs DNAts OxyTs DNAcs OxyMCs DNAts DNAts DNAts DNAas DNAcs DNAcs DNAcs OxyAs OxyMCs OxyAs OxyMC |
| 15 | 7,604 | 7,620 | 238 | 254 | DES-005460 | AttCCtttacaccACAC | ASO-005460 | OxyAs DNAts DNAts OxyMCs OxyMCs DNAts DNAts DNAts DNAas DNAcs DNAcs DNAcs OxyAs OxyMCs OxyAs OxyMC |
| 15 | 7,604 | 7,620 | 238 | 254 | DES-005461 | AttCcttacaccACAC | ASO-005461 | OxyAs DNAts DNAts OxyMCs DNAcs DNAts DNAts DNAts DNAas DNAcs DNAcs DNAcs OxyAs OxyMCs OxyAs OxyMC |
| 15 | 7,604 | 7,620 | 238 | 254 | DES-005462 | AttcCTttacaccACAC | ASO-005462 | OxyAs DNAts DNAts DNAcs OxyMCs OxyTs DNAts DNAts DNAas DNAcs DNAcs DNAcs OxyAs OxyMCs OxyAs OxyMC |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 14 | 7,604 | 7,621 | 238 | 255 | DES-005463 | AAttcctttacaCCAcAC | ASO-005463 | OxyAs OxyAs DNAts DNAts DNAcs DNAts DNAts DNAts DNAas DNAcs DNAcs OxyMCs OxyMCs DNAcs OxyAs DNAcs OxyAs OxyMC |
| 14 | 7,604 | 7,621 | 238 | 255 | DES-005464 | AattcctttacaCCAcAC | ASO-005464 | OxyAas DNAas DNAts DNAts DNAts DNAts DNAts DNAts DNAas DNAcs DNAcs OxyMCs OxyMCs DNAcs OxyAs DNAcs OxyAs OxyMC |
| 14 | 7,604 | 7,621 | 238 | 255 | DES-005465 | AAttCctttacaCCacAC | ASO-005465 | OxyAs OxyAs DNAts DNAts OxyMCs DNAcs DNAts DNAts DNAas DNAcs DNAcs OxyMCs OxyMCs DNAcs OxyAs DNAcs OxyAs OxyMC |
| 14 | 7,604 | 7,621 | 238 | 255 | DES-005466 | AaTtCctttacaCCacAC | ASO-005466 | OxyAs DNAas OxyTs DNAts OxyMCs DNAcs DNAts DNAts DNAas DNAcs DNAcs OxyMCs OxyMCs DNAas DNAcs OxyAs DNAts OxyMC |
| 14 | 7,604 | 7,621 | 238 | 255 | DES-005467 | AaTtcctttacaCCacAC | ASO-005467 | OxyAs DNAas OxyTs DNAts DNAcs DNAcs DNAts DNAts DNAas DNAcs DNAcs OxyMCs OxyMCs DNAcs OxyAs DNAcs OxyAs OxyMC |
| 14 | 7,604 | 7,621 | 238 | 255 | DES-005468 | AattCctttacaCCacAC | ASO-005468 | OxyAs DNAas DNAts DNAts OxyMCs DNAcs DNAts DNAts DNAas DNAcs DNAcs OxyMCs OxyMCs DNAcs OxyAs DNAcs OxyAs OxyMC |
| 14 | 7,604 | 7,621 | 238 | 255 | DES-005469 | AATtcctttacaCcACAC | ASO-005469 | OxyAs OxyAs OxyTs DNAts DNAcs DNAcs DNAts DNAts DNAas DNAcs DNAcs OxyMCs DNAcs OxyAs OxyMCs OxyMCs OxyAs OxyMC |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 14 | 7,604 | 7,621 | 238 | 255 | DES-005470 | AAttCctttacaCcACAC | ASO-005470 | OxyAs OxyAs DNAts DNAts OxyMCs DNAcs DNAts DNAts DNAas DNAas DNAcs DNAcs OxyMCs DNAcs OxyAs OxyMCs OxyAs OxyMC |
| 14 | 7,604 | 7,621 | 238 | 255 | DES-005471 | AAttcctttacaCcACAC | ASO-005471 | OxyAs OxyAs DNAts DNAts OxyMCs DNAcs DNAts DNAts DNAas DNAas DNAcs DNAcs OxyMCs DNAcs OxyAs OxyMCs OxyAs OxyMC |
| 14 | 7,604 | 7,621 | 238 | 255 | DES-005472 | AaTtCctttacaCcACAC | ASO-005472 | OxyAs DNAas OxyTs DNAts OxyMCs DNAcs DNAts DNAts DNAas DNAas DNAcs DNAcs OxyMCs DNAcs OxyAs OxyMCs OxyAs OxyMC |
| 14 | 7,604 | 7,621 | 238 | 255 | DES-005473 | AaTtcctttacaCcACAC | ASO-005473 | OxyAs DNAas OxyTs DNAts DNAts DNAcs DNAts DNAts DNAas DNAas DNAcs DNAcs OxyMCs DNAcs OxyAs OxyMCs OxyAs OxyMC |
| 14 | 7,604 | 7,621 | 238 | 255 | DES-005474 | AattCctttacaCcACAC | ASO-005474 | OxyAs DNAas OxyTs DNAts OxyMCs DNAcs DNAts DNAts DNAas DNAas DNAcs DNAcs OxyMCs DNAcs OxyAs OxyMCs OxyAs OxyMC |
| 14 | 7,604 | 7,621 | 238 | 255 | DES-005475 | AATtCctttacaCcAcAC | ASO-005475 | OxyAs OxyAs OxyTs DNAts OxyMCs DNAcs DNAts DNAts DNAas DNAas DNAcs DNAcs OxyMCs DNAcs OxyAs DNAcs OxyAs OxyMC |
| 14 | 7,604 | 7,621 | 238 | 255 | DES-005476 | AaTTCctttacaCcACAC | ASO-005476 | OxyAs DNAas OxyTs OxyTs OxyMCs DNAcs DNAts DNAts DNAas DNAas DNAcs DNAcs OxyMCs DNAcs OxyAs DNAcs OxyAs OxyMC |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 14 | 7,604 | 7,621 | 238 | 255 | DES-005477 | AATtcctttacaCcaCAC | ASO-005477 | OxyAs OxyAs OxyTs DNAts DNAcs DNAts DNAcs DNAts DNAts DNAts DNAas DNAcs DNAas OxyMCs DNAas OxyAs OxyMC |
| 14 | 7,604 | 7,621 | 238 | 255 | DES-005478 | AAttCctttacaCcaCAC | ASO-005478 | OxyAs OxyAs DNAts OxyMCs DNAts OxyTs DNAts DNAts DNAts DNAas DNAcs DNAas OxyMCs DNAas OxyAs OxyMC |
| 14 | 7,604 | 7,621 | 238 | 255 | DES-005479 | AaTtCctttacaCcaCAC | ASO-005479 | OxyAs DNAas OxyTs DNAts OxyMCs DNAts DNAcs DNAts DNAts DNAts DNAas DNAcs DNAas OxyMCs DNAas OxyAs OxyMC |
| 14 | 7,604 | 7,621 | 238 | 255 | DES-005480 | AattCctttacaCcaCAC | ASO-005480 | OxyAs DNAas DNAts OxyMCs DNAts OxyTs DNAts DNAcs DNAts DNAts DNAts DNAas DNAcs DNAas OxyMCs DNAas OxyAs OxyMC |
| 14 | 7,604 | 7,621 | 238 | 255 | DES-005481 | AaTTCctttacaCcacAC | ASO-005481 | OxyAs DNAas OxyTs OxyTs OxyMCs DNAts DNAcs DNAts DNAts DNAts DNAas DNAcs DNAas OxyMCs DNAcs DNAas OxyAs OxyMC |
| 14 | 7,604 | 7,621 | 238 | 255 | DES-005482 | AATtCctttacacAcAC | ASO-005482 | OxyAs OxyAs OxyTs DNAts OxyMCs DNAts DNAcs DNAts DNAts DNAts DNAas DNAcs DNAas DNAcs OxyAs DNAcs OxyAs OxyMC |
| 14 | 7,604 | 7,621 | 238 | 255 | DES-005483 | AATtcCtttacacACaC | ASO-005483 | OxyAs OxyAs OxyTs DNAts DNAcs OxyMCs DNAts DNAts DNAts DNAts DNAas DNAcs DNAas OxyMCs OxyAs DNAcs OxyAs OxyMC |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 14 | 7,604 | 7,621 | 238 | 255 | DES-005484 | AAttCctttacacCAcAC | ASO-005484 | OxyAs OxyAs DNAts OxyTs OxyMCs DNAcs DNAts DNAts DNAas DNAas DNAcs DNAcs OxyMCs OxyAs DNAcs OxyAs OxyMC |
| 14 | 7,604 | 7,621 | 238 | 255 | DES-005485 | AAttCctttacacCAcAC | ASO-005485 | OxyAs OxyAs DNAts OxyTs DNAcs OxyMCs DNAts DNAts DNAas DNAas DNAcs DNAcs OxyMCs OxyAs DNAcs OxyAs OxyMC |
| 14 | 7,604 | 7,621 | 238 | 255 | DES-005486 | AAttCctttacacCAcAC | ASO-005486 | OxyAs OxyAs DNAts DNAts DNAcs OxyMCs DNAts DNAts DNAas DNAas DNAcs DNAcs OxyMCs OxyAs DNAcs OxyAs OxyMC |
| 14 | 7,604 | 7,621 | 238 | 255 | DES-005487 | AAttCctttacacCAcAC | ASO-005487 | OxyAs OxyAs DNAts DNAts OxyTs OxyMCs DNAts DNAts DNAas DNAas DNAcs DNAcs OxyMCs OxyAs DNAcs OxyAs OxyMC |
| 14 | 7,604 | 7,621 | 238 | 255 | DES-005488 | AaTTCctttacacCAcAC | ASO-005488 | OxyAs OxyAs DNAts OxyTs OxyTs DNAcs DNAts DNAts DNAas DNAas DNAcs DNAcs OxyMCs OxyAs DNAcs OxyAs OxyMC |
| 14 | 7,604 | 7,621 | 238 | 255 | DES-005489 | AaTTCctttacacCAcAC | ASO-005489 | OxyAs DNAts OxyTs OxyTs DNAcs OxyMCs DNAts DNAts DNAas DNAas DNAcs DNAcs OxyMCs OxyAs DNAcs OxyAs OxyMC |
| 14 | 7,604 | 7,621 | 238 | 255 | DES-005490 | AaTTCctttacacCAcAC | ASO-005490 | OxyAs DNAas OxyTs OxyTs DNAcs DNAts DNAts DNAas DNAas DNAcs DNAcs OxyMCs OxyAs DNAcs OxyAs OxyMC |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 14 | 7,604 | 7,621 | 238 | 255 | DES-005491 | AaTtCctttacacCaCAC | ASO-005491 | OxyAs DNAas OxyAs DNAts DNAcs DNAcs OxyMCs DNAts DNAts DNAts DNAas DNAas DNAcs DNAas DNAcs OxyAs DNAcs OxyAs OxyMC |
| 14 | 7,604 | 7,621 | 238 | 255 | DES-005492 | AatTCctttacacCaCAC | ASO-005492 | OxyAs DNAas DNAts OxyTs OxyMCs DNAcs OxyMCs DNAts DNAts DNAts DNAas DNAas DNAcs DNAas DNAcs OxyAs DNAcs OxyAs OxyMC |
| 14 | 7,604 | 7,621 | 238 | 255 | DES-005493 | AaTcCctttacacCaCAC | ASO-005493 | OxyAs DNAas DNAts OxyCs DNAts DNAcs OxyMCs DNAts DNAts DNAts DNAas DNAas DNAcs DNAas DNAcs OxyAs DNAcs OxyAs OxyMC |
| 14 | 7,604 | 7,621 | 238 | 255 | DES-005494 | AATtCctttacacCaCAC | ASO-005494 | OxyAs OxyAs OxyTs DNAts OxyCs DNAcs OxyMCs DNAts DNAts DNAts DNAas DNAas DNAcs DNAas DNAcs OxyAs DNAcs OxyAs OxyMC |
| 14 | 7,604 | 7,621 | 238 | 255 | DES-005495 | AATtccttacacCaCAC | ASO-005495 | OxyAs OxyAs OxyTs DNAts DNAcs DNAcs OxyMCs DNAts DNAts DNAts DNAas DNAas DNAcs DNAas DNAcs OxyAs DNAcs OxyAs OxyMC |
| 14 | 7,604 | 7,621 | 238 | 255 | DES-005496 | AAttCctttacacCaCAC | ASO-005496 | OxyAs OxyAs DNAts DNAts OxyMCs DNAcs OxyMCs DNAts DNAts DNAts DNAas DNAas DNAcs DNAas DNAcs OxyAs DNAcs OxyAs OxyMC |
| 14 | 7,604 | 7,621 | 238 | 255 | DES-005497 | AAttcCtttacacCaCAC | ASO-005497 | OxyAs OxyAs DNAts DNAts DNAcs OxyMCs OxyMCs DNAts DNAts DNAts DNAas DNAas DNAcs DNAas DNAcs OxyAs DNAcs OxyAs OxyMC |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 14 | 7,604 | 7,621 | 238 | 255 | DES-005498 | AaTtCctttacacCaCAC | ASO-005498 | OxyAs DNAas OxyTs DNAts OxyMCs DNAcs DNAts DNAts DNAas DNAas DNAcs DNAts DNAcs OxyMCs DNAas OxyMCs OxyAs OxyMC |
| 14 | 7,604 | 7,621 | 238 | 255 | DES-005499 | AaTtCctttacacCaCAC | ASO-005499 | OxyAs DNAas OxyTs DNAts DNAcs DNAcs DNAts DNAts DNAas DNAas DNAcs DNAts DNAcs OxyMCs DNAas OxyMCs OxyAs OxyMC |
| 14 | 7,604 | 7,621 | 238 | 255 | DES-005500 | AaTTCctttacacCaCAC | ASO-005500 | OxyAs DNAas DNAts OxyTs OxyMCs DNAcs DNAts DNAts DNAas DNAas DNAcs DNAts DNAcs OxyMCs DNAas OxyMCs OxyAs OxyMC |
| 14 | 7,604 | 7,621 | 238 | 255 | DES-005501 | AatTcCtttacacCaCAC | ASO-005501 | OxyAs DNAas DNAts OxyTs DNAcs OxyMCs DNAts DNAts DNAas DNAas DNAcs DNAts DNAcs OxyMCs DNAas OxyMCs OxyAs OxyMC |
| 14 | 7,604 | 7,621 | 238 | 255 | DES-005502 | AattCctttacacCaCAC | ASO-005502 | OxyAs DNAas DNAts DNAts OxyMCs DNAcs DNAts DNAts DNAas DNAas DNAcs DNAts DNAcs OxyMCs DNAas OxyMCs OxyAs OxyMC |
| 14 | 7,604 | 7,621 | 238 | 255 | DES-005503 | AattcCtttacacCaCAC | ASO-005503 | OxyAs DNAas DNAts DNAts DNAcs OxyMCs DNAts DNAts DNAas DNAas DNAcs DNAts DNAcs OxyMCs DNAas OxyMCs OxyAs OxyMC |
| 14 | 7,604 | 7,621 | 238 | 255 | DES-005504 | AATTcCtttacacCacAC | ASO-005504 | OxyAs OxyAs OxyTs OxyTs DNAcs OxyMCs DNAts DNAts DNAas DNAas DNAcs DNAts DNAcs OxyMCs DNAas OxyAs OxyMC |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 14 | 7,604 | 7,621 | 238 | 255 | DES-005505 | AAttCCtttacacCacAC | ASO-005505 | OxyAs OxyAs DNAts DNAts OxyMCs OxyMCs DNAts DNAts DNAas DNAas DNAas OxyMCs DNAas DNAcs OxyAs OxyMC |
| 14 | 7,604 | 7,621 | 238 | 255 | DES-005506 | AaTtCCtttacacCacAC | ASO-005506 | OxyAs DNAas OxyTs DNAts OxyMCs OxyMCs DNAts DNAts DNAas DNAas DNAas OxyMCs DNAas DNAcs OxyAs OxyMC |
| 14 | 7,604 | 7,621 | 238 | 255 | DES-005507 | AatTcCtttacacCacAC | ASO-005507 | OxyAs DNAas DNAas OxyTs OxyMCs OxyMCs DNAts DNAts DNAas DNAas DNAas OxyMCs DNAas DNAcs OxyAs OxyMC |
| 14 | 7,604 | 7,621 | 238 | 255 | DES-005508 | AattCCtttacacCacAC | ASO-005508 | OxyAs DNAas DNAas DNAts OxyMCs OxyMCs DNAts DNAts DNAas DNAas DNAas OxyMCs DNAas DNAcs OxyAs OxyMC |
| 14 | 7,604 | 7,621 | 238 | 255 | DES-005509 | AATTcctttacacCacAC | ASO-005509 | OxyAs OxyAs OxyTs OxyTs DNAcs DNAcs DNAts DNAts DNAas DNAas DNAas OxyMCs DNAas DNAcs OxyAs OxyMC |
| 14 | 7,604 | 7,621 | 238 | 255 | DES-005510 | AATtCctttacaccACAC | ASO-005510 | OxyAs OxyAs OxyTs DNAts OxyMCs DNAcs DNAts DNAts DNAas DNAas DNAas DNAcs DNAas DNAcs OxyAs OxyMC |
| 14 | 7,604 | 7,621 | 238 | 255 | DES-005511 | AATtcCtttacaccACAC | ASO-005511 | OxyAs OxyAs OxyTs DNAts DNAcs OxyMCs DNAts DNAts DNAas DNAas DNAas DNAcs DNAas DNAcs OxyAs OxyMC |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 14 | 7,604 | 7,621 | 238 | 255 | DES-005512 | AATtcctttacaccACAC | ASO-005512 | OxyAs OxyAs OxyTs DNAts DNAcs DNAcs DNAts DNAts DNAts DNAas DNAcs DNAcs DNAcs OxyMCs OxyMCs OxyAs OxyMC |
| 14 | 7,604 | 7,621 | 238 | 255 | DES-005513 | AAtTCcTtttacaccACAC | ASO-005513 | OxyAs OxyAs DNAts OxyTs OxyMCs DNAcs OxyTs DNAts DNAts DNAas DNAcs DNAcs DNAcs OxyMCs OxyAs OxyAs OxyMC |
| 14 | 7,604 | 7,621 | 238 | 255 | DES-005514 | AAtTCctttacaccACAC | ASO-005514 | OxyAs OxyAs DNAts OxyTs OxyMCs DNAcs DNAts DNAts DNAts DNAas DNAcs DNAcs DNAcs OxyMCs OxyAs OxyAs OxyMC |
| 14 | 7,604 | 7,621 | 238 | 255 | DES-005515 | AAtTcCTttacaccACAC | ASO-005515 | OxyAs OxyAs DNAts OxyTs DNAcs OxyMCs OxyTs DNAts DNAts DNAas DNAcs DNAcs DNAcs OxyMCs OxyAs OxyAs OxyMC |
| 14 | 7,604 | 7,621 | 238 | 255 | DES-005516 | AAtTcctttacaccACAC | ASO-005516 | OxyAs OxyAs DNAts OxyTs DNAcs DNAcs DNAts DNAts DNAts DNAas DNAcs DNAcs DNAcs OxyMCs OxyAs OxyAs OxyMC |
| 14 | 7,604 | 7,621 | 238 | 255 | DES-005517 | AAttCcTttacaccACAC | ASO-005517 | OxyAs OxyAs DNAts DNAts OxyMCs DNAcs OxyTs DNAts DNAts DNAas DNAcs DNAcs DNAcs OxyMCs OxyAs OxyAs OxyMC |
| 14 | 7,604 | 7,621 | 238 | 255 | DES-005518 | AAttCctttacaccACAC | ASO-005518 | OxyAs OxyAs DNAts DNAts OxyMCs DNAcs DNAts DNAts DNAts DNAas DNAcs DNAcs DNAcs OxyMCs OxyAs OxyAs OxyMC |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 14 | 7,604 | 7,621 | 238 | 255 | DES-005519 | AAttcCTtttacaccACAC | ASO-005519 | OxyAs OxyAs DNAts DNAcs DNAts DNAcs OxyMCs OxyTs DNAts DNAts DNAas DNAcs DNAas DNAcs DNAts DNAcs OxyAs OxyMCs OxyAs OxyMC |
| 14 | 7,604 | 7,621 | 238 | 255 | DES-005520 | AAttcCtttacaccACAC | ASO-005520 | OxyAs OxyAs DNAts DNAcs DNAts DNAcs OxyMCs DNAts DNAts DNAas DNAcs DNAas DNAcs DNAts DNAcs OxyAs OxyMCs OxyAs OxyMC |
| 14 | 7,604 | 7,621 | 238 | 255 | DES-005521 | AAttccttttacaccACAC | ASO-005521 | OxyAs OxyAs DNAts DNAcs DNAts DNAcs DNAts DNAts DNAas DNAcs DNAas DNAcs DNAts DNAcs OxyAs OxyMCs OxyAs OxyMC |
| 14 | 7,604 | 7,621 | 238 | 255 | DES-005522 | AaTTCcttttacaccACAC | ASO-005522 | OxyAs DNAas OxyTs OxyTs OxyMCs DNAts DNAcs DNAts DNAas DNAcs DNAas DNAcs DNAts DNAcs OxyAs OxyMCs OxyAs OxyMC |
| 14 | 7,604 | 7,621 | 238 | 255 | DES-005523 | AaTTccttttacaccACAC | ASO-005523 | OxyAs DNAas OxyTs OxyTs DNAcs DNAts DNAcs DNAts DNAas DNAcs DNAas DNAcs DNAts DNAcs OxyAs OxyMCs OxyAs OxyMC |
| 14 | 7,604 | 7,621 | 238 | 255 | DES-005524 | AaTtCCttttacaccACAC | ASO-005524 | OxyAs DNAas OxyTs DNAts OxyMCs OxyMCs DNAts DNAts DNAas DNAcs DNAas DNAcs DNAts DNAcs OxyAs OxyMCs OxyAs OxyMC |
| 14 | 7,604 | 7,621 | 238 | 255 | DES-005525 | AaTtCcttttacaccACAC | ASO-005525 | OxyAs DNAas OxyTs DNAts OxyMCs DNAcs DNAts DNAts DNAas DNAcs DNAas DNAcs DNAts DNAcs OxyAs OxyMCs OxyAs OxyMC |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 14 | 7,604 | 7,621 | 238 | 255 | DES-005526 | AaTtcCtttacaccACAC | ASO-005526 | OxyAs DNAas OxyTs DNAts DNAcs OxyMCs DNAts DNAts DNAas DNAcs DNAcs OxyAs OxyMCs OxyAs OxyMC |
| 14 | 7,604 | 7,621 | 238 | 255 | DES-005527 | AaTtccTttacaccACAC | ASO-005527 | OxyAs DNAas OxyTs DNAts DNAcs DNAts DNAts DNAas DNAcs DNAcs OxyAs OxyMCs OxyAs OxyMC |
| 14 | 7,604 | 7,621 | 238 | 255 | DES-005528 | AatTCcTtttacaccACAC | ASO-005528 | OxyAs DNAas DNAts OxyTs OxyMCs DNAcs OxyTs DNAts DNAas DNAcs DNAcs OxyAs OxyMCs OxyAs OxyMC |
| 14 | 7,604 | 7,621 | 238 | 255 | DES-005529 | AatTCctttacaccACAC | ASO-005529 | OxyAs DNAas DNAts OxyTs OxyMCs DNAcs DNAts DNAts DNAas DNAcs DNAcs OxyAs OxyMCs OxyAs OxyMC |
| 14 | 7,604 | 7,621 | 238 | 255 | DES-005530 | AatTccTtttacaccACAC | ASO-005530 | OxyAs DNAas DNAts OxyTs DNAcs DNAcs OxyTs DNAts DNAts DNAas DNAcs DNAcs OxyAs OxyMCs OxyAs OxyMC |
| 14 | 7,604 | 7,621 | 238 | 255 | DES-005531 | AattCcTttacaccACAC | ASO-005531 | OxyAs DNAas DNAts DNAts OxyMCs DNAcs OxyTs DNAts DNAts DNAas DNAcs DNAcs OxyAs OxyMCs OxyAs OxyMC |
| 14 | 7,604 | 7,621 | 238 | 255 | DES-005532 | AattCctttacaccACAC | ASO-005532 | OxyAs DNAas DNAts DNAts OxyMCs DNAcs DNAts DNAts DNAas DNAcs DNAcs OxyAs OxyMCs OxyAs OxyMC |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 14 | 7,604 | 7,621 | 238 | 255 | DES-005533 | AattcCTtttacaccACAC | ASO-005533 | OxyAs DNAas DNAts DNAcs OxyMCs OxyTs DNAts DNAaas DNAas DNAcs DNAas OxyMCs OxyAs DNAts OxyMC |
| 14 | 7,604 | 7,621 | 238 | 255 | DES-005534 | AATtCctttacaccAcAC | ASO-005534 | OxyAs OxyAs OxyTs DNAts OxyMCs DNAts DNAts DNAaas DNAas DNAcs DNAas OxyAs DNAcs OxyAs OxyMC |
| 14 | 7,604 | 7,621 | 238 | 255 | DES-005535 | AAtTCCtttacaccAcAC | ASO-005535 | OxyAs OxyAs DNAts OxyTs OxyMCs OxyMCs DNAts DNAts DNAaas DNAas DNAcs DNAas OxyAs DNAcs OxyMC |
| 14 | 7,604 | 7,621 | 238 | 255 | DES-005536 | AAtTCctttacaccAcAC | ASO-005536 | OxyAs OxyAs DNAts DNAts OxyMCs DNAts DNAts DNAaas DNAas DNAcs DNAas OxyAs DNAcs OxyMC |
| 14 | 7,604 | 7,621 | 238 | 255 | DES-005537 | AAttCCTttacaccAcAC | ASO-005537 | OxyAs OxyAs DNAts DNAts OxyMCs OxyMCs OxyTs DNAts DNAaas DNAas DNAcs DNAas OxyAs DNAcs OxyMC |
| 14 | 7,604 | 7,621 | 238 | 255 | DES-005538 | AAttCCtttacaccAcAC | ASO-005538 | OxyAs OxyAs DNAts DNAts OxyMCs OxyMCs DNAts DNAts DNAaas DNAas DNAcs DNAas OxyAs DNAcs OxyMC |
| 14 | 7,604 | 7,621 | 238 | 255 | DES-005539 | AaTTCcTtttacaccAcAC | ASO-005539 | OxyAs DNAas OxyTs OxyTs OxyMCs DNAcs DNAts DNAts DNAaas DNAas DNAcs DNAas OxyAs DNAcs OxyMC |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 14 | 7,604 | 7,621 | 238 | 255 | DES-005540 | AaTtCctttacaccAcAC | ASO-005540 | OxyAs DNAas OxyAs OxyTs OxyMCs DNAcs DNAts DNAts DNAas DNAas DNAcs DNAas OxyAs DNAcs OxyMC |
| 14 | 7,604 | 7,621 | 238 | 255 | DES-005541 | AaTtCCtttacaccAcAC | ASO-005541 | OxyAs DNAas OxyAs OxyTs DNAcs OxyMCs OxyMCs DNAts DNAts DNAas DNAas DNAcs DNAas OxyAs DNAcs OxyMC |
| 14 | 7,604 | 7,621 | 238 | 255 | DES-005542 | AatTCctttacaccAcAC | ASO-005542 | OxyAs DNAas DNAts OxyAs OxyTs OxyMCs DNAcs DNAts DNAts DNAas DNAas DNAcs DNAas OxyAs DNAcs OxyMC |
| 14 | 7,604 | 7,621 | 238 | 255 | DES-005543 | AATTccttacaccAcAC | ASO-005543 | OxyAs OxyAs OxyTs OxyTs DNAcs DNAcs DNAts DNAts DNAas DNAas DNAcs DNAas OxyAs DNAcs OxyMC |
| 14 | 7,604 | 7,621 | 238 | 255 | DES-005544 | AATtccTttacaccAcAC | ASO-005544 | OxyAs OxyAs OxyTs DNAts DNAcs DNAcs OxyTs DNAts DNAas DNAas DNAcs DNAas OxyAs DNAcs OxyMC |
| 14 | 7,604 | 7,621 | 238 | 255 | DES-005545 | AATtcctTtacaccaCAC | ASO-005545 | OxyAs OxyAs OxyTs DNAts DNAcs DNAcs OxyMCs DNAts DNAas DNAas DNAcs DNAas OxyAs DNAcs OxyMC |
| 14 | 7,604 | 7,621 | 238 | 255 | DES-005546 | AATtCctttacaccaCAC | ASO-005546 | OxyAs OxyAs DNAts OxyTs DNAcs DNAcs OxyMCs DNAts DNAas DNAas DNAcs DNAas OxyAs DNAcs OxyMC |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 14 | 7,604 | 7,621 | 238 | 255 | DES-005547 | AATtcCtTtacaccaCAC | ASO-005547 | OxyAs OxyAs OxyTs DNAcs DNAts DNAcs OxyMCs DNAts OxyTs DNAts DNAas DNAcs DNAts DNAcs DNAts DNAcs OxyMCs OxyAs OxyMC |
| 14 | 7,604 | 7,621 | 238 | 255 | DES-005548 | AATtcCtttacaccaCAC | ASO-005548 | OxyAs OxyAs OxyTs DNAcs DNAts DNAcs OxyMCs DNAts DNAts DNAts DNAas DNAcs DNAts DNAcs DNAts DNAcs OxyMCs OxyAs OxyMC |
| 14 | 7,604 | 7,621 | 238 | 255 | DES-005549 | AATtcctttacaccaCAC | ASO-005549 | OxyAs OxyAs OxyTs DNAcs DNAts DNAcs DNAts DNAts DNAts DNAts DNAas DNAcs DNAts DNAcs DNAts DNAcs OxyMCs OxyAs OxyMC |
| 14 | 7,604 | 7,621 | 238 | 255 | DES-005550 | AAtTCcTttacaccaCAC | ASO-005550 | OxyAs OxyAs DNAts OxyTs OxyMCs DNAcs OxyTs DNAts DNAts DNAts DNAas DNAcs DNAts DNAcs DNAts DNAcs OxyMCs OxyAs OxyMC |
| 14 | 7,604 | 7,621 | 238 | 255 | DES-005551 | AAtTCcTtTacaccaCAC | ASO-005551 | OxyAs OxyAs DNAts OxyTs OxyMCs DNAcs OxyTs DNAts OxyTs DNAts DNAas DNAcs DNAts DNAcs DNAts DNAcs OxyMCs OxyAs OxyMC |
| 14 | 7,604 | 7,621 | 238 | 255 | DES-005552 | AAtTCcttTacaccaCAC | ASO-005552 | OxyAs OxyAs DNAts OxyTs OxyMCs DNAcs DNAts DNAts OxyTs DNAts DNAas DNAcs DNAts DNAcs DNAts DNAcs OxyMCs OxyAs OxyMC |
| 14 | 7,604 | 7,621 | 238 | 255 | DES-005553 | AAtTCcTttacaccaCAC | ASO-005553 | OxyAs OxyAs DNAts OxyTs OxyMCs DNAcs OxyTs DNAts DNAts DNAts DNAas DNAcs DNAts DNAcs DNAts DNAcs OxyMCs OxyAs OxyMC |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 14 | 7,604 | 7,621 | 238 | 255 | DES-005554 | AAtTcCtTtacaccaCAC | ASO-005554 | OxyAs OxyAs DNAts OxyTs DNAcs OxyMCs DNAts OxyTs DNAts DNAas DNAts DNAcs DNAcs DNAas OxyMCs OxyAs OxyMC |
| 14 | 7,604 | 7,621 | 238 | 255 | DES-005555 | AAtTcctttacaccaCAC | ASO-005555 | OxyAs OxyAs DNAts OxyTs DNAcs DNAcs DNAts DNAts DNAas DNAts DNAcs DNAcs DNAas OxyMCs OxyAs OxyMC |
| 14 | 7,604 | 7,621 | 238 | 255 | DES-005556 | AAttCcTTtacaccaCAC | ASO-005556 | OxyAs OxyAs DNAts DNAts OxyMCs DNAts OxyTs DNAts DNAas DNAts DNAcs DNAcs DNAas OxyMCs OxyAs OxyMC |
| 14 | 7,604 | 7,621 | 238 | 255 | DES-005557 | AAttCcTttacaccaCAC | ASO-005557 | OxyAs OxyAs DNAts DNAts OxyMCs DNAts OxyTs DNAts DNAas DNAts DNAcs DNAcs DNAas OxyMCs OxyAs OxyMC |
| 14 | 7,604 | 7,621 | 238 | 255 | DES-005558 | AAttCctTtacaccaCAC | ASO-005558 | OxyAs OxyAs DNAts DNAts DNAcs OxyMCs DNAts OxyTs DNAts DNAas DNAts DNAcs DNAcs DNAas OxyMCs OxyAs OxyMC |
| 14 | 7,604 | 7,621 | 238 | 255 | DES-005645 | Aattcctttacaccacac | ASO-005645 | OxyAs DNAas DNAts DNAcs DNAcs DNAts DNAts DNAts DNAas DNAcs DNAas DNAcs DNAcs DNAas DNAcs OxyAs DNAcs OxyMC |
| 14 | 7,604 | 7,621 | 238 | 255 | DES-005646 | AATtcctttaCACcacAC | ASO-005646 | OxyAs OxyAs OxyTs DNAts DNAcs DNAcs DNAts DNAts DNAas OxyMCs OxyAs OxyMCs OxyAs DNAcs DNAas DNAcs OxyAs OxyMC |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 14 | 7,604 | 7,621 | 238 | 255 | DES-005647 | AAttcctttaCACcacAC | ASO-005647 | OxyAs OxyAs DNAts DNAcs DNAts DNAts DNAts DNAts DNAas OxyMCs OxyAs DNAas DNAcs OxyAs OxyMC |
| 14 | 7,604 | 7,621 | 238 | 255 | DES-005648 | AaTtcctttaCACcacAC | ASO-005648 | OxyAs DNAas OxyTs DNAts DNAcs DNAts DNAts DNAts DNAts DNAas OxyMCs OxyAs DNAas DNAcs OxyAs OxyMC |
| 14 | 7,604 | 7,621 | 238 | 255 | DES-005649 | AattcctttaCAcCACAC | ASO-005649 | OxyAs OxyAs DNAts DNAcs DNAts DNAts DNAts DNAts DNAas OxyMCs OxyAs DNAcs OxyAs DNAcs OxyAs OxyMC |
| 14 | 7,604 | 7,621 | 238 | 255 | DES-005650 | AAttcctttacACCAcAC | ASO-005650 | OxyAs OxyAs DNAts DNAcs DNAts DNAts DNAts DNAts DNAas DNAcs OxyAs OxyMCs OxyMCs OxyAs DNAcs OxyAs OxyMC |
| 14 | 7,604 | 7,621 | 238 | 255 | DES-005651 | AATtcctttacACCAcAC | ASO-005651 | OxyAs OxyAs OxyTs DNAts DNAcs DNAts DNAts DNAts DNAas DNAcs OxyAs OxyMCs OxyMCs OxyAs DNAcs OxyAs OxyMC |
| 14 | 7,604 | 7,621 | 238 | 255 | DES-005652 | AAttcctttacACcaCAC | ASO-005652 | OxyAs OxyAs DNAts DNAcs DNAts DNAts DNAts DNAts DNAas DNAcs OxyAs OxyMCs DNAas DNAcs OxyAs OxyMC |
| 14 | 7,604 | 7,621 | 238 | 255 | DES-005653 | AaTtcctttacACcaCAC | ASO-005653 | OxyAs DNAas OxyTs DNAts DNAcs DNAts DNAts DNAts DNAts DNAas DNAcs OxyAs OxyMCs DNAas DNAcs OxyAs OxyMC |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 14 | 7,604 | 7,621 | 238 | 255 | DES-005654 | AATtccttacAcCaCAC | ASO-005654 | OxyAs OxyAs OxyTs DNAts DNAcs DNAts DNAts DNAts DNAas DNAcs DNAas DNAcs OxyAs DNAcs OxyAs OxyMC |
| 15 | 7,604 | 7,620 | 238 | 254 | DES-005749 | AttccttacaccACAC | ASO-005749 | OxyAs DNAts DNAts DNAcs DNAcs DNAts DNAts DNAas DNAas DNAcs DNAas DNAcs OxyAs OxyMCs OxyAs OxyMC |
| 15 | 7,604 | 7,620 | 238 | 254 | DES-005750 | ATtCcTttacaccAcAC | ASO-005750 | OxyAs OxyTs OxyTs OxyMCs DNAcs OxyTs DNAts DNAas DNAcs DNAas DNAcs OxyAs DNAcs OxyAs OxyMC |
| 15 | 7,604 | 7,620 | 238 | 254 | DES-005751 | ATTCcTttacaccAcAC | ASO-005751 | OxyAs OxyTs OxyTs OxyMCs DNAcs OxyTs DNAts DNAas DNAcs DNAas DNAcs OxyAs DNAcs OxyAs OxyMC |
| 15 | 7,604 | 7,620 | 238 | 254 | DES-005752 | ATTCCtttacaccAcAC | ASO-005752 | OxyAs OxyTs OxyTs OxyMCs OxyMCs DNAcs OxyTs DNAts DNAas DNAcs DNAas DNAcs OxyAs DNAcs OxyAs OxyMC |
| 15 | 7,604 | 7,620 | 238 | 254 | DES-005753 | ATtCCtttacaccAcAC | ASO-005753 | OxyAs OxyTs DNAts OxyMCs OxyMCs DNAcs OxyTs DNAts DNAas DNAcs DNAas DNAcs OxyAs DNAcs OxyAs OxyMC |
| 15 | 7,604 | 7,620 | 238 | 254 | DES-005754 | AtTCCtttacaccAcAC | ASO-005754 | OxyAs DNAts OxyTs OxyMCs OxyMCs DNAcs OxyTs DNAts DNAas DNAcs DNAas DNAcs OxyAs DNAcs OxyAs OxyMC |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 15 | 7,604 | 7,620 | 238 | 254 | DES-005755 | AtTCctttacaccAcAC | ASO-005755 | OxyAs DNAts OxyTs OxyMCs DNAcs DNAts DNAts DNAas DNAcs DNAts DNAas DNAcs DNAts DNAas DNAcs OxyAs DNAcs OxyMC |
| 15 | 7,604 | 7,620 | 238 | 254 | DES-005756 | AttCCTttacaccAcAC | ASO-005756 | OxyAs DNAts DNAts OxyMCs OxyTs DNAts DNAas DNAcs DNAts DNAas DNAcs DNAts DNAas DNAcs OxyAs DNAcs OxyMC |
| 15 | 7,604 | 7,620 | 238 | 254 | DES-005757 | ATTCctttacaccaCAC | ASO-005757 | OxyAs OxyTs OxyTs DNAcs DNAts DNAts DNAts DNAas DNAcs DNAts DNAas DNAcs DNAts DNAas OxyMCs OxyAs OxyMC |
| 15 | 7,604 | 7,620 | 238 | 254 | DES-005758 | ATTccttTacaccaCAC | ASO-005758 | OxyAs OxyTs OxyTs DNAcs DNAcs DNAts DNAts DNAas DNAcs DNAts DNAas DNAcs DNAts DNAas OxyMCs OxyAs OxyMC |
| 15 | 7,604 | 7,620 | 238 | 254 | DES-005759 | ATtCcTttacaccaCAC | ASO-005759 | OxyAs OxyTs DNAts OxyMCs DNAcs OxyTs DNAts DNAas DNAcs DNAts DNAas DNAcs DNAts DNAas OxyMCs OxyAs OxyMC |
| 15 | 7,604 | 7,620 | 238 | 254 | DES-005760 | ATtCccTtacaccaCAC | ASO-005760 | OxyAs OxyTs DNAts OxyMCs DNAcs DNAcs OxyTs DNAts DNAas DNAcs DNAts DNAas DNAcs DNAts DNAas OxyMCs OxyAs OxyMC |
| 15 | 7,604 | 7,620 | 238 | 254 | DES-005761 | ATtCctttacaccaCAC | ASO-005761 | OxyAs OxyTs DNAts OxyMCs DNAcs DNAts DNAts DNAts DNAas DNAcs DNAts DNAas DNAcs DNAts DNAas OxyMCs OxyAs OxyMC |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 15 | 7,604 | 7,620 | 238 | 254 | DES-005762 | ATtcCtTtacaccaCAC | ASO-005762 | OxyAs OxyTs DNAts DNAcs OxyMCs DNAts DNAts OxyTs DNAts DNAas DNAcs DNAts DNAcs DNAas OxyMCs OxyAs OxyMC |
| 15 | 7,604 | 7,620 | 238 | 254 | DES-005763 | ATtCcTtttacaccaCAC | ASO-005763 | OxyAs OxyTs DNAts DNAcs OxyMCs DNAts DNAts DNAcs DNAts DNAas DNAcs DNAts DNAcs DNAas OxyMCs OxyAs OxyMC |
| 15 | 7,604 | 7,620 | 238 | 254 | DES-005764 | ATtccttttacaccaCAC | ASO-005764 | OxyAs OxyTs DNAts DNAcs DNAts DNAts DNAcs DNAts DNAas DNAcs DNAts DNAcs DNAas OxyMCs OxyAs OxyMC |
| 15 | 7,604 | 7,620 | 238 | 254 | DES-005765 | AtTcCTttacaccaCAC | ASO-005765 | OxyAs DNAts DNAts OxyTs OxyMCs DNAts OxyTs DNAts DNAas DNAcs DNAts DNAcs DNAas OxyMCs OxyAs OxyMC |
| 15 | 7,604 | 7,620 | 238 | 254 | DES-005766 | AtTcCtttacaccaCAC | ASO-005766 | OxyAs DNAts DNAts OxyTs OxyMCs DNAts DNAts DNAcs DNAts DNAas DNAcs DNAts DNAcs DNAas OxyMCs OxyAs OxyMC |
| 15 | 7,604 | 7,620 | 238 | 254 | DES-005767 | AtTcCtTtacaccaCAC | ASO-005767 | OxyAs DNAts OxyTs DNAcs OxyMCs DNAts OxyTs DNAts DNAas DNAcs DNAts DNAcs DNAas OxyMCs OxyAs OxyMC |
| 15 | 7,604 | 7,620 | 238 | 254 | DES-005768 | AtTcCtTtacaccaCAC | ASO-005768 | OxyAs DNAts OxyTs DNAcs OxyMCs DNAts DNAas DNAcs DNAts DNAcs DNAas OxyMCs OxyAs OxyMC |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 15 | 7,604 | 7,620 | 238 | 254 | DES-005769 | AtTcctttacaccaCAC | ASO-005769 | OxyAs DNAts OxyTs DNAcs DNAcs DNAts DNAts DNAas DNAcs DNAts DNAas DNAcs DNAas OxyMCs OxyAs OxyMC |
| 15 | 7,604 | 7,620 | 238 | 254 | DES-005770 | AttCCtttacaccaCAC | ASO-005770 | OxyAs DNAts DNAts OxyMCs OxyMCs DNAts DNAts DNAas DNAcs DNAts DNAas DNAcs DNAas OxyMCs OxyAs OxyMC |
| 15 | 7,604 | 7,620 | 238 | 254 | DES-005771 | AttCcCTttacaccaCAC | ASO-005771 | OxyAs DNAts DNAts OxyMCs DNAcs OxyTs DNAts DNAas DNAcs DNAts DNAas DNAcs DNAas OxyMCs OxyAs OxyMC |
| 15 | 7,604 | 7,620 | 238 | 254 | DES-005772 | AttCcttttacaccaCAC | ASO-005772 | OxyAs DNAts DNAts OxyMCs DNAcs DNAts OxyTs DNAas DNAcs DNAts DNAas DNAcs DNAas OxyMCs OxyAs OxyMC |
| 15 | 7,604 | 7,620 | 238 | 254 | DES-005773 | AttCCTttacaccaCAC | ASO-005773 | OxyAs DNAts DNAts OxyMCs DNAcs DNAts DNAts OxyTs DNAcs DNAts DNAas DNAcs DNAas OxyMCs OxyAs OxyMC |
| 15 | 7,604 | 7,620 | 238 | 254 | DES-005774 | AttcCTTtacaccaCAC | ASO-005774 | OxyAs DNAts DNAts DNAcs OxyMCs OxyTs OxyTs DNAas DNAcs DNAts DNAas DNAcs DNAas OxyMCs OxyAs OxyMC |
| 15 | 7,604 | 7,620 | 238 | 254 | DES-005775 | AttcCtTTacaccaCAC | ASO-005775 | OxyAs DNAts DNAts DNAcs OxyMCs DNAts OxyTs OxyTs DNAas DNAcs DNAts DNAas DNAcs DNAas OxyMCs OxyAs OxyMC |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 15 | 7,604 | 7,620 | 238 | 254 | DES-005776 | ATTCcTTtacaccacAC | ASO-005776 | OxyAs OxyTs OxyTs OxyMCs DNAcs OxyTs OxyTs DNAts DNAas DNAcs DNAas DNAcs DNAcs OxyAs OxyMC |
| 15 | 7,604 | 7,620 | 238 | 254 | DES-005777 | ATTCcTtttacaccacAC | ASO-005777 | OxyAs OxyTs OxyTs OxyMCs DNAcs OxyTs DNAts DNAts DNAas DNAcs DNAas DNAcs DNAcs OxyAs OxyMC |
| 15 | 7,604 | 7,620 | 238 | 254 | DES-005778 | ATTCcdTtacaccacAC | ASO-005778 | OxyAs OxyTs OxyTs OxyMCs DNAcs DNAts OxyTs DNAts DNAas DNAcs DNAas DNAcs DNAcs OxyAs OxyMC |
| 15 | 7,604 | 7,620 | 238 | 254 | DES-005779 | ATTCcttttacaccacAC | ASO-005779 | OxyAs OxyTs OxyTs OxyMCs DNAcs DNAts DNAts DNAts DNAas DNAcs DNAas DNAcs DNAcs OxyAs OxyMC |
| 15 | 7,604 | 7,620 | 238 | 254 | DES-005780 | ATtCCtttacaccacAC | ASO-005780 | OxyAs OxyTs DNAts OxyMCs OxyMCs DNAts DNAts DNAts DNAas DNAcs DNAas DNAcs DNAcs OxyAs OxyMC |
| 15 | 7,604 | 7,620 | 238 | 254 | DES-005781 | AtTCCtttacaccacAC | ASO-005781 | OxyAs DNAts OxyTs OxyMCs OxyMCs DNAts DNAts DNAts DNAas DNAcs DNAas DNAcs DNAcs OxyAs OxyMC |
| 15 | 7,604 | 7,620 | 238 | 254 | DES-005782 | AtTCCtttacaccacAC | ASO-005782 | OxyAs DNAts OxyTs OxyMCs OxyMCs DNAts DNAts DNAts DNAas DNAcs DNAas DNAcs DNAcs OxyAs OxyMC |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 15 | 7,604 | 7,620 | 238 | 254 | DES-005783 | AtTCctttacaccacAC | ASO-005783 | OxyAs DNAts OxyTs OxyMCs DNAcs DNATs DNAts DNAts DNAts DNAas DNAcs DNAas DNAcs DNAas DNAcs OxyAs OxyMC |
| 15 | 7,604 | 7,620 | 238 | 254 | DES-005784 | AttCCTTtacaccacAC | ASO-005784 | OxyAs DNAts DNAts OxyMCs OxyMCs OxyTs OxyTs DNAts DNAas DNAcs DNAas DNAcs DNAas DNAcs OxyAs OxyMC |
| 15 | 7,604 | 7,620 | 238 | 254 | DES-005785 | AttCCTttacaccacAC | ASO-005785 | OxyAs DNAts DNAts OxyMCs OxyMCs OxyTs DNAts DNAts DNAas DNAcs DNAas DNAcs DNAas DNAcs OxyAs OxyMC |
| 13 | 7,604 | 7,622 | 238 | 256 | DES-008413 | GAAttccttacaccacaCAC | ASO-008413 | OxyGs OxyAs OxyAs DNAts DNAts DNAas DNAcs DNAas DNAcs DNAas DNAcs OxyMCs OxyAs OxyMC |
| 12 | 7,604 | 7,619 | 238 | 253 | DES-287031 | tTCctttacaccACAC | ASO-287031 | OMets OxyTs OxyMCs DNAcs DNATs DNAts DNAas DNAcs DNAcs OxyAs OxyMCs OxyAs OMec |
| 12 | 7,604 | 7,619 | 238 | 253 | DES-287957 | ttCctttacaccAcAc | ASO-287957 | OMets OMets OxyMCs DNAcs DNATs DNAts DNAas DNAcs DNAcs OxyAs OMecs OxyAs OMec |
| 12 | 7,604 | 7,619 | 238 | 253 | DES-287959 | TtcctttacaccaCaC | ASO-287959 | OxyTs OMets OMecs DNAcs DNATs DNAts DNAas DNAcs DNAcs OMeas DNAcs OMeas OxyMCs OMeas OxyMC |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 12 | 7,604 | 7,619 | 238 | 253 | DES-287962 | ttCctttacaccACac | ASO-287962 | OMets OMets OxyMCs DNAcs DNAts DNAts DNAts DNAas DNAcs DNAas DNAcs DNAcs OxyAs OxyMCs OMeas OMec |
| 12 | 7,604 | 7,619 | 238 | 253 | DES-288906 | ttccTttacaccacac | ASO-288906 | OMets OMets OMecs OxyTs DNAts DNAts DNAas DNAcs DNAas DNAcs DNAcs DNAcs OMeas OMec |
| 12 | 7,604 | 7,619 | 238 | 253 | DES-313413 | ttcctttacaccacac | ASO-313413 | OMets OMets OMecs DNAcs DNAts DNAts DNAts DNAas DNAcs DNAas DNAcs DNAcs OMecs OMeas OMec |
| 14 | 7,604 | 7,621 | 238 | 255 | DES-319536 | AattCctTtacaccacAc | ASO-319536 | OxyAs DNAas DNAts DNAts OxyMCs OMecs OMets OxyTs DNAts DNAas DNAcs DNAas DNAcs DNAcs OxyAs OMec |
| 14 | 7,604 | 7,621 | 238 | 255 | DES-319537 | aattCctTtacaccacAc | ASO-319537 | OMeas DNAas DNAts DNAts OxyMCs OMecs OMets OxyTs DNAts DNAas DNAcs DNAas DNAcs DNAcs OxyAs OMec |
| 15 | 7,604 | 7,620 | 238 | 254 | DES-324636 | AtTcctttacaccACac | ASO-324636 | OxyAs DNAts OxyTs DNAcs DNAcs DNAts DNAts DNAas DNAcs DNAas DNAcs DNAcs OxyAs OxyMCs OMeas OMec |
| 15 | 7,604 | 7,620 | 238 | 254 | DES-324637 | AtTcctttacaccAcAc | ASO-324637 | OxyAs DNAts OxyTs DNAcs DNAcs DNAts DNAts DNAas DNAcs DNAas DNAcs DNAcs OxyAs OMecs OxyAs OMec |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 15 | 7,604 | 7,620 | 238 | 254 | DES-324638 | AtTcctttacaccAcAc | ASO-324638 | OxyAs OMets OxyTs DNAcs DNAcs DNAts DNAts DNAas DNAcs DNAas DNAcs DNAcs OxyAs OMecs OxyAs OMec |
| 15 | 7,604 | 7,620 | 238 | 254 | DES-324639 | atTcctttacaccAcAc | ASO-324639 | OMeas OMets OxyTs DNAcs DNAcs DNAts DNAts DNAas DNAcs DNAas DNAcs DNAcs OxyAs OMecs OxyAs OMec |
| 15 | 7,604 | 7,620 | 238 | 254 | DES-324640 | atTcctttacaccAcac | ASO-324640 | OMeas OMets OxyTs DNAcs DNAcs DNAts DNAts DNAas DNAcs DNAas DNAcs DNAcs OxyAs OMecs OMeas OMec |
| 15 | 7,604 | 7,620 | 238 | 254 | DES-324641 | AtTcctttacaccAcaC | ASO-324641 | OxyAs DNAts OxyTs DNAcs DNAcs DNAts DNAts DNAas DNAcs DNAas DNAcs DNAcs OxyAs OMecs OMeas OMec |
| 15 | 7,604 | 7,620 | 238 | 254 | DES-324642 | AtTcctttacaccAcaC | ASO-324642 | OxyAs OMets OxyTs DNAcs DNAcs DNAts DNAts DNAas DNAcs DNAas DNAcs DNAcs OxyAs OMecs OMeas OMec |
| 15 | 7,604 | 7,620 | 238 | 254 | DES-324643 | AtTcctttacaccAcaC | ASO-324643 | OxyAs OMets OxyTs DNAcs DNAcs DNAts DNAts DNAas DNAcs DNAas DNAcs DNAcs OxyAs OMecs OMeas OxyMC |
| 15 | 7,604 | 7,620 | 238 | 254 | DES-324644 | AtTcctttacacCaCac | ASO-324644 | OxyAs OMets OxyTs DNAcs DNAcs DNAts DNAts DNAas DNAcs DNAas DNAcs DNAcs OxyMCs OMeas OxyMCs OMeas OMec |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 15 | 7,604 | 7,620 | 238 | 254 | DES-324645 | AttCctttacaccAcAc | ASO-324645 | OxyAs OMets OMets OxyMCs DNAcs DNAts DNAts DNAts DNAts DNAas DNAcs DNAcs DNAas DNAcs OxyAs OMecs OMec |
| 15 | 7,604 | 7,620 | 238 | 254 | DES-324646 | AtTcctttacacCAcac | ASO-324646 | OxyAs OMets OxyTs DNAcs DNAts DNAts DNAts DNAts DNAas DNAcs DNAas DNAcs OxyMCs OxyAs OMecs OMeas OMec |
| 15 | 7,604 | 7,620 | 238 | 254 | DES-324647 | AtTcctttacacCacaC | ASO-324647 | OxyAs OMets OxyTs DNAcs DNAts DNAts DNAts DNAts DNAas DNAcs DNAas DNAcs OxyMCs OMeas DNAcs OMeas OxyMC |
| 14 | 7,604 | 7,621 | 238 | 255 | DES-325058 | AatttcctTtacaccacAc | ASO-325058 | OxyAs DNAas DNAts DNAts DNAts OMets OMecs OMets OxyTs DNAts DNAas DNAcs DNAas DNAcs DNAas OxyAs OMec |
| 14 | 7,604 | 7,621 | 238 | 255 | DES-325059 | AatttcctTtacaccacaC | ASO-325059 | OxyAs DNAas DNAts DNAts DNAts OMets DNAts OxyMCs OMets OxyTs DNAts DNAas DNAcs DNAas DNAcs OMeas OxyMC |
| 14 | 7,604 | 7,621 | 238 | 255 | DES-325060 | AatttcctTtacaccacAC | ASO-325060 | OxyAs DNAas DNAts DNAts DNAts OMets DNAts DNAts OMets OxyTs DNAts DNAas DNAcs DNAas DNAcs OxyAs OxyMC |
| 14 | 7,604 | 7,621 | 238 | 255 | DES-325061 | AattCctTtacaccacAc | ASO-325061 | OxyAs OMeas OMets OMets OxyMCs OMets OxyTs DNAts DNAas DNAcs DNAas DNAcs DNAas DNAcs OxyAs OMec |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 14 | 7,604 | 7,621 | 238 | 255 | DES-325062 | AattcctTtacaccacAc | ASO-325062 | OxyAs DNAaas DNAts DNAts OMecs OMecs DNAts OxyTs DNAts DNAaas DNAas DNAas DNAcs DNAas DNAcs OxyAs OMec |
| 14 | 7,604 | 7,621 | 238 | 255 | DES-325063 | AattcctTtacaccaCaC | ASO-325063 | OxyAs DNAaas DNAts DNAts OMecs OMecs DNAts OxyTs DNAts DNAas DNAas DNAas DNAcs DNAaas OxyMCs OMeas OxyMC |
| 14 | 7,604 | 7,621 | 238 | 255 | DES-325064 | AattcctTtacaccaCac | ASO-325064 | OxyAs DNAaas DNAts DNAts OMecs OMecs DNAts OMets OxyTs DNAts DNAaas DNAas DNAas DNAcs DNAas OxyMCs OMeas OMec |
| 14 | 7,604 | 7,621 | 238 | 255 | DES-325065 | AattcctTtacaccacAc | ASO-325065 | OxyAs OMeas DNAts DNAts OMecs DNAts OMecs OMets OxyTs DNAaas DNAas DNAas DNAcs DNAas DNAcs OxyAs OMec |
| 14 | 7,604 | 7,621 | 238 | 255 | DES-325066 | AattccttTacaccacAc | ASO-325066 | OxyAs OMeas DNAts DNAts OMecs OMecs DNAts DNAcs OMets OxyTs DNAas DNAas DNAas DNAcs DNAas DNAcs OxyAs OMec |
| 14 | 7,604 | 7,621 | 238 | 255 | DES-325067 | AattcctTtacaccAcAc | ASO-325067 | OxyAs DNAaas DNAts DNAts OMecs OMecs DNAts OMecs OMets OxyTs DNAts DNAas DNAas DNAcs DNAas OxyAs OMec |
| 14 | 7,604 | 7,621 | 238 | 255 | DES-325068 | AattcctTtacaccACac | ASO-325068 | OxyAs DNAaas DNAts DNAts OMecs OMecs DNAts OMecs OMets OxyTs DNAts DNAas DNAas DNAcs OxyAs OxyMCs OMeas OMec |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 14 | 7,604 | 7,621 | 238 | 255 | DES-325069 | AattcctttAcaccacAc | ASO-325069 | OxyAs OMeas OMets OMets DNAts DNAcs DNAcs OMets OMets OMets OxyAs DNAas DNAcs DNAcs DNAcs DNAcs OxyAs OMec |
| 17 | 7,605 | 7,620 | 239 | 254 | DES-001255 | ATTcctttacacCACA | ASO-001255 | OxyAs OxyTs OxyTs DNAcs DNAcs DNAts DNAts DNAts DNAas DNAcs DNAcs DNAcs OxyMCs OxyAs OxyMCs OxyA |
| 17 | 7,605 | 7,620 | 239 | 254 | DES-001412 | ATtcctttacaccaCA | ASO-001412 | OxyAs OxyTs DNAts DNAcs DNAcs DNAts DNAts DNAts DNAas DNAcs DNAcs DNAcs DNAcs OxyMCs OxyA |
| 17 | 7,605 | 7,622 | 239 | 256 | DES-008412 | GAAttcctttacaccACA | ASO-008412 | OxyGs OxyAs OxyAs DNAts DNAcs DNAcs DNAts DNAts DNAts DNAas DNAcs DNAcs DNAcs OxyAs OxyMCs OxyA |
| 18 | 7,606 | 7,623 | 240 | 257 | DES-008414 | TGAattcctttacacCAC | ASO-008414 | OxyTs OxyGs OxyAs OxyAs DNAts DNAcs DNAcs DNAts DNAts DNAts DNAas DNAcs DNAcs DNAcs OxyAs OxyMCs |
| 19 | 7,607 | 7,624 | 241 | 258 | DES-008415 | ATGAattcctttacacCA | ASO-008415 | OxyAs OxyTs OxyGs OxyAs DNAts DNAts DNAcs DNAcs DNAts DNAts DNAts DNAts DNAcs DNAcs DNAcs OxyMCs OxyA |
| 20 | 7,608 | 7,625 | 242 | 259 | DES-008416 | AATgaattcctttaCACC | ASO-008416 | OxyAs OxyAs OxyTs DNAgs DNAas DNAas DNAts DNAts DNAts DNAcs DNAts DNAts DNAcs OxyMCs OxyAs OxyMCs OxyMC |

FIG. 2 (cont.)

| Sequence ID No. | NG_011851.1 Start | NG_011851.1 End | NM_000345.3 Start | NM_000345.3 End | DES No. | ASO with Design | ASO No. | ASO with Chemical Structure |
|---|---|---|---|---|---|---|---|---|
| 21 | 7,611 | 7,627 | 245 | 261 | DES-008417 | CTAatgaattcctTTAC | ASO-008417 | OxyMCs OxyTs OxyAs DNAas DNAts DNAgs DNAas DNAgs DNAas DNAts DNAts DNAcs DNAts OxyTs OxyAs OxyMC |

FIG. 3.

| SEQ ID No. | NG_0118 51.1 Start | NG_0118 51.1 End | DES No. | ASO with Design | ASO No. | ASO with Chemical Structure |
|---|---|---|---|---|---|---|
| 7 | 7,603 | 7,620 | DES-316392 | ATTCctttacaccACACT<br>A design for SEQ ID NO: 7 OMe3-L1-D9-L2-OMe3 | ASO-316392 | OMeas OMets OMets OxyMCs DNAcs DNAts DNAts DNAts DNAas DNAts DNAcs DNAcs DNAcs OxyAs OxyMCs OMeas OMecs OMet |
| 7 | 7,603 | 7,620 | DES-316393 | ATTCctttacaccACACT<br>A design for SEQ ID NO: 7 OMe3-L1-D9-L1-OMe1-L1-OMe2 | ASO-316393 | OMeas OMets OMets OxyMCs DNAcs DNAts DNAts DNAts DNAas DNAts DNAcs DNAcs DNAcs OxyAs OMecs OxyAs OMecs OMet |
| 7 | 7,603 | 7,620 | DES-316394 | ATTCctttacaccACACT<br>A design for SEQ ID NO: 7 L1-OMe2-L1-D9-L1-OMe1-L1-OMe2 | ASO-316394 | OxyAs OMets OMets OxyMCs DNAcs DNAts DNAts DNAts DNAas DNAcs DNAcs DNAcs OxyAs OMecs OxyAs OMecs OMet |
| 7 | 7,603 | 7,620 | DES-316395 | ATTCctttacaccACACT<br>A design for SEQ ID NO: 7 L1-OMe2-L1-D9-L1-OMe1-L1-OMe3 | ASO-316395 | OxyAs OMets OMets OxyMCs DNAcs DNAts DNAts DNAts DNAas DNAcs DNAcs DNAcs OxyAs OxyMCs OMeas OMecs OMet |
| 12 | 7,604 | 7,619 | DES-287031 | TTCctttacaccACAC<br>A design for SEQ ID NO: 12 OMe1-L2-D9-L3-OMe1 | ASO-287031 | OMets OxyTs OxyMCs DNAcs DNAts DNAts DNAas DNAcs DNAcs DNAcs OxyAs OxyMCs OxyAs OMec |
| 12 | 7,604 | 7,619 | DES-287957 | TTCctttacaccACAC<br>A design for SEQ ID NO: 12 OMe2-L1-D9-L1-OMe1-L1-OMe1 | ASO-287957 | OMets OMets OxyMCs DNAcs DNAts DNAts DNAas DNAcs DNAcs DNAcs OxyAs OMecs OxyAs OMec |

FIG. 3 (cont.)

| | | | | | |
|---|---|---|---|---|---|
| 12 | 7,604 | 7,619 | DES-287959 | TTCctttacaccACAC<br>A design for SEQ ID NO: 12<br>L1-OMe2-D9-OMe1-L1-OMe1-L1 | ASO-287959 | OxyTs OMets OMecs DNAts DNAts<br>DNAas DNAas DNAcs DNAcs DNAts<br>OMeas OxyMC OMeas OxyMCs |
| 12 | 7,604 | 7,619 | DES-287962 | TTCctttacaccACAC<br>A design for SEQ ID NO: 12<br>OMe2-L1-D9-L2-OMe2 | ASO-287962 | OMets OMets OxyMCs DNAts DNAts<br>DNAas DNAcs DNAas DNAcs OxyAs OxyMCs<br>OMeas OMec |
| 12 | 7,604 | 7,619 | DES-288906 | TTCttacaccACAC<br>A design for SEQ ID NO: 12<br>OMe4-L1-D9-OMe2 | ASO-288906 | OMets OMets OMecs OxyTs DNAts<br>DNAas DNAcs DNAas DNAcs DNAas<br>OMeas OMec |
| 12 | 7,604 | 7,619 | DES-313413 | TTCctttacaccACAC<br>A design for SEQ ID NO: 12<br>OMe3-D9-OMe4 | ASO-313413 | OMets OMets OMecs DNAts DNAts<br>DNAas DNAcs DNAas DNAcs OMeas OMecs<br>OMeas OMec |
| 14 | 7,604 | 7,621 | DES-319536 | AattCCTtacaccacAC<br>A design for SEQ ID NO: 14<br>L1-D3-L1-OMe2-L1-D8-L1-OMe1 | ASO-319536 | OxyAs DNAas DNAts DNAts OxyMCs OMecs OMets<br>OxyTs DNAts DNAts DNAas DNAas DNAcs<br>DNAas DNAcs OxyAs OMec |
| 14 | 7,604 | 7,621 | DES-319537 | AattCCTtacaccacAC<br>A design for SEQ ID NO: 14<br>OMe1-D3-L1-OMe2-L1-D8-L1-OMe1 | ASO-319537 | OMeas DNAas DNAts DNAts OxyMCs OMecs OMets<br>OxyTs DNAts DNAts DNAas DNAas DNAcs<br>DNAas DNAcs OxyAs OMec |
| 14 | 7,604 | 7,621 | DES-325058 | AattCCTtacaccacAC<br>A design for SEQ ID NO: 14<br>L1-D3-OMe3-L1-D8-L1-OMe1 | ASO-325058 | OxyAs DNAas DNAts DNAts OMecs OMecs OMets<br>OxyTs DNAts DNAas DNAas DNAcs<br>DNAas DNAcs OxyAs OMec |

FIG. 3 (cont.)

| | | | | | |
|---|---|---|---|---|---|
| 14 | 7,604 | 7,621 | DES-325059 | AattCCTTtacaccacAC<br>A design for SEQ ID NO: 14 L1-D3-L1-OMe2-L1-D8-OMe1-L1 | ASO-325059 | OxyAs DNAas DNAts DNAts OxyMCs OMets<br>OxyTs DNATs DNAas DNAcs OMeas DNAcs DNAcs<br>DNAas DNACs OMeas OxyMC |
| 14 | 7,604 | 7,621 | DES-325060 | AattCCTTtacaccacAC<br>A design for SEQ ID NO: 14 L1-D3-OMe3-L1-D8-L2 | ASO-325060 | OxyAs DNAas DNAts DNAts OMecs OMets<br>OxyTs DNATs DNAas DNAas DNAcs DNAcs<br>DNAas DNACs OxyAs OxyMC |
| 14 | 7,604 | 7,621 | DES-325061 | AATTCCTTtacaccacAC<br>A design for SEQ ID NO: 14 L1-OMe3-L1-OMe2-L1-D8-L1-OMe1 | ASO-325061 | OxyAs OMeas OMets OMets OxyMCs OMets<br>OxyTs DNATs DNAts DNAas DNAas DNAcs DNAcs<br>DNAas DNACs OxyAs OMec |
| 14 | 7,604 | 7,621 | DES-325062 | AattCCTTtacaccacAC<br>A design for SEQ ID NO: 14 L1-D3-OMe2-D1-L1-D8-L1-OMe1 | ASO-325062 | OxyAs DNAas DNAts DNAts OMecs OMets<br>OxyTs DNATs DNAas DNAas DNAcs DNAcs<br>DNAas DNACs OxyAs OMec |
| 14 | 7,604 | 7,621 | DES-325063 | AattCCTTtacaccacAC<br>A design for SEQ ID NO: 14 L1-D3-OMe3-L1-D7-L1-OMe1-L1 | ASO-325063 | OxyAs DNAas DNAts DNAts OMecs OMets<br>OxyTs DNATs DNAas DNAas DNAcs DNAcs<br>DNAas OxyMCs OMeas OxyMC |
| 14 | 7,604 | 7,621 | DES-325064 | AattCCTTtacaccacAC<br>A design for SEQ ID NO: 14 L1-D3-OMe3-L1-D7-L1-OMe2 | ASO-325064 | OxyAs DNAas DNAts DNAts OMecs OMets<br>OxyTs DNATs DNAas DNAas DNAcs DNAcs<br>DNAas OxyMCs OMeas OMec |
| 14 | 7,604 | 7,621 | DES-325065 | AAttCTTtacaccacAC<br>A design for SEQ ID NO: 14 L1-OMe1-D3-OMe3-L1-D7-L1-OMe1 | ASO-325065 | OxyAs OMeas DNAts DNAts DNAts OMecs OMets<br>OMets OxyTs DNAas DNAas DNAcs DNAcs<br>DNAas DNAcs OxyAs OMec |

FIG. 3 (cont.)

| | | | | | |
|---|---|---|---|---|---|
| 14 | 7,604 | 7,621 | DES-325066 | AAItcCTTacaccacAC<br>A design for SEQ ID NO: 14 L1-OMe2-D2-OMe3-L1-D7-L1-OMe1 | ASO-325066 | OxyAs OMeas OMets DNAts DNAcs OMets<br>OMets OxyTs DNAas DNAcs DNAas DNAcs<br>DNAas DNAcs OxyAs OMec |
| 14 | 7,604 | 7,621 | DES-325067 | AattCCTTacaccACAC<br>A design for SEQ ID NO: 14 L1-D3-OMe3-L1-D6-L1-OMe1-L1-OMe1 | ASO-325067 | OxyAs DNAas DNAts DNAcs OMecs OMets<br>OxyTs DNAts DNAas DNAcs DNAas DNAcs<br>OxyAs OMecs OxyAs OMec |
| 14 | 7,604 | 7,621 | DES-325068 | AattCCTTacaccACAC<br>A design for SEQ ID NO: 14 L1-D3-OMe3-L1-D6-L2-OMe3 | ASO-325068 | OxyAs DNAas DNAts DNAcs OMecs OMets<br>OxyTs DNAts DNAas DNAcs DNAas DNAcs<br>OxyAs OxyMCs OMeas OMec |
| 14 | 7,604 | 7,621 | DES-325069 | AAItcCTTAcaccacAC<br>A design for SEQ ID NO: 14 L1-OMe2-D3-OMe3-L1-D6-L1-OMe1 | ASO-325069 | OxyAs OMeas OMets DNAts DNAcs OMets<br>OMets OMets OxyAs DNAas DNAcs DNAcs<br>DNAas DNAcs OxyAs OMec |
| 15 | 7,604 | 7,620 | DES-324636 | AtTccttacaccACAC<br>A design for SEQ ID NO: 15 L1-D1-L1-D10-L2-OMe2 | ASO-324636 | OxyAs DNAts OxyTs DNAcs DNAts DNAts<br>DNAts DNAas DNAcs DNAas DNAcs OxyAs<br>OxyMCs OMeas OMec |
| 15 | 7,604 | 7,620 | DES-324637 | AtTccttacaccACAC<br>A design for SEQ ID NO: 15 L1-D1-L1-D10-L1-OMe1-L1-OMe1 | ASO-324637 | OxyAs OMets OxyTs DNAcs DNAts DNAts<br>DNAts DNAas DNAcs DNAas DNAcs OxyAs<br>OMecs OxyAs OMec |
| 15 | 7,604 | 7,620 | DES-324638 | ATTccttacaccACAC<br>A design for SEQ ID NO: 15 L1-OMe1-L1-D10-L1-OMe1-L1-OMe1 | ASO-324638 | OxyAs OMets OxyTs DNAcs DNAts DNAts<br>DNAts DNAas DNAcs DNAas DNAcs OxyAs<br>OMecs OxyAs OMec |

FIG. 3 (cont.)

| | | | | | | |
|---|---|---|---|---|---|---|
| 15 | 7,604 | 7,620 | DES-324639 | A<u>TT</u>cctttacacc<u>ACAC</u><br>A design for SEQ ID NO: 15 OMe2-L1-D10-L1-OMe1-L1-OMe1 | ASO-324639 | OMeas OMets OxyTs DNAcs DNAts DNATs<br>DNAts DNAas DNAcs DNAcs DNAcs<br>OMecs OxyAs OMec OxyAs |
| 15 | 7,604 | 7,620 | DES-324640 | A<u>TT</u>cctttacacc<u>ACAC</u><br>A design for SEQ ID NO: 15 OMe2-L1-D10-L1-OMe3 | ASO-324640 | OMeas OMets OxyTs DNAcs DNAts DNATs<br>DNAts DNAas DNAcs DNAcs DNAcs<br>OMecs OMeas OMec OxyAs |
| 15 | 7,604 | 7,620 | DES-324641 | A<u>t</u>Tcctttacacc<u>ACAC</u><br>A design for SEQ ID NO: 15 L1-D1-L1-D10-L1-OMe2-L1 | ASO-324641 | OxyAs DNAts OxyTs DNAcs DNAts DNATs<br>DNAts DNAas DNAcs DNAcs DNAcs<br>OMecs OMeas OxyMC OxyAs |
| 15 | 7,604 | 7,620 | DES-324642 | A<u>TT</u>cctttacacc<u>ACAC</u><br>A design for SEQ ID NO: 15 L1-OMe1-L1-D10-L1-OMe3 | ASO-324642 | OxyAs OMets OxyTs DNAcs DNAts DNATs<br>DNAts DNAas DNAcs DNAcs DNAcs<br>OMecs OMeas OMec OxyAs |
| 15 | 7,604 | 7,620 | DES-324643 | A<u>TT</u>cctttacacc<u>ACAC</u><br>A design for SEQ ID NO: 15 L1-OMe1-L1-D10-L1-OMe2-L1 | ASO-324643 | OxyAs OMets OxyTs DNAcs DNAts DNATs<br>DNAts DNAas DNAcs DNAcs DNAcs<br>OMecs OMeas OxyMC OxyAs |
| 15 | 7,604 | 7,620 | DES-324644 | A<u>TT</u>cctttacacc<u>CACAC</u><br>A design for SEQ ID NO: 15 L1-OMe1-L1-D9-L1-OMe1-L1-OMe2 | ASO-324644 | OxyAs OMets OxyTs DNAcs DNAts DNATs<br>DNAts DNAas DNAcs DNAcs OMeas<br>OxyMCs OMeas OMec |
| 15 | 7,604 | 7,620 | DES-324645 | A<u>TT</u>Cctttacacc<u>ACAC</u><br>A design for SEQ ID NO: 15 L1-OMe2-L1-D9-L1-OMe1-L1-OMe1 | ASO-324645 | OxyAs OMets OMets OxyMCs DNAcs DNATs<br>DNAts DNAas DNAcs DNAcs DNAcs<br>OMecs OxyAs OMec |

FIG. 3 (cont.)

| | | | | | |
|---|---|---|---|---|---|
| 15 | 7,604 | 7,620 | DES-324646 | A<u>TT</u>ccttacac<u>CACAC</u><br>A design for SEQ ID NO: 15<br>L1-OMe1-L1-D9-L2-OMe3 | ASO-324646 | OxyAs OMets OxyTs DNAcs DNAcs DNAts DNAts<br>DNAts DNAas DNAcs DNAas DNAcs DNAcs OxyMCs OxyAs<br>OMecs OMeas OMec |
| 15 | 7,604 | 7,620 | DES-324647 | A<u>TT</u>ccttacac<u>CACAC</u><br>A design for SEQ ID NO: 15<br>L1-OMe1-L1-D9-L1-OMe3-L1 | ASO-324647 | OxyAs OMets OxyTs DNAcs DNAcs DNAts DNAts<br>DNAts DNAas DNAcs DNAas DNAcs DNAcs OxyMCs OMeas<br>OMecs OMeas OxyMC |

FIG. 4.

| ASO_NO | SK cells a-syn/GAPDH %con@25 uM | PAC neurons asyn/tub %inh @40nM | PAC neurons aysn/tub % Inh@5 uM |
|---|---|---|---|
| ASO-001255 | | | 96.27 |
| ASO-001263 | | | 94.38 |
| ASO-001412 | | | 91.64 |
| ASO-001421 | | | 97.37 |
| ASO-001435 | | | 90.75 |
| ASO-001464 | | | 92.75 |
| ASO-001490 | | | 97.14 |
| ASO-001649 | | | 99.02 |
| ASO-002030 | | | 93.54 |
| ASO-002031 | | | 97.60 |
| ASO-002032 | | | 94.93 |
| ASO-002040 | | | 97.13 |
| ASO-002041 | 4.13 | 82.56 | 94.36 |
| ASO-002042 | | | 85.68 |
| ASO-002050 | | | 97.11 |
| ASO-002051 | | | 89.93 |
| ASO-002052 | | | 93.98 |
| ASO-002060 | | | 95.80 |
| ASO-002061 | | | 83.94 |
| ASO-002069 | | | 96.98 |
| ASO-002070 | | | 79.43 |
| ASO-002078 | | | 94.90 |
| ASO-002079 | | | 80.79 |
| ASO-002087 | | | 97.69 |
| ASO-002088 | | | 84.11 |
| ASO-002096 | | | 97.35 |
| ASO-002097 | | | 95.75 |
| ASO-002098 | | | 86.51 |
| ASO-002755 | | 48.78 | |
| ASO-002780 | 2.15 | 96.97 | |
| ASO-002816 | 2.66 | 95.73 | |
| ASO-005367 | 17.52 | 76.59 | |
| ASO-005368 | 10.20 | 91.00 | |
| ASO-005369 | 15.71 | 90.38 | |
| ASO-005370 | 14.17 | 72.42 | |
| ASO-005371 | 27.99 | 75.29 | |
| ASO-005372 | 41.24 | 29.83 | |
| ASO-005373 | 12.27 | 73.27 | |
| ASO-005374 | 19.62 | 74.00 | |
| ASO-005375 | 20.75 | 65.07 | |
| ASO-005376 | 8.16 | 73.51 | |

FIG. 4 (cont.)

| ASO_NO | SK cells a-syn/GAPDH %con@25 uM | PAC neurons asyn/tub %inh @40nM | PAC neurons aysn/tub % Inh@5 uM |
|---|---|---|---|
| ASO-005377 | 23.37 | 66.56 | |
| ASO-005378 | 15.67 | 65.45 | |
| ASO-005379 | 34.80 | 25.13 | |
| ASO-005380 | 7.76 | 85.92 | |
| ASO-005381 | 4.30 | 88.49 | |
| ASO-005382 | 13.12 | 84.63 | |
| ASO-005383 | 15.22 | 65.97 | |
| ASO-005384 | 10.24 | 66.42 | |
| ASO-005385 | 13.05 | 92.49 | |
| ASO-005386 | 19.84 | 83.76 | |
| ASO-005387 | 10.28 | 91.48 | |
| ASO-005388 | 20.26 | 90.49 | |
| ASO-005389 | 28.17 | 81.70 | |
| ASO-005390 | 9.41 | 85.83 | |
| ASO-005391 | 5.19 | 99.52 | |
| ASO-005392 | 6.01 | 99.57 | |
| ASO-005393 | 17.03 | 96.08 | |
| ASO-005394 | 30.75 | 59.58 | |
| ASO-005395 | 14.70 | 81.46 | |
| ASO-005396 | 6.85 | 92.89 | |
| ASO-005397 | 10.05 | 92.35 | |
| ASO-005398 | 6.56 | 97.44 | |
| ASO-005399 | 5.27 | 97.52 | |
| ASO-005400 | 5.07 | 95.08 | |
| ASO-005401 | 64.21 | 56.38 | |
| ASO-005402 | 63.39 | 21.96 | |
| ASO-005403 | 42.13 | 47.14 | |
| ASO-005404 | 42.98 | 29.14 | |
| ASO-005405 | 44.76 | 59.53 | |
| ASO-005406 | 31.80 | 56.43 | |
| ASO-005407 | 40.75 | 60.14 | |
| ASO-005408 | 66.02 | 3.89 | |
| ASO-005409 | 36.08 | 58.65 | |
| ASO-005410 | 19.48 | 80.74 | |
| ASO-005411 | 17.06 | 81.58 | |
| ASO-005412 | 36.68 | 49.33 | |
| ASO-005413 | 22.64 | 74.63 | |
| ASO-005414 | 46.39 | 73.75 | |
| ASO-005415 | 13.06 | 80.06 | |
| ASO-005416 | 31.18 | 64.65 | |
| ASO-005417 | 21.46 | 72.97 | |
| ASO-005418 | 12.08 | 66.35 | |

FIG. 4 (cont.)

| ASO_NO | SK cells a-syn/GAPDH %con@25 uM | PAC neurons asyn/tub %inh @40nM | PAC neurons aysn/tub % Inh@5 uM |
|---|---|---|---|
| ASO-005419 | 25.12 | 65.05 | |
| ASO-005420 | 40.03 | 43.34 | |
| ASO-005421 | 55.96 | 48.69 | |
| ASO-005422 | 26.95 | 77.58 | |
| ASO-005423 | 37.07 | 56.12 | |
| ASO-005424 | 11.62 | 80.17 | |
| ASO-005425 | 25.48 | 63.45 | |
| ASO-005426 | 20.08 | 88.79 | |
| ASO-005427 | 27.37 | 92.82 | |
| ASO-005428 | 18.00 | 93.99 | |
| ASO-005429 | 26.63 | 65.88 | |
| ASO-005430 | 33.05 | 80.49 | |
| ASO-005431 | 40.18 | 63.84 | |
| ASO-005432 | 7.35 | 88.12 | |
| ASO-005433 | 12.11 | 91.26 | |
| ASO-005434 | 33.73 | 74.38 | |
| ASO-005435 | 9.22 | 84.22 | |
| ASO-005436 | 37.40 | 73.35 | |
| ASO-005437 | 14.63 | 90.18 | |
| ASO-005438 | 6.32 | 85.04 | |
| ASO-005439 | 11.22 | 80.77 | |
| ASO-005440 | 27.81 | 77.10 | |
| ASO-005441 | 15.42 | 72.69 | |
| ASO-005442 | 15.12 | 81.85 | |
| ASO-005443 | 13.96 | 86.70 | |
| ASO-005444 | 39.33 | 66.39 | |
| ASO-005445 | 13.73 | 87.60 | |
| ASO-005446 | 15.44 | 88.84 | |
| ASO-005447 | 13.29 | 95.26 | |
| ASO-005448 | 21.56 | 91.47 | |
| ASO-005449 | 17.37 | 94.11 | |
| ASO-005450 | 8.14 | 85.96 | |
| ASO-005451 | 9.09 | 83.84 | |
| ASO-005452 | 7.01 | 98.29 | |
| ASO-005453 | 8.89 | 91.53 | |
| ASO-005454 | 3.11 | 98.02 | |
| ASO-005455 | 6.45 | 96.22 | |
| ASO-005456 | 19.19 | 81.26 | |
| ASO-005457 | 12.05 | 88.17 | |
| ASO-005458 | 4.49 | 91.08 | |
| ASO-005459 | 8.22 | 84.28 | |
| ASO-005460 | 4.66 | 92.48 | |

FIG. 4 (cont.)

| ASO_NO | SK cells a-syn/GAPDH %con@25 uM | PAC neurons asyn/tub %inh @40nM | PAC neurons aysn/tub % Inh@5 uM |
|---|---|---|---|
| ASO-005461 | 3.76 | 94.95 | |
| ASO-005462 | 6.04 | 92.21 | |
| ASO-005463 | 41.73 | 55.32 | |
| ASO-005464 | 40.76 | 50.43 | |
| ASO-005465 | 17.21 | 86.33 | |
| ASO-005466 | 24.24 | 76.29 | |
| ASO-005467 | 37.11 | 58.36 | |
| ASO-005468 | 15.25 | 76.09 | |
| ASO-005469 | 26.16 | 73.60 | |
| ASO-005470 | 19.38 | 78.82 | |
| ASO-005471 | 18.41 | 61.75 | |
| ASO-005472 | 31.76 | 44.09 | |
| ASO-005473 | 21.32 | 55.00 | |
| ASO-005474 | 11.69 | 70.99 | |
| ASO-005475 | 36.40 | 64.16 | |
| ASO-005476 | 47.05 | 43.68 | |
| ASO-005477 | 35.61 | 50.26 | |
| ASO-005478 | 17.39 | 86.08 | |
| ASO-005479 | 26.06 | 81.92 | |
| ASO-005480 | 17.24 | 79.79 | |
| ASO-005481 | 27.71 | 81.71 | |
| ASO-005482 | 21.97 | 88.04 | |
| ASO-005483 | 22.44 | 85.20 | |
| ASO-005484 | 18.68 | 86.95 | |
| ASO-005485 | 26.39 | 78.71 | |
| ASO-005486 | 9.23 | 96.25 | |
| ASO-005487 | 12.20 | 85.38 | |
| ASO-005488 | 32.36 | 67.32 | |
| ASO-005489 | 29.16 | 65.11 | |
| ASO-005490 | 18.67 | 81.62 | |
| ASO-005491 | 20.33 | 72.46 | |
| ASO-005492 | 8.62 | 89.30 | |
| ASO-005493 | 16.96 | 85.74 | |
| ASO-005494 | 10.40 | 81.16 | |
| ASO-005495 | 16.61 | 83.19 | |
| ASO-005496 | 6.75 | 83.08 | |
| ASO-005497 | 10.12 | 83.69 | |
| ASO-005498 | 10.46 | 67.89 | |
| ASO-005499 | 17.00 | 75.48 | |
| ASO-005500 | 8.84 | 92.75 | |
| ASO-005501 | 11.64 | 81.61 | |
| ASO-005502 | 5.71 | 79.52 | |

FIG. 4 (cont.)

| ASO_NO | SK cells a-syn/GAPDH %con@25 uM | PAC neurons asyn/tub %inh @40nM | PAC neurons aysn/tub % Inh@5 uM |
|---|---|---|---|
| ASO-005503 | 10.24 | 85.75 | |
| ASO-005504 | 22.71 | 84.93 | |
| ASO-005505 | 8.60 | 87.28 | |
| ASO-005506 | 16.22 | 82.42 | |
| ASO-005507 | 13.39 | 92.55 | |
| ASO-005508 | 7.56 | 83.23 | |
| ASO-005509 | 11.42 | 88.58 | |
| ASO-005510 | 8.12 | 92.37 | |
| ASO-005511 | 7.71 | 89.05 | |
| ASO-005512 | 18.55 | 82.94 | |
| ASO-005513 | 16.46 | 85.23 | |
| ASO-005514 | 6.99 | 94.59 | |
| ASO-005515 | 18.10 | 91.10 | |
| ASO-005516 | 10.97 | 91.27 | |
| ASO-005517 | 7.71 | 92.14 | |
| ASO-005518 | 4.80 | 93.80 | |
| ASO-005519 | 8.31 | 96.29 | |
| ASO-005520 | 6.31 | 89.99 | |
| ASO-005521 | 13.97 | 72.63 | |
| ASO-005522 | 9.76 | 85.28 | |
| ASO-005523 | 10.80 | 88.76 | |
| ASO-005524 | 13.08 | 90.00 | |
| ASO-005525 | 5.99 | 86.16 | |
| ASO-005526 | 8.42 | 89.68 | |
| ASO-005527 | 20.32 | 71.11 | |
| ASO-005528 | 8.79 | 83.91 | |
| ASO-005529 | 3.64 | 94.41 | |
| ASO-005530 | 10.15 | 88.68 | |
| ASO-005531 | 5.41 | 88.57 | |
| ASO-005532 | 5.87 | 96.01 | |
| ASO-005533 | 5.63 | 95.42 | |
| ASO-005534 | 12.76 | 90.92 | |
| ASO-005535 | 15.05 | 86.34 | |
| ASO-005536 | 8.06 | 90.50 | |
| ASO-005537 | 8.08 | 98.60 | |
| ASO-005538 | 5.95 | 97.96 | |
| ASO-005539 | 27.93 | 78.89 | |
| ASO-005540 | 12.96 | 86.36 | |
| ASO-005541 | 9.25 | 86.44 | |
| ASO-005542 | 7.74 | 94.22 | |
| ASO-005543 | 16.90 | 83.78 | |
| ASO-005544 | 11.72 | 85.03 | |

FIG. 4 (cont.)

| ASO_NO | SK cells a-syn/GAPDH %con@25 uM | PAC neurons asyn/tub %inh @40nM | PAC neurons aysn/tub % Inh@5 uM |
|---|---|---|---|
| ASO-005545 | 18.34 | 79.65 | |
| ASO-005546 | 9.64 | 77.52 | |
| ASO-005547 | 18.34 | 80.26 | |
| ASO-005548 | 16.30 | 76.04 | |
| ASO-005549 | 41.60 | 55.94 | |
| ASO-005550 | 12.08 | 86.02 | |
| ASO-005551 | 15.17 | 82.85 | |
| ASO-005552 | 5.58 | 89.33 | |
| ASO-005553 | 12.25 | 90.80 | |
| ASO-005554 | 24.32 | 78.47 | |
| ASO-005555 | 15.67 | 71.34 | |
| ASO-005556 | 13.06 | 88.62 | |
| ASO-005557 | 10.12 | 92.53 | |
| ASO-005558 | 11.15 | 82.24 | |
| ASO-005559 | 31.15 | 61.01 | |
| ASO-005560 | 48.65 | 39.08 | |
| ASO-005561 | 22.05 | 44.35 | |
| ASO-005562 | 27.70 | 72.64 | |
| ASO-005563 | 29.40 | 77.21 | |
| ASO-005564 | 45.52 | 65.95 | |
| ASO-005565 | 49.46 | 38.01 | |
| ASO-005566 | 31.19 | 32.04 | |
| ASO-005567 | 32.63 | 66.89 | |
| ASO-005568 | 14.97 | 73.19 | |
| ASO-005569 | 8.14 | 63.26 | |
| ASO-005570 | 12.70 | 77.29 | |
| ASO-005571 | 26.22 | 78.65 | |
| ASO-005572 | 19.52 | 72.48 | |
| ASO-005573 | 17.21 | 83.21 | |
| ASO-005574 | 34.79 | 48.47 | |
| ASO-005575 | 52.96 | 53.50 | |
| ASO-005576 | 7.71 | 84.01 | |
| ASO-005577 | 6.47 | 64.67 | |
| ASO-005578 | 5.77 | 56.00 | |
| ASO-005579 | 8.46 | 71.63 | |
| ASO-005580 | 22.35 | 41.74 | |
| ASO-005581 | 21.63 | 78.89 | |
| ASO-005582 | 4.79 | 80.15 | |
| ASO-005583 | 12.36 | 76.91 | |
| ASO-005584 | 6.19 | 90.23 | |
| ASO-005585 | 8.69 | 89.56 | |
| ASO-005586 | 22.41 | 57.10 | |

FIG. 4 (cont.)

| ASO_NO | SK cells a-syn/GAPDH %con@25 uM | PAC neurons asyn/tub %inh @40nM | PAC neurons aysn/tub % Inh@5 uM |
|---|---|---|---|
| ASO-005587 | 15.26 | 84.62 | |
| ASO-005588 | 49.66 | 3.17 | |
| ASO-005589 | 11.56 | 68.38 | |
| ASO-005590 | 40.19 | 77.77 | |
| ASO-005591 | 18.55 | 72.08 | |
| ASO-005592 | 22.32 | 66.94 | |
| ASO-005593 | 18.70 | 51.87 | |
| ASO-005594 | 29.63 | 68.96 | |
| ASO-005595 | 63.56 | 18.94 | |
| ASO-005596 | 9.38 | 85.78 | |
| ASO-005597 | 5.60 | 74.43 | |
| ASO-005598 | 29.73 | 54.03 | |
| ASO-005599 | 8.41 | 64.80 | |
| ASO-005600 | 7.08 | 71.57 | |
| ASO-005601 | 11.18 | 47.74 | |
| ASO-005602 | 10.85 | 26.77 | |
| ASO-005603 | 18.91 | 72.08 | |
| ASO-005604 | 19.16 | 64.77 | |
| ASO-005605 | 39.87 | 59.61 | |
| ASO-005606 | 5.55 | 78.07 | |
| ASO-005607 | 4.70 | 82.38 | |
| ASO-005608 | 7.43 | 51.91 | |
| ASO-005609 | 6.22 | 70.54 | |
| ASO-005610 | 8.04 | 67.95 | |
| ASO-005611 | 9.43 | 81.08 | |
| ASO-005612 | 8.27 | 64.64 | |
| ASO-005613 | 10.66 | 83.82 | |
| ASO-005614 | 47.26 | 51.68 | |
| ASO-005615 | 16.73 | 71.59 | |
| ASO-005616 | 83.87 | 33.94 | |
| ASO-005617 | 10.37 | 45.48 | |
| ASO-005618 | 10.65 | 70.21 | |
| ASO-005619 | 13.35 | 71.26 | |
| ASO-005620 | 11.31 | 85.73 | |
| ASO-005621 | 15.13 | 79.80 | |
| ASO-005622 | 25.06 | 82.29 | |
| ASO-005623 | 39.53 | 39.38 | |
| ASO-005624 | 28.57 | 53.47 | |
| ASO-005625 | 28.91 | 86.31 | |
| ASO-005626 | 34.57 | 74.88 | |
| ASO-005627 | 5.41 | 48.03 | |
| ASO-005628 | 5.53 | 38.80 | |

FIG. 4 (cont.)

| ASO_NO | SK cells a-syn/GAPDH %con@25 uM | PAC neurons asyn/tub %inh @40nM | PAC neurons aysn/tub % Inh@5 uM |
|---|---|---|---|
| ASO-005629 | 23.54 | 70.29 | |
| ASO-005630 | 5.00 | 73.02 | |
| ASO-005631 | 6.67 | 59.62 | |
| ASO-005632 | 7.54 | 65.77 | |
| ASO-005633 | 21.55 | 66.66 | |
| ASO-005634 | 11.62 | 69.81 | |
| ASO-005635 | 37.58 | 82.46 | |
| ASO-005636 | 16.77 | 69.66 | |
| ASO-005637 | 2.21 | 50.43 | |
| ASO-005638 | 6.16 | 61.83 | |
| ASO-005639 | 7.26 | 65.48 | |
| ASO-005640 | 3.99 | 75.14 | |
| ASO-005641 | 4.49 | 86.53 | |
| ASO-005642 | 6.16 | 66.69 | |
| ASO-005643 | 13.04 | 76.38 | |
| ASO-005644 | 25.82 | 43.49 | |
| ASO-005645 | 49.96 | 45.31 | |
| ASO-005646 | 63.52 | 57.26 | |
| ASO-005647 | 54.30 | 78.19 | |
| ASO-005648 | 53.98 | 56.54 | |
| ASO-005649 | 55.87 | 39.04 | |
| ASO-005650 | 50.66 | 56.59 | |
| ASO-005651 | 42.78 | 67.05 | |
| ASO-005652 | 36.20 | 71.48 | |
| ASO-005653 | 44.44 | 61.74 | |
| ASO-005654 | 39.37 | 71.08 | |
| ASO-005655 | 51.39 | 44.52 | |
| ASO-005656 | 26.08 | 71.15 | |
| ASO-005657 | 37.42 | 60.52 | |
| ASO-005658 | 35.54 | 56.37 | |
| ASO-005659 | 44.06 | 41.29 | |
| ASO-005660 | 39.62 | 50.33 | |
| ASO-005661 | 35.48 | 63.11 | |
| ASO-005662 | 29.02 | 75.97 | |
| ASO-005663 | 19.70 | 80.74 | |
| ASO-005664 | 25.65 | 72.56 | |
| ASO-005665 | 25.22 | 66.40 | |
| ASO-005666 | 40.44 | 56.99 | |
| ASO-005667 | 26.80 | 69.22 | |
| ASO-005668 | 48.27 | 61.42 | |
| ASO-005669 | 28.64 | 35.01 | |
| ASO-005670 | 29.85 | 68.91 | |

FIG. 4 (cont.)

| ASO_NO | SK cells a-syn/GAPDH %con@25 uM | PAC neurons asyn/tub %inh @40nM | PAC neurons aysn/tub % Inh@5 uM |
|---|---|---|---|
| ASO-005671 | 12.43 | 78.77 | |
| ASO-005672 | 14.05 | 61.03 | |
| ASO-005673 | 18.02 | 68.90 | |
| ASO-005674 | 28.33 | 54.33 | |
| ASO-005675 | 46.00 | 49.50 | |
| ASO-005676 | 11.02 | 76.17 | |
| ASO-005677 | 7.11 | 83.63 | |
| ASO-005678 | 21.73 | 66.67 | |
| ASO-005679 | 9.69 | 80.73 | |
| ASO-005680 | 21.39 | 46.52 | |
| ASO-005681 | 6.36 | 83.60 | |
| ASO-005682 | 4.92 | 86.72 | |
| ASO-005683 | 7.08 | 86.98 | |
| ASO-005684 | 18.54 | 70.49 | |
| ASO-005685 | 8.30 | 77.42 | |
| ASO-005686 | 24.20 | 54.35 | |
| ASO-005687 | 10.20 | 77.36 | |
| ASO-005688 | 25.74 | 37.26 | |
| ASO-005689 | 14.02 | 76.61 | |
| ASO-005690 | 30.03 | 47.95 | |
| ASO-005691 | 12.56 | 75.54 | |
| ASO-005692 | 15.25 | 67.24 | |
| ASO-005693 | 28.03 | 57.68 | |
| ASO-005694 | 61.88 | 17.27 | |
| ASO-005695 | 21.11 | 61.00 | |
| ASO-005696 | 52.16 | 10.18 | |
| ASO-005697 | 10.92 | 77.73 | |
| ASO-005698 | 37.94 | 40.77 | |
| ASO-005699 | 24.66 | 66.73 | |
| ASO-005700 | 4.91 | 75.64 | |
| ASO-005701 | 21.94 | 42.48 | |
| ASO-005702 | 11.87 | 73.48 | |
| ASO-005703 | 10.65 | 74.13 | |
| ASO-005704 | 14.74 | 70.60 | |
| ASO-005705 | 34.73 | 31.12 | |
| ASO-005706 | 10.48 | 68.44 | |
| ASO-005707 | 16.74 | 65.66 | |
| ASO-005708 | 47.42 | 16.65 | |
| ASO-005709 | 9.20 | 78.53 | |
| ASO-005710 | 8.54 | 84.21 | |
| ASO-005711 | 8.47 | 77.04 | |
| ASO-005712 | 10.69 | 83.96 | |

FIG. 4 (cont.)

| ASO_NO | SK cells a-syn/GAPDH %con@25 uM | PAC neurons asyn/tub %inh @40nM | PAC neurons aysn/tub % Inh@5 uM |
|---|---|---|---|
| ASO-005713 | 14.89 | 65.35 | |
| ASO-005714 | 41.78 | 37.75 | |
| ASO-005715 | 10.90 | 78.63 | |
| ASO-005716 | 41.43 | 21.63 | |
| ASO-005717 | 5.64 | 87.92 | |
| ASO-005718 | 12.24 | 64.33 | |
| ASO-005719 | 15.27 | 70.11 | |
| ASO-005720 | 20.57 | 70.98 | |
| ASO-005721 | 17.19 | 64.77 | |
| ASO-005722 | 94.39 | 61.00 | |
| ASO-005723 | 23.13 | 48.71 | |
| ASO-005724 | 27.43 | 72.96 | |
| ASO-005725 | 70.13 | 13.89 | |
| ASO-005726 | 23.66 | 51.36 | |
| ASO-005727 | 20.12 | 69.40 | |
| ASO-005728 | 39.49 | 41.79 | |
| ASO-005729 | 21.72 | 59.97 | |
| ASO-005730 | 20.21 | 48.89 | |
| ASO-005731 | 51.12 | 37.02 | |
| ASO-005732 | 26.64 | 72.72 | |
| ASO-005733 | 27.16 | 80.88 | |
| ASO-005734 | 27.44 | 68.45 | |
| ASO-005735 | 34.00 | 71.72 | |
| ASO-005736 | 37.14 | 48.04 | |
| ASO-005737 | 31.92 | 52.36 | |
| ASO-005738 | 32.60 | 61.80 | |
| ASO-005739 | 56.46 | 32.50 | |
| ASO-005740 | 33.66 | 34.94 | |
| ASO-005741 | 34.74 | 45.25 | |
| ASO-005742 | 40.78 | 49.09 | |
| ASO-005743 | 19.35 | 54.46 | |
| ASO-005744 | 13.96 | 66.39 | |
| ASO-005745 | 14.90 | 81.24 | |
| ASO-005746 | 23.45 | 53.69 | |
| ASO-005747 | 13.94 | 65.28 | |
| ASO-005748 | 28.51 | 42.03 | |
| ASO-005749 | 21.54 | 71.11 | |
| ASO-005750 | 21.61 | 72.90 | |
| ASO-005751 | 8.23 | 76.02 | |
| ASO-005752 | 7.73 | 86.50 | |
| ASO-005753 | 5.79 | 81.68 | |
| ASO-005754 | 6.93 | 93.67 | |

FIG. 4 (cont.)

| ASO_NO | SK cells a-syn/GAPDH %con@25 uM | PAC neurons asyn/tub %inh @40nM | PAC neurons aysn/tub % Inh@5 uM |
|---|---|---|---|
| ASO-005755 | 4.92 | 96.48 | |
| ASO-005756 | 6.83 | 97.29 | |
| ASO-005757 | 6.81 | 84.03 | |
| ASO-005758 | 14.54 | 77.69 | |
| ASO-005759 | 6.52 | 86.25 | |
| ASO-005760 | 11.44 | 66.99 | |
| ASO-005761 | 8.84 | 76.38 | |
| ASO-005762 | 21.45 | 70.47 | |
| ASO-005763 | 12.47 | 74.10 | |
| ASO-005764 | 37.49 | 48.58 | |
| ASO-005765 | 8.67 | 89.78 | |
| ASO-005766 | 5.10 | 89.86 | |
| ASO-005767 | 7.79 | 85.09 | |
| ASO-005768 | 22.44 | 72.49 | |
| ASO-005769 | 23.25 | 58.54 | |
| ASO-005770 | 5.92 | 93.99 | |
| ASO-005771 | 10.39 | 91.62 | |
| ASO-005772 | 10.42 | 74.11 | |
| ASO-005773 | 10.29 | 94.89 | |
| ASO-005774 | 8.67 | 84.25 | |
| ASO-005775 | 19.04 | 86.96 | |
| ASO-005776 | 30.28 | 55.15 | |
| ASO-005777 | 19.12 | 60.23 | |
| ASO-005778 | 10.57 | 77.39 | |
| ASO-005779 | 9.30 | 73.83 | |
| ASO-005780 | 6.88 | 93.58 | |
| ASO-005781 | 13.29 | 90.31 | |
| ASO-005782 | 5.47 | 93.02 | |
| ASO-005783 | 6.61 | 90.10 | |
| ASO-005784 | 8.05 | 98.15 | |
| ASO-005785 | 4.46 | 99.46 | |
| ASO-005796 | 35.65 | 52.21 | |
| ASO-005797 | 32.17 | 47.64 | |
| ASO-005798 | 49.94 | 48.31 | |
| ASO-005799 | 29.98 | 67.91 | |
| ASO-005800 | 39.95 | 54.08 | |
| ASO-005801 | 45.76 | 31.52 | |
| ASO-005802 | 40.51 | 44.56 | |
| ASO-005803 | 49.27 | 41.01 | |
| ASO-005804 | 56.83 | 14.00 | |
| ASO-005805 | 27.06 | 36.65 | |
| ASO-005806 | 27.98 | 46.90 | |

FIG. 4 (cont.)

| ASO_NO | SK cells a-syn/GAPDH %con@25 uM | PAC neurons asyn/tub %inh @40nM | PAC neurons aysn/tub % Inh@5 uM |
|---|---|---|---|
| ASO-005807 | 39.09 | 47.18 | |
| ASO-005808 | 38.57 | 23.05 | |
| ASO-005809 | 53.61 | 40.32 | |
| ASO-005810 | 12.51 | 83.48 | |
| ASO-005811 | 19.14 | 70.83 | |
| ASO-005812 | 39.20 | 62.10 | |
| ASO-005813 | 33.79 | 45.31 | |
| ASO-005814 | 29.59 | 54.93 | |
| ASO-005815 | 41.93 | 41.91 | |
| ASO-005816 | 41.43 | 27.45 | |
| ASO-005817 | 39.13 | 32.85 | |
| ASO-005818 | 20.11 | 64.45 | |
| ASO-005819 | 10.14 | 60.97 | |
| ASO-005820 | 50.05 | 41.48 | |
| ASO-005821 | 26.69 | 53.16 | |
| ASO-005822 | 21.22 | 48.81 | |
| ASO-005823 | 14.22 | 66.30 | |
| ASO-005824 | 26.25 | 49.14 | |
| ASO-005825 | 22.50 | 58.36 | |
| ASO-005826 | 71.09 | 21.17 | |
| ASO-005827 | 51.00 | 35.81 | |
| ASO-005828 | 57.25 | 24.88 | |
| ASO-005829 | 39.68 | 58.56 | |
| ASO-005830 | 31.70 | 52.40 | |
| ASO-005831 | 39.12 | 29.07 | |
| ASO-005832 | 32.59 | 54.19 | |
| ASO-005833 | 30.08 | 43.10 | |
| ASO-005834 | 42.79 | 48.37 | |
| ASO-005835 | 43.88 | 27.04 | |
| ASO-005836 | 38.62 | 35.19 | |
| ASO-008412 | 12.07 | 50.84 | |
| ASO-008413 | 25.19 | 18.45 | |
| ASO-008414 | 4.40 | 52.18 | |
| ASO-008415 | 4.95 | 71.50 | |
| ASO-008416 | 9.05 | 51.86 | |
| ASO-008417 | 19.29 | 14.90 | |
| ASO-319536 | | 88.06 | |
| ASO-319537 | | 68.15 | |
| ASO-324636 | | 68.54 | |
| ASO-324637 | | 91.53 | |
| ASO-324638 | | 68.30 | |
| ASO-324639 | | 54.07 | |

FIG. 4 (cont.)

| ASO_NO | SK cells a-syn/GAPDH %con@25 uM | PAC neurons asyn/tub %inh @40nM | PAC neurons aysn/tub % Inh@5 uM |
|---|---|---|---|
| ASO-324640 | | 42.02 | |
| ASO-324641 | | 61.84 | |
| ASO-324642 | | 70.52 | |
| ASO-324643 | | 67.13 | |
| ASO-324644 | | 19.76 | |
| ASO-324645 | | 83.39 | |
| ASO-324646 | | 53.72 | |
| ASO-324647 | | 68.75 | |
| ASO-325058 | | 28.14 | |
| ASO-325059 | | 87.43 | |
| ASO-325060 | | -20.25 | |
| ASO-325061 | | 71.98 | |
| ASO-325062 | | 39.19 | |
| ASO-325063 | | 2.76 | |
| ASO-325064 | | 43.49 | |
| ASO-325065 | | 41.68 | |
| ASO-325066 | | 35.88 | |
| ASO-325067 | | 51.66 | |
| ASO-325068 | | 24.58 | |
| ASO-325069 | | 24.48 | |

FIG. 5

| ASO_NO | LE PAC A-Syn/Tub IC50 (uM) |
|---|---|
| ASO-001412 | 0.11 |
| ASO-001435 | 0.02 |
| ASO-001464 | 0.02 |
| ASO-002816 | 0.24 |
| ASO-005376 | 0.08 |
| ASO-005392 | 0.01 |
| ASO-005400 | 0.01 |
| ASO-005430 | 0.02 |
| ASO-005432 | 0.27 |
| ASO-005433 | 0.01 |
| ASO-005435 | 0.01 |
| ASO-005439 | 0.01 |
| ASO-005440 | 0.02 |
| ASO-005441 | 0.02 |
| ASO-005442 | 0.02 |
| ASO-005445 | 0.01 |
| ASO-005446 | 0.01 |
| ASO-005450 | 0.004 |
| ASO-005451 | 0.01 |
| ASO-005452 | 0.25 |
| ASO-005453 | 0.01 |
| ASO-005454 | 0.005 |
| ASO-005455 | 0.01 |
| ASO-005458 | 0.21 |
| ASO-005459 | 0.01 |
| ASO-005460 | 0.01 |
| ASO-005465 | 0.01 |
| ASO-005480 | 0.02 |
| ASO-005483 | 0.004 |
| ASO-005486 | 0.01 |
| ASO-005496 | 0.01 |
| ASO-005500 | 0.01 |
| ASO-005508 | 0.31 |
| ASO-005512 | 0.01 |
| ASO-005514 | 0.01 |
| ASO-005517 | 0.30 |
| ASO-005518 | 0.28 |
| ASO-005525 | 0.11 |
| ASO-005529 | 0.06 |
| ASO-005530 | 0.01 |
| ASO-005531 | 0.01 |
| ASO-005532 | 0.27 |

FIG. 5 (cont.)

| ASO_NO | LE PAC A-Syn/Tub IC50 (uM) |
|---|---|
| ASO-005533 | 0.13 |
| ASO-005558 | 0.01 |
| ASO-005571 | 0.03 |
| ASO-005573 | 0.04 |
| ASO-005576 | 0.01 |
| ASO-005578 | 0.02 |
| ASO-005581 | 0.04 |
| ASO-005582 | 0.01 |
| ASO-005584 | 0.01 |
| ASO-005585 | 0.02 |
| ASO-005597 | 0.02 |
| ASO-005599 | 0.31 |
| ASO-005606 | 0.01 |
| ASO-005608 | 0.29 |
| ASO-005610 | 0.10 |
| ASO-005611 | 0.13 |
| ASO-005612 | 0.01 |
| ASO-005613 | 0.02 |
| ASO-005621 | 0.02 |
| ASO-005625 | 0.04 |
| ASO-005626 | 0.05 |
| ASO-005628 | 0.01 |
| ASO-005631 | 0.01 |
| ASO-005632 | 0.15 |
| ASO-005633 | 0.04 |
| ASO-005635 | 0.09 |
| ASO-005637 | 0.43 |
| ASO-005640 | 0.28 |
| ASO-005641 | 0.27 |
| ASO-005642 | 0.05 |
| ASO-005649 | 0.21 |
| ASO-005650 | 0.11 |
| ASO-005651 | 0.02 |
| ASO-005652 | 0.04 |
| ASO-005671 | 0.01 |
| ASO-005679 | 0.14 |
| ASO-005682 | 0.08 |
| ASO-005685 | 0.24 |
| ASO-005687 | 0.01 |
| ASO-005703 | 0.02 |
| ASO-005709 | 0.43 |
| ASO-005711 | 0.22 |

FIG. 5 (cont.)

| ASO_NO | LE PAC A-Syn/Tub IC50 (uM) |
|---|---|
| ASO-005717 | 0.21 |
| ASO-005751 | 0.25 |
| ASO-005753 | 0.01 |
| ASO-005755 | 0.01 |
| ASO-005757 | 0.08 |
| ASO-005761 | 0.01 |
| ASO-005762 | 0.04 |
| ASO-005763 | 0.02 |
| ASO-005764 | 0.04 |
| ASO-005766 | 0.01 |
| ASO-005768 | 0.02 |
| ASO-005770 | 0.02 |
| ASO-005783 | 0.27 |
| ASO-005784 | 0.25 |
| ASO-005785 | 0.004 |
| ASO-008414 | 0.02 |
| ASO-008415 | 0.02 |
| ASO-287031 | 0.01 |
| ASO-287957 | 0.02 |
| ASO-287959 | 0.03 |
| ASO-287962 | 0.02 |
| ASO-288906 | 0.08 |
| ASO-313413 | 1.11 |
| ASO-316392 | 0.01 |
| ASO-316393 | 0.02 |
| ASO-316394 | 0.01 |
| ASO-316395 | 0.01 |
| ASO-319536 | 0.01 |
| ASO-319537 | 0.02 |
| ASO-324636 | 0.02 |
| ASO-324637 | 0.02 |
| ASO-324638 | 0.02 |
| ASO-324639 | 0.02 |
| ASO-324641 | 0.04 |
| ASO-324642 | 0.02 |
| ASO-324643 | 0.02 |
| ASO-324644 | 0.02 |
| ASO-324645 | 0.01 |
| ASO-324646 | 0.03 |
| ASO-324647 | 0.03 |
| ASO-325059 | 0.01 |
| ASO-325061 | 0.02 |

FIG. 5 (cont.)

| ASO_NO | LE PAC A-Syn/Tub IC50 (uM) |
|---|---|
| ASO-325067 | 0.03 |
| ASO-002041 | 0.04 |

FIG. 6

| ASO_NO | Tox Score @1D | 3D mRNA %KD | Tox Score @28D | Tox Score WT @28D | 28D mRNA %KD Hippo | 28D mRNA %KD BS | 28D mRNA %KD Str | 28D protein %KD Hippo | 28D protein %KD BS | 28D protein %KD Str |
|---|---|---|---|---|---|---|---|---|---|---|
| ASO-001464 | 8 | | | | | | | | | |
| ASO-002780 | 14.67 | | 20 | | | | | | | |
| ASO-002816 | 0.15 | 95.05 | | | | | | | | |
| ASO-005376 | 5.20 | 92.24 | | 0.60 | | | | | | |
| ASO-005381 | 2.10 | 96.36 | | 20.00 | | | | | | |
| ASO-005390 | 9.20 | | | | | | | | | |
| ASO-005392 | 0.00 | 92.56 | | 0.00 | | | | | | |
| ASO-005396 | 0.20 | | | 20.00 | | | | | | |
| ASO-005399 | 0.10 | 77.33 | | 20.00 | | | | | | |
| ASO-005400 | 0.10 | 94.56 | | 2.33 | | | | | | |
| ASO-005432 | 0.00 | | | 20.00 | | | | | | |
| ASO-005435 | 0.60 | | | 20.00 | | | | | | |
| ASO-005450 | 0.00 | | | 20.00 | | | | | | |
| ASO-005451 | 0.40 | 81.58 | | 20.00 | | | | | | |
| ASO-005452 | 0.00 | | | 20.00 | | | | | | |
| ASO-005453 | 0.00 | 80.42 | | 20.00 | | | | | | |
| ASO-005454 | 2.20 | 95.73 | | 20.00 | | | | | | |
| ASO-005455 | 2.30 | 93.45 | | 4.00 | | | | | | |
| ASO-005458 | 0.20 | | | 20.00 | | | | | | |
| ASO-005459 | 0.50 | 90.83 | | 0.00 | | | | | | |
| ASO-005460 | 0.00 | 92.84 | | 20.00 | | | | | | |
| ASO-005486 | 0.40 | 95.80 | | 0.20 | | | | | | |
| ASO-005492 | 0.20 | | | 20.00 | | | | | | |

FIG. 6 (cont.)

| ASO_NO | Tox Score @1D | 3D mRNA %KD | Tox Score @28D | Tox Score WT @28D | 28D mRNA %KD Hippo | 28D mRNA %KD BS | 28D mRNA %KD Str | 28D protein %KD Hippo | 28D protein %KD BS | 28D protein %KD Str |
|---|---|---|---|---|---|---|---|---|---|---|
| ASO-005496 | 0.00 | 85.02 | | 0.00 | | | | | | |
| ASO-005500 | 0.20 | | | 20.00 | | | | | | |
| ASO-005502 | 1.00 | 97.50 | | 1.20 | | | | | | |
| ASO-005508 | 0.00 | | | 20.00 | | | | | | |
| ASO-005514 | 0.00 | | | 20.00 | | | | | | |
| ASO-005517 | 0.00 | | | 20.00 | | | | | | |
| ASO-005518 | 0.40 | 98.02 | | 2.00 | | | | | | |
| ASO-005525 | 0.20 | 95.31 | | | | | | | | |
| ASO-005532 | 0.00 | 97.17 | | | | | | | | |
| ASO-005576 | 1.20 | 72.40 | | 20.00 | | | | | | |
| ASO-005578 | 0.10 | 87.45 | | 0.00 | | | | | | |
| ASO-005582 | 0.00 | 87.64 | | 5.67 | | | | | | |
| ASO-005584 | 0.00 | 83.95 | | 0.00 | | | | | | |
| ASO-005597 | 2.10 | 85.21 | | 0.00 | | | | | | |
| ASO-005599 | 0.40 | | | 20.00 | | | | | | |
| ASO-005606 | 0.00 | 94.42 | | 3.00 | | | | | | |
| ASO-005607 | 0.40 | | | 20.00 | | | | | | |
| ASO-005608 | 0.60 | 95.86 | | 1.60 | | | | | | |
| ASO-005610 | 1.60 | 98.41 | | 0.80 | | | | | | |
| ASO-005611 | 0.80 | 94.82 | | 0.00 | | | | | | |
| ASO-005612 | 0.60 | | | 20.00 | | | | | | |
| ASO-005628 | 0.60 | | | 2.00 | | | | | | |
| ASO-005631 | 1.20 | | | 1.00 | | | | | | |

FIG. 6 (cont.)

| ASO_NO | Tox Score @1D | 3D mRNA %KD | Tox Score @28D | Tox Score WT @28D | 28D mRNA %KD Hippo | 28D mRNA %KD BS | 28D mRNA %KD Str | 28D protein %KD Hippo | 28D protein %KD BS | 28D protein %KD Str |
|---|---|---|---|---|---|---|---|---|---|---|
| ASO-005632 | 0.60 | | | 3.40 | | | | | | |
| ASO-005637 | 0.00 | | | 5.20 | | | | | | |
| ASO-005638 | 0.00 | | | 20.00 | | | | | | |
| ASO-005640 | 0.40 | | | 20.00 | | | | | | |
| ASO-005641 | 0.00 | | | 4.60 | | | | | | |
| ASO-005650 | 0.00 | | | 0.00 | | | | | | |
| ASO-005651 | 0.00 | | | 1.00 | | | | | | |
| ASO-005652 | 0.00 | | | 0.40 | | | | | | |
| ASO-005671 | 0.00 | | | 1.40 | | | | | | |
| ASO-005677 | 1.20 | 96.05 | | | | | | | | |
| ASO-005679 | 0.00 | 95.70 | | | | | | | | |
| ASO-005682 | 8.00 | 92.07 | | | | | | | | |
| ASO-005685 | 0.00 | 85.75 | | | | | | | | |
| ASO-005700 | 0.00 | 92.82 | | 0.00 | | | | | | |
| ASO-005703 | 0.40 | | | 0.40 | | | | | | |
| ASO-005709 | 3.10 | 96.15 | | 1.00 | | | | | | |
| ASO-005710 | 0.20 | 95.05 | | 0.20 | | | | | | |
| ASO-005711 | 0.30 | 91.78 | | 0.40 | | | | | | |
| ASO-005717 | 0.00 | 96.58 | | 0.00 | | | | | | |
| ASO-005751 | 0.40 | | | 20.00 | | | | | | |
| ASO-005753 | 2.50 | 91.85 | | 5.17 | | | | | | |
| ASO-005755 | 0.60 | | | 20.00 | | | | | | |
| ASO-005757 | 0.40 | | | 20.00 | | | | | | |

FIG. 6 (cont.)

| ASO_NO | Tox Score @1D | 3D mRNA %KD | Tox Score @28D | Tox Score WT @28D | 28D mRNA %KD Hippo | 28D mRNA %KD BS | 28D mRNA %KD Str | 28D protein %KD Hippo | 28D protein %KD BS | 28D protein %KD Str |
|---|---|---|---|---|---|---|---|---|---|---|
| ASO-005762 | 0.00 | | | 1.00 | | | | | | |
| ASO-005763 | 0.60 | | | 0.20 | | | | | | |
| ASO-005764 | 0.00 | | | 1.00 | | | | | | |
| ASO-005766 | 0.00 | 94.10 | | 20.00 | | | | | | |
| ASO-005770 | 0.60 | | | 20.00 | | | | | | |
| ASO-005779 | 0.60 | | | 20.00 | | | | | | |
| ASO-005783 | 0.00 | | | 20.00 | | | | | | |
| ASO-005784 | 0.00 | | | 20.00 | | | | | | |
| ASO-005785 | 0.00 | | | 20.00 | | | | | | |
| ASO-287031 | 0.00 | | | 0.00 | | | | | | |
| ASO-287957 | 0.00 | 68.80 | | 0.00 | | | | | | |
| ASO-287959 | 0.00 | 80.59 | | 0.00 | | | | | | |
| ASO-287962 | 0.00 | 90.88 | | 0.00 | | | | | | |
| ASO-288906 | 0.00 | 67.73 | | 0.00 | | | | | | |

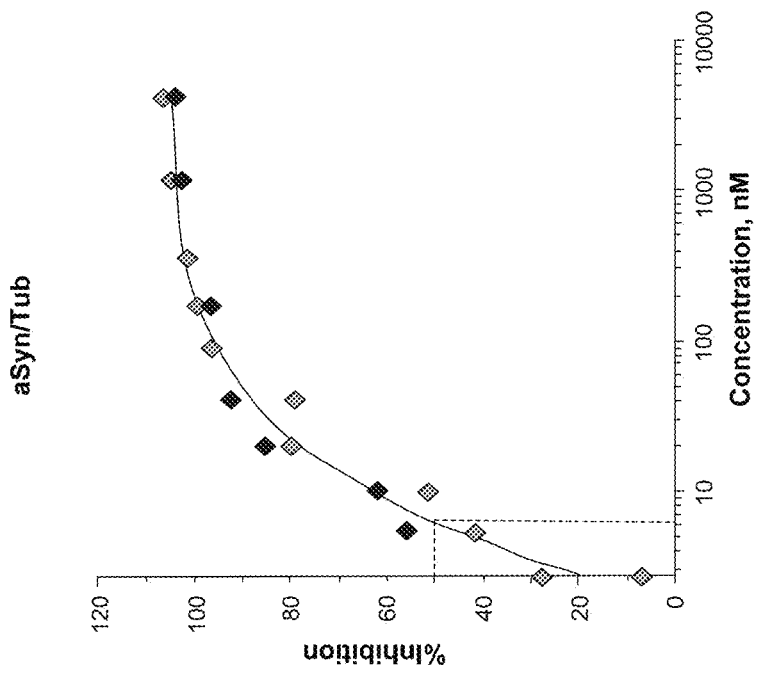
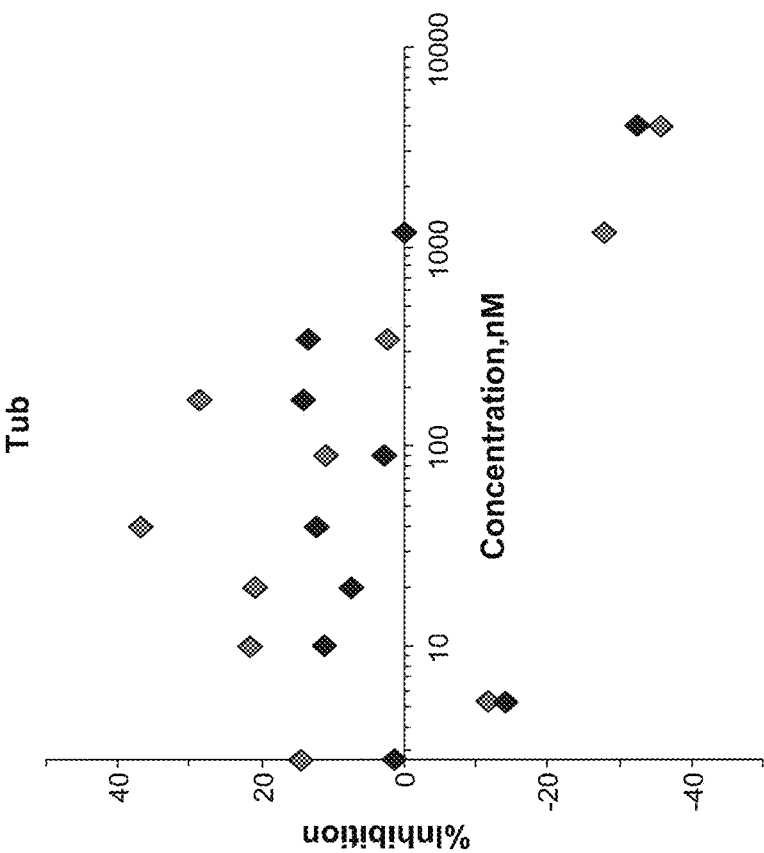

OxyAs DNAts OxyTs DNAcs DNAcs DNAcs DNAts DNAts DNAcs DNAcs DNAas DNAcs OxyAs OxyMCs OxyAs OxyMC

ANTISENSE OLIGONUCLEOTIDES TARGETING ALPHA-SYNUCLEIN AND USES THEREOF

REFERENCE TO SEQUENCE LISTING SUBMITTED ELECTRONICALLY

The content of the electronically submitted sequence listing (Name: 3338.1090001_SequenceListing_ST25.txt, Size: 176,128 bytes; and Date of Creation: Apr. 9, 2024) submitted in this application is incorporated herein by reference in its entirety.

FIELD OF THE DISCLOSURE

The present disclosure relates to antisense oligomeric compounds (ASOs) that target an intron exon junction of alpha-synuclein (SNCA) transcript in a cell, leading to reduced expression of alpha-synuclein (SNCA) protein. Reduction of SNCA protein expression can be beneficial for a range of medical disorders, such as multiple system atrophy, Parkinson's disease, Parkinson's Disease Dementia (PDD), and dementia with Lewy bodies.

BACKGROUND OF THE DISCLOSURE

Alpha-synuclein (SNCA), a member of the synuclein protein family, is a small soluble protein that is expressed primarily within the neural tissues. See Marques O et al., *Cell Death Dis.* 19: e350 (2012). It is expressed in many cell types but is predominantly localized within the presynaptic terminals of neurons. While the precise function has yet to be fully elucidated, SNCA has been suggested to play an important role in the regulation of synaptic transmission. For instance, SNCA functions as a molecular chaperone in the formation of SNARE complexes, which mediate the docking of synaptic vesicles with the presynaptic membranes of neurons. SNCA can also interact with other proteins like the microtubule-associated protein tau, which helps stabilize microtubules and regulate vesicle trafficking.

Due to SNCA's role in the regulation of synaptic transmission, alterations of SNCA expression and/or function can disrupt critical biological processes. Such disruptions have been thought to contribute to α-synucleinopathies, which are neurodegenerative diseases characterized by abnormal accumulation of SNCA protein aggregates within the brain. Accordingly, insoluble inclusions of misfolded, aggregated, and phosphorylated SNCA protein are a pathological hallmark for diseases such as Parkinson's disease (PD), Parkinson's Disease Dementia (PDD), dementia with Lewy bodies (DLB), and multiple system atrophy (MSA). See Galvin J E et al., *Archives of Neurology* 58: 186-190 (2001); and Valera E et al., *J Neurochem* 139 Suppl 1: 346-352 (October 2016).

α-Synucleinopathies, such as Parkinson's disease, are highly prevalent progressive neurodegenerative brain disorders, especially among the elderly. See Recchia A et al., *FASEB J.* 18: 617-26 (2004). It is estimated that approximately seven to ten million people worldwide are living with such disorders, with about 60,000 new cases each year in the United States alone. Medication costs for an individual person can easily exceed $2,500 a year and therapeutic surgery can cost up to $100,000 per patient. Therefore, a more robust and cost-effective treatment options are greatly needed.

BRIEF SUMMARY OF THE DISCLOSURE

The present disclosure is directed to an antisense oligonucleotide (ASO) comprising a contiguous nucleotide sequence of 10 to 30 nucleotides in length that are complementary to a nucleic acid sequence within an alpha-synuclein (SNCA) transcript, wherein the nucleic acid sequence comprises nucleotides 7592-7637 of SEQ ID NO: 28. In some embodiments, the nucleic acid sequence comprises nucleotides 7602-7627 of SEQ ID NO: 28. In other embodiments, the nucleic acid sequence corresponds to nucleotides 7603-7620 of SEQ ID NO: 28. In certain embodiments, the nucleic acid sequence corresponds to nucleotides 7604-7620 of SEQ ID NO: 28. In some embodiments, the SNCA transcript comprises SEQ ID NO: 28. In some embodiments, the contiguous nucleotide sequence comprises SEQ ID NO: 4 to SEQ ID NO: 21 with one, two, three, or four mismatches. In other embodiments, the contiguous nucleotide sequence comprises SEQ ID NO: 4 to SEQ ID NO: 21. In certain embodiments, the contiguous nucleotide sequence comprises SEQ ID NO: 15 or SEQ ID NO: 7.

In some embodiments, the antisense oligonucleotide of the present disclosure is capable of inhibiting the expression of the human SNCA transcript in a cell which is expressing the human SNCA transcript.

In some embodiments, the contiguous nucleotide sequence comprises at least one nucleotide analogue. In some embodiments, the antisense oligonucleotide is a gapmer. In other embodiments, the antisense oligonucleotide is an alternating flank gapmer.

In some embodiments, the antisense oligonucleotide as disclosed herein comprises the formula of 5'-A-B—C-3', wherein, (i) region B is a contiguous sequence of at least 6 DNA units, which are capable of recruiting RNase; (ii) region A is a first wing sequence of 1 to 10 nucleotides, wherein the first wing sequence comprises one or more nucleotide analogues and optionally one or more DNA units and wherein at least one of the nucleotide analogues is located at the 3' end of A; and (iii) region C is a second wing sequence of 1 to 10 nucleotides, wherein the second wing sequence comprises one or more nucleotide analogues and optionally one or more DNA units and wherein at least one of the nucleotide analogues is located at the 5' end of C.

In some embodiments, region A comprises a combination of nucleotide analogues and DNA unit selected from (i) 1-10 nucleotide analogs and 0 DNA unit; (ii) 1-9 nucleotide analogues and 1 DNA unit; (iii) 1-8 nucleotide analogues and 1-2 DNA units; (iv) 1-7 nucleotide analogues and 1-3 DNA units; (v) 1-6 nucleotide analogues and 1-4 DNA units; (vi) 1-5 nucleotide analogues and 1-5 DNA units; (vii) 1-4 nucleotide analogues and 1-6 DNA units; (viii) 1-3 nucleotide analogues and 1-7 DNA units; (ix) 1-2 nucleotide analogues and 1-8 DNA units; and (x) 1 nucleotide analogue and 1-9 DNA units. In some embodiments, region C comprises a combination of nucleotide analogues and DNA unit selected from (i) 1-10 nucleotide analogs and 0 DNA unit; (ii) 1-9 nucleotide analogues and 1 DNA unit; (iii) 1-8 nucleotide analogues and 1-2 DNA units; (iv) 1-7 nucleotide analogues and 1-3 DNA units; (v) 1-6 nucleotide analogues and 1-4 DNA units; (vi) 1-5 nucleotide analogues and 1-5 DNA units; (vii) 1-4 nucleotide analogues and 1-6 DNA units; (viii) 1-3 nucleotide analogues and 1-7 DNA units; (ix) 1-2 nucleotide analogues and 1-8 DNA units; and (x) 1 nucleotide analogue and 1-9 DNA units. In some embodiments, region A is a first wing design selected from any ASOs in FIGS. 2 and 3 and/or region C is a second wing design selected from any ASOs in FIGS. 2 and 3, wherein the upper letter is a nucleoside analog and the lower letter is a DNA.

In some embodiments, the antisense oligonucleotide of the present disclosure comprises at least two, at least three, at least four, at least five, at least six, at least seven, at least eight, at least nine, or at least ten nucleotide analogues. In certain embodiments, the nucleotide analogue or analogues are one or more sugar modified nucleosides selected from the group consisting of Locked Nucleic Acid (LNA); 2'-O-alkyl-RNA; 2'-amino-DNA; 2'-fluoro-DNA; arabino nucleic acid (ANA); 2'-fluoro-ANA, hexitol nucleic acid (HNA), intercalating nucleic acid (INA), constrained ethyl nucleoside (cEt), 2'-O-methyl nucleic acid (2'-OMe), 2'-O-methoxyethyl nucleic acid (2'-MOE), and any combination thereof. In some embodiments, the nucleotide analogue or analogues comprise a bicyclic sugar. In certain embodiments, the bicyclic sugar comprises cEt, 2',4'-constrained 2'-O-methoxyethyl (cMOE), LNA, α-L-LNA, β-D-LNA, 2'-0,4'-C-ethylene-bridged nucleic acids (ENA), amino-LNA, oxy-LNA, or thio-LNA. In some embodiments, the nucleotide analogue or analogues comprise an LNA.

In some embodiments, the antisense oligonucleotide comprises one or more 5' methyl cytosine nucleobases. In some embodiments, the antisense oligonucleotide comprises two to five LNAs on the 5' region of the antisense oligonucleotide. In some embodiments, the antisense oligonucleotide comprises two to five LNAs on the 3' region of the antisense oligonucleotide.

In some embodiments, the antisense oligonucleotide has an in vivo tolerability less than or equal to a total score of 4, wherein the total score is the sum of a unit score of five categories, which are 1) hyperactivity; 2) decreased activity and arousal; 3) motor dysfunction and/or ataxia; 4) abnormal posture and breathing; and 5) tremor and/or convulsions, and wherein the unit score for each category is measured on a scale of 0-4. In certain embodiments, the in vivo tolerability is less than or equal to the total score of 3, the total score of 2, the total score of 1, or the total score of 0.

In some embodiments, the antisense oligonucleotide reduces expression of SNCA mRNA in a cell by at least about 20%, at least about 30%, at least about 40%, at least about 50%, at least about 60%, at least about 70%, at least about 80%, at least about 90%, or about 100% compared to a cell not exposed to the antisense oligonucleotide. In other embodiments, the antisense oligonucleotide reduces expression of SNCA protein in a cell by at least about 60%, at least about 70%, at least about 80%, at least about 90%, or at least about 95% compared to a cell not exposed to the antisense oligonucleotide.

In some embodiments, the antisense oligonucleotide comprises the nucleotides A, T, C, and G and at least one analogue of the nucleotides A, T, C, and G, and has a sequence score greater than or equal to 0.2, wherein the sequence score is calculated by formula I:

$$\text{\#of C nucleotides and analogues thereof} - \text{\#of G nucleotides and analogues thereof/Total nucleotide length.} \quad (I)$$

In some embodiments, the antisense oligonucleotide has from 10 to 24 nucleotides in length or from 14 to 21 nucleotides in length. In other embodiments, the antisense oligonucleotide has 14, 15, 16, 17, 18, 19, 20, or 21 nucleotides in length.

In some embodiments, the nucleotide sequence of the antisense oligonucleotide comprises, consists essentially of, or consists of a sequence selected from the group consisting of SEQ ID NOs: 4 to 21 with a design selected from the group consisting of the designs in FIGS. 2 and 3, wherein the upper case letter is a sugar modified nucleoside and the lower case letter is DNA. In certain embodiments, the nucleotide sequence comprises, consists essentially of, or consists of SEQ ID NO: 15 with the design of ASO-005459 and SEQ ID NO: 7 with the design of ASO-005578 or ASO-005584. In other embodiments, the nucleotide sequence comprises, consists essentially of, or consists of a sequence selected from the group consisting of SEQ ID NOs: 4-21 with the corresponding chemical structure in FIGS. 2 and 3. In certain embodiments, the nucleotide sequence comprises, consists essentially of, or consists of ASO-005459, ASO-005578, and ASO-005584. In some embodiments, the ASO of the present disclosure comprises a molecular formula of $C_{171}H_{214}N_{56}O_{90}P_{16}S_{16}$. In some embodiments, the ASO comprises a molecular formula of $C_{182}H_{229}N_{58}O_{96}P_{17}S_{17}$. In other embodiments, the ASO comprises a molecular formula of $C_{181}H_{227}N_{58}O_{96}P_{17}S_{17}$.

In some embodiments, the antisense oligonucleotide of the present disclosure comprises an internucleoside linkage selected from: a phosphodiester linkage, a phosphotriester linkage, a methylphosphonate linkage, a phosphoramidate linkage, a phosphorothioate linkage, and combinations thereof. In certain embodiments, the internucleoside linkage comprises one or more stereo-defined, modified phosphate linkages.

The present disclosure also provides a conjugate comprising the antisense oligonucleotide as disclosed herein, wherein the antisense oligonucleotide is covalently attached to at least one non-nucleotide or non-polynucleotide moiety. In some embodiments, the non-nucleotide or non-polynucleotide moiety comprises a protein, a fatty acid chain, a sugar residue, a glycoprotein, a polymer, or any combinations thereof.

Also provided herein is a pharmaceutical composition comprising the antisense oligonucleotide or the conjugate as disclosed herein and a pharmaceutically acceptable carrier. In some embodiments, the composition further comprises a therapeutic agent. In certain embodiments, the therapeutic agent is an alpha-synuclein antagonist. In some embodiments, the alpha-synuclein antagonist is an anti-alpha-synuclein antibody or fragment thereof.

The present disclosure further provides a kit comprising the antisense oligonucleotide, the conjugate, or the composition as disclosed herein. Also disclosed is a diagnostic kit comprising the antisense oligonucleotide, the conjugate, or the composition of the present disclosure.

The present disclosure is also directed to method of inhibiting or reducing SNCA protein expression in a cell, the method comprising administering the antisense oligonucleotide, the conjugate, or the composition as disclosed herein to the cell expressing SNCA protein, wherein the SNCA protein expression in the cell is inhibited or reduced after the administration. In some embodiments, the antisense oligonucleotide inhibits or reduces expression of SNCA mRNA in the cell after the administration. In certain embodiments, the expression of SNCA mRNA is reduced by at least about 20%, at least about 30%, at least about 40%, at least about 50%, at least about 60%, at least about 70%, at least about 80%, at least about 90%, or about 100% after the administration compared to a cell not exposed to the antisense oligonucleotide. In other embodiments, the antisense oligonucleotide reduces expression of SNCA protein in the cell after the administration by at least about 60%, at least about 70%, at least about 80%, or at least about 90% compared to a cell not exposed to the antisense oligonucleotide. In some embodiments, the cell is a neuron.

Provided herein is a method for treating a synucleinopathy in a subject in need thereof, comprising administering an effective amount of the antisense oligonucleotide, the conjugate, or the composition of the present disclosure. In some embodiments, the synucleinopathy is selected from the group consisting of Parkinson's disease, Parkinson's Disease Dementia (PDD), multiple system atrophy, dementia with Lewy bodies, and any combinations thereof.

Also provided herein is a use of the antisense oligonucleotide, the conjugate, or the composition of the present disclosure for the manufacture of a medicament. The present disclosure also provides the use of the antisense oligonucleotide, the conjugate, or the composition for the manufacture of a medicament for the treatment of a synucleinopathy in a subject in need thereof. In some embodiments, the antisense oligonucleotide, the conjugate, or the composition of the present disclosure is for use in therapy of a synucleinopathy in a subject in need thereof. In other embodiments, the antisense oligonucleotide, the conjugate, or the composition of the present disclosure is for use in therapy.

In some embodiments, the subject is a human. In some embodiments, the antisense oligonucleotide, the conjugate, or the composition is administered orally, parenterally, intrathecally, intra-cerebroventricularly, pulmonarily, topically, or intraventricularly.

In some embodiments, the nucleotide analog comprises a sugar modified nucleoside. In some embodiments, the sugar modified nucleoside is an affinity enhancing sugar modified nucleoside.

BRIEF DESCRIPTION OF THE FIGURES

FIGS. 1A, 1, and 1C show alpha-synuclein genomic (partial), mRNA, and protein sequences. The sequence in FIG. 1A represents a partial SNCA genomic sequence (i.e., residues 6001 to 8400 of SEQ ID NO: 28; SEQ ID NO: 1). SEQ ID NO: 1 is identical to a SNCA pre-mRNA sequence except that the nucleotide "t" in SEQ ID NO: 1 is shown as "u" in the pre-mRNA. SEQ ID NO: 2 in FIG. 1B represents a SNCA mRNA sequence except that the nucleotide "t" in SEQ ID NO: 2 is shown as "u" in the mRNA. FIG. 1C shows SNCA protein sequence (SEQ ID NO: 3).

FIG. 2 shows exemplary ASOs targeting the intron exon junction of the SNCA pre-mRNA. Each column of FIG. 2 shows the Sequence ID number (SEQ ID No.) designated for the sequence only, the target start and end positions on the SNCA pre-mRNA sequence, the target start and end positions on the SNCA mRNA sequence, the design number (DES No.), the ASO sequence with a design, the ASO number (ASO No.), and the ASO sequence with a chemical structure.

FIG. 3 shows ASOs targeting the intron exon junction of the SNCA pre-mRNA with exemplary wing design modification. Each column of FIG. 3 shows the Sequence ID number (SEQ ID No.) designated for the sequence only, the target start and end positions on the SNCA pre-mRNA sequence, the design number (DES No.), the ASO sequence with a design, the ASO number (ASO No.), and the ASO sequence with a chemical structure and wing design modification identified. DES-316392, DES-316393, DES-316394, and DES-316395 show various ASO designs possible for SEQ ID NO: 7. DES-287031, DES-287957, DES-287959, DES-287962, DES-288906, and DES-313413 show various ASO designs possible for SEQ ID NO: 12. DES-319536, DES-319537, DES-325058, DES-325059, DES-325060, DES-325061, DES-325062, DES-325063, DES-325064, DES-325065, DES-325066, DES-325067, DES-325068, and DES-325069 show various ASO designs possible for SEQ ID NO: 14. DES-324636, DES-324637, DES-324638, DES-324639, DES-324640, DES-324641, DES-324642, DES-324643, DES-324644, DES-324645, DES-324646, and DES324647 show various ASO designs possible for SEQ ID NO: 15. For the ASO designs, the upper letters indicate nucleotide analogues (e.g., LNA or 2'-O-Methyl (OMe)), and the lower letters indicate DNAs. The upper letters with or without underlines indicate the two letters can be different nucleotide analogues, e.g., LNA and 2'-O-Methyl. For example, the underlined upper letters can be 2'-O-Methyl while the upper letters without underlines are LNA. In the ASOs with chemical structure column, OMe is 2'-O-Methyl nucleotide, L is LNA, D is DNA, and the numbers followed by L or D mean the number of LNAs or DNAs FIG. 4 shows the percent reduction of SNCA protein expression in both a human neuroblastoma cell line SK—N-BE(2) ("SK cells") and primary neurons isolated from A53T-PAC transgenic mice ("PAC neurons") after in vitro culture with various ASOs as described in Example 2A for PAC neurons and Example 2E for SK cells. For the SK cells, the cells were treated with 25 µM of ASO and the SNCA mRNA expression (normalized to GAPDH) is shown as a percent of the control. For the PAC neurons, the cells were treated with either 40 nM or 5 µM of ASO and the SNCA protein expression (normalized to tubulin) is shown as percent inhibition. Where no value is provided, the particular ASO was not tested under the particular conditions.

FIG. 5 shows the potency of the various ASOs in reducing SNCA protein expression in primary neurons isolated from A53T-PAC transgenic mice in vitro. As described in Example 2A, the PAC neurons were cultured in vitro with a 10-point titration of the different ASOs and the potency ($IC_{50}$) of the ASOs is shown as a ratio of SNCA to tubulin expression (µM).

FIG. 6 shows the tolerability score ("Tox Score") and the percent reduction (or knockdown, "KD") of both the SNCA mRNA and SNCA protein expression in ASO-treated A53T-PAC transgenic or WT (wild-type) mice (see Example 4). The tolerability scores are provided for days 1 (1 D) and 28 (28 D) post ASO administration. The percent reduction in SNCA mRNA and SNCA protein expression is shown for days 3 and 28 post ASO administration in the hippocampus (Hippo), brain stem (BS), and striatum (Str).

FIGS. 7A and 7B show the effect of ASO-005459 on SNCA and tubulin (Tub) protein expression in primary neurons isolated from A53T-PAC transgenic mice. Neurons were treated with a 10-point titration of ASO-005459 and amounts of SNCA and tubulin protein measured. Percent inhibition of α-Syn/Tub ratio (FIG. 7A) and Tub levels (FIG. 7B) are shown. Each data point represents an individual replicate.

In FIG. 10A, the A53T-PAC mice were dosed with 3.13 µg, 12.5 µg, 25 µg, or 50 µg of ASO-005459 and their bodyweights measured at weeks 0, 1, and 2 post-treatment. In FIG. 10B, C57BL/6 mice were dosed with 100 µg of ASO-005459 and the animals' body weight was measured once a week during a course of 28 days. In both FIGS. 10A and 10B, animals receiving the vehicle control were used as controls. Data shown represents the mean±SD from multiple animals (n=5). Statistics shown is based on 2-way ANOVA.

FIG. 13D shows the data from the hippocampus (circle), brainstem (square), and striatum (triangle) in combination. Each data point represents an individual animal. A four-parameter, nonlinear fit is shown for the hippocampus (FIG. 13A) and the brainstem (FIG. 13B).

In FIG. 18A, the animals received one of the following: vehicle control (circle), ASO-005578 (square, 4 mg), or ASO-005584 (triangle, 4 mg). Then, the animals were sacrificed at 2 weeks post-dosing. In FIG. 18B, the animals received either the vehicle control or ASO-005584 (8 mg per animal) and then were sacrificed at 2 weeks (square) and 4 weeks post dosing (triangle). In both FIGS. 18A and 18B, the SNCA mRNA expression level in the following tissues was assessed: medulla (top left panel), caudate putamen (top middle panel), pons (top right panel), cerebellum (bottom left panel), lumbar spinal cord (bottom middle panel), and frontal cortex (bottom right panel). The SNCA mRNA expression levels shown in FIGS. 18A and 18B were normalized to GAPDH and then shown relative to the mean of the control group ("vehicle"). Both the data for the individual animals and the mean are shown. The horizontal line marks the reference value of 100% (i.e., value at which the SNCA mRNA expression would be equivalent to expression level observed in the vehicle control group).

DETAILED DESCRIPTION OF DISCLOSURE

I. Definitions

Figure 8:
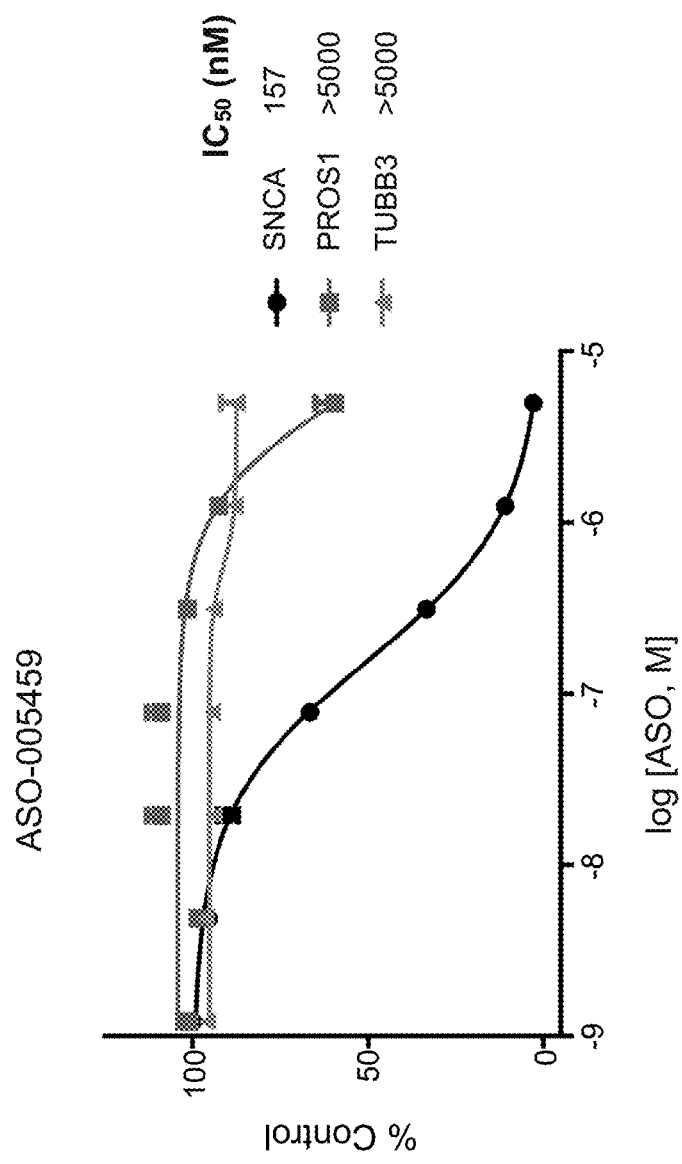
FIG. 8 shows the effect of ASO-005459 on the expression level of SNCA (circle), Protein S (alpha) (PROS1 (square)), and Tubulin (TUBB3 (triangle)) mRNAs in human neurons. The neurons were treated with various concentrations of ASO-005459 for 6 days, and then, the mRNA levels were measured by QUANTIGENE® assay. The expression level of the mRNAs is shown as a percent of the control. Data shown represents the mean±SD from duplicate determinations.

It is to be noted that the term "a" or "an" entity refers to one or more of that entity; for example, "a nucleotide sequence," is understood to represent one or more nucleotide sequences. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. Unless otherwise indicated, nucleotide sequences are written left to right in 5' to 3' orientation. Amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

The term "about" is used herein to mean approximately, roughly, around, or in the regions of. When the term "about" is used in conjunction with a numerical range, it modifies that range by extending the boundaries above and below the numerical values set forth. In general, the term "about" can modify a numerical value above and below the stated value by a variance of, e.g., 10 percent, up or down (higher or lower). For example, if it is stated that "the ASO reduces expression of SNCA protein in a cell following administration of the ASO by at least about 60%," it is implied that the SNCA levels are reduced by a range of 50% to 70%.

The term "antisense oligonucleotide" (ASO) refers to an oligomer or polymer of nucleosides, such as naturally-occurring nucleosides or modified forms thereof, that are covalently linked to each other through internucleotide linkages. The ASO useful for the disclosure includes at least one non-naturally occurring nucleoside. An ASO is complementary to a target nucleic acid, such that the ASO hybridizes to the target nucleic acid sequence. The terms "antisense ASO," "ASO," and "oligomer" as used herein are interchangeable with the term "ASO."

The term "nucleic acids" or "nucleotides" is intended to encompass plural nucleic acids. In some embodiments, the term "nucleic acids" or "nucleotides" refers to a target sequence, e.g., pre-mRNAs, mRNAs, or DNAs in vivo or in vitro. When the term refers to the nucleic acids or nucleotides in a target sequence, the nucleic acids or nucleotides can be naturally occurring sequences within a cell. In other embodiments, "nucleic acids" or "nucleotides" refer to a sequence in the ASOs of the disclosure. When the term refers to a sequence in the ASOs, the nucleic acids or nucleotides are not naturally occurring, i.e., chemically synthesized, enzymatically produced, recombinantly produced, or any combination thereof. In one embodiment, the nucleic acids or nucleotides in the ASOs are produced synthetically or recombinantly, but are not a naturally occurring sequence or a fragment thereof. In another embodiment, the nucleic acids or nucleotides in the ASOs are not naturally occurring because they contain at least one nucleotide analog that is not naturally occurring in nature. The term "nucleic acid" or "nucleoside" refers to a single nucleic acid segment, e.g., a DNA, an RNA, or an analog thereof, present in a polynucleotide. "Nucleic acid" or "nucleoside" includes naturally occurring nucleic acids or non-naturally occurring nucleic acids. In some embodiments, the terms "nucleotide", "unit" and "monomer" are used interchangeably. It will be recognized that when referring to a sequence of nucleotides or monomers, what is referred to is the sequence of bases, such as A, T, G, C or U, and analogs thereof.

The term "nucleotide" as used herein, refers to a glycoside comprising a sugar moiety, a base moiety and a covalently linked group (linkage group), such as a phosphate or phosphorothioate internucleotide linkage group, and covers both naturally occurring nucleotides, such as DNA or RNA, and non-naturally occurring nucleotides comprising modified sugar and/or base, which are also referred to as "nucleotide analogs" herein. Herein, a single nucleotide (unit) can also be referred to as a monomer or nucleic acid unit. In certain embodiments, the term "nucleotide analogs" refers to nucleotides having modified sugar moieties. Non-limiting examples of the nucleotides having modified sugar moieties (e.g., LNA) are disclosed elsewhere herein. In other embodiments, the term "nucleotide analogs" refers to nucleotides having modified nucleobase moieties. The nucleotides having modified nucleobase moieties include, but are not limited to, 5-methylcytosine, isocytosine, pseudoisocytosine, 5-bromouracil, 5-propynyluracil, 6-aminopurine, 2-aminopurine, inosine, diaminopurine, and 2-chloro-6-aminopurine.

The term "nucleoside" as used herein is used to refer to a glycoside comprising a sugar moiety and a base moiety, which can be covalently linked by the internucleotide linkages between the nucleosides of the ASO. In the field of biotechnology, the term "nucleoside" is often used to refer to a nucleic acid monomer or unit. In the context of an ASO, the term "nucleoside" can refer to the base alone, i.e., a nucleobase sequence comprising cytosine (DNA and RNA), guanine (DNA and RNA), adenine (DNA and RNA), thymine (DNA) and uracil (RNA), in which the presence of the sugar backbone and internucleotide linkages are implicit. Likewise, particularly in the case of oligonucleotides where one or more of the internucleotide linkage groups are modified, the term "nucleotide" can refer to a "nucleoside." For example the term "nucleotide" can be used, even when specifying the presence or nature of the linkages between the nucleosides.

The term "nucleotide length" as used herein means the total number of the nucleotides (monomers) in a given sequence. For example, the sequence of AtTcctttacaccACAC (SEQ ID NO: 15) has 17 nucleotides; thus the nucleotide length of the sequence is 17. The term "nucleotide length" is therefore used herein interchangeably with "nucleotide number."

As one of ordinary skill in the art would recognize, the 5' terminal nucleotide of an oligonucleotide does not comprise a 5' internucleotide linkage group, although it can comprise a 5' terminal group.

As used herein, a "coding region" or "coding sequence" is a portion of polynucleotide which consists of codons translatable into amino acids. Although a "stop codon" (TAG, TGA, or TAA) is typically not translated into an amino acid, it can be considered to be part of a coding region, but any flanking sequences, for example promoters, ribosome binding sites, transcriptional terminators, introns, untranslated regions ("UTRs"), and the like, are not part of a coding region. The boundaries of a coding region are typically determined by a start codon at the 5' terminus, encoding the amino terminus of the resultant polypeptide, and a translation stop codon at the 3' terminus, encoding the carboxyl terminus of the resulting polypeptide.

The term "non-coding region" as used herein means a nucleotide sequence that is not a coding region. Examples of non-coding regions include, but are not limited to, promoters, ribosome binding sites, transcriptional terminators, introns, untranslated regions ("UTRs"), non-coding exons and the like. Some of the exons can be wholly or part of the 5' untranslated region (5' UTR) or the 3' untranslated region (3' UTR) of each transcript. The untranslated regions are important for efficient translation of the transcript and for controlling the rate of translation and half-life of the transcript.

The term "region" when used in the context of a nucleotide sequence refers to a section of that sequence. For example, the phrase "region within a nucleotide sequence" or "region within the complement of a nucleotide sequence" refers to a sequence shorter than the nucleotide sequence, but longer than at least 10 nucleotides located within the particular nucleotide sequence or the complement of the nucleotides sequence, respectively. The term "sub-sequence" or "subsequence" can also refer to a region of a nucleotide sequence.

The term "downstream," when referring to a nucleotide sequence, means that a nucleic acid or a nucleotide sequence is located 3' to a reference nucleotide sequence. In certain embodiments, downstream nucleotide sequences relate to sequences that follow the starting point of transcription. For example, the translation initiation codon of a gene is located downstream of the start site of transcription.

The term "upstream" refers to a nucleotide sequence that is located 5' to a reference nucleotide sequence.

Unless otherwise indicated, the sequences provided herein are listed from 5' end (left) to 3' end (right).

As used herein, the term "regulatory region" refers to nucleotide sequences located upstream (5' non-coding sequences), within, or downstream (3' non-coding sequences) of a coding region, and which influence the transcription, RNA processing, stability, or translation of the associated coding region. Regulatory regions can include promoters, translation leader sequences, introns, polyadenylation recognition sequences, RNA processing sites, effector binding sites, UTRs, and stem-loop structures. If a coding region is intended for expression in a eukaryotic cell, a polyadenylation signal and transcription termination sequence will usually be located 3' to the coding sequence.

The term "transcript" as used herein can refer to a primary transcript that is synthesized by transcription of DNA and becomes a messenger RNA (mRNA) after processing, i.e., a precursor messenger RNA (pre-mRNA), and the processed mRNA itself. The term "transcript" can be interchangeably used with "pre-mRNA" and "mRNA." After DNA strands are transcribed to primary transcripts, the newly synthesized primary transcripts are modified in several ways to be converted to their mature, functional forms such as mRNA, tRNA, rRNA, lncRNA, miRNA and others. Thus, the term "transcript" can include exons, introns, 5' UTRs, and 3' UTRs.

The term "expression" as used herein refers to a process by which a polynucleotide produces a gene product, for example, a RNA or a polypeptide. It includes, without limitation, transcription of the polynucleotide into messenger RNA (mRNA) and the translation of an mRNA into a polypeptide. Expression produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation or splicing, or polypeptides with post translational modifications, e.g., methylation, glycosylation, the addition of lipids, association with other protein subunits, or proteolytic cleavage.

The terms "identical" or percent "identity" in the context of two or more nucleic acids refer to two or more sequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences.

One such non-limiting example of a sequence alignment algorithm is the algorithm described in Karlin et al., 1990, *Proc. Natl. Acad. Sci.*, 87:2264-2268, as modified in Karlin et al., 1993, *Proc. Natl. Acad. Sci.*, 90:5873-5877, and incorporated into the NBLAST and XBLAST programs (Altschul et al., 1991, *Nucleic Acids Res.*, 25:3389-3402). In certain embodiments, Gapped BLAST can be used as described in Altschul et al., 1997, *Nucleic Acids Res.* 25:3389-3402. BLAST-2, WU-BLAST-2 (Altschul et al., 1996, *Methods in Enzymology*, 266:460-480), ALIGN, ALIGN-2 (Genentech, South San Francisco, California) or Megalign (DNASTAR) are additional publicly available software programs that can be used to align sequences. In certain embodiments, the percent identity between two nucleotide sequences is determined using the GAP program in the GCG software package (e.g., using a NWSgapdna.CMP matrix and a gap weight of 40, 50, 60, 70, or 90 and a length weight of 1, 2, 3, 4, 5, or 6). In certain alternative embodiments, the GAP program in the GCG software package, which incorporates the algorithm of Needleman and Wunsch (*J. Mol. Biol*. (48):444-453 (1970)) can be used to determine the percent identity between two amino acid sequences (e.g., using either a BLOSUM 62 matrix or a PAM250 matrix, and a gap weight of 16, 14, 12, 10, 8, 6, or 4 and a length weight of 1, 2, 3, 4, 5). Alternatively, in certain embodiments, the percent identity between nucleotide or amino acid sequences is determined using the algorithm of Myers and Miller (CABIOS, 4:11-17 (1989)). For example, the percent identity can be determined using the ALIGN program (version 2.0) and using a PAM120 with residue table, a gap length penalty of 12 and a gap penalty of 4. One skilled in the art can determine appropriate parameters for maximal alignment by particular alignment software. In certain embodiments, the default parameters of the alignment software are used.

In certain embodiments, the percentage identity "X" of a first nucleotide sequence to a second nucleotide sequence is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence.

Different regions within a single polynucleotide target sequence that align with a polynucleotide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

As used herein, the terms "homologous" and "homology" are interchangeable with the terms "identity" and "identical."

The term "naturally occurring variant thereof" refers to variants of the SNCA polypeptide sequence or SNCA nucleic acid sequence (e.g., transcript) which exist naturally within the defined taxonomic group, such as mammalian, such as mouse, monkey, and human. Typically, when referring to "naturally occurring variants" of a polynucleotide the term also can encompass any allelic variant of the SNCA-encoding genomic DNA which is found at Chromosomal position 17q21 by chromosomal translocation or duplication, and the RNA, such as mRNA derived therefrom. "Naturally occurring variants" can also include variants derived from alternative splicing of the SNCA mRNA. When referenced to a specific polypeptide sequence, e.g., the term also includes naturally occurring forms of the protein, which can therefore be processed, e.g., by co- or post-translational modifications, such as signal peptide cleavage, proteolytic cleavage, glycosylation, etc.

In determining the degree of "complementarity" between ASOs of the disclosure (or regions thereof) and the target region of the nucleic acid which encodes mammalian SNCA protein (e.g., the SNCA gene), such as those disclosed herein, the degree of "complementarity" (also, "homology" or "identity") is expressed as the percentage identity (or percentage homology) between the sequence of the ASO (or region thereof) and the sequence of the target region (or the reverse complement of the target region) that best aligns therewith. The percentage is calculated by counting the number of aligned bases that are identical between the two sequences, dividing by the total number of contiguous monomers in the ASO, and multiplying by 100. In such a comparison, if gaps exist, it is preferable that such gaps are merely mismatches rather than areas where the number of monomers within the gap differs between the ASO of the disclosure and the target region.

The term "complement" as used herein indicates a sequence that is complementary to a reference sequence. It is well known that complementarity is the base principle of DNA replication and transcription as it is a property shared between two DNA or RNA sequences, such that when they are aligned antiparallel to each other, the nucleotide bases at each position in the sequences will be complementary, much like looking in the mirror and seeing the reverse of things. Therefore, for example, the complement of a sequence of 5'"ATGC"3' can be written as 3'"TACG"5' or 5'"GCAT"3'. The terms "reverse complement", "reverse complementary" and "reverse complementarity" as used herein are interchangeable with the terms "complement", "complementary" and "complementarity."

The terms "corresponding to" and "corresponds to," when referencing two separate nucleic acid or nucleotide sequences can be used to clarify regions of the sequences that correspond or are similar to each other based on homology and/or functionality, although the nucleotides of the specific sequences can be numbered differently. For example, different isoforms of a gene transcript can have similar or conserved portions of nucleotide sequences whose numbering can differ in the respective isoforms based on alternative splicing and/or other modifications. In addition, it is recognized that different numbering systems can be employed when characterizing a nucleic acid or nucleotide sequence (e.g., a gene transcript and whether to begin numbering the sequence from the translation start codon or to include the 5'UTR). Further, it is recognized that the nucleic acid or nucleotide sequence of different variants of a gene or gene transcript can vary. As used herein, however, the regions of the variants that share nucleic acid or nucleotide sequence homology and/or functionality are deemed to "correspond" to one another. For example, a nucleotide sequence of a SNCA transcript corresponding to nucleotides X to Y of SEQ ID NO: 28 ("reference sequence") refers to an SNCA transcript sequence (e.g., SNCA pre-mRNA or mRNA) that has an identical sequence or a similar sequence to nucleotides X to Y of SEQ ID NO: 28. A person of ordinary skill in the art can identify the corresponding X and Y residues in the SNCA transcript sequence by aligning the SNCA transcript sequence with SEQ ID NO: 28.

The terms "corresponding nucleotide analog" and "corresponding nucleotide" are intended to indicate that the nucleobase in the nucleotide analog and the naturally occurring nucleotide have the same pairing, or hybridizing, ability. For example, when the 2-deoxyribose unit of the nucleotide is linked to an adenine, the "corresponding nucleotide analog" contains a pentose unit (different from 2-deoxyribose) linked to an adenine.

The term "DES Number" or "DES No." as used herein refers to a unique number given to a nucleotide sequence having a specific pattern of nucleosides (e.g., DNA) and nucleoside analogs (e.g., LNA). As used herein, the design of an ASO is shown by a combination of upper case letters and lower case letters. For example, DES-005459 refers to an ASO sequence of AtTcctttacaccACAC (SEQ ID NO: 15) with an ASO design of LDLDDDDDDDDDDLLLL (i.e., AtTcctttacaccACAC), wherein the L (i.e., upper case letter) indicates a nucleoside analog (e.g., LNA) and the D (i.e., lower case letter) indicates a nucleoside (e.g., DNA).

The term "ASO Number" or "ASO No." as used herein refers to a unique number given to a nucleotide sequence having the detailed chemical structure of the components, e.g., nucleosides (e.g., DNA), nucleoside analogs (e.g., beta-D-oxy-LNA), nucleobase (e.g., A, T, G, C, U, or MC), and backbone structure (e.g., phosphorothioate or phosphodiester). For example, ASO-005459 refers to OxyAs DNAts OxyTs DNAcs DNAcs DNAts DNAts DNAts DNAas DNAcs DNAas DNAcs DNAcs OxyAs OxyMCs OxyAs OxyMC.

"Potency" is normally expressed as an $IC_{50}$ or $EC_{50}$ value, in µM, nM or pM unless otherwise stated. Potency can also be expressed in terms of percent inhibition. $IC_{50}$ is the median inhibitory concentration of a therapeutic molecule. $EC_{50}$ is the median effective concentration of a therapeutic molecule relative to a vehicle or control (e.g., saline). In functional assays, $IC_{50}$ is the concentration of a therapeutic molecule that reduces a biological response, e.g., transcription of mRNA or protein expression, by 50% of the biological response that is achieved by the therapeutic molecule. In functional assays, $EC_{50}$ is the concentration of a therapeutic molecule that produces 50% of the biological response, e.g., transcription of mRNA or protein expression. $IC_{50}$ or $EC_{50}$ can be calculated by any number of means known in the art.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, sports animals, and zoo animals including, e.g., humans, non-human primates, dogs, cats, guinea pigs, rabbits, rats, mice, horses, cattle, bears, and so on.

The term "pharmaceutical composition" refers to a preparation which is in such form as to permit the biological activity of the active ingredient to be effective, and which contains no additional components which are unacceptably toxic to a subject to which the composition would be administered. Such composition can be sterile.

An "effective amount" of an ASO as disclosed herein is an amount sufficient to carry out a specifically stated purpose. An "effective amount" can be determined empirically and in a routine manner, in relation to the stated purpose.

Terms such as "treating" or "treatment" or "to treat" or "alleviating" or "to alleviate" refer to both (1) therapeutic measures that cure, slow down, lessen symptoms of, and/or halt progression of a diagnosed pathologic condition or disorder and (2) prophylactic or preventative measures that prevent and/or slow the development of a targeted pathologic condition or disorder. Thus, those in need of treatment include those already with the disorder; those prone to have the disorder; and those in whom the disorder is to be prevented. In certain embodiments, a subject is successfully "treated" for a disease or condition disclosed elsewhere herein according to the methods provided herein if the patient shows, e.g., total, partial, or transient alleviation or elimination of symptoms associated with the disease or disorder.

II. Antisense Oligonucleotides

The present disclosure employs antisense oligonucleotides for use in modulating the function of nucleic acid molecules encoding mammalian α-Syn, such as the SNCA nucleic acid, e.g., SNCA transcript, including SNCA pre-mRNA, and SNCA mRNA, or naturally occurring variants of such nucleic acid molecules encoding mammalian α-Syn. The term "ASO" in the context of the present disclosure, refers to a molecule formed by covalent linkage of two or more nucleotides (i.e., an oligonucleotide).

The ASO comprises a contiguous nucleotide sequence of from about 10 to about 30, such as 10-20, 16-20, or 15-25 nucleotides in length. The terms "antisense ASO," "antisense oligonucleotide," and "oligomer" as used herein are interchangeable with the term "ASO."

A reference to a SEQ ID number includes a particular nucleobase sequence, but does not include any design or full chemical structure shown in FIG. 2 or 3. Furthermore, the ASOs disclosed in the FIGs. herein show a representative design, but are not limited to the specific design shown in the FIGs. unless otherwise indicated. Herein, a single nucleotide (unit) can also be referred to as a monomer or unit. When this specification refers to a specific ASO number, the reference includes the sequence, the specific ASO design, and the chemical structure. When this specification refers to a specific DES number, the reference includes the sequence and the specific ASO design. For example, when a claim (or this specification) refers to SEQ ID NO: 15, it includes the nucleotide sequence of attcctttacaccacac only. When a claim (or the specification) refers to DES-005459, it includes the nucleotide sequence of attcctttacaccacac with the ASO design shown in the FIGs. (i.e., AtTcctttacaccACAC). Alternatively, the design of ASO-005459 can also be written as SEQ ID NO: 15, wherein each of the first nucleotide, the third nucleotide, and the $14^{th}$-$17^{th}$ nucleotides from the 5' end is a modified nucleotide, e.g., LNA, and each of the other nucleotides is a non-modified nucleotide (e.g., DNA). The ASO number includes the sequence and the ASO design as well as the specific details of the ASO. Therefore, ASO-005459 referred in this application indicates OxyAs DNAts OxyTs DNAcs DNAcs DNAts DNAts DNAts DNAas DNAcs DNAas DNAcs DNAcs OxyAs OxyMCs OxyAs OxyMC, wherein "s" indicates a phosphorothioate linkage.

In various embodiments, the ASO of the disclosure does not comprise RNA (units). In some embodiments, the ASO comprises one or more DNA units. In one embodiment, the ASO according to the disclosure is a linear molecule or is synthesized as a linear molecule. In some embodiments, the ASO is a single stranded molecule, and does not comprise short regions of, for example, at least 3, 4 or 5 contiguous nucleotides, which are complementary to equivalent regions within the same ASO (i.e. duplexes)—in this regard, the ASO is not (essentially) double stranded. In some embodiments, the ASO is essentially not double stranded. In some embodiments, the ASO is not a siRNA. In various embodiments, the ASO of the disclosure can consist entirely of the contiguous nucleotide region. Thus, in some embodiments the ASO is not substantially self-complementary.

In one embodiment, the ASO of the disclosure can be in the form of any pharmaceutically acceptable salts. The term "pharmaceutically acceptable salts" as used herein refers to derivatives of the ASOs of the disclosure wherein the ASO is modified (e.g., addition of a cation) by making salts thereof. Such salts retain the desired biological activity of the ASOs without imparting undesired toxicological effects. In some embodiments, the ASO of the disclosure is in the form of a sodium salt. In other embodiments, the ASO is in the form of a potassium salt.

II.A. The Target

Suitably the ASO of the disclosure is capable of down-regulating (e.g., reducing or removing) expression of the SNCA mRNA or protein. In this regard, the ASO of the disclosure can affect indirect inhibition of SNCA protein through the reduction in SNCA mRNA levels, typically in a mammalian cell, such as a human cell, such as a neuronal cell. In particular, the present disclosure is directed to ASOs that target one or more regions of the SNCA pre-mRNA.

Synonyms of SNCA are known and include NACP, non A-beta component of AD amyloid, PARK1, PARK4, and PD1. The sequence for the SNCA gene can be found under publicly available Accession Number NC_000004.12 and the partial sequence for the SNCA pre-mRNA transcript (residues 6001 to 8400) can be found under publicly available Accession Number NG_011851.1 (SEQ ID NO: 28). The sequence for SNCA protein can be found under publicly available Accession Numbers: P37840, A8K2A4, Q13701, Q4JHI3, and Q6IAU6, each of which is incorporated by reference herein in its entirety. Natural variants of the SNCA gene product are known. For example, natural variants of SNCA protein can contain one or more amino acid substitutions selected from: A30P, E46K, H50Q, A53T, and any combinations thereof. Therefore, the ASOs of the present disclosure can be designed to reduce or inhibit expression of the natural variants of the SNCA protein.

Mutations in SNCA are known to cause one or more pathological conditions. The ASOs of the disclosure can be used to reduce or inhibit the expression of a SNP or alternatively spliced SNCA transcript containing one or more mutations and consequently reduce the formation of a mutated SNCA protein. Examples of SNCA protein mutants include, but are not limited to a SNCA protein comprising one or more mutations selected from: D2A, E35K, Y39F, H50A, E57K, G67_V71del, V71_V82del, A76_V77del, A76del, V77del, A78del, A85_F94del, Y125F, Y133F, Y136F, and any combination thereof. The ASO of the disclosure can be designed to reduce or inhibit expression of any mutants of SNCA proteins.

An example of a target nucleic acid sequence of the ASOs is SNCA pre-mRNA. SEQ ID NO: 1 in FIG. 1A represents a partial SNCA genomic sequence (residues 6001 to 8400 of SEQ ID NO: 28). SEQ ID NO: 1 is identical to a SNCA pre-mRNA sequence except that the nucleotide "t" in SEQ ID NO: 1 is shown as "u" in the pre-mRNA. In certain embodiments, the "target nucleic acid" comprises an intron region of an SNCA protein-encoding nucleic acids or naturally occurring variants thereof, and RNA nucleic acids derived therefrom, e.g., pre-mRNA. In other embodiments, the "target nucleic acid" comprises an exon region of an SNCA protein-encoding nucleic acids or naturally occurring variants thereof, and RNA nucleic acids derived therefrom. In some embodiments, for example when used in research or diagnostics the "target nucleic acid" can be a cDNA or a synthetic oligonucleotide derived from the above DNA or RNA nucleic acid targets. In one embodiment, the partial SNCA genomic sequence is shown as GenBank Accession No. NG_011851.1 (residues 6001 to 8400 of SEQ ID NO: 28) (SEQ ID NO: 1). The mRNA encoding SNCA protein is shown as SEQ ID NO: 2. See FIG. 1B. The SNCA protein sequence encoded by the SNCA mRNA is shown as SEQ ID NO: 3. See FIG. 1C.

In one embodiment, the ASO according to the disclosure comprises a contiguous nucleotide sequence of 10 to 30 nucleotides in length that are complementary to a nucleic acid sequence within a SNCA transcript, e.g., a region corresponding to an intron exon junction of SEQ ID NO: 28, wherein the nucleic acid sequence corresponds to nucleotides 7,602-7,627 of SEQ ID NO: 28.

In certain embodiments, the ASOs hybridize to or are complementary to a region within a SNCA transcript, e.g., nucleotides 7,602-7,627 of SEQ ID NO: 28, and have a sequence score equal to or greater than about 0.1, 0.2, 0.3, 0.4, 0.5, 0.6, 0.7, 0.8, 0.9, or 1.0. Calculation methods of the sequence score are disclosed elsewhere herein.

In some embodiments, the ASOs of the present disclosure hybridize to an intron exon junction of a SNCA transcript, e.g., a region corresponding to a junction between intron 1 and exon 2 of SEQ ID NO: 28. In some embodiments, the ASO of the disclosure comprises a contiguous nucleotide sequence that hybridizes to a nucleic acid sequence, or a region within the sequence, of a SNCA transcript ("target region"), wherein the nucleic acid sequence corresponds to nucleotides 7,602-7,627 of SEQ ID NO: 28. In another embodiment, the ASO of the disclosure comprises a contiguous nucleotide sequence that hybridizes to a nucleic acid sequence, or a region within the sequence, of a SNCA transcript, wherein the nucleic acid sequence corresponds to nucleotides 7,602-7,627 of SEQ ID NO: 28, and wherein the ASO has one of the designs described herein (e.g., Section II.H. e.g., a gapmer design, e.g., an alternating flank gapmer design) or a chemical structure shown elsewhere herein (e.g., FIGS. 2 and 3).

In some embodiments, the target region corresponds to nucleotides 7,604-7,620 of SEQ ID NO: 28. In other embodiments, the target region corresponds to nucleotides 7,603-7,620 of SEQ ID NO: 28. In other embodiments, the target region corresponds to nucleotides 7,602-7,619 of SEQ ID NO: 28. In certain embodiments, the ASOs hybridize to a region within an exon of a SNCA transcript, e.g., SEQ ID NO: 28, and have a sequence score equal to or greater than about 0.1, 0.2, 0.3, 0.4, 0.5, 0.6, 0.7, 0.8, 0.9, or 1.0. Calculation methods of the sequence score are disclosed elsewhere herein.

In certain embodiments, the target region corresponds to nucleotides 7,602-7,627 of SEQ ID NO: 28±10 nucleotides at the 3' end, the 5' end, or both. In other embodiments, the target region corresponds to nucleotides 7,604-7,620 of SEQ ID NO: 28±1, ±2, ±3, ±4, ±5, ±6, ±7, ±8, ±9, or ±10 nucleotides at the 3' end, the 5' end, or both.

In certain embodiments, the ASO of the disclosure is capable of hybridizing to the target nucleic acid (e.g., SNCA transcript) under physiological condition, i.e., in vivo condition. In some embodiments, the ASO of the disclosure is capable of hybridizing to the target nucleic acid (e.g., SNCA transcript) in vitro. In some embodiments, the ASO of the disclosure is capable of hybridizing to the target nucleic acid (e.g., SNCA transcript) in vitro under stringent conditions. Stringency conditions for hybridization in vitro are dependent on, inter alia, productive cell uptake, RNA accessibility, temperature, free energy of association, salt concentration, and time (see, e.g., Stanley T Crooks, Antisense Drug Technology: Principles, Strategies and Applications, $2^{nd}$ Edition, CRC Press (2007)). Generally, conditions of high to moderate stringency are used for in vitro hybridization to enable hybridization between substantially similar nucleic acids, but not between dissimilar nucleic acids. An example of stringent hybridization conditions include hybridization in 5× saline-sodium citrate (SSC) buffer (0.75 M sodium chloride/0.075 M sodium citrate) for 1 hour at 40° C., followed by washing the sample 10 times in 1×SSC at 40° C. and 5 times in 1×SSC buffer at room temperature. In vivo hybridization conditions consist of intracellular conditions (e.g., physiological pH and intracellular ionic conditions) that govern the hybridization of antisense oligonucleotides with target sequences. In vivo conditions can be mimicked in vitro by relatively low stringency conditions. For example, hybridization can be carried out in vitro in 2×SSC (0.3 M sodium chloride/0.03 M sodium citrate), 0.1% SDS at 37° C. A wash solution containing 4×SSC, 0.1% SDS can be used at 37° C., with a final wash in 1×SSC at 45° C.

IIB. ASO Sequences

The ASOs of the disclosure comprise a contiguous nucleotide sequence which corresponds to the complement of a region of SNCA transcript, e.g., a nucleotide sequence corresponding to SEQ ID NO: 1 (i.e., nucleotides 6001 to 8400 of SEQ ID NO: 28).

In certain embodiments, the disclosure provides an ASO which comprises a contiguous nucleotide sequence of a total of from 10-30 nucleotides, such as 10-15 nucleotides, 10-20 nucleotides, or 10-25 nucleotides in length wherein the contiguous nucleotide sequence has at least about 85%, at least about 90%, at least about 95%, at least about 98%, or at least about 99% sequence identity to a region within the complement of a mammalian SNCA transcript, such as SEQ ID NO: 1 or SEQ ID NO: 2.

The ASO can comprise a contiguous nucleotide sequence which is fully complementary (perfectly complementary) to the equivalent region of a nucleic acid which encodes a mammalian SNCA protein (e.g., SEQ ID NOs: 1 and 2). The ASO can comprise a contiguous nucleotide sequence which is fully complementary (perfectly complementary) to a nucleic acid sequence, or a region within the sequence, corresponding to nucleotides X—Y, wherein X and Y are the pre-mRNA start site and the pre-mRNA end site of NG_011851.1 (SEQ ID NO: 28), respectively, as shown in FIG. 2. Furthermore, the ASO can have a design described elsewhere herein (e.g., Section II.G. e.g., a gapmer design, e.g., an alternating flank gapmer design) or a chemical structure shown elsewhere herein (e.g., FIGS. 2 and 3). In some embodiments, the ASO comprises a contiguous nucleotide sequence which is fully complementary (perfectly complementary) to a nucleic acid sequence, or a region within the sequence, corresponding to nucleotides X—Y of SEQ ID NO: 2, wherein X and Y are the mRNA start site and the mRNA end site, respectively.

In certain embodiments, the nucleotide sequence of the ASOs of the disclosure or the contiguous nucleotide sequence has at least about 80% sequence identity to a sequence selected from SEQ ID NOs: 4 to 21 (i.e., the sequences in FIGS. 2 and 3), such as at least about 85%, at least about 90%, at least about 91%, at least about 92%, at least about 93%, at least about 94%, at least about 95%, at least about 96% sequence identity, at least about 97% sequence identity, at least about 98% sequence identity, at least about 99% sequence identity, such as about 100% sequence identity (homologous). In some embodiments, the ASO has a design described elsewhere herein (e.g., Section II.G.I, e.g., a gapmer design, e.g., an alternating flank gapmer design) or a nucleoside chemical structure shown elsewhere herein (e.g., FIGS. 2 and 3).

In some embodiments, the ASO of the disclosure comprises at least one ASO with the design (e.g., DES number) disclosed in FIGS. 2 and 3. In some embodiments, the ASO of the disclosure comprises at least one ASO with the design (e.g., DES number) disclosed in FIGS. 2 and 3, wherein the ASO is one nucleotide, two nucleotides, three nucleotides, or four nucleotides shorter at the 3' end than the ASOs disclosed in FIGS. 2 and 3. In other embodiments, the ASO of the disclosure comprises at least one ASO with the design (e.g., DES number) disclosed in FIGS. 2 and 3, wherein the ASO is one nucleotide, two nucleotides, three nucleotides, or four nucleotides shorter at the 5' end than the ASOs disclosed in FIGS. 2 and 3. In yet other embodiments, the ASO of the disclosure comprises at least one ASO with the design (e.g., DES number) disclosed in FIGS. 2 and 3, wherein the ASO is one nucleotide, two nucleotides, three nucleotides, or four nucleotides shorter at the 5' end and/or the 3' end than the ASOs disclosed in FIGS. 2 and 3.

In other embodiments, the ASO of the disclosure comprises at least one ASO with the chemical structure (e.g., ASO number) disclosed in FIGS. 2 and 3. In some embodiments, the ASO of the disclosure comprises at least one ASO with the chemical structure (e.g., ASO number) disclosed in FIGS. 2 and 3, wherein the ASO is one nucleotide, two nucleotides, three nucleotides, or four nucleotides shorter at the 3' end than the ASOs disclosed in FIGS. 2 and 3. In other embodiments, the ASO of the disclosure comprises at least one ASO with the chemical structure (e.g., ASO number) disclosed in FIGS. 2 and 3, wherein the ASO is one nucleotide, two nucleotides, three nucleotides, or four nucleotides shorter at the 5' end than the ASOs disclosed in FIGS. 2 and 3. In yet other embodiments, the ASO of the disclosure comprises at least one ASO with the chemical structure (e.g., ASO number) disclosed in FIGS. 2 and 3, wherein the ASO is one nucleotide, two nucleotides, three nucleotides, or four nucleotides shorter at the 5' end and/or the 3' end than the ASOs disclosed in FIGS. 2 and 3.

In some embodiments the ASO (or contiguous nucleotide portion thereof) is selected from, or comprises, one of the sequences selected from the group consisting of SEQ ID NOs: 4 to 21 and a region of at least 10 contiguous nucleotides thereof, wherein the ASO (or contiguous nucleotide portion thereof) can optionally comprise one, two, three, or four mismatches when compared to the corresponding SNCA transcript.

In one embodiment, the ASO comprises a sequence selected from the group consisting of SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and SEQ ID NO: 21. In some embodiments, the ASO comprises a sequence selected from the group consisting of SEQ ID NO: 7 (e.g., the sequence of ASO-005578 and ASO-005584) and SEQ ID NO: 15 (e.g., the sequence of ASO-005459).

In some embodiments, the ASOs of the disclosure bind to the target nucleic acid sequence (e.g., SNCA transcript) and are capable of inhibiting or reducing expression of the SNCA transcript by at least about 10%, at least about 20%, at least about 30%, at least about 40%, at least about 50%, at least about 60%, at least about 70%, at least about 80%, at least about 90%, or about 100% in a tissue (e.g., a brain region) of a mouse expressing a human SNCA gene (e.g., A53T-PAC) when administered in vivo at doses of 3.13 µg, 12.5 µg, 25 µg, 50 µg, or 100 µg compared to the control (e.g., an internal control such as GADPH or tubulin, or a mouse administered with vehicle control alone), as measured by an assay, e.g., quantitative PCR or QUANTI-GENE® analysis disclosed herein.

In some embodiments, the ASOs are capable of reducing expression of SNCA protein by at least about 10%, at least about 20%, at least about 30%, at least about 40%, at least about 50%, at least about 60%, at least about 70%, at least about 80%, at least about 90%, or about 100% in a tissue (e.g., a brain region) of a mouse expressing a human SNCA gene (e.g., A53T-PAC) when administered in vivo at doses of 3.13 µg, 12.5 µg, 25 µg, 50 µg, or 100 µg compared to the control (e.g., an internal control such as GADPH or tubulin, or a mouse administered with vehicle control alone), as measured by an assay, e.g., High Content Assay disclosed herein (see Example 2A).

In some embodiments, the ASOs of the disclosure bind to the target nucleic acid sequence (e.g., SNCA transcript) and are capable of inhibiting or reducing expression of the SNCA transcript by at least about 10%, at least about 20%, at least about 30%, at least about 40%, at least about 50%, at least about 60%, at least about 70%, at least about 80%, at least about 90%, or about 100% in a tissue (e.g., a brain region) of a cyno expressing the wild-type SNCA gene when administered once or twice in vivo at doses of 2 mg, 4 mg, or, 8 mg, compared to the control (e.g., an internal control such as GADPH or tubulin, or a cyno administered with vehicle control alone), as measured by an assay, e.g., quantitative PCR or QUANTIGENE® analysis disclosed herein.

In some embodiments, the ASOs are capable of reducing expression of SNCA protein by at least about 10%, at least about 20%, at least about 30%, at least about 40%, at least about 50%, at least about 60%, at least about 70%, at least about 80%, at least about 90%, or about 100% in a tissue (e.g., a brain region) of a cyno expressing the wild-type SNCA gene when administered once or twice in vivo at doses of 2 mg, 4 mg, or 8 mg, compared to the control (e.g., an internal control such as GADPH or tubulin, or a cyno administered with vehicle control alone), as measured by an assay, e.g., High Content Assay disclosed herein (see Example 2A).

In other embodiments, the ASOs of the disclosure are capable of reducing expression of SNCA mRNA in vitro by at least about 20%, at least about 30%, at least about 40%, at least about 50%, at least about 60%, at least about 70%, at least about 80%, at least about 90%, or about 100% in mouse primary neurons expressing a full-length human SNCA gene (e.g., PAC neurons) when the neurons are in contact with 5 µM, 3.3 µM, 1 µM, 4 nM, 40 nM, or 200 nM of the antisense oligonucleotide compared to a control (e.g., an internal control such as GADPH or tubulin, or a mouse primary neurons expressing a full-length human SNCA gene in contact with saline alone), as measured by an assay, e.g., QUANTIGENE® analysis disclosed herein.

In yet other embodiments, the ASOs are capable of reducing expression of SNCA protein in vitro by at least about 60%, at least about 70%, at least about 80%, at least about 90%, or at least about 95% in mouse primary neurons expressing a full-length human SNCA gene (e.g., PAC neurons) when the neurons are in contact with 5 µM, 3.3 µM, 1 µM, 4 nM, 40 nM, or 200 nM of the antisense oligonucleotide compared to control (e.g., an internal control such as GADPH or tubulin, or a mouse primary neurons expressing a full-length human SNCA gene (in contact with saline alone), as measured by an assay, e.g., High Content Assay disclosed herein (see Example 2A).

In some embodiments, the ASOs are capable of reducing expression of SNCA mRNA in vitro by at least about 10%, at least about 20%, at least about 30%, at least about 40%, at least about 50%, at least about 60%, at least about 70%, at least about 80%, at least about 90%, or about 100% in human neuroblastoma cell line (e.g., SK—N—BE(2)) expressing a full-length human SNCA gene when the neuroblastoma cells are in contact with 25 µM of the antisense oligonucleotide compared to control (e.g., an internal control such as GADPH or tubulin, or neuroblastoma cells expressing a full-length human SNCA gene in contact with saline alone), as measured by an assay, e.g., quantitative PCR disclosed herein.

In some embodiments, the ASOs disclosed herein are capable of reducing expression of SNCA protein in vitro by at least about 10%, at least about 20%, at least about 30%, at least about 40%, at least about 50%, at least about 60%, at least about 70%, at least about 80%, at least about 90%, or about 100% in human neuroblastoma cell line (e.g., SK—N—BE(2)) expressing a full-length human SNCA gene when the neuroblastoma cells are in contact with 25 µM of the antisense oligonucleotide compared to control (e.g., an internal control such as GADPH or tubulin, or neuroblastoma cells expressing a full-length human SNCA gene in contact with saline alone), as measured by an assay, e.g., High Content Assay analysis disclosed herein (see Example 2A).

In certain embodiments, the ASOs of the disclosure bind to the SNCA transcript and inhibit or reduce expression of the SNCA mRNA by at least about 10% or about 20% compared to the normal (i.e. control) expression level in the cell, e.g., at least about 30%, about 40%, about 50%, about 60%, about 70%, about 80%, about 90% or about 95% compared to the normal expression level (such as the expression level in the absence of the ASO(s) or conjugate(s)) in the cell. In certain embodiments, the ASO reduces expression of SNCA protein in a cell following administration of the ASO by at least 60%, at least 70%, at least 80%, or at least 90% compared to a cell not exposed to the ASO (i.e., control). In some embodiments, the ASO reduces expression of SNCA protein in a cell following administration of the ASO by at least about 60%, at least about 70%, at least about 80%, or at least about 90% compared to a cell not exposed to the ASO (i.e., control).

In certain embodiments, the ASO of the disclosure has at least one property selected from: (1) reduces expression of SNCA mRNA in a cell, compared to a control cell that has not been exposed to the ASO; (2) does not significantly reduce calcium oscillations in a cell; (3) does not significantly reduce tubulin intensity in a cell; (4) reduces expression of α-Syn protein in a cell; and (5) any combinations thereof compared to a control cell that has not been exposed to the ASO.

In some embodiments, the ASO of the disclosure does not significantly reduce calcium oscillations in a cell, e.g., neuronal cells. If the ASO does not significantly reduce calcium oscillations in a cell, this property of the ASO corresponds with a reduced neurotoxicity of the ASO. In some embodiments, calcium oscillations are greater than or equal to 95%, greater than or equal to 90%, greater than or equal to 85%, greater than or equal to 80%, greater than or equal to 75%, greater than or equal to 70%, greater than or equal to 65%, greater than or equal to 60%, greater than or equal to 55%, or greater than or equal to 50% of oscillations in a cell not exposed to the ASO.

Calcium oscillations are important for the proper functions of neuronal cells. Networks of cortical neurons have been shown to undergo spontaneous calcium oscillations resulting in the release of the neurotransmitter glutamate. Calcium oscillations can also regulate interactions of neurons with associated glia, in addition to other associated neurons in the network, to release other neurotransmitters in addition to glutamate. Regulated calcium oscillations are required for homeostasis of neuronal networks for normal brain function. (See, Shashank et al., *Brain Research,* 1006 (1): 8-17 (2004); Rose et al., *Nature Neurosci.,* 4:773-774 (2001); Zonta et al., *J Physiol Paris.,* 96(3-4):193-8 (2002); Pasti et al., *J. Neurosci.,* 21(2): 477-484 (2001).) Glutamate also activates two distinct ion channels, α-amino-3-hydroxy-5-methyl-4-isoxazolepropionic acid (AMPA) receptors and N-methyl-D-aspartate (NMDA) receptors.

In some embodiments, the calcium oscillations measured in the present methods are AMPA-dependent calcium oscillations. In some embodiments, the calcium oscillations are NMDA-dependent calcium oscillations. In some embodiments, the calcium oscillations are gamma-aminobutyric acid (GABA)-dependent calcium oscillations. In some embodiments, the calcium oscillations can be a combination of two or more of AMPA-dependent, NMDA-dependent or GABA-dependent calcium oscillations.

In certain embodiments, the calcium oscillations measured in the present methods are AMPA-dependent calcium oscillations. In order to measure AMPA-dependent calcium oscillations, the calcium oscillations can be measured in the presence of $Mg^{2+}$ ions (e.g., $MgCl_2$). In certain embodiments, the method further comprises adding $Mg^{2+}$ ions (e.g., $MgCl_2$) at an amount that allows for detection of AMPA-dependent calcium oscillations. In some embodiments, the effective ion concentration allowing for detection of AMPA-dependent calcium oscillations is at least about 0.5 mM. In other embodiments, the effective ion concentration to induce AMPA-dependent calcium oscillations is at least about 0.6 mM, at least about 0.7 mM, at least about 0.8 mM, at least about 0.9 mM, at least about 1 mM, at least about 1.5 mM, at least about 2.0 mM, at least about 2.5 mM, at least about 3.0 mM, at least about 4 mM, at least about 5 mM, at least about 6 mM, at least about 7 mM, at least about 8 mM, at least about 9 mM, or at least about 10 mM. In a particular embodiment, the concentration of $Mg^{2+}$ ions (e.g., $MgCl_2$) useful for the methods is 1 mM. In certain embodiments, the concentration of $Mg^{2+}$ ions (e.g., $MgCl_2$) useful for the present methods is about 1 mM to about 10 mM, about 1 mM to about 15 mM, about 1 mM to about 20 mM, or about 1 mM to about 25 mM. $Mg^{2+}$ ions can be added by the addition of magnesium salts, such as magnesium carbonate, magnesium chloride, magnesium citrate, magnesium hydroxide, magnesium oxide, magnesium sulfate, and magnesium sulfate heptahydrate.

In some embodiments, calcium oscillations are measured in the present method through the use of fluorescent probes which detect the fluctuations of intracellular calcium levels. For example, detection of intracellular calcium flux can be achieved by staining the cells with fluorescent dyes which bind to calcium ions (known as fluorescent calcium indicators) with a resultant, detectable change in fluorescence (e.g., Fluo-4 AM and Fura Red AM dyes available from Molecular Probes. Eugene, OR, United States of America).

In other embodiments, the ASOs of the disclosure do not significantly reduce the tubulin intensity in a cell. In some embodiments, tubulin intensity is greater than or equal to 95%, greater than or equal to 90%, greater than or equal to 85%, greater than or equal to 80%, greater than or equal to 75%, greater than or equal to 70%, greater than or equal to 65%, greater than or equal to 60%, greater than or equal to 55%, or greater than or equal to 50% of tubulin intensity in a cell not exposed to the ASO (or exposed to saline).

In some embodiments, such property is observed when using from 0.04 nM to 400 μM concentration of the ASO of the disclosure. In the same or a different embodiment, the inhibition or reduction of expression of SNCA mRNA and/or SNCA protein in the cell results in less than 100%, such as less than 98%, less than 95%, less than 90%, less than 80%, such as less than 70%, mRNA or protein levels compared to cells not exposed to the ASO. Modulation of expression level can be determined by measuring SNCA protein levels, e.g., by methods such as SDS-PAGE followed by western blotting using suitable antibodies raised against the target protein. Alternatively, modulation of expression levels can be determined by measuring levels of SNCA mRNA, e.g., by northern blot or quantitative RT-PCR. When measuring inhibition via mRNA levels, the level of down-regulation when using an appropriate dosage, such as from about 0.04 nM to about 400 μM concentration, is, in some embodiments typically to a level of from about 10-20% the normal levels in the cell in the absence of the ASO.

In certain embodiments, the ASO of the disclosure has an in vivo tolerability less than or equal to a total score of 4, wherein the total score is the sum of a unit score of five categories, which are 1) hyperactivity; 2) decreased activity and arousal; 3) motor dysfunction and/or ataxia; 4) abnormal posture and breathing; and 5) tremor and/or convulsions, and wherein the unit score for each category is measured on a scale of 0-4. In certain embodiments, the in vivo tolerability is less than or equal to the total score of 3, the total score of 2, the total score of 1, or the total score of 0. In some embodiment, the assessment for in vivo tolerability is determined as described in the examples below.

In some embodiments, the ASO can tolerate 1, 2, 3, or 4 (or more) mismatches, when hybridizing to the target sequence and still sufficiently bind to the target to show the desired effect, i.e., down-regulation of the target mRNA and/or protein. Mismatches can, for example, be compensated by increased length of the ASO nucleotide sequence and/or an increased number of nucleotide analogs, which are disclosed elsewhere herein.

In some embodiments, the ASO of the disclosure comprises no more than 3 mismatches when hybridizing to the target sequence. In other embodiments, the contiguous nucleotide sequence comprises no more than 2 mismatches when hybridizing to the target sequence. In other embodiments, the contiguous nucleotide sequence comprises no more than 1 mismatch when hybridizing to the target sequence.

In some embodiments the ASO according to the disclosure comprises a nucleotide sequence, or a region within the sequence, according to any one of SEQ ID NOs: 4 to 21, the ASO sequences with the design as described in FIGS. 2 and 3, and the ASO sequence with the chemical structure as described in FIGS. 2 and 3.

However, it is recognized that, in some embodiments, the nucleotide sequence of the ASO can comprise additional 5' or 3' nucleotides, such as, independently, 1, 2, 3, 4 or 5 additional nucleotides 5' and/or 3', which are non-complementary to the target sequence. In this respect the ASO of the disclosure, can, in some embodiments, comprise a contiguous nucleotide sequence which is flanked 5' and/or 3' by additional nucleotides. In some embodiments the additional 5' and/or 3' nucleotides are naturally occurring nucleotides, such as DNA or RNA.

In some embodiments, the ASO of the disclosure has a sequence score greater than or equal to 0.2, wherein the sequence score is calculated by formula I.

of C nucleotides and analogs thereof–#of G nucleotides and analogs thereof/Total nucleotide length. (I)

In other embodiments, the ASO of the disclosure has a sequence score greater than or equal to 0.2, wherein the sequence score is calculated by formula IA:

of C nucleotides and 5-methylcytosine nucleotides–#of G nucleotides/Total nucleotide length. (IA)

In these embodiments, a sequence score of greater than or equal to a cut off value corresponds to a reduced neurotoxicity of the ASO.

In certain embodiments, the ASO of the disclosure has a sequence score greater than or equal to about 0.1, 0.2, 0.25, 0.3, 0.35, 0.4, 0.45, 0.5, 0.55, 0.6, 0.65, 0.7, 0.75, 0.8, 0.85, 0.9, 0.95, or 1.0. In one embodiment, the ASO of the disclosure comprises a contiguous nucleotide sequence hybridizing to a non-coding region of a SNCA transcript, wherein the sequence score of the ASO is greater than or equal to about 0.1, 0.2, 0.25, 0.3, 0.35, 0.4, 0.45, 0.5, 0.55, 0.6, 0.65, 0.7, 0.75, 0.8, 0.85, 0.9, 0.95, or 1.0. In another embodiment, the ASO of the disclosure comprises a contiguous nucleotide sequence hybridizing to an intron region of a SNCA transcript, wherein the sequence score of the ASO is greater than or equal to about 0.1, 0.2, 0.25, 0.3, 0.35, 0.4, 0.45, 0.5, 0.55, 0.6, 0.65, 0.7, 0.75, 0.8, 0.85, 0.9, 0.95, or 1.0. In another embodiment, the ASO of the disclosure comprises a contiguous nucleotide sequence hybridizing to an intron exon junction of a SNCA transcript, wherein the sequence score of the ASO is greater than or equal to about 0.1, 0.2, 0.25, 0.3, 0.35, 0.4, 0.45, 0.5, 0.55, 0.6, 0.65, 0.7, 0.75, 0.8, 0.85, 0.9, 0.95, or 1.0. In all of these embodiments, when the sequence score is greater than or equal to the cut off value, the ASO is considered to have reduced neurotoxicity.

IIC. ASO Length

The ASOs can comprise a contiguous nucleotide sequence of a total of 10, 11, 12, 13, 14, 15, 16, 17, 18, 19, 20, 21, 22, 23, 24, 25, 26, 27, 28, 29, or 30 contiguous nucleotides in length.

In some embodiments, the ASOs comprise a contiguous nucleotide sequence of a total of about 10-22, such as 10-21 or 12-18, such as 13-17 or 12-16, such as 13, 14, 15, 16, 17, 18, 19, 20, or 21 contiguous nucleotides in length.

In some embodiments, the ASOs comprise a contiguous nucleotide sequence of a total of 16, 17, 18, 19, or 20 (16 to 20) contiguous nucleotides in length.

In some embodiments, the ASO according to the disclosure consists of no more than 22 nucleotides, such as no more than 21 or 20 nucleotides, such as no more than 18 nucleotides, such as 15, 16 or 17 nucleotides. In some embodiments the ASO of the disclosure comprises less than 22 nucleotides. It should be understood that when a range is given for an ASO, or contiguous nucleotide sequence length, the range includes the lower and upper lengths provided in the range, for example from (or between) 10-30, includes both 10 and 30.

II.D. Nucleosides and Nucleoside Analogs

In one aspect of the disclosure, the ASOs comprise one or more non-naturally occurring nucleotide analogs. "Nucleotide analogs" as used herein are variants of natural nucleotides, such as DNA or RNA nucleotides, by virtue of modifications in the sugar and/or base moieties. Analogs could in principle be merely "silent" or "equivalent" to the natural nucleotides in the context of the oligonucleotide, i.e. have no functional effect on the way the oligonucleotide works to inhibit target gene expression. Such "equivalent" analogs can nevertheless be useful if, for example, they are easier or cheaper to manufacture, or are more stable to storage or manufacturing conditions, or represent a tag or label. In some embodiments, however, the analogs will have a functional effect on the way in which the ASO works to inhibit expression; for example by producing increased binding affinity to the target and/or increased resistance to intracellular nucleases and/or increased ease of transport into the cell. Specific examples of nucleoside analogs are described by e.g. Freier & Altmann; *Nucl. Acid Res.*, 1997, 25, 4429-4443 and Uhlmann; *Curr. Opinion in Drug Development*, 2000, 3(2), 293-213, and in Scheme 1.

II.D.1. Nucleobase

The term nucleobase includes the purine (e.g., adenine and guanine) and pyrimidine (e.g., uracil, thymine and cytosine) moiety present in nucleosides and nucleotides which form hydrogen bonds in nucleic acid hybridization. In the context of the present disclosure the term nucleobase also encompasses modified nucleobases which may differ from naturally occurring nucleobases, but are functional during nucleic acid hybridization. In some embodiments the nucleobase moiety is modified by modifying or replacing the nucleobase. In this context "nucleobase" refers to both naturally occurring nucleobases such as adenine, guanine, cytosine, thymidine, uracil, xanthine and hypoxanthine, as well as non-naturally occurring variants. Such variants are for example described in Hirao et al., (2012) *Accounts of Chemical Research* vol 45 page 2055 and Bergstrom (2009) Current Protocols in Nucleic Acid Chemistry Suppl. 37 1.4.1.

In a some embodiments the nucleobase moiety is modified by changing the purine or pyrimidine into a modified purine or pyrimidine, such as substituted purine or substituted pyrimidine, such as a nucleobase selected from isocytosine, pseudoisocytosine, 5-methyl cytosine, 5-thiozolocytosine, 5-propynyl-cytosine, 5-propynyl-uracil, 5-bromouracil 5-thiazolo-uracil, 2-thio-uracil, 2'thio-thymine, inosine, diaminopurine, 6-aminopurine, 2-aminopurine, 2,6-diaminopurine and 2-chloro-6-aminopurine.

The nucleobase moieties may be indicated by the letter code for each corresponding nucleobase, e.g., A, T, G, C or U, wherein each letter may optionally include modified nucleobases of equivalent function. For example, in the exemplified oligonucleotides, the nucleobase moieties are selected from A, T, G, C, and 5-methyl cytosine. Optionally, for LNA gapmers, 5-methyl cytosine LNA nucleosides may be used.

II.D.2. Sugar Modification

The ASO of the disclosure can comprise one or more nucleosides which have a modified sugar moiety, i.e. a modification of the sugar moiety when compared to the ribose sugar moiety found in DNA and RNA. Numerous nucleosides with modification of the ribose sugar moiety have been made, primarily with the aim of improving certain properties of oligonucleotides, such as affinity and/or nuclease resistance.

Such modifications include those where the ribose ring structure is modified, e.g. by replacement with a hexose ring (HNA), or a bicyclic ring, which typically have a biradical bridge between the C2' and C4' carbons on the ribose ring (LNA), or an unlinked ribose ring which typically lacks a bond between the C2' and C3' carbons (e.g., UNA). Other sugar modified nucleosides include, for example, bicyclohexose nucleic acids (WO2011/017521) or tricyclic nucleic acids (WO2013/154798). Modified nucleosides also include nucleosides where the sugar moiety is replaced with a non-sugar moiety, for example in the case of peptide nucleic acids (PNA), or morpholino nucleic acids.

Sugar modifications also include modifications made via altering the substituent groups on the ribose ring to groups other than hydrogen, or the 2'-OH group naturally found in RNA nucleosides. Substituents may, for example be introduced at the 2', 3', 4' or 5' positions. Nucleosides with modified sugar moieties also include 2' modified nucleosides, such as 2' substituted nucleosides. Indeed, much focus has been spent on developing 2' substituted nucleosides, and numerous 2' substituted nucleosides have been found to have beneficial properties when incorporated into oligonucleotides, such as enhanced nucleoside resistance and enhanced affinity.

In some embodiments, the sugar modification comprises an affinity enhancing sugar modification, e.g., LNA. An affinity enhancing sugar modification increases the binding affinity of the ASOs to the target RNA sequence (e.g., intron1/exon2 junction of SNCA mRNA). In some embodiments, an ASO comprising a sugar modification disclosed herein has a binding affinity to a target RNA sequence that is enhanced by at least 5%, at least 10%, at least 20%, at least 30%, at least 40%, at least 50%, at least 60%, at least 70%, at least 80%, at least 90%, or at least 100% compared to a control (e.g., an ASO without such sugar modification).

II.D.2.a 2' Modified Nucleosides

A 2' sugar modified nucleoside is a nucleoside which has a substituent other than H or —OH at the 2' position (2' substituted nucleoside) or comprises a 2' linked biradical, and includes 2' substituted nucleosides and LNA (2'-4' biradical bridged) nucleosides. For example, the 2' modified sugar may provide enhanced binding affinity and/or increased nuclease resistance to the oligonucleotide. Examples of 2' substituted modified nucleosides are 2'-O-alkyl-RNA, 2'-O-methyl-RNA, 2'-alkoxy-RNA, 2'-O-methoxyethyl-RNA (MOE), 2'-amino-DNA, 2'-Fluoro-RNA, and 2'-F-ANA nucleoside. For further examples, please see e.g. Freier & Altmann; Nucl. Acid Res., 1997, 25, 4429-4443 and Uhlmann; Curr. Opinion in Drug Development, 2000, 3(2), 293-213, and Deleavey and Damha, Chemistry and Biology 2012, 19, 937. Below are illustrations of some 2' substituted modified nucleosides.

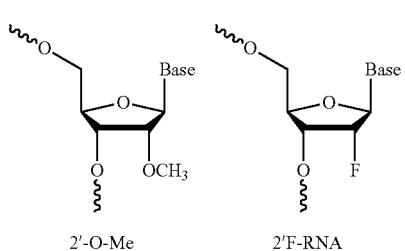

2'-O-Me    2'F-RNA

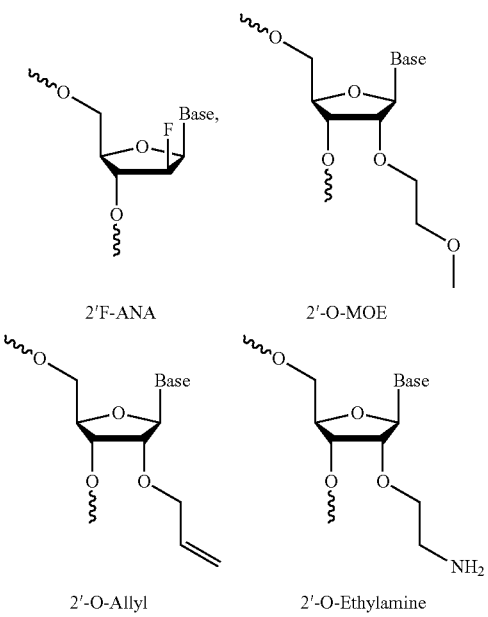

2'F-ANA    2'-O-MOE

2'-O-Allyl    2'-O-Ethylamine

II.D.2.b Locked Nucleic Acid Nucleosides (LNA).

LNA nucleosides are modified nucleosides which comprise a linker group (referred to as a biradical or a bridge) between C2' and C4' of the ribose sugar ring of a nucleotide. These nucleosides are also termed bridged nucleic acid or bicyclic nucleic acid (BNA) in the literature.

In some embodiments, the modified nucleoside or the LNA nucleosides of the ASO of the disclosure has a general structure of the formula II or III:

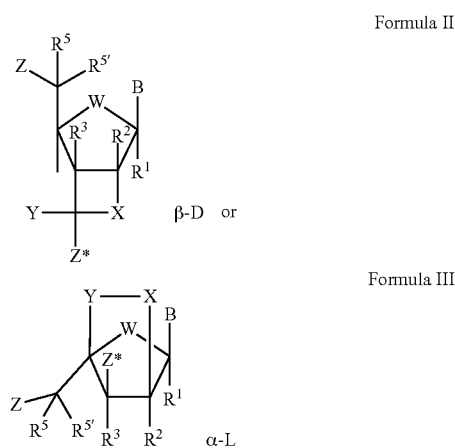

Formula II

Formula III wherein W is selected from —O—, —S—, —N(R$^a$)—, —C(R$^a$R$^b$)—, such as, in some embodiments—O—; B designates a nucleobase or modified nucleobase moiety; Z designates an internucleoside linkage to an adjacent nucleoside, or a 5'-terminal group; Z* designates an internucleoside linkage to an adjacent nucleoside, or a 3'-terminal group; and X designates a group selected from the group consisting of —C(R$^a$R$^b$)—, —C(R$^a$)=C(R$^b$)—, —C(R$^a$)=N—, —O—, —Si(R$^a$)$_2$—, —S—, —SO$_2$—, —N(R$^a$)—, and >C=Z.

In some embodiments, X is selected from the group consisting of: —O—, —S—, NH—, NR$^a$R$^b$, —CH$_2$—, CR$^a$R$^b$, —C(=CH$_2$)—, and —C(=CR$^a$R$^b$)—. In some embodiments, X is —O—.

In some embodiments, Y designates a group selected from the group consisting of —C(R$^a$R$^b$)—, —C(R$^a$)=C(R$^b$)—, —C(R$^a$)=N—, —O—, —Si(R$^a$)$_2$—, —S—, —SO$_2$—, —N(R$^a$)—, and >C=Z. In some embodiments, Y is selected from the group consisting of: —CH$_2$—, —C(R$^a$R$^b$)—, —CH$_2$CH$_2$—, —C(R$^a$R$^b$)—C(R$^a$R$^b$)—, —CH$_2$CH$_2$CH$_2$—, —C(R$^a$R$^b$)C(R$^a$R$^b$)C(R$^a$R$^b$)—, —C(R$^a$)=C(R$^b$)—, and —C(R$^a$)=N—.

In some embodiments, Y is selected from the group consisting of: —CH$_2$—, —CHR$^a$—, —CHCH$_3$—, CR$^a$R$^b$—, and —X—Y— together designate a bivalent linker group (also referred to as a radicle) together designate a bivalent linker group consisting of 1, 2, 3 or 4 groups/atoms selected from the group consisting of —C(R$^a$R$^b$)—, —C(R$^a$)=C(R$^b$)—, —C(R$^a$)=N—, —O—, —Si(R$^a$)$_2$—, —S—, —SO$_2$—, —N(R$^a$)—, and >C=Z.

In some embodiments, —X—Y— designates a biradical selected from the groups consisting of: —X—CH$_2$—, —X—CR$^a$R$^b$—, —X—CHR$^a$—, —X—C(HCH$_3$)$^-$, —O—Y—, —O—CH$_2$—, —S—CH$_2$—, —NH—CH$_2$—, —O—CHCH$_3$—, —CH$_2$—O—CH$_2$—, —O—CH(CH$_3$CH$_3$)—, —O—CH$_2$—CH$_2$—, OCH$_2$—CH$_2$—, —O—CH$_2$OCH$_2$—, —O—NCH$_2$—, —C(=CH$_2$)—CH$_2$—, —NR$^a$—CH$_2$—, N—O—CH$_2$, —S—CR$^a$R$^b$— and —S—CHR$^a$—.

In some embodiments —X—Y— designates —O—CH$_2$— or —O—CH(CH$_3$)—.

In certain embodiments, Z is selected from —O—, —S—, and —N(R$^a$)—, and R$^a$ and, when present R$^b$, each is independently selected from hydrogen, optionally substituted C$_{1-6}$-alkyl, optionally substituted C$_{2-6}$-alkenyl, optionally substituted C$_{2-6}$-alkynyl, hydroxy, optionally substituted C$_{1-6}$-alkoxy, C$_{2-6}$-alkoxyalkyl, C$_{2-6}$-alkenyloxy, carboxy, C$_{1-6}$-alkoxycarbonyl, C$_{1-6}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di(C$_{1-6}$-alkyl)amino, carbamoyl, mono- and di(C$_{1-6}$-alkyl)-amino-carbonyl, amino-C$_{1-6}$-alkyl-aminocarbonyl, mono- and di(C$_{1-6}$-alkyl)amino-C$_{1-6}$-alkyl-aminocarbonyl, C$_{1-6}$-alkyl-carbonylamino, carbamido, C$_{1-6}$-alkanoyloxy, sulphono, C$_{1-6}$-alkylsulphonyloxy, nitro, azido, sulphanyl, C$_{1-6}$-alkylthio, halogen, where aryl and heteroaryl may be optionally substituted and where two geminal substituents R$^a$ and R$^b$ together may designate optionally substituted methylene (=CH$_2$), wherein for all chiral centers, asymmetric groups may be found in either R or S orientation.

In some embodiments, R$^1$, R$^2$, R$^3$, R$^5$ and R$^{5*}$ are independently selected from the group consisting of: hydrogen, optionally substituted C$_{1-6}$-alkyl, optionally substituted C$_{2-6}$-alkenyl, optionally substituted C$_{2-6}$-alkynyl, hydroxy, C$_{1-6}$-alkoxy, C$_{2-6}$-alkoxyalkyl, C$_{2-6}$-alkenyloxy, carboxy, C$_{1-6}$-alkoxycarbonyl, C$_{1-6}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di(C$_{1-6}$-alkyl)amino, carbamoyl, mono- and di(C$_{1-6}$-alkyl)-amino-carbonyl, amino-C$_{1-6}$-alkyl-aminocarbonyl, mono- and di(C$_{1-6}$-alkyl)amino-C$_{1-6}$-alkyl-aminocarbonyl, C$_{1-6}$-alkyl-carbonylamino, carbamido, C$_{1-6}$-alkanoyloxy, sulphono, C$_{1-6}$-alkylsulphonyloxy, nitro, azido, sulphanyl, C$_{1-6}$-alkylthio, and halogen, where aryl and heteroaryl may be optionally substituted, and where two geminal substituents together may designate oxo, thioxo, imino, or optionally substituted methylene.

In some embodiments R$^1$, R$^2$, R$^3$, R$^5$ and R$^{5*}$ are independently selected from C$_{1-6}$ alkyl, such as methyl, and hydrogen.

In some embodiments R$^1$, R$^2$, R$^3$, R$^5$ and R$^{5*}$ are all hydrogen.

In some embodiments R$^1$, R$^2$, R$^3$, are all hydrogen, and either R$^5$ and R$^{5*}$ is also hydrogen and the other of R$^5$ and R$^{5*}$ is other than hydrogen, such as C$_{1-6}$ alkyl such as methyl.

In some embodiments, R$^a$ is either hydrogen or methyl. In some embodiments, when present, R$^b$ is either hydrogen or methyl.

In some embodiments, one or both of R$^a$ and R$^b$ is hydrogen.

In some embodiments, one of R$^a$ and R$^b$ is hydrogen and the other is other than hydrogen.

In some embodiments, one of R$^a$ and R$^b$ is methyl and the other is hydrogen.

In some embodiments, both of R$^a$ and R$^b$ are methyl.

In some embodiments, the biradical —X—Y— is —O—CH$_2$—, W is O, and all of R$^1$, R$^2$, R$^3$, R$^5$ and R$^{5*}$ are all hydrogen. Such LNA nucleosides are disclosed in WO99/014226, WO00/66604, WO98/039352 and WO2004/046160 which are all hereby incorporated by reference, and include what are commonly known as beta-D-oxy LNA and alpha-L-oxy LNA nucleosides.

In some embodiments, the biradical —X—Y— is —S—CH$_2$—, W is O, and all of R$^1$, R$^2$, R$^3$, R$^5$ and R$^{5*}$ are all hydrogen. Such thio LNA nucleosides are disclosed in WO99/014226 and WO2004/046160.

In some embodiments, the biradical —X—Y— is —NH—CH$_2$—, W is O, and all of R$^1$, R$^2$, R$^3$, R$^5$ and R$^{5*}$ are all hydrogen. Such amino LNA nucleosides are disclosed in WO99/014226 and WO2004/046160.

In some embodiments, the biradical —X—Y— is —O—CH$_2$—CH$_2$— or —O—CH$_2$—CH$_2$—CH$_2$—, W is O, and all of R$^1$, R$^2$, R$^3$, R$^5$ and R$^{5*}$ are all hydrogen. Such LNA nucleosides are disclosed in WO00/047599 and Morita et al., Bioorganic & Med. Chem. Lett. 12 73-76, which are hereby incorporated by reference, and include what are commonly known as 2'-O-4'C-ethylene bridged nucleic acids (ENA).

In some embodiments, the biradical —X—Y— is —O—CH$_2$—, W is O, and all of R$^1$, R$^2$, R$^3$, and one of R$^5$ and R$^{5*}$ are hydrogen, and the other of R$^5$ and R$^{5*}$ is other than hydrogen such as C$_{1-6}$ alkyl, such as methyl. Such 5' substituted LNA nucleosides are disclosed in WO2007/134181.

In some embodiments, the biradical —X—Y— is —O—CR$^a$R$^b$—, wherein one or both of R$^a$ and R$^b$ are other than hydrogen, such as methyl, W is O, and all of R$^1$, R$^2$, R$^3$, and one of R$^5$ and R$^{5*}$ are hydrogen, and the other of R$^5$ and R$^{5*}$ is other than hydrogen such as C$_{1-6}$ alkyl, such as methyl. Such bis modified LNA nucleosides are disclosed in WO2010/077578.

In some embodiments, the biradical —X—Y— designate the bivalent linker group —O—CH(CH$_2$OCH$_3$)—(2' O-methoxyethyl bicyclic nucleic acid—Seth at al., 2010, J. Org. Chem. Vol 75(5) pp. 1569-81). In some embodiments, the biradical —X—Y— designate the bivalent linker group —O—CH(CH$_2$CH$_3$)—(2'O-ethyl bicyclic nucleic acid—Seth at al., 2010, J. Org. Chem. Vol 75(5) pp. 1569-81). In some embodiments, the biradical —X—Y— is —O—CHR$^a$—, W is O, and all of R$^1$, R$^2$, R$^3$, R$^5$ and R$^{5*}$ are all hydrogen. Such 6' substituted LNA nucleosides are disclosed in WO10036698 and WO07090071.

In some embodiments, the biradical —X—Y— is —O—CH(CH$_2$OCH$_3$)—, W is O, and all of R$^1$, R$^2$, R$^3$, R$^5$ and R$^{5*}$ are all hydrogen. Such LNA nucleosides are also known as cyclic MOEs in the art (cMOE) and are disclosed in WO07090071.

In some embodiments, the biradical —X—Y— designates the bivalent linker group —O—CH(CH$_3$)—. —in either the R- or S-configuration. In some embodiments, the biradical —X—Y— together designate the bivalent linker group —O—CH$_2$—O—CH$_2$—(Seth et al., 2010, *J. Org. Chem*). In some embodiments, the biradical —X—Y— is —O—CH(CH$_3$)—, W is O, and all of R$^1$, R$^2$, R$^3$, R$^5$ and R$^{5*}$ are all hydrogen. Such 6' methyl LNA nucleosides are also known as cET nucleosides in the art, and may be either (S)cET or (R)cET stereoisomers, as disclosed in WO07090071 (beta-D) and WO2010/036698 (alpha-L)).

In some embodiments, the biradical —X—Y— is —O—CR$^a$R$^b$—, wherein in neither R$^a$ or R$^b$ is hydrogen, W is O, and all of R$^1$, R$^2$, R$^3$, R$^5$ and R$^{5*}$ are all hydrogen. In some embodiments, R$^a$ and R$^b$ are both methyl. Such 6' di-substituted LNA nucleosides are disclosed in WO 2009006478.

In some embodiments, the biradical —X—Y— is —S—CHR$^a$—, W is O, and all of R$^1$, R$^2$, R$^3$, R$^5$ and R$^{5*}$ are all hydrogen. Such 6' substituted thio LNA nucleosides are disclosed in WO11156202. In some 6' substituted thio LNA embodiments R$^a$ is methyl.

In some embodiments, the biradical —X—Y— is —C(=CH$_2$)—C(R$^a$R$^b$)—, such as —C(=CH$_2$)—CH$_2$—, or —C(=CH$_2$)—CH(CH$_3$)—W is O, and all of R$^1$, R$^2$, R$^3$, R$^5$ and R$^{5*}$ are all hydrogen. Such vinyl carbo LNA nucleosides are disclosed in WO08154401 and WO09067647.

In some embodiments the biradical —X—Y— is —N(OR$^a$)—, W is O, and all of R$^1$, R$^2$, R$^3$, R$^5$ and R$^{5*}$ are all hydrogen. In some embodiments R$^a$ is C$_{1-6}$ alkyl such as methyl. Such LNA nucleosides are also known as N substituted LNAs and are disclosed in WO2008/150729. In some embodiments, the biradical —X—Y— together designate the bivalent linker group —O—NR$^a$—CH$_3$—(Seth et al., 2010, *J. Org. Chem*). In some embodiments the biradical —X—Y— is —N(R$^a$)—, W is O, and all of R$^1$, R$^2$, R$^3$, R$^5$ and R$^{5*}$ are all hydrogen. In some embodiments R$^a$ is C$_{1-6}$ alkyl such as methyl.

In some embodiments, one or both of R$^5$ and R$^{5*}$ is hydrogen and, when substituted the other of R$^5$ and R$^{5*}$ is C$_{1-6}$ alkyl such as methyl. In such an embodiment, R$^1$, R$^2$, R$^3$, may all be hydrogen, and the biradical —X—Y— may be selected from —O—CH$_2$—or —O—CH(CR$^a$)—, such as —O—CH(CH$_3$)—.

In some embodiments, the biradical is —CR$^a$R$^b$—O—CR$^a$R$^b$—, such as CH$_2$—O—CH$_2$—, W is 0 and all of R$^1$, R$^2$, R$^3$, R$^5$ and R$^{5*}$ are all hydrogen. In some embodiments R$^a$ is C$_{1-6}$ alkyl such as methyl. Such LNA nucleosides are also known as conformationally restricted nucleotides (CRNs) and are disclosed in WO2013036868.

In some embodiments, the biradical is —O—CR$^a$R$^b$—O—CR$^a$R$^b$—, such as O—CH$_2$—O—CH$_2$—, W is O and all of R$^i$, R$^2$, R$^3$, R$^5$ and R$^{5*}$ are all hydrogen. In some embodiments R$^a$ is C$_{1-6}$ alkyl such as methyl. Such LNA nucleosides are also known as COC nucleotides and are disclosed in Mitsuoka et al., *Nucleic Acids Research* 2009 37(4), 1225-1238.

It will be recognized than, unless specified, the LNA nucleosides may be in the beta-D or alpha-L stereoisoform.

Certain examples of LNA nucleosides are presented in Scheme 1.

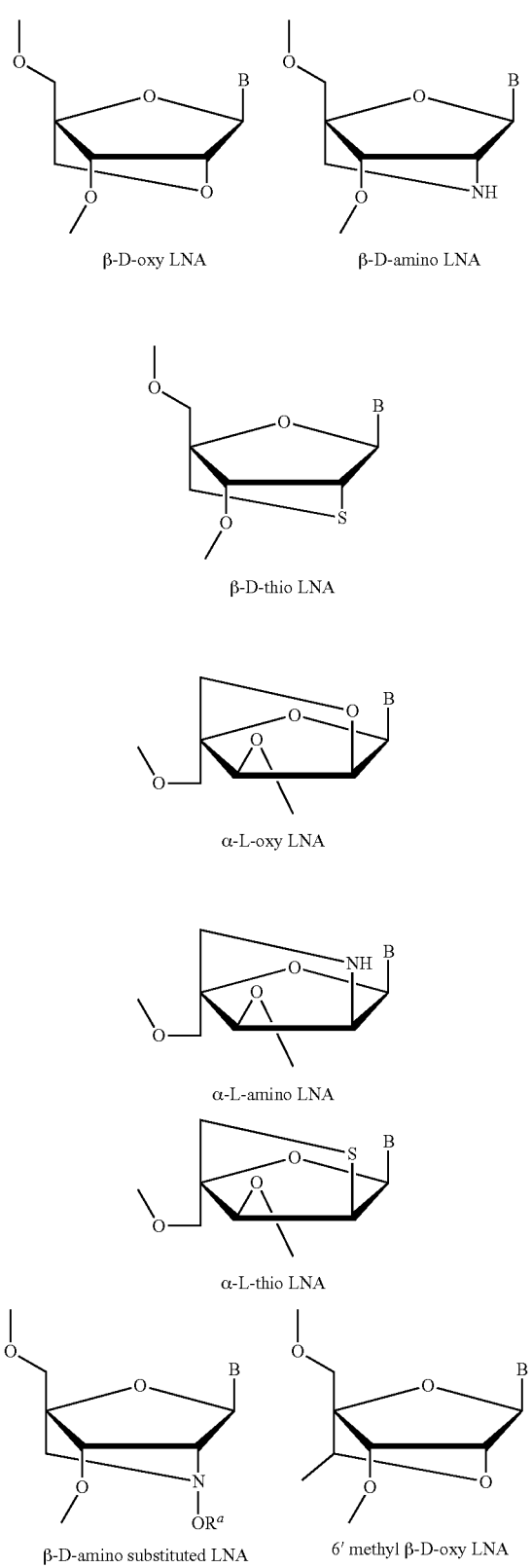

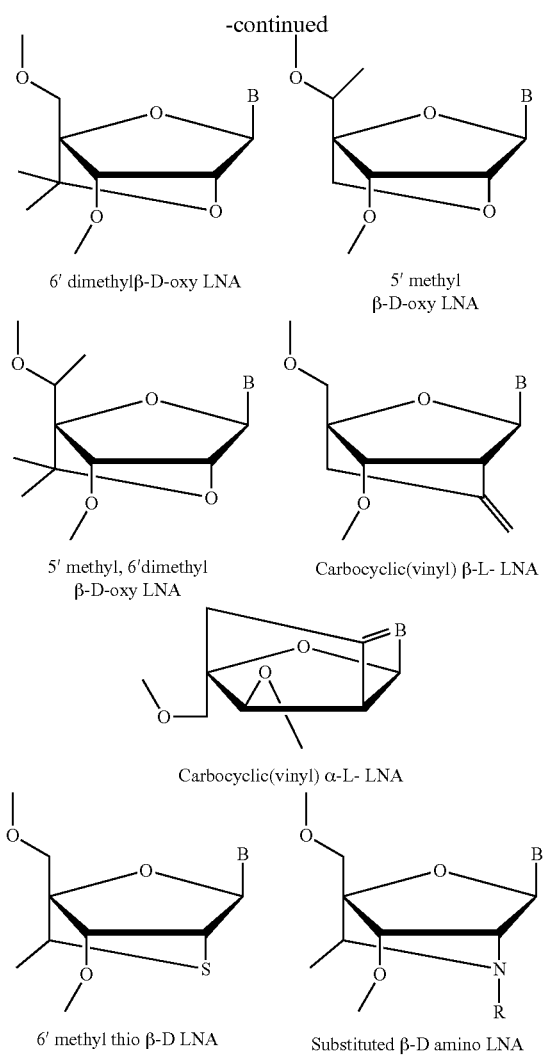

As illustrated in the examples, in some embodiments of the disclosure the LNA nucleosides in the oligonucleotides are beta-D-oxy-LNA nucleosides.

II.E. Nuclease Mediated Degradation

Nuclease mediated degradation refers to an oligonucleotide capable of mediating degradation of a complementary nucleotide sequence when forming a duplex with such a sequence.

In some embodiments, the oligonucleotide may function via nuclease mediated degradation of the target nucleic acid, where the oligonucleotides of the disclosure are capable of recruiting a nuclease, particularly and endonuclease, preferably endoribonuclease (RNase), such as RNase H. Examples of oligonucleotide designs which operate via nuclease mediated mechanisms are oligonucleotides which typically comprise a region of at least 5 or 6 DNA nucleosides and are flanked on one side or both sides by affinity enhancing nucleosides, for example gapmers.

II.F. RNase H Activity and Recruitment

The RNase H activity of an antisense oligonucleotide refers to its ability to recruit RNase H when in a duplex with a complementary RNA molecule and induce cleavage and subsequent degradation of the complementary RNA molecule. WO01/23613 provides in vitro methods for determining RNase H activity, which may be used to determine the ability to recruit RNase H. Typically an oligonucleotide is deemed capable of recruiting RNase H if it, when provided with a complementary target nucleic acid sequence, has an initial rate, as measured in pmol/l/min, of at least 5%, such as at least 10% or more than 20% of the of the initial rate determined when using a oligonucleotide having the same base sequence as the modified oligonucleotide being tested, but containing only DNA monomers, with phosphorothioate linkages between all monomers in the oligonucleotide, and using the methodology provided by Example 91-95 of WO01/23613.

In some embodiments, an oligonucleotide is deemed essentially incapable of recruiting RNaseH if, when provided with the complementary target nucleic acid, the RNaseH initial rate, as measured in pmol/l/min, is less than 20%, such as less than 10%, such as less than 5% of the initial rate determined when using a oligonucleotide having the same base sequence as the oligonucleotide being tested, but containing only DNA monomers, with no 2' substitutions, with phosphorothioate linkages between all monomers in the oligonucleotide, and using the methodology provided by Example 91-95 of WO01/23613.

II.G. ASO Design

The ASO of the disclosure can comprise a nucleotide sequence which comprises both nucleotides and nucleotide analogs, and can be in the form of a gapmer. Examples of configurations of a gapmer that can be used with the ASO of the disclosure are described in U.S. Patent Appl. Publ. No. 2012/0322851.

The term gapmer as used herein refers to an antisense oligonucleotide which comprises a region of RNase H recruiting oligonucleotides (gap) which is flanked 5' and 3' by one or more affinity enhancing modified nucleosides (flanks). Various gapmer designs are described herein. The term LNA gapmer is a gapmer oligonucleotide wherein at least one of the affinity enhancing modified nucleosides is an LNA nucleoside. The term mixed wing gapmer refers to a LNA gapmer wherein the flank regions comprise at least one LNA nucleoside and at least one DNA nucleoside or non-LNA modified nucleoside, such as at least one 2' substituted modified nucleoside, such as, for example, 2'-O-alkyl-RNA, 2'-O-methyl-RNA, 2'-alkoxy-RNA, 2'-O-methoxyethyl-RNA (MOE), 2'-amino-DNA, 2'-Fluoro-RNA and 2'-F-ANA nucleoside(s). In some embodiments the mixed wing gapmer has one flank which comprises LNA nucleosides (e.g., 5' or 3') and the other flank (3' or 5' respectfully) comprises 2' substituted modified nucleoside(s).

In some embodiments, in addition to enhancing affinity of the ASO for the target region, some nucleoside analogs also mediate RNase (e.g., RNaseH) binding and cleavage.

II.G.1. Gapmer Design

In one embodiment, the ASO of the disclosure is a gapmer. A gapmer ASO is an ASO which comprises a contiguous stretch of nucleotides which is capable of recruiting an RNase, such as RNaseH, such as a region of at least 6 DNA nucleotides, referred to herein in as region B (B), wherein region B is flanked both 5' and 3' by regions of affinity enhancing nucleotide analogs, such as from 1-10 nucleotide analogs 5' and 3' to the contiguous stretch of nucleotides which is capable of recruiting RNase—these regions are referred to as regions A (A) and C (C) respectively.

In certain embodiments, the gapmer is an alternating flank gapmer, examples of which are discussed below. In certain embodiments, the alternating flank gapmer exhibits less off target binding than a traditional gapmer. In certain embodiments, the alternating flank gapmer has better long term tolerability than a traditional gapmer.

An alternating flank gapmer can comprise a (poly)nucleotide sequence of formula (5' to 3'), A-B—C, wherein: region A (A) (5' region or a first wing sequence) comprises at least one nucleotide analog, such as at least one LNA unit, such as from 1-10 nucleotide analogs, such as LNA units, and; region B (B) comprises at least six consecutive nucleotides which are capable of recruiting RNase (when formed in a duplex with a complementary RNA molecule, such as the pre-mRNA or mRNA target), such as DNA nucleotides, and; region C (C) (3'region or a second wing sequence) comprises at least one nucleotide analog, such as at least one LNA unit, such as from 1-10 nucleotide analogs, such as LNA units; wherein regions A and C can include at any position in A and C 1-3 insertions of DNA nucleotide regions (e.g., DNA Insertions), in which these DNA insertions can each be 1-6 DNA units long.

In certain other embodiments, the gapmer, e.g., an alternating flank gapmer, comprises a (poly)nucleotide sequence of formula (5' to 3'), A-B—C, or optionally A-B—C-D or D-A-B—C, wherein: region A (A) (5' region) comprises at least one nucleotide analog, such as at least one LNA unit, such as from 1-10 nucleotide analogs, such as LNA units, and; region B (B) comprises at least five consecutive nucleotides which are capable of recruiting RNase (when formed in a duplex with a complementary RNA molecule, such as the mRNA target), such as DNA nucleotides, and; region C (C) (3'region) comprises at least one nucleotide analog, such as at least one LNA unit, such as from 1-10 nucleotide analogs, such as LNA units, and; region D (D), when present comprises 1, 2 or 3 nucleotide units, such as DNA nucleotides.

In some embodiments, region A comprises 1, 2, 3, 4, 5, 6, 7, 8, 9, or 10 nucleotide analogs, such as LNA units, such as from 2-5 nucleotide analogs, such as 2-5 LNA units, such as 2-5 nucleotide analogs, such as 3-5 LNA units; and/or region C consists of 1, 2, 3, 4, 5, 6, 7, 8, 9, or 10 nucleotide analogs, such as LNA units, such as from 2-5 nucleotide analogs, such as 2-5 LNA units, such as 2-5 nucleotide analogs, such as 3-5 LNA units.

In some embodiments B comprises 5, 6, 7, 8, 9, 10, 11, 12, 13, 14, 15, 16, 17, 18, 19, 20, 21, 22, or 23 consecutive nucleotides which are capable of recruiting RNase, or from 6-14, 7-14, 8-14, or from 7-10, or from 7-9, such as 8, such as 9, such as 10, or such as 14 consecutive nucleotides which are capable of recruiting RNase. In some embodiments region B comprises at least five DNA nucleotide unit, such as 5-23 DNA units, such as from 5-20 DNA units, such as from 5-18 DNA units, such as from 6-14 DNA units, such as from 8-14 DNA units, such as 5, 6, 7, 8, 9, 10, 11, 12, 13, or 14 DNA units.

In some embodiments region A comprises 3, 4, or 5 nucleotide analogs, such as LNA, region B consists of 5, 6, 7, 8, 9, 10, 11, 12, 13, or 14 DNA units, and region C consists of 3, 4, or 5 nucleotide analogs, such as LNA. Such designs include (A-B—C) 5-10-5, 3-14-3, 3-10-3, 3-10-4, 4-10-3, 3-9-3, 3-9-4, 4-9-3, 3-8-3, 3-8-4, 4-8-3, 3-7-3, 3-7-4, and 4-7-3, and can further include region D, which can have one to 3 nucleotide units, such as DNA units.

In some embodiments, the ASO of the disclosure, e.g., an alternating flank gapmer, comprises the formula of 5'-A-B—C-3', wherein (i) region B is a contiguous sequence of at least 5, 6, 7, 8, 9, or 10, e.g., 5 to 18 DNA units, which are capable of recruiting RNase;

(ii) region A is a first wing sequence of 1 to 10 nucleotides, wherein the first wing sequence comprises one or more nucleotide analogs and optionally one or more DNA units (e.g., DNA insertion) and wherein at least one of the nucleotide analogs is located at the 3' end of A; and (iii) region C is a second wing sequence of 1 to 10 nucleotides, wherein the second wing sequence comprises one or more nucleotide analogs and optionally one or more DNA units (e.g., DNA insertion) and wherein at least one of the nucleotide analogs is located at the 5' end of C.

In some embodiments, the first wing sequence (region A in the formula) comprises a combination of nucleotide analogs and DNA units selected from (i) 1-10 nucleotide analogs and 0 DNA unit; (ii) 1-9 nucleotide analogs and 1 DNA unit; (iii) 1-8 nucleotide analogs and 1-2 DNA units; (iv) 1-7 nucleotide analogs and 1-3 DNA units; (v) 1-6 nucleotide analogs and 1-4 DNA units; (vi) 1-5 nucleotide analogs and 1-5 DNA units; (vii) 1-4 nucleotide analogs and 1-6 DNA units; (viii) 1-3 nucleotide analogs and 1-7 DNA units; (ix) 1-2 nucleotide analogs and 1-8 DNA units; (x) 1 nucleotide analog and 1-9 DNA units.

In certain embodiments, the second wing sequence (region C in the formula) comprises a combination of nucleotide analogs and DNA unit selected from (i) 1-10 nucleotide analogs and 0 DNA unit; (ii) 1-9 nucleotide analogs and 1 DNA unit; (iii) 1-8 nucleotide analogs and 1-2 DNA units; (iv) 1-7 nucleotide analogs and 1-3 DNA units; (v) 1-6 nucleotide analogs and 1-4 DNA units; (vi) 1-5 nucleotide analogs and 1-5 DNA units; (vii) 1-4 nucleotide analogs and 1-6 DNA units; (viii) 1-3 nucleotide analogs and 1-7 DNA units; (ix) 1-2 nucleotide analogs and 1-8 DNA units; (x) 1 nucleotide analog and 1-9 DNA units.

In some embodiments, region A in the ASO formula has a sub-formula selected from the first wing design of any ASOs in FIGS. 2 and 3, and/or region C in the ASO formula has a sub-formula selected from the second wing design of any ASOs in FIGS. 2 and 3, wherein the upper letter is a nucleotide analog (e.g., sugar modified analog, which can also be written as L) and the lower letter is DNA (which can also be written as D).

In certain embodiments, the ASO, e.g., an alternating flank gapmer, has the formula of 5' A-B—C 3', wherein region B is a contiguous sequence of 5 to 18 DNA units, region A has a formula of LLDLL, LDLLL, or LLLDL and region C has a formula of LLDLL or LDLDLL, and wherein L is an LNA unit and D is a DNA unit.

In some embodiments, the ASO has the formula of 5' A-B—C 3', wherein region B is a contiguous sequence of 10 DNA units, region A has the formula of LDL, and region C has the formula of LLLL, wherein L is an LNA unit and D is a DNA unit.

Further gapmer designs are disclosed in WO2004/046160, which is hereby incorporated by reference in its entirety. WO2008/113832 hereby incorporated by reference in its entirety, refers to 'shortmer' gapmer ASOs. In some embodiments, ASOs presented herein can be such shortmer gapmers.

In some embodiments the ASO, e.g., an alternating flank gapmer, comprises a contiguous nucleotide sequence of a total of 10, 11, 12, 13, 14, 15, 16, 17, 18, 19, or 20 nucleotide units, wherein the contiguous nucleotide sequence is of formula (5'-3'), A-B—C, or optionally A-B—C-D or D-A-B—C, wherein; region A consists of 1, 2, 3, 4, or 5 nucleotide analog units, such as LNA units; region B consists of 5, 6, 7, 8, 9, 10, 11, 12, 13, or 14 contiguous nucleotide units which are capable of recruiting RNase when formed in a duplex with a complementary RNA molecule (such as a mRNA target); and region C consists of 1, 2, 3, 4, or 5 nucleotide analog units, such as LNA units. When present, region D consists of a single DNA unit.

In some embodiments A comprises 1 LNA unit. In some embodiments region A comprises 2 LNA units. In some embodiments region A comprises 3 LNA units. In some embodiments region A comprises 4 LNA units. In some embodiments region A comprises 5 LNA units. In some embodiments region C comprises 1 LNA unit. In some embodiments C comprises 2 LNA units. In some embodiments region C comprises 3 LNA units. In some embodiments region C comprises 4 LNA units. In some embodiments region C comprises 5 LNA units. In some embodiments region B comprises 6 nucleotide units. In some embodiments region B comprises 7 nucleotide units. In some embodiments region B comprises 8 nucleotide units. In some embodiments region B comprises 9 nucleotide units. In certain embodiments, region B comprises 10 nucleoside units. In certain embodiments, region B comprises 11 nucleoside units. In certain embodiments, region B comprises 12 nucleoside units. In certain embodiments, region B comprises 13 nucleoside units. In certain embodiments, region B comprises 14 nucleoside units. In certain embodiments, region B comprises 7-23 DNA monomers or 5-18 DNA monomers. In some embodiments region B comprises from 6-23 DNA units, such as 6, 7, 8, 9, 10, 11, 12, 13, 14, 15, 16, 17, 18, 19, 20, 21, 22, or 23 DNA units. In some embodiments region B consists of DNA units. In some embodiments region B comprises at least one LNA unit which is in the alpha-L configuration, such as 2, 3, 4, 5, 6, 7, 8, 9, 10, 11, 12, 13, 14, 15, 16, 17, 18, 19, 20, 21, 22, or 23 LNA units in the alpha-L-configuration. In some embodiments region B comprises at least one alpha-L-oxy LNA unit or wherein all the LNA units in the alpha-L-configuration are alpha-L-oxy LNA units. In some embodiments the number of nucleotides present in A-B—C are selected from (nucleotide analog units—region B—nucleotide analog units): 1-8-1, 1-8-2, 2-8-1, 2-8-2, 3-8-3, 2-8-3, 3-8-2, 4-8-1, 4-8-2, 1-8-4, 2-8-4, or; 1-9-1, 1-9-2, 2-9-1, 2-9-2, 2-9-3, 3-9-2, 1-9-3, 3-9-1, 4-9-1, 1-9-4, or; 1-10-1, 1-10-2, 2-10-1, 2-10-2, 1-10-3, and 3-10- 1. In some embodiments the number of nucleotides in A-B—C is selected from: 2-7-1, 1-7-2, 2-7-2, 3-7-3, 2-7-3, 3-7-2, 3-7-4, and 4-7-3. In other embodiments, the ASO contains 10 DNA units in B, LDLLL in A (first wing) and LLDLL in C (second wing). In yet other embodiments, the ASO contains 9 DNA units in B, LDDLL in A, and LDLDLL in C. In still other embodiments, the ASO contains 10 DNA units in B, LLDLL in A, and LLDLL in C. In further embodiments, the ASO contains 9 DNA units in B, LLLLL in A, and LDDLL in C. In certain embodiments, each of regions A and C comprises three LNA monomers, and region B consists of 7, 8, 9, 10, 11, 12, 13, or 14 nucleoside monomers, for example, DNA monomers. In some embodiments both A and C consist of two LNA units each, and B consists of 7, 8, or 9 nucleotide units, for example DNA units. In various embodiments, other gapmer designs include those where regions A and/or C consists of 3, 4, 5 or 6 nucleoside analogs, such as monomers containing a 2'-O-methoxyethyl-ribose sugar (2'-MOE) or monomers containing a 2'-fluoro-deoxyribose sugar, and region B consists of 7, 8, 9, 10, 11, 12, 13, 14, 15, 16, 17, 18, 19, 20, 21, 22, or 23 nucleosides, such as DNA monomers, where regions A-B—C have 3-8-3, 3-9-3, 3-10-3, 5-10-5 or 4-12-4 monomers. Further gapmer designs are disclosed in WO 2007/146511A2, hereby incorporated by reference in its entirety.

In some embodiments, the alternating flank ASO has at least 10 contiguous nucleotides, comprising region A, region B, and region C (A-B—C), wherein region B comprises at least 5 consecutive nucleoside units and is flanked at 5' by region A of 1-8 contiguous nucleoside units and at 3' by region C of 1-8 contiguous nucleoside units, wherein region B, when formed in a duplex with a complementary RNA, is capable of recruiting RNaseH, and wherein region A and region C are selected from the group consisting of:
(i) region A comprises a 5' LNA nucleoside unit and a 3' LNA nucleoside unit, and at least one DNA nucleoside unit between the 5' LNA nucleoside unit and the 3' LNA nucleoside unit, and, region C comprises at least two 3' LNA nucleosides;
(ii) region A comprises at least one 5' LNA nucleoside and region C comprises a 5' LNA nucleoside unit, at least two terminal 3' LNA nucleoside units, and at least one DNA nucleoside unit between the 5' LNA nucleoside unit and the 3' LNA nucleoside units, and
(iii) region A comprises a 5' LNA nucleoside unit and a 3' LNA nucleoside unit, and at least one DNA nucleoside unit between the 5' LNA nucleoside unit and the 3' LNA nucleoside unit; and region C comprises a 5' LNA nucleoside unit, at least two terminal 3' LNA nucleoside units, and at least one DNA nucleoside unit between the 5' LNA nucleoside unit and the 3' LNA nucleoside units.

In some embodiments, region A or region C comprises 1, 2, or 3 DNA nucleoside units. In other embodiments, region A and region C comprise 1, 2, or 3 DNA nucleoside units. In yet other embodiments, region B comprises at least five consecutive DNA nucleoside units. In certain embodiments, region B comprises 6, 7, 8, 9, 10, 11, 12, 13 or 14 consecutive DNA nucleoside units. In some embodiments, region B is 8, 9 10, 11, or 12 nucleotides in length. In other embodiments, region A comprises two 5' terminal LNA nucleoside units. In some embodiments, region A has formula 5'[LNA]$_{1-3}$[DNA]$_{1-3}$[LNA]$_{1-3}$, or 5'[LNA]$_{1-2}$[DNA]$_{1-2}$[LNA]$_{1-2}$[DNA]$_{1-2}$[LNA]$_{1-2}$. In other embodiments, region C has formula [LNA]$_{1-3}$[DNA]$_{1-3}$[LNA]$_{2-3}$ 3', or [LNA]$_{1-2}$[DNA]$_{1-2}$[LNA]$_{1-2}$[DNA]$_{1-2}$[LNA]$_{2-3}$ 3'. In yet other embodiments, region A has formula 5'[LNA]$_{1-3}$[DNA]$_{1-3}$[LNA]$_{1-3}$, or 5'[LNA]$_{1-2}$[DNA]$_{1-2}$[LNA]$_{1-2}$[DNA]$_{1-2}$[LNA]$_{1-2}$, and region C comprises 2, 3, 4 or 5 consecutive LNA nucleoside units. In some embodiments, region C has formula [LNA]$_{1-3}$[DNA]$_{1-3}$[LNA]$_{2-3}$ 3' or [LNA]$_{1-2}$ [DNA]$_{1-2}$ [LNA]$_{1-2}$ [DNA]$_{1-2}$ [LNA]$_{2-3}$ 3', and region A comprises 1, 2, 3, 4 or 5 consecutive LNA nucleoside units. In still other embodiments, region A has a sequence of LNA and DNA nucleosides, 5'-3' selected from the group consisting of L, LL, LDL, LLL, LLDL, LDLL, LDDL, LLLL, LLLLL, LLLDL, LLDLL, LDLLL, LLDDL, LDDLL, LLDLD, LDLLD, LDDDL, LLLLLL, LLLLDL, LLLDLL, LLDLLL, LDLLLL, LLLDDL, LLDLDL, LLDDLL, LDDLLL, LDLLDL, LDLDLL, LDDDLL, LLDDDL, and LDLDLD, wherein L represents a LNA nucleoside, and D represents a DNA nucleoside. In yet other embodiments, region C has a sequence of LNA and DNA nucleosides, 5'-3' selected from the group consisting of LL, LLL, LLLL, LDLL, LLLLL, LLDLL, LDLLL, LDDLL, LDDLLL, LLDDLL, LDLDLL, LDDDLL, LDLDDLL, LDDLDLL, LDDDLLL, and LLDLDLL. In a further embodiment, region A has a sequence of LNA and DNA nucleosides, 5'-3' selected from the group consisting of LDL, LLDL, LDLL, LDDL, LLLDL, LLDLL, LDLLL, LLDDL, LDDLL, LLDLD, LDLLD, LDDDL, LLLLDL, LLLDLL, LLDLLL, LDLLLL, LLLDDL, LLDLDL, LLDDLL, LDDLLL, LLLDLL, LDLDLL, LDDDLL, LLDDDL, and LDLDLD, and region C has a sequence of LNA and DNA nucleosides, 5'-3' selected from the group consisting of LDLL, LLDL, LLLLL, LLDLL, LDLLL, LDDLL, LDDLLL, LLDDLL, LDLDLL, LDDDLL, LDLDDLL, LDDLDLL, LDDDLLL, and LLDLDLL.

In certain embodiments, the alternating flank ASO has contiguous nucleotides comprising a sequence of nucleosides, 5'-3', selected from the group consisting of LDLDDDDDDDDDDLLLL, LLDDDLLDDDDDDDDLL, LDLLDLDDDDDDDDDLL, LLLLDDDDDDDDDDLDLL, LLLLDDDDDDDDDLDDLL, LLLLDDDDDDDLDDDLL, LLLLDDDDDDDLDLDLL, LLLDLDDDDDDDDDLLL, LLLDLDDDDDDDDLDLL, LLLLDDDDDDDDDLDLL, LLLLDDDDDDDDLDDLL, LLLDDLDDDDDDDDDLL, LLLDDLDDDDDDDDLL, LLLDDDLDDDDDDDDLL, LLLDDLLDDDDDDDDLLL, LLLLLDDDDDDDDLDDLL, LDLLLDDDDDDDDDLL, LDLLLDDDDDDDDLDDLL, LDLLLLDDDDDDDDDLL, LLDLLLDDDDDDDDDLL, LLLDLDDDDDDDDDDLL, LLLDLDDDDDDDDDDLL, LLLLDDDDDDDDDDLL, LLLLDDDDDDDDLDDDLL, LDDLDDDDDDDDLDLL, LDDLDDDDDDDD-DLLDLL, LLLLLDDDDDDDDLDLL, LLLL-DDDDDDDDDLDLL, LLLDDDDDDDDDDLDLL, LLDLDDDDDDDDDLDLL, LDLLLDDDDDDDD-DLDLL, LLLDDDDDDDDDLDDLL, LLL-DDDDDDDDLDDDLL, LLLDDDDDDDDLDLDLL, LLLLDDDDDDDDDLDDLL, LLLLDDDDDDDDDLD-LLL, LLLLDDDDDDDDLDDDLL, LLLLDDDDDDD-DLDDLLL, LLLLDDDDDDDDLDLDLL, LLLL-DDDDDDDLDDLDLL, LLLLDDDDDDDLDLDLL, LLDLLDDDDDDDDDDDLL, LLDLLLDDDDDDD-DLDLL, LLLDLDDDDDDDDDDLL, LLLD-LDDDDDDDDLDLL, LLLDLDDDDDDDLDDLL, LLLDLDDDDDDDLDLDLL, LLLLDDDDDDDD-DLLDLL, LLLLLDDDDDDDDDLDLLL, LLLLLL-DDDDDDDDDLDDLL, LLLLDDDDDDDDDLLDLL, LLLLDDDDDDDDDLDLLL, LLLLDDDDDDDDD-DLDDLL, LLLDDDDDDDDDDLLDLL, LLL-DDDDDDDDDDLDLLL, LLLLLDDDDDDDD-DLLDLL, LLDDDDDDDDDDDLDDLL, LLDLLDDDDDDDDDLDDLL, LLLDDDDDDDDDDDDLL, LLLLDDDDDDDDDDLDDLL, LLLL-DDDDDDDDDLDLDLL, LLLLDDDDDDDLLDLDLL, LDLLLLDDDDDDDDLLDLL, LLDLLDDDDDDDDDD-DLLDLL, LLDLDDDDDDDDDDLLLL, LLD-DLDDDDDDDDDLLLL, LLLDLDDDDDDDDDD-DLLLL, LLDLDDDDDDDDDDDLLL, LLDLLDDDDDDDDDDLLLL, LLD-DLDDDDDDDDDDLLL, LLLDDDDDDDDDDLD-DLLL, LLLDLDDDDDDDDDDDLLL, LLDLL-DDDDDDDDDDLLL,
LLLLDDDDDDDDDDLLDLL, LLLLDDDDDDDDD-DLLDDLL, LLDDLDDDDDDDDLDLLL, LLDDLD-LDDDDDDDDDLLLL, LLDDLDDDDDDDDLDLLL, LLLDLDDDDDDDDLDLDLL, LLDLLDDDDDDDD-DLDDLLL, LLLDLDDDDDDDDDLDLLL, LLDLD-LDDDDDDDDDLLLL, LLLLDDDDDDDDDDLDLD-DLL, LLLDLDDDDDDDDDLDLLL, LLDLDLDDDDDDDDLLLLL, LLDLLDDDDDDDD-DLLLLL, LLDLDDDDDDDDDDDLLLL, LLDDDLL-DDDDDDDDDDLLDLL, LLLDLDDDDDDDDDDDDLLL, LLDDLLDDDDDDDDDLLDLL, DLLLL, LLDLLDDDDDDDDDLDLDLL, LLLLDDDDDDDDDLDDLLL, LLLD-DLDDDDDDDDDLLLL, LLLDLDDDDDDDD-DLLDLL, LLLLDDDDDDDDDLDLDLL, LLLL-DDDDDDDDDDLDLLL, and LLDDLLDDDDDDDDDDDLDLL; wherein L represents a LNA nucleoside, and D represents a DNA nucleoside. In other embodiments, the LNA nucleoside is beta-D-oxy LNA.

In yet other embodiments, an alternating flank ASO has contiguous nucleotides comprising an alternating sequence of LNA and DNA nucleoside units, 5'-3', selected from the group consisting of: 1-1-1-10-4, 1-2-1-9-2-1-2, 1-2-1-9-1-1-3, 2-3-2-8-2, 1-1-2-1-1-9-2, 3-10-1-1-2, 3-9-1-2-2, 3-8-1-3-2, 3-8-1-1-1-1-2, 3-1-1-9-3, 3-1-1-8-1-1-2, 4-9-1-1-2, 4-8-1-2-2, 3-3-1-8-2, 3-2-1-9-2, 3-2-2-8-2, 3-2-2-7-3, 5-7-1-2-2, 1-1-3-10-2, 1-1-3-7-1-2-2, 1-1-4-9-2, 2-1-3-9-2, 3-1-1-10-2, 3-1-1-7-1-2-2, 3-1-2-9-2, 4-7-1-3-2, 5-9-1-1-2, 4-10-1-1-2, 3-11-1-1-2, 2-1-1-10-1-1-2, 1-1-3-9-1-1-2, 3-10-1-2-2, 3-9-1-3-2, 3-8-1-1-1-2-2, 4-9-1-2-2, 4-9-1-1-3, 4-8-1-3-2, 4-8-1-2-3, 4-8-1-1-1-1-2, 4-7-1-2-1-1-2, 4-7-1-1-1-2-2, 2-1-2-11-2, 2-1-3-8-1-1-2, 3-1-1-11-2, 3-1-1-9-1-1-2, 3-1-1-8-1-2-2, 3-1-1-7-1-1-1-1-2, 4-9-2-1-2, 4-7-1-3-3, 5-9-1-1-3, 5-9-1-2-2, 4-10-2-1-2, 4-10-1-1-3, 4-10-1-2-2, 3-11-2-1-2, 3-11-1-1-3, 5-9-2-1-2, 3-11-1-2-2, 2-1-2-9-1-2-2, 3-1-1-10-1-1-2, 3-1-1-9-1-2-2, 4-9-1-1-1-1-2, 4-8-2-1-1-1-2, 1-1-3-10-2-1-2, 2-1-2-10-2-1-2, 2-1-1-12-4, 2-2-1-11-4, 3-1-1-11-4, 2-1-1-13-3, 2-1-2-11-4, 2-2-1-12-3, 3-11-1-2-3, 3-1-1-12-3, 2-1-2-12-3, 4-11-2-1-2, 4-10-2-2-2, 3-2-1-9-1-1-3, 2-2-1-1-1-9-4, 2-2-2-9-1-1-3, 3-1-1-9-1-1-1-1-2, 2-1-2-9-1-2-3, 3-1-1-10-1-1-3, 2-1-1-2-1-9-4, 4-9-1-1-1-2-2, 3-1-1-9-1-2-3, 2-1-1-1-1-10-4, 2-1-2-10-1-1-3, 2-1-1-1-1-9-2-1-2, 2-2-2-9-2-1-2, 4-9-1-2-1-1-2, 3-2-1-9-2-1-2, 2-1-2-9-2-2-2, 2-1-1-1-1-9-1-1-3, 3-1-1-9-2-2-2, 2-2-2-10-4, 2-1-2-9-1-1-1-2, 4-10-1-2-3, 3-2-1-10-4, 3-1-1-10-2-1-2, 4-10-1-1-1-2, 4-11-1-1-3, and 2-2-2-10-1-1-2; wherein the first numeral represents an number of LNA units, the next a number of DNA units, and alternating LNA and DNA regions thereafter.

In other embodiments, the ASOs of the disclosure are represented as any one of ASO numbers selected from FIGS. 2 and 3.

Figures 21A, 21B:
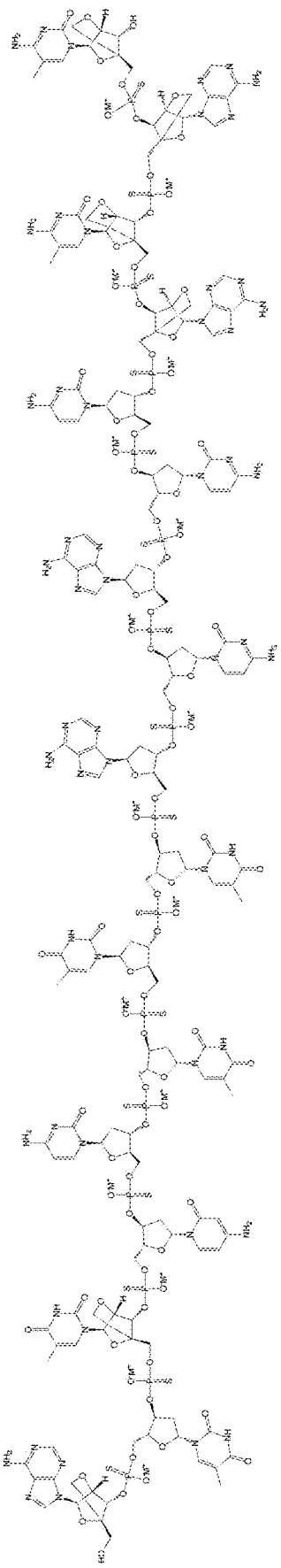
FIG. 21A shows the contiguous nucleotide sequence of ASO-005459. OxyA, OxyT, and Oxy MC are adenine beta D-oxy-LNA, thymine beta D-oxy-LNA, and methyl cytosine beta D-oxy-LNA, respectively; DNAt, DNAc, and DNAa are thymine DNA, cytosine DNA, and adenine DNA, respectively; and s is a phosphorothioate linkage.
FIG. 21B shows the molecular structure of ASO-005459 as disclosed herein. The provided structure has a molecular formula of $C_{171}H_{214}N_{56}O_{90}P_{16}S_{16}$ and each of the M+ is a pharmaceutically acceptable counterion such as $H^+$, $Na^+$, or $NH_4^+$.

In some embodiments, the ASO of the disclosure (i.e., ASO-005459) comprises a contiguous nucleotide sequence of 17 nucleotides in length, which corresponds to the complement of a region (i.e., junction between intron 1 and exon 2) of SNCA transcript, i.e., nucleotides 7,604-7,620 of SEQ ID NO: 28. In some embodiments, the ASO of the disclosure has the nucleotide sequence as set forth in SEQ ID NO: 15 (i.e., attcctttacaccacac) with an ASO design of LDLDDDDDDDDDDLLLL (i.e., AtTcctttacaccACAC), wherein the L indicates a locked nucleic acid nucleoside (i.e., LNA, e.g., beta-D-oxy-LNA) and the D indicates a deoxyribonucleic acid (DNA). Accordingly, the $1^{st}$, $3^{rd}$ and the $14^{th}$-$17^{th}$ nucleotides from the 5' end of ASO-005459 is beta-D-oxy-LNA and each of the other nucleotides is, DNA. In other embodiments, the ASO disclosed herein also has the following chemical structure: OxyAs DNAts OxyTs DNAcs DNAcs DNAts DNAts DNAts DNAas DNAcs DNAas DNAcs DNAcs OxyAs OxyMCs OxyAs OxyMC, wherein "s" indicates a phosphorothioate linkage. The structural formula for ASO-005459 is provided in FIG. 21B, wherein M+ is a pharmaceutically acceptable counterion. The term "pharmaceutically acceptable counterion," as used herein," refers to an ion that accompanies an ionic species in order to maintain electric neutrality that is not biologically or otherwise undesirable and thereby, allowing for the production of a pharmaceutically acceptable salt form. Accordingly, in some embodiments, pharmaceutically acceptable counterion can be H$^+$, Na$^+$, K$^+$, NH$_4^+$, Li$^+$, or any other cation, e.g., a cation with a charge of 1+. In some embodiments, the pharmaceutically acceptable counterion is H$^+$, Na$^+$, NH$_4^+$, or combinations thereof.

II.H. Internucleotide Linkages

The monomers of the ASOs described herein are coupled together via linkage groups. Suitably, each monomer is linked to the 3' adjacent monomer via a linkage group.

The person having ordinary skill in the art would understand that, in the context of the present disclosure, the 5' monomer at the end of an ASO does not comprise a 5' linkage group, although it may or may not comprise a 5' terminal group.

The terms "linkage group" and "internucleotide linkage" are intended to mean a group capable of covalently coupling together two nucleotides. Specific and preferred examples include phosphate groups and phosphorothioate groups.

The nucleotides of the ASO of the disclosure or contiguous nucleotides sequence thereof are coupled together via linkage groups. Suitably each nucleotide is linked to the 3' adjacent nucleotide via a linkage group.

Suitable internucleotide linkages include those listed within WO2007/031091, for example the internucleotide linkages listed on the first paragraph of page 34 of WO2007/031091 (hereby incorporated by reference in its entirety).

Examples of suitable internucleotide linkages that can be used with the disclosure include phosphodiester linkage, a phosphotriester linkage, a methylphosphonate linkage, a phosphoramidate linkage, a phosphorothioate linkage, and combinations thereof.

It is, in some embodiments, preferred to modify the internucleotide linkage from its normal phosphodiester to one that is more resistant to nuclease attack, such as phosphorothioate or boranophosphate—these two, being cleavable by RNaseH, also allow that route of antisense inhibition in reducing the expression of the target gene.

Suitable sulphur (S) containing internucleotide linkages as provided herein may be preferred. Phosphorothioate internucleotide linkages are also preferred, particularly for the gap region (B) of gapmers. Phosphorothioate linkages can also be used for the flanking regions (A and C, and for linking A or C to D, and within region D, as appropriate).

Regions A, B and C, can, however, comprise internucleotide linkages other than phosphorothioate, such as phosphodiester linkages, particularly, for instance when the use of nucleotide analogs protects the internucleotide linkages within regions A and C from endo-nuclease degradation—such as when regions A and C comprise LNA nucleotides.

The internucleotide linkages in the ASO can be phosphodiester, phosphorothioate or boranophosphate so as to allow RNaseH cleavage of targeted RNA. Phosphorothioate is preferred for improved nuclease resistance and other reasons, such as ease of manufacture. In some embodiments, the internucleotide linkages comprise one or more stereo-defined internucleotide linkages (e.g., such as stereo-defined modified phosphate linkages, e.g., phosphodiester, phosphorothioate, or boranophosphate linkages with a defined stereochemical structure). The term "stereo-defined internucleotide linkage" is used interchangeably with "chirally controlled internucleotide linkage" and refers to a internucleotide linkage in which the stereochemical designation of the phosphorus atom is controlled such that a specific amount of R$_p$ or S$_p$ of the internucleotide linkage is present within an ASO strand. The stereochemical designation of a chiral linkage can be defined (controlled) by, for example, asymmetric synthesis. An ASO having at least one stereo-defined internucleotide linkage can be called as a stereo-defined ASO, which includes both a fully stereo-defined ASO and a partially stereo-defined ASO.

In some embodiments, an ASO is fully stereo-defined. A fully stereo-defined ASO refers to an ASO sequence having a defined chiral center (R$_p$ or S$_p$) in each internucleotide linkage in the ASO. In some embodiments, an ASO is partially stereo-defined. A partially stereo-defined ASO refers to an ASO sequence having a defined chiral center (R$_p$ or S$_p$) in at least one internucleotide linkage, but not in all of the internucleotide linkages. Therefore, a partially stereo-defined ASO can include linkages that are achiral or stereo-nondefined in addition to the at least one stereo-defined linkage. When an internucleotide linkage in an ASO is stereo-defined, the desired configuration, either R$_p$ or S$_p$, is present in at least 10%, at least 20%, at least 30%, at least 40%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or essentially 100% of the ASO.

In one aspect of the ASO of the disclosure, the nucleotides and/or nucleotide analogs are linked to each other by means of phosphorothioate groups.

It is recognized that the inclusion of phosphodiester linkages, such as one or two linkages, into an otherwise phosphorothioate ASO, particularly between or adjacent to nucleotide analog units (typically in region A and or C) can modify the bioavailability and/or bio-distribution of an ASO—see WO2008/113832, hereby incorporated by reference.

In some embodiments, such as the embodiments referred to above, where suitable and not specifically indicated, all remaining linkage groups are either phosphodiester or phosphorothioate, or a mixture thereof.

In some embodiments all the internucleotide linkage groups are phosphorothioate.

When referring to specific gapmer oligonucleotide sequences, such as those provided herein it will be understood that, in various embodiments, when the linkages are phosphorothioate linkages, alternative linkages, such as those disclosed herein can be used, for example phosphate (phosphodiester) linkages can be used, particularly for linkages between nucleotide analogs, such as LNA, units. Likewise, when referring to specific gapmer oligonucleotide sequences, such as those provided herein, when the C residues are annotated as 5-'methyl modified cytosine, in various embodiments, one or more of the Cs present in the ASO can be unmodified C residues.

US Publication No. 2011/0130441, which was published Jun. 2, 2011 and is incorporated by reference herein in its entirety, refers to ASO compounds having at least one bicyclic nucleoside attached to the 3' or 5' termini by a neutral internucleoside linkage. The ASOs of the disclosure can therefore have at least one bicyclic nucleoside attached to the 3' or 5' termini by a neutral internucleoside linkage, such as one or more phosphotriester, methylphosphonate, MMI (3'-CH$_2$—N(CH$_3$) O-5'), amide-3 (3'-CH$_2$—C(=O)—N(H)-5'), formacetal (3'-O—CH$_2$—O-5') or thioformacetal (3'-S—CH$_2$—O-5'). The remaining linkages can be phosphorothioate.

In some embodiments, the ASOs of the disclosure have internucleotide linkages described in FIGS. 2 and 3. As used herein, e.g., FIGS. 2 and 3, phosphorothioate linkages are indicated as "s", and phosphodiester linkages are indicated by the absence of "s."

II.I. Conjugates

The term conjugate as used herein refers to an oligonucleotide which is covalently linked to a non-nucleotide moiety (conjugate moiety or region C or third region).

Conjugation of the oligonucleotide of the disclosure to one or more non-nucleotide moieties may improve the pharmacology of the oligonucleotide, e.g. by affecting the activity, cellular distribution, cellular uptake or stability of the oligonucleotide. In some embodiments the conjugate moiety modify or enhance the pharmacokinetic properties of the oligonucleotide by improving cellular distribution, bioavailability, metabolism, excretion, permeability, and/or cellular uptake of the oligonucleotide. In particular the conjugate may target the oligonucleotide to a specific organ, tissue or cell type and thereby enhance the effectiveness of the oligonucleotide in that organ, tissue or cell type. At the same time the conjugate may serve to reduce activity of the oligonucleotide in non-target cell types, tissues or organs, e.g., off target activity or activity in non-target cell types, tissues or organs. WO 93/07883 and WO2013/033230 provides suitable conjugate moieties. Further suitable conjugate moieties are those capable of binding to the asialoglycoprotein receptor (ASGPr). In particular tri-valent N-acetylgalactosamine conjugate moieties are suitable for binding to the ASGPr, see for example WO 2014/076196, WO 2014/207232 and WO 2014/179620.

Oligonucleotide conjugates and their synthesis has also been reported in comprehensive reviews by Manoharan in Antisense Drug Technology, Principles, Strategies, and Applications, S. T. Crooke, ed., Ch. 16, Marcel Dekker, Inc., 2001 and Manoharan, Antisense and Nucleic Acid Drug Development, 2002, 12, 103.

In an embodiment, the non-nucleotide moiety (conjugate moiety) is selected from the group consisting of carbohydrates, cell surface receptor ligands, drug substances, hormones, lipophilic substances, polymers, proteins, peptides, toxins (e.g. bacterial toxins), vitamins, viral proteins (e.g. capsids), and combinations thereof.

II.J. Activated ASOs

The term "activated ASO," as used herein, refers to an ASO of the disclosure that is covalently linked (i.e., functionalized) to at least one functional moiety that permits covalent linkage of the ASO to one or more conjugated moieties, i.e., moieties that are not themselves nucleic acids or monomers, to form the conjugates herein described. Typically, a functional moiety will comprise a chemical group that is capable of covalently bonding to the ASO via, e.g., a 3'-hydroxyl group or the exocyclic $NH_2$ group of the adenine base, a spacer that can be hydrophilic and a terminal group that is capable of binding to a conjugated moiety (e.g., an amino, sulfhydryl or hydroxyl group). In some embodiments, this terminal group is not protected, e.g., is an $NH_2$ group. In other embodiments, the terminal group is protected, for example, by any suitable protecting group such as those described in "Protective Groups in Organic Synthesis" by Theodora W Greene and Peter G M Wuts, 3rd edition (John Wiley & Sons, 1999).

In some embodiments, ASOs of the disclosure are functionalized at the 5' end in order to allow covalent attachment of the conjugated moiety to the 5' end of the ASO. In other embodiments, ASOs of the disclosure can be functionalized at the 3' end. In still other embodiments, ASOs of the disclosure can be functionalized along the backbone or on the heterocyclic base moiety. In yet other embodiments, ASOs of the disclosure can be functionalized at more than one position independently selected from the 5' end, the 3' end, the backbone and the base.

In some embodiments, activated ASOs of the disclosure are synthesized by incorporating during the synthesis one or more monomers that is covalently attached to a functional moiety. In other embodiments, activated ASOs of the disclosure are synthesized with monomers that have not been functionalized, and the ASO is functionalized upon completion of synthesis.

III. Pharmaceutical Compositions and Administration Routes

The ASO of the disclosure can be used in pharmaceutical formulations and compositions. Suitably, such compositions comprise a pharmaceutically acceptable diluent, carrier, salt or adjuvant.

The ASO of the disclosure can be included in a unit formulation such as in a pharmaceutically acceptable carrier or diluent in an amount sufficient to deliver to a patient a therapeutically effective amount without causing serious side effects in the treated patient. However, in some forms of therapy, serious side effects may be acceptable in terms of ensuring a positive outcome to the therapeutic treatment.

The formulated drug may comprise pharmaceutically acceptable binding agents and adjuvants. Capsules, tablets, or pills can contain for example the following compounds: microcrystalline cellulose, gum or gelatin as binders; starch or lactose as excipients; stearates as lubricants; various sweetening or flavoring agents. For capsules the dosage unit may contain a liquid carrier like fatty oils. Likewise coatings of sugar or enteric agents may be part of the dosage unit. The oligonucleotide formulations can also be emulsions of the active pharmaceutical ingredients and a lipid forming a micellular emulsion.

The pharmaceutical compositions of the present disclosure can be administered in a number of ways depending upon whether local or systemic treatment is desired and upon the area to be treated. Administration can be (a) oral (b) pulmonary, e.g., by inhalation or insufflation of powders or aerosols, including by nebulizer; intratracheal, intranasal, (c) topical including epidermal, transdermal, ophthalmic and to mucous membranes including vaginal and rectal delivery; or (d) parenteral including intravenous, intraarterial, subcutaneous, intraperitoneal or intramuscular injection or infusion; or intracranial, e.g., intrathecal, intra-cerebroventricular, or intraventricular, administration. In one embodiment the ASO is administered IV, IP, orally, topically or as a bolus injection or administered directly in to the target organ. In another embodiment, the ASO is administered intrathecal or intra-cerebroventricular as a bolus injection.

Pharmaceutical compositions and formulations for topical administration can include transdermal patches, ointments, lotions, creams, gels, drops, sprays, suppositories, liquids and powders. Conventional pharmaceutical carriers, aqueous, powder or oily bases, thickeners and the like may be necessary or desirable. Examples of topical formulations include those in which the ASO of the disclosure are in admixture with a topical delivery agent such as lipids, liposomes, fatty acids, fatty acid esters, steroids, chelating agents and surfactants. Compositions and formulations for oral administration include but are not limited to powders or granules, microparticulates, nanoparticulates, suspensions or solutions in water or non-aqueous media, capsules, gel capsules, sachets, tablets or minitablets. Compositions and formulations for parenteral, intrathecal, intra-cerebroventricular, or intraventricular administration can include sterile aqueous solutions which can also contain buffers, diluents and other suitable additives such as, but not limited to, penetration enhancers, carrier compounds and other pharmaceutically acceptable carriers or excipients.

Pharmaceutical compositions of the present disclosure include, but are not limited to, solutions, emulsions, and liposome-containing formulations. These compositions may be generated from a variety of components that include, but are not limited to, preformed liquids, self-emulsifying solids and self-emulsifying semisolids. Delivery of drug to the target tissue can be enhanced by carrier-mediated delivery including, but not limited to, cationic liposomes, cyclodextrins, porphyrin derivatives, branched chain dendrimers, polyethylenimine polymers, nanoparticles and microspheres (Dass C R. *J Pharm Pharmacol* 2002; 54(1):3-27).

The pharmaceutical formulations of the present disclosure, which can conveniently be presented in unit dosage form, can be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

For parenteral, subcutaneous, intradermal or topical administration the formulation can include a sterile diluent, buffers, regulators of tonicity and antibacterials. The active ASOs can be prepared with carriers that protect against degradation or immediate elimination from the body, including implants or microcapsules with controlled release properties. For intravenous administration the carriers can be physiological saline or phosphate buffered saline. International Publication No. WO2007/031091 (A2), published Mar. 22, 2007, further provides suitable pharmaceutically acceptable diluent, carrier and adjuvants—which are hereby incorporated by reference.

IV. Diagnostics

This disclosure further provides a diagnostic method useful during diagnosis of SNCA related diseases, e.g., a synucleinopathy. Non-limiting examples of synucleinopathy include, but are not limited to, Parkinson's disease, Parkinson's Disease Dementia (PDD), dementia with Lewy bodies, and multiple system atrophy.

The ASOs of the disclosure can be used to measure expression of SNCA transcript in a tissue or body fluid from an individual and comparing the measured expression level with a standard SNCA transcript expression level in normal tissue or body fluid, whereby an increase in the expression level compared to the standard is indicative of a disorder treatable by an ASO of the disclosure.

The ASOs of the disclosure can be used to assay SNCA transcript levels in a biological sample using any methods known to those of skill in the art. (Touboul et. al., *Anticancer Res.* (2002) 22 (6A): 3349-56; Verjout et. al., *Mutat. Res.* (2000) 640: 127-38); Stowe et. al., *J. Virol. Methods* (1998) 75 (1): 93-91).

By "biological sample" is intended any biological sample obtained from an individual, cell line, tissue culture, or other source of cells potentially expressing SNCA transcript. Methods for obtaining tissue biopsies and body fluids from mammals are well known in the art.

V. Kits Comprising ASOs

This disclosure further provides kits that comprise an ASO of the disclosure described herein and that can be used to perform the methods described herein. In certain embodiments, a kit comprises at least one ASO in one or more containers. In some embodiments, the kits contain all of the components necessary and/or sufficient to perform a detection assay, including all controls, directions for performing assays, and any necessary software for analysis and presentation of results. One skilled in the art will readily recognize that the disclosed ASO can be readily incorporated into one of the established kit formats which are well known in the art.

VI. Methods of Using

The ASOs of the disclosure can be utilized for therapeutics and prophylaxis.

SNCA is a 140 amino acid protein preferentially expressed in neurons at presynaptic terminals where it is thought to play a role in regulating synaptic transmission. It has been proposed to exist natively as both an unfolded monomer and a stable tetramer of α-helices and has been shown to undergo several posttranslational modifications. One modification that has been extensively studied is phosphorylation of SNCA at amino acid serine 129 (S129). Normally, only a small percentage of SNCA is constitutively phosphorylated at S129 (pS129), whereas the vast majority of SNCA found in pathological intracellular inclusions is pS129 SNCA. These pathological inclusions consist of aggregated, insoluble accumulations of misfolded SNCA proteins and are a characteristic feature of a group of neurodegenerative diseases collectively known as synucleinopathies.

In synucleinopathies, SNCA can form pathological aggregates in neurons known as Lewy bodies, which are characteristic of both Parkinson's Disease (PD), Parkinson's Disease Dementia (PDD), and dementia with Lewy bodies (DLB). The present ASOs therefore can reduce the number of the SNCA pathological aggregates or prevent formation of the SNCA pathological aggregates. Additionally, abnormal SNCA-rich lesions called glial cytoplasmic inclusions (GCIs) are found in oligodendrocytes, and represent the hallmark of a rapidly progressing, fatal synucleinopathy known as multiple systems atrophy (MSA). In some embodiments, the ASOs of the disclosure reduce the number of GCIs or prevent formation of GCIs. Reports of either undetectable or low levels of SNCA mRNA expression in oligodendrocytes suggest that some pathological form of SNCA is propagated from neurons, where it is highly expressed, to oligodendrocytes. In certain embodiments, the ASOs of the disclosure reduce or prevent propagation of SNCA, e.g., pathological form of SNCA, from neurons.

The ASOs can be used in research, e.g., to specifically inhibit the synthesis of SNCA protein (typically by degrading or inhibiting the mRNA and thereby prevent protein formation) in cells and experimental animals thereby facilitating functional analysis of the target or an appraisal of its usefulness as a target for therapeutic intervention. Further provided are methods of down-regulating the expression of SNCA mRNA and/or SNCA protein in cells or tissues comprising contacting the cells or tissues, in vitro or in vivo, with an effective amount of one or more of the ASOs, conjugates or compositions of the disclosure.

For therapeutics, an animal or a human, suspected of having a disease or disorder, which can be treated by modulating the expression of SNCA transcript and/or SNCA protein is treated by administering ASO compounds in accordance with this disclosure. Further provided are methods of treating a mammal, such as treating a human, suspected of having or being prone to a disease or condition, associated with expression of SNCA transcript and/or SNCA protein by administering a therapeutically or prophylactically effective amount of one or more of the ASOs or compositions of the disclosure. The ASO, a conjugate or a pharmaceutical composition according to the disclosure is typically administered in an effective amount. In some embodiments, the ASO or conjugate of the disclosure is used in therapy.

The disclosure further provides for an ASO according to the disclosure, for use in treating one or more of the diseases referred to herein, such as a disease selected from the group consisting of Parkinson's disease, Parkinson's Disease Dementia (PDD), dementia with Lewy bodies, multiple system atrophy, and any combinations thereof.

The disclosure further provides for a method for treating α-synucleinopathies, the method comprising administering an effective amount of one or more ASOs, conjugates, or pharmaceutical compositions thereof to an animal in need thereof (such as a patient in need thereof).

In certain embodiments, the disease, disorder, or condition is associated with overexpression of SNCA gene transcript and/or SNCA protein.

The disclosure also provides for methods of inhibiting (e.g., by reducing) the expression of SNCA gene transcript and/or SNCA protein in a cell or a tissue, the method comprising contacting the cell or tissue, in vitro or in vivo, with an effective amount of one or more ASOs, conjugates, or pharmaceutical compositions thereof, of the disclosure to affect degradation of expression of SNCA gene transcript thereby reducing SNCA protein.

In certain embodiments, the ASOs are used to reduce the expression of SNCA mRNA in one or more sections of brain, e.g., hippocampus, brainstem, striatum, or any combinations thereof. In other embodiments, the ASOs reduce the expression of SNCA mRNA, e.g., in brain stem and/or striatum, less than 70%, less than 60%, less than 50%, less than 40%, less than 30%, less than 20%, less than 10%, or less than 5% compared to the SNCA mRNA expression after administration of or exposure to a vehicle (no ASO), at day 3, day 5, day 7, day 10, day 14, day 15, day 20, day 21, or day 25. In some embodiments, the expression of SNCA mRNA is maintained below 70%, below 60%, below 50%, below 40%, below 30%, below 20%, below 10%, or below 5% compared to the SNCA mRNA expression after administration of or exposure to a vehicle (no ASO) until day 28, day 30, day 32, day 35, day 40, day 42, day 45, day 49, day 50, day 56, day 60, day 63, day 70, or day 75.

In other embodiments, the ASOs of the present disclosure reduces SNCA mRNA and/or SNCA protein expression in medulla, caudate putamen, pons cerebellum, lumbar spinal cord, frontal cortex, and/or any combinations thereof.

The disclosure also provides for the use of the ASO or conjugate of the disclosure as described for the manufacture of a medicament. The disclosure also provides for a composition comprising the ASO or conjugate thereof for use in treating a disorder as referred to herein, or for a method of the treatment of as a disorder as referred to herein. The present disclosure also provides ASOs or conjugates for use in therapy. The present disclosure additionally provides ASOs or conjugates for use in the treatment of synucleinopathy.

The disclosure further provides for a method for inhibiting SNCA protein in a cell which is expressing SNCA comprising administering an ASO or a conjugate according to the disclosure to the cell so as to affect the inhibition of SNCA protein in the cell.

The disclosure includes a method of reducing, ameliorating, preventing, or treating neuronal hyperexcitability in a subject in need thereof comprising administering an ASO or a conjugate according to the disclosure.

The disclosure also provides for a method for treating a disorder as referred to herein the method comprising administering an ASO or a conjugate according to the disclosure as herein described and/or a pharmaceutical composition according to the disclosure to a patient in need thereof.

The ASOs and other compositions according to the disclosure can be used for the treatment of conditions associated with over expression or expression of mutated version of SNCA protein.

The disclosure provides for the ASO or the conjugate according to disclosure, for use as a medicament, such as for the treatment of α-Synucleinopathies. In some embodiments the α-Synucleinopathy is a disease selected from the group consisting of Parkinson's disease, Parkinson's Disease Dementia (PDD), dementia with Lewy bodies, multiple system atrophy, and any combinations thereof.

The disclosure further provides use of an ASO of the disclosure in the manufacture of a medicament for the treatment of a disease, disorder or condition as referred to herein. In some embodiments, the ASO or conjugate of the disclosure is used for the manufacture of a medicament for the treatment of a α-Synucleinopathy, a seizure disorder, or a combination thereof.

Generally stated, one aspect of the disclosure is directed to a method of treating a mammal suffering from or susceptible to conditions associated with abnormal levels of SNCA i.e., a α-synucleinopathy), comprising administering to the mammal and therapeutically effective amount of an ASO targeted to SNCA transcript that comprises one or more LNA units. The ASO, a conjugate or a pharmaceutical composition according to the disclosure is typically administered in an effective amount.

The disease or disorder, as referred to herein, can, in some embodiments be associated with a mutation in the SNCA gene or a gene whose protein product is associated with or interacts with SNCA protein. Therefore, in some embodiments, the target mRNA is a mutated form of the SNCA sequence.

An interesting aspect of the disclosure is directed to the use of an ASO (compound) as defined herein or a conjugate as defined herein for the preparation of a medicament for the treatment of a disease, disorder or condition as referred to herein.

The methods of the disclosure can be employed for treatment or prophylaxis against diseases caused by abnormal levels of SNCA protein. In some embodiments, diseases caused by abnormal levels of SNCA protein are α-synucleinopathies. In certain embodiments, α-synucleinopathies include Parkinson's disease, Parkinson's Disease Dementia (PDD), dementia with Lewy bodies, and multiple system atrophy.

Alternatively stated, in some embodiments, the disclosure is furthermore directed to a method for treating abnormal levels of SNCA protein, the method comprising administering a ASO of the disclosure, or a conjugate of the disclosure or a pharmaceutical composition of the disclosure to a patient in need thereof.

The disclosure also relates to an ASO, a composition or a conjugate as defined herein for use as a medicament.

The disclosure further relates to use of a compound, composition, or a conjugate as defined herein for the manufacture of a medicament for the treatment of abnormal levels of SNCA protein or expression of mutant forms of SNCA protein (such as allelic variants, such as those associated with one of the diseases referred to herein).

A patient who is in need of treatment is a patient suffering from or likely to suffer from the disease or disorder.

The practice of the present disclosure will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986);); Crooke, Antisense drug Technology: Principles, Strategies and Applications, $2^{nd}$ Ed. CRC Press (2007) and in Ausubel et al. (1989) Current Protocols in Molecular Biology (John Wiley and Sons, Baltimore, Md.).

All of the references cited above, as well as all references cited herein, are incorporated herein by reference in their entireties.

The following examples are offered by way of illustration and not by way of limitation.

EXAMPLES

Example 1: Construction of ASOs

Antisense oligonucleotides described herein were designed to target various regions in the SNCA pre-mRNA. See FIG. 1A for genomic SNCA sequence and FIG. 1B for SNCA cDNA. For example, the ASOs were constructed to target the regions denoted using the pre-mRNA start site and pre-mRNA end site of NG_011851.1 as shown in FIG. 2 and/or mRNA start site and end site of its mRNAs. The exemplary sequences of the ASOs (e.g., SEQ ID Numbers) are described in FIGS. 2 and 3. In some embodiments, the ASOs were designed to be gapmers (e.g., alternating gapmers). See DES Numbers.

FIGS. 2 and 3 show non-limiting examples of the ASO design for selected sequences. The same methods can be applied to any other sequences disclosed herein. The gapmers were constructed to contain locked nucleic acids—LNAs (upper case letters). For example, a gapmer can have Beta-deoxy LNA at the 5' end and the 3' end and have a phosphorothioate backbone. But the LNAs can also be substituted with any other nucleotide analogs and the backbone can be other types of backbones (e.g., a phosphodiester linkage, a phosphotriester linkage, a methylphosphonate linkage, a phosphoramidate linkage, or combinations thereof).

The ASOs were synthesized using methods well known in the art. Exemplary methods of preparing such ASOs are described in Barciszewski et al., Chapter 10—"Locked Nucleic Acid Aptamers" in *Nucleic Acid and Peptide Aptamers: Methods and Protocols*, vol. 535, Gunter Mayer (ed.) (2009), the entire contents of which is hereby expressly incorporated by reference herein.

Example 2A: High Content Assay to Measure Reduction of SNCA Protein in Primary Neurons ASOs targeting SNCA were tested for their ability to reduce SNCA protein expression in primary mouse neurons. The primary neuronal cultures were established from the forebrain of PAC-Tg(SNCA$^{A53T}$)$^{+/+}$; SNCA$^{-/-}$ ("PAC-A53T") mice carrying the entire human SNCA gene with a A53T mutation on a mouse SNCA knockout background. See Kuo Y et al., *Hum Mol Genet.*, 19: 1633-50 (2010). All procedures involving mice were conducted according to Animal Test Methods (ATM) approved by the Bristol-Myers Squibb Animal Care and Use Committee (ACUC). Primary neurons were generated by papain digestion according to manufacturer's protocol (Worthington Biochemical Corporation, LK0031050). Isolated neurons were washed and resuspended in Neurobasal medium (NBM, Invitrogen) supplemented with B27 (Gibco), 1.25 μM Glutamax (Gibco), 100 unit/ml penicillin, 100 μg/ml streptomycin, and 25 μg/ml Amphotericin B.

Cells were plated on multi-well poly D-Lysine coated plates at 5,400 cells/cm$^2$ (for example in 384 well plates 6,000 cells/well in 25 μl NBM). ASOs were diluted in water and added to the cells at DIV01 (i.e., 1 day post plating). ASOs were added to 2× final concentration in medium then delivered to cells manually. Alternatively, ASOs in water were dispensed using a Labcyte ECHO acoustic dispenser. For ECHO dispense, 250 nl of ASO in water was added to cells in medium followed by the addition of an equal volume aliquot of fresh aliquot of NBM. For primary screening, the ASOs were added to final concentrations of 5 μM, 3.3 μM, 1 μM, 200 nM, or 40 nM. For potency determination, 8-10 point titrations of the ASOs were prepared from 0.75 mM stock then delivered to cultured cells for a final concentration range of 2.7-4000 nM or 4.5-10,000 nM. ASO-000010 (TCTgtcttggctTTG, SEQ ID NO: 22) and ASO-000838 (AGAaataagtggtAGT, SEQ ID NO: 23) (5 μM) were included in each plate as reference control inhibitors for tubulin and SNCA, respectively. The cells were incubated with the ASOs for 14 days to achieve steady state reduction of mRNA.

After the 14-day incubation, the cells were fixed by the addition of fixative to final concentrations of 4% formaldehyde (J. T. Baker) and 4% sucrose (Sigma) in the wells. The cells were fixed for 15 minutes, and then, the fixative aspirated from the wells. Then, the cells were permeabilized for 20 minutes with a phosphate buffered saline (PBS) solution containing 0.3% Triton-X 100 and 3% bovine serum albumin (BSA) or 3% Normal goat serum. Afterwards, the permeabilization buffer was aspirated from the wells, and the cells were washed once with PBS. The primary antibodies were then diluted in PBS containing 0.1% Triton X-100 and 3% BSA. Dilutions of 1:1000 of rabbit anti-SNCA (Abcam) and 1:500 of chicken anti-tubulin (Abcam) were used. Cells were incubated with the primary antibodies between 2 hours to overnight. Following the incubation, the primary antibody staining solution was aspirated, and the cells were washed 2-times with PBS. A secondary staining solution containing 1:500 dilution of goat-anti-chicken Alexa 567 antibody, goat anti-rabbit-Alexa 488 antibody, and Hoechst (10 µg/ml) in PBS containing 0.1% Triton X-100 with 3% BSA was added to the wells, and the plates were incubated for 1 hour. Afterwards, the secondary staining solution was aspirated from the wells, and the cells were washed 3-times with PBS. After washing the cells, 60 µl of PBS was added to each well. Plates were then stored in the PBS until imaging.

For imaging, the plates were scanned on a Thermo-Fisher (Cellomics) CX5 imager using the Spot Detector bio-application (Cellomics) to quantify nuclei (Hoechst stain, Channel 1), tubulin extensions (Alexa 567, channel 2) and SNCA (Alexa 488, channel 3). Object count (nuclei) was monitored but not published to the database. The total area covered by tubulin was quantified as the feature SpotTotalAreaCh2 and total intensity of staining for SNCA quantified as SpotTotalIntenCh3. The tubulin measure was included to monitor toxicity. To determine the reduction of SNCA protein, the ratio of SNCA intensity to the tubulin staining area was calculated and results normalized as % inhibition median using the median of vehicle treated wells as total and ASO-000010 or ASO-000838 wells as maximally inhibited wells for tubulin or SNCA, respectively.

Example 2B: Spontaneous Calcium Oscillation Measurement

Reduced oscillations in intracellular free calcium concentration (calcium oscillation) corresponds to increased neurotoxicity and therefore, can indicate reduced tolerability in vivo. To measure primary cortical neuron spontaneous calcium oscillation, rat primary cortical neurons were prepared from Sprague-Dawley rat embryos (E19). Briefly, the brain cortex was dissected and incubated at 37° C. for 30-45 minutes in papain/DNase/Earle's balanced salt solution (EBSS) solution. After trituration and centrifugation of the cell pellet, the reaction was stopped by incubation with EBSS containing protease inhibitors, bovine serum albumin (BSA), and DNase. The cells were then triturated and washed with Neurobasal (NB, Invitrogen) supplemented with 2% B-27, 100 µg/ml penicillin, 85 µg/ml streptomycin, and 0.5 mM glutamine.

The cells were plated at a concentration of 25,000 cells/well onto 384-well poly-D-lysine coated fluorescent imaging plates (BD Biosciences) in 25 µl/well supplemented Neurobasal (NB) media (containing B27 supplement and 2 mM glutamine). The cells were grown for 12 days at 37° C. in 5% $CO_2$ and fed with 25 µl of additional media on DIV04 (i.e., 4 days after plating) and DIV08 (i.e., 8 days after plating) for use on DIV12 (i.e., 12 days after plating).

On the day of the experiment, the NB media was removed from the plate and the cells were washed once with 50 µl/well of 37° C. assay buffer (Hank's Balanced Salt Solution, containing 2 mM $CaCl_2$) and 10 mM Hopes pH 7.4). Oscillations were tested both in the presence and in the absence of 1 mM $MgCl_2$. The cells were loaded with a cell permanent fluorescent calcium dye, Fluo-4-AM (Invitrogen, Molecular Probes F14201). Fluo-4-AM was prepared at 2.5 mM in DMSO containing 10% pluronic F-127 and then diluted 1:1000 in the assay buffer for a final concentration of 2.5 µM. The cells were incubated for 1 hr with 20 µl of 2.5 µM Fluo-4-AM at 37° C. in 5% $CO_2$. After the incubation, an additional 20 µl of room temperature assay buffer was added, and the cells were allowed to equilibrate to room temperature in the dark for 10 minutes.

The plates were read on a FDSS 7000 fluorescent plate reader (Hamamatsu) at an excitation wavelength of 485 nm and emission wavelength of 525 nm. The total fluorescence recording time was 600 seconds at 1 Hz acquisition rate for all 384 wells. An initial baseline signal (measurement of intracellular calcium) was established for 99 seconds before the addition of the ASOs. ASOs were added with a 384 well head in the FLIPR in 20 µl of assay buffer at 75 µM for a final concentration of 25 µM. In some instances an ASO targeting tau such as ASO-000013 (OxyAs OxyTs OxyTs DNAts DNAcs DNAcs DNAas DNAas DNAas DNAts DNAts DNAcs DNAas OxyMCs OxyTs OxyT; ATTtccaaattcaCTT, SEQ ID NO: 24) or ASO-000010 (TCTgtcttggctTTG, SEQ ID NO: 22) was included as controls.

Fluorescence time sequence intensity measurements (described above) were exported from the Hamamatsu reader, and transferred to an in-house proprietary application in IDBS E-Workbook suite for data reduction and normalization. In each 384 well screening plate, up to a maximum of 48 individual ASOs were tested in quadruplicate wells. 12 wells were exposed to a positive control (ASO-000010), which significantly inhibits the calcium oscillations counted during the 300 sec acquisition time frame and 12 wells were exposed to an negative control inactive ASO (ASO-000013) which does not inhibit the observation of calcium oscillations. Finally, 24 wells were dedicated to a vehicle control consisting of RNase-DNase-free water at the same concentration used to dilute the test ASOs. The effects of test ASOs in individual wells on calcium oscillation frequency (over the 300 sec period) were expressed as a % control of the median number of calcium oscillations counted in the 24 vehicle control wells. Individual 384 well assay plates passed QC standards if the positive and negative ASO controls (ASO-000010 and ASO-000013) exhibited well characterized pharmacology in the Ca assay, and if the vehicle and pharmacological control wells generated a minimum of ~20 calcium oscillations over the 300 sec experimental time period.

Example 2C: QUANTIGENE® Analysis (96-Well Assay) to Measure mRNA Reduction in Human Neurons The ability of ASOs to reduce human SNCA mRNA and/or possible human off target mRNA species was measured in vitro by QUANTIGENE® analysis. Human neurons (Cellular Dynamics Inc., "iNeurons"), were thawed, plated, and cultured per manufacturer's specifications. These iNeurons are highly pure population of human neurons derived from induced pluripotent stem (iPS) cells using Cellular Dynamic's proprietary differentiation and purification protocols.

Lysis: Cells were plated on poly-L-ornithine/laminin coated 96-well plates at 50,000 to 100,000 cells per well (dependent on the expression of the off target being investigated) and maintained in Neurobasal media supplemented with B27, glutamax, and Penicillin-Streptomycin. The ASOs were diluted in water and added to cells at DIV01 (i.e., 1 day post plating). For single point measurements, a final ASO concentration of 0.5 µM was typically used. For $IC_{50}$ determinations, the neurons were treated with a seven-point concentration response dilution of 1:4, with the highest concentration as 5 µM to define the IC$_{50}$. The cells were then incubated at 37° C. and 5% CO$_2$ for 6 days to achieve steady state reduction of mRNA.

After the incubation, the media was removed and cells were washed 1× in DPBS and lysed as follows. Measurement of lysate messenger RNA was performed using the QUANTIGENE® 2.0 Reagent System (AFFYMETRIX®), which quantitates RNA using a branched DNA-signal amplification method reliant on the specifically designed RNA capture probe set. The working cell lysis buffer solution was made by adding 50 µl proteinase K to 5 ml of pre-warmed (37° C.) Lysis mix and diluted in dH$_2$O to a 1:4 final dilution. The working lysis buffer was added to the plates (100 to 150 µl/well, depending on the expression of the off target being investigated), triturated 10 times, sealed and incubated for 30 min at 55° C. Following the lysis, the wells were triturated 10 more times, and the plates were stored at −80° C. or assayed immediately.

Assay: Depending on the specific capture probe used (i.e., SNCA, PROS1, or tubulin), the lysates were diluted (or not diluted) in the lysis mix. Then, the lysates were added to the capture plates (96-well polystyrene plate coated with capture probes) at a total volume of 80 µl/well. Working probe sets reagents were generated by combining nuclease-free water (12.1 µl), lysis mixture (6.6 µl), blocking reagent (1 µl), and specific 2.0 probe set (0.3 µl) (human SNCA catalogue #SA-50528, human PROS1 catalogue #SA-10542, or human beta 3 tubulin catalogue #SA-15628) per manufacturer's instructions (QUANTIGENE® 2.0 AFFYMETRIX®). Next, 20 µl working probe set reagents were added to 80 µl lysate dilution (or 80 µl lysis mix for background samples) on the capture plate. Plates were centrifuged at 240 g for 20 seconds and then incubated for 16-20 hours at 55° C. to hybridize (target RNA capture).

Signal amplification and detection of target RNA began by washing plates with buffer 3 times (300 µl/well) to remove any unbound material. Next, the 2.0 Pre-Amplifier hybridization reagent (100 µl/well) was added, incubated at 55° C. for 1 hour, then aspirated, and wash buffer was added and aspirated 3 times. The 2.0 Amplifier hybridization reagent was then added as described (100 µl/well), incubated for 1 hour at 55° C. and the wash step repeated as described previously. The 2.0 Label Probe hybridization reagent was added next (100 µl/well), incubated for 1 hour at 50° C. and the wash step was repeated as described previously. The plates were again centrifuged at 240 g for 20 seconds to remove any excess wash buffer and then, the 2.0 Substrate was added (100 µl/well) to the plates. Plates were incubated for 5 minutes at room temperature and then, the plates were imaged on a PerkinElmer Envision multilabel reader in luminometer mode within 15 minutes.

Data determination: For the gene of interest, the average assay background signal was subtracted from the average signal of each technical replicate. The background-subtracted, average signals for the gene of interest were then normalized to the background-subtracted average signal for the housekeeping tubulin RNA. The percent inhibition for the treated sample was calculated relative to the control treated sample lysate. Results of QUANTIGENE® assays for cells treated with the ASOs are shown in e.g., FIG. 8.

Example 2D: QUANTIGENE® Analysis (96-Well Assay) to Measure mRNA Reduction in Ramos Cells To measure possible human off target IKZF3 (IKAROS family zinc finger 3) mRNA reduction, Ramos cells (a human lymphocytic cell line) were used. Since Ramos cells do not express SNCA, RB1 (RB transcriptional corepressor 1), which is expressed in Ramos cells, was used as a positive control for assessing ASO-mediated knockdown IKZF3 mRNA expression. Two ASOs were synthesized to bind to and knockdown human RB1 mRNA expression. Beta-2 microglobulin (02M) was used as a housekeeping gene control. The Ramos cells were grown in suspension in RPMI media supplemented with FBS, glutamine, and Pen/Strep.

Lysis: Cells were plated on poly-L-ornithine/laminin coated 96 well plates at 20,000 cells per well and maintained in Neurobasal media containing B27, glutamax and Penicillin-Streptomycin. ASOs were diluted in water and added to cells at 1 day post plating (DIV01) to a final concentration of 1 µM. Following ASO treatment, the cells were incubated at 37° C. for 4 days to achieve steady state reduction of mRNA. After the incubation, the media was removed and cells lysed as follows. Measurement of lysate messenger RNA was performed using the QUANTIGENE® 2.0 Reagent System (AFFYMETRIX®), which quantitated RNA using a branched DNA-signal amplification method reliant on the specifically designed RNA capture probe set. Lysis mix (QUANTIGENE®2.0 AFFYMETRIX®) was pre-warmed in an incubator at 37° C. for 30 minutes. For lysing cells in suspension, 100 µl of 3× Lysis Buffer (with 10 µl/ml proteinase K) was added to 200 µl of cells in suspension. The cells were then triturated 10 times to lyse, and the plate sealed and incubated for 30 min at 55° C. Afterwards, the lysates were stored at −80° C. or assayed immediately.

Assay: Depending on the specific capture probe used (i.e., IKZF3, RB1, and β2M), the lysates were diluted (or not diluted) in the lysis mix. Then, the lysates were added to the capture plate (96 well polystyrene plate coated with capture probes) at a total volume of 80 µl/well. Working probe sets reagents were generated by combining nuclease-free water 12.1 µl, lysis mixture 6.6 µl, blocking reagent 1 µl, specific 2.0 probe set 0.3 µl (human IKZF3 catalogue #SA-17027, human RB1 catalogue #SA-10550, or human beta-2 microglobulin catalogue #SA-10012) per manufacturer instructions (QUANTIGENE® 2.0 AFFYMETRIX®). Then 20 µl working probe set reagents were added to 80 µl lysate dilution (or 80 µl lysis mix for background samples) on the capture plate. Plates were then incubated for 16-20 hours at 55° C. to hybridize (target RNA capture). Signal amplification and detection of target RNA was begun by washing plates with buffer 3 times (300 µl/well) to remove any unbound material. Next, the 2.0 Pre-Amplifier hybridization reagent (100 µl/well) was added, incubated at 55° C. for 1 hour then aspirated and wash buffer was added and aspirated 3 times. The 2.0 Amplifier hybridization reagent was then added as described (100 µl/well), incubated for 1 hour at 55° C. and the wash step was repeated as described previously. The 2.0 Label Probe hybridization reagent was added next (100 µl/well), incubated for 1 hour at 50° C. and the wash step again was repeated as described previously. The plates were again centrifuged at 240 g for 20 seconds to remove any excess wash buffer and then, the 2.0 Substrate was added (100 µl/well) to the plates. Plates were incubated for 5 minutes at room temperature, and then, the plates were imaged on a PerkinElmer Envision multilabel reader in luminometer mode within 15 minutes.

Data determination: For the gene of interest, the average assay background signal (i.e., no lysate, just 1× lysis buffer) was subtracted from the average signal of each technical replicate. The background-subtracted, average signals for the gene of interest were then normalized to the background-subtracted average signal for the housekeeping mRNA (for Ramos cells, it was beta-2-microglobulin). The percent inhibition for the treated sample was calculated relative to the average of the untreated sample lysate. Results of QUANTIGENE® assays for cells treated with the ASOs are shown in Table 4.

Example 2E: qPCR Assay to Measure Reduction of SNCA mRNA in SK—N-BE(2) Cells ASO SAN-005459 targeting SNCA was tested for its ability to reduce SNCA mRNA expression in human SK—N-BE(2) neuroblastoma cell acquired from ATCC (CRL-2271).

SK—N-BE(2) cells were grown in cell culturing media (MEM [Sigma, cat.no M2279] supplemented with 10% Fetal Bovine Serum [Sigma, cat.no F7524], 1× GLUTAMAX™ [Sigma, cat.no 3050-038] 1x MEM Non-essential amino acid solution [Sigma, cat.no M7145] and 0.025 mg/ml Gentamycin [Sigma, cat.no G1397]). Cells were trypsinized every 5 days, by washing with Phosphate Buffered Saline (PBS), [Sigma cat.no 14190-094] followed by addition of 0.25% Trypsin-EDTA solution (Sigma, T3924), 2-3 minutes incubation at 37° C., and trituration before cell seeding. Cells were maintained in culture for up to 15 passages.

For experimental use, 12,500 cells per well were seeded in 96 well plates (Nunc cat.no 167008) in 100 μL growth media. Oligonucleotides were prepared from a 750 μM stock. ASO dissolved in PBS was added approximately 24 hours after the cells were seeded to a final concentration of 25 μM for single point studies. Cells were incubated for 4 days without any media change. For potency determination, 8 concentrations of ASO were prepared for a final concentration range of 16-50,000 nM. ASO-004316 (CcAAAtct-tataataACtAC, SEQ ID NO: 25) and ASO-002816 (TTCctt-tacaccACAC, SEQ ID NO: 12) were included as controls.

After incubation, cells were harvested by removal of media followed by addition of 125 μL PURELINK® Pro 96 Lysis buffer (Invitrogen 12173.001A) and 125 μL 70% ethanol. RNA was purified according to the manufacture's instruction and eluted in a final volume of 50 μL water resulting in an RNA concentration of 10-20 ng/μl. RNA was diluted 10 fold in water prior to the one-step qPCR reaction. For one-step qPCR reaction qPCR-mix (qScript TMXLE 1-step RT-qPCR TOUGHMIX®Low ROX from QauntaBio, cat.no 95134-500) was mixed with two Tagman probes in a ratio 10:1:1 (qPCR mix: probe1:probe2) to generate the mastermix. Taqman probes were acquired from LifeTechnologies: SNCA: Hs01103383_m1; PROS1: Hs00165590_m1: TBP: 4325803; GAPDH 4325792. Mastermix (6 μL) and RNA (4 μL, 1-2 ng/μL) were then mixed in a qPCR plate (MICROAMP© optical 384 well, 4309849). After sealing, the plate was given a quick spin, 1000 g for 1 minute at RT, and transferred to a Viia™ 7 system (Applied Biosystems, Thermo), and the following PCR conditions used: 50° C. for 15 minutes; 95° C. for 3 minutes; 40 cycles of: 95° C. for 5 sec followed by a temperature decrease of 1.6° C./see followed by 60° C. for 45 sec. The data was analyzed using the QUANTSTUDIO™ Real-Time PCR Software.

Example 3: In Vitro Analysis of ASO-005459 on the Reduction of Human SNCA mRNA ASO-005459 is a 17-base, LNA-modified ASO that targets the intron1/exon2 boundary of human SNCA pre-mRNA (see FIG. 2, SEQ ID NO: 15).

Potency of ASO-005459 in Mouse Neurons

Using the methods described above in Example 2A, ASO-005459 was tested for its ability to reduce SNCA protein expression as a downstream result of reduction in SNCA mRNA. Briefly, primary neurons derived from PAC-A53T mice were treated with ASO-005459 or control ASOs for 14 days. Cells were then fixed and the levels of SNCA protein and tubulin protein were measured by high content imaging. Tubulin levels were measured to monitor toxicity and to normalize SNCA protein reduction.

As shown in Table 1 below, incubation of cells with 4 nM of ASO-005459 resulted in a 21% reduction in the SNCA protein expression. With 40 nM and 5 μM of ASO-005459, the SNCA protein expression was reduced by 84% and 86%, respectively. In contrast, ASO-005459 had minimal to no effect on the level of tubulin protein expression.

TABLE 1

| ASO-005459 activity in A53T-PAC neurons | | | | | | |
|---|---|---|---|---|---|---|
| ASO-005459 concentration | aSyn/tub % inh | SD | N | Tub % inh | SD | N |
| 4 nM | 21.11 | 33.71 | 3 | −8.60 | 12.07 | 4 |
| 40 nM | 84.28 | 13.21 | 8 | 4.32 | 28.65 | 7 |
| 5 μM | 86.45 | 7.91 | 2 | 29.01 | 18.06 | 2 |

SD = standard deviation
N = number of tests

To further evaluate potency, A53T-PAC neurons were treated with a 10-point titration of ASO-005459, as described above in Example 2A, and the $IC_{50}$s for the effect on SNCA and tubulin proteins determined. As shown in FIGS. 7A and 7B, and Table 2 (below), a concentration-dependent reduction in α-Syn/tubulin ratio was observed, with an average $IC_{50}$ of 7.4 nM. This observation was consistent with the single point activity data shown in Table 1 (above). Moreover, ASO-005459 produced negligible effects on Tub levels. Taken together these results indicate that ASO-005459 potently reduces SNCA protein levels with minimal effect on overall cell viability.

TABLE 2

| Potency and selectivity estimate for ASO-005459 for SNCA and tubulin protein in A53T-PAC neurons | | | | | |
|---|---|---|---|---|---|
| aSyn/tub $IC_{50}$ (nM) | SD | N | tub $IC_{50}$ (nM) | SD | N |
| 7.42 | 2.73 | 6 | >4000 | NA | 5 |

SD = standard deviation
N = number of tests

Efficacy of ASO-005459 in SK—N-BE(2) cells

Using the method described in Example 2E, ASO-005459 was tested for its ability to reduce SNCA mRNA in SK—N-BE(2) after 4 days treatment.

Incubation of cells with 25 μM ASO-005459 resulted in 92% reduction in SNCA mRNA in SK—N-BE(2) cells.

Potency of ASO-005459 in Human Neurons

ASO-005459 potency for SNCA was confirmed using primary human neurons as described above in Example 2C. Briefly, human neurons were derived from induced pluripotent stem (iPS) cells. Cells were treated with ASO-005459 or control ASOs for 6 days and then, mRNA levels were measured by QUANTIGENE® Assay. Because human neurons also express PROS1, a potential off-target for ASO-005459, the PROS1 mRNA level was also measured to assess the effect of ASO-005459 on off-target genes. In addition, tubulin (TUBB) mRNA was measured to monitor toxicity.

As shown in FIG. 8 and Table 3 (below), ASO-005459 induced a concentration-dependent reduction in SNCA expressed in human neurons, with an average $IC_{50}$ of 100 nM. This $IC_{50}$ is ~13-fold weaker than the $IC_{50}$ for reducing SNCA protein in PAC-A53T neurons (Table 2, above). The reason for this potency shift is not clear but could be due to differences in ASO uptake, metabolism, or kinetics of SNCA knock-down. While ASO-005459 also exhibited concentration-dependent reductions of PROS1 mRNA in the human neurons; the $IC_{50}$ was 30-50 fold weaker than the $IC_{50}$ for SNCA. These results confirm ASO-005459 activity for SNCA in human neurons and indicate that ASO-005459 is 30-50-fold more selective for SNCA compared to PROS1.

TABLE 3

Potency and Selectivity of ASO-005459 on SNCA and PROS1 mRNA in human neurons

| Assay Date | Batch | SNCA $IC_{50}$ (nM) | PROS1 $IC_{50}$ (nM) | TUBB3 $IC_{50}$ (nM) | PROS1/ SNCA $IC_{50}$ ratio |
|---|---|---|---|---|---|
| Aug. 26, 2016 | 01-001 | 42 | 2127 | >5000 | 51 |
| Dec. 8, 2016 | 01-004 | 157 | >5000 | >5000 | >32 |

Batch = particular lot-number of ASO-005459 used

Potency of ASO-005459 in Ramos Cells

IKZF3 is another potential off-target for ASO-005459, but, unlike PROS1, it is not expressed in human neurons. Instead, IKZF3 is robustly expressed in Ramos cells, a human lymphocytic cell line. Ramos cells were treated with 1 μM ASO-005459 and the effect on IKZF3 mRNA expression was measured. To monitor toxicity, beta-2 microglobulin mRNA was also measured. Since Ramos cells do not express SNCA, another gene, RB1 (RB transcriptional corepressor 1), was used as a positive control for ASO-mediated knockdown. ASO-006754 (GGTgaggtttggtaGA, SEQ ID NO: 26) and ASO-006755 (GGTgaggtttggtagaAG, SEQ ID NO: 27) target RB1 and were included the study. As shown in Table 4 (below), at 1 μM concentration, ASO-005459 did not affect IKZF3 mRNA expression, demonstrating ASO-005459's specificity for SNCA. ASO-005459 also did not affect the expression of RB1 and 02M mRNAs, indicating that ASO-005459 is not toxic to Ramos cells. In contrast, ASO-006754 and ASO-006755 (the control ASOs) reduced RB1 levels by 87% and 83%, respectively, confirming the ASO activity in Ramos cells.

TABLE 4

Effect of 1 μM ASO-005459 on IKZF3 in Ramos cells

| ASO | Target | Batch | IKZ F3 (% con) | RB1 (% con) | β2M (% con) |
|---|---|---|---|---|---|
| ASO-005459 | SNCA | 01-004 | 102 | 99 | 94 |
| ASO-006754 | RB1 | 01-001 | 104 | 13 | 87 |
| ASO-006755 | RB1 | 01-001 | 116 | 17 | 83 |

Batch = particular lot-number of the ASO used

Collectively, the results presented here demonstrate that ASO-005459 is potent and highly selective for reducing SNCA mRNA, which in turn mediates the reduction of SNCA protein levels. The results also show ASO-005459 is well tolerated both in mouse and in human neurons. These findings support the continued development of ASO-005459 as a disease-modifying therapeutic for the treatment of synucleinopathies.

Example 4: In Vivo Tolerability and In Vivo SNCA mRNA Reduction

The in vivo tolerability of selected ASOs was tested to see how the ASOs were tolerated when injected into different animal models (i.e., mice and cynomolgus monkeys):

Mice

Subjects: Male and female (2-3 months old) PAC-Tg ($SNCA^{A53T}$)$^{+/+}$; $SNCA^{-/-}$ ("PAC-A53T") mice carrying the entire human SNCA gene with a A53T mutation on a mouse SNCA knockout background were used for acute, long term, and PK/PD in vivo efficacy studies. In some cases wild-type (WT) C57B/6 mice were used for long term (i.e., 4 weeks) health assessment. Mice were housed in groups of 4 or 5 in a temperature controlled housing room with food and water available ad libitum. All procedures involving mice were conducted according to Animal Test Methods (ATM) approved by the Bristol-Myers Squibb Animal Care and Use Committee (ACUC).

ASO Dosing Solution Preparation: Sterile saline (1 mL) syringes fitted with 0.2 m Whatman filters and nuclease free centrifuge tubes were used to prepare dosing solutions. Indicated volume of water or saline was added to an ASO powder and was vortexed (~1 min) to dissolve the ASO powder. The solution was then allowed to sit for 10 min and was vortexed again for ~1 min. The tubes were briefly centrifuged to return all of the liquid to the bottom of the tube, and then, the solution was filtered through a 0.2 μm sterile filter into a 2nd RNase free tube. A small aliquot of the primary stock was diluted to 1 mg/ml for analysis of the concentration using Nanodrop. The analytical sample was vortexed three times with manual inversion to mix thoroughly. Then, the UV absorbance of the sample was measured twice at 260 nm with Nanodrop (the pedestal was rinsed and wiped three times before applying the sample). The test sample was discarded once the analysis was complete. The sample was considered ready for dosing if UV absorbance was between 90 and 110% of the sample. If UV absorbance exceeded 110% of the sample, a secondary dilution was prepared; if the absorbance was <90%, the sample was prepared at a higher initial concentration and similar steps were followed as described above. Samples were stored at 4° C. until use.

Freehand Intracerebroventricular (ICV) Injection: ICV injections were performed using a Hamilton micro syringe fitted with a 27 or 30-gauge needle, according to the method of Haley and McCormick. The needle was equipped with a polyethylene guard at 2.5-3 mm from the tip in order to limit its penetration into the brain. Mice were anesthetized using isoflurane anesthetic (1-4%). Once sufficiently anesthetized, the mice were held by the loose skin at the back of the neck with the thumb and first fingers of one hand. Applying gentle but firm pressure, the head of the animal was then immobilized by pressing against a firm flat level surface. Dosing was conducted using 10 μL Hamilton syringes fitted with a 27½ g needle. The needle tip was then inserted through the scalp and the skull, about 1 mm lateral and 1 mm caudal to bregma (i.e., right of the midline, about 3 mm back as measured from the eye line). Once the needle was positioned, the ASO was given in a volume of 5 μl in saline vehicle and injected over ~30 seconds. The needle was left in place for 5-10 seconds before removal. The mice were returned to their home cage and allowed to recover for ~2-4 min. Mice were observed continuously for 30 minutes immediately after dosing for adverse behavioral effects of drug and/or dosing. During this time, any mouse that convulsed more than 3 separate times was immediately euthanized and given an automatic score of 20. Drug tolerability was scored 1 hr±15 min post dosing. Animals dosed with non-tolerated compounds (tolerability score >4) were euthanized immediately following the 1 hr evaluation.

ASO Tolerability Assessment: Animals dosed with the ASOs were evaluated right after the dosing and monitored for 2 hours for any adverse effects. For acute tolerability (AT) studies, mice were evaluated at the time of dosing and again at the takedown, i.e., 3 days post ASO injection. For long term health assessment, the mice were weighed weekly and monitored for any health and behavioral issues until the completion of the experiment. Mice that had weight losses of greater than 15% of their initial body weight or exhibited tolerability issues were removed from the studies and euthanized. Health and tolerability assessments were conducted according to the following chart:

regions were dissected from the second hemisphere for protein/PK measurements in the dose-response time course PK/PD studies.

In some of the studies, the blood and the cerebrospinal fluid (CSF) were also collected for PK (blood) and PK/protein (CSF) measurements. To collect the blood and the CSF, the mice were deeply anesthetized with Isoflurane (4%). Blood was collected via cardiac puncture using 23G needle. Once removed, the blood was transferred into 2 ml BD Microtainer (K2EDTA BD #365974) tubes and placed on ice until processing. To process the blood, the tubes were centrifuged at 4500×g for 10 min at 4° C. Then, the plasma was removed and placed into 0.5 ml Eppendorf tubes and stored at −80° C. until use. To collect the CSF, the thoracic cavity was opened exposing the heart, and as much of the blood was drained to avoid contamination of the CSF. The CSF samples were collected via Cisterna magna using micropipettes and placed into lo-bind protein Eppendorf tubes. Then, the tubes were centrifuged at 4500×g for 15 min

TABLE 5

Tolerability scoring system[a]

| Category | Score 1 | Score 2 | Score 3 | Score 4 |
|---|---|---|---|---|
| Hyperactivity, stereotypies, home cage behavior controls | Very slightly increased home cage exploration or rearing compared to controls | Increased home cage exploration (e.g. digging, burying, etc.) Increased grooming | Moderately increased home cage activity Detectable stereotypies (e.g. circling, repetitive behaviors, etc.) | Marked hyperactivity Marked stereotypies |
| Decreased vigilance, exploration and responsiveness | Some reduction in exploratory activity Responds normally to stimulation | Drowsiness Slightly reduced response to touch or handling | Stupor (reduced responsiveness, decreased corneal reflex) | Coma (does not respond to stimulation, e.g. pinch), no corneal reflex |
| Motor coordination and strength | Mild change to gait or grip strength (falls between 5-10 sec) No falls, normal righting response | Reduced grip strength (falls in less than 5 sec) Mild ataxia (e.g. slow righting response, swaying) | Highly reduced grip strength (falls in less than 2 sec) Ataxia (e.g. staggering, falling impaired walking) | Severe ataxia (e.g. crawling, fails to grip bar) No ability to right |
| Posture, appearance, breathing | Very slight abnormal posture (subtle) | Slight abnormal posture (e.g. hunched, extended, low posture, tail position, straub tail) Piloerection or ptosis unkempt coat | Moderately abnormal posture (e.g. ventral recumbency) Shallow breathing | Markedly abnormal posture (e.g. lateral recumbency) Facial paralysis (e.g. drooling, protruding tongue) Labored breathing |
| Tremor, hyperactivity, convulsion | Detectable tremor | Hyper-responsive to stimuli (e.g. noise) Marked tremors | Few or partial seizures, rearing and falling as part of convulsing | Repeated or continuous seizure (miming, bouncing, clonic and/or tonic) |

[a]Normal is scored as "0". Animals are scored on an individual basis at successive time points post dosing. Observations are rated at 1 h ± 15 min, then 24 h ± 2 h, then 7 days (if appropriate). Convulsions count for the 1 hr timepoint, even if they occur prior to the observation window. A total tolerability score is calculated based on the sum of the individual category scores, with a maximum possible score of 20.

Tissue Collection: Following final behavioral and health assessments, mice were decapitated on a guillotine and the brains were quickly removed. Each brain was split into two hemispheres and a) hippocampus was dissected for mRNA measurements in the 3-day acute tolerability studies; b) hippocampus, brain stem, and striatum from one hemisphere were dissected for mRNA measurements, whereas the same at 4° C. The CSF was carefully transferred to clean lo-bind 0.5 ml Eppendorf tubes and stored at −80° C. until further use.

Cyno Data

Subject: Male cynomolgus monkeys weighing 3.5-10.0 kg at the start of the study were used. Each was implanted with an intrathecal cerebrospinal fluid (CSF) catheter entering at the L3 or L4 vertebrae. The distal tip of the polyurethane catheter extended within the intrathecal space to approximately the L1 vertebrae. The proximal end was connected to a subcutaneous access port located on the animal's lower back. Animals were allowed to heal for at least two weeks prior to the start of the study. Laboratory animal care was according to Public Health Service Policy on the Humane Care and Use of Laboratory Animals and the Guide for the Care and use of Laboratory Animals NRC (2011) (National Research Council: Guide for the Care and Use of Laboratory Animals (The National Academies Collection: Reports funded by National Institutes of Health). National Academies Press (US), Washington (DC)). The protocol was approved by the Wallingford Animal Care and Use Committee of the Bristol-Myers Squibb Company.

CSF & BloodSampling: The CSF port was accessed subcutaneously using aseptic techniques, and CSF was sampled from awake animals sitting upright in a primate restraint chair. Approximately 0.1 ml of CSF was discarded at the start of collection to clear dead space in the catheter and port. CSF was collected by gravity flow to a maximum of 0.5 ml CSF per sample. CSF was spun at 2,000 g at 4° C. for 10 min. The supernatant was frozen on dry ice or in liquid nitrogen and kept at −90° C. until analyzed.

Blood was sampled from an available vein, typically the saphenous vein. Blood samples were prepared in a number of procedures depending upon the particular measure in question. For plasma, blood was collected into EDTA-treated tubes. For serum, blood was collected into serum-separator tubes and allowed to clot for at least 30 min prior to centrifugation. For measures of clotting and clotting factors, blood was collected into citrated tubes, and for analysis of RNA, blood was collected into tubes containing RNA later. After processing, samples were frozen on dry ice or in liquid nitrogen and kept frozen until analyzed.

Intrathecal Dosing: Animals were trained to be dosed while awake and using modified commercially-available restraint chairs, animals were maintained in a prone position. SNCA-targeted anti-sense oligonucleotides (ASOs) were dissolved in saline, sterilized by filtration, and administered at 0.33 ml/min in a 1.0 ml volume followed by a 0.5 ml sterile water flush. Total infusion time was 4.5 min. Animals remained in the prone position for 30 min post infusion.

Necropsy: Cynomolgus monkeys were administered the appropriate volume of a commercially available euthanasia solution while anesthetized with ketamine and/or isoflurane. Necropsy tissues were obtained immediately thereafter and the brain was transferred to wet ice for dissection. Areas of interest were dissected using 4-6 mm slices in an ASI Cyno Brain Matrix as well as free handed techniques. Samples were placed fresh in RNAlater, or frozen on dry ice for later analysis. CNS tissue was rapidly dissected form cynomolgus monkeys and pieces no longer than 4 mm on any axis were collected and placed in 5 mLs of RNA later. Samples were stored at 4° C. overnight then transferred to −20° C. for storage until analyzed.

Brain regions analyzed included medulla, pons, midbrain, cerebellum, caudate-putamen (left and right), hippocampus (left and right), frontal cortex (left and right), temporal cortex (left and right), parietal cortex (left and right), occipital cortex (left and right) and cortical white matter. Additionally, spinal cord was sampled at the cervical, thoracic and lumbar regions. Samples were also collected from liver, kidney and heart. On some occasions, samples of trigeminal nuclei, tibial nerve and the aorta were collected to examine off-target pharmacology in those areas.

ELISA Quantitation of ASO Concentration in Mouse or Monkey Tissue, Plasma, and CSF:

Tissue was homogenized with plasma and water in a 1:1 ratio. Standard curve was generated by 2-fold serial dilution from 5000 to 4.9 nM in plasma (for plasma and CSF) and in plasma:water (for tissues samples) and then further diluted to 5000-fold total with 5×SSCT (750 mM NaCl, and 75 mM sodium citrate, pH 7.0, containing 0.05% (v/v) Tween-20) alone and in 5×SSCT containing 35 nM capture and 35 nM detection reagents to obtain a standard range of 1-1000 µM. The dilution factor used varied depending on the expected sample concentration range. The capture probe was AAAGGAA with a 3' Biotin (Exiqon) and the detection probe was 5' DigN-isopropyl 18 linker—GTGTGGT (Exiqon).

Experimental samples and standards were added to Clarity lysis buffer (Phenomenex, cat #ALO-8579) in a 1:1 ratio prior to dilution with capture and detection buffer and before transferring to the ELISA plate. CSF samples were diluted with plasma (2-fold) prior to addition of lysis buffer. A streptavidin-coated plate (Thermo 15119) was washed 3 times with 5×SSCT buffer. 100 µl samples were added and incubated for 60 min at room temperature. The detection probe, 100 µl anti-Dig-AP Fab fragment diluted 1:4000 in PBS containing 0.05% Tween-20 (Roche Applied Science, Cat. No. 11 093 274 910), was added and incubated for 60 min at room temperature. After washing the plate with 2×SSCT buffer, 100 µl Tropix CDP-star Sapphire II substrate (Applied Biosystems) was added for 30 min at room temperature. Antisense oligonucleotide concentrations were measured by luminescence (Enspire-PerkinElmer).

Alpha-Synuclein Protein Measurements:

Brain tissue samples were homogenized at 10 ml/g tissue in RIPA buffer (50 mM Tris HCl, 150 mM NaCl, 1% NP-40, 0.5% sodium deoxycholate, 0.1% sodium dodecyl sulfate) using bead homogenizer Qiagen Tissuelyser II for 25 cycles/ sec, with a 5 mm stainless steel bead for 2 min total. Homogenized samples were incubated 30 min on ice. 50 µL aliquot of each sample was retained for PK analysis. The remaining samples were centrifuged 20,800 g, for 60 min, 4° C. The supernatant was retained and used for analysis. Total protein was measured using Pierce BCA protein assay kit (23227).

Brain tissue extracts: SNCA protein was measured using the MJFR1+4B12 ELISA. Briefly, ELISA plates (Costar) were coated with 100 µl of the anti-SNCA antibody MJFR1 (Abcam) at a concentration of 0.1 µg/ml diluted in BupH carbonate-bicarbonate buffer, pH 9.4 (Thermo Scientific) overnight (O/N) at 4° C. The next day plates were washed 4-times with Dulbecco's PBS (Life Technologies) and blocked with 3% BSA (bovine serum albumin, protease free, Fraction V, Roche Diagnostic) in PBS for 2~3 h at room temperature (RT) or overnight at 4° C. Both the standards and the brain samples were diluted with 1% BSA/0.05% Tween/PBS containing Roche protease inhibitor (Roche 11836145001, 1 pellet/25 ml) and Phosphatase Inhibitor 2&3 (Sigma, 1:100). SNCA wild-type (rPeptide) was used as a standard. Samples were loaded in duplicate (50 µl/well) and incubated for O/N at 4° C. After plates were equilibrated to RT, 50 µl of the detection antibody 4B12 (Biolegend) (diluted 1:4000 in 1% BSA/0.1% Tween/DPBS) was added to each well and co-incubated with the samples at RT for ~2 hours. Detection antibody was pre-conjugated with alkaline phosphatase (AP kit from Novus Biologicals). Plates were then washed 4-times with 0.05% Tween/PBS and developed with 100 µl of alkaline phosphatase substrate (Tropix CDP Star Ready-to-Use with Sapphire II, T-2214, Life Technologies) for 30 minutes. Luminescence counts were measured with Perkin Elmer EnVision (2102 Multilabel Reader). The plates were kept constant shaking (Titer plate shaker, speed 3) during the assay. Data was analyzed using GraphPad Prism. Total protein in brain tissue was measured using a Micro protein assay kit (Thermofisher #23235) according to manufacturer's instructions.

Cerebral spinalfluid (CSF): SNCA protein was measured using the U-PLEX Human SNCA Kit: (cat #K151WKK-2, Meso Scale Discovery) according to manufacturer's instructions. CSF samples were diluted 10-fold. Hemoglobin was measured in CSF samples using the Abcam mouse Hemoglobin ELISA kit (ab157715). CSF samples were diluted 40-fold for the hemoglobin measurements.

mRNA measurements by qRT-PCR

Brain regions were harvested and placed in 1.5 ml RNAlater Tissue Protect tubes (Qiagen cat #76514) that were prefilled with RNA-later, a RNA stabilization solution. Tissue in RNA-later solution can be stored at 4° C. for 1 month, or at −20° C. or −80° C. indefinitely.

RNA Isolation: RNeasy Plus Mini Kit: RNA from mouse hippocampus and cortex was isolated using the RNeasy Plus Mini Kit (Qiagen cat #74134). Tissue samples were homogenized in a volume of 600 µL or 1200 µL RLT Plus buffer containing 10 µl/ml of 2-mercaptoethanol and 0.5% Reagent Dx. 600 µL lysis buffer was used if the tissue sample was <20 mg, 1200 µl lysis buffer was used for tissue samples >20 mg. For homogenization, tissue sample was transferred to a 2.0 mL round-bottom Eppendorf Safe-Lock tube (Eppendorf cat #022600044) containing 600 µL RLT Plus Buffer (plus 10 ul/ml of 2-mercaptoethanol and 0.5% Reagent Dx), and a 5 mm stainless steel Bead (Qiagen cat #69989) Samples were homogenized, using a Qiagen's TissueLyser II instrument. Samples were processed for 2.0 min at 20 Hz, samples rotated 1800 and processed for another 2.0 min at 20 Hz. Samples were then processed 2.0 min at 30 Hz, samples rotated 180° and processed for another 2.0 min at 30 Hz. Longer and/or at higher frequency homogenization used if processing not complete. A 600 µL of the tissue lysate was then transferred into a gDNA Eliminator spin column in a 2.0 mL collection tube and samples centrifuged for 30 secs at 10,000 g. All centrifugation steps were performed at RT. The flow-through was collected and an equal volume of 70% ethanol added and mixed. 600 µL was transferred to RNeasy spin column placed in a 2.0 mL collection tube and samples centrifuged for 15 secs at 10,000 g. The flow-through was discarded and the remaining 600 µL sample added to the spin column. The spin columns were centrifuged and the flow-through discarded. Columns were washed with 700 µL of Wash Buffer RW1, centrifuged for 15 secs at 10,000 g, and the flow-through discarded The columns were then washed 2-times with 500 µL of Buffer RPE containing 4 volumes of ethanol as described in kit protocol. Columns were first centrifuged for 15 secs at 10,000 g for first wash and then for 2.0 min at 10,000 g for the second wash. After second wash, columns were centrifuged once for 1.0 min at 10,000 g to dry the membranes. Columns were then transferred to a new 1.5 mL collection tube and 30 µL of RNase-free water was added directly to the center of the membrane. The membranes were allowed to incubate for 10 min at RT. Then, the columns were centrifuged for 1.0 min at 10,000 g to elute the RNA. The elution, containing the RNA, was collected and stored on ice until the RNA concentrations could be determined by UV absorbance using a NanoDrop Spectrophotometer (Thermo). RNA samples were stored at −80° C.

RNA Isolation: RNEASY® Plus Universal Mini Kit: RNA from all other Cyno, Mouse, and Rat tissue samples was isolated using RNEASY® Plus Universal Mini Kit (Qiagen cat #73404). For homogenization, 50 µg or less of tissue sample was transferred to a 2.0 mL round-bottom Eppendorf Safe-Lock tube (Eppendorf cat #022600044) containing 900 µL QIAZOL® Lysis Reagent, and a 5 mm stainless steel Bead (Qiagen cat #69989) Samples were homogenized, using a Qiagen's TissueLyser II instrument. Samples were processed for 2.0 min at 20 Hz, samples rotated 180° and processed for another 2.0 min at 20 Hz. Samples were then processed 2.0 min at 30 Hz, samples rotated 180° and processed for another 2.0 min at 30 Hz. Longer and/or at higher frequency homogenization used if processing not complete. Homogenized tissue lysate was then transferred into a new 2.0 mL round-bottom Eppendorf Safe-Lock tube and left at RT for 5.0 min. 100 µL of gDNA Eliminator Solution was added to each tube and tubes were vigorously shaken for 30 secs. 180 µL of Chloroform (Sigma cat #496189) was added to each tube and tubes were vigorously shaken for 30 secs. Tubes were left at RT for 3 min. Centrifuge tubes at 12,000 g for 15 min at 4° C. After centrifugation the upper aqueous phase was transferred to a new 2.0 mL round-bottom Eppendorf Safe-Lock tube ~500 µL. An equal volume of 70% ethanol added and mixed. All future centrifugation steps were performed at RT. 500 µL was transferred to RNeasy spin column placed in a 2.0 mL collection tube and samples centrifuged for 15 secs at 10,000 g. The flow-through was discarded and the remaining 500 µL sample added to the spin column. The spin columns were centrifuged and the flow-through discarded and the columns washed with 700 µL of Wash Buffer RWT containing 2 volumes of ethanol. Columns were centrifuged for 15 secs at 10,000 g, the flow-through discarded. The columns were then washed twice with 500 µL of Buffer RPE containing 4-volumes of ethanol as described in kit protocol. Columns were first centrifuged for 15 secs at 10,000 g for first wash and then for 2.0 min at 10,000 g for the second wash. After second wash, columns were centrifuged once for 1.0 min at 10,000 g to dry the membranes. Columns were then transferred to a new 1.5 mL collection tube and 30 µL of RNase-free water added directly to the center of the membrane. Membranes were allowed to incubate for 10 min at RT. Columns were centrifuged for 1.0 min at 10,000 g to elute the RNA. The elutions, containing the RNA, were collected and stored on ice until RNA concentration determined by UV absorbance using a NanoDrop Spectrophotometer (Thermo). RNA samples were stored at −80° C.

cDNA Synthesis by Reverse Transcription: 300 ng of RNA was diluted to a final volume of 10.8 µL using nuclease-free water (Invitrogen cat #10977-015) in a PCR-96-AB-C microplate (Axygen cat #321-65-051). Added 6.0 µL to each well of reaction mix 1 containing the following: 2.0 µL of 50 µM random decamers (Ambion cat #AM5722G) and 4.0 µL of a 1×dNTP mix (Invitrogen cat #10297-018). The plate was sealed with optical sealing tape (Applied Biosystems cat #4360954) and centrifuged for 1.0 min at 1,000×g at RT. Next, the plate was heated for 3.0 min at 70° C. using a 96-well Thermal Cycler GeneAmp PCR System 9700 (Applied Biosystems). The plate was then cooled completely on ice. Next, 3.25 µL of the reaction mix 2 (containing 2 µL of lOX strand buffer, 1.0 µL of MMLV-RT 200 U/µL reverse transcriptase enzyme (Ambion cat #2044), and 0.25 µL of RNase inhibitor 40 U/µL (Ambion cat #AM2682)) were added to each of the wells. Plate was sealed with optical sealing tape and centrifuged for 1.0 min at 1,000×g at RT. Using a 96-well Thermal Cycler, the plate was heated at 42° C. for 60 min proceeded by 95° C. for 10 min. Then, the plates were cooled on ice. The cDNA plates were stored at −20° C. until ready to use for PCR analysis.

qPCR for amplification and quantification of SNCA and GAPDH mRNA expression: cDNA was diluted 5-fold in nuclease free water in a PCR-96-AB-C microplate. 16 μL of Master Mix solution consisting of the following: 10 μL of 2× Taqman Gene Expression Master Mix (Applied Biosystems cat #4369016), 1.0 μL of 20× Taqman primer-probe set (Applied Biosystems), and 5.0 μL of nuclease-free water, was added to each well of a 384-well optical PCR plate (Applied Biosystems cat #4483315). 4.0 μL of diluted cDNA was added to each well of the 384-well optical PCR plate. Plate was sealed with optical sealing tape and centrifuged for 1.0 min at 1,000×g at RT. PCR was performed on the Applied Biosystems 700 HT Fast Real-Time PCR System using the following parameters in standard mode: 50° C. for 2.0 min, 95° C. for 10 min, followed by 40 cycles of 95° C. for 15 secs and 60° C. for 1.0 min.

qRT-PCR primer-probe sets: Primer-probes sets from Applied Biosystems (Thermo Fisher) included the following:

Human alpha synuclein (cat #Hs01103383_m1) FAM labelled
Human PROS1 (cat #HS00165590_m1) FAM labelled
Cyno alpha synuclein (cat #Mf02793033_m1) FAM labelled
Cyno GAPDH (cat #Mf04392546_g1) FAM labelled
Cyno GAPDH (cat #Mf04392546_g1) VIC labelled Primer Limited
Rat alpha synuclein (cat #Rn01425141_m1) FAM labelled
Rat GAPDH (cat #Rn01775763-g1) FAM labelled
Rat GAPDH (cat #4352338E) VIC labelled Primer Limited
Mouse GAPDH (cat #Mm99999915-g1) FAM labelled
Mouse GAPDH (cat #4352339E) VIC labelled Primer Limited.

Example 5: Analysis of In Vivo Activity and Tolerability of ASO-005459 in Mice

ASO-005459 is a LNA-modified ASO specific for human SNCA. The in vitro results (described above) demonstrate that ASO-005459 is potent and selective for reducing SNCA mRNA in primary neurons. The in vitro results also suggest that that ASO-005459 is well tolerated.

A53T-PAC mice

To evaluate whether these results are also true in vivo, 100 μg of ASO-005459 was administered to A53T-PAC mice via ICV injection, and both the tolerability and the SNCA mRNA knockdown (KD) in the hippocampus were assessed at 3 days post injection, as described in Example 4 (above).

Figure 9:
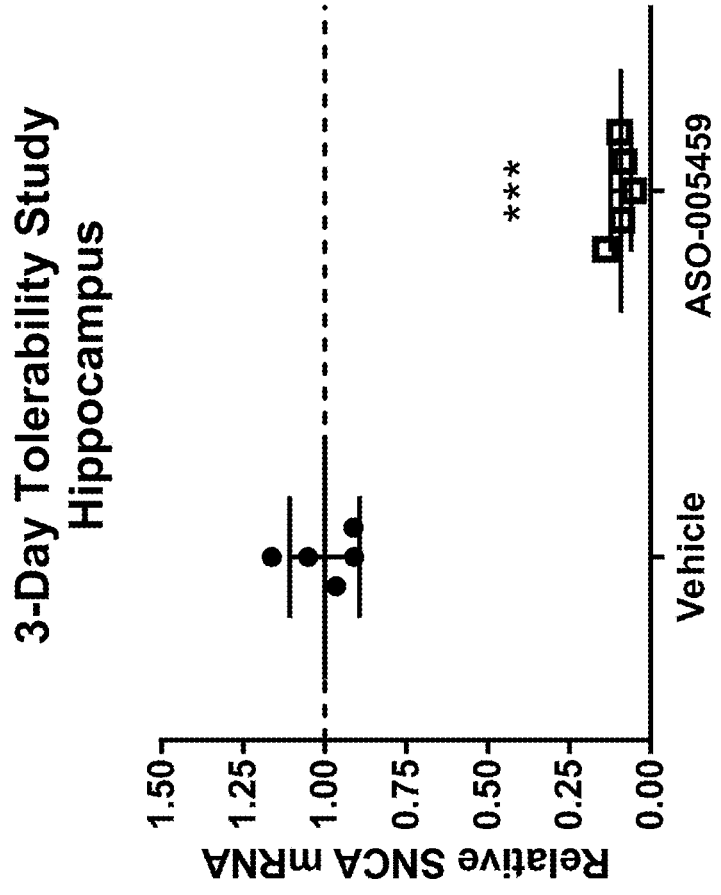
FIG. 9 shows the SNCA mRNA expression levels in the hippocampus of A53T-PAC mice at three days post ICV administration of 100 µg of ASO-005459 (open square) or control vehicle (closed circle). SNCA mRNA expression levels were measured by qRT-PCR, normalized to GAPDH mRNA, and then expressed relative to the mean expression level of the vehicle group. The horizontal line marks the reference value of 1 (i.e., value at which the SNCA mRNA expression would be equivalent to expression level observed in the vehicle control group). Data shown represents the mean±SD from duplicate determination. Statistics shown is based on 1-way ANOVA with Dunnett's post-test. ***p<0.001.

As shown in Table 6 (below), ASO-005459 was well tolerated with an overall mean tolerability score of 1. In addition, ASO-005459 significantly reduced SNCA mRNA levels by >90% in the hippocampus at 3 days post administration. (FIG. 9).

TABLE 6

ASO-005459 tolerability in A53T-PAC mice, 3-day study

| Animal # | Hyper-activity | Vigilance | Motor S&C | Posture/ Breathing | Tremor/ Convulsions | Total Score |
|---|---|---|---|---|---|---|
| 31 | 0 | 2 | 1 | 2 | 0 | 5 |
| 32 | 0 | 0 | 0 | 0 | 0 | 0 |
| 33 | 0 | 0 | 0 | 0 | 0 | 0 |

TABLE 6-continued

ASO-005459 tolerability in A53T-PAC mice, 3-day study

| Animal # | Hyper-activity | Vigilance | Motor S&C | Posture/ Breathing | Tremor/ Convulsions | Total Score |
|---|---|---|---|---|---|---|
| 34 | 0 | 0 | 0 | 0 | 0 | 0 |
| 35 | 0 | 0 | 0 | 0 | 0 | 0 |
| mean |  |  |  |  |  | 1.00 |
| SEM |  |  |  |  |  | 1.00 |

To evaluate activity in vivo, A53T-PAC mice were dosed with ASO-005459 at 3.13 μg, 12.5 μg, 25 μg, or 50 μg concentration via ICV injection. Tolerability was assessed by measuring body weights at days 7 and 14 post dosing. The expression of SNCA mRNA was assessed at 14 days post dosing, when the animals were sacrificed and their tissues harvested. SNCA mRNA knockdown was measured in three brain regions: Hippocampus, brainstem, and striatum. Brainstem and striatum are two of the regions that are most affected in the brains of MSA and PD patients. In a separate study, C57BL/6 mice were dosed with 100 μg of ASO-005459 and tolerability was assessed by measuring the body weight of the animals at days 7, 14, 21, and 28 post dosing. 100 μg ASO-005459 was dosed ICV in wild-type (WT) C57BL/6 mice, and the body weight and behavior were monitored over a 4-week period. Because ASO-005459 does not target mouse SNCA, reduction in SNCA mRNA expression was not measured in these animals.

Figure 10A:
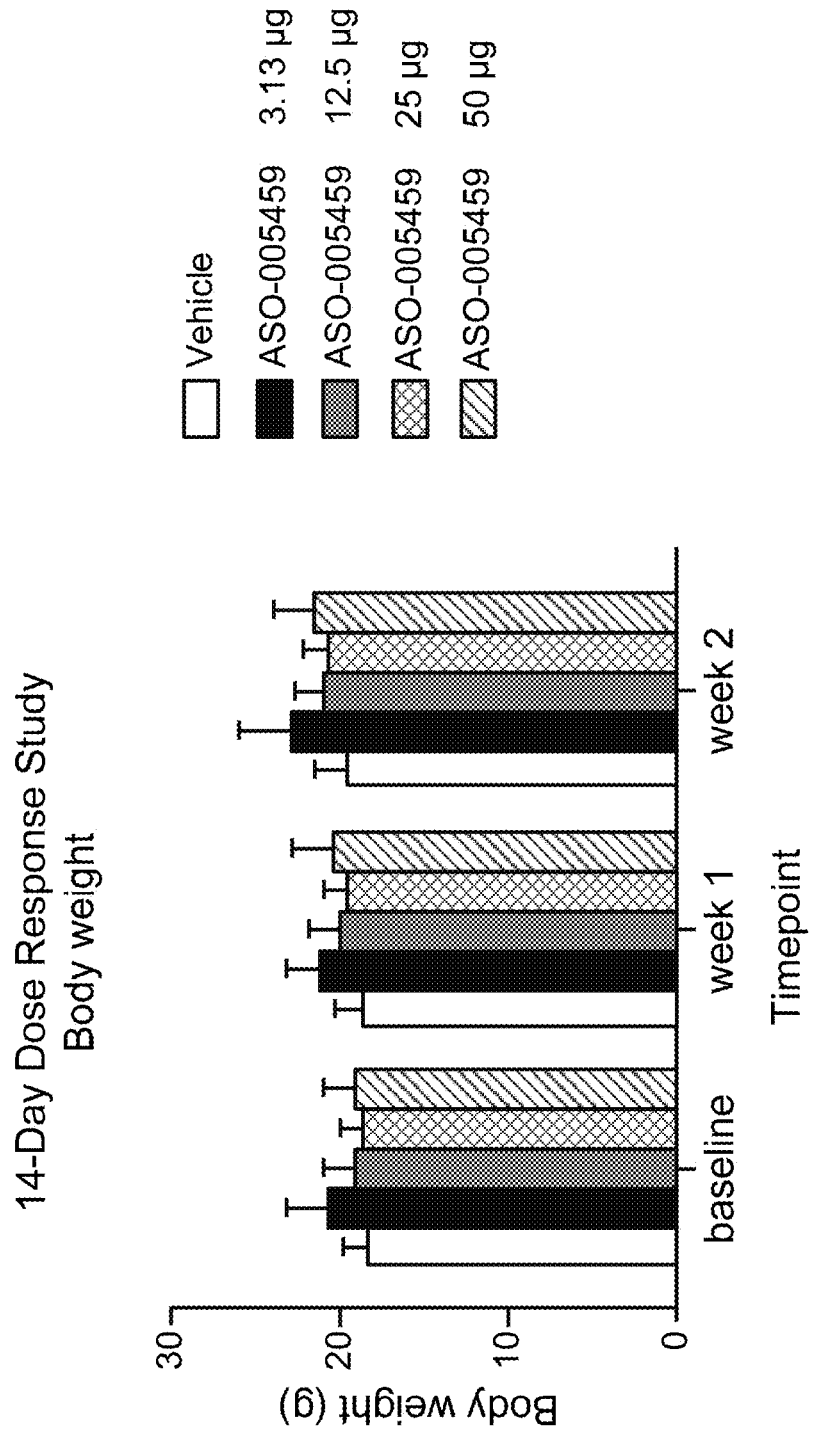
FIGS. 10A and 10B show a comparison of the average body weight of mice treated with ASO-005459.
Figure 10B:
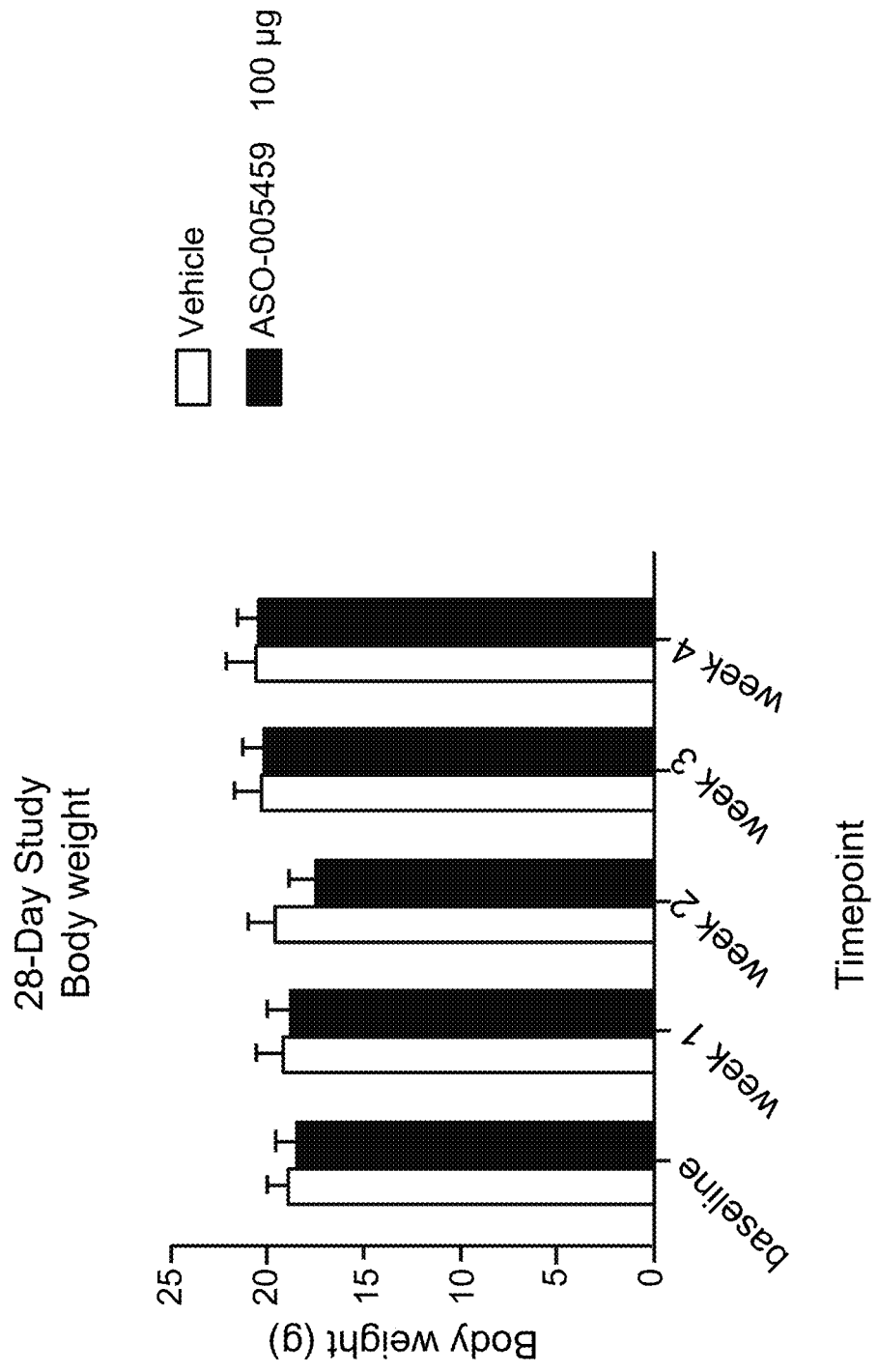
Figure 11A:
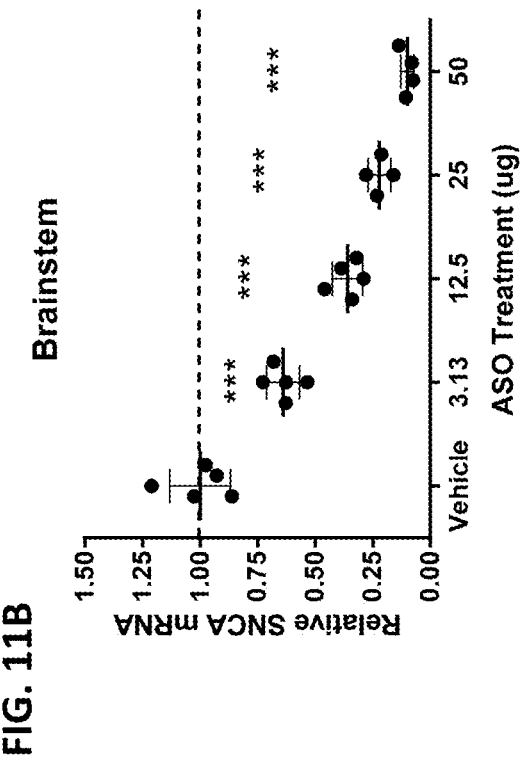
FIGS. 11A, 11B, and 11C show the SNCA mRNA expression levels in the hippocampus (FIG. 11A), brainstem (FIG. 11B), and striatum (FIG. 11C) of A53T-PAC mice at 14 days post ICV administration of ASO-005459 (3.13 µg, 12.5 µg, 25 µg, or 50 µg) or the vehicle control. SNCA mRNA levels were measured by qRT-PCR, normalized to GAPDH mRNA, and then expressed relative to the mean of the vehicle group. Data shown represents the mean±SD from multiple animals (n=5). Each circle represents an individual animal. The horizontal line marks the reference value of 1 (i.e., value at which the SNCA mRNA expression would be equivalent to expression level observed in the vehicle control group). Statistics shown is based on 1-way ANOVA with Dunnett's post-test. ***p<0.001.
Figure 11C:
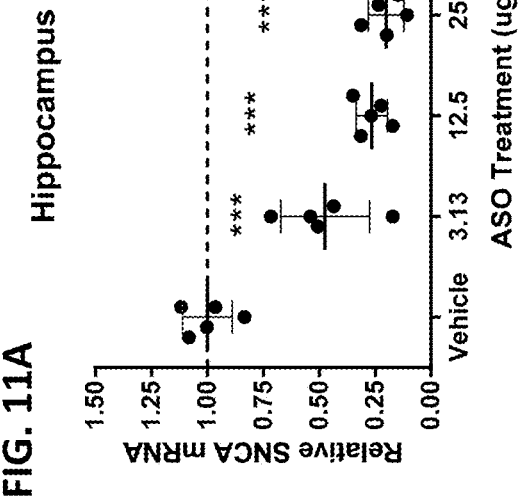
Figure 11B:
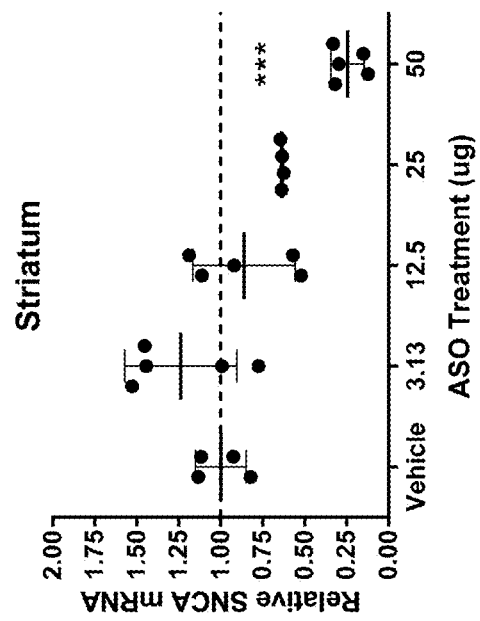

As shown in FIGS. 10A and 10B, there were no significant differences in the body weight of the mice (both A53T-PAC mice and C57BL/6 mice) treated with ASO-005459 (for all concentrations) and those treated with the control vehicle. The animals (C57BL/6) did not exhibit any abnormal behaviors during the course of the experiment. See Table 7 (below). Such results demonstrate that ASO-005459 was well tolerated. Also, in mice treated with ASO-005459, there was a significant and dose-dependent reduction in SNCA mRNA expression in all three brain regions tested. See FIGS. 11A-11C. In the hippocampus, the SNCA mRNA expression was reduced by 53%, 73%, 80%, and 96% for 3.13, 12.5, 25, and 50 μg ASO-005459, respectively. Similar dose-dependent knockdowns were also observed in the brainstem. In the striatum, SNCA mRNA knockdowns were more variable and less robust compared to the other regions (FIGS. 11A-11C): a 75% and 46% knockdown was observed with 50 μg and 25 μg of ASO-005459, respectively. However, with 12.5 μg and 3.13 μg of ASO-005459, there was no significant reduction in SNCA mRNA expression. Possible explanations for the lower activity observed in the striatum could be due to differences in the ASO levels or the kinetics of SNCA mRNA knockdown.

TABLE 7

ASO-005459 tolerability in 28-day study

| Animal # | Time-point (day) | Hyper-activity | Vigilance | Motor S&C | Posture/ Breathing | Tremor/ Convulsions | Total Score |
|---|---|---|---|---|---|---|---|
| 26 | 1 | 0 | 0 | 0 | 0 | 0 | 0 |
| 26 | 28 | 0 | 0 | 0 | 0 | 0 | 0 |
| 27 | 1 | 0 | 0 | 0 | 0 | 0 | 0 |
| 27 | 28 | 0 | 0 | 0 | 0 | 0 | 0 |
| 28 | 1 | 0 | 0 | 0 | 0 | 0 | 0 |
| 28 | 28 | 0 | 0 | 0 | 0 | 0 | 0 |

TABLE 7-continued

ASO-005459 tolerability in 28-day study

| Animal # | Time-point (day) | Hyper-activity | Vigilance | Motor S&C | Posture/ Breathing | Tremor/ Convul-sions | Total Score |
|---|---|---|---|---|---|---|---|
| 29 | 1 | 0 | 0 | 0 | 0 | 0 | 0 |
| 29 | 28 | 0 | 0 | 0 | 0 | 0 | 0 |
| 30 | 1 | 0 | 0 | 0 | 0 | 0 | 0 |
| 30 | 28 | 0 | 0 | 0 | 0 | 0 | 0 |

Figure 12:
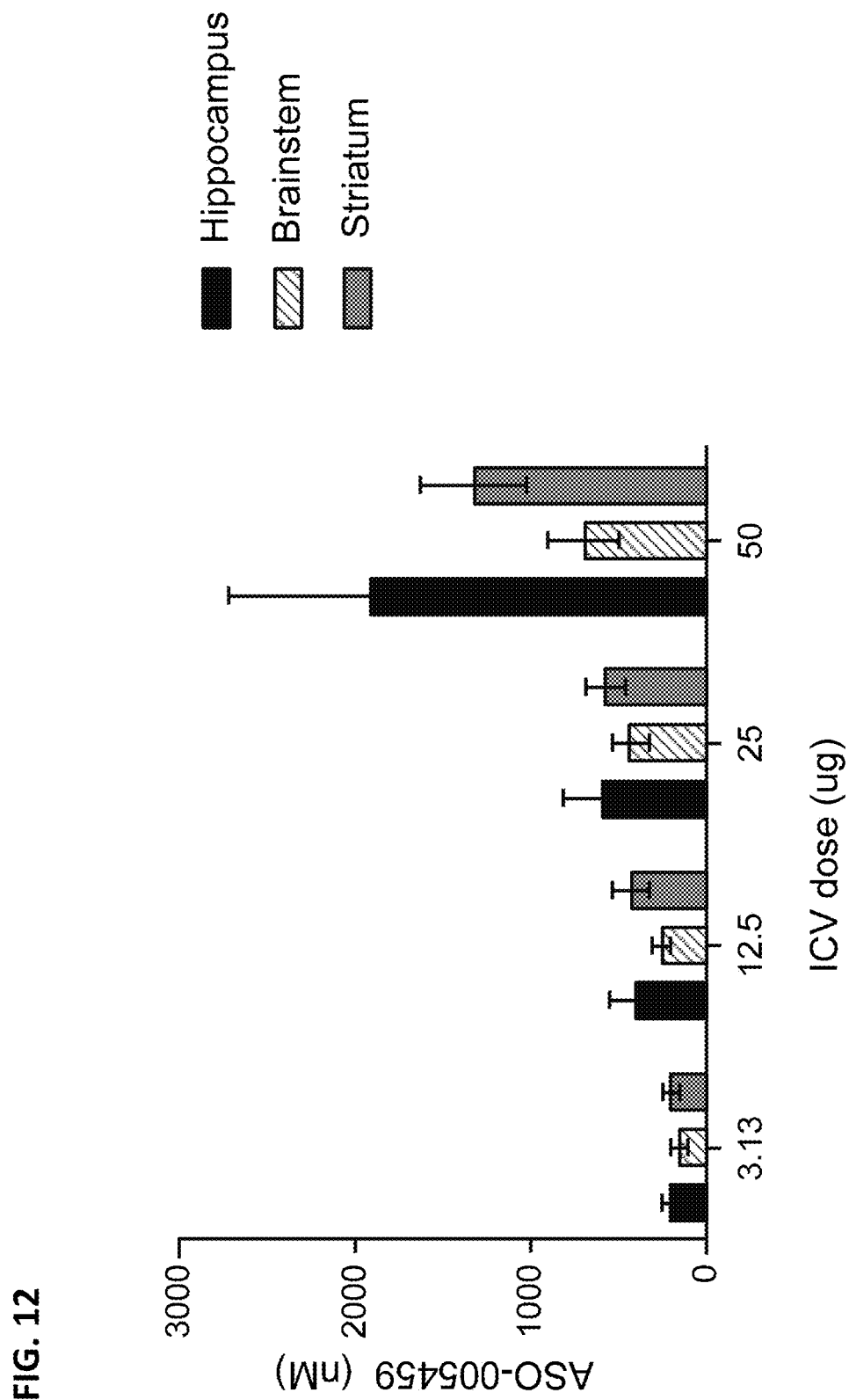
FIG. 12 shows the level of ASO-005459 detected in the hippocampus (black), brainstem (light gray), and the striatum (dark gray) of A53T-PAC mice at 14 days post ASO-005459 treatment. The mice received 3.13 µg, 12.5 µg, 25 µg, or 50 µg of ASO-005459 via ICV administration. Data shown represents the mean±SD from multiple animals (n=5).
Figure 13A:
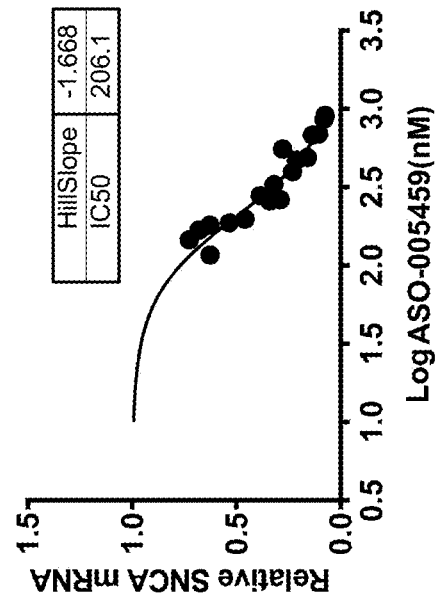
FIGS. 13A, 13B, 13C, and 13D show the relationship between ASO-005459 exposure levels and SNCA mRNA expression in the hippocampus (FIG. 13A), brainstem (FIG. 13B), and striatum (FIG. 13C) of A53T-PAC mice at fourteen days post ASO-005459 treatment.
Figure 13B:
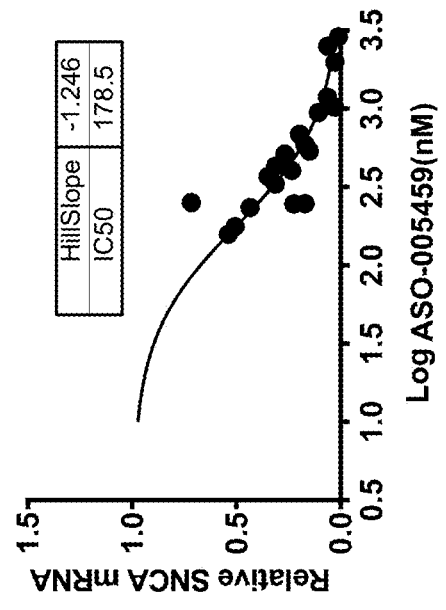
Figure 13C:
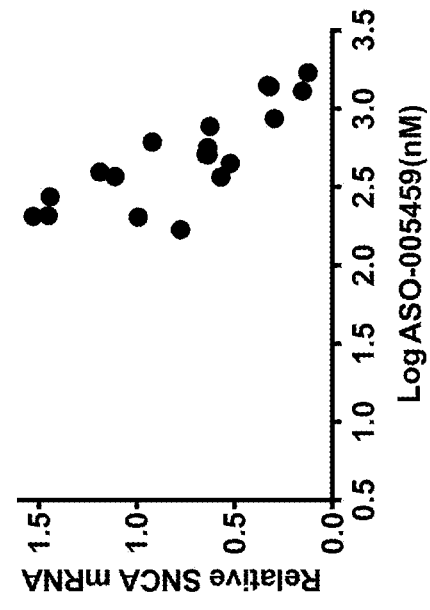
Figure 13D:
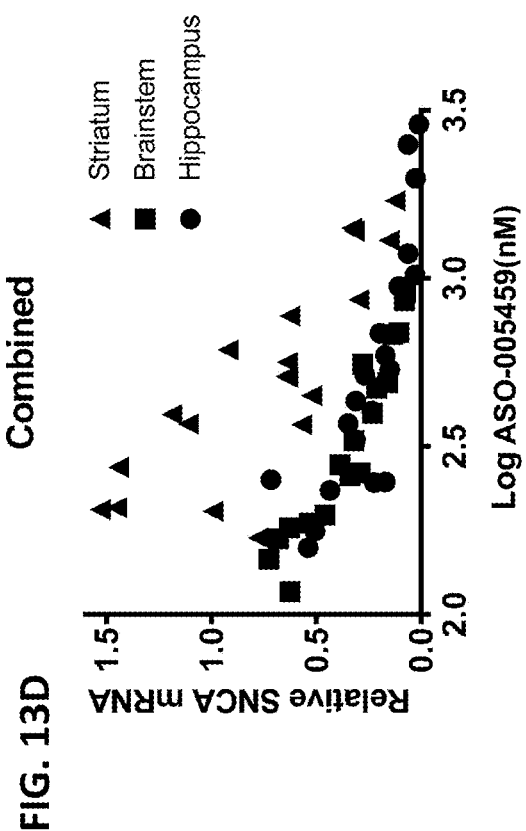

The ASO-005459 levels were measured in all three brain regions of the A53T-PAC mice. As shown in FIG. 12 and Table 8 (below), brain exposures were approximately dose proportional and similar across all three regions, including the striatum. The ASO-005459 exposure-response relationships for the different brain regions are shown in FIGS. 13A-13D. Similar exposure-response relationships were observed in the hippocampus and brainstem with estimated $IC_{50}$s of 179 and 206 nM, respectively. In comparison, the exposure response relationship in the striatum was relatively steep suggesting slower kinetics of SNCA mRNA reduction in that region. See FIG. 13C.

TABLE 8

Summary of ASO-005459 brain exposure in 14-day A53T-PAC study

| | Dose (μg) | Mean (nM) | SD | Relative to hippo |
|---|---|---|---|---|
| Hippocampus | 3.13 | 214 | 43 | |
| | 12.5 | 411 | 140 | |
| | 25 | 600 | 223 | |
| | 50 | 1916 | 807 | |
| Brainstem | 3.13 | 160 | 47 | 0.7 |
| | 12.5 | 266 | 47 | 0.6 |
| | 25 | 440 | 102 | 0.7 |
| | 50 | 707 | 202 | 0.4 |
| Striatum | 3.13 | 212 | 38 | 1.0 |
| | 12.5 | 438 | 103 | 1.1 |
| | 25 | 586 | 109 | 1.0 |
| | 50 | 1332 | 302 | 0.7 |

To provide a more extensive dose-response/time course data, ASO-005459 was again administered (0, 12.5, 25, or 50 μg) directly into the cerebral ventricles of A53T-PAC mice by ICV freehand injection. The animals were sacrificed at 24 hours, 3 days, 4, 8, 12, 16, and 20 weeks post dosing and the SNCA mRNA expression in the brain stem and the striatum was assessed.

Figure 14A:
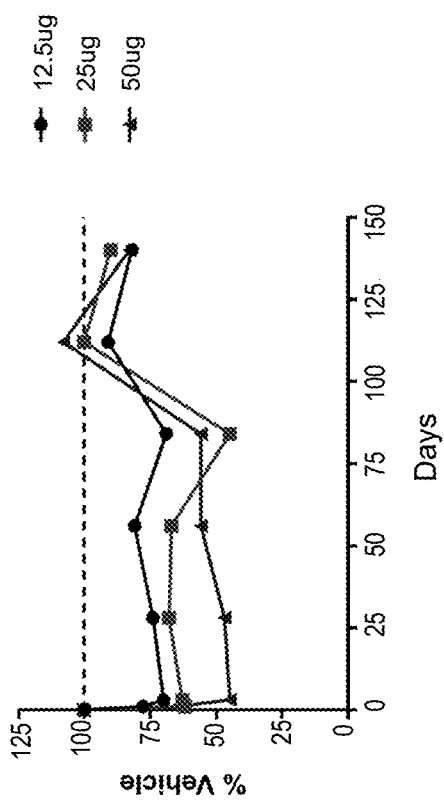
FIGS. 14A and 14B show the dose response curve of the effect of ASO-005459 on SNCA mRNA expression level in A53T-PAC mice. The animals received (via ICV injection) 12.5 µg (circle), 25 µg (box), or 50 µg (triangle) of ASO-005459 and were sacrificed at 24 hours, 3 days, 4, 8, 12, 16, and 20 weeks post-dosing. SNCA mRNA expression levels both in the brain stem (FIG. 14A) and in the striatum (FIG. 14B) were assessed via qRT-PCR and then normalized to the vehicle control. The mean data is shown. The horizontal line marks the reference value of 100% (i.e., value at which the SNCA mRNA expression would be equivalent to expression level observed in the vehicle control group).
Figure 14B:
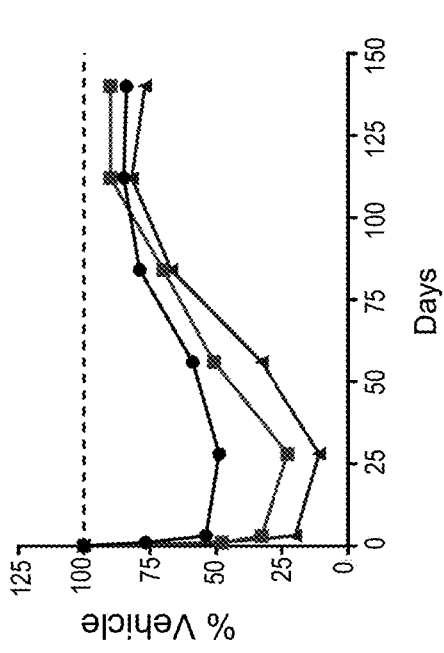
Figure 15B:
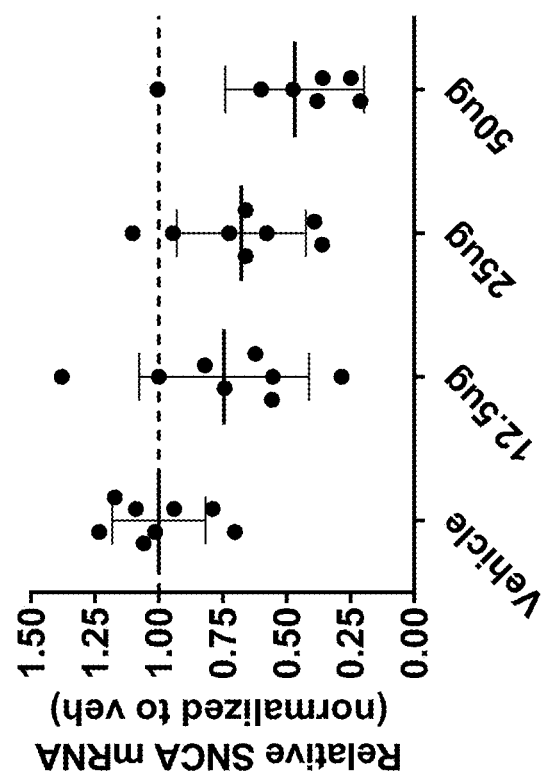
FIGS. 15A and 15B show the effect of ASO-005459 on SNCA mRNA expression level in A53T-PAC mice after 4 weeks post ASO-005459 administration. The animals received either the vehicle control or varying concentrations of ASO-005459 (12.5, 25, or 50 µg). The relative SNCA mRNA expression level (normalized to the vehicle control) are shown for both the brain stem (FIG. 15A) and the striatum (FIG. 15B). Each data point represents an individual animal. The mean±SD from multiple animals is also shown. Statistics shown is based on comparison to the vehicle group using 1-way ANOVA with Dunnett's correction for multiple comparisons. The horizontal line marks the reference value of 1 (i.e., value at which the SNCA mRNA expression would be equivalent to expression level observed in the vehicle control group). *p<0.05, p<0.01, *p<0.001, ****p<0.0001.
Figure 15A:
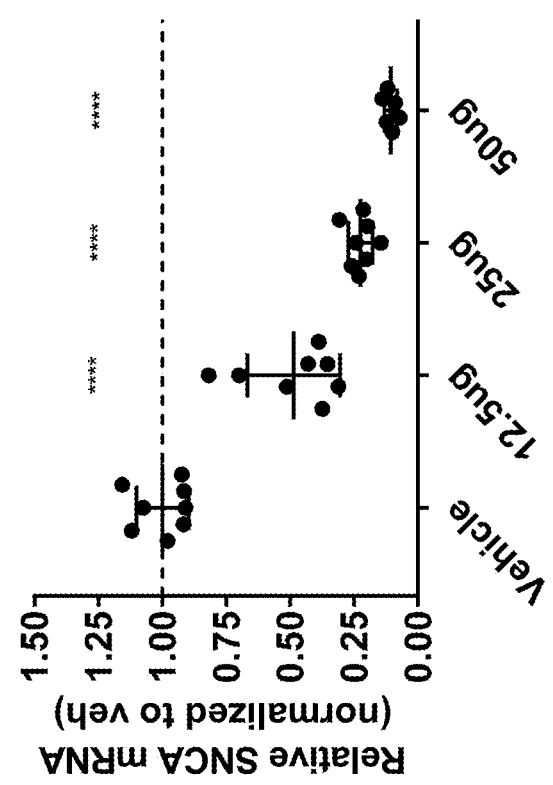

As shown in FIGS. 14A and 14B (and in agreement with the data provided above), administration of ASO-005459 to the A53T-PAC mice resulted in significant reduction of SNCA mRNA expression level (relative to the vehicle control) in both the brain stem and the striatum. The reduction appeared to be both time- and dose-dependent, with peak reduction (~90%) observed in the brain stem with 50 μg ASO-005459 at about 4 weeks post dosing (FIG. 14A). In the striatum, peak reduction (~55%) was observed with 50 μg ASO-005459 at about 3 days post dosing (FIG. 14B). SNCA mRNA expression levels remained significantly reduced compared to the vehicle control at 4 weeks post dosing (FIGS. 15A and 15B) and returned to baseline control by about 16 weeks post-dosing (FIGS. 14A and 14B).

Figure 16A:
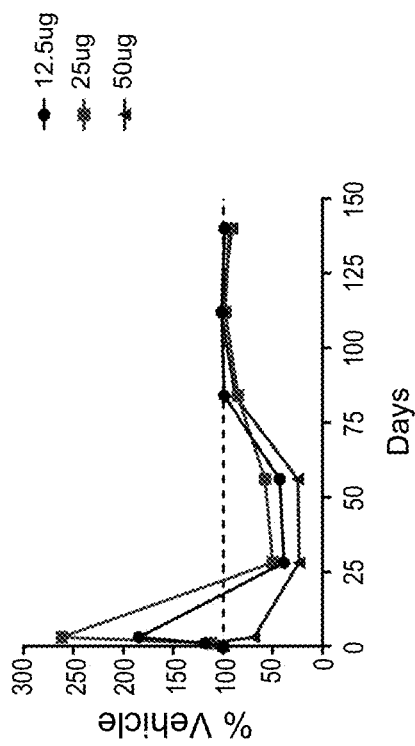
FIGS. 16A and 16B show the dose response curve of the effect of ASO-005459 on SNCA protein expression level in the brain tissues of A53T-PAC mice. The animals received (via ICV injection) 12.5 µg (circle), 25 µg (box), or 50 µg (triangle) of ASO-005459 and were sacrificed at 24 hours, 3 days, 4, 8, 12, 16, and 20 weeks post-dosing. SNCA proteins levels were measured both in the brain stem (FIG. 16A) and in the striatum (FIG. 16B) by ELISA and then normalized to the vehicle control. The mean data is shown. The horizontal line marks the reference value of 100% (i.e., value at which the SNCA mRNA expression would be equivalent to expression level observed in the vehicle control group).
Figure 16B:
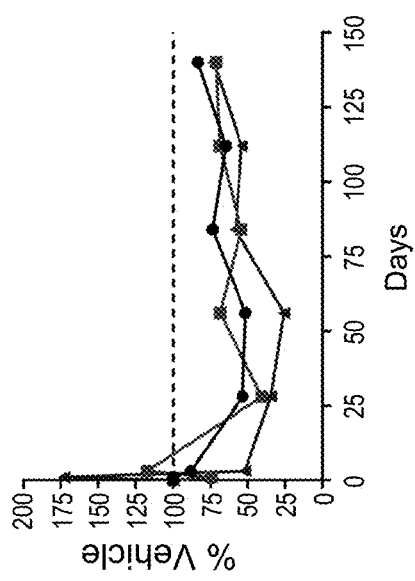
Figure 17B:
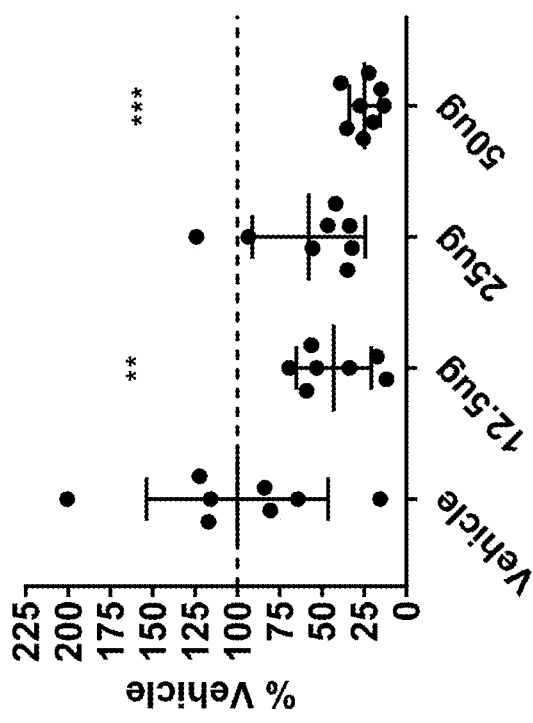
FIGS. 17A and 17B show the effect of ASO-005459 on SNCA protein expression level in A53T-PAC mice at 8 weeks post ASO-005459 administration. The animals received either the vehicle control or varying concentrations of ASO-005459 (12.5, 25, or 50 µg). The relative SNCA protein expression levels (normalized to the vehicle control) are shown for both the brain stem (FIG. 17A) and the striatum (FIG. 17B). Each data point represents an individual animal. The horizontal line marks the reference value of 100% (i.e., value at which the SNCA mRNA expression would be equivalent to expression level observed in the vehicle control group). The mean±SD from multiple animals is also shown. Statistics shown is based on comparison to the vehicle group using 1-way ANOVA with Dunnett's correction for multiple comparisons.
Figure 17A:
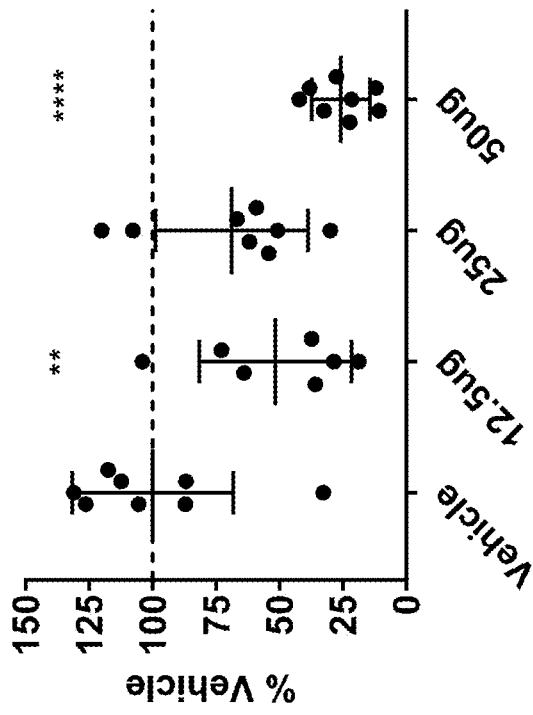

As shown in FIGS. 16A and 16B, administration of ASO-005459 to the animals also resulted in a time- and dose-dependent reduction in the SNCA protein level in both the brain stem and the striatum brain tissue. Peak reduction (~75%) was observed in the brain stem with a dose of 50 μg at 8 weeks post dosing (FIG. 16A). For the striatum brain tissue, peak reduction (~75%) was also observed with the 50 μg dose but at 4 weeks post dosing (FIG. 16B). Expression levels for the individual mice at 8 weeks post dosing are provided in FIGS. 17A (brain stem) and 17B (striatum). While SNCA protein level returned close to baseline by about 12 weeks post dosing in the striatum, expression level was still significantly reduced (~25%) in the brain stem as far out as 16 weeks post-dosing.

Example 7: Analysis of In Vivo Activity and Tolerability of SNCA-Targeted Antisense Oligonucleotides (ASOs) in Cynomolgus Monkeys To further evaluate the ASO activity and tolerability in vivo, an intrathecal ported Cynomolgus monkey model (Cyno IT) was developed. This model enables the evaluation of ASO-005459-mediated knockdown of SNCA as well as knockdown of the potential 1-basepair mismatch off-targets PROS1 and IKZF3. The ASO-005459 target sites in SNCA, PROS1, and IKZF3 are completely conserved between human and cyno.

As described above in Example 3, each animal was implanted with an intrathecal cerebrospinal fluid (CSF) catheter entering at the L3 or L4 vertebrae. The ASOs (ASO-005459, ASO-005584, and ASO-005578) were dissolved in saline and administered to the animals, infused over 4.5 min using the IT port (2 animals per dose group). Each of the animals received one of the following: (i) ASO-005578 (4 mg total), (ii) ASO-005584 (4 or 8 mg total), and (iii) ASO-005459 (8 mg total). Animals were then euthanized at various time points post dosing, when the tissues were harvested for analysis of the ASO exposure and activity. Brain regions analyzed included medulla (Med), pons (V-Pons), midbrain (V-MB), cerebellum (CBL), caudate-putamen (left and right) (CauP), hippocampus (left and right) (Hip), frontal cortex (left and right) (FrC), temporal cortex (left and right) (TeC), parietal cortex (left and right) (PaC), occipital cortex (left and right) (Occ), and cortical white matter (WM). Additionally, spinal cord was sampled at the cervical (CSC), thoracic (TSC), and lumbar (LSC) regions. Samples were also collected from liver, kidney, heart, trigeminal nuclei, tibial nerve, and aorta to examine off-target pharmacology in those areas.

Figure 18A:
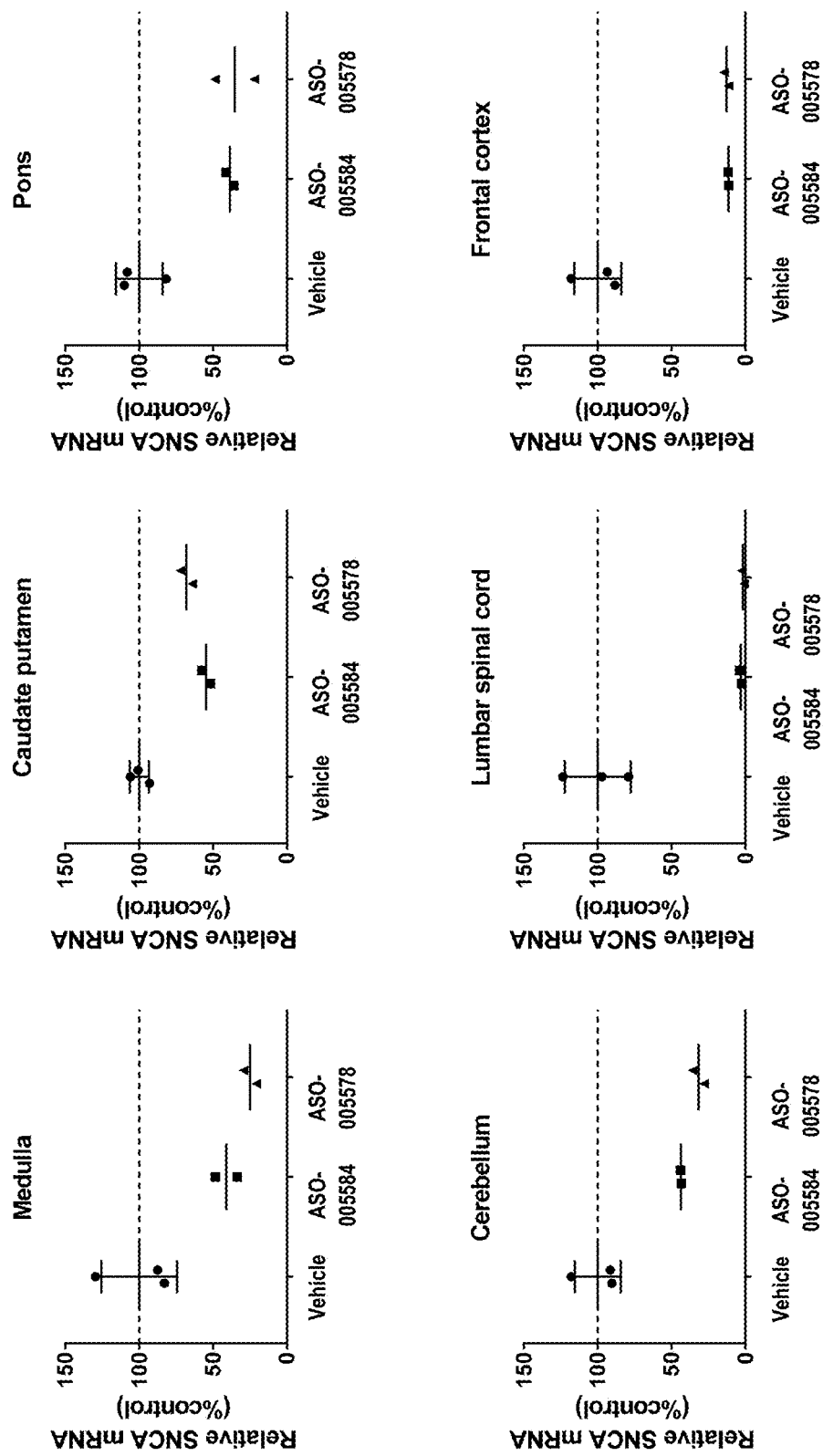
FIGS. 18A and 18B show the effect of ASO-005578 and ASO-005584 on SNCA mRNA expression level in the brain tissues of cyno monkeys.
Figure 18B:
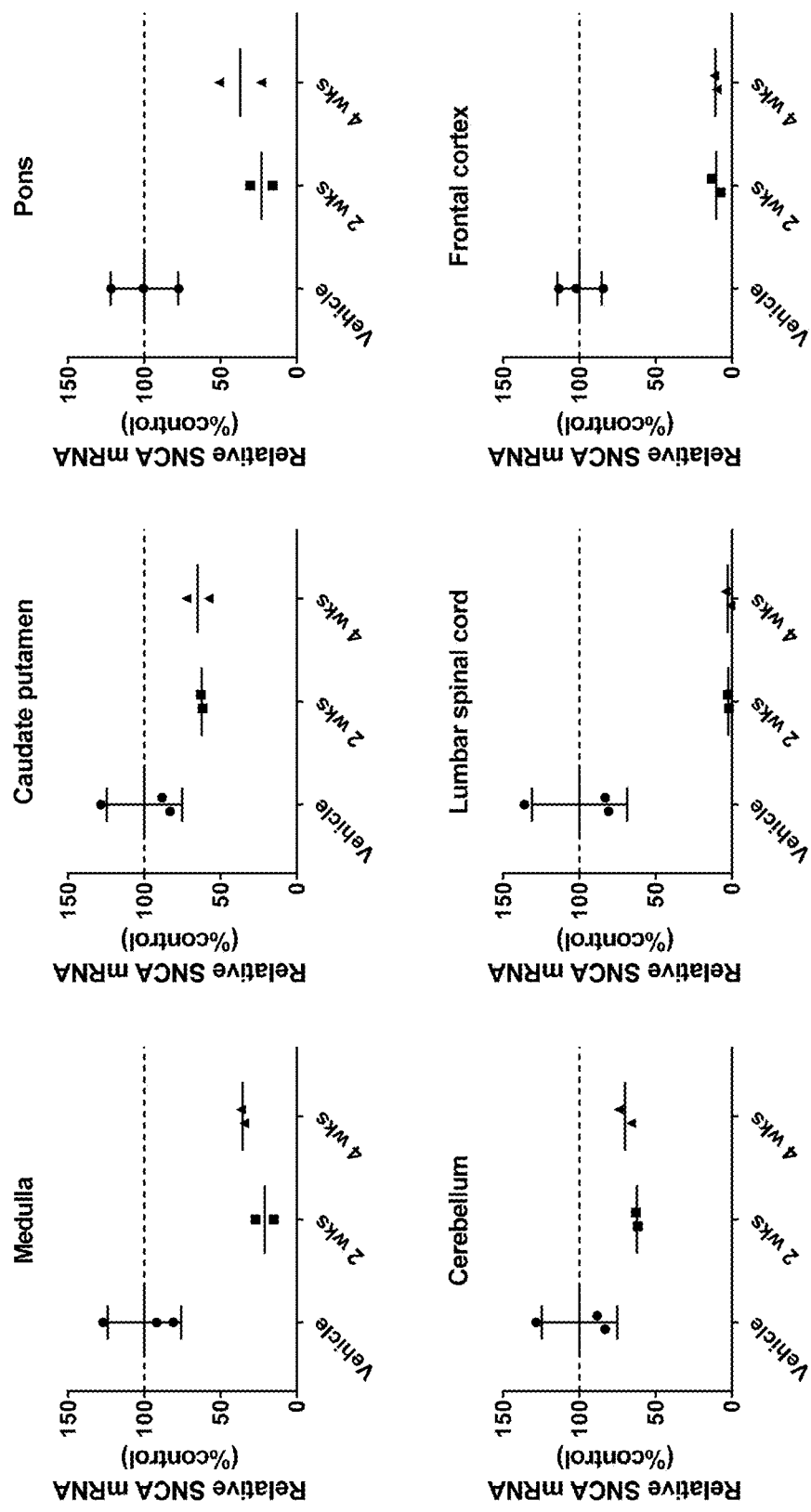

As was observed in mice, the ASOs were well tolerated in cyno with no adverse effects being observed (data not shown). And as shown in FIG. 18A and Table 9 below, the administration of ASO-005578 or ASO-005584 to the animals resulted in significant reduction of SNCA mRNA levels in all brain tissues analyzed. At 2 weeks post dosing, ASO-005578 induced reductions of 75%, 32%, 65%, 69%, 98% o and 87% o in the medulla, caudate-putamen, pons, cerebellum, lumbar spinal cord and frontal cortex, respectively. ASO-005584 induced reductions of 59%, 45%, 61%, 57%, 97% and 88% in the medulla, caudate-putamen, pons, cerebellum, lumbar spinal cord and frontal cortex, respectively. Similar reductions were observed at the 2-week and 4-week post-dose timepoints following administration of 8 mg ASO-005584 (FIG. 18B). ASO-005459 also exhibited robust knockdown of SNCA mRNA in various regions of the cyno brain (Table 9).

TABLE 9

Effect of ASOs on brain SNCA mRNA levels in cyno brain

| ASO No. | Dose (mg) | Timepoint (weeks) | Med | CBL | FrC | PaC | CauP | TeC | Occ | Hip | V-MB | V-Pons | CSC | TSC | LSC | WM |
|---|---|---|---|---|---|---|---|---|---|---|---|---|---|---|---|---|
| ASO-005578 | 4 | 2 | 25 | 32 | 13 | 27 | 68 | 24 | 38 | 45 | 27 | 35 | 15 | 7 | 2 | 64 |
| ASO-005584 | 4 | 2 | 41 | 44 | 12 | 34 | 55 | 8 | 38 | 44 | 53 | 39 | 16 | 9 | 3 | 45 |
|  | 8 | 2 | 21 | 62 | 10 | 16 | 62 | 6 | 19 | 36 | 34 | 23 | 2 | 2 | 2 | 38 |
|  | 8 | 4 | 36 | 70 | 11 | 23 | 65 | 7 | 28 | 48 | 48 | 37 | 5 | 4 | 3 | 78 |
| ASO-005459 | 8 | 24 hours | 174 | 140 | 146 |  | 149 |  |  |  |  | 137 |  |  | 73 |  |
|  | 8 | 24 hours | 129 | 108 | 138 |  | 133 |  |  |  |  | 145 |  |  | 90 |  |
|  | 8 | 3 days | 162 | 69 | 69 |  | 112 |  |  |  |  | 62 |  |  | 19 |  |
|  | 8 | 3 days | 127 | 67 | 72 |  | 114 |  |  |  |  | 87 |  |  | 31 |  |
|  | 2 | 2 | 133 | 140 | 109 |  | 161 |  |  |  |  | 104 |  |  | 21 |  |
|  | 2 | 2 | 117 | 127 | 100 |  | 126 |  |  |  |  | 180 |  |  | 111 |  |
|  | 4 | 2 | 62 | 86 | 22 |  | 116 |  |  |  |  | 49 |  |  | 4 |  |
|  | 4 | 2 | 81 | 72 | 50 |  | 145 |  |  |  |  | 97 |  |  | 13 |  |
|  | 8 | 2 | 31 | 97 | 7 |  | 124 |  |  |  |  | 66 |  |  | 14 |  |
|  | 8 | 2 | 30 | 38 | 15 | 26 | 75 | 12 | 29 | 29 | 86 | 29 | 13 | 6 | 2 | 79 |
|  | 8 | 4 | 26 | 50 | 4 | 12 | 53 | 3 | 13 | 9 | 24 | 21 | 4 | 6 | 4 | 87 |
|  | 8 | 4 | 38 | 61 | 9 |  | 120 |  |  |  |  | 30 |  |  | 10 |  |
|  | 8 | 8 | 121 | 85 | 40 |  | 98 |  |  |  |  | 78 |  |  | 5 |  |
|  | 8 | 8 | 93 | 52 | 14 |  | 61 |  |  |  |  | 36 |  |  | 11 |  |
|  | 8 | 13 | 30 | 63 | 8 |  | 81 |  |  |  |  | 27 |  |  | 1 |  |
|  | 8 | 13 | 25 | 28 | 8 |  | 49 |  |  |  |  | 22 |  |  | 1 |  |
|  | 8 | 20 | 40 | 38 | 35 |  | 76 |  |  |  |  | 63 |  |  | 9 |  |
|  | 8 | 20 | 22 | 52 | 35 |  | 76 |  |  |  |  | 26 |  |  | 11 |  |

Figure 19A:
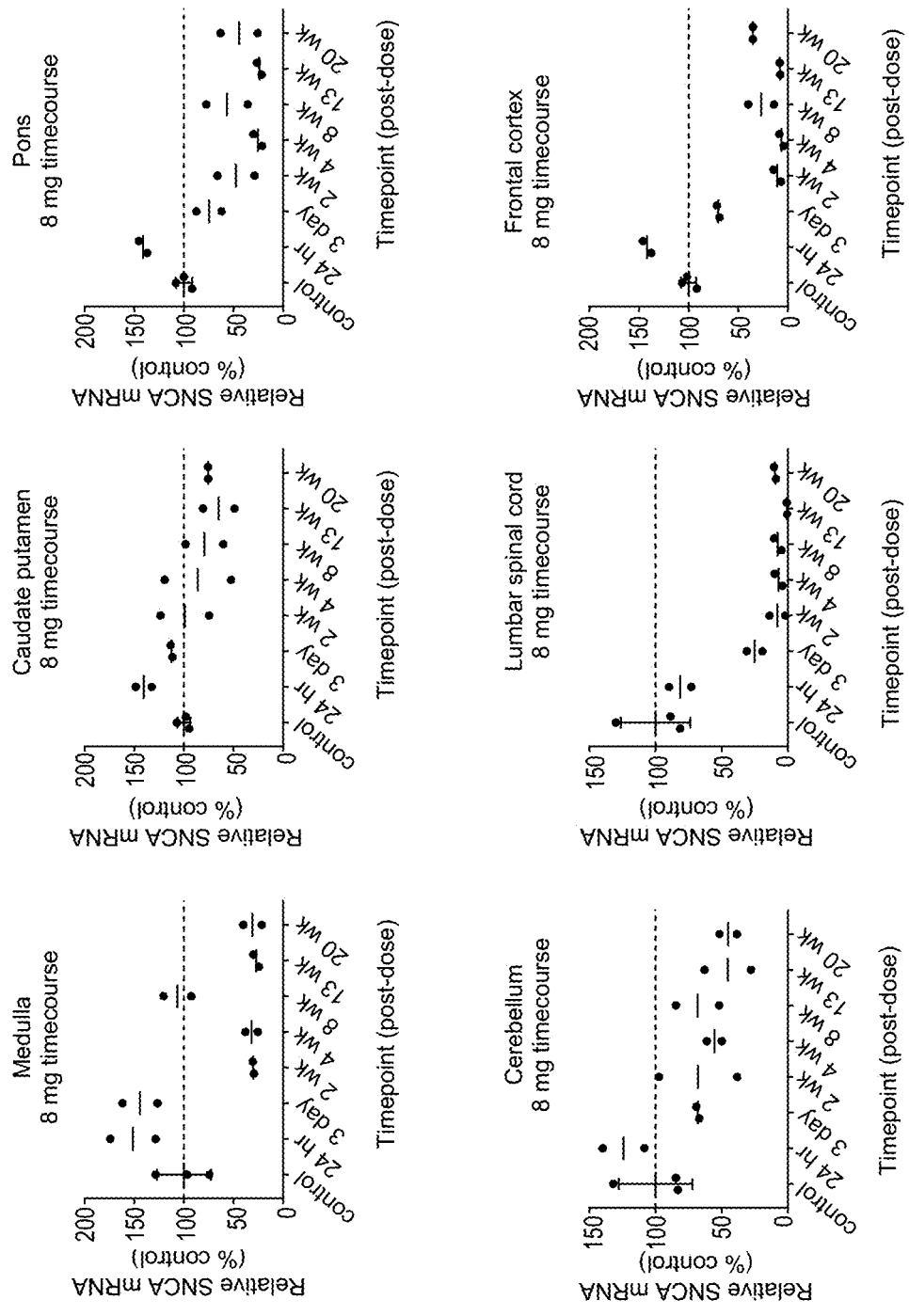
FIGS. 19A and 19B show the kinetics of SNCA mRNA and SNCA protein expression levels in cyno monkeys after ASO-005459 administration. Each of the animals received either the vehicle control or ASO-005459 (8 mg) and then were sacrificed at 24 hours, 3 days, 2, 4, 8, 13, or 20 weeks post-dosing. At each time point, the expression levels of SNCA mRNA (FIG. 19A) and SNCA protein (FIG. 19B) were assessed in the following tissues: medulla (top left panel), caudate putamen (top middle panel), pons (top right panel), cerebellum (bottom left panel), lumbar spinal cord (bottom middle panel), and frontal cortex (bottom right panel). The expression levels are shown as a percentage of the vehicle control. Both the data for the individual animals and the mean are shown. The horizontal line marks the reference value of 100% (i.e., value at which the SNCA mRNA expression would be equivalent to expression level observed in the vehicle control group).
Figure 19B:
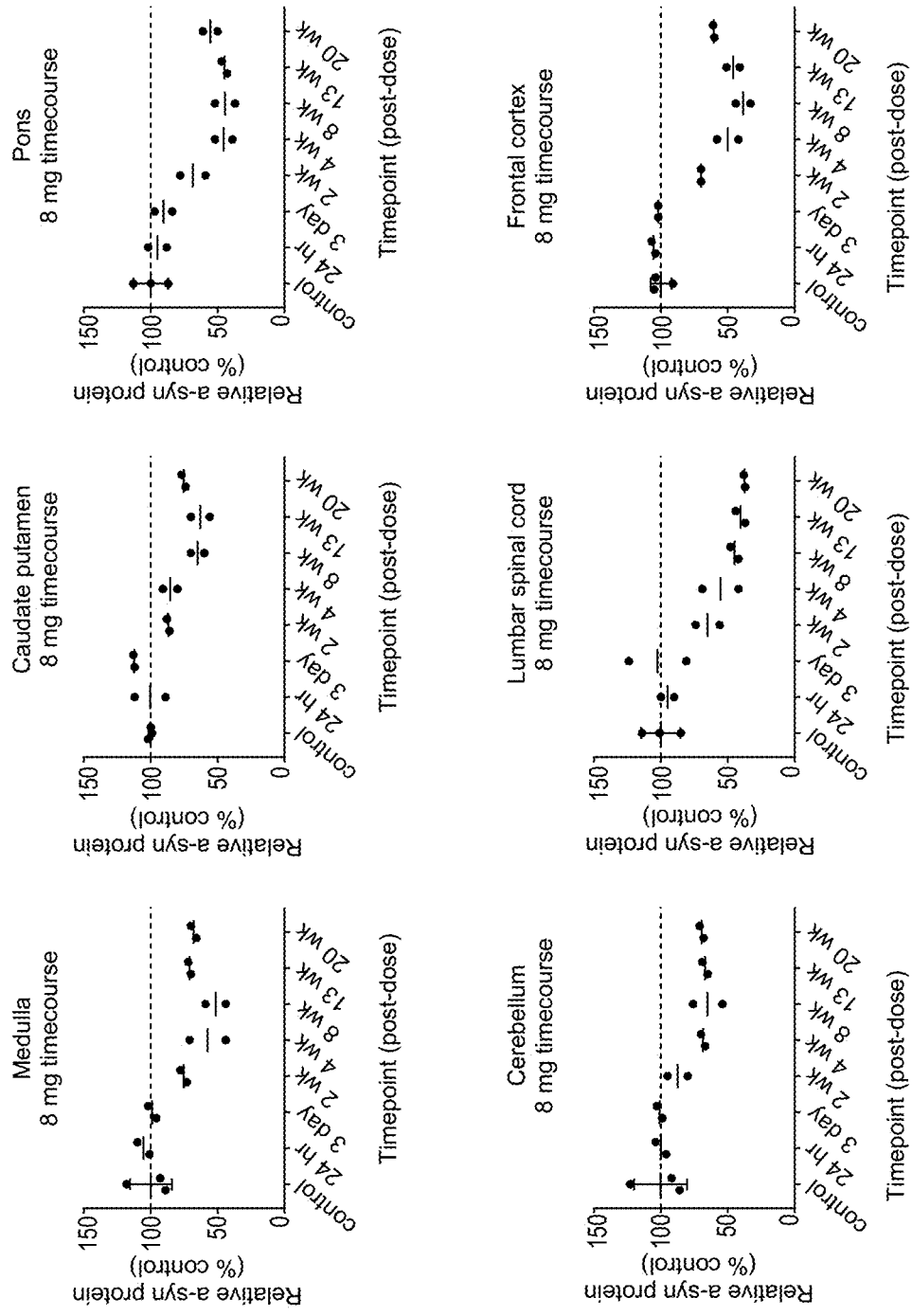

To further characterize the time-dependent reduction of SNCA mRNA described-above, cyno monkeys were dosed with ASO-005459 (8 mg total per animal) and sacrificed at 24 hour, 3 days, 2, 4, 8, 13, or 20 weeks post-dosing to assess the SNCA mRNA expression level in the different tissues. As shown in FIG. 19A, peak reduction was observed between 2 weeks and 13 weeks post-dosing. Peak reductions of 700%, 65%, 7500, 3500, 94% o and 99% o were observed in the medulla, cerebellum, pons, caudate-putamen, frontal cortex and lumbar spinal cord, respectively. This reduction in SNCA mRNA expression level also correlated with a time-dependent reduction in the SNCA protein expression level (FIG. 191B).

Figure 20A:
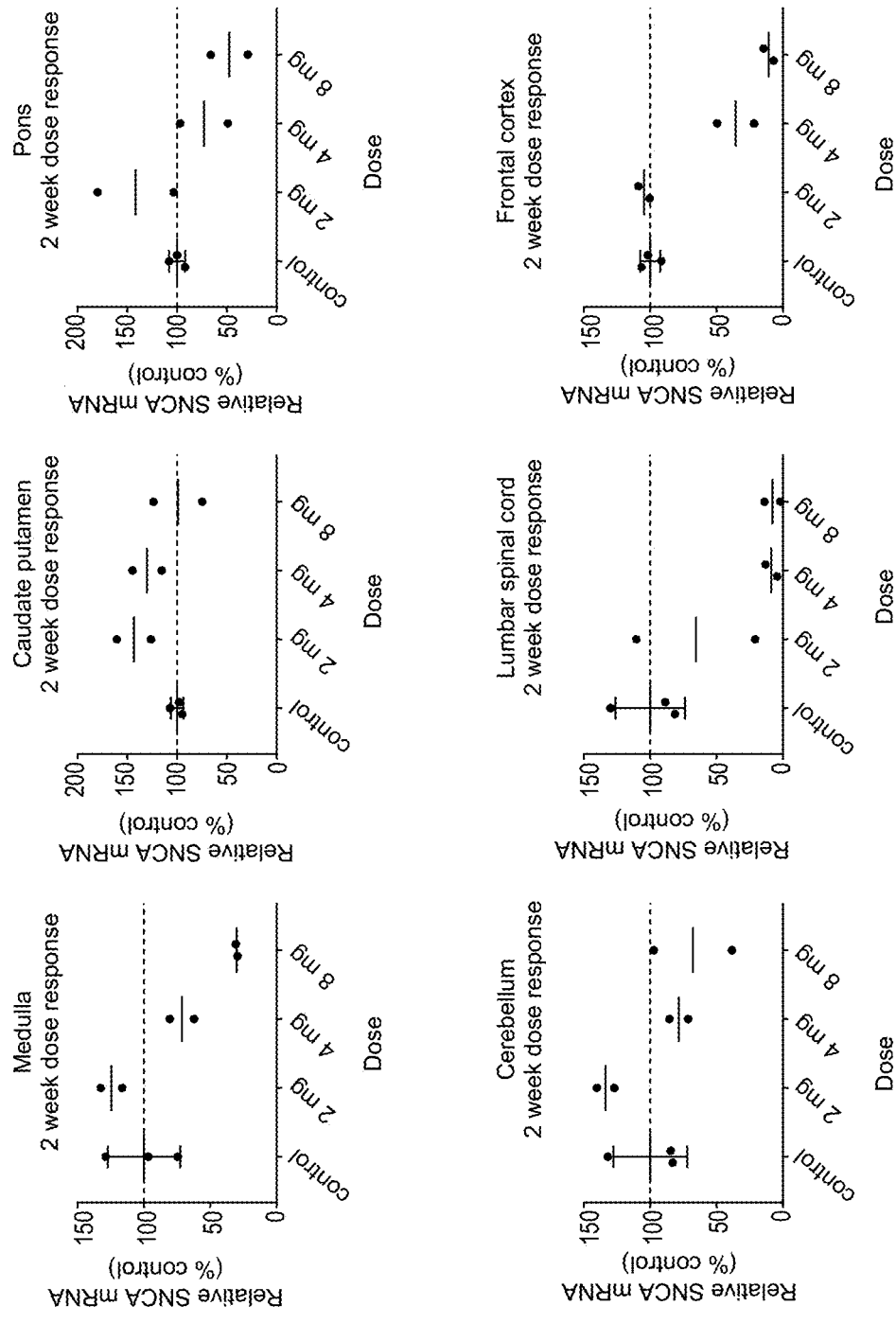
FIGS. 20A and 20B show the relative expression level (as percentage of the vehicle control) for both the SNCA mRNA (FIG. 20A) and SNCA protein (FIG. 20B) in cyno monkeys at 2 weeks post ASO-005459 administration. The animals received either the vehicle control or varying concentrations of the ASO-005459 (2, 4, or 8 mg). The expression levels were assessed in the following tissues: medulla (top left panel), caudate putamen (top middle panel), pons (top right panel), cerebellum (bottom left panel), lumbar spinal cord (bottom middle panel), and frontal cortex (bottom right panel). The expression levels are shown as a percentage of the vehicle control. Both the data for the individual animals and the mean are shown. The horizontal line marks the reference value of 100% (i.e., value at which the SNCA mRNA expression would be equivalent to expression level observed in the vehicle control group).
Figure 20B:
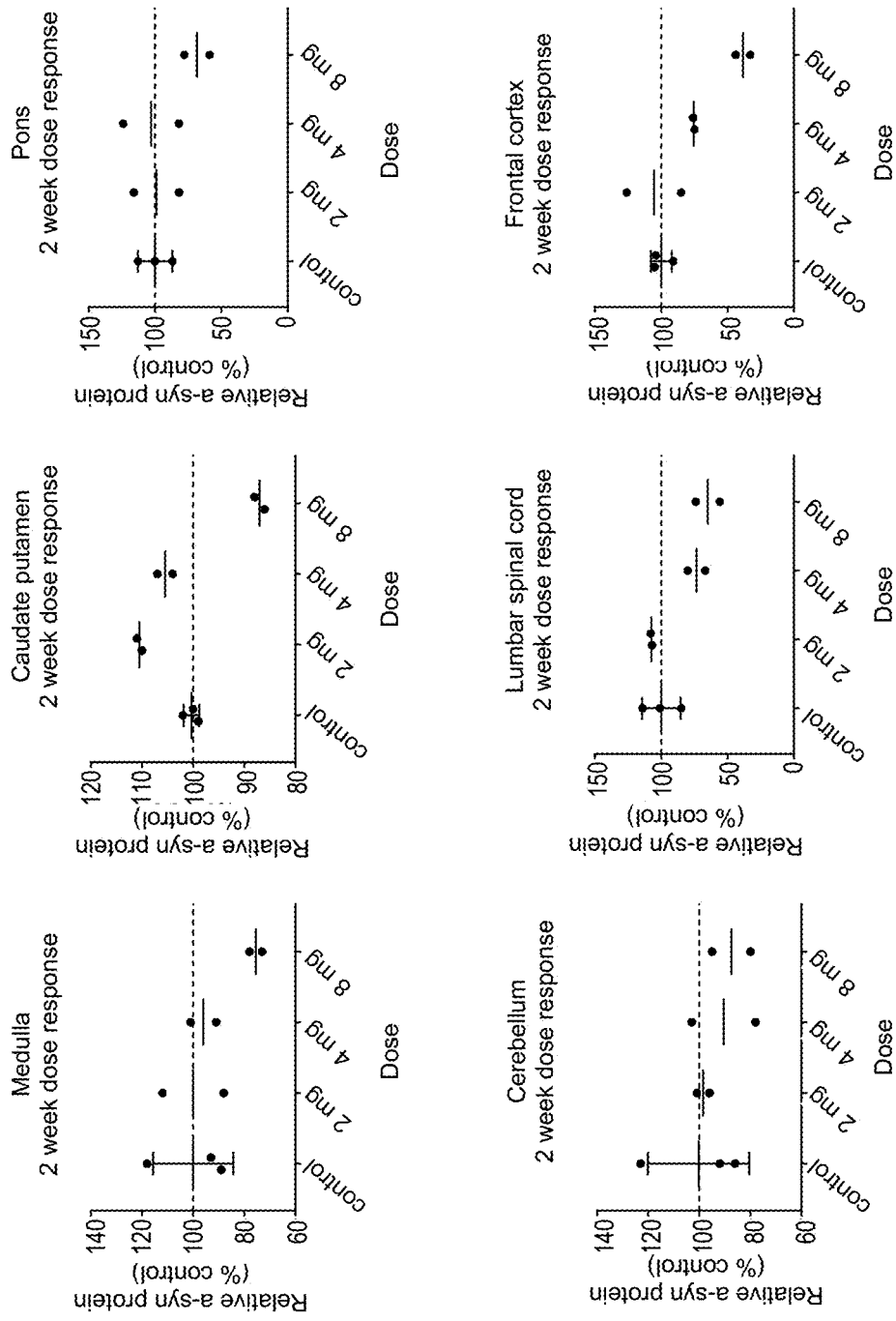

Next, to further assess whether the reduction in expression level in the cyno monkeys was also dependent on the dose, the animals received 2, 4, or 8 mg of ASO-005459 and then, were sacrificed at 2 weeks post-dosing. As shown in FIGS. 20A and 201B, the reduction in both the SNCA mRNA and the SNCA protein expression levels was also dependent on the dose, with the greatest reduction observed with 8 mg of ASO-005459.

The results presented here demonstrate that ASO-005459 is potent and selective for reducing SNCA mRNA and that ASO-005459 is well tolerated in neurons and studies in preclinical species in vivo. Moreover, results from the A53T-PAC neurons confirm that ASO-005459-mediated reductions of mRNA result in reductions of SNCA protein levels in vitro and in vivo. In addition, results in A53T-PAC mice and cyno monkeys demonstrate that ASO-005459 reduces SNCA mRNA and SNCA protein in brain at doses that are well tolerated. Taken together, these findings support the continued development of ASO-005459 as a disease-modifying therapeutic for the treatment of synucleinopathies.

This PCT application claims priority benefit of U.S. Provisional Application No. 62/616,994, filed Jan. 12, 2018, which is incorporated herein by reference in its entirety.

What is claimed:

1. An antisense oligonucleotide comprising a contiguous nucleotide sequence of 10 to 30 nucleotides in length that are complementary to a nucleic acid sequence within an alpha-synuclein (SNCA) transcript, wherein the contiguous nucleotide sequence comprises a sequence as set forth in:
   (i) SEQ ID NO: 7 with the design of AttCctttacaccACaCT (ASO-005578), AttCctttacaccAcACT (ASO-005584), AttCctttacaccaCACT (ASO-005597), or AttCctttacaccacACT (ASO-005611);
   (ii) SEQ ID NO: 9 with the design of AatTCctttacaccacACT (ASO-005717) or AAttCctttacaccaCACT (ASO-005700);
   (iii) SEQ ID NO: 12 with the design of ttccTttacaccacac (ASO-288906), ttCctttacaccAcAc (ASO-287957), TtcctttacaccaCaC (ASO-287959), or ttCctttacaccACac (ASO-287962); or
   (iv) SEQ ID NO: 14 with the design of AAttcctttacACCAcAC (ASO-005650), AAttCctttacacCaCAC (ASO-005496), or AAttCCtTtacaccacAC (ASO-005392);
   wherein the upper case letter is a beta-D-oxy-locked nucleic acid (LNA) and the lower case letter is a DNA.

2. The antisense oligonucleotide of claim 1, wherein the antisense oligonucleotide comprises one or more 5' methyl cytosine nucleobases.

3. The antisense oligonucleotide of claim 1, wherein the nucleotide sequence comprises, consists essentially of, or consists of SEQ ID NO 7 with the design of ASO-005578 or ASO-005584.

4. The antisense oligonucleotide of claim 3, wherein the ASO comprises:
   (i) a molecular formula of $C_{182}H_{229}N_{58}O_{96}P_{17}S_{17}$; or
   (ii) a molecular formula of $C_{181}H_{227}N_{58}O_{96}P_{17}S_{17}$.

5. The antisense oligonucleotide of claim 1, which comprises an internucleoside linkage selected from: a phosphodiester linkage, a phosphotriester linkage, a methylphosphonate linkage, a phosphoramidate linkage, a phosphorothioate linkage, and combinations thereof.

6. The antisense oligonucleotide of claim 1, wherein the antisense oligonucleotide is covalently attached to at least one non-nucleotide or non-polynucleotide moiety.

7. A pharmaceutical composition comprising the antisense oligonucleotide of claim 1 and a pharmaceutically acceptable carrier.

8. A kit comprising the antisense oligonucleotide of claim 1 and instructions for use.

9. A method of inhibiting or reducing SNCA mRNA expression or SNCA protein expression in a cell, the method comprising administering the antisense oligonucleotide of claim 1 to the cell expressing SNCA mRNA or SNCA protein, wherein the SNCA mRNA expression or SNCA protein expression in the cell is inhibited or reduced after the administration.

10. A method for treating a synucleinopathy in a subject in need thereof, comprising administering an effective amount of the antisense oligonucleotide of claim 1 to the subject.

11. The method of claim 10, wherein the synucleinopathy is selected from the group consisting of Parkinson's disease, Parkinson's Disease Dementia (PDD), multiple system atrophy, dementia with Lewy bodies, and any combinations thereof.

* * * * *

SEQUENCE LISTING

```
<160> NUMBER OF SEQ ID NOS: 28

<210> SEQ ID NO 1
<211> LENGTH: 2400
<212> TYPE: DNA
<213> ORGANISM: Homo sapiens
<220> FEATURE:
<221> NAME/KEY: misc_feature
<222> LOCATION: (6001)..(8400)
<223> OTHER INFORMATION: partial SNCA genomic sequence

<400> SEQUENCE: 1
gagatbggga cgaggagcac gctgcaggga aagcagcgag cgccgggaga ggggcgggca        60
gaagcgctga caaatcagcg gtggggggcgg agagccgagg agaaggagaa ggaggaggac       120
taggaggagg aggacggcga cgaccagaag gggcccaaga gaggggggcga gcgaccgagc       180 gccgcgacgc ggaagtgagg tgcgtgcggg ctgcagcgca gaccccggcc cggcccctcc        240
```

| | | | |
|---|---|---|---|
| gagagcgtcc | tgggcgctcc | ctcacgcctt | gccttcaagc cttctgcctt tccaccctcg | 300 |
| tgagcggaga | actgggagtg | gccattcgac | gacaggttag cgggtttgcc tcccactccc | 360 |
| ccagcctcgc | gtcgccggct | cacagcggcc | tcctctgggg acagtccccc ccgggtgccg | 420 |
| cctccgccct | tcctgtgcgc | tccttttcct | tcttctttcc tattaaatat tatttgggaa | 480 |
| ttgtttaaat | tttttttta | aaaaagaga | gaggcgggga ggagtcggag ttgtggagaa | 540 |
| gcagagggac | tcaggtaagt | acctgtggat | ctaaacgggc gtctttggaa atcctggaga | 600 |
| acgccggatg | ggagacgaat | ggtcgtgggc | accgggaggg ggtggtgctg ccatgaggac | 660 |
| ccgctgggcc | aggtctctgg | gaggtgagta | cttgtccctt tggggagcct aaggaaagag | 720 |
| acttgacctg | gctttcgtcc | tgcttctgat | attcccttct ccacaagggc tgagagatta | 780 |
| ggctgcttct | ccgggatccg | cttttccccg | ggaaacgcga ggatgctcca tggagcgtga | 840 |
| gcatccaact | tttctctcac | ataaaatctg | tctgcccgct ctcttggttt ttctctgtaa | 900 |
| agtaagcaag | ctgcgtttgg | caaataatga | aatggaagtg caaggaggcc aagtcaacag | 960 |
| gtggtaacgg | gttaacaagt | gctggcgcgg | ggtccgctag ggtggaggct gagaacgccc | 1020 |
| cctcgggtgg | ctggcgcggg | gttggagacg | gcccgcgagt gtgagcggcg cctgctcagg | 1080 |
| gtagatagct | gagggcgggg | gtggatgttg | gatggattag aaccatcaca cttgggcctg | 1140 |
| ctgtttgcct | gagtttgaac | cacaccccga | gtgagcagtt agttctgttg cctacgcctt | 1200 |
| tccaccatca | acctgttagc | cttcttctgg | gattcatgtt aaggataccc ctgaccctaa | 1260 |
| gcctccagct | tccatgcttc | taactcatac | tgttacccct tagaccccgg gaatttaaaa | 1320 |
| aaggggttaa | tcttttcatg | caactccact | tctgaaatgc agtaataaca actcagagga | 1380 |
| ttcatcctaa | tccgtggtta | ggtggctaga | cttttactag ccaagatgga tgggagatgc | 1440 |
| taaattttta | atgccagagc | taaaaatgtc | tgctttgtcc aatggttaaa tgagtgtaca | 1500 |
| cttaaaagag | tctcacactt | tggagggttt | ctcatgattt ttcagtgttt tttgtttatt | 1560 |
| tttccccgaa | agttctcatt | caaagtgtat | tttatgtttt ccagtgtggt gtaaaggaat | 1620 |
| tcattagcca | tggatgtatt | catgaaagga | cttttcaaagg ccaaggaggg agttgtggct | 1680 |
| gctgctgaga | aaaccaaaca | gggtgtggca | gaagcagcag gaaagacaaa agagggtgtt | 1740 |
| ctctatgtag | gtaggtaaac | cccaaatgtc | agtttggtgc ttgttcatga gtgatgggtt | 1800 |
| aggataatca | atactctaaa | tgctggtagt | tctctctctt gattcatttt tgcatcattg | 1860 |
| cttgtcaaaa | aggtggactg | agtcagaggt | atgtgtaggt aggtgaatgt gaacgtgtgt | 1920 |
| atttgagcta | atagtaaaaa | atgcgactgt | ttgcttttcc agatttttaa ttttgcccta | 1980 |
| atatttatga | cttttttaaaa | atgaatgttt | ctgtacctac ataattctat ttcagagaac | 2040 |
| agttttaaaa | actcatagtc | ttttaaaaaa | taatcaagaa tattcttaag aatcaaaatc | 2100 |
| attgatggat | ctgtgatttc | ttttaccatc | atgaaaaatg tttgtcaatt ttaatccatt | 2160 |
| ctgattttta | aaatatgact | tgatatgcc | cctgtgatgt gtataaagag acctatttgt | 2220 |
| ggccctaaaa | tggaaagaac | agattagtct | ttgatagagt tacttcatgt gatcatttgg | 2280 |
| tctctgtgaa | cactgaggac | agagaaaagt | gcttgagggc tgctactaat ctctcagaaa | 2340 |
| catttgtata | gttcatccat | caaatgacac | acatactaaa agaataaaga aattgatgct | 2400 |

<210> SEQ ID NO 2
<211> LENGTH: 3215
<212> TYPE: DNA
<213> ORGANISM: Homo sapiens

<400> SEQUENCE: 2

```
aggagaagga gaaggaggag gactaggagg aggaggacgg cgacgaccag aagggggccca      60 agagaggggg cgagcgaccg agcgccgcga cgcggaagtg aggtgcgtgc gggctgcagc     120 gcagacccccg gcccggcccc tccgagagcg tcctgggcgc tccctcacgc cttgccttca    180
agccttctgc ctttccaccc tcgtgagcgg agaactggga gtggccattc gacgacagtg    240
tggtgtaaag gaattcatta gccatggatg tattcatgaa aggactttca aaggccaagg    300
agggagttgt ggctgctgct gagaaaacca acagggtgt ggcagaagca gcaggaaaga    360
caaaagaggg tgttctctat gtaggctcca aaccaagga gggagtggtg catggtgtgg    420
caacagtggc tgagaagacc aaagagcaag tgacaaatgt tggaggagca gtggtgacgg    480
gtgtgacagc agtagcccag aagacagtgg agggagcagg gagcattgca gcagccactg    540
gctttgtcaa aaaggaccag ttgggcaaga atgaagaagg agccccacag gaaggaattc    600
tggaagatat gcctgtggat cctgacaatg aggcttatga aatgccttct gaggaagggt    660
atcaagacta cgaacctgaa gcctaagaaa tatctttgct cccagtttct tgagatctgc    720
tgacagatgt tccatcctgt acaagtgctc agttccaatg tgcccagtca tgacatttct    780
caaagttttt acagtgtatc tcgaagtctt ccatcagcag tgattgaagt atctgtacct    840
gcccccactc agcatttcgg tgcttccctt tcactgaagt gaatacatgg tagcagggtc    900
tttgtgtgct gtggattttg tggcttcaat ctacgatgtt aaaacaaatt aaaaacacct    960
aagtgactac cacttatttc taaatcctca ctattttttt gttgctgttg ttcagaagtt   1020
gttagtgatt tgctatcata tattataaga ttttttaggtg tcttttaatg atactgtcta   1080
agaataatga cgtattgtga aatttgttaa tatatataat acttaaaaat atgtgagcat   1140
gaaactatgc acctataaat actaaatatg aaatttttacc attttgcgat gtgttttatt   1200
cacttgtgtt tgtatataaa tggtgagaat taaaataaaa cgttatctca ttgcaaaaat   1260
attttatttt tatcccatct cactttaata ataaaaatca tgcttataag caacatgaat   1320
taagaactga cacaaaggac aaaaatataa agttattaat agccatttga agaaggagga   1380
attttagaag aggtagagaa aatggaacat taaccctaca ctcggaattc cctgaagcaa   1440
cactgccaga agtgtgtttt ggtatgcact ggttccttaa gtggctgtga ttaattattg   1500
aaagtggggt gttgaagacc ccaactacta ttgtagagtg gtctatttct cccttcaatc   1560
ctgtcaatgt ttgctttacg tattttgggg aactgttgtt tgatgtgtat gtgtttataa   1620
ttgttataca ttttttaattg agccttttat taacatatat tgttattttt gtctcgaaat   1680
aattttttag ttaaaatcta ttttgtctga tattggtgtg aatgctgtac cttctgaca   1740 ataaataata ttcgaccatg aataaaaaaa aaaaaaagt gggttcccgg gaactaagca    1800
gtgtagaaga tgattttgac tacaccctcc ttagagagcc ataagacaca ttagcacata   1860
ttagcacatt caaggctctg agagaatgtg gttaactttg tttaactcag cattcctcac   1920
tttttttttt taatcatcag aaattctctc tctctctctc tcttttttctc tcgctctctt   1980 tttttttttt ttttttacagg aaatgccttt aaacatcgtt ggaactacca gagtcacctt   2040
aaaggagatc aattctctag actgataaaa atttcatggc ctccttaaa tgttgccaaa    2100 tatatgaatt ctaggatttt tccttaggaa aggttttct ctttcaggga agatctatta    2160
actccccatg ggtgctgaaa ataaacttga tggtgaaaaa ctctgtataa attaatttaa    2220
aaattatttg gttctctttt ttaattattc tggggcatag tcatttctaa aagtcactag    2280
tagaaagtat aatttcaaga cagaatattc tagacatgct agcagtttat atgtattcat    2340
```

-continued

```
gagtaatgtg atatatattg ggcgctggtg aggaaggaag gaggaatgag tgactataag    2400
gatggttacc atagaaactt cctttttac ctaattgaag agagactact acagagtgct    2460
aagctgcatg tgtcatctta cactagagag aaatggtaag tttcttgttt tatttaagtt    2520
atgtttaagc aaggaaagga tttgttattg aacagtatat ttcaggaagg ttagaaagtg    2580
gcggttagga tatattttaa atctacctaa agcagcatat tttaaaaatt taaaagtatt    2640
ggtattaaat taagaaatag aggacagaac tagactgata gcagtgacct agaacaattt    2700
gagattagga aagttgtgac catgaattta aggatttatg tggatacaaa ttctccttta    2760
aagtgtttct tcccttaata tttatctgac ggtaattttt gagcagtgaa ttactttata    2820
tatcttaata gtttatttgg gaccaaacac ttaaacaaaa agttcttaa gtcatataag    2880 ccttttcagg aagcttgtct catattcact cccgagacat tcacctgcca agtggcctga    2940
ggatcaatcc agtcctaggt ttattttgca gacttacatt ctcccaagtt attcagcctc    3000
atatgactcc acggtcggct ttaccaaaac agttcagagt gcactttggc acacaattgg    3060
gaacagaaca atctaatgtg tggtttggta ttccaagtgg ggtcttttc agaatctctg    3120 cactagtgtg agatgcaaac atgtttcctc atctttctgg cttatccagt atgtagctat    3180
ttgtgacata ataaatatat acatatatga aaata    3215
```

<210> SEQ ID NO 3
<211> LENGTH: 140
<212> TYPE: PRT
<213> ORGANISM: Homo sapiens

<400> SEQUENCE: 3

```
Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140
```

<210> SEQ ID NO 4
<211> LENGTH: 16
<212> TYPE: DNA
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(16)
<223> OTHER INFORMATION: Antisense Oligonucleotide

<400> SEQUENCE: 4
cctttacacc acactg                                              16

<210> SEQ ID NO 5
<211> LENGTH: 18
<212> TYPE: DNA
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(18)
<223> OTHER INFORMATION: Antisense Oligonucleotide

<400> SEQUENCE: 5
ttcctttaca ccacactg                                            18

<210> SEQ ID NO 6
<211> LENGTH: 20
<212> TYPE: DNA
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(20)
<223> OTHER INFORMATION: Antisense Oligonucleotide

<400> SEQUENCE: 6
aattccttta caccacactg                                          20

<210> SEQ ID NO 7
<211> LENGTH: 18
<212> TYPE: DNA
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(18)
<223> OTHER INFORMATION: Antisense Oligonucleotide

<400> SEQUENCE: 7
attcctttac accacact                                            18

<210> SEQ ID NO 8
<211> LENGTH: 16
<212> TYPE: DNA
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(16)
<223> OTHER INFORMATION: Antisense Oligonucleotide

<400> SEQUENCE: 8
tcctttacac cacact                                              16

<210> SEQ ID NO 9
<211> LENGTH: 19
<212> TYPE: DNA
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(19)
<223> OTHER INFORMATION: Antisense Oligonucleotide

<400> SEQUENCE: 9

-continued aattcccttta caccacact        19

<210> SEQ ID NO 10
<211> LENGTH: 20
<212> TYPE: DNA
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(20)
<223> OTHER INFORMATION: Antisense Oligonucleotide

<400> SEQUENCE: 10
gaattccttt acaccacact        20

<210> SEQ ID NO 11
<211> LENGTH: 17
<212> TYPE: DNA
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(17)
<223> OTHER INFORMATION: Antisense Oligonucleotide

<400> SEQUENCE: 11
ttcctttaca ccacact        17

<210> SEQ ID NO 12
<211> LENGTH: 16
<212> TYPE: DNA
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(16)
<223> OTHER INFORMATION: Antisense Oligonucleotide

<400> SEQUENCE: 12
ttcctttaca ccacac        16

<210> SEQ ID NO 13
<211> LENGTH: 19
<212> TYPE: DNA
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(19)
<223> OTHER INFORMATION: Antisense Oligonucleotide

<400> SEQUENCE: 13
gaattccttt acaccacac        19

<210> SEQ ID NO 14
<211> LENGTH: 18
<212> TYPE: DNA
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(18)
<223> OTHER INFORMATION: Antisense Oligonucleotide

```
<400> SEQUENCE: 14
aattccttta caccacac                                               18

<210> SEQ ID NO 15
<211> LENGTH: 17
<212> TYPE: DNA
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(17)
<223> OTHER INFORMATION: Antisense Oligonucleotide

<400> SEQUENCE: 15
attcctttac accacac                                                17

<210> SEQ ID NO 16
<211> LENGTH: 18
<212> TYPE: DNA
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(18)
<223> OTHER INFORMATION: Antisense Oligonucleotide

<400> SEQUENCE: 16
gaattccttt acaccaca                                               18

<210> SEQ ID NO 17
<211> LENGTH: 16
<212> TYPE: DNA
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(16)
<223> OTHER INFORMATION: Antisense Oligonucleotide

<400> SEQUENCE: 17
attcctttac accaca                                                 16

<210> SEQ ID NO 18
<211> LENGTH: 18
<212> TYPE: DNA
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(18)
<223> OTHER INFORMATION: Antisense Oligonucleotide

<400> SEQUENCE: 18
tgaattcctt tacaccac                                               18

<210> SEQ ID NO 19
<211> LENGTH: 18
<212> TYPE: DNA
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(18)
<223> OTHER INFORMATION: Antisense Oligonucleotide
```

```
<400> SEQUENCE: 19
atgaattcct ttacacca                                           18

<210> SEQ ID NO 20
<211> LENGTH: 18
<212> TYPE: DNA
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(18)
<223> OTHER INFORMATION: Antisense Oligonucleotide

<400> SEQUENCE: 20
aatgaattcc tttacacc                                           18

<210> SEQ ID NO 21
<211> LENGTH: 17
<212> TYPE: DNA
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(17)
<223> OTHER INFORMATION: Antisense Oligonucleotide

<400> SEQUENCE: 21
ctaatgaatt cctttac                                            17

<210> SEQ ID NO 22
<211> LENGTH: 15
<212> TYPE: DNA
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(15)
<223> OTHER INFORMATION: Antisense Oligonucleotide

<400> SEQUENCE: 22
tctgtcttgg ctttg                                              15

<210> SEQ ID NO 23
<211> LENGTH: 16
<212> TYPE: DNA
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(16)
<223> OTHER INFORMATION: Antisense Oligonucleotide

<400> SEQUENCE: 23
agaaataagt ggtagt                                             16

<210> SEQ ID NO 24
<211> LENGTH: 16
<212> TYPE: DNA
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(16)
```

<223> OTHER INFORMATION: Antisense Oligonucleotide

<400> SEQUENCE: 24
atttccaaat tcactt                                                     16

<210> SEQ ID NO 25
<211> LENGTH: 20
<212> TYPE: DNA
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(20)
<223> OTHER INFORMATION: Antisense Oligonucleotide

<400> SEQUENCE: 25
ccaaatctta taataactac                                                 20

<210> SEQ ID NO 26
<211> LENGTH: 16
<212> TYPE: DNA
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(16)
<223> OTHER INFORMATION: Antisense Oligonucleotide

<400> SEQUENCE: 26
ggtgaggttt ggtaga                                                     16

<210> SEQ ID NO 27
<211> LENGTH: 18
<212> TYPE: DNA
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(18)
<223> OTHER INFORMATION: Antisense Oligonucleotide

<400> SEQUENCE: 27
ggtgaggttt ggtagaag                                                   18

<210> SEQ ID NO 28
<211> LENGTH: 121198
<212> TYPE: DNA
<213> ORGANISM: Homo sapiens

<400> SEQUENCE: 28
gcacatacaa ctttaacttc aatattttaa tgacgaaatt taaggataat ttaaatagaa     60
atggactcag aaaagaatca gtaagactta gtgaaggatc attgtctatt atagagaagt    120
tgatttaaga ttaacttatt agtaatattt aacatatata aagaattatt agactgggta    180
tatagacaag cgttttattc ttggaagaca aaagaagaa aaattgaatt caaccgatgt     240
atacgaaaat aaaaagtaac agtaaattaa aaatagataa ttaaataaat atatgataca    300
gtataacgtt ttatagccaa gatgatgtta caaatccata tttattgaca tggatatgtt    360
tttatactaa agtgtttatc aaatagccat taagagataa cttctttgaa taatttgctt    420
tctaaatttc ttaactacat aaatttccag ctttatatgg aacaccaagt tttcaaacca    480
ttagtgatgt gctttttata tggtgttaaa aagtttcttt cttctttttt tctttttccc    540

```
ccaagatgga gtcttgctct gtcgcccagg ctggagcgca gtagtgcgat ctcggctcag    600
tgcaacaacc acctcctggg tacaagcaat tctcctgcct cagcccccca gtagctggg     660 attacaggca cctgccacca cgtccagctg attttttgtat ttttagtaga cgggggttt    720 taccatcttg gccaggctgg tctctaactc ctgacctcag gtaatctgcc cacctcagcc    780
tcccaaagtg ctgagattac aggcgtgagc caccatgccc gacctaaaaa gtttcttaaa    840 cgtcactttta tactctcaaa ttatctagaa aggaaaacgt attagattcc tggatatttt    900
ggatattgta aggaacatac ttatttgctg tatatactct gtttgtaaca gtattgtaac    960
ttcagttcaa acaatacac aaaacattac aagttcccgt gatatttttaa aaattcattt   1020 attttcttcc tttctgaata caaatgctgt tcagtctgtt gattcttcac taatctgaaa   1080
tattagggac tgatttctga attggatatt cattctgaag cctttcagag ccactggcac   1140
aaagggtctg tcaaacttgg aacaccattt gttgtatcat ttttatttttt tctcttggca   1200 aatccacata attcatacag gactatgcca gtgtctttttg aaagaaacaa ggtttaagaa   1260
agtaaaaatg ttaataaaga tagtgaatgt taattctgtc attgttactg tatttcttca   1320
agctgtggct gcaaactgct ttgagtgatg ttattgtaac tcgcacatta gggagagaaa   1380
gagatgtttg gtagattttt aattaatgat ccctatcaat gctccttgag ctttcccact   1440
ctatctctcc acaacttcca tccctggttg gaattttttt gcttacccat actaagtgag   1500
agttattgat gggaaggcat cagatatctc acgtgtgttg ctggtgggat gggagactgt   1560
ggaggatggg aacaggtgga aatctactgc aatggaaaaa aaaaaaaagc atgtcctagg   1620
acacccaaaa catggaggct agataataac aatagctact tgtactgaga gcttccactc   1680
tgcctggctc tttgctatga gccacattat tcattcctta caacaatcaa acaagacaag   1740
taaaatatca tgcccatttt ttaatgagaa aactagagat tagagaggtt atagatactt   1800
gctctgagtc actagtaatg agtagtagag ctttaataag tccctgaatt taggttgtat   1860
ctagtacatt tactcttaga agtctatcat gctcaccaga gttgcagagt tgcgtgtatt   1920
tcttgggctc attaatgtgt tttttttcttt ctaaaactaa agtcatttga acttgttaga   1980
ttttgaaata tttaaatatc ttttctatct ggctttaaca tctttaatct tggaatcttg   2040
catgccttca tattcttagg accacgaaac cacaggaata tttaaaatga tatctagtgg   2100
aaacaatatg aagttggcca tgggggtcaaa ttagagaatc tgaatactat gcttctcctt   2160
gattgctctt cccatttctt cagagtaacc ctattccccc atctcatgct cacccccttt   2220
ccaaaatcat acataatgat ctcccaacag tatgcattag gctttctcta ctctacccac   2280
tatgaaatta cacaagaagc ctatcgcaat ctcactacct cgtctctctc acaggtttac   2340
agaaggtgag aggaaggtgc agatagagaa taagaagcag gtggctccag catcaacatt   2400
acatcacccc ttgtgttcac aacaaatacg gaatattatc caaagataat aaacgttgta   2460
ttttcttaac ttaaacacat aaatcagtc ctctctttaa tcaattgtta atgggcagca   2520
tctttatttt catgccattc tactctgctg tctttgctat agcacaagtt taccacatac   2580
catacctaaa aattcagttg ttctatgggg gtaaacaaag tctaggttaa gcatatattt   2640
catagaatgt taatctatag caaaattaat gaattaaatc cagataaaag aatcctatta   2700
tggtctggta aaatatttat atttcactta gcaaagagaa aacaaaacat gaatattgta   2760
gttatgaaca gaatatgcat gttagtaatg cttccaaata tgttattact tcataacttc   2820
atatttctta tgaggtacaa gccattcaat tagtttaacg ttatattcag agaggctaaa   2880
```

```
gatttactga agaccatgct gtccatcaat aatgaaaaga aaaattaaaa aaactttatt    2940
ttaacttcta gttcccttct ttgtacttga gcagctttcc ctccttaaga atacagacct    3000
agaacatatg caatatcact atcaatatta tgtgtaatta aaagttcatt ggatgtttac    3060
tgtgttcaag gcattttaag gagtgacaag agttaaacat atagttgtaa ttcaaaatga    3120
caacgaaatt agtttacagt tttcttttt tgtaggtagt aagaaatcat ctcccctat      3180 tgaggaatac caatatagaa aaggcaaaac tttaaatatg aatgaactgt tcataataa     3240 cataagttct tcttgatttc cattgtcaca tccaaatttg aaggctattt ctaacacagc    3300
tgggttctac cttttttcctt ctcactcttt accacaccca atctgtgagg cttcagacac   3360
aaactgctaa ttcaggagac aattgtgcct tctgtaacag tttctgctaa attgtctcag    3420
ctctgccact taaaatagct aggtgatctc agcatatcac caaaactctt ggagctcagt    3480
ttctctgtct ataaaagtta cataaaatgt aattgatctg cttgttatga ctaaataaca    3540
tagtacatta gtccttttgcc aaaggactaa caaattacca aataaaagtt tggaatcatg   3600
ttaaacgttt ataagaagtg caactgtcca gaaataattc tctcacattg gtctgttgta    3660
atgagaccta aaatatctca ttttatttac ctctttgact taaagcacta ggtctcaagg    3720
aggtcatggt tatactataa atatgtcatg tgaataata tattaaataa ttgttgtaat     3780
actctattga gatactagtt gtaaagaggc acaatggaaa acttatacta ttaacagtag    3840 taaaagaaa caacaaaaag caataaaaaa caaacaccc attcatgcaa cgacatgaac      3900
gaacctcaca atattatac tgagtaaaag aagtcagaca aatataaaac aaagtttata     3960
ctacgtgatt agatctttat gacattctag aatatgcaca tgaaggtaca aggtaactgt    4020
ctggaatgat gaaaatgtcc tgtgtcttca aaatagtgtg ggttacacta atgcatggct    4080
ttttcaaaac tgatttaaag ggacacaaca tctgagcatt tccctaggtg taaattacac    4140 tgcaattta aagaatcatc taatgatatt gtggttattt ttaaacagtc cttaaatttt     4200
gtggatgcat actgaatgtt tacagctgaa aagatatata taaagcttga atttggtaaa    4260
aaaaaaaaaa aaagagggag gattggtagt gataaagtga gtggacttat ggatgagaca    4320
tgatcagcca tgcattgaaa aaatgtaaaa gttggatgat cttcacatga gagtccttta    4380
ttctgtctac ttttgcatat gtttgaatat ttcccataac aaaaagttga aaatagagtg    4440
atcacatgag ttaatctcct aatttacaaa aaagaaaact ggaacagaa ggagaacaaa     4500 acttgttcaa ggtctcaaag ccagacagca aactagctcc caagtccaac cttcttgctc    4560
tggtcctaag caaacaaaaa atattaatat gagctactgc attaaggaaa gtctgctttt    4620
ccaaagggca gaccaatagt tcaaggaaga gtttaaataa taaatatttg tgatcttact    4680
ttcatgcttt tctatttttcc actgaacaca tatgcattat cttctatatg tctttatgt    4740 ataatcattt gcttcctgtt ccttgtggtt ttaaagttgt tttgtatgtt taaatttgat    4800
tttactcaaa tttcagaacc caaattagcg caagaatcag acaaagcata actttctata    4860
aatataaaaa caattaaaaa aaaacatac agcaaaaacg agttgttgtt tccccctcc     4920 tcttccagtg cttaactaat cttccgaatc caggcacaga aagcaaaggc tttctgctag    4980
tgggaggagc ttgcttctcc attctggtgt gatccaggaa cagctgtctt ccagctctga    5040
aagaggtgaa aatgtgttaa gcgatgcaaa aattgtcttg aagttcgcgt gtgtatgtct    5100
gtgtgcatgt gcgtgtggtg ggtggggga gagaaaaggg ggtgtcaatt ctgagggcaa     5160
cgagaatcag aagtcagaaa ggtgagtggt gtgtagcatc tcccttcag aaggggctga     5220 agaagaaatt ggatatgatg gtccggtagg ctaaatcacg ctggatttgt ctcccagata    5280
```

```
aagggaggtc tgcaaagtaa gtcccatttc tagagcgaaa agccttagga ccgcttgttt    5340
tagacggctg gggaatattt attccttgtt ccactgatgg gaaaatcagc gtctggcagg    5400
cgctgattgg tggaaaggaa aatggtgata gtggcgtgga aagaggattt gctgagcctt    5460
ctcctgcctc ctcaacctgt gactcttcct tagtagtctc cctttcaccc tcaggaccct    5520
ttccggctct tcctagatta agagcaaacg aaaaccttga agatatttga actaaagcga    5580
cccctaacgt tgtaacctgt gaccgtgatt aaatttcagc gatgcgaggg caaagcgctc    5640
tcggcggtgc ggtgtgagcc acctcccggc gctgcctgtc tcctcagca gctccccaag    5700 ggataggctc tgcccttggt ggtcgaccct caggccctcg gctctcccag gcgactctg    5760 acgaggggta gggggtggtc cccgggagga cccagaggaa aggcggggac aagaagggag    5820
gggaagggaa aagaggaaga ggcatcatcc ctagcccaac cgctcccgat ctccacaaga    5880
gtgctcgtga ccctaaactt aacgtgaggc gcaaaagcgc ccccactttc ccgccttgcg    5940
cggccaggca ggcggctgga gttgatggct caccccgcgc ccctgcccc atccccatcc     6000 gagataggga cgaggagcac gctgcaggga aagcagcgag cgccgggaga ggggcgggca    6060
gaagcgctga caaatcagcg gtgggggcgg agagccgagg agaaggagaa ggaggaggac    6120
taggaggagg aggacggcga cgaccagaag gggcccaaga gaggggggcga gcgaccgagc    6180 gccgcgacgc ggaagtgagg tgcgtgcggg ctgcagcgca gacccggcc cggcccctcc     6240 gagagcgtcc tgggcgctcc ctcacgcctt gccttcaagc cttctgcctt tccaccctcg    6300
tgagcggaga actgggagtg gccattcgac gacaggttag cgggtttgcc tcccactccc    6360
ccagcctcgc gtcgccggct cacagcggcc tcctctgggg acagtccccc ccgggtgccg    6420
cctccgccct tcctgtgcgc tccttttcct tcttctttcc tattaaatat tatttgggaa    6480
ttgtttaaat ttttttttta aaaaagaga gaggcgggga ggagtcggag ttgtggagaa    6540
gcagagggac tcaggtaagt acctgtggat ctaaacgggc gtctttggaa atcctggaga    6600
acgccggatg ggagacgaat ggtcgtgggc accgggaggg ggtggtgctg ccatgaggac    6660
ccgctgggcc aggtctctgg gaggtgagta cttgtcccct tggggagcct aaggaaagag    6720
acttgacctg gctttcgtcc tgcttctgat attcccttct ccacaagggc tgagagatta    6780
ggctgcttct ccgggatccg ctttttccccg ggaaacgcga ggatgctcca tggagcgtga    6840
gcatccaact tttctctcac ataaaatctg tctgcccgct ctcttggttt ttctctgtaa    6900
agtaagcaag ctgcgtttgg caaataatga aatggaagtg caaggaggcc aagtcaacag    6960
gtggtaacgg gttaacaagt gctggcgcgg ggtccgctag ggtggaggct gagaacgccc    7020
cctcgggtgg ctggcgcggg gttggagacg gcccgcgagt gtgagcggcg cctgctcagg    7080
gtagatagct gagggcgggg gtggatgttg gatggattag aaccatcaca cttgggcctg    7140
ctgtttgcct gagtttgaac cacaccccga gtgagcagtt agttctgttg cctacgcctt    7200
tccaccatca acctgttagc cttcttctgg gattcatgtt aaggataccc ctgaccctaa    7260
gcctccagct tccatgcttc taactcatac tgttacccctt tagaccccgg gaatttaaaa    7320
aaggggttaa tcttttcatg caactccact tctgaaatgc agtaataaca actcagagga    7380
ttcatcctaa tccgtggtta ggtggctaga cttttactag ccaagatgga tgggagatgc    7440
taaattttta atgccagagc taaaaatgtc tgctttgtcc aatggttaaa tgagtgtaca    7500
cttaaaagag tctcacactt tggagggttt tcatgattt ttcagtgttt tttgtttatt     7560
tttccccgaa agttctcatt caaagtgtat tttatgtttt ccagtgtggt gtaaaggaat    7620
```

```
tcattagcca tggatgtatt catgaaagga ctttcaaagg ccaaggaggg agttgtggct    7680
gctgctgaga aaaccaaaca gggtgtggca gaagcagcag gaaagacaaa agagggtgtt    7740
ctctatgtag gtaggtaaac cccaaatgtc agtttggtgc ttgttcatga gtgatgggtt    7800
aggataatca atactctaaa tgctggtagt tctctctctt gattcatttt tgcatcattg    7860
cttgtcaaaa aggtggactg agtcagaggt atgtgtaggt aggtgaatgt gaacgtgtgt    7920
atttgagcta atagtaaaaa atgcgactgt ttgcttttcc agattttttaa ttttgcccta    7980 atatttatga cttttttaaaa atgaatgttt ctgtacctac ataattctat ttcagagaac    8040
agttttaaaa actcatagtc ttttaaaaaa taatcaagaa tattcttaag aatcaaaatc    8100
attgatggat ctgtgatttc ttttaccatc atgaaaaatg tttgtcaatt ttaatccatt    8160 ctgatttta aaatatgact ttgatatgcc cctgtgatgt gtataaagag acctatttgt    8220
ggccctaaaa tggaaagaac agattagtct ttgatagagt tacttcatgt gatcatttgg    8280
tctctgtgaa cactgaggac agagaaaagt gcttgagggc tgctactaat ctctcagaaa    8340
catttgtata gttcatccat caaatgacac acatactaaa agaataaaga aattgatgct    8400
tattacctac ttgttcctaa agttccacct tggggtatac acccaaactc tgactctctt    8460
ttctgtaact tgaactgtat tcaattgagt gttattttac aaaccacttt gaattccttg    8520
gaaaagaata gacacacact ctcatccaca ggcatagaca cacacactca acacagacac    8580
attgcccatt cttcctctct tctttctcct ctgagctttt tcacattctc tggtggcaac    8640
tatagcagta agagtcacag gatgaacagt caggtggagg atgaccacat tgagttgcct    8700
agctgaaaca tgtgctccgt ctatgtctgc aaagtgaaag aaagctacac tatctcttca    8760
acatagatca gtggggggaaa ttttatactt gggatgattt atatgaatgc atctcatcaa    8820
agttcacaac acatttttttt ttcagttttt tattttcagt ttttagagtc agggccttgc    8880
tctgtcgccc aggctggact gcagtgatgc tatcatagct cactgcatcc ttgaattcct    8940
gggctcaagt catgcccccca cctcagcctc ctgagtagcc aggattatag gcatgtgcca    9000
ctgcctcatt atttagactt ttcttatgtt gacttaatct tcccacaaat cttcaattaa    9060 attactttt ttctaccttta aaacatattt tcagaaagtc attgaaatag ggtgttacaa    9120
gaggaaaaaa ttgatgagtt aatttttaaat attttatgaa gtgtgaatta taccttttta    9180
gatgaaattt ggaatactga atcagtgaca tgcagtttat caatatcttt ccgtttgtcc    9240
tcagatttcc aagttctgca agcacaagtt tctttgactt agttacccttt taactgttca    9300 ttgaaatcat tttcaatgtc tctcatggca tttaacacat agcacattct ataaatttt    9360 tattggttac attctgagtt ctaattgaga gttgaactta cacacagaat ttaagataaa    9420
aaatgaccat gtgaagacac aatagtatag tccagggatt ggcaaaattt tgggtaagga    9480
atcagatagc acgtatttta agccatgaga tctatgtctt ggccaggtgc cgtggctcag    9540
gtctttaatc ccagcacttt gagagcccga ggctggtgga tcacttgagc ccaggggttt    9600
gagaccagcc tgggccacat ggtgaaaccc tgtgtctaca aacaacgcaa aaattagccg    9660
ggtatggtag catgcatgtg tattgccagc tacccaggag gctgaggtag gaggatggct    9720
tgagccatac agctcactgc agaggttgca gtgagctgag atcgagccac tgcactccag    9780
cctgggtggc agagtgatac cctgtctaaa aaaagaaaa aaaatctat gtctcaattc    9840 tgctgttgaa gtgtgaaggt agtcataaac aataactagt gtggctgtgt cccaataaaa    9900
cttcatttat caaacaggt ggtgggctgg aattgtcttg tatgttgtag cttgctgact    9960
actgatagag tggaaagaac atgcactaat cacacaaacc aaagttttag ttgagactac    10020
```

```
atcacttatc acctttaggg tcttggggaa gcgtacttaa catctctgag catcacttcc   10080
ctgattagta aaaatatga tttagaaaac tgcaactacc ttgcagtttt tgtgggaatg   10140
tcataataag acaggacata tgaataattg agcacacttt tatatatagg aaccatggtt   10200
attattatca aataaactct ccaacggaat aattactttg ccaacacgtt ttccatttat   10260
tcttttatcc ttcattacat aactagtttg aaagattgga ggcgaccaaa gaccatttta   10320
taatttcact tatggctgaa gatgtttggt agaagcctca taagaaaagt aatctcattc   10380
ctttataaga atatactttt aacaactact ttttaactca ttgaagaact accttaatga   10440
tcagtgttat ttttatgggt tttgttccct ccattttgt tatctgcgta caccaatttt   10500
caatcaacat acttcaattt aatagacaaa aatttcttca aatgactcag aaattaatta   10560
gatctaaatc caaaagcaga aagatttaat tatctttata taatgctcag taatataaat   10620
gcaataaata caagaaaatg atgatctttg agtgtcttcc aatgccactc tgctcaataa   10680
gcagcagtgg ccatcagtga aattgatagc aaattctcaa gtcaaaatgt gcttcacctc   10740
actaagctga caaagtcaac ataacatgca caacagggat aactgagttc tcaaaactct   10800
caggtattac ttctgacctt cttctccact ctgtgctctt ttgaggttgg aagacaaga   10860 tagggtgtgt gtgggacacc tccgctcagg gaagccatca gctctggtgt ccctacagca   10920
tttataccct gctagtcaca taaccacttg gcacctattt tgtaggtgta cgttatcaat   10980
tacagattac tcataaatta aaggctaacc atcaattaca gattattagt aaataattat   11040
gacctcaaag aacaactgat tggtttgata catggtaacc ttatgaggac tctcatttat   11100
ctcgtttttt taagttatat acctatctct ttggggttgc actacaaaaa tataaaatat   11160
gttgcataag atatttataa aaaataatta attataagtt ctaatggtgt ggtttagtgg   11220
cattcttttt tttttctttt tttctgagat agggtctcaa tctgtcattt cactccaggc   11280
tgaagtgcag tggtgtgatc tcggctcact gcaacctccg cctcctgggt tcaagttatt   11340
ctcctgactc agcctcctga gtagctgaaa ttacaggcat gcaccaccat gcccggctaa   11400
tttttgtatt tttagtagag atggggtttc accatgttag ccaggatggt ctcgaactcc   11460
tgatctcatc atccccgacc tcggcctccc aaaatgctgg gattacaggc gtgagccatt   11520
gcacccggcc tagtggcatt cttttttaaa aataaattta attgtgtata tttagggtat   11580
gcaacatgat gctatcagat acattagaca ctaaaaaatt actatattga agcaaattaa   11640
tatattcata atctctcata gttaccttt ttgttgtttt tgtggcaagg gcagctaaaa   11700
tccacttatt tatcatgaat ctcaaatata gtacaatttt atcacctaca gtcctctac   11760 attagatctg tacacttttt catcttacac atctgctact tgcttggatc ctatggccta   11820
tatgtcccta ttttctacct acttttccac ccctattaac cctgtttttt acgtagtctc   11880
tgtatatttg aattttgttt caagcttcca catatatgtg agataatgta atattttct   11940 ttctgtgttt ggcttatttc acttagcata attttgtctg ggttcatcca tgttgtaaat   12000
ggtaggatct tgtttttta gggctgactg atattccatt gtatctatgt accacaatct   12060
ttttatctac ctatctatca gtagacactt tagttgtggc tattatgttt ttctttttt   12120 cttttttgga gacagggtct tgctgtcacc caggctgcaa tggagtggtg ttatcatagc   12180
tcactgtaac ctcaaacttc tgggctcaag agatcctcct gccttggcct cccaagtagc   12240
tgagactaca ggcatacatt accatgcctg gctaattttt aatatttttt gtagatatag   12300
catctcactc tgttgcccag actggtctca aactcctaat tcaaatttag aatagagtat   12360
```

```
gacaattctg taaaatataa aaaacatgtc cactccgtat aggaagttat acaatgagaa    12420
gaagacaaac actatttaca ttactcttga taagttttt acaaagaaat aaaacacttt    12480
aatttctaat gttttaaatt ctggtttgct aaataaataa atattagttt tagtgttttt    12540
aaaattcctt atatagttat aagtgatctt cctgcctcag cctcccaaag cactgggatt    12600
ccaagcaaga gccactgtgt tggggcccctt ggaaacagat atgctgaaat cttttcttgt    12660
ggatctacac ccagaagagg gattgctggg tcatatgcta ctctatttt aattttctt    12720 ttattttag tgaatatgta ataattgtat ataattgtgg gatccagaat tatatttcca    12780
tacatgtata caatgtgtga taatcaaatt agggtaatta acatatccat tacctgaaac    12840
atttatcatt cctttgtggt gggaacagta aaaattaaaa attctctctt ctagattttt    12900
gaacatatgc aataaactat tgttaagtat atcaccctac agtactacag aatgctagaa    12960
ctcattcctc atatttggct ccaatttcat attctttaac caacctctcc atatcctccc    13020
ctccctctta ccgttgtcag cctctaataa tcataattct actctctact tctatctcat    13080
tgtctttgat ttagaatatg tttcataatt taaccaaagg tcaaattctt aggtactgct    13140
aaggcaaaga acaaagatcg cattccagct gttagacatt tcttactact agtcattttt    13200
aagacaacat ggggtgcagg tggtgaggat gagagataga gattgaaaca tattctctta    13260
aatatcagct gttctcactc tgcatagttc cagcacaaac aaattccagg tactatggtt    13320
agttaaataa caccagccac taacaacaca attcaaattt ctgttaccac agtataccga    13380
aagtcattgc ataaagtaca aactttgctg ctaactcttc agccttcaaa tcattacata    13440
aataacagaa acccattata atcagtgaca aaaccacagc acttctttca aagctttttg    13500
gagattggtt gcttcacatc tgttatgcag ttcatacaga cagcaatgcc cggacttgtg    13560
tggccacatt gtctcccagt ggtgagccca tgtgatgttt cacgaaaatg cgcaatcaaa    13620
agaggaaact ggccagcaaa gatgaaagag tagcaaacaa aggaagtgaa acattctgga    13680
agtaaaattt gaatcaaaca taagttgatg tatacaggaa gtagctaccc tgaggatgtt    13740
gtcactgctg caattcagga gactctaaat atgcagtcag aggaacgtag tgaggtgaag    13800
gtatccgtat aatggggaaa gaggttgtga taaagagtga aggtgtccca gaggaagtgt    13860
tgctgaaaaa tacaccttat gttaaataca ctgtcagtat atcatgacat taaagtgcaa    13920
atgataacat tttgtaaact gatccaaact taaaaggag tatgataatt ctgtaaaaca    13980
taaaaatcat gccgattcca taaattatac agtgtgaatt acactgaaaa atccaacatt    14040
agagaggata tgaatacaat ttttacaag cataattta ataatacaca taataattat    14100
ttgtattcaa gtttagtaat gttcaaggtt tggaagaaat tctgatcctg tgtagagacc    14160
ctagtttgaa tgtgcttata gcctattatt acatgtgtaa tgttacataa attacttaac    14220
tcggattttt aatttcatca gctatttaaa atgggcataa tataactata ttaaatggct    14280
gttatgaaga ttaaataaga tgatatgtaa aatgtgtttt ttgtttgttt gtttgtttgt    14340
ctgtttgttt ttttgagaca gagtcttgct ctgttaccca ggctggagtg cagtggcaca    14400
atcttggctc actgcaagtt ctgcctcccg agttcatgcc attctcctgc ctcagcccct    14460
cccaagtagc tgggactaca ggcacccgcc accacgcctg gctaattttt tgtattttg    14520 gtagagatgg ggtttcacca tattagccag gatggtctcg atctcctgac ctcgtgatct    14580
gcccacctcg gcctcccaaa ttgctgggat tacaggcatg agccactgcg cccagcctaa    14640 aatgttttt ttacataatg ggtgttcagc acatgttaaa gccttctctc catccttctt    14700
cccttttgtt tcatgggttg actgatctgt ctctagtgct gtacttttaa agcttctaca    14760
```

```
gttctgaatt caaaattatc ttctcactgg gccccggtgt tatctcattc tttttctcc    14820 tctgtaagtt gacatgtgat gtgggaacaa aggggataaa gtcattattt tgtgctaaaa    14880
tcgtaattgg agaggacctc ctgttagctg ggctttcttc tatttattgt ggtggttact    14940
ggagttcctt cttctagttt taggatatat atatatattt ttttctttcc ctgaagatat    15000
aataatatat atacttctga agattgagat ttttaaatta gttgtattga aaactagcta    15060
atcagcaatt taaggctagc ttgagactta tgtcttgaat ttgttttgt aggctccaaa     15120 accaaggagg gagtggtgca tggtgtggca acaggtaagc tccattgtgc ttatatccaa    15180
agatgatatt taaagtatct agtgattagt gtggcccagt attcaagatt cctatgaaat    15240
tgtaaaacaa tcactgagca ttctaagaac atatcagtct tattgaaact gaattcttta    15300 taaagtatt ttaaataggt aaatattgat tataaataaa aaatatactt gccaagaata     15360
atgagggctt tgaattgata agctatgttt aatttatagt aagtgggcat ttaaatattc    15420
tgaccaaaaa tgtattgaca aactgctgac aaaaataaaa tgtgaatatt gccataattt    15480 taaaaaagt aaaatttctg ttgattacag taaaatattt tgaccttaaa ttatgttgat     15540
tacaatattc ctttgataat tcagagtgca tttcaggaaa cacccttgga cagtcagtaa    15600
aatgtttatt gtatttatct ttgtattgtt atggtatagc tatttgtaca aatattattg    15660
tgcaattatt acatttctga ttatattatt catttggcct aaatttaccg agaatttgaa    15720
caagtcaatt aggtttacaa tcaagaaata tcaaaaatga tgaaaaggat gataatcatc    15780
atcagatgtt gaggaagatg aggatgagag tgccagaaat agagaaatca aaggagaacc    15840
aaaatttaac aaattaaaag cccacagact tgctgtaatt aagttttctg ttgtaagtac    15900
tccacgtttc ctggcagatg tggtgaagca aagatataa tcagaaatat aatttatata     15960
atcggaaagc attaaacaca atagtgccta tacaataaaa atgttcctat cactgacttc    16020
taaaatggaa atgaggacaa tgatatggga atcttaatac agtgttgtgg atatgactaa    16080
aaacacagga gtcagatctt cttggttcaa cttcctgctt actccttacc agctgtgtgt    16140 ttttgcaag attcttcacc tctgtgtgat ttagcttcct catctataaa ataattcagt     16200
gaattaatgt acacaaaaca tctggaaaac aaaagcaaac aatatgtatt ttataagtgt    16260
tacttatagt tttatagtga actttcttgt gcaacatttt tacaactagt ggagaaaaat    16320 atttcttta atgaatactt tgatttaaa atcagagtg taaaaataaa acagactcct        16380
ttgaaactag ttctgttaga agttaattgt gcacctttaa tgggctctgt tgcaatccaa    16440
cagagaagta gttaagtaag tggactatga tgccttctag ggacctccta taaatatgat    16500
attgtgaagc atgattataa taagaactag ataacagaca ggtggagact ccactatctg    16560
aagacggtca acctagatga atggtgttcc atttagtagt tgaggaagaa cccatgaggt    16620
ttagaaagca gacaagcatg tggcaagttc tggagtcagt ggtaaaaatt aaagaaccca    16680
actattactg tcacctgatg atctaatgga gactgtggag atgggctgca ttttttagt     16740 cttttccaga atgccaaaat gtaaacacat atctgtgtgt gtgtgtgtgt gtgtgtgtgt    16800
gtgcgtgtgt gtgagagaga gagagagact gaagtttgta caattagaca ttttataaaa    16860
tgttttctga aggacagtgg ctcacaatct taagtttcta acattgtaca atgttgggag    16920
actttgtata ctttattttc tctttagcgt attaaggaat ctgagatgtc ctacagtaaa    16980
gaaatttgca ttcatagtt aaaatcaggg ttattcaaac ttttttgatta ttgaaaactt    17040 tcttcattag ttactagggt tgaatgaaac tagtgttcca cagaaaacta tgggaaatgt    17100
```

```
tgctaggcag taaggacatg gtgatttcag catgtgcaat atttacagcg attgcaccca    17160
tggaccaccc tggcagtagt gaaataacca aaaatgctgt cataactagt atggctatga    17220
gaaacacatt gggataaatc ggctgctatc ataatcattc ctctcccaca tcagataaat    17280
gaattaactt tttgaatagg gttatttaat ataaagtgct taagtctaat tatgagaaga    17340
aataagataa ttacacttca atggttaaag agagggagaa taatttgcat attatgcctg    17400
atgtaaaatg tttattatgg gtacatatta agtgctaact aattgttaat tgttcttgct    17460
acaagtctta atgcagggaa acaagaaatt attacatagt acctaatatt atcttctaat    17520
attaaagaaa caatttcccc taaattcatc ccattagctt ttttttttc ggtggggcag     17580 gggagaaata cagacttcag taaacttggg ctgggaactt tctacctaca aagttcaaat    17640
aaaataaatt atcctagtta gataatatca atgaaaaatc caccaactta aatcctggct    17700
gtttgatctc aggaaattat ttcagttatc aacttaatgc atcatattat agaaatatat    17760
gaaaatgtgt ttaattaaac ttactgaatg atatgttttt tcaggtactt taaaaataaa    17820
ctatgatata aagttaccta tttttcatgc aagtatagta taaagaaatt tctaacactg    17880
gagattttct gaaggttttg attcttataa atttattaca tcataatgaa caaaactaat    17940
tttcaacata ttatgattta aatttcctta gtaaattgtt tcaaatttat tttctttaaa    18000
tccatattta catatgtata tttaaatata catatttact tgtataacaa ttcaaaacca    18060
tatattaatt ttataatttt gtttaatgtc aaaggttaga tttggctata tctattctaa    18120
aagttggtat cacatttcct ttttggaatt ttattttta agtagctaaa gtcaaatata    18180
aacctattat ttatattaat gcagacatta gaggtagaca ctaaattcat tttagtatat    18240
tctaaattat ttattatcta ctatgaaata atataaagaa aaataaagca gaatccctga    18300
tttcaaagaa ctcaattgcc gaaaaacagt taccatttat tagacccaaa atgtactaat    18360
atgagtgtgt ctcttttcct tttgtttttgt cacccgtcat ttggaatgtc agtgagtaga    18420
gagatagtgt gaaaggccct caaggggaaa aatagaggtt aaaggtcagc agagacccta    18480
ctagagaaat cagttctaca gaaatgtttt taaatgtgtc gattattgct acatgtacac    18540
tctgtcattt tgtaatgtag ccattttatt tatgattata ataataaaac aacaaaatta    18600
taataatgtg tagagtacat tttactgtgc agtgtattgc attaaaacta gattaaaatt    18660
tatacatata taaaaggcta tctagatatt ataaaattta tggctggatc tgtaaaaaat    18720
tcaaaaccta tttttaatct cgctttgaga ttttataaca agaaaatgtt cgtttcaagc    18780
aaaattttca attcacgtcc ttgaaaagga aaaaaatgac aacttgaaac acataattga    18840 ctattttaa aggatcaaca tttcagaaat gttttaaaac ataagatttt cagtacagct     18900
tttcgctggc atttaaatcg aactttgaat tgtaaatagc tcttgctctt aaggagacat    18960
cagccatatc cttagaagtg gcacggagtt gttaggtagt tgtacaaaat tctagcctaa    19020
aagacaaata gggagcaaca ctactgtgga ccgtttctgg tcttgggctg tgtggctatg    19080
tcaggcttgc ccacattgcc tgtactaagg agaaagcctc ttgtccttac agacccccctt   19140 agcttacata gtctatttga aaacaaattg ctttgtccac accatttaaa tattggcttc    19200
aggccaggcg cggtggctca cgcctgttat cccagcactt tgggaggctg aggcgggcag    19260
atcacgaggt caggagatcg agaccatcct ggctaacacg gtgaaaccct gtctctacta    19320
aaaatataaa aaaattagcc gggtgtggtg gcgcgcacct gtagtcccag ctgctgggga    19380
ggctgaggca ggagaatggc ctgaacccgg gagtcggagt ttgcagtgag ccgacatcgt    19440
gccactgcac tccagcctgg gtgacagagc aagactccgt ctcaaaataa ataaataaat    19500
```

```
aaataaataa gtaaatattg gcttcttcaa ctggtgagat gaaacctata caatagtcat   19560
gtgaatagca ctaaacagct gacatggtgt aactcctctc agactgaggc ttatctgggg   19620
agtacaaagc atgtcaagaa aatgtgcctt catttcctta gatgagtgtc cccatcctcc   19680
actctcctcc actgttctcc tctctgcttc tatgatatca acttttcttt ttctttagat   19740
tccacatgag tgagatcatg tggttgtttg cctttctgtt tctggcttat ttaactgaac   19800
aagaaagttt ttgacatgaa attaaacttc tgcttgtaaa ctcaattcaa actatttaca   19860
ctgtcttctc aaaaatgtta acttatttta ataaatctac tgaatgaccg tatctcattt   19920
tgttttatga aaagaaattg taagggtgct caatagcctc ttcattttca tactgtctag   19980
ctcctgtgct cctattaaaa ttactgcaaa tttagctttt taagaaccct tgtttcact    20040
acctgaagtt ctataaaaag atccaagttc cttcacaacc gtttcttatg ctgttattcg   20100
tacatatgtg ataataccac gtctgaacac gtagataata agtagggggct gggtgcggtg   20160
gatcatgcct ataatcctag cactttggga ggctaaggcg ggtggatcac ctgaggttag   20220
gagttcgaga ccggcctggc caacatgatg aaaccctgtt tctactaaaa atacaaataa   20280
taataataat aataattagc caggtgtggt tgtgggcacc tgtaatccca gctactcggg   20340
agactgaggc aggagaatag cttgaactca ggaggcggag gttgctgtga gctgagattg   20400
tgccattgca ttccagcctg aacaacaaga atgaaactcc atctcaaata aataaataaa   20460
tagaagtatg tattgtgttg cttagaaggt gtggtggaaa ttaacttgct gagtgagatc   20520
aaaggattgg cactgaattg aaataaagaa atattcatgc tgagtctggt tcaaatataa   20580
ctgcacctgt aagaattgct ttctgtaaac tttccatagt ataaaccaaa tccaaatcac   20640
tcatggcttt acattcctga tcgttaaact tgaagcactt tttaatactg catgacttta   20700
gccaaaatat cttagccaag attcaatgtt tggttgaacc acactcactt ggacatcttg   20760
gtggcttttg ttcttctga ccactcagtt atctatggca tgtgtagata caggtgtatg    20820
gaagccgatg gctagtggaa gtggaatgat tttaagtcac tgttattcta ccacccttta   20880
atctgttgtt gctctttatt tgtaccagtg gctgagaaga ccaaagagca agtgacaaat   20940
gttggaggag cagtggtgac gggtgtgaca gcagtagccc agaagacagt ggagggagca   21000
gggagcattg cagcagccac tggctttgtc aaaaaggacc agttgggcaa ggtatggctg   21060
tgtacgtttt gtgttacatt tataagctgg tgagattacg gttcattttc atgtgaggcc   21120
tggaggcagg agcaagatac ttactgtggg gaacggctac ctgaccctcc ccttgtgaaa   21180
aagtgctacc tttatattgg tcttgcttgt ttcaggcatt aacccagata atgccatgc    21240
aaatttata attattatga ttgtttcaat ttctggaaga aagttaatga aacaaaaaat    21300
gtagtaaaat gccaaaggaa cagtgacatt tcagaaagaa tgagggcttt catgttaatt   21360
gtaagtcttg gaatttctct tccttggagt aacaaatccc tttgtgccta atttcctaat   21420
ttccaaaata aagttctttt acttatttct ttatagtgac atcatctctt attaaatggc   21480
atatctgcat attacataac agttcattgc caaatacata tttgtgggaa atgagagact   21540
taaaatacat accaaccaga gatatagttt tgaggtagat tttaaaattc tgagaagaat   21600
tttgactgaa ttttttttgac aaacatggga cacgaataag attataccaa agatattata  21660
actttcattt taaatatgga actaatacag tatgaggtgt caacaacgtt gaagtttcac   21720
aaacatcacc actacaacag caaaataatt tttgcttttt ccctgccaca atgacctcct   21780
tgctatttct tgaataaatc aagcataccc ttgccctgac acgttcttgg ggaggcctgc   21840
```

```
cctaatctat ataaaattgg agccattctt ctcacctctg gtattcccag tctccctact   21900 tttttttcctt ctttctttct ttttcttttt ctttctttct ttccttcttt ctctctttcc   21960
tttctttctt ttcccttcct tccttccttt ctcccttcct tccttcctcc ctctctccct   22020 ccctccttc ctcccttct ttctttctct ttttcttttc ttgcttcctt ccttccttct   22080 ttcctttct ttctttttcc tttctttgcc aaagtgttat tcacctttaa atataataca   22140
taatgtgctt acttaatgt atgattttta tttattttct cccttctaga atgtaggcac   22200
catgagagtg aaatatattt attttgttca ttgatatttc acaagtgtct gggagagttt   22260
ccaacttaca gtagacaatt aacaaacatt tattaaatta aggagggaag gaagtgagta   22320
agcacaacaa ctttcatttc tgggtctttt ataatcatat gcttagtata agaacagtgc   22380
tattcagcta tccaaaagtt acaatcaaaa tgattttgga tgaatatctt gaaaattgtg   22440
agaaagaagt tttatttgct ggcaaactat tctgggttgt ttccacttca tgtaatccta   22500
agtagcagcc ttaccttgat agcccattaa aactctgata ataaaaggc agaacaaaaa   22560 tatctgtgat atatttagat ttactacatg tacttacatg tctagtgtct ggtgcaatgg   22620
atgctaatga tggcaaatcc ttactgggct tctagtgaag ttcttcagct aatgtttgaa   22680
tgcatggttg gtcatggtgg tacccctttg tacaaaatat gcttttcaaa taatcttatt   22740
agggataata attatattaa ttcctggttt ccatctaaaa ttttaattct atttatagct   22800
tcgtaagatt tcacaagtta agagggacct cagattaaat tagtacacag gcaattaatc   22860
agttttgtgt ctccgaccct tttcacgggc taatagaagc tatagaccct cttagcttca   22920
gaaaaatgcg cactcacata cgcacatcaa agagcttaat gggaagtcca ttgacagacc   22980
ctctgttcag atcaatcttc tgattgtaga gatgaggaaa cagaaatcta cagaggaagt   23040
gggtagtcca agattgcaca gtcatttgga atagactgga caccagtagt acttttccag   23100
ccactatatc acttccccaa gcacttcctc aaaacttacc ttcctttggg tctttataca   23160
ttcagttatg gacaactaga tttaactaga ggattttatt gcttcagaat attaagcaac   23220
agggaaacat gtaccgtctt ttattcacct gcatttaagg catacaatat aaattgcaaa   23280
tggagcatga aagtgcttaa tcttttacaa aactgggttt gctttccacc catctaaaaa   23340
tacttctatt tattttaata tttaaagcag aaatctaagt gatgtgacaa aattaatcat   23400
ttggagatat ttcccttata ggtagtatag tttcttactg attcctaata tgaaaatgaa   23460
gccatagaac ctagaaattg cagcatagtt gtggaaataa acattggact gagagtgaaa   23520
atggctagtc ttcctctctg ctcatacacc acctgactgg ataacctttc gcagatctcc   23580
taaaagtctt tctcataaaa tgaggaagct ctactagaaa attgttgaag tctaatttag   23640
caataaagtt ctgagtttct ataataattc aaagaatact ctaataaatg tctgcaattg   23700
tggtcacatc tatgggatgc taaaaaatct ggatggtttc aatgaaagta tttaatttgt   23760
tcattatgaa ctttgaaata atttatttca tttttaaac tttgatcaaa atgaccctgg   23820
taaatagaaa taagcaaact ctttttgctt gaaatgctta ttaatgactg cattgagaca   23880
ctcattcatc attcaagaaa gaatgtttgc tcacactgtg ccagaaactt ggaggaagag   23940
ggatgtgaca agtaggggta ctggatgtct agcttgtaga agtggattaa tggctctgct   24000
tttaagatca ggaacactga aagggagtaa tggcaccggt tttcacctttt catgcccttt   24060 gagggtatct ggtccatcac cctctagttg atgagggagg gaaagttccc tctcccttca   24120
caaataggtg gaaattaaat gacataattc tgaacaacca ataaatcgag agtaaatcaa   24180
agcagatacc tgttttgtta atttgatcat atgaatgtag ctgcccttag taataatttc   24240
```

```
taagtataag actagttaaa ggacaaatga gttatcttga attataagat tttgttttac    24300
agaacaatat taactcttgt gtttagtaca ttagaataat agatcttttg atccatattt    24360
ttactcatgt gcacataaga agttatcagt catacaattc atttcttgaa gttcatacct    24420
ttcattggca gagtagaaac aggttaaaag tgcacaggca gaaattttaa gtgcaaagca    24480
acagtgatgt tatatagaga aaatttatat ttcctacttc tattgaagaa gaaagatctg    24540
cttgttctaa gaatattgta caaagaaagt gacttgaatc agcgttattc tgtaatgcta    24600
ctatgcgtgc agtgtggagt agccactaga acacttggtc tatcccagct cctcaacagt    24660
gtcttgcttg tggctggtgc tcaaataaat ccttgctgaa ctaatgagca tctctttcat    24720
gccacatgga atgctctaaa agagttggat cctgaagttt ttatattttt gtaattttct    24780
ggagttttag agagcaaaag tcctgaataa actgtgaagc cactgcctga caaataatac    24840
agcagtcagc ttcgttatca tatcccattg agacacgact tatctacatg atgattaata    24900
gttttcacgc aagaaataag cttgaaatgt ctgttgcctt ggatacttaa aacatccagg    24960
ttcagcgatg ttatttattg ttgttcaaaa tcagaatgaa gttcctaagc aatgccattt    25020
tggaaaaatt acatcaatat attatgaaca acttttttta aatcttgatt tcaaatggat    25080
tgacacgtgt atattctgta ataatcctga cttaattcat aaaaggatag ctagccagtt    25140
gtgtgctaga tgaataaaaa aaaagcaggt tttaaaatgt caggtttgac attgtgaata    25200
taatatctaa gtatcctttt actcatttcc tttgacttac tatggctgtc atgttgggct    25260
tcatgaaaat ttattttaa acacttgagt gttatggacc ctctgattaa atgattaatc    25320
agatgatgta tgttgccatc agctgaatca tttaatgttg atttcacaaa caagcacagg    25380
tcacaggcaa catttcagat ttcttttgaag aagcacacac aggtcacagg cataatctta    25440
aaataatttt ataacaaggt agtaataaga gatgtcagga ctggagaaat atttttaattt   25500 atagtaagct ttccccttaa gtgtctaata attgttaata taatacattg cctcaaataa    25560
ttaaaagttt ggttcttgtc cttgtgcttg acttcagaag ataaccagat gactattagg    25620
tatatttaga cctaaattaa aagctttgag acacaatgaa ttgcctgatt tgtatttgtg    25680
tttcgagtgg catatactat tactggcact ataatcttag attaaagcat actgtgatta    25740
ttaaagaaaa atttaagatt gatttgtttc taaaggtatg taacagtgac attttgcaat    25800
gtggtatgta aaagttggta tttctcactc atatgagagc ccactaatgg tacataaact    25860
gtccccactt agaaacacaa ttattatggc ctttctttgt atctgacaaa atttcactgg    25920
gttcaagatg gatgaatagt gaattctaat gacccttaat cctgtaaggt tctaggtggg    25980
aaagtactct gtaattatgt ataaaattat aaggaaaata ggcttactgc tatgttttca    26040
ttaaaaatca ttaactgagt acttaatatg tgccagacac tcagctgggc accatgaaga    26100
atacaaaact gagtaacata tgggtggctc ctgccttcaa gaaatgggca gttcaggccg    26160
ggagactgac atatttaccc tgggaaaaag ggagcagctg tggtctctga gaacaatatg    26220
gtttgttaca agtatatatc catcatggaa aaaagagat ttatcttaga aatgagagag     26280
gctgatgctc tcaataaaata tcatacatta aattgtgttt ttgtcagtag actgaaatta    26340
cctcacatac acgcacagat agtagccatg atattttagc tgcttagata tagagacaaa    26400
tacttccacc caaatcttag gatcagtggt taatagtctg taagcattac aatcccacaa    26460
catatgcatg actatacatc caatttaat attcaaagaa ctgattgcga tgatagtttt     26520
gtttgtcaaa gaaatgtatt ataggatgag tgggatagaa ctgcatcacg ttacaccaac    26580
```

```
aaataggttt aaatcatatt tgtgcacttc ccttgttcct tcataaatgt ttaacatagc      26640
ttaaaattct gtggactgca acgtgagagc aatgaccaca cttctgtgaa cccattttta      26700
ctgtgcatgt gctaacgtct attgttagta ttccttcact tgcaaagatg gcatgataat      26760
tttgctggtt tcattaatga gatactgtta aatgtaggat gacttcaaac ttagttgtat      26820
tgtaaaatta tttttaattg tatacattta agttgtacag catgatgttt tgagatactt      26880
atctttattt atatatatat ataatataca cacgtatata aaagtgattc ctacattgaa      26940
gcaaattaac atacccatca tcatatggtt atctttgctt ttttactatc agtgcctaaa      27000
atctactttc ttgaaaaatt accagtatgc actacaatat tattaacaat aatcttcatg      27060
ttgtacatta gatctttaga cttactcatc ttacatgact taggtttgtt tttacctcta      27120
ctaccatctg agccatattt ccactttgta atttgataat aaacttggaa aaatagcact      27180
tatatgttta ggtgacgggc ataaatagga taagatgtgt ttatatatta ttccatatat      27240
cttgtctcca actacaatga taaacaacct gtttgtccct aaaaagtaag aaataacttg      27300
acttttctgc cccttcaagc ataggctgtt agcttttaag ttttagggag acattgatga      27360
tgctatttgc tttatcaaga ggaaattgtc aaaagaggtc ttttggttct caaactattc      27420
aaagtattta aaaatcagga caaaatatgt ttacgtgata ttcaagggta cagaaatgag      27480
gtaaatgaga tgccaattgt atttgtcatg caaatatata attacgtgta tgagagttag      27540
atgatacatc tcatcaattt aattgttctt ctacaaggag aaaatgaaca atttgtcaac      27600
tcgtatatga agtaattttt ataagaaatt ttattaaaac ttttaacaac atttggattt      27660
ttaagttgca atttaaatat ccccttctac caggtgattc tggaatcact aagcagttac      27720
ttgtgaaaat tccaaagtag catttaattc ttattaatgt catagtgaat actaatgcaa      27780
agaatactga gccagaaatt atgcttgttg aataaaataga ttatttattg aacaagtaag      27840
tgaaaaaatg gaaataaaga acggatatat attttatctt cctgcttaga tgtgggactg      27900
tcctactttt ctctggtgtt cacaacaaca atatgataaa tctaattgga attcagttca      27960
taggaatgaa ttcagttaca ttatggattg tgatgaataa tgtacacttt taatttaatg      28020
aaatcaaata gattttaact atctatgctt acaatgggt gacataagtc tgacaatcct      28080
taatatcaag tcatctccaa ttcacatgta tacacacttt ttttctattt ggctattggg      28140
aatcctcaca aaaatcgaaa attgcccttt cagtgtacgt tacggtattt catgccacac      28200
agattttctg aggttgtaca tacagctttg ccttgaggtt ccaattttg ctcagtggat      28260 tgagtatata ttatttgcta tatatcagaa gaggcatgtg cttcctactt atgtcaggta      28320
actttgggat taatataatt gtcctacaaa gcatagatag atagaaatac ttcatcctta      28380
atttctaata ttatgacata tctaaagtag gcacctttaa aagttaatct ccactaaata      28440
ctaatgactg cttatagtgg caattcatct ttcatggtag tcctcctaca aaggtatact      28500
aacatttatg agtttgaaac aaaggcaatt cacaagtgtt ctgctagaga tggtctatat      28560
ctgctgtttg atccagcatg atggccagct ggccctcctg tgcatgacgg ctcgtggttt      28620
aactgcacca ttttgtttgg tcatatacag ggaaaacatg gcatggtgtg gagggcatgg      28680
gcttgaattc agggaacaga gagttggtct tctctctctc actctactgg atgatgtcat      28740
ctcccctctc taagcatgag ttttcttatc tgtgaaataa aaatgttgaa ttaaatgagt      28800
tcaaaatgct ttcagtctgt gtttaatagc ttgaatctta agacaatgta ttcaattatg      28860
cgttgccaga tccctggcaa ctcatgtaac ctttctaaac catagctact catctgtaac      28920
tggccagcca actgcccagg gttggagtgt gaatgaaata agataatgca gacaaaagat      28980
```

```
ttttaaaaat tgtagtgcat tatacagttg taatattttg ccaagaactt acattttctc   29040
taagaagtgt gtcgatacat gatcacagaa aatcttttcc atattccttt gtagtttgat   29100
gatattaagt aagtaaattg tataacacaa agagggaaaa gcatcactga acatgccgtt   29160
ttatttagct aaataaaatg taatcactat tagttttcct ctgatttccc caaagtcatg   29220
tgattccatt gagtattatg cacatggtat aattagaatg gattctctgc tcaaataatt   29280
ttgggaaaca tttaaattaa caaagtttaa aagtatctct gttaagctga agcaaatctc   29340
aaaggcctta atattgtatg taagaggaat agttaccatc tttcctaatg cctctttgac   29400
gccaaaccca tggagaatag ttctaggtgt tcagtaaaac acagatttgg gatgccacag   29460
gttaattgga actgtcccct gcaatccttt tctctttttc ttaataatgg ctgattgcag   29520
gtcctagatg aaagacattt agagagatta tcaggactca gcatcccata tcagaatcca   29580
ttcttttata gtcattttct gttacatttc ttgggacaac accaaagaaa tgaccatctt   29640
cattcacata ggctttgtac caaatgctga caaagatcct tggtgaccta gatgggggca   29700
ggtctaagta gattgcagct gtaaaattgg ctgatgaatg atctcagccc cttttactca   29760
cactcaaagg caggacagtc cattaagggg aaggagggca gagttttcc ttaggccaat    29820
tccctatgcc agaactttt agaatggaag catttccaga ggagaaacaa ccccaagcac    29880
agttcaaagc cccctcctcc caagttcatt tgaaagtggg atggtttatc tgcaaagggg   29940
gaaaagatga gggataggga cgggaatatc cctacccttc agagagtctg gtttcatcct   30000
gcactttac tgcacagcca caaatgcctt ggggtgaatc tacaatatga tacatcatat    30060
ggtctaaacg tgcctggctg atcctctcta atacttcagg ggtctaaaag ggataacatg   30120
ctctcctgtt actcaccgac tctgtccgcc atatttcacc cagccagcca ctgccttcac   30180
ttccgtccga ggcctaatct gagcccatgg gaaacctaag aaccccctacc acaactgcct  30240
caactcttgg gaatcagggt gtatgggggt gacaggaagt gagcatacat tctccaactt   30300
gatatgtcag ccccccacgtc tgtatgaatg tttgctcaca ctgtgactgc cggccttgct  30360
cctcaggctg catcctacca gggagtaaga cccaagtcct tcctgctttc agacaacacc   30420
aagcctcatg agtccccact cagaggaagg accagagaca aactctaatg ttccactaat   30480
acttcccttc ttattacttt ccttgaaaat cccttctccc tctttctttt tatacttcgc   30540
taatgaaagg taatgaaagg gtctggcact tggaatttag aattgataca tggttttaa    30600
cccgcggacg tattccacaa taaccctgc atcttctact aagatgtggg ctaggaaggg    30660
accagccagt tccagggtc acagtgcctc agctgatgtt tcatattttc agcaacttta    30720
tgttagagat gtccatcaat cagaacaata tggttagaga ataaactaat aaaagtcatt   30780
tttgaggaca tgttggaagt ctatcaaaag cattgaaatt atgcatgctc tgaccagtcg   30840
catgtctaag aatttaaata tgatcataag tttaaatatg aagatgttta tcacagaatt   30900
gattataaaa caaattgaa aaaaatagtg ctagaagttt gatcataggg acctcattaa    30960
atgcattatg gttgatccat gcagtggttt gctgaacagc cattaaaatg ttgtagaata   31020
attattaatg gtgtggaagg atgctattgt tgcagtatgt gaaagaaca aattacaaag    31080
cagtttgtgc agcataatat tttatttttt taaaaacctg tatgtggctt atgtacatat   31140
aaagacgtgg aataaatgca caaggtactc agttttctc agtgaagccc atttgcatt     31200
ttgggctggg taattcttcg ctgtggagaa ctctcattca ttgtaggatg tttacaagcc   31260
ctgggcctta cctctttaac gccagtaggc acccccagca tggcaacaag cacaaaatgg   31320
```

```
tctctctcat attgcccttg aggaaatttt gcaactaagt aactattact gggtcctaga    31380
ttacagtctg gattattgcg ttcctttctt atttttattt tctccaattc cctttaataa    31440
gcatgtactg gattcataaa aaaacaacat aaatggtaat tacaatattc cgcactggtt    31500
aaaacttatg taaataagca ttctgctgct ttagccacaa ttgcaattta tgctccttct    31560
ctttcttaag ttcccagttc ccacgtacat tcattcgact gattcaaaag tcattttagc    31620
ttgatagact cttaaaagtt agagttatca tttctgctat ttattctttc aattatccat    31680
ttgtccaccc atccatctga tccattttgt tgatgcatgc tgtgtataaa atactacacc    31740
agcctggtgc ggtggctcac gcctgtaatt ccaggacttt gggaggccaa ggcgggtgga    31800
tcacctgaag tcaggtgttt gagaccagcc tggccaacgt ggaaaaaccc tgtctctact    31860
aaaaatacaa aaattagcca ggcatggtgg cagacgactc taatcccagc tacttaggag    31920
gctgaaccag gagaatcgct cgaacccagg agatggagtt tgcagtgagc tgagatcatg    31980
ccaatacact ccagcctggg tgacagagca agactccgtc tcaaaaacaa acaaaaaaaa    32040
tacaatgcca agcatcataa aaaatatagt gatatataag acctatttgt tgtgctctag    32100
gcattgacat ctagctgtca accattaata tgtgtaggag tctatctatc aatattatgg    32160
actgtgcttg aagacttctt ccccaatctt tttctcttcc cattaagttt gaagtgaggt    32220
tttctgagtg aagtatcata gtacatacag tctcattatt tttcaaaaat ctctggttat    32280
agtacatttc tttcctttat cccctttgtt cccaactatc aaaccatttt ggatatccag    32340
tattggtatc cagtattatt aaaaagcaaa acagagaact attaacaaaa aaatttgtag    32400
gagtaattgg ttgtatggta tccagtacta ttagatagta aatcagaaaa ttattaacaa    32460 aaatttttaga cgaataatgg attgtcttgc ccaagtgaat tgagtgattt agttgttctt    32520
tcatttttag caagtacagc tgatcatttg aggccttact cattgtttga ttttgcaaat    32580
tcttactatt ataaatgttt tgggctctga gaaagctgtt gtcttaatct gtttgtgctg    32640
ttataacaaa atacatgaga ctgggtaatt tacaaacaac agaaatttat ttctcatagc    32700
tctggaggct gggaactcca agatcaaggc atttgtcttc aggttcagta tctggcgagg    32760
gccggttctc tactcccaag atggtgtctt gtcactgtat cctccagagg gccaaatgct    32820
gtgttctcac atggtagaga gatagaaagg gccaactcac tccctcaagg cctttcataa    32880
tgttaccaat tccacttgtc agggctctgc ccccgtgact ttattacctc tgcaaggccc    32940
caccacttaa tactatcacg ttggttatta cgatttatca catgaatttc gaccatacta    33000
gttgccatcc tttcattttc atatatcctt aaaactttgc cttctcatt ttaatgtact     33060 ttatccacag tatgccaact tttcgatact tttgttaacc tgtctgacga tatataggaa    33120
actgtaaaag tgcagttttt gatacactct ttagctgccc gtttacttct actgtcgtta    33180
gagaacccca tccatagtgc atgtgtttat tttgtgtatg aacaaagact ttatatatag    33240
tttgggtcat ttttattcat tagtgcttcc cttataatct ctgaataccq ttttattagt    33300 acatactgct attcttaata gtaactagca tgcctgatca tcccaaatgt ctaggttcac    33360
attttaaaat aagttatatc tttgggctta acagtttatt gaaaggtaac aaggattgag    33420
tcatagttgt atgtttttgg aagtagaatt caactgtaaa tagaaattgg ttgtttagat    33480
ctcactatat atgaaaaaat gaaggcttta ggagaaaatc tccccaaagt acccattttt    33540
catgtgataa atatcatgaa atgatttgag aaaaaaatgt atatttgtta cagctaacaa    33600
atatttgtgt tttttattct tcatggagag aatgaaattt cttctcttct ttacacattt    33660
cttttcttta ttagaaacta attggtgcct ttataaaaat taactgcaga gcactaacgt    33720
```

```
gtatatataa gtattatgta gggtgtaggg tatgttcagg gtatggtgtg tgtgtgtgtg   33780
tgtgtgtgtg tgtgtgtgtg tagctgtgtg tgtatataat gaaatatatg gtagtgttgt   33840
ttcagaaatc tgcttggtct tcccagagtt cattcatctt ataaattcat ctacattgat   33900
ctctattttt ggaatccatg aaatgttttt tggcagtact tcctttaata tagtgtgctg   33960
gaaatctgga aatttctagc cagattagtt acaaaaaatt agccagtggt tttgcactct   34020
ctatagaatc aaggcccaag gcctactctt gttactcagg gccttgtttt atctggcctc   34080
tttcttttca gccatatagc tctcaaatac tcaacaaaat tcttcattct aggtagacaa   34140
gtatcttcaa aatacttccc aattatctaa taactgtctt accactaaga aggcttttat   34200
gtctcctgtc tgaattttat ccatgcaaaa aagtccagcc caagcctcca gaactccaaa   34260
aagttatccc taactgctga aacacagtaa tttcactatg tgaaatttca ctttggtctc   34320
ctagcatttg cagatatacc atacatatcc ttgatccttt tcctttcata cctttatat    34380 ctaacccttaa agctaataat tttacctaca ctgtaattca aaatgtatcc ccagtcttac   34440
catgtctccc ttctctactg ttaccaccct aggctaggcc ttcatcattt ctcacctgga   34500
ctccttccct aacctctgaa ctgatctgcc tgcttccact tagacaccca acctagtcca   34560
ttcttgagca gtcggaataa ttcttttaag aaagaaacca gatcacatcc ccctctgctc   34620
ccaaccatcc agtgacctct tatcatacat agaatgaaat gcaaatcttt actgtgtttt   34680
aaaggcccta cattatctgg acctcagtaa cttcttactt cctatccctt ttctccttgt   34740
atgccaccct ccaactacac tctaactaca ctgtcttttt ccctgttctt cagacctgcc   34800
aaccatattt tcactgctca attaatatgt agaaaatgaa ttgtttgtta aatgtagact   34860
gtttccttct taaagcaaag ataaatgaca ttgtcttcaa aaacaactaa ctgcccagaa   34920
ttcctgattt taatttttaaa aagacaaact gcaagaatgt gttaaacagt aaggaaacaa   34980
ttcactactt cagaattcta tatgatttca ctgcacgtta gtaattttgt atattataga   35040
atatgagggt attctaataa acttaactct atgctgtata cttatcatga tagctcattt   35100
tcttatatgt ttataacagc actacttatt gtacatggat acgtgggaaa taaattaatt   35160
ttctccttaa gaacaaagca accatttcac tcatgagata aatcttgaag atttaaaaac   35220
tacttataat taattataca ttattcatat aatgttaagt attttcttag taaaccacat   35280
aatttagaat ggcaattgga cagatgggca gaaccacatg catccactat taggcagttg   35340
gtgagcataa gatgccagaa agaagattag gaatatcaag gcagggagct tccgatcgct   35400
cttgaaaaca ttgacccttc actcctcact ctccacgatg catttccttt gaaaagtaat   35460
gccttccaaa acaaagttct ctgttttata tctaaactta ctcaatagtt tctcatggtt   35520
attgatatat aaaaaataaa gtaaaatgtt taggcagacc aaaagaagaa tttcccctc    35580 cctctgcctt ttatgccaag gtgacagcta tgaaatgtac agtacgtttc ctctgcaagg   35640
aatgtagcag tgttccattg caagaagatg agagggagag aaaggttgca cgctgaggaa   35700
tatagtgtca tttgtcactg cctagactca tcagctgtgt ggaactctga gaggcaccag   35760
gcttctttat ttatttcttc agaaacttca gcaaaaaaga tttcattagg agcagagaaa   35820
aatgtgaaaa acgaattagc ttttgtgatg gggagtagtc atctctgaat attgatcaag   35880
attaagaggg ttgtcttcgt aacttctttt atccatagtc tatactgatt taactagaaa   35940
actaatttca ggtggtattt cgggtgtggc agatctttat agtaaatgaa gaatctagtc   36000
aaatctactg aaaaactctg cttactttaa tgtttgatct ggttgaaacc attttagctt   36060
```

-continued

```
aacaatcctt cctctgaaac agggaatcaa ttgatatcct acagcaaaat tatgtggaag    36120
ggccattagc ttcacatcca atgcaaattt tgcctgtgtt tactcttccc caatccaaaa    36180
tatatcagat cctagatgcc agtgaaatcg tttgagctag atggcttgag ggtcatagct    36240
tttttcattt cctgttctca gacctcttat aattgataga ataaaatcag aagagcccta    36300
gagctgtccc acctattctg cctcacaaaa gtagaagtaa tggcaaccac tatcataggg    36360
atcatgctca cctttttctt accagacaaa tttggatatt agcttgaaat taataccttc    36420
cttaaaatgt tggaatttgg ttatatgcga aattttgctc tatttattca ttatattttg    36480
tatggaatta ttttttgccct atattttcac ttaagtgttc tctacccaag atttttaattg    36540 aacccaaatc agccagacac acagacatgg attttgctgc caccaaggtt aattcttctt    36600
ttaaagttaa cttttaaaat ttggtaaaat atagctttga aaatttgcat tcgtctagtg    36660
tttgttatgt atttcccct tttgtttgat tatatgtcta tattttctt gtagaaattg     36720 attttttaacc tgcttttttat gttagctttt atgagcttct gtctgaattc tgaatatgtc    36780
tttcttaatg tcttctaaat gtttcttct ggattattaa aagatttatt aggcttttaa    36840
taattatatt tgttacctta gggaatgtgt ttgaaaatat tttaaatgga attgccagtt    36900
aacacagcat tgaactttt cttgttagag atacattgtt ttctaggcat tttattggga    36960
gagaagttag tatgatataa tgtctttggc tgatattaac tcttctaaga tgcattgttt    37020
ctgagaacac cattgtctga tttcattcag ggaaatttca cacaagccag tagagtcaat    37080 actttttttca agacctgtta attgatatat ataaaaactt gccattgttt acatgcccat    37140
ttcagatcct ttatgtgacc taagctagaa atgcatttta acagcatttg ttttttccaaa    37200 aatatttatt tattttatta ttatagagat agcgtctctc tatgttgccc aggctggcct    37260
cgaactcctg ggctcaagca attcctctgc ctcggcctcc caacagtgct gggatacagg    37320
tgtgagccat tgtgccaggc ccttgttttt atttttttg aacattgtat tttgaaaggg    37380
gtttgaaggt gatccctaga tagcaaccag taatgattcg agcagcaaaa caatctaaaa    37440 agtaattta taagaaaatg cagaacataa atgagcccat aaaaaattat attaggttct    37500
atttacatta ctaccttctt tcacatgtaa tatttcacta acatttaatg aatttctgtg    37560
cagtgccata taccattatg aattctagga tagaagaatg agtgagaaat gttcttaggc    37620
cttaggaaga aggaacaagc atctctgtgt aatagttatt tcaactcttc ttttacacct    37680
cattcccata ttaaatctca gaaaagctaa agtaatagct atcccagatc tattttagac    37740
tccagacact tacttcaatg tcttgttctc cttatcagac tggaatcatt ccaaacctct    37800
taacttctgg gcaaccatga taatgcgaca gaaaggacac taaatctgtc gcaaatttat    37860
cttgatattc tatccagtct tacttggtac tgaaggtcac aagtaaaata aggtggttgt    37920
tttttgtttg tttttttttt tttgacagaa gagaaaagaa cactgtgagc acagagtgaa    37980
tgtctaacat tgattcttga gtagcaggaa ttctctatgc gagaggatct ctatgcaaaa    38040
agatctcata ttctagcaca atttaaggat ctctatgcaa agatatccca tattttagca    38100
ttatcaataa gctatggggt aatatattgt atgtggtgtg gcttgaattc tagaaatttg    38160
atttctagaa atggtccctg tagttaagga tatataatgt ggccgtctcc agttttctat    38220
gaggaatagg aaaatactat cattattagc tgtgtgacca tggacaactt gcttcgttct    38280
tcagttgcat catctgtata aaataagaat aagaaaattt acatctgcaa ggtgtgatgg    38340
agatcacatg ggataattgt ggtcccagag cctggcacaa aagggcttaa tatttataat    38400 cctcccatt tctccgtata ctctaaagga agtttattgc ttatcaaatt gtgccgtggt    38460
```

```
tagttgtaca gcttccctgc caaattgtaa actccaacac taatgtgacg ttacatttta    38520
tatagtgcta tgattttcaa attgtttgca taatttcaaa tacacagtaa attgcttttt    38580
attagtataa ttattgctat tgtcaatatt attattacaa cagcttcaca gtaagatggg    38640
cagaaaaaaa tttaatttcc attttacaaa tgcacttttg aggctcacag aagtcaaata    38700
gaccaaagtc acagggctag tgagggaccc agaagaaaca aattgtaatt cactgattcc    38760
aagttcagtg gttgccttac tgcatcataa aggctattac acaatccagg tgtatcatat    38820
gattcttgtc tatatattca tacatatcag aaaaagtgtt ctactcaaaa ttgctagcaa    38880
tcaacagata ctgatagtca ttagtactta aatctttatc aaatgaaata ttaataccca    38940
tgaaagagag gacaatgaaa ggtttgtatc atttgtatgt cacaagtcaa cttttttcaa    39000
tcactcatta ttagtttaac tgtaaaaaat tatttacatt tagcgtgaaa ctttcctgta    39060
ttctcaacat atttccttcg gtagaaaagc aaacctccag ttctctgttc tttgcttgga    39120
tacttgccag tttgtaactc agctatcaaa cagtaaagct cacaaaacac ttattaaaat    39180
gactaaaatc caaacacca agagcacagc atgctggtga gatgtggagc aacaagaact    39240
ttcattcatt cactaatgct ggcaatacaa aatggtacag taactttgga agataggttg    39300
acaatttctt acgaagctaa actatactta acatatatat ttgtccatttt tcacagtgct    39360
aaaaagaagt tcccgagact gggaaattta taaggaaag aggtttatttt aattgactca    39420
cagctcagca tggctgagga ggcctcagaa agcttataat catggtggaa ggagaagggg    39480
aagcaaggca cctacttcac aaggtgacag gaaggagaat gaatgcagga ggaactacca    39540
aacacataaa accattagct ctcgtgagaa ctcactcgct atcatgagaa cagcatgggg    39600
gaaacagctc tcatgatcta gttacctcca cctggtctct cccttgacat gtggggatta    39660
tggggattat aattcaagat gagatttggg tggggacaca aagcctaacc atatcaccat    39720
atgatccaaa atcatgctac atgatattca cccaaaggaa atgtaaactg tgtccacacc    39780
aaaacctgca catgcacgtt tatagcagct ttattcataa ttgccaaaac ttggaagcaa    39840
ccaagatgtt cctcaatagg tgaatgaaca aaaagactgg cacatgtact caatggaata    39900
ttattcagtg ataaaagaa atgagctatc aagccacaaa aacacatgga gaaaacttag    39960
gtacgtaagc cagtttgaaa ggttgcattc tatatgattc caatatatga cattctgaaa    40020
gagacaaaat tctggagaca gtaaaaagat cagtgattgc ctggggctct gagaaagtgc    40080
agagggatga atgggtgaag cacatggcat gtttaggaca gtgaaactat tctctatgat    40140
actgtcatgt tggatacatg accttatacc tttgttaaaa ctcagaatttt tacaatacag    40200
agtgaattct aatataaact atggacttta gttgtaataa ggtatcaatg ttatttcata    40260
agttttaata atgtaccaca ctaatgcaaa attataataa tagggaatt ggggaaggg    40320
taatggagta tatgggaatg cactgtaatc tcagtacaat tattccacaa acctaaaact    40380
tctttcaaaa atacaagcta ttggtcaggt gtgatggctt ataccagtaa tctcagcact    40440
ttgggaagtc aagaccctca gatcacttga ggccaggagt tcgagaccag cctggccaac    40500
atggtgaaat cctgtctcta ctaaaaatac aaaaaaaaaa aagaaagaa agaaagaaa     40560
gaaagaacag aagaaataaa agaaagaaag gaaagaaaga aagaaaagaaa gaaagaaga    40620
gaaagagaga aagaaagaag gaaagaaaga aacagaaaga gagaaagaaa gaaagaaaaa    40680
gaaagaaaga aagaaagaaa gaaagaaag acagatgcgg ttgctcatgc ttgtaatcac    40740
aactactcgg gagactgagg catgagaatc gcctgaactc agaaggtgga ggttgcagta    40800
```

-continued

```
gggtgagatt acgccactgc actccagcct gggtgacaga gcaaggctct gtctcaaaaa    40860
aaaaaaaaaa aagctattaa aaatatgtaa agctcagtct agatacagta ccagaatagt    40920
aggaacttta tttcacctgt cctacaaatt atggttgtgt gccacttggg taaaactcag    40980
aatccaaata tgtgaatgta agatttatgg ggaaattatt tgtatttcaa ataatccttt    41040
aatgaatgca ctccttctaa agtagccatt aataaagcag ttaatgtttc atttaattat    41100
agattaatgt acataagata tgccaggaat gcaattagga actgggaagg gggtgttatt    41160
ctaataactt ccacatagca ttgtgagaca ttttctgctt tcttcaaatt tcatttaatt    41220
acattttaaa caaatatttt tgtgagccta ttatatagtc cttcgctagc actgaggaga    41280
catgctttgt gaccttggtg atttcacatt caaatttccc tttcacctac actcttcctt    41340
gttttttcat gcctgtgtag attgtaaatt cttcctcaga ttaagacatt ttattcacct    41400
ttgtaacatc cacagtatct agcacaatca gtgccttcaa aaacaattgg cctcaagaat    41460
tgattgactc aatgagtgac tgaaagacta aattaataag tacacatcta tttgtacttc    41520
cctgcttact tataaggtat gacaatgaaa tactgagaca gttatacatt acttacggac    41580
tcaatctcat ttctttacaa tctctattct tctttttga gtataatgtt atttttacaat    41640
tccactaact tgtcactctt tattataaat tcatatctcc atttcacctg agaataataa    41700
aggcaaggaa gtattttaaa tgatcttgtt ttttataact agcattcatt gagcaaatca    41760
aagtatgaaa ataatatagg tgtcagtgat tattataaag ttgtatgcac aaaacattcc    41820
aatgattggg gccaatacag agaaaacatc tcaatatttg gaattttgct tttctgtaaa    41880
tactttgata tgtacttaca tcatatcaat tataactcct gctgaaaaca aacagtgcac    41940
acaaatttgg tagttggagg agactttata aagggactaa ttacgaaggt ttagaccggg    42000
ttaggaaaaa cacacggaat agtgcaatac tttaggatgg caacagcgag caccgttata    42060
accactaggc caaatgaac taaatgaaca gggagattac catttatcag aaaagaggg    42120
agaaaggaag gagagatgac caagcaagtc ctatgtgaag acggctgcct gacttgagct    42180
gtgtgatctt tggactgata ccacctgcct gcactggcct agcagggcga gaatagtcaa    42240
tatctggaaa atggatcacc tgaccttact ttcctccctc cctgtttcct ctttgtggtg    42300
tttccactgg ccaaactcac agcgtagaca aaggagtgc attgatgtag cagtggttct    42360
aatccagggc caattgtgct cccagggaac attagtggtt atcacagctc aggggaggaa    42420
gggagaggag tggagtgcta ctatgattca ctgagggatt ttttttaaaca tctacaatgc    42480
acaggacatc cttccacaac aaagtatcca gttaaaaaat gtcattactg ccaaggttga    42540
aaaaccgtgg tgtagtcagt acaattcatc ttctccaggc acagtgcagg agtggggtgg    42600
agtgtctgaa ggggaagaag gaagaaacca gcacacccca caaagtaac caatgcaaat    42660
accaaatagg aaaagacagc acttaaaata caaaagtctc aggaatatat ctgatagtgt    42720
tttatggaat ttattaaaat ttagcctgga gtgagtaata tttagcaagc caggtttgtc    42780
tttagagaaa tccttgtggg gtttatacaa ggatttatta acaaagggca cacacaatac    42840
tcatattaca gtcagtctgg ttatgtaaaa catgggcaag aatgtaatag acaatgtga    42900
tgtattcaca aaggattta ggactacaca gataatcctc taatgctttc acttacgtac    42960
tatgaaaggc tatagtttgc atagtgatat agccacgtaa gatagtaaac ttgacattca    43020
tgcagctata catgtttgca cacaccagga tgcatgccct ttctacctgg ttgattttt    43080
attcttttat taatctctaa tttattcccc agaacactct ccataaaac tttctcacaa    43140
cttaaatctt taatctattg tgtggatttc tgactcattc tccaagctttt tcctcttccc    43200
```

```
tccgcaatgc cttatagtct tatgactatt tatcccttg cctacatttc tagccagatc    43260
tcttgcctga tacacactct catatttctc tttgcacgct acacattttt atttagatat    43320
cacactacta ctttgatttc aacaggtctc agtttaactt aattttcct tcaagcaagg    43380
agtcccttca tatcagttat caccattggc accagaattt ttcttatgac ttcccatgac    43440
ctacaatata aaccatataa atcactgatg cctccatagt tccctccctc tcaaatttag    43500
ccataagatg atttttaggat ccttgttttt tccaatctct ctttcattct ctcccccatc    43560
tcttccatta tgaaggtttg gataggacac aactcatgcc tagattagtg caatagatgc    43620
tgagcctgtg cagcggtagt ttagctttct ctcctggtta actttaactg ccacatatat    43680
cacttcacac gtcattttc attcaaacgt atttaactgg ctcttcattc ataagaagct    43740
ggaatttgtc gtttgactga tatttaaag attttatatt ttttctccat cctcgttcta    43800
atgttgtatc ttgtgtcatt tgttcattca taaacttaag acttagctaa ccactgagca    43860
tccaggaaat tcagtatcta tcatgtgaat tctctaatac tggttgatcc attgtcacca    43920
gagcatagca ggcttctcct gcctttatgt atgtttgtca tatagttcat gcctaaaatt    43980
cttcttaaa tcttaaattc ctaagataca cacttttgcc caagatcaca gtaatctctg    44040
ccataatctc tgctggaatc tgttcactgt gttgctcctg ctaaacttct tacagatgac    44100
tttttttctt tttggtttcc ctggtatcta gtataattc ttataggt actcaataaa    44160
tgtttcctgt tgatctctac acctactctg tacaataca tagtgactag acacatgttg    44220
ctatcaagca tttcaaaagt agctagcctg agttgagata taggggtaaa atacacaaca    44280
gatttcaaga catattatga aaaaaaccca taaaatttct cagtaatttt tttatagatt    44340
acatgtagaa actataacat tttgaataag ttgtatcaaa taaatataa aattcacccg    44400
gttcttttta atttgttaaa tgtggtggct agaaaattta aaattacata attggctcac    44460
agaataatta taatgatgg tattgcttta gatcaagttt gtctaacccg tggcccatgg    44520
gccacaagcg gcccaggatg gttttgaatg agatccaaca caaatgtgtg aacttcctta    44580
aaacattatg aatttttgt ttgtttgtt tttgtttttt tctcatcagc tatcatgagt    44640
gttagtgtat tttatgcatg gctcaagaca attaattctt cttcaaatat ggcccaggga    44700
agccaaaaga ctggacaacc ctgctttaga tagtaaagca tatgagtagt taatgtgtac    44760
tataagcagt gtgatctgat agactattta atgttgtttg atggtacatt attcaagtcg    44820
attattatgt ctacctatgc agtttaacga cggtaatgag agagggcagc ttgattacag    44880
gtcttatctt ttgactaact tgctaggcca cctgagaagg acccaaatta ctgaatgct    44940
taactcaact aatttgtatt cacttgaaga atttcaagga tgtttatatg ccatcaactt    45000
gctttaaatt ttttctctca gtgaaaattt ttccttaaat gagtatgtgg tattcaaatt    45060
tatccttgtt ttctatgatt atcttttcat agcactgtgg tttccaggaa cctttttttt    45120
tttgagatgc attctacatg taactattgc acagtttgca tgtagtaagg ttcattattc    45180
ttctactttt ccaaacacct ggcatgttta cttgaggttg gtacaccttg tatcccagat    45240
tttgctgttt ttaacttaaa tattgaatat tttgattaaa cattatggaa agtttaaatg    45300
ggtcaagaaa aatagctttt cttcccatga agaacaatac ggcataggag ttaagagcat    45360
agatttaaag tcagaaaacc tgtgctgcct acttgtgcaa agtcacttac atgctgtact    45420
tctgtttctt catctgtaag ttctacccct aggtatttac ttaagattaa tggaagcata    45480
tgttcataca atgacttgta cagaattatt cacgatagca ttactcttaa tagctctaac    45540
```

```
tggtaacaac acaataatca atcaacaatt gtgctgtatt catacagcag aatactactt    45600
agcaacaaaa atggaatgga ctactgataa cctcaacaac atggatgaat ctcaaaacta    45660
tcatgctgtg tgatgccagg cacaaatcag tacatactat aattccagaa aagacaaatg    45720
tcatccatgg taacaacaag atccatgctt gctggaggta gaggcatcag ttcagtcatt    45780
caggaagctg attccaagat ggtgttagaa ttacaaccat ccacaagaga tttattgcag    45840
gcaatagcta tgaaaggtag aaagagaaca ggagaaaaac caggcaagga aaaccacaa     45900 tgtagttgtg atatcacttc aaagggaggc agaaggaagg agaattgggt aggaatagcc    45960
acagattaca gtgcagttac aagaaagtct tggcttccaa caaaggttac ttgttgagga    46020
gtcatgcatt aggcagacat gtctgggctg tagtttcctt gctgctccca gtcattggct    46080
ggaggccagt ctgggttcct gtgctgtggt ggatcccatt gctgctgcag caggaggcca    46140
atagcactcc tggcagctaa ttggagagaa aagatccaag aggtgtacct tcatggctac    46200
ccccatgggg ctgggtgga ggtggaggag aaggagaagg aattaactag aaaaaggcac     46260
aaaggaaaat tgggaaaat aatgaagata tatgatttct caattgtggt ggtcgttaca     46320
tgggtttatt aatgcatcaa aactcaagaa atgtacattt aaaatgagtg catatgattg    46380
taagtgaatt atacctcaat atagttaatt ttttaaaaat catagatttc tttatattta    46440
atgcatgaac ataaacctaa gacactcctc cactccaaaa cttaattacc ttgtgatcag    46500
cagagcagaa ggtactttgt gatatatagg tagagaagat gaagtcttgt gacatttaac    46560
aagggacagg aaaatggacc ttgtcctaag ttaccaaact gcaaaatat cacctacaaa     46620 ggctattcat aacatacatt ttcaaggggg ttacaatatt tgcctactat aaaatttttgg   46680 atctgtaaag gggttaaatt atttgtgcag gggaataaac atcaaagaaa cattaagagg    46740
tccagagaag taaaatagga agggtctttt ggctagagga gatatttaac tttcagaaca    46800
tgtggaatta agttgtattg attatgatct gatcttcttc cccctaaatt tgatcctctt    46860
cctgtaatct attgtttcca tcatcttcaa ctcttccctt tccctctccc ttgtccctca    46920
gttctagtca atcacaaagt cctacagttt cactttctgt ataccttatt tctggaattc    46980
atctctagac ttcaaaatat atatatatat atttttttt tgagatgga gtctcgctct      47040 gttgcccagg ctggagtgcc gtggtgcaat ctcagctcac agcagcctct gccacccagg    47100
ttcaagcgat tctcctagtt cagcctcctg agtagctggg attacaggca tctgccacca    47160
cgcctggtta atttttgtat tttcagtaga gatggggttt cgccatgttg gccaggctga    47220
tctcgaactc ctgacctcag gtgatccacc cgcgtcagcc tcccaaagtg ctggaattac    47280
aggtgtgagc cactgcttcc agcccaaaat atcttaagta gataattgca cgactaatct    47340
ctgcttttct ctcccagcag ccttccaaat tcatgtctca cagctgacag agttgttcct    47400
gccttcagat tcatgacctg gctctgtgtt ctagctcagg ctttctctct catatcacct    47460
cttgcctctc tgttgccccc atatttccc ctctggttgg ttggtgctcc tttgaaccc      47520 tctgcatatc ttttcaagaa tattatgact tattatgcct ataaactttg tttaattatt    47580
tatttctaaa atttgacagg gaactttccg aaggcaggta ttgtgtcttt ctcatttaaa    47640
agcaaattct cgcctggcat ggtggctcat gcctgtaatc ccacactttg ggaggctaag    47700
gtggacagat cacttgagcc taggagttca tgaccagcct gggcaacaca gttagaccaa    47760
aaaaaaaata tatacgaaaa ttagcctggc atggtggcac accccgtag tctcagctag     47820 tctggtagct gaggtgagag gatcacttga gcctggatgg ttgaggttgc agtgagctgt    47880
gattgtatca ctgcactcca gcctgggcaa aaaagtaaga tcctgtctca aaaaaaaaaa    47940
```

```
aaaaaaaaat tagtgaatcc tcagtgttta aaaagtccat aaacatacta aacatagaag   48000
acctccaaat gaaattaatc aattattatt tagtgggttg cttctctttt gttttaatat   48060
agttttaaca aagagtaaaa gttatgatct ttttatatgt aaaataaata atgccgggtt   48120
tgacataaat tttaggaaaa ctagagacgc tacttcctaa aaattttctt tctataatct   48180
tcctaaatat ttttccataa agtacaaaat aatagaaaaa aattaagaga ttgagtatcc   48240
tttcaggaag tgatatgaca aatagggttc gagaactatt tgaattctca ccacttttca   48300
taagggcaga tctcaagtta aattttcta ttcgaattta aatgactttc actggaatac    48360
cattacagaa aagcttctgt gtttagatgg caatatggag tttctttct tggaatatta    48420 attgaaggag aagtcttaat tttttaagtc tatatctccg tatatatttg aacctatttt   48480
atatgttagt ccttctcttt agtaaccttc atccacagtg aacaagattt acccttacct   48540
ttaagcagta gcggctactt tatgtgaagt gaacagctgc ttttttatc tgcatctaga    48600 catcaagtag tccagagtcc tttctaacac cctagcaata gaagtaagaa tattttgacc   48660
attccatgac ttgatgatac ttctagtaat aatactgtat tattaaaaac aaacaaacct   48720
ttgtgcagtg gtaattgaag cagttccttg ggaacatgta ttaagtactt tttagcagtt   48780
aagtccactc tctgtaggtt aaggaatatt taaataaaat aatgtggcaa atgagttcaa   48840
gatgataaat gcgatgagaa ctaaaacagc tttaattta tgtgggaaat aaatagagga    48900
aaagtacatt acagggctcc tggacttatt tctttcttca aagtgtttct cctagcgaat   48960
attattacta ttttttctct taagtaaaaa atacacaaag tatgaatcta cacaggataa   49020
taatattgaa gttaaggatg atgtctcctc cttcactctc caaatacta tttacttggc    49080 ttcatggaaa tctctctcac tccaattcca ccgtgtcaac tgaggtcttc tgttctttct   49140
ctccctatag catattcctg ttacataaat cctaaactgt gtcgtgttag tcacacactg   49200
taacctctag ataagcgcct gtccagaggt tctcaatcag agccttgcaa atatgtatta   49260
aatcaatggg tcatcttcag tgtctcagtg ggcccttgga tatgttttgc agactgctgt   49320
gagtatgtag ggatgtccag tatcgaggga agtgtggatg gctttcattg gttcttatag   49380
ggctgaagaa cacatagagc agtaagcact tctactgtag ggagagatcg agcttctccc   49440
atccccactg ctggcaccac caccaccta caccccattt tgagttctga aagtgaatcc    49500
ttgagaaaga acacacaaaa caaccatcat aatagtgggc acagctgtgg gtggtagaat   49560
aacattccca agcttctttt cctacacatg attaatatta attcagcaaa catttattca   49620
gctcctactt ttaaacaggc actattctag gtactaaaga catagaggca aagcatacaa   49680
gactctgcct ttgtgaaaca attaagaaat aagtaaaaag aaaagaaaca gaaaaggcaa   49740
tttggatagt gtcaggtgct ataaagaaaa caaaatgcca ttttaataaa taataataat   49800
acaatgtttt catactatgt gctagacact atgctagtag gtatttatag acataacctc   49860
aattaatcct caaaatggca tgttgatatc aatacccaa gtttacatat gagacttaag    49920
atgtctgagt atattccccc aggtaacaat taatatgcac aataaaactt tttgctcatt   49980
catttattaa cctatgttga ttgagtacct attttgtgtc aggcatcatt ttaaggcacc   50040
tggatatagt tatgaacaaa caataaaaa tctctgccct caaataatta atatctcaca    50100
gaggttaggc aaaatataat cagaaaataa gtataacgta taggatgcca gatcatgaaa   50160
gaagctatga atggcatcaa gaagctggaa aaggcaagga gacagatttt tcctagagt    50220 ctccaaaaca gaacacagtc ctgccgacac cttaacttta ggctagtgag acccctattg   50280
```

```
gacttcagac ttacaatccc acaatgtaat aaatttgtgg taattcagta ggggaacaat    50340
agaaaactaa tacgatatca aaacaaatta tatcatagaa caagaaaatg taattgtgac    50400
aaataatacc tacaaaaatg ttgtaaatgc taggcaaata atgtgtttaa agcacttagg    50460
ccaatgttca acgtaaagta attcatgcta taatatcatc atcatcatta ccaatattta    50520
ggggctctaa caaatgatgt acgtgtaagc agatgtaaga aaatttcctt gctgaagagg    50580
aggtattaat agagtatata acaatagata acaaattcca aataaaggca aactaaatgt    50640
tttattggat taaatttaat tttaaaaact acaagaggcc gggcgcggtg gctcacgcct    50700
ataatcccag cactttggaa ggctgaggtg ggtggatcac gaggtcagga gatcgagacc    50760
atcctggcca acatggtgaa acgctgtctc tactaaaaat acaaaaatta gctgggcctg    50820
gtggcgcgtg cctgtaatct cagctatttg ggaggctgag gcaagagaat cacttgaaca    50880
accaaggagt cggaggttgc agtgagccaa gattgtgcca ctgcactcca gcctggcaac    50940
agagtgagat cccgtctcaa caacaacaac aacaacaaca acaacaacaa caacaacaac    51000
aacaaaactg tgagatccat ggtgggcttt taagaggaaa atgcaagcta aggtttgttt    51060
agactctgag tactgcatgt gtaaaaataa aggcatgatg aaaagatcaa gagattagag    51120
tgatactttt tatctactag tgtcagagtc atgaccaggg gattggctat gagaatacat    51180
aagctgtgcc aggagtaatc caaggagatt gtttcaattt ggaagagtgt ccacagaatg    51240
attctcatac tagacgttgg gctattgtaa agaaagttgg taggtactcc atcgctagga    51300
tcatatcagg gagaaattga acaggatggc cctaatgacc ctgttgtacc cctagcttat    51360
ggattaggca agtcacttct actcgtatac cctgtttccc catttgtaaa taagaggatg    51420
tgttactcta aggatctcta agattctttg cagttgttaa attgcatagc tctccactga    51480
ttccatggtg gaaatttgct attctattac aaatattcta aatgtatgag atatcagaca    51540
tactcattta aaaaacaaaa tacaaaaaat aagtattcta caaataaaca cagataatgt    51600
ttaaattcta tatgtctttg tttctcttca gaagcatcca aaatacaaac catctaagag    51660
gcaagaaaat gtcgtgatgt tcctagtgca agttaaaaag atttgctttc ctcaagtcgg    51720
aaagcccttc tcattttga ggttttttc ttcttttttt tttcaagtga agcattttg    51780 gaggagtcaa tatccatctt taaaggtagc caggtcacat gtatacatat gtaactaacc    51840
tgcacaatgt gcacatgtac cctaaaactt aaagtataat ttaaaaaaaa agaatttaaa    51900 taaaaaaga aaatcagaga gaaaaaaaaa aagatgcatg tgcaccctga tactaccatc    51960
catagtgata cggtttggct ttgtgtcccc acccaaatct catcttgaat tgtaaccccc    52020
atgtgttgag ggagggacct tatgggaggt gattggatca tgggggtagt ttctccatgc    52080
tgttctcatg atagtgaatg agttctcata agatctaatg gtttaaaatc atggcacttc    52140
cttttgctct ctcttttctcc tgccatgtga ggtgtgcctt gcttccctt cccttctgc    52200 tatgattgta agtttcctga ggcctcctca gctatgcaga acggtgagtc aattaaactt    52260
ctttctttat aaaaaaaaaa aaaaaaaaaa aggtagccag gtaaaaatta cttgtttcca    52320 ggacatttc acctgaaaga agcattgtca tataacatag aagcaagaaa tccagtagtg    52380
ggggttattt aaaaatagct ggaaaatttc aatcagcatg agtttgaagc aacaatttat    52440
catcaccttt tatggtgggt ggggttaaga acatttcagc gggcaaagtg gtggtgatgg    52500
ggaagagaca ccaggggagg tgattcccat tgcattgctt tgtaaacaga ggcacaggtt    52560
cttcattttt gtcacacaaa atcacagcta tgcagaattt attaatttat tcttctgaga    52620
caagaaaaaa gccaccaaag gaaaccaaca gcttgctcct ctcacactgg gggaaccata    52680
```

```
tgagagactt atctatccct gactttaatt ttgacctgag gagagctcct cttaaggaaa    52740
acaaattaat tcaatgacta tactacttaa tcattgacct ttatttaata agagattttt    52800
ccataggata tgctgagctg tctcacttac atcagttgtg tctcctgagg tgggtgacag    52860
gagaccacaa atattgcata gcacacaaat cgttaatagc agctgtatac caaaccatta    52920
cctaaatatg tagagtacaa ttcattctca ctaatgtcag agagcatgct ataaaatggt    52980
gaatccggac agctgaagat actgaataat aacctctatt ttgaacaagt ttacagtgtt    53040
ccaatcagta attaaattga tacctgatga atatatgtgt gtgtatgtat tcatagcaga    53100
gatggttttc ctgagataag gattttgtta ttcggatagg ctgctgctgg aattgtcctt    53160
ctacccttgt ttctttgtcc ttagtcatca ctcatacctc tttccactct tctgccatca    53220
cttttgtcac caaagtcatg gtcctttccc cgccgattgc tgctgcaggt ctagggcacc    53280
aagacttagg cagcactcac catgtgccaa gaactggacc acaggtacca tccagcattg    53340
ctcatggaga ctctgtccct ttctgtagga caccctcctt ttagctagca accccctccac   53400 cacctagagc ctctggacct ctcattttaa tattaagaac taggaaaact taccgctgag    53460
aataactagt acaactagaa ctggtagaga atctgggtc tcttgggaat ggattttttag    53520 gctttattga ttagaggtgt attaataatg cagtgttata gtttcatgac ataacgaata    53580
aaaaagttca ttttggactt gcctttcagc tccctaggag ctaaaagacg tatttaatgt    53640
aacttgtgtg gtggaaataa gttctttttt caggcaaaag atgtgcaaac ccatctgggg    53700
aagaaacatt aaaaactaag gagacagtgt cctagataac tatgttcttt tcctgttta    53760 gtctaaaata atgattagtt ttcttatata tcttcatttg tcttggttcc ttttagccca    53820
atttaataat attattgcag atattgatga aaacctttac cttcctctta attcatcaaa    53880
gtacttgata aaatttatac atagtacatt aattgggagg tttttatgag attaattaat    53940
ataatgaact gatgttgaaa ttatttaaaa cctgaattat tattgtatta agtaggacac    54000
ttaatacagt taatcagttc tgtctttatt catttgtgag aattttttggc aagctattgt    54060 gaatattcag ggaagggaat gtattttttag caggaatctt atacctccta catgaaaatg    54120
aagcatttac tgaaacatcc atgaaacaaa atgtttctga atgtgtacta tacacttgtt    54180
ataagcccct tttcttctgt agctatattt tggagaaaaa tctttgcttt gacaaaaaaa    54240
attatgttga cttacacata tattttataa ctaagcagtg tttggtttgt gataaaggat    54300
acaaaaatat aaaaatgttc agcacacgta agtaaggcct tgttgacagt gtgagttatg    54360
ctactggata ctcaaaagga acattcagtg ttctcaggtg gtctctagac tgtctcaagc    54420
ctaggaagat attttataag caaaggaata agagaaggaa gattcagatt taatccaagt    54480
gaagaattca gttttgtgtg ccttatcctg ttattttgag aggcagccaa agatgctgg    54540 tcagcaagga gaattgtaag ttgggcagcc aactctgatt tctcaacctc ttagctgttt    54600
tcttaaactc agaatttta atgaatttaa atgtccatat caggtagact ttggggatgc    54660
ttttaccagt gattttcaga atgttacttt ctggcatttc ttttcacgta gcattatatt    54720
aaaaatgaat tcattcatcc accttcccct gtccttacta attttccctc ctactccctt    54780 ccccccttgtt cttgccatgg ggacatgcaa acactggtgg ttgatgtctg agcaaggctg    54840
ctgacagggg gaggaaggag atgtcaagca gaggtcaatg gcagtgtgcc cagcagccta    54900
ggaagtagga gggaaaagag agagagacag agatggtgga tgaaagagaa agccaggatg    54960
attatggtgg ttatgatact tgtcatgctg aacacccaat tgagcaccca ataagcacat    55020
```

```
aataatttaa tcatcctctg gcttggatgg cagtgttcta tcagtgttga cttcctggtt   55080
gtgacagttt tacagtgtta gtgtagaaga gaatccttgc tttagagagg tacttactga   55140
agtacttagg gttaatgcac cattgtgctg gaaaaagata cgcacacaca cgcacacaca   55200
cacacacaca cactctcaca cacacgcaca aatacatcca tgtgttaggc agagggagca   55260
aatgaggtaa aatgttaaca attaggaatt ctgggtgaag tggatagagg gactctttga   55320
ctgttcttga aacttctcta tacatttgat ctgtttcaaa ttcttcagaa aatcaaacta   55380
caaaaactta attcatttag tgaacatcta ctgaacatct gtatattaaa tagtgttaaa   55440
tgaatgtcaa ttaaaatgct caaacacagt agaggttgat tctcattcac ataagtccat   55500
ggtaggtgtt tttggcaggt gggtgagttt ctcccttagg gagattgagg aacccagact   55560
cctcccaagt tgcagcccca ccgtcttctg aggggatgca tccatacccca cttcgaagta   55620 gcatacatta tttcctttct cattcctttg gataccagcc acaatttatt caaggtagac   55680
agaaaattgt agtatatagc catatgccct gacaaagaag ggagaacaga ttttggtgga   55740
caactagcaa actctgatac aatctgttat taagcactgt gtgtggatag atgctaacta   55800
gaaggagatt atcttcccctt cagcaaatat aaactgaatg ccgtttattt ggttgaaact   55860
aagctagatc atgggagtat agaaatttta taagaagaca tagtcacttc tgtcagtgag   55920
ctcaagaaga attagtatgc ggaatgtaat catacctaca gggggcttgt gccacttaag   55980
taaaatgaaa cattatttttg agtacaattt agcaataaat gtactacgag atcattaaaa   56040
atcatgtttg aatgttattg tgtcaaggat gggaaaaaga cttttgggtt gtagacttga   56100
taattatagt taaaaacagt ttttattctt gtttagtctt atttttttatg tttaaacata   56160 tttatacttg ctaacattta tacttgctaa gtaaagactg ttttttacaac catgacaaga   56220 acaaaacata ttagtaatgc aaatgccaca tttcctacaa tcaactaatc acactaacat   56280
atttgcatgg aagaatcact gggattgatc tggccacgtg tgtagtcatg cccaaaatgt   56340
gaagtccatc tgttttgcaa tttttttttaa ccactgttat ccaaatgctc cttggatttt   56400
ttttattagt ggatatattt tggaggtcag acaccctctt ggctagatca tcacctttat   56460
aacaaatata tatactattc tcatggaaat atatttagac attgccctac tgggaatttt   56520
tttcaagtaa ttaatgtaca gcttgtgcaa cagcttgatc ttggcttcat ggaaataatt   56580
cactcttagc agcatctaat gccacaaagc atttatggat gtcagctcag aacttacttt   56640
tatttatctc tgagttactt tttttttttt tttttttgaga cagagtctca ctctgtctttt   56700 ggcttgtccc taacctctta acagacttaa tattaagctc catttcactc agtcgttctg   56760
ttgtcatata aatgagacat tctacaagca tagtttttag tttctgccag agcatcatac   56820
aacattgtga gctatgatga agataaagac ctagagaaga tatttaatat gaagttcatt   56880
atctaatatt tggtatgtgt ggcaaaatag caatctactg cttggttctg ctgtaatcta   56940
tttacccacc catcccatct ttctttcaat ttaaaaggat aatgattta gtcacgatta   57000 tacataaacc cattaccata ggcaataaac aatggggcaa accattggtc ccatagttgg   57060
agtgtggtct gaagtgtgtt ttggtggaga gagatctatg tctggagata gctaacatgg   57120
atttggatcc cagatctgct cctacctgtt gctgtgcctg tgaccaaatc atgtgatctc   57180
tctggtttca gtttacttgt gaataaagta aataccttca tcaacacctg ttttttgaata   57240 caatgttttt ctgtaatttt tgcttcttat aatgttataa tgatcatcct tacatctaaa   57300
tcttggttta cattttcatc aattcttttg gaaagattgg agaagtaaat tttggagatg   57360
tatgtcggct attaaaaatg tttaatttttt taattaaaaa ttaaaacgtt gaaaaatcct   57420
```

```
gatgcaaaat aaatgcatta tgcttagtga actcttctca tttcgaagtt tattcacctt    57480 cttgttttg caagtttcct gaaaaatgca tataaagtca ctaagttagc agaactttat     57540
aaaattatat aactatatat aatcttttga tatcagtgaa gccagctgat cctatagaaa    57600
taatgtagga attataatca ctagcacata atttaagagt cctgtggtct tattcatgtt    57660
atttaccctc tctgaatctt acatatagta agagggttat tatacataat atgtgtacat    57720
gtatacaggt aagtaagtat atatgcttat gtgtaaaagc agagttattg tgagagtcaa    57780
atggaaatgt gaaagtactt tgtagttttt tattactatt attaattttt aataaaatgg    57840
taacattcat ttaataatca ttagttttaa cttcagattg tactggattt cctctagtat    57900
ttcttaagat tagtgaataa agtatttctc ctaataaata tattgactac tgtctttcga    57960
tcaaacatat taggtatatt tttacagtag catcaggcag tgaaaatttg aagctcttta    58020
tagaggactg atttatgatg aaaaggaata acatgaacaa atggaattat atgaagcttc    58080
cccagaaata tctaagaggg gccaattta agaaatatct gacttctttt tcatggacat      58140
ttcaaaataa acctaactca tatggtacag ttttaagag ggaaaagaaa aaaccatctg      58200
agaatctctg gaattctgcc gaaagtatca cttggcattt tattctacct tctggatgca    58260
gttgattgac agtagtgtta tgatgccagg ggtatagtga ctagaaaaag aaaaccaggg    58320
aattcagtgt tcttgctcat gaagaacagc ttggttcttt aaaaacaatg agattttgcc    58380
accccatctc acaaacctat gatttgtgag aacaatccct tttgtgttgc aagacttta     58440 catttctctt cccacactat attagaagaa taaacattgc ttcataagta ccgattgata    58500
gtctcatttc atatttttaa aatagagtta ctttaaggtt aaatttttca tgtagattaa    58560
aatgactaag taaccattca catatttcaa ataaaatata ttttactac aaaaggaaaa     58620 taactagatt cttaagtgtt atagtcaagt gtaattgagt aatatgaatt ctaaatgaat    58680
ttctaagatc tgctcagctt tcactacttt aggaaggaac aacttaagaa aaatttaat    58740 aaagatatct cttcacacac atggcagtgt tgtacttaga gaacatgacc caaaattttt    58800
tatgactgca tattgaattc ctgatactct tgggaagctc caaaagcacc agtggagttt    58860
ccagatgtaa ctgtggctgc agacccgcca gtcccggtgt tggaagggat cattataggc    58920
tcttgtgtgc agactcatct tcagacccag aggaattaaa taacttgccc aaagtcgcac    58980
aactttctca tggtaggttg ggcactagaa taaatattgc ttttttcttaa gagttttagc    59040 ctccgtatta tgaaatcttc tatgttctgc tgatgatatc tcctttcttc atctgttttc    59100 tattttaag caatggaaat acaaacttgc aactccccat ttccaacaca acttagaaaa     59160
aacaatattt aagaaaaaa ttacaggcat ctcatctcct ttacctgaca gatgcttgat     59220
agtaatggcc tctagatagg gatgacatct aatataaatg tgtcctttca agtcaagctt    59280
tctctgttca ttagtagaaa tattgtatat caagtgtgca aaaattttct tcaacaggga    59340
gctttgtttc cctccttta ttataacaat ctgagctttg tggtcccagg gtctcctagt     59400
gcctgtcttt aggtctgttt attcacatga agaaagcatg tcatatagta ttatctaaga    59460
ctcaggctgc ttatgcatga tgacagaagg gttcccaggc acaaacattc atccatgcat    59520
tcatccatcc acctattcat ccattgattt ggctgataat tattgactac tgttgagttg    59580
ccctcagatt tagtttctgt ccttctgcca tggggaaata tggggttaag ccacaacata    59640
ctcttctctt cttttctgc accttcttag tatatttagt tccatttgt ctagccctgc      59700 ctctgacttc tttgttgtac ttcaggtttt ttatcattga aagttattc tggatcatag     59760
```

```
atcattctct tggtcactttt gcttgttcac ttataaaatt aattcagaaa aaatgaccca   59820
cagtaattac cgtaaatcac agaccataaa ctataatact gtatattgta ttatagtaca   59880
gaaatattta tactttaaaa tgttttaaat atagatatta taaaaagata tgtctcatat   59940
aagtaatata aatactttt tattacctct tctctcccta ttctccaggc cagtgtttta    60000
aaaatccatc tttatatgtc catcctggaa aaaactcatg atcataaatg agtttctcaa   60060
tagagtttat aagcccacag ttgaaacaca attgtcttag catccattta gttgtcatac   60120
ttttaagatt taatggcaaa tattatgttt tgtttcttca aaagaaatat tttaaaattt   60180
tagtaaaggc agttagagaa ggtagagata atggactgtt taatcctact tttcatccca   60240
caagtgaaca aaaaaatgat aaaacatttt tcccaaaatg tagctttaac tatacttaaa   60300
tttggactaa aatgggagat atcttttcta ctattgaaaa gccgtgtctg tagattaatg   60360
ctaaaatcgg gtgtaaaagc aaaatttgtt tggcttgatt gccaatggcc cattcatttg   60420
gctacagaaa caatagcaca tagcaacaga taatgatgtg agatcaccta gctcaagtaa   60480
gagtgtctga tccgtcaaaa atatatacat caagattcaa aagaaatgtg tgttttctca   60540
agtcatctct gtaaaaatac attaaataga ggaatagaag tttgactttg aaaatacatt   60600
gcagacccaa tccgtctttc ctatttttctg gtgaaaagta tcaaatatgt ggaacctgga   60660
actgctattc tccttcttaa aaatcttttct taatattcta ttgataactg gtgcaagcct   60720 aacttttgt cttacccgat tcttctcaca ccaaagtgat aggaccttca ggtagccttt    60780
ggatagaaga taaataataa tttaactatt gatggaagtt agtattagaa ttagacttgg   60840
aagtctatgg aataaaatga ttctacaaca atttgtactt cagacattag tataacaaaa   60900
catgtttgcc cgtgcatgcg gaaacaacca atttcatgtg gatgcttata ttcacaaagg   60960
agtaaccacc tggggtttcc cactgttgct ccagagaaaa ctagcagcag gagaacttct   61020
ctgaaggtat caagacatct ttaaaaaaca cttgttaagt gttggttcag ctaaagcagg   61080
gagttttcag ttagtaatgg cttttaaaaa ttaaaacaag tttagcatgt aggtcattaa   61140
ccttgaatca ctgtcatgat tattattaac catctgttct caaatcgaaa gatattttc    61200 ttttctagat cacatttatt ctcacattgc tcaatttcac tatatatcaa gacatgaaaa   61260
ctgtaaaaat cacaccttct acattattat ttttattgaa aaattcctaa tgaaacagtg   61320
cgctctggga tagagaaagg aactaactga cattttgctt cttaacttgt ttttatgcaa   61380
gttctaagtg gtttctggcc atgtacataa aagacaaata tctggaaaaa aaactagcag   61440
aagtcagtta tttggctcta tctactttga gaattatgtt atataaatgt taggaaattt   61500
tttgtaatat tcttatttag aaatgaaata taaaagtttt taaaaatatc taaggacagt   61560
atacagtcct aaagtaaagc tgttaggtaa atgctacaca atcctcttat tacagagtca   61620
cttacctgag aatataagaa gagggcctct tgtttaagag taaatgtgag ctgcaatcag   61680
gattctgcac tcatttggac acttagtttt gttttccat gactggtgtt gcctgttact    61740
gagacaccta cctgtcatgt gaccacagct tatgttacaa tgtgtctagt cagacttaga   61800
gatgtgtgaa agagcagtac ctagacggga aactatgggt ctataaaggt tttgccttct   61860
tgggcggagt tcaaactagg aagccacaaa acttccagtt gcattttcac agattaatga   61920
aatatatttt acacttttcc tgaaagatat tttatttgtg caaaccttgt tacaaagtac   61980
agccagttga ttaatcgatg aagtgatttg tagtggattc ttatattttg tgtaagggta   62040
tatgtgaggc cctatatatg aggctttcta tataatgaag tataattcag ttcagcattt   62100
caattcagca atcacttatt gggcctctac tcagttgcct tcagggcttt ataatttaat   62160
```

```
tgataaaggg aggttaatta attaattata acaacagatc gcttaatagt gtaactacta    62220
atttaattaa tgacaaataa caatacatta aagaaatgc attaataaaa ataatatatt    62280
ggtgttatag acaataattt tctgattaac tttattatta ttatttcaat agcttttggg    62340
gagcaggtgg tttttggtta tatggagaag ttgtttaggt atgatttctg agattttggt    62400
acactcataa cctgagcagc atacactgca cccaatgtgt agtctttcat tcctcacctt    62460
cctcccaccc ttcccctcaa gtctccagag tccattatat cattcttatg cctttgcatc    62520
ctttagttta ggtggcagtt ataaatgaga acatgtaatg tttggttttc cactcctgag    62580
ttacttcact tagaataatg gtctccaact ctatctacgt agctacaaat gccattattt    62640
tgttcctttt tatggctgag tagtattcca tagcatccac acacaccccc ctatgcttta    62700
tatatatatg taaatatatc acattttctt tatccactca ttggttgatg ggtatttagg    62760
ctggttccat attttttgcaa ttgtgaattg tgcagctata aacatgcatg tgcaagtgtc    62820
ttttttcatat aatgacttct tttcctctgg gtagatacct aggagtggga tcgctggaac    62880
aaatgattgt tctacttta gttctttaag gaatctccat aacttttcca tggtggttgt    62940
actagtttac attcctacca gcagtgtaaa aaaatgttcc cttttacca cttccatgcc    63000
aacgttatt tttttatttt ttaattatgg caattcttgc aggagtaagg tggtatcaca    63060
ttgtggtttt gatttgcatt tccctggtca ttaaagatgt tgagcatttt ttcatatgtt    63120
tgttggctgt ttgtctatct tcttttgaga attgtctatt catgtcctta gcccactttt    63180
tgataggatt atttgttttt tcttactgat ttgtttgagt tccttgtaga ttctggatat    63240
tagtcctttg tcagatggat agtttgcaga tatttctccc attctgtggg ttgtctgttt    63300
actctgatga ttatttcttt tgctgtgcag aagctttata gttttaggtc ccatctattt    63360
atcttttttg ttgttgttgc atttgctttt ggtttcttgg tcatgaactc tttgcttaag    63420
ccagtgtcta gaagagtttt accaatgtta tcttctataa ttttttaaggt tttgggtctt    63480
agattaaagt ctttgatcca tcttgagtgg atttttgtat aagttgagag atgaggatcc    63540
agcttcattc ttctacatgt ggcttgccaa ttatcccaac accatttgtt gaataggatg    63600
tccttttccc accttatgtt tttgtttgct ttgttgaaga tcagttggct gtaagtatt    63660
agctttattt ctggattttc tattctgctc cattgatcta catgtctatt tttatagtag    63720
taccatgctg ttttcctaac tatagtcttg tagtatagtt tgaagttggg taatctagtg    63780
cctccagatt tgttattttt tgcttagtct tgctttggct gtatgggctg ttgttttgtt    63840
ccatgtgaat tttaagattt tttttcttgt tctttgaaga atgatggtgg catttttgatg   63900
ggagtcgcat tgaatttata gattgttttt ggcagtgtgc tcattttcac aatattgatt    63960
ctgccaatcc atgaataagg gatgtgtttt cattagtttc tgttgtctgt gatttctttc    64020
agcaatattt tgtagttttc ctgtagagat cttccacctc tttggttagg tatattccta    64080
agcattttt tttttgcag ctgttgtaaa aaggctcaag ttcttaattt gattctcagt    64140
tttgttgctg ttggtgtata gcactggtac tgatttgtgt acattgattt tgtatctgga    64200
aactttactg aattaactta tcagatctag gagcttttg gatgagtctt taggtttct    64260
aggtatacaa acatatcatc ggcaaagagc aacagtttga cttcctcttt agcagtttgg    64320
atgctctta tttctttctc ttgtctgatt gctctggcta ggatttccag tactatgttg    64380
aatagaagtg gtgaaagcag gcattcttgt cttattccag ttctcggggg aaatgctttc    64440
aaattttccc ccgttcaata taatgttggc tgtgggtttg tcataagtgg cttttattac    64500
```

```
cttaaggtgt gtatcttata tgccagtttt gctgagggtt ttaatcataa agcaatactg    64560 aatttttgtca aatgctttt ctgcatctat tgagtttatc atatgatttt tgttttact     64620 cctgcttata tggtgtatca catttattga cttgcatatg ttaaagcaac cctgcatccc    64680
cggtatgaaa cccacctgat catggtggat tatcttttg atatgctgct ggattcattt     64740
agctagtatt ttattgagga ttttacatc tctgttcatc agggatattg gtctgtagtt     64800
ttcttttttt gttatgtcct tttctggttt tgatattagg gtaatactgg cttcatagaa    64860
tgatttaggg aggattccct ctgtctctat cttttggaac agtttcaata gaatttgtac    64920 caattttttct ttgaatttct gatagcattc acctgtgaat ccatctggtc ctagactttt   64980
tttgtttcct gacatttttt ctattattgt ttcactctca ctatgcatta ttggtctgtt   65040
aataatttct atttcttcct gttttaatct aggaggtttg tatatatgca ggaatttgtc    65100
catctcttct tggttttcta gtttgtgtac gtaaatgtgt tcacagtagt cttgaataat   65160
ctttttattt tctgtggtat cagttgtagt atctcccatt tcatttctaa ttgagcttgt   65220
ttagatcttt tttcttgttt tcttggttaa tcttgccaat ggtctattga ttttgtttat   65280
cttttcaaag aagcaggttt tgtttcatt tatcttttgt attgtatttt gtgtttcaat    65340
tttatttatt tatttattta tttttatttt tattttttga gatggagtct cactcttgtt   65400
acccaggctg gaatgcaaca gtatgatctt ggctcactgc aacatctgcc ttccaggttc   65460
aagtgattct cttgcctcag ctgcccgagt agctgggact acaggtgcct gccaccacac   65520
ctggctaatt tttgtatttt tagtagagac ggggtttcac catgttggcc aggcaggtct   65580
caaactcctg acttatggtg atccgcctgc cttggcctcc caaagtgctg cgattacagg   65640
tgtgagccac cacactaaga ctcaattta tttatttcta ttctgatctt tgttatttct    65700
tttcttctgc tgggtttggg tttgcttgt cttgtttttc cagttcctag aggtgtaagc    65760
tcagattgtc tatttgtgct ctttcagact ttttgatgta gatatttaat gctatgaact   65820
ttgctcttaa catggctttt gctgtatccc agaggttgtg ataggttttg tcattattat   65880
tgttgaattc aaatatttt aaaattttca tctttcttga tttcattgtt gacccaaaga    65940
tcattcagga gcagattatt cgatttccat gtattgtat agttttgagg gttcttttg     66000 gagttaattt ttaatttat tccactgtgg tctgagagaa tacttgatat aattttgatt    66060
ttcttaaatt tattgagact tgttcatatg gtctgtcttg gagaatattc catgtgttga   66120
tgaaaaggat gtagttgttg ggtaggattt tttgtaaata tctgttaagt ccatttgttc   66180
tagggtatag tttaagtcca tgtttctttg ttgactttct gtcttgatga cctgtctagt   66240
gctgtcagtg gagtactgaa gtcccccact attattgtgt tgctgtctat ctcatgtctt   66300
aggtctagta gtgattgctt tataaatttg ggagcccaag tgttagatgc atatacactt   66360
aagattgtaa atttttcctg ttgaactaat tattttatca ttatataatg tctctctttg   66420
tcttttttaa ttgttgttgc tttaaaatct tttttgtctg atataagaat tgctattctt   66480
tctcactttg agtttccatt tgcatggaat atcttttcc acccctttac cttaagttta    66540
tgtgagtcct tacgtgttag gtgagtctct tgaagacagc agatacttgg ttgatggatt   66600
tttatccatt ctgccattct gtatctttta agtggagcat ttaggccatt tacattcaac   66660
attagtattg aggtatgagg tactgttcta ttcatcatga tagttgttgc ctcaatacct   66720
tcttgttgtt gctgttgtta attgtgttat tattttatgg gtcctgttaa atttatgctt   66780
taaggaggtt ctatttgat gtattcaagt tactgtttca agatttagag ctccttttag    66840
catttctcag tgctggcttg gtagtggcaa attcagcatt tgtttgtctg aaaaagactt   66900
```

```
tatctctctt tcatttatga agcttagttt cactggatac aaaattcttg gctgataatt    66960
attttgttta agaggctaaa tatagggccc aatctcttct ggctagcagg gtttatgctg    67020
agaaatctgc tattaatctg ctatgttttc ttttatagga tacctgatgc ttttgcctca    67080
cagctcttaa gattctttcc ttcatcttga ctttagacaa cctgatggct gtgtgcccag    67140
gtggtaatct ttttgcattg aatttcccag gtgttctttg tgcttcttat atttggatat    67200
ctagatctct agcaagacta ggaagttttt cttgattatt ccctcaaata agtccttaat    67260
gaccccacta tataacatga aatatctgtt attggtactg aggtgctggc cacaaacaat    67320
tctgtgtgtc ctgaaaactc ttcagaatat tcgtcatctt tagcacttgt tatcttagtg    67380
tttgggcttg gcttagagtg atacatctca taacagggca acagaaagaa ccaggaacca    67440
agatttatat aacataagtc agtaaaacta gaggcaccag aggtttacat ttacattagg    67500
ttacattttc taacaggtag caaagcacat gaatgaagtt cagtggaagg ccttcctcag    67560
gaatccagta aaaaccaaac atacacacac acacacggac atccgtgagg caggaaggga    67620
tgtccactat agtacagaca agcatcctgg aaggccatca aggagtaggt gggtttcagt    67680
tgcctcagga atgtggcatg gacccaaact aagtgagtac agatacttgt cattgaggag    67740
aagattcaaa atagcatcct aggtgtaaaa actgaggcac ctggggcagg ggaactaggt    67800
ctctggaatg ttggcttaaa agcacccctc tcaggaaagg cctcatatgc catgcagggg    67860
gttatatatg tgttgtggga cacagatggc aaggagataa ttctatgcac caggctccac    67920
tactaacagg taaacagacc aacattaaca gagacttagg taaaaaggta ggtgcccagt    67980
ggtcagttct caggcacttc caagatgcac ctaacagaaa tgtaacttgg tgtctattgt    68040
gtcctaggtc taacaactga agagaagtga attagtacct cttgtggaca gagaaacagg    68100
ggcagagacc cattacaaag ctgtctcaga taggcatttg aagctgttta agtatgtaga    68160
ggcttaagtc aggctggttc tgaaatgtga gagagggtta agcttcatgg gaaatcagca    68220
gggtagtttg ctattttta ttataaccaa tctcacaata gtttgggaca tcaaatatca    68280
aattgttggg aatatttatc catattagtc tttttgccac taatatttaa aaatagttta    68340
caatatacaa caaaaagttg taaaatttcc atctccactt aatcgatctt atgtaaccca    68400
tacaatacat caaatgtcct ttccccactt tatgttttta tttgctttgt caaagatcac    68460
ttggctgtta gcatttgggt ttatttctag gttctctatt ctgttttatt ggtctgtgtg    68520
cctattttta taccagtgcc atgctgtttt ggtgactatg gccttatagt atagtttgaa    68580
agcaggtaat gtgatgcctc cagatttttc tttttgctta atcttgcttt ggctatgtgg    68640 gctcttttt ggttccatat gaattttagg attgtttttt ctagttctgt gaagaatgat    68700
ggtggtattt tgatgggaat tgcatttaat tgtagatttc tcttggcagt attacccagg    68760
cttttcttat tttggcaccc tgtgctgctg tctccttttc cttctttctg cttctcttaa    68820
ccaactgtta cctacacttc aatactttct gagggcaatt catcctccag taagtctccc    68880
tgaatcttct cttccttccc tggcttatta tatatccttc ctcttggttc ccatagcacc    68940
tatgcacact tctgtcattg cacttgccaa tttgttttat aatgatctgc tcatctgtct    69000
cctcacttag actatgagct cactgagagc aatggctgtt gcattcacct tatatcctca    69060
acaccattct gaaggcaaga gaaagaatac ccagaggtgg agctgggaag ctggttgtcc    69120
aagtagtgaa tgactctagt ttgaattgaa ctctatagcc agtgggcaat gtggatgtgt    69180
tgacagtttt ttaacagggg actagtgaaa acacattttg ggtttagaaa aaattgcaag    69240
```

```
tctgatgaca tacataggag aagagattag agataggaat ttcacttcag aaatttaacc    69300
acaagagcaa gtgacagatc acggaagtct gaaccagact ataaatgtga gaatagagaa    69360
aaaagttaac aatttgggtg tgaaagggcg agggagagag gtgtgaagaa tgactaagtg    69420
tggatctgtt tttaaggatt gaatggaaat ttgagcattt tagctaatca ggcctaatat    69480
tgagcaaagc aaaactcttg caaattgtta tttcaagtgt gggctgagaa aatgaaaaaa    69540
tataaattct cacgttataa cctcttccgt gtgtctgatt tgatagaatc cagccccatt    69600
gcctccaaat tccattgcat cttagaccag caaacacaag tgaattctac ttaaccccag    69660
aattctgtat gaaaatctta ctgccttttt ttttctaatc atgtgtcaaa gtgtgggaag    69720
aacttttatt tatgttttaa taaattgtca gtataaccat ttttacttga aaatattata    69780 attttttcaag taaacaaatt gtttctctaa gttgaaaatt ttatgatgga ataaaagtat    69840
ttttcctcaa aacacataga aattttacaa caatatttta gagttaacta aatgtttctt    69900
tagtagttta gtcacttaaa aagtgatatg attatgaaaa tacttaaact ttgtcttttta    69960 actatttcta ataatgctat tggtataatt tcatattttt atactgatct tttctccaaa    70020
ctttagtaaa acatacttct gtaaacccct gcccacaaaa ctgaagtcca catttacttc    70080
tgaatgactg ataagtttgt aaaagtatgc atgaatttcg ttattaaatt aaagttttta    70140
ttatatttta tgcacaatgg tataaattat taaattaatt ttcaagctta tagaacattg    70200
ataaagattg tcattagaaa accctgagtt gattgttata cattacataa cctttcattg    70260
gtggattagt gaatatgtta tagggtgacc atgaatccaa agaatcaaag ctggctacag    70320
caaacagagg gtcaaaagga tatggaacta tgcatgatcc agcaaaacac tcaatatctg    70380
ttttcctgga atgttaaaag acaaagaaga aaacttgggg aacactagat gcatatagtt    70440
ctggttcttt aagaataaaa atatgggccg ggccggtgg ctcatgcctg taatcccagc    70500
actttgtggg aggccaaggc gggtggatca caaggttagg agttcaagac cagccaggcc    70560
aacatagtga aaccctgtct ctactaaaaa tacaaaaaaa aattacaaaa aaaatacaaa    70620
aaaaaaaata gccaggtgtg gtgacaggca cctgtattcc cagctacttg ggaggctgag    70680
gcaggagaat cacttgaacc cgggaggcag aggttgcagt gagccaagat agtgccactg    70740
tgctccagcc tgggtgacat agtgagactc tgtctcaaaa aaaaaaaaa gaataaaaac    70800 aagaatggtc agagtcctag taccttgtcc agtgtagtgc tgccttgaga ttgcattgca    70860
atctgtctga gagatagtaa aagaaagtga taccttcctt agccctgttt ctctttagac    70920 tatgcttttcc cctctccaag ttaatatctc tcagtctaaa gcctgggaaa aggtgccaat    70980
tttgtttttc tttcttcctc acacctccta gaagttacac tgggacacta ttactttttt    71040
ccaggctttg gccatgtgta ttgttttgga gagtcaactt ccttttttct ttcattctgc    71100
aaatagtttt gagctgtcac tctgtactag gtgctataaa acttacaggt gcattttaca    71160
tgcctatttc ctataggcca cgatttaaca aaatgttcat aaatgagaat taggagtgca    71220
tgtattgaat caccacacat taactgaaca gctttcattg ccagagact atattgacag    71280 tggagattca aagataaact agagaaatct catgcttaaa taactttcta taataaatta    71340
tataagagaa gtaggttcag ggatcttggg agctcagaag caggatgagt taaacaaaag    71400
ttggattttg cctttagctt ggtttcatta tcctgaagga agagcctgaa atatagtgta    71460
gggtgcaagt agtatatgtg ggtggcaatc tcgggaaaca ggagcatgtg atgaataagg    71520
agaaaaagcc aatataaagg tactgcattg agggcaatga gggctctaat tctctgcacc    71580
ttctcaagca ttgtgcagat tggttttctg gattatcagc ctgaaggaca aaacgaagaa    71640
```

```
acagccatta gctcctgtct cccattgtct gagagctgcc actaggatat taacttcctg    71700
aaattctgca gaaatctcct cttactttgg cactggagat gcccatacgc agaaagcaaa    71760
aaggcacagc atatttaagg aagctcataa gaaacagtgc atccagaagt ggcgagaatt    71820
ggaggaatgg acatgagact ctaagaacca gcgcctttga tgttccttt gatctgttat     71880 gtagctcttc ttgtacacag gtgagcaaag gcatgctgga caaatggatt cacatgtgct    71940
aaagcatggg gcaaaaacca catattaatt caggaaaaga caagatgcgt ggccctctct    72000
gtctctgtct aagggtgaat taaagagggg atatatgtac agagtggcag gcaggactt     72060 gagataagaa ggctaggtgg gtgctctcat gctagtagca ttatagtaca ggtgatgaga    72120
agctcctgaa gaatcatctt aacatttgta ttttagagca acagtattga gttctgactt    72180
agagacagca aaactaaaga cagaaagact atttttgatta ttaatgatgt agatataaga   72240
atatcgtcaa tgtgaactaa agcatgaagc tacttatgat atatcattaa aaggatttaa    72300
ctgattggag acaaacgaga gggatgggga aaagaattca tttgttttta gttgctcttt    72360
ttttcctact tattcctttg ttccgagtgt gaataaactt tgtaaacttt tatactaaaa    72420
cattctgctc attcatactt atttctttga tgaaacaagg aaaccccttgt atagttataa   72480 acgtgtgaat caatttaaat attaggaaat ttttttaaat aaagctagtt ttctgaaggg    72540
gaaaaacttg gttcaatttt ttgctggcaa tctgctttgt gattttgaa catgatatct     72600 acatctagac tcatgttttg ctagctggaa tttttttca aattaacgct accattatta    72660
tatgctttac tatttagctt ttgcagcctt ggaaatctat gattaataca ataattctc     72720 tatggcaatt ttaaaaatac atgtaaaagc cttcaatcta cattgctact gtgtcgtagc    72780
acaaaaaaag aaaatgtgat caaattttaa taaaatctac aatttattcc cttctaaata    72840
cagtcctagc tcaggagaaa ggaagctatt tgtattttc agaatcaaat ttccctaaat     72900
gaatatagag aaagaattat aactgaaata ttgttgaaac agtggtcatc tcaaatctga    72960
aggtcattcc aaaaaagttt ctgagttttc attgcctcaa tctaaaagtt ggccttttttg   73020 gtaatagatg aaagtaaaat aattgaaagg gtctgttgca gttttggaat atcttgaaaa    73080
tatagtagag tgaagccttc ttcccttaaa taaaagacaa gttgctgatt gttttctttc    73140
tagccagata gaataatgc cttctttctc ttgttagtct taacacctca cttgttacta     73200
tgtgtcagaa aggcgagaca ccataaatgg agatactact gatggaggtc atctgacatg    73260
gggctggtag gcagtgggaa gactggtatg gacacaggtg gcttaggggt tggggaatga   73320
tatgaaacta aggaaatgat aattagcaga acccagtgtg catgtgtgtg cattcgtgtg    73380
tccgtgtatg tgtgtactgt agcacaatgc aagaaagaaa aaacaaggca gacttttcat    73440
aatttcaggg ataaataaat cctttatcac ttcatgtaga atattggcta cttggaggta    73500
tatctaaacg taaatatata actatataac tacatgctaa ttaaaaacat acaaagaaga    73560
agtgcctaaa gaattacaac agaaagtggc atagtgatta ttagagttaa tataatataa    73620
ataaggccag gcatggtggc tcatgcctat aatcccagca cttttggagg tcaagttgca    73680
gggatcactt gaggacaggg gatagagaca agcctagcca acatggtgaa acccatctct    73740
actaaaaata cagaaattag ctgggtgtgg tgatgggcgc tggtaatccc agctactcaa    73800
gaaactgaag caggagaatt gcttgaaccc ggaagctggg gctgcagtga gccaagatcg    73860
cgcactgcac tccagactgg gtgacagaga aagacccggt ctcaaaaaat taaaaaatag    73920
tataaataat atttcaaaac acaagtctgt taagataaaa ggtacagagg aatggtgaga    73980
```

```
tgactttttt atttgtgtga taagggactg ttttctgtga ttgtgagaaa gaccaggagt    74040
taagaaaaag tggccatcaa taaatcagcc acttatgggg aagaaccata aaccactctc    74100
agatgaaata caaatgcagt cattatttaa tattattgga atatttgtat tagttttttgg   74160 tatgtgctgc tagtgctggt acattttagt agtcaattaa tattttgtta atcttaattt    74220
ctaactaaat tccagagtga aatggaaata ataatgaaaa aattttattt acaaaacaga    74280
ttttgttttt ttctgttaag aatgatacac agttgtcctt cagtagccat aggggattgg    74340
tttcaggacc tcccttgggt actaaaatct gcagatgcct aagcccctgt tataaaatgg    74400
cttagtattt gtatataacc tatgcacatc ctctcatata ctttcaatca ggggtcccca    74460
accccagggc catgaccagt actggtccat agcctgttag gctgttcgat accaggctgc    74520
acagcaagag ctgagctcct cctcctgtca gctcagtggt ggcattagat tgccatagga    74580
gcacgaaccc tattgtgaac tgcacatgtg agggatctag gttgtgcgct ccttatgaga    74640
atctaatgat aaatgtaatg tgcttgaatc atcccaaaac cattcccctt ccctcacca    74700 tccctgtccg tggaaacatt tcttccagaa aaccagtccc tggtgccaga aaggttgggg    74760
actgctgctt taaataatct ctagattact gataatgccc aatacaatgt aaattctatg    74820
taaatagttt ttatactata ttgtttagag aataatgaaa agaaaaagtc tacatgttca    74880
gtttaagtgt tgataagtgt gtagagaaaa gggaacccctt gtacattgtt ggtggaaata   74940
tagattggtg cagtcattat ggacaatagt acggaggttc ctaaagaaat taaaattaga    75000
attacctaag acccagcaat ccctcctctg gatgtaccca aaggaaataa aatcatcacc    75060
tcataaagat atctgcactg ctatattcat tgcagcatta tttacagtag ccaagatatg    75120
gaaaccacct aggtatgtgt tggtgcatga atggataaaa gaaactgtgg tatatgtata    75180
tacaatggaa tattattcag ccttaaaaaa ggagaagacc ctgtcatttg ccacaacatg    75240
catggacctg gaggatatta agctgtggga aataagtcca acacacatcc acacacaaaa    75300
ttgcataatc tcacttatat gtggaatcta aaaagaaaaa gttcaaatat aaagttagaa    75360
taaaacagtg gttaccggcc ggatgtggta gctcacgcct gtaatcctag ccctttggga    75420
agccgaggtg ggtgaatcac ctgaggtcag gagttcaaga ccagcctgac caacatggtg    75480
aaatcctgtt tctactaaaa gtacaaaaat tagccgggca tagtggcagg tgcctgtaat    75540
cccagctact caggcagttg agaaaggaga atcacttgaa ctcaggaggc ataggttgca    75600
gtgagccgag atggcgccac ttcactccag cctgggcaaa agagcaaaac tctgtctcaa    75660
aataaaaaaa caaaaacac agtccacaca ctggttacca tgagtgaggt ggcagggagg     75720
agattgggag atgtagatct aaggatacaa agtagcagat atgtaggagg aactaaaaag    75780
ctgacatgca ggatgacaac tatagttagt aatagtgtat tgtattcagg attttttgcta   75840 attgagtaga ttatagctgc tcttgccaca ggggaaaaag tgggtaacta cgtgagatag    75900
acaatggatg tgttaattt tgtcactata ataacctttt caccatatac attcatctta     75960
taacagcatg ttgtttactg taaatatata caataaaatt tatttttaaa tatctgagta    76020
tgatttgatg atttgtgaaa atagagtgaa ttataataat tttaaatgta agttaatgtt    76080
attagaaaag aaacagaaag aacataccac acagaaagtc tgtctgaagg atctttgttt    76140
tctccaccaa tacaagtgtt cattgattca gaggtggatt atgagatatg accataaaac    76200
aaaaatttca agggaaatat atttttattca atgaaaaatt ctcaacacaa ctgttatatg    76260
ccagtaaaca ctatatcttt taaataacag gtcatatcta ttatatttaa aattcaagga    76320
gagactacat tagagatgct attagatcaa cttctaatttt caaagatttc taagatatgg    76380
```

```
aacagttact ccttatacaa attaaaaaag caaatgctga agaaattcag ctacatggat    76440
acaccatgag gtggaaagat gctccataac tcttagttaa actgcactaa ttacacataa    76500
aaggaaaatg tttcatttca ctgtaatttg gaaaccaaag aaagaaaaga ctgaattttt    76560
acatactgtt aaagagattg cgtatctgtt ctaagtttaa gacagaggca aaatgtattt    76620
tattcatttg tcctgcaccg tttagaaata aaattcaact tcctttaat ttttttaag    76680 aataaaaaac tcagtctaag gaaagtctta aagtttcat tttaagtgat ccactgttct    76740
agaagtttaa tattttgttt aaaatgttta tgttctgtat tccaccaagt ctagttttaa    76800
aacaaaacaa caacaacaa aatacttctc taacttggag tttaaggtga agaaaccaa    76860 ttacgtggtt tggaaatgtc acactttca tctctttttt aaaaaatttt ttaattcagg    76920
acagaaattg tatggattta gtgtaagtct tgggatctca caagtgtcag tatttcactc    76980
tcctccatat cttgatagca ataacttgaa ataggatctc agtagctcaa gcaatactgg    77040
gctctgagag ttggttaaaa attatttggc tgagcgcctg ttgctgaggg aagaactaat    77100
ctcgagcata ttttttggagc caaataccaa attgtttgtg cttagcaaca cagcaccagg    77160
cttgcccttc agaatgattc tagaccaaat gccagaaatg ctctggttct gactacagag    77220
ttctattcac aaatgacagg aggcaagagg tcctcctcac tttcagaaga aggtcctttt    77280
gctttcttag tcaatggtag gaaaaccatt gtggttttca ttgcattaca taatttttaa    77340
ggtgattact tcaataagaa gtgctctgtg tatatgtgtg tttatagacg catttttaa    77400 acactggaga atttctgaaa gtagtacaaa ccttgtaatg tcaagtagat gtgggaaaaa    77460
gggagtttac aacattctct cctgacattg ctctcctttg gcatctgcat ttttaaaatg    77520
ttaaaaatgt ttaaaaacgt gtgcttaaca cttaatttgg tgatagttgc tgttaccaag    77580
gcaactctgt aactccaccc agataaaaat aaatcttgaa gatgagtttc tgtgtctctg    77640
agcaaatatt tttgtgaata gtagaagcag agaaagttaa agatacctga gcttttgatc    77700
tttactagtt ttatagatat gtttatagtt atacattttt attcatacat tttagataaa    77760
taactttgta aagcaattga ttcttcttgt aaaaatcaag tatattctta atagactgat    77820
aaactttctt ttttttgagac agagtcttgc tctattgccc aggctggaat acagtgccat    77880
gatcttggct cactgcaacc tacctctgcc tcctgggttc aagcaattct cctgcctcag    77940
cctcttgagt agctgagatt acaggtgcat ggtaccacac cccactaatt tttgtattct    78000
tagtagagat ggggttttgc catttggcc aggctctgag aaactttta aggtctcttt    78060 tgcagccagc tatttgtcta ccttatttca ttcttaatct cactagccaa tatttttct    78120 gtttaagtgc tttcagcaaa tattaaatgc ttgtgccttc agtcttatcc tgtggaaaca    78180
ctggtaatga caaaaacaca tatttcaacc taatatacaa tagaaacaga atgccagtta    78240
ttcatggagg agaagaatag acttctgtat ttaaaataac atttttgctct gtgttttaaa    78300 atcattcttc cttcatcaat tgtaagcatc ttgactataa tttatacacc taaagataaa    78360
taattcagta gcaatgataa ctgaaaacag gacacataca atgaactagc taaattacca    78420
tacattctca tccatttcaa aaatagctct gtactttttt cagattttgt tagaagaata    78480
ttcaatacaa atttttattc aatgaacact tcagatgtca agattgttac ccacatggac    78540
aacagtaacc taggtaaaga ttctgcagcc aggcgtggtg gctcacacct gtaatcccag    78600
cactttggga ggctgaggcg ggcagatcat gaggtcagga gatcgagact atccggcta    78660 acatggtgaa accccatctc tactaaaaat acaaaaaatt agccaggtgt ggtgtcatgt    78720
```

```
gcttgtagtc ccagctgctc gggaggctaa ggcaggagaa tcgcttgaac ccgggaggtg   78780
gaggttgcgg tgagccgaga ttgcaccact gcactccagc ctgggtgaca gagcgagact   78840
ctgtctcaaa aaaaaaaaaa aaaaatttta tacctgggct ctgtgctcac cagcagaagg   78900
ggtaacatgg cttcttagga caaccttact tgaccattta cttctttgac actagggta   78960
ttcttagatc agcaggtcct tccctccact tatgcacatg aggctacag agagtctggg   79020
aggcagggaa tttatgattg gaaacagtat acttttate taagaaatta ttaatgtcac   79080
tgcattcaag tgattaacac catcaatatc ttcaagacta aggggattac atgatgtgta   79140
aaattagaaa actgtcatct actagtggct aggcactta attatattaa gcatgcaaca   79200
agagaactct tcaaatgaat ccatctctcc tctgtattat ttccaaccct tggatcccca   79260
tctgtttctg cagacaacag ctatgctgct gaatgtctta atggtttgct gccccaacta   79320
gcttcaagat actgcaggtc aagcatagca tcttactctt ccctgcatct ccagcacctc   79380
tcagaatgtt ggtcacatag aagatgtttg ctgaggagtt gaataagaat atgtacaagg   79440
gacacaatta gcattgttta aaaagatgt aacaagatag ggtaaggaa agctttggag   79500
gataaatctt tagaacaatc aataatatct tctcctctgt tggttagttg cccttcaatc   79560
tcagccactg aatcaaatac aacataatta ctattctgat atgttcttga atcgaatatc   79620
caataataag atattcggat gcatagccat gtctaatatc aaagcccatg cttttcgcta   79680
ttattgtact ccatacatta gcttccaaat ttatttgcaa tccaaatatt aaaagcaagt   79740
cataagctta gtatcgccaa tgtgatacta agtatccact tactaaactt tattttcaaa   79800
atgtggtttt atctcagttt aatgaacacg gcatgtttta atttacactt tcatattata   79860
tagtaagggc gtggttacag atatgttaat ttcctgtgct gcttcacaat gatggaacat   79920
aatagcaaat gaaactgtta atttgcagat acccataggc ctttggtgtc tgaatagaaa   79980
taaacacacc tacaactgag agaggaagca tgtgaagcat tccagtgaac agaggccatt   80040
tattcagtca cagacacagg agaaaaacaa caattaaaaa aaaatctctg atgaaaagtt   80100
cataaaaagt tcactcagtt taagcatatg tcctataact acttaaaata gagttcttct   80160
taaatatcat tctttgctgt ttttagattt cttctgcctg tatcaaatta atagaacaca   80220
gcatactttt aatttgctct ggtttcttag tggggcattt attaaacaca ttaaaacaat   80280
agtctcaggg ttttactgct gatgttaaag ttctgctttc ctacttacca actgtgtcat   80340
cttaaggcac atactttgcc tctctctcaa atctcccaaa tggagaatga taagaatacg   80400
tacctcaatt aaagaagcta taacaagtag aatgtttgga aaagtgccgg gtacaccata   80460
agcccactat gagtattgga ttgtattacc tctgaaagct gcagaatgga attctcaaag   80520
ttatatgtcc ctaaaatcct cttaagtgac agaaatggag aaattagcag tctgtctaag   80580
agagcttttc tagagtctgg gcatatgttt ttaggacaag acagttcagc ttcagcttaa   80640
aatgagagag cacgtctgtg tccttactcc tgggtgccag gtttcttgtc cccatcttaa   80700
gacaaataat tttggtggag aagaggcagt ctctttgatt tcgctctaaa aaccttttct   80760
ggaggaggta gacactctcc accccgtttt tgagactcat gcagctgagg atgactggct   80820
gagtacaagc aattgttcct tctaagcagt ttcaattctt ataacttgtg gagatattct   80880
taagtccagg ggattttgtg tatggtggat ttttattaca aagtcctgta cttcatagga   80940
acaaaataat tcaaagtcag gaaccagatc aaagccacaa ctcagatatg gcaccttgag   81000
aagttcattt gtatttcact tgcataaaaa ccctcaccac tgctatctga ttttcacaaa   81060
tcattcaaca gctatccatg aagcacccac tgtgtgtctg gtctctgtgt cagtccctgg   81120
```

```
cttcatgtgt ctttccttct gtaccctgac tccccaactc atgaacacat gaagtaaaaa   81180
aatgaaaatc ttttttctgac ctctcttcaa aatcactttt ttcaaaacaa acacctctca   81240
cctgctcatc ctccagccag taaatcacag gggcctagaa atgtcactta caaatatttt   81300
ctgattctgt ccctcccttc aagcttgcca acattatcac agtttagggc ctgctcatct   81360
ttcccccaat ctccaattag atctctccac aatgcaattc tgcacattcc ctgttacaac   81420
ccttcaatta tttcccagcc catccaaaat aaaatctaag cctcttacta acacattcag   81480
gaactctgtg gcctacggtt ttctacagac taattttcca gcagttgact tccagtgcaa   81540
gtgaaaacct agtgtcatgc ctgcatgata gataaatttg aagctgaaga gcccaaatgt   81600
atagaccatg ccatgaaagg tttatagtca tgacacagtg gccctatagt acagtgcttg   81660
aagctggctc tctactgtca gacagaccac ttgccagcca tgagacctgg ggcaaaatgc   81720
cttaattttt atgtgcctca agttctcatg tgagatgaga ataaaaatta cccctatttc   81780
ataagatttg ataaagtgtt tagcataata cctcataaca attgcaattc agtggtggtt   81840
attattataa agaaaagatg attaacttta tcttaatgtt taacttgttc tgatagttat   81900
tgatctatag ctttgatatg gaggtttgag aatgacctgg aaagaattgg ccacaatgat   81960
tgaagatagt gatacaagaa taaagatgaa ctgcaaaatg taaacctgca ataacagaaa   82020
gaatgaagtc actggtctca tgggaactga tatgggagaa aaaacagat caaaaggcta   82080 ttcatgtttt gggcctcttt gtcaaaatgg aaatgagaaa ctggggaata aaaattaaag   82140
caattctagc atctggtttt aacataattc ttatccctaa aaagaatcta taagaaactc   82200
ccaaaatgac aggcagccgt gggtagcatt gcatttcaag taatctttta attgttaaaa   82260
tttaagtttc caacatgaac ataaaatttt caacctaaaa gaaatgagtt ccaaatctga   82320
gacaagtgaa aaaggataaa gcctactagg gggtaaattc catctcttta gagatctagt   82380 acccaatttta gcaatgtcca atcaagcctt taactactac atttgaacac ctcatcattt   82440
caaaatgtta cttaatgatg ccaattaact gtacaatgtc tctgcatagc acatagccct   82500
aaaatgattt gtgcaatgtt actgtcagta aaactgaact acagggaatg ctcatattct   82560
atgtcattat atacagaaat gcaatatcaa taaagtgata tctgttggta ttagaaaaaa   82620
gtgaaaattt tcatatcttt ctattttctt ttttcctcaa tgggatgctc ttgttaaaga   82680
tagctctgca tagtaaggtt tgtataaaca ttatttagct aaagttaaaa ggggtaacat   82740
actggttcta gcacagatat taaaacaaat tagtttgtag gtagggcagc aatcaattat   82800
attactaacc atagctttgg tccttttatc ctttcccatt tgattttaca cagtgggatg   82860
ttaaaggttg aatgtctttg gtatctataa acttaattga aagctgttat ttgtttgttt   82920
aagtctgttg atttttataa tcataatttt actcctatag atttcttgta ggagtactat   82980
atgaatttat gttgcactga attttgttat gttatacaaa ttaataggct tttatttatg   83040
gaaagctact attgatctgt catttcttaa aaaattacta aaaagtgtta aaactttaaa   83100
tgttggagag tttatatttt aaaagttaca tgctagaaaa acatgatgtc tgagtatatt   83160
agaagttata gataattcat ctgtcaacta taaaactctc caacactgcc tttctttaat   83220
gaataatatg aaatttagca gtgaaaatgt gacaatgtac aatcctaaat aaatcaacaa   83280
atttagagat gtacctctaa aaccattgta aattcaacag tgtaattttc cattggactt   83340
tcacttattc attcattaaa caaatgtttg tgagtgcctg caatgtatga acattgtac   83400 tgaagctagg cagtgtgagt tatcatatgg gattatcctt taaatacttc tgagggcaaa   83460
```

```
aaaaaaaaaa aaaagaagag aaaaggtgtg aggaaagata aagggttaat tcattaaaaa   83520
ataacacttg aggactgttt tctttgcaag gcataaagtt atcacccttt caaacagtag   83580
atatttcaca tttaggatgc gagactccag ttccaacaaa gctcattgca cagctgctac   83640
cctgattaaa ctgctacatg aactctgagc aatgtagcat ggtagccgca tgcttctgct   83700
tgcatgatgg ttaattcctt ccattctcat tagtgatttt ctgagctttg aaattctgat   83760
ggtacctagg atataaagca tatttatcta actgaaaaac agataattag atgtaacata   83820
aaatatgaat ggctttgtca ctttattgta gcagagaatg aatgtgggat aaattaaagc   83880
tgatgctaga acatatgcct attttttagc tggaaaattt caagattat gtactttggg    83940
cttgagaaag aaatggagtt tattttttat gcactgacat ctcttttttt ttttttttgg   84000
aagagctctc ttaggaatga atggtatgta aatacagtag gaatgtaatt atagattttc   84060
ctgacccagt tcctaaataa tagatatcat ttcagaagtg ccccaatacc tgaccttttg   84120
ctccaagcca tatcaaagca cacatctagt ctacttttca ctctcattcc tagccactat   84180
gacaatacta ttcagataaa acttctagtc ctctacttat gtgactcata ccaacttgac   84240
cttacgatag tgactggggg tgcatatcta ggttcatgct gtttgtccat tattatggtt   84300
ttgtgagaaa aggcaaaatt tctaggtaaa gtgttatgag gacgaataat ccaccaggca   84360
accaactgac cctttcattt gccatcttgt cacttcaaac agctctccag aacctgcagc   84420
cagcacagac caaagtcagg tttgtctcct cttctgttga tgaacaaagg ttgattccat   84480
atcgtggcta ttgtgaatag tggcagtaaa catggcagta ttgtatgaaa atatcacaga   84540
tagcccttaa atatgtgcaa ctatgatgat ctatcaaaat taaaaattaa aatttatttt   84600
taaaagttca gttagaaagc ttgtagttcc tggcaaacta ctacctttct cggcaaaaga   84660
atttgatatc tcttaaatat tttctgccta atgctgatag attgtattta catattccat   84720
taatgcaata aataaaatta caccaaaaca tcagcattat ttatttccag gggcatctct   84780
caaaataaat tcctccaaaa ttcacaaaac caaaaccaat gtgaaattgt actcaggat    84840
gcaaatgtag cccagtgaag catttgccca cttgtttggt attattgaag cacaattaga   84900
aaaatgtgca atgtatgccc aaaaattcta taataagggc caggcgcggt ggctcacacc   84960
tgtaatctca gcattttggg aggccaaggt gggcaaatca tgaggtcagg agatcgagac   85020
catcctagct aacaccatga aacccagtct ttactaaaaa tacaaaaaat tggcccagac   85080
gtggtggcgg gatcctgtag tcccagctac tcgggaggct gaggcaggag aatggcatga   85140
acccaggagg cagagtttgc actgagccta ctctccagcc tgaacgacag agcgagaccc   85200
catctcaaaa aaaaaaacca taataagaac tttttaatat actatattat aatgtaaaaa   85260
gactagatgt caaacaaatt aggtgatggg aaggaattga gggagaattt tagactaagc   85320
aattgagcag cacctgtttt tcaccacaaa tctgttacat gtattgctca attgtgctga   85380
atccatattg ggtcctggtg gctatgtaat agtctctttc ttggataaat gtttgtcctc   85440
tcttatggtt tactaatggt gtacagaaca gcattgaata gtggttattt cctatgactt   85500
cctagatatc tctctcataa tcctgaatgt tttaaagatc attcttagat agagtacagc   85560
tagacacgaa cctagtggaa atcaggtag acaaaattta aaaggagtct taattgaagg    85620
tcattttatt gtcctcagta ttaatcttac ttaaaacaaa cctgtcactg agcagaactc   85680
aaaacaccag agcccttgc caaatgtgat ttttacaac aggagcgctg gcagttgaga     85740
ggagtattct gtcacacttg agagaattcg agtccctgaa gatttatatg aatgcttagc   85800
tattatcgaa ccatctcttc acagatgact tagtaaatgt ctgccttgc atcagataat    85860
```

```
ggcttacaag ttaatctcct cttgctccct gttacacaca tatacacctt cttcctaaac    85920
agctcataag gtgaaagaaa gactcagatt tctgactatg taattgataa tatcacacgg    85980
actgcctgct catcatctgc tagtcacatt ggcagagttg acagttttgg agacactgaa    86040
gacagtgcat atattaggaa ataagcagtt tcctgatata aattttcttg tagtttataa    86100
attacatagc atttattatt ccctcatatt ttataacatt taataataga actgacacat    86160
atattcattt taaactcaat tgtgtataat aactatcata gcaacccttc agtgcctaaa    86220
tatcaaatct tccattcctc ccatgaacat cttgaatata taggtactgt ggttagctcc    86280
aacaagcttt tggttagaat tcattgcact gatacataga cattgtttta aaggcaattt    86340
caaatcaaag ctgtcagctg tgaatcaagc acaccttaaa aagtgacaca tttgtcacta    86400
gattccagcc tctcaaatta ctgacacgca tccttttat gtaaagatga cattgttctt    86460
tcctgatata ttgcattcct catgaatttc ttatagtcat agaattttta taaaccattt    86520
cagaatcgct gaaataaaca tcaatatttt taacttttc attctgtcaa aaatattgta    86580
tgcagagata ttgctgtaag tgtgtatacc tgtgcttaag agactagggc tgaagagaag    86640
taatcaaccg aaccactggt gtaaatgtgc gtcacatttt tagtgactag aaattgaaat    86700
aattccaaca aatttatgtg cttgggctt gagaattcag actgccttag gctaagataa    86760
aaatcttttc ctggtactat ataccttctt ttattgaatg actacctggc tctttctatt    86820
atatatgcag attttgtacc tctggtcatc tttgtaaatg gtgcctaaaa gatatttgaa    86880
gaataagtga ccagcaataa gaacaaatgt ctatacaaaa gcacccttta gttggatgta    86940
attcactact ttgagttgtt aataacctct aaggatgaca gtagctatta gttgaataaa    87000
ccattatgtc tattattaga acactagata gtttataagt ccaaacaatg cataaaatac    87060
ctatctcatg ttaccattgt ttaggttacc agataattgt tctgtccaat tattccactt    87120
aattttttgc ttgcccatta gctaaatggc aagataaaat ttgtcaaacg ggggggaatg    87180
tattgaaaat gctagacaac tacacttaaa atgaaaacag gccaggcgcg gtggctcagg    87240
cctgtaatcc cagcactttg ggaggccaag gcgggtggat cacctgaggt cgggagttca    87300
agaccagctt gaccaacatg gagaaactcc atctctacta aaaatacaaa attagccggg    87360
catggtggca catacctgta atcccaacta ctggggaggc tgaggcagaa gaatcgtttg    87420
aacccaggag gcggtggttg cagtgagccg agattgtgcc actgtattct agcctaggca    87480
acatgagcga aactccatct caaaaaaaaa aaaaaaaga agaaaagaa aacaaatgca    87540 taatttgcaa atattatttt tatattgtat gttatctagg gcttctaaat gcattcttct    87600
tataagccta ggtttgcaat aacattcatt tagaattgag taatttttaaa tataatattt    87660 tataaaataa aatataataa tttctcttaa ttcttttgaaa atattaaatt aaaaggggggt    87720 tgcaaactct gcattccaca tttccatccc aacatttaat tttagcaatt ttgtagtctg    87780
cctaaaatgc aatccatcat ttactgttta gaaaataggg aatgtacaca aaggccttc    87840 agctttccct gaactccata aaaatctttt tgcttcttta ctgcccccct ttgtcaggag    87900
ttctgaggaa ctgttttta tcttaagtct cacaaagcat ttaggagaat atttaaactt    87960
aaattctttt aaaacttatg ttcaggacaa agtaacattg tatgcattgg tgtcatatgt    88020
atttaaattt tgaatttttt aatactggca aaatgaggtt tcaattttaa tataaattat    88080
ttaacaatct taaatcatta aatatattac ttaatatatt taatatatct aaacagtcac    88140
aattttccca tactaataat cataaaaaat cttacccaat ggtcatatag atatacttaa    88200
```

```
tggagttttg ggggggtatt tttgtatatt aaaaaattca tatatttgcc ttacttagaa      88260
gaactgatta aatgaaagta taatattaac aaacatattg ttattttata tttgcatttg      88320
tgataattat atttgaaacg ttcaagattt tccaatgaat ttcttttgca tttgcgtatt      88380
tgtgcctttt tattataaaa ataggtggct ttttagttcc actgcataag tttcaacata      88440
ggtctacaaa tagtgcatct ttttgaagtt aatcattata atcacaaatt gaagttgcct      88500
gagctccaat tggagtctaa atggatgact gaatcttatt attcgaaacc cactgttgct      88560
acacaatatg ccacacaag agagtacaca agacccgtct gattcagcct cagtgccata      88620 aatatttttaa tggtttcgtt ggaatctgga aatggagctc accacaggag atgcttcttc      88680
ctttgactct cattattatt tcctttacaa attaattaat aaaaacttag atgctaaatt      88740
agcacttgat gaaaacttat atagccttga cattttgatt ctgtgagtga ataaaaatac      88800
ttggagaaat aaaaatccta atcatgttca ggaatacccca caaggtaaca agtacatttt      88860
taaactttaa aaacatttat tattcatgat aaaacatgtt gtgtgattta aatataaatt      88920
tttattattt gctttaactt atttccggat taaaaagtaa atgttaccct agctgttcta      88980
aatggtaatc ctcatgatta aaacagcaat ttgtcatatt tcagttacaa atgatctttt      89040
attattagtt atagaacata agtttcttca ttgactgagg cgatgtttca agtagataaa      89100
tctgttaaaa aaattgtggt catattctgt taaattctca taccaggcaa tttgtttgat      89160
attcaggaaa aacctagcca ctgaccaaaa actctacctg ccttctcagt tgtatcctct      89220
tggacttaaa ggggactggg aaagttataa gatggttcat gatagtccat caacatccca      89280
agaacaaaaa cagatgttgt actgacagca tcatatgatc atatgcatgt aagagcacat      89340
tcatattgcc aaatcagttg gaattttttca cggttgaaag ttaaatgaaa tgcttagatg      89400
tatgagtcat cggagttaaa gacaattaca gccagattta tggctgtgct aaaataaagc      89460
tagttagaaa acagaccaaa ttccatgacg ataccaagtc tgactaatga ttcaccttaa      89520
atttcggagc aacattttatc ctcacttgtt tgtttatttg acaatgtgcc cttatccatt      89580
aagtaactag gaggaaggga aaagcactac gtgggtgagt gacaagacac tgacactgat      89640
ttgtgacttt ggataattcc tggatgctgt tatctgtttt ggcatagaga tggatctgta      89700
actgctaata attgccgact gtgaccatcc cagaggccat ttacttaacc caggtatttc      89760
agacctgaca gcccgaggat aaacacgatt tccctccatc actaacttca tctgcagggc      89820
ctaagcctcc ttcacagtct ctccagtgat ttattggcat ctccaagggt atctcacatg      89880
tgctgaagaa caaatctgct cactttcatc tgcttggttt tccctttga atctgctgc       89940 tttaaaatta ctaagggagg aatcatgcct gctgctaccc ttgccagtga ccttgcagtt      90000
tgtgccctga ttgttccaat taccacaatc aaaacagaag cgtttgcagt tactgcagtg      90060
ctctctctgt ggatgtcagg tctgactcag agagccaggc tggggaacag ccatttccac      90120
tcttgtacct ctgcaaaagg acttccatgt tccgtaaaca gactcccacc tctcattttc      90180
cccccaagca aagcatcata aattagagag catgtaacgg gaaagaaaat ccattagcca      90240
tttgggttca gtcagacaag ccagctcatg gaaagtttat acaggaaggt cacatttcaa      90300
ttgagatcag gagggtgaaa gggtccagct gtgtgatgag agagagaatg ttcgggaatg      90360
tggaacagag gtatccaagg cagaacaaac tcgtatatga aggctttaag ggtgtgcaaa      90420
tctagcatat tttatgacat aaaagagtcc tgattagcta gaatatgatg aatgtgagaa      90480
gaggtgaagg ctggagatag gaaaaattat tccagatctt ataagctata gtaagaaatt      90540
tgcatattat atatagactt gtgggaagcc attggatttt gtaagaagga gattaacatt      90600
```

```
atcttattta tgttatttgt gatttataac cccaaatgtg ccagatacaa acaaaccaaa    90660
aataataata ataataataa gaagaagaac aacaacagca atggaactgt ggtgatggtt    90720
ttggtcacaa aatgcatata tatctattt tcacaatgca aaaatatttc attatttcaa     90780
attttaacat aaatgtgggt atgcatgagc ttacaaatct tgaagtttat tggggaatat    90840
tggtgagcat ggttttatt gcatggtcac aacttactaa tgggaaacat ctgaataacct    90900 attgagttaa tgcatgcaca ttttatttt cctggaatac tgagaaaaag gttgctacat     90960
aatgtcttga tagcttctaa gtcatggctc aaaagtgaat gtggaatctg ctaatcggaa    91020
tggactcaga ttcagccaag ttctcaaaaa catttgcttt catagatgtc ttcaagaaac    91080
aaggagtctt gaatttaaat tgtgaagtgt ctatcttaga atagagagat ttaaaatctg    91140
actgtatttt gtttaaaaaa gcctatataa ctgtattata taaaattatt tatactacag    91200
ttaaaaaaag aatcccatcc tatttgtgcc taaataagtg cctgcttgta gcatgaaaac    91260
tatttgttga gggtccttag atcctcagag catgctgtga aagtaggtac aattgttctt    91320
tctatataag cctcttaaga taacagataa ttgccagaaa tacagcacac agtacaaaat    91380
taccttgttt tacttttgcc acaaaaaaca atttctttg gctttgagca ataaagtcca     91440
atgatttttt tcctttcaaa atatcttcct ccctctccat aagttttata tttattcacg    91500
aaggaatatt ccaatatcgg atgttttgt ctgtgtctct tcctggaaca aatgttaatt     91560
aatctctttg ggtttgtatg tcaagtggag gggtgggat tggggacagg tgatagttgt     91620
ctagggagtt aacttcatct ctataggaga gtggatagac gctgtatacg aaaagctctt    91680
gaaaagggaa atacagcagc cacttcctca gggcttccat ggtggtcaga ctccttgatt    91740
gctttagatt aactctggct tttgtccttc ggaggccacc agattgggtg gatagacatt    91800
gtccttgctg ttcttttgac ctacctactt gtacttagg ggaaaaaaat gcctgtaata     91860
ggttaaatgc tttctcaaag atcaccaaag tatataacac atggcaaata gacagagaaa    91920
tgagacagta taatcagtat aatttataaa agtaccttac agcaggatcc catgggatat    91980 gggtttttt taaaaaaaat ctacctaatc tttttcattga actcctattc aggattcatt     92040
atattgaata tggctcagag acctggaaaa ttgtttccac ctttttaatt tattcaccat    92100
catttatgga agttttcaag gacgtttact tacctacctc agttaacaga ttgtactact    92160
tgggaagtct ataaatatga gcttaaagca ttttctgagt tttaaaataa tttagattgt    92220
gtagaatgtt aaaactaaaa gaggaaaaaa ttattcagtt cctcagttga acctagcaat    92280
ttatcttttc acagtgtgct caagtatagt ttttgaaaag taagaagat ggttttata      92340 caaacataaa cacatttcaa agatttatt caactaatta attagtagtg gagccaataa     92400
gctggtaaga ctggtttaaa ggaatatctg aggaataaag atttatagaa acagtcaaag    92460
aaattctaaa gagaattgac taatagatat aaatctagta aatatttgat taataatagc    92520
agtaacctat ggaattatgt tttctactga gcataaatga gcatgaatct ctttgggttt    92580
gtatgtcaag tggaagggtg gggattgggg acaagtgata gttgtcaagg gagttaactt    92640
catctctata ggagagtgga tagatgctgt ataagaaaag ctcttgaaaa gggaaataaa    92700
gcagccactg cacatctgca catataacct gtagatctgg gggctctaat aaaaaagtta    92760
atggcaatgt caaaatctgg tgttttatct tagataactt catagtcatt gattgagccc    92820
cttaaaaata acatttaaag gacatgtagt cattctgttt ctttattgcc aagttttcag    92880 caattttct catgagaatg agtgctaaga aacttttggt ggagcgtggt ggctcaagcc     92940
```

```
tgcagtcttg cactttggga cgccaaggct ggccaattac ttgagatcag tagtttgaga    93000
ccaccctggc caacatggtg aaaccttgtc tctactaaaa atacaaaaaa aaaaaaaagt    93060
gggatgtggt ggcatgcgcc tgtaatcctg gctactctgg aggctgaggc acgagagtca    93120
cttgaacccg ggaggcagag gttgcagtga gccgagatcc tgccactgca ctccagcctg    93180
ggctacagag ggagactcca tctcaaacaa acaaacaaac aaaaagaaa cttttaaaat    93240 ataacaatag agacattaca taggcccaca aaaccacctc caaaaaagca ttctatcacc    93300
tgcaagaaag catatatata tatctgcttt tgtgtatata tatatatata tatatatctg    93360
cttttgtgta tatatatata cacacacaca cacatatg tgtgatatca gcatgtgtat     93420
ttacacatat attttgtgca tgtatatttt taactaaaaa tgtgctagga gttagatatg    93480
aactgatttt ggaggaggtg atatgctgta gagagagaga atgggagaat agcagtatta    93540
taatctctct ccattgtatt cagttttttt ctttgtctga atttttaata gaagtcagcc    93600
agaagatgtt agtttctggg aaatgtgttg agatttacag tcaaatccag agagaactag    93660
aggcttatga gtaaataagt aaaggttatg cagagaaagt attcttttc ctgtgtaaac    93720 ttgaatattg gccaggcgcg gtggacacct gtaatccagc actttgggag gccaaggcgg    93780
gtggatcgac tgaggtcagg agttcatgac cagcctgtcc aacatggtga aacccattct    93840
ctaccaaaaa tacaaaaatt agtgggtgtg gtggcaggat cctgtaatcc cagctactac    93900
ggaggctgag gcaggagaat tgctttaacc taggaggcgg aggttgcagt gagctgagac    93960
agcgccattg cactatagct acggcgataa gagtgagact tcatctaaaa aaaaaaaaga    94020
aaagaaaacc ttgaatattt cttgtacttg tgttcaaatc atacagttat gaaagtttac    94080
ccctagctgt tacacttaaa atgtacttct gaaatataca gagagatgat acagactatt    94140
aatgagttcc actaaacttt taatggttta gaaaatacaa atattttctt atttttctgg    94200
aattccagcc attaatgtaa acattggtt tcaacataaa taacacactg gcatgcacat    94260
atgcctaagc atgggccccc acacatacag acattctgaa agaccacttt ttaaaaatat    94320
tcagtaccgt atattgtgca ttccttcttt atccacatac ttaagctgct gcaagcatcc    94380
cattgataac accagtaata aaagatggga ccatcagtaa tgagatttga aagcccctt     94440 tgcaagaaag taaggactag aaggtggaaa tcactctgtc ttagagtcat atggattggg    94500
gctttgctag aagtgtgtgc tctcagggaa agctgccttt ttattttctc cagagaaaag    94560 ccttttgtc agtaaaagaa gatgtatcat ccaatgcata tgtaaaattc taaacagcag     94620
ataaaacaac attcactatt aatctctgca aaagaagata tattgaaaaa atcctcaagt    94680
gtccctcttt gggtttcttt gttatatatt aaagcagtta tctttagatg catgagaatc    94740
acctgaagac cttattttta aaattcagat tcctgtcagt tcactcccaa agattccgat    94800
tcagtagtta agagacaaag cctaggaatg tgaatttaca atcaacacct caggtgatag    94860
ccatgcatgt tcttaatgct ctactactat ctatgcataa aaggaagata aagtttttaaa   94920 aacttgaaat gtggtataac agtttagtat tgaataatat acatttttac ttattgtaac    94980
aaattatgat atctacttgg ggcaacagta tcttttattt tggatctgaa tcctaatttt    95040
ggctaggtat cactgaggga ttcttagtct aaaacaatta aatggagtta gtggttttt     95100 ttagtaactc ttgattttct gtttttttcc attggcatct tacaaaattt attcattcat    95160 ttttccctt ttcacttggc attatttgtt agacagtgga caaagaact atagaaagta     95220 gagaagcatg tgatgttgtc ctgctcttag attctcgcaa ctcaggagag gacattcgct    95280
tacaccaatc atctcaaaac atggcagttt atgctgaact cagtccaatg ggagagcatt    95340
```

```
tgactgagca cataggggaga gaagttagct ctgttgaagg ataatcaacg aagaattctt    95400
aggaaaggta cagtcattca ttgaatattt gctcggcact tactaggtgc atatgtgcac    95460
taagatctaa ggatgggctg atgaagaacc caggtccctt ttcttctagt ggacatgcag    95520
actggcctaa aaaaaaaaag gtaactggaa aatggataag gaaactgagt cactcggttt    95580
atttattatc actcggttta tttgcttttg tttgtatttt cattttgaca cagcacagtg    95640
tcatcttaac gcatcctcca aagtgaagga tggggtggat aacactttag ttggcatttc    95700
tgtagccagg agccaggatc tttctcccat aattgcatta acctgggaag gcaccctcta    95760
ggtagatttg tatagcaccc tggttaatca attatcagtt tacttcttgt ctcactaagc    95820
tttaacacct tacatttatg aagcagtgta aatataactt tagcatcttg atcacagcaa    95880
gcacctgatt tgtattttt tattagctca agtgaaatca gatcagagaa gtacattaca     95940
ggtcataaaa tatgtgcaaa tttcataatg acctccttt aaaatgtgca aaaataagat     96000
tgttaaggca cattccagag ccttggggg tgtgtgtgtg tgtgtgtgtg tgtgtgtgtg     96060
cgtgtgtgtg tgtgcttgtc ttttgagaat atctgtatat cagaaattt ggctgagaag     96120 caatcttctt cttagtggtt ctttttctct tttgaaaata aagtactaaa atacttaaa     96180 gatgcagaac agcaacctgt tcccagtgag actctcgttt aattaatgtg gtgatctata    96240
tagagaaaag ggacaattgc aaaagtccct caataattat ctaaccacag tctttaggta    96300
attacagcag aaagattttc aagacacaaa acaccctgga aaatttgacc tcttattttg    96360
attcaggcct ttcatttctt aaatatttc tttaatgttg atgtttatgc ttgacaaggt     96420
cagcctaatg ccagatgaat ccctggaact caaaacattg ctgaattcac agttgaagga    96480
ttttaatata atataccagc ttttaaaaat cctacagtga gaataacagg actgaataaa    96540
aaaattaaga aatgctcagg tagaaataaa tagagaaatt tagaaaaaaa ataaaacgta    96600
ttcaaaataa gtattaagca ttggcaaaga aaaatagta gcagacaatt acatgttcca     96660
tttgtaaaga tgattattaa ttagtggtct tgcaaaacat tggagaaaat ttgctgaacc    96720
atcacattca taaatattaa aaccacccat tagtgaaaat cttttacta aacttcacaa     96780 ctgatagtca aataatgttc agttttctc cattgcaata aaaaataaag gcttttgcct     96840
tcagatcagt ctctgggcct tattaattca gtcagccaga agccacatgg aaatattttg    96900
ttttgttaaa agccagcttg ccctcatgat ctttttaaaat cttttaaaaa tcttccatca    96960
gccctctccc tgacttgaat tatggcagtg cttttctaaac tggtaaactc aatctccttg    97020
gtgtgcctca agatagagta cataaaccct ccttagaaat tgagctctca attctaaatt    97080
gcactctcca tgagagcaag caagaatgct ttgctttgta ttaagtggtc acaatattaa    97140
atataaccat agacagcact gtattttcta aacaccttat tttctttaa tgactgacat     97200 aaattagatc ataagtatac aaatgcatat ctgttgtatt tttcagcacc atgtgttttt    97260
ttttcttttt tctgagttat tttcctgctt tcggcagcct tttctctcag gtgccttgtg    97320
atccacagtg gtgtgtgttc acactaacca aagcaatagt cttacctgcc agaaatagct    97380
gtgacattta aagagaggtc caggggaagg cacagtgctt aacatccaag tctgaagagc    97440
taatagtgaa attgggcat cagctacaga gagatttagg ggaagtaaca ggcaggttaa      97500
atattttatg gaaatgattt ctgttctgta tatgattgca attaacacat gtcaatctgt    97560
ttcattaatt tgttaactca tctattatgc tatgccatga agaaaataaa attggagttc    97620
tttatttttt tgagatggag tctcactctc ttgcccaggc tggagtgcag tggcaggatc    97680
```

-continued

```
tcagctcact gcaatctcca ccacccaggt tcaagcgatt cttctgcctc agccacctga  97740
gtaactggga ctacaggtgc gtgcaaccat gcctggctaa ttttttgtatt tttagtagag  97800 atggggtttc accatgtggg ccaggctggt cccaaactcc tgacctcaag tgatccgcct  97860
gtcttggcct cccaaggtgc tgggattaca ggcgtgagcc accgcgcccc gccacaaaac  97920
tgaagttcta agcttcagtt tagatgctca ctaaatgctt gttttgcaat acctgactgt  97980
aactggcagg aatatgtttt gaaagtcctc attttccagg tatgcagatg aaatataggg  98040
gcattatcta ctatgtcaaa ttataatgat ttatcagtgg cacatgaaag tcgcctcaca  98100
tttcttaatc agtgatatac cattatgtca tgccaccttt taatgtaata tgtttacatc  98160
tttctttaga tgtaagcatt catttagttc atcacggtgg ctttcacact tactccaaga  98220
acgctatgag ttcctttgat gtgctcaagt ctcctgcccc agggagaaag ggagtggtga  98280
gcaggaatcg ctttaatcta tttacacaga tatttttctt tccatttatt ttaaaggaat  98340 ttttttttaac ttaatgagta tgcagtgacg gtggtgatga tgatgatact aaggtttaaa  98400
tgattagata gtcaaatctg gctggaatt gtaatactgt tttgactttt aatcttagag  98460
aagctccagt ctgcttattt tctgggcata aacacatgag aacaataaca cagttctgtt  98520
atctgaatgt tgttatattt tgtttgaaac attcagtgac tttcaaatat tgtatttgcc  98580
taagaaaatt caacagagtc agacattctc ttccaggtta aatttggtga gtctgctagg  98640
aaaataaatt ttgtgcactg gtcattctga tctagtggac gttctaataa aagcacctt  98700 gtgctgccta cgtcttcact ttaaagataa gatacctggg tactcgacac caaattatag  98760
tttgagatct caaaaatggg ataggaaac cacagctcaa aaacaaaaat actagcactg  98820
gaaaagatag aactagtgaa gatgaatcat tctctagact ttaaattcag agatatcaaa  98880
attaagaaaa agtaggagga ataaaaaaag agggtaagca aaacaatata agtttgtata  98940
gcaagagggt ataaagcaaa tacaatattt tcagaaaaa ttaaataaaa atagatttac  99000
ataacattgt ttttaatctc aaagatcaaa tttcaatttt catctcattt taaaacccat  99060
atgcacagtc tcctttatat acatcagttg ggtgtcaaag tgactttttt cttgtttcca  99120
aatacagtta ttttttaaaat ttaattgtat gatttaggaa tttgaaagca agccagtttg  99180
cacacacata tgttattata tgtgtgcttt agacttggtt tttagttaat gtaacatgac  99240
agggccacct gagttatttg tttacaaact agctggaaag ccaccctgga ggagaaacct  99300
ggcaacaaaa tggtctgcag ctttgttatt gttatctata ggattggatg ccattattgc  99360
tgtaaaatag ttcacaagaa ctcagtctat gggaaagact caaaaattct ttgcctgtta  99420
aagaaaaatc aggatattgg actggttagt ttaactaaaa agtgatgata ctcagattct  99480
gcttggattc actgcttctc agcagttgtt ttgtttcttt ctaattgata tttttatttttt  99540 cagagaaccc attataaaac tcttcttctt cccttaaaat cacaaccaca caacagcaat  99600
taaaacatgc tttgacgtaa gactgatatg gttttaaacc cagcttgact atcgaatttt  99660
ttactttagg caaaacacct ctgacattta tgtcttatcg tcagtaaaaa ggggtgatta  99720
acagttttac aagattattc aataaataaa tataaattcc tccttttcct tcctttcctt  99780
tcttcatctt cagcatctgc atgccataag ctcattttag ttctctggac tcatgttaac  99840
atgtcccacc tttcccaaat taaacatcat ctctgttatt ggctccattc ttttcctctc  99900
atttgagaca attctttatc aaccaacacc ctctctgctc tgtattgtga aactctgctc  99960
ctactacatt aacagtctct tggtttcttt aaaaagaaga caaaacaatt aagaacaga  100020 agcaaaaaat ctactcaaat ccccaattgt taccctcaaa attaattgtc ccacccctag 100080
```

```
ctttctcatt gcacaactct ttgtcaaaat gttttctacc atcacagcct tcaatgatct   100140
ttctggttcc tttatctcct gaagtctgac ttctacctcc atctttttct ggactattca   100200
acacactttg agaaaaaaca tacttttgtt aaacaggtat gcatccctga agcataaaat   100260
acatagtact gaaagtgcac atgtgtggtt cttcccattt tttttacagc acttgaaact   100320
gacaagtagt agtaccaatt acttagtaaa agaccttttt catttcattt ctgaaatatt   100380 gttatttttcc tttttcatct tccatctctg actacacctc caattttacc tctttgctgc   100440
cttccttcct aagaaagttc ttcatgcaat gccatcttgt ttttcttcac ttgcctcttt   100500
ttctcacttt aattttatga actctgatga cttacctctg tagtgtaact actcaaaata   100560
tgtatttctg aagtctcaac tccaatctca tattttcaac ttatatttat ggaggcatct   100620
cagactcaac ctacctaaaa aatggcttat ctgccctaaa atctactttg ttcttttttt   100680
ctctactgct aataattatc ttcctagttg gtcaagctca aaacctaatc attttactc   100740 cttgtccctg tgtcagctgt ccacattcaa gcagcgtatc atttctgcac attttttcaag  100800 caagtcagta actgcctttt gtttgggact gtcttttcat atagtgaaca gccttggaag   100860
atagaaatca tttctccttc taaaacaaaa ggcaggtgtg cttgcagcct tggatagagg   100920
tagtgcctct ttctaaagca aagggacatc tttactggcc attataaaat atccatgttt   100980
cctgagctct gcgttcctct tttctaatgc aacccactga gcatgtaggt gtcacctgag   101040
cttttctgtg ggaattgcgg cttgaggaat cagtgcaaga aaatcatgat actcttgcta   101100
atgctattaa tgtgagtagt aaagttaatt gtctctgacc cagcactatt gtgtctttgc   101160
ccagcactca aaagactggc aggcttgcaa gtaggacaaa atgttagatt tttcacagtt   101220
cttctgctta taagtacttg ttaaaaccaa ttaaaacaca acttgtagtt tgcacctata   101280
attttgtagc atttgcttct tatctatgtc actaggatgt gcttagtgac agacccatct   101340
atcatctatt actcaagttt ttggctgtat tcctaggcaa cagagagaag gggaacaaac   101400
aagaggacct gtgcacagtt tgagaaaggc aaaacaccga gcttaattgc agacttgaat   101460
gtagctagca aacgaagtaa ggcaaaaggt tccttttttt tttttttaga tggagtctca   101520
ctctgtcgcc agtctggagt gcagtggtgc tgtctcggct cactgcaacc tccgcctcct   101580
gggttccagc gattcttctg cctcagcctc ccgagtagct gggactacag gcatgtgcca   101640
ccatgcccag ctaactttg tattttagt agagacggag tttcaccacg ttggccagga   101700
tggtctcaat ctcttgacct tgtgatccgc ccattcggcc tcccaaagtg ctgagattat   101760
aggtgtgagc ctccgttccc ggccaaaagt ttccattttt taaatagttg ggttttagt   101820 ttcgattctt tccaaaaaaa ggttttctta aaaaataaa attagcaata agatgaaata   101880
taacaacaat ataatcttat taagacaata tatgatatac atttatcaaa atacttatat   101940
tttcaaaagt gcttaaaata atctagcaca tagtagatgc tcagtaaata tttgatatta   102000
tgactgtgca tgggtcatta taggctactt tatgtatatc atttcattta gtacaacatc   102060
actctgaaaa atgttttatt gttaccgttt ttcagttgaa acatttacgt tgctcaagat   102120
ctcactggta ccatctacta ttaggtcagt ctgccaccaa atctcatgct cttaaatgcc   102180 cttttctcc tgagcttcca acaaatagtg tactgtatat aattgttgaa gggagggggac  102240 tgtgagacaa atatttaga gtgaatgtgt agccacaatt tcagttcctc aacaaagtga   102300
taaaattagg aatcatcctc aatatatatt cttccaacac acacacacac atacacacac   102360
acacacacac aaataccaca agcccacttg aatgcaccc acctacacat tgcaaccata   102420
```

```
gagacaattg cagcattaaa tacagaatat tctgtgtgtt gtttgtttgt tctcccttttg   102480 ctacaaaaat cagaatttct actcaataaa cagcaaaggg agatacaaat gaaccaaatt   102540
aaagaaggaa aaaatgttga aaaaattata tacagaacta tgtattgatt tattgagagt   102600
tcagtaatgt aatccagaaa taatggatgc cttaaaagta attaaaagaa tgcaaataaa   102660
catttagtgc caattaaaga aaaagaaata caacattaga caaaataaaa gatattcatt   102720
tgatgcaatg aggaaataat cttttattcc tctttaaatt ctctgtggaa taaggcatgg   102780
ttataaataa ataaacatct gccccatgga cttaatggat cgttatattt tattgcgata   102840
atcataatga aattgttggg agggattagt atctctagtg taatgctaag aaagataaag   102900
cctgtgccca ggcaaaagct ttcttggttg gtcaaaaggt ttgaagacat ttcaaactat   102960
tctaaaacaa acaacaagc aaacaaacaa aaaacataca atgtctttgc cacatattta   103020
ggaaacaaaa tgaacaattt atttctgaca acctcatagt cttttgttctg tcagaacaat   103080 aatggaaagg tctaaaccag aaaatgctat gcattgaatt tataataaac tattttttcc   103140
tgtaacaaaa aattgataaa cttgatattt gcagatttaa tgattatgtg tttaaaaaaa   103200
atctggtttt tgcccttgca aaaaatcata tatatacaca tagatatgta tgtgtgtgtg   103260
tgcatagtat atatatatgt atatacatat atatacacac atttatatat ataaacattt   103320
cctttaacct cctattttat tccaataaaa atattggtat tagagatagt tctgatattt   103380
catcatgaat agttaacatt gcatttggaa aggattaatt tttttgaaac gtaattttac   103440
cttaataagt agcccagcgt aatattttag taattacaca gattttttt tcaagacatt   103500 tgacaactaa tattgcataa tagttaagag tgtgggcttt ggagccagac ttcctatctc   103560
tgttcattca ctgataaaat ggagacagta gtaacttcct caaagagttg tttttttaaga   103620 tcaaataatg catataaaac tcttgaaatg gtaccaaata cagagtaagc accaaataaa   103680
cattaactgt tattgttatt ccatgtccga ataacacaga aaagtaagaa ttttaatatt   103740
tcatttgaat gacctttaaa ggatacacct agcccattat cttttcttgat aatcttgtaa   103800 gatgattcct tttttatctc cgatctgttg aggcatggat agaggttttc agagaaaaca   103860
ttttctaggt aactgaaaga aagtagcaac aacaaactgt gacaaaactt aacaatgaga   103920
gaatttacaa gatagaataa ttgcaactcc ttttgaaatc aaccactatg gtcctctggc   103980
tgggatagct aagcaaagat attccagcct gaaggttgag atctacttga agagttttct   104040
atccagattg tgagggcccc tcaaacttca cttagtatct gtttctatta gtatggaaac   104100
ttctggaacc ttgtggtatc acattcactt gactacttta ttcctgctct agctatctta   104160
aagcctttct taatctttta tcttttagag aagatacttc taggttttaa atccaccgat   104220
cttgaagcta ttgccttcac tctctgcttc agagcccatc cttttgtata tgagtagttt   104280
gttttgccta aagtactttc tcccagtcag attttaagtc cagtttctca tctgtttttg   104340
agagcaaact cctgggcctt ggctcactaa catcttgaca gcatatttct tctttcctat   104400
gggcttttca gcattccctg gttttttcta aaatatgaaa gcagactctt tatctcttac   104460
tttgtcaaag cctacccctcc ccactgattt ctcacccagt tgctagtttt aagacctgcc   104520 tctgccggg cgcagtggct cacgcctgta atcccagcac tttgggaggc caaggtaggt   104580
ggatcacgag gtcaggagat cgagaccatc ctggctaaca cagtgaaacc ctgtctctac   104640
taaaattaca aaaaaattag ccaggcgtgg tggtgagcgc ctgtagtccc agctactcgg   104700
gaggctgaag caggagaatg gcgtgatccc gtgaggcaga gcttgcagtg agctgagatc   104760
gcgccactgc actccagcct gggcgacaga gcgagactct gtctcaaaaa aaaaaaaaaa   104820
```

```
aaaaaaaaaa aaaaaagacc tgcctccaaa tatcattgta tttgcaaaca tgaaatgact 104880
tattgattct gagctcagca caagagcaaa cctttctcag cttgacccat cttcacatcg 104940
ttaatgtctt attcagtcac tacccaaggg gctgaccttc aagattctaa tccatgaaag 105000
cttaaaatag taaacaaatt tgaatatagt ttaacataca taataaattt tatttctaga 105060
agaggaggat cagcccttag acatgaaaag taaaaatagt ttattcccag atttcccttt 105120
gtgcattagt atattcaacc gagtctatcc aagtaacagg acaaaaaaag ctggcagttg 105180
ttgctgcgct gtgaagtctt attaggtgag tcagctaatt atatggcact accataaata 105240
cagcaggcac tgccctgctt gttaggcttg ccaaggaaaa taaggattta aagcagcata 105300
ctacctcttt gctatataat gacattttct tcttaaaaat gattttgcac caattcctga 105360
tttatccacc aattatttt taatttatgg ttgaatgtat ttaaacctga attcagagat 105420
aaaactagta aatagctccc caaaataacc ccaaatatat ttaatatatt agctttactc 105480
tctcctccac tgccaaacct ttaaaaactg aaataaattg ttttttattc atctttctc 105540 tttttctctc tctctaaggt gattgccaag actaaagaaa cagctagaag ggcaaaagac 105600
aagaaaatca gtaagatagt aacagattat ccaaagtaga gcacggctca ggtgcagtgg 105660
ctcatgcctg taatcccagc actttcggag gctgacgcag gaggatcact tgagtccagg 105720
agtttgagac cagcctgggc aacataatga aacttcatct ctataaaaaa aaaaaattta 105780
aatagccgag catggtggtg taagcctata gtcccagcta tttgggaggc tgaggctgga 105840
ggatcacttg ggcccaggag ttggagacta cagtgagcta tgattgtatc actgcattac 105900
agcctgggca atagggcaag accctgcctc taaacaaaag ataaacaaag tagagcataa 105960
atggcttcta aatatatgtt atttatgtgt aagactgggt tctctaaagg tatcatttaa 106020
ttaaaataga tttgcattct caatctgtag gtatggatta tgtataatgt atttaagata 106080
tgacttacag cgttcaccaa tgtgactatt cccaagtgat ccagatggct gatgacatag 106140
taatttgtac atttgctgag acctgatctg agtaggtatg taacataact gagggagagc 106200
aagtccattt gccgaaagaa agcctagcat atgacccagg agccacatct tcactcagcc 106260
ttgttgctag gtttggctta gcatatataa tagcatagca tgtataattt atgacaaaaa 106320
attatacttt gcacttttta attagaacat tcaaaatgat ctcaggaagt ggcaccagag 106380
atcatcagtg gtctactgta cttcgtgtgt atgtgtctgt gagtatgtat gtgtttgtgt 106440
gtgttcccac attctaaggc atgtcttta caggttagta gaaaatgttg atagaaaatt 106500
atagatttca acatctaaaa cacagtaggt cactacattg ttaaaacttg gaattttta 106560 tcttgttgta aagtcaggcc aaccaaacct aaaatactgc tacattgaaa tagtgcaaaa 106620
tattcaaaat actatagtta tagatttggt agtaggactg taccagacct gtcactctat 106680
acaagactta tgccttgccc tttcacttac ctgttccctt ttacatctat cttactagat 106740
gtaatgctat aaattatatt tctaatatat tataatttat catgtattat aatgtatcaa 106800
atattacaaa ttatgttgca actccccta cctttcgtct gcatattgcc tcagaaagaa 106860
cagatggatc caacagactt caaccacagg cccttagtga caaatagctc ttaatgctgg 106920
gcttgccact ttgatgcatt tctaaagtta tagaatgtta aatgcaccaa gtcctttggt 106980
catttatttt ctaccttaga tctaagccat aactatactt tcccaaaaat taaagtttga 107040
attttaactt aaccatatat aattggaaaa ggaggttggg ttcgttaagt gtaatttat 107100 catgctttat tatcctttgg gcattggata cagcagaaca tgccaatttc tatggcttct 107160
```

```
catgtgacag aatatactta ctaggatgca attaaatact cctcagagta tgtaaacaat  107220
aaatgtaatc attacattat ttttatattg ttctttctta tgcataatag taagactgaa  107280
aatatagtgt tatttctgaa atatgcatat tgttttgctt ttgatgatta aataacattg  107340
tccaaagttt taggttttt gaaatcttat attttttaac aaaatatcta gcctttccaa  107400
aacaagacct caataattcg tttaagaccc agagttgttc ctctccacat agatctctta  107460
aaaaggcaga ggatttatga cctcaagaga aatcagagta tccaaagttt gctttaattc  107520
aatgttttaa aaataaaatt ccttagattt tatcaaaaat tgagattagt ttgatttga  107580 atcagatgcc ctttgctccc cacccaaaa tggcattatg agcagactag gaattgataa  107640
tagaaaattg aacatatgaa atatatcttt accttgcttt ttaacaaggt attcatgtct  107700
atcgccttca tttttaagtg catcaataaa atacatggta attctcttag tgaaatatac  107760
tatctacact atgtacacac tcccctgtct gaggtagaga agtagagaat attcacattt  107820
ttgaaacgtc tatgctattt ttatttaaat acgagttctg ggcttgattt cattttggaa  107880
cacgggtgtg tgcttaagtt gaaccttttt ttcctcttaa gtcaaagttc tttttagtt  107940 tcttcttta tcttttggc tactatctct ctccttcatc ctcctggtgt gagttgttga  108000
gtgaaggtat taattccatt atttgaggct aagtgacatt gttcaataat gcagcaaaac  108060
aatggttcta cccaaaatat cttcaagtgt aaaagcagtg ggcaaaagag aaagtgcgct  108120
tctgctgctt tgaatgttta aggctgtgaa agttgatcac acaaattggg tcattcttgt  108180 tatcccaac taaaacaatc aagaagcctg ggaggaaaag cattcaagaa acatcacatt  108240
gctccaaaag tgtaatttc tacaagtccg catgctgagg ctgcctgttg taacctggga  108300
ccaatttttt ctgtaactgc tgaaaaaact tgctgcagct ctaggactaa ttttgcccac  108360
cactgtcact caccaattga agcttactag ctccccagaa cctttctagt gccaatgaac  108420
tttctcaaag agcagcgtgt atcatttctc tttttcagaa cacctccaac ctcctctttg  108480
ttctttgggt ataccaaaga ccaaccagcc ttgaatttca attttcttc ccacataaaa  108540 gtttaatt agaaatgtat ctctacattt ctaactttga caaagcatag ataccagata  108600
attgatgaaa ccttgctatt ttaacgatca ccatggatta cttcccagtg tcttcagata  108660
accctcaaca tttgccaaca tttgatggac ttcaaatga gcatatcttt tttaaaaaaa  108720
attattcaca ctgacagcaa gtacattggt atactctata ttaaattata ccacagggtt  108780
tacaaacaat tggtgatgtc gggcagtggt ttccaaggaa catacttaac aagacactca  108840
caaggcccta caaacctgca ttttaacaa gggccctaga tgattctaga agagtgtggt  108900
ttggaaagca atttttgcct ttattatgtg tcatttaaa tatatttaaa attaaagtta  108960
taagtcatag aattgaataa agataatttc cttacagaaa gtattactag gtatctaaat  109020
acaatatggt tcaaaacagg aaatttaaaa agattatgta aattctgtag ttgtattcct  109080
aaagacagta gctgaaattt ttttcctactt ctccttgtat cacttccctt ttccttcact  109140
ttcacttccc tggaattgta cttcccaata agctattagc agtgaaggaa gcttcgtctc  109200
atgatctgtt ttatagagca cttcagctgg gacgagtacg aaatgataat cagttatatc  109260
agctattcaa ccctacaggt ttatttaaaa agaacttgaa taagcttttt agggagaaag  109320
aggtcagtct cagccatttc tgtttcctaa tatagctttt aagtctttcc ttattagcaa  109380
tgagggtcat tccattgtaa tttttgata accatttttc tttctgtgtg tcaaatgcag  109440
atataagata ctgaactgag tctatttcac tgttcgtaaa acaatcccat ttgaaaaaaa  109500
aaagtctaca gctattccag ggatagggcc tagtagagag agaataaaag gtattttctt  109560
```

```
actatgtctc tatatcctac cctgtaggtt ctcttattaa gcatacaggc atataccaaa    109620
atccagacgt ttttctcatt tattttattg ccctaacata ttctgggtta atataatatc    109680
ataatgaaaa tttgagaaaa aattgatttt ttcaaaagtg tttaacattt gttatattgg    109740
tagttttttt tcttgtttgt ggtaaaaata aatagaaggt gcacttcaca ccttcaagta    109800
tgattatatt ttgaaaacaa gtcatgaata ctcataaaat gcaattttta atgttctttt    109860
tttgttacag ccaaactata ttaggcacag ttgtaaattg gagttgaaat ttaatatttc    109920
tttatagata acaatgtttt tagaaatagg tttatgaaac agtaaatata caggtatagg    109980
gataaaattg tgtctgatgg tcatatgaag tgtttgttgt tatattctcc ttggaatagc    110040
tgccaaatat tttagtatgc ttaaaatcta cgaatgtgat agagtcaaca aatttagatc    110100
acatattcag aaaaacatag ttagagaact aactattgaa atgagcatac agcagtcttc    110160
ctttatctac agggatacat tctgaaaccc ccactaggac acctgaaatt gcggatagta    110220
gcaaaccccta catatactgt tttttccaat gcttatgtac ctatgaaaaa gtttaattta    110280
taaactaggc acagtaagag attaacaaca ataactaata acaaaagaga acaattataa    110340
taatatactg taataaaagt tatgtgggta tggtctcgct ttctctttcc ctctctctct    110400
gtctctaaat atcttagtat tttggggttg caattggtgg tgggcaactg aaaccatgga    110460
aaacaaaacc acggataaaa ggagactact gtatatactt tttaaaactg atgaaatatt    110520
aaactcatgt ttcttctata tcccacccat ttcccccacc caaacctaga tagatatctt    110580
atttgatctg taaacatttta attaatttgt aaaagttaag aacttttttga agtaaaactg    110640
caatatatca tcacacctaa agaaataaac aataattctt aaatatcaag tcagtgttca    110700
aatttcccca actacctcat atgtgttttc catttgctta tgtagggttc ccaatgagaa    110760
tgaaataaag ttcttaggtt gcaattggct aatgctctct cacttctact ttaagcggca    110820
ggttcccact aacttctttt tagttgcaat ttacttattg aaattagacg tattctttgt    110880
cttgtgtagt ttctcacagt gcaaaatttg ctgattgtag ccactgttgt aagcaatgaa    110940
catgtttttc accaccttat atttgctgta agttgtcagt gatagttaaa tgttaatcaa    111000
attcaaattc ggatcacgta gggcttttct tttttgttt tcttttttcta tttatatatt    111060
tatttattta ttttgagacg gagtctcact ccgtcaccag gctggagtgc aatggtgtga    111120
tctgggctca ctgcaatctc cacctcccgg gttcaagtga ttcccctggc tcagtctccc    111180
gagtagctgg gactatagga gaaccaccac gcccggctaa cttttttgtat tttagtagag    111240
atggggtttc accatgttgg ccaggatgct atagatctcc tgacctcacc gatcatgtag    111300
gacttcaatt gtcgaacaaa cgaacccttta atagcagtta caccattagg atgacctgat    111360
ccaacatcga ggtcgtaaac cctattgtcg atttggactc tagaatagga ttgtgctgtc    111420
atccctagtg tagcttgttc ccacttgatg aagttattgg atcagtgaac aatagcccac    111480
ttaaactagt acagtcttag tttaagatgg tgatgtgtat gtacttccat cagagggcac    111540
ataatacagt aaatcctcac ttaacttcat caatagtttc tggaaactgt gacttgaagc    111600
aaaacaacat ataacaaaac cagtttttacc attggctaat tgatataagc aagaattaag    111660
tcctatggca aatttctgga cacaaaaaca ccatcaaact cctaaataaa gataaatcac    111720
ttctgacatt aaacattgaa attaatgtga gctatatata cgtttaagaa agattaatac    111780
aaacaagtca aataacttac ctaattattt cggtggaggc cgcaggtggt tggagcctat    111840
cctggcagct cagggagcaa tatgggaacc caccccggac aggacgctgt tccattactg    111900
```

```
cagggtgctc ttgtacacac ccactcaccc aggctggaac catgcagaca cacacactca    111960
cctaacctac acatctgtgt acatccttca aagttcagcc aaataacata taaacaaatc    112020
cagtaatatc catcagtctt agttccgtca taacaactcc tttttgatca tcaaacaaca    112080
aacagggtag gtctgccata tttacttgtc tggtccatat caaaattttc taacaaatta    112140
tattagaaaa tcaaatctct gtcagtttca aaatcatgga aaaaaatttg ccttatttcc    112200
cttatacttg gatatcctaa cagtaatcta aatattaatg agaaagttaa tgatgtcgtt    112260
tccttctccc tgttgtaaag aaggttttgc tgtcccgttt gatcactaag actaattgac    112320
actcagaaaa agcataggaa acttctcagc atcacaaaag ctctgtcatc tagagaagct    112380
aggacttgag ctcaagtcct gtgacatgga aggccttgtg cctagccatc ctgcagcaga    112440
ggcgtatcta ccaagaagtg aaacactacg aaaacagtat gtttactcca cattttaaag    112500
tgaggtagtt tggggtggtt catattttat ttaatttata tattatttgg attttttta     112560 gtttataaaa agggcattgg caagggcaga atgatctgta agcttctctg cccacctacc    112620
ataagcatga tctttagtgt gaccttttct tactgttagc cattttctta tacttctgcg    112680
tccctgtcag tcacttccat gtgaagacat ggggaagctt ttttacatca gacatgttgt    112740
tgaaaatcag ccgcgttggc tgagggatta tttgatctct ttctccaagt ccctttaggc    112800
tcacattgcc tctctgttct ttgaattttc acttaccttt atcttcttat aattactttg    112860
ctgaaataaa tgcaaagcaa caaaaggtat ttagtgaaga ataccaacaa agccatgacc    112920
atttcaggct gagttttgta gtattctttg tctaggaaga gatacctaga aaaattttct    112980
gaccatgtat ttgattattt tccttcaata tgtatagtct cagtcttcaa atttcagaaa    113040
agaatttgtt tcttcattgt catttaaaat taatgtgtta aatatgtatg cttttacatt    113100
ataagtggtt ataaaagtta aacacttaga aaaaagtca aataacata catactatcc     113160 aacaaaataa ctttcatatt ttattgtgtt ttcttccaaa cttttttacct ttgcgtctga   113220 attctgtgta ggttgtatct ataatataga caacacttta tagcctgcta aatattatac   113280
cataaatagg tagttgttac ataattctca ggtaatagta atacaggtct ttatcataat   113340
ctactgagta gttgaatgat aattttttttt aagacaaggt ctccctctgt cacccaggct   113400
agaatgcagt ggcatgcaca tggctcactg tagcctctac ctcccaggct caagtgatcc    113460
tcctgcctca gcctcccaag tggctgggac tgtaggcatg tgccaccatg cccagctatt    113520
tatttgtatt tttagtagag atggggtttc attgtaacag cccaggctgg tcttgaactc    113580
ctggactcaa atgatccacc tgcctcagcc tcccaaagtg ctgaaatcac aggagtgaac    113640
cactgcaccc agcaataatt ttttaactct tcattattca ttgaacattt agttaacaat    113700
tctaaaaatt ttgttttcctg ctgtcattga tcttgtgaaa aatatctttg gactatagct    113760
gtggattatt tcctaaatag taaattactt gagcaaaaag tttacatact ttgagggttg    113820
ataacccatg ttgccgcaat gttttcccgg aggcattgtg gagtttagaa tgccagtagt    113880
aatattaagg tgtgccattt tcaagatccg tggccaacat ccctatatgt aagatttttc    113940
caaaacatgg ttctgatttt taaaagtgaa aaatgctact tcatcatgtt cttttttgtgc   114000 ttcttacttt aaatattaga atgaagaagg agccccacag gaaggaattc tggaagatat    114060
gcctgtggat cctgacaatg aggcttatga aatgccttct gaggtaggag tccaagctga    114120
atctttctaa caagacagta ccaaaaaacct gtcattgtca catttctctt tcattagtgc    114180
ttagtgagaa tcatttgctc tctacatgct cattacgtgg acaacttgca agttaagaat    114240 agttttttaca ttttttaaagg gtccttaaaa aaaaagagga ggaggaagat gaagaagagg    114300
```

```
aagaaaggat gtaaaagaaa tcatatgtag tccacatagc ttaatatact tactacttga 114360 cccctttacag gaaaagttta ctaacccctg cattagagaa tatattttta gaaactttac 114420
attctaaaat aaatttctaa atggaaagtt agggaaatca atggaatgcc aaaggaaggt 114480
tattattttt tgccatacat gtccaatggg atgacgcata gtaaaataaa agttacccac 114540
acaagttata gaataaaaag ataaatgcat gatttgcgac aattgatata ttccagtata 114600
atgttttaaa caacacaata tgattgttaa ttttattttg attgaaaatg aaagtatctt 114660
taatagaaaa tgtatcaaaa gggaaattag aaaatactgt tagatgaata aaactggccc 114720
aagaagaaac agtaaatctg aatagatttg taacacagcg aatagattaa attagtaata 114780
aaaaaaaaaa cctacctgca aagaaaatcc caggccgaga tggcatcact ggtaaattct 114840
accaaacatt taaagaggaa ttaatactaa ttagttaaca ccaattaata tctcttacaa 114900
aacagaagag gagacatttc ccaactaatt ttgtgagacc aatattaccc tgataatcaa 114960
aaccaaatga agatatcaca agaaaagaaa ctatataatg gctccattaa aaattgagtt 115020
caagtatgtt gtagtttggt tatgtattat tcctcacggc attattaaaa ggcatgtcga 115080
ggatgggcac agcagttcac acctgtaatc ccgcactttg tgagccaaag tggccaggtt 115140
acttgaggcc aggagttgga gaccagtctg gccaacatgg tgaaacccca tctctactaa 115200
aaatacaaaa attagccggg catggtggta cacgcctatg gttccagcta cttgggaggc 115260
tgaggcatga gagtcacttg aacccaggag gcagaggttg cagtgagctg agatggcacc 115320
cctgcactcc aatcttggta acagagcaag actgtctcac acagacacac gaaaggcata 115380
ttgataataa ttcaacttat agaaattgag attaaattgt ttgtttgcct aataagaatt 115440
tccaatattt tggggtcttt tatgcaagac acagtactaa acacaatgga aaactataga 115500
gtaattgaca ttaccaggac ataaggagtt tacagtctgg taggtttgat gaaaaaaaat 115560
agaaattcat tcattcattt cttcattatg attcctttaa caaacataat tgattgtctt 115620
cgatgtacca ggcatcacag gagcaaaaat atataagaca tactaaaaag taaaacattt 115680
taaagatctg tttcaatcaa tcaggagaag ttttattgag gaggtaatgt tgatctgggt 115740
gggaaaaggt aagagatata gtaggtcaaa acaaacagag gacattctgg cacaagggaa 115800
tatcagaagc aaaggcatgt atgtctgagc atgcaaatgg atatgtctga gaacagtgaa 115860
taattatgac tcaagcttag gaacaaggaa aatggtgata gattgaattt gcagctatgg 115920
gtcaaagaca agttatagag tattaggata atcttgtcat ttcagcttgt attctattca 115980
gaaaacaact tgagttattg aagttatgct tatttgtttg ttttttaagca gaatcctgat 116040 attattagag ttgctcttta ggaggaataa tctgatccct ttaattaaat ccattaatat 116100
ttgtgttgtg gatgctatcc agatactgta tggagagctt gaggtttgaa atacaagtaa 116160
taattgaagc catagatgaa gacgaaattt tcaactggga gagtgaaagt agggaaaatg 116220
tatcttgcct tcaaacatct taatttcctt ctgagaatta gagcatctta gtctggaaaa 116280
ggctttatag acagcttgat tttgttctca catttttacag gtgaagaaac tgagaaccag 116340
acagtccaac ttatttgtcc taccaaacta ggtatatgat cattaaatgg tgcatccgga 116400
tcagaaccta gatattttaa ctctgactac tactgtaatt cacttttata tcagacaaga 116460
aagacacaac tattaaaaat aagataatat ttgctgcaga atatttgcaa aaacattgat 116520
tgtaaatttt agtgtaagtg gggagccatt tcctatctca ttggctgtca gtgctgatgc 116580
gtaattgaaa cttatactaa cagtgtgtgc tgtctttttg attttctaa tattaggaag 116640
```

```
ggtatcaaga ctacgaacct gaagcctaag aaatatcttt gctcccagtt tcttgagatc   116700
tgctgacaga tgttccatcc tgtacaagtg ctcagttcca atgtgcccag tcatgacatt   116760
tctcaaagtt tttacagtgt atctcgaagt cttccatcag cagtgattga agtatctgta   116820 cctgcccca ctcagcattt cggtgcttcc cttcactga agtgaataca tggtagcagg    116880
gtctttgtgt gctgtggatt tgtggcttc aatctacgat gttaaaacaa attaaaaaca   116940
cctaagtgac taccacttat ttctaaatcc tcactatttt tttgttgctg ttgttcagaa   117000
gttgttagtg atttgctatc atatattata agattttag gtgtcttta atgatactgt     117060 ctaagaataa tgacgtattg tgaaatttgt taatatatat aatacttaaa aatatgtgag   117120
catgaaacta tgcacctata aatactaaat atgaaatttt accattttgc gatgtgtttt   117180
attcacttgt gtttgtatat aaatggtgag aattaaaata aaacgttatc tcattgcaaa   117240 aatatttat ttttatccca tctcacttta ataataaaaa tcatgcttat aagcaacatg    117300
aattaagaac tgacacaaag gacaaaaata taaagttatt aatagccatt tgaagaagga   117360
ggaattttag aagaggtaga gaaaatggaa cattaacccct acactcggaa ttccctgaag   117420
caacactgcc agaagtgtgt tttggtatgc actggttcct taagtggctg tgattaatta   117480
ttgaaagtgg ggtgttgaag accccaacta ctattgtaga gtggtctatt tctcccttca   117540
atcctgtcaa tgtttgcttt acgtattttg gggaactgtt gtttgatgtg tatgtgttta   117600
taattgttat acattttaa ttgagccttt tattaacata tattgttatt tttgtctcga    117660
aataattttt tagttaaaat ctattttgtc tgatattggt gtgaatgctg tacctttctg   117720
acaataaata atattcgacc atgaataaaa aaaaaaaaa agtgggttcc cgggaactaa    117780
gcagtgtaga agatgatttt gactacaccc tccttagaga gccataagac acattagcac   117840
atattagcac attcaaggct ctgagagaat gtggttaact tgtttaact cagcattcct    117900 cactttttt ttttaatcat cagaaattct ctctctctct ctctcttttt ctctcgctct   117960 ctttttttt tttttttac aggaaatgcc tttaaacatc gttggaacta ccagagtcac    118020
cttaaaggag atcaattctc tagactgata aaaatttcat ggcctccttt aaatgttgcc   118080
aaatatatga attctaggat ttttccttag gaaaggtttt tctctttcag ggaagatcta   118140
ttaactcccc atgggtgctg aaaataaact tgatggtgaa aaactctgta taaattaatt   118200 taaaattat ttggtttctc tttttaatta ttctggggca tagtcatttc taaaagtcac    118260
tagtagaaag tataatttca agacagaata ttctagacat gctagcagtt tatatgtatt   118320
catgagtaat gtgatatata ttgggcgctg gtgaggaagg aaggaggaat gagtgactat   118380
aaggatggtt accatagaaa cttccttttt tacctaattg aagagagact actacagagt   118440
gctaagctgc atgtgtcatc ttacactaga gagaaatggt aagtttcttg tttatttaa    118500 gttatgttta agcaaggaaa ggatttgtta ttgaacagta tatttcagga aggttagaaa   118560
gtggcggtta ggatatattt taaatctacc taaagcagca tattaaaaa atttaaagt     118620 attggtatta aattaagaaa tagaggacag aactagactg atagcagtga cctagaacaa   118680
tttgagatta ggaaagttgt gaccatgaat ttaaggattt atgtggatac aaattctcct   118740
ttaaagtgtt tcttcccta atatttatct gacggtaatt tttgagcagt gaattacttt    118800
atatatctta atagtttatt tgggaccaaa cacttaaaca aaaagttctt taagtcatat   118860 aagcctttc aggaagcttg tctcatattc actcccgaga cattcacctg ccaagtggcc    118920
```

```
tgaggatcaa tccagtccta ggtttatttt gcagacttac attctcccaa gttattcagc   118980
ctcatatgac tccacggtcg gctttaccaa aacagttcag agtgcacttt ggcacacaat   119040
tgggaacaga acaatctaat gtgtggtttg gtattccaag tggggtcttt ttcagaatct   119100
ctgcactagt gtgagatgca aacatgtttc ctcatctttc tggcttatcc agtatgtagc   119160
tatttgtgac ataataaata tatacatata tgaaaatatg tatttggttt ctgcctccag   119220
ttcttacaaa gagctcctaa aacccttgta atttcctgag tagtaggggt gctagggtca   119280
tcttttgttc taatatttgg tctttgactc tgctttctga cagagctcct tagtccctgg   119340
gtgagagtag catcttctct tctaatgaag tgactcttgc tgggttcctg gatgggggct   119400
ggtcaccaga aaggtcaagc catgataaga agcttgaagc ttttggcccc attcacatct   119460
tctggggacg ggagagaaga ggagctggag attgagttaa taagcaacaa tgcttccatg   119520
atgaagactc cataaaaatc cctaaaagac aggattcaga gtgctttgaa ataggtgaac   119580
atgcagaggt gctgggaatt gtggtgtgtc cagagaaggc atgcaagctc cccacgcctc   119640
ccccatacct ttccctgtgc atctcttcca tctggctgtt cctgagttgt atccttttat   119700
aacaaactgg taatctagta agcaaactgt tttcctgaag tctgtgaatc acactagcaa   119760
attatcaaac ctgaggagag ggccgtggag accttggatt tgtagacaag tcaaacagaa   119820
gctatgagta acatgaggac tcattgcttg tgattgtcat cttcagtggg aaggggaaaa   119880
atcttgtaaa actgagtcct taacctgtgg gtcaatgcta actccaggta gatagtgtcc   119940
gatttgaatt acgggacacc cagttggtag ccacaaagaa tgggagaatt gcttggtgta   120000
gaaaacacac cccacacaca catgtggtgt cagaaatgaa ccggaaatat tgtgttccgg   120060
aaatattgag tgttgtgagt gagtgtatag aaagaaaaac agcgtttcct tttcactact   120120
agattaaaac aaacacactc atgcattcac acatctcaaa gacaactatt aattctcaaa   120180
gacagtgctg tctaaatcca tactgaggaa gaaaacacat tttcttttca aatctgtaaa   120240
cctgacagac tgcctctgtc cacacactaa tggaactctg tgtttcatct gaaatgtgtt   120300
catcccactt tgttctttct gtcttgggca gggcaagagt gcaacagggc tgacattttc   120360
atatgagctc tgtccctgtt attggctata ctttagacaa attattatgt gtcaaatata   120420
gatgtaagtg atttatcaat attaagtcat ttaattctca aaacaacctt aataggttcc   120480
attatgattc taattttaca cataagccaa aggaggcacc cacaggctag ataactttcc   120540
cacggccaca cagctagtaa gcggcagagc caagaggccc aacattacag caccacagtc   120600
tgtgctctca gccccttggc cacatagtgt cagagtgagg acacacagct atttaagaaa   120660
acttccagaa gtctaggaaa tggggtgata gccccacttt tctaggtata ataattagat   120720
atttgttttt cttcaggtac ctaaagaaaa tttactagag tttgagcctt tagtaagttt   120780
tgctagtaca tctgtttttc ttcaggtgcc tgaagacaaa catatacaca cacacacaca   120840
cacaaacaca cacaaaatgt gtatctatat atatgtgtac acatatctct catctctata   120900
tatatgtctc tgtatatcta tatatctata aacatatcta tatctataga tacatataga   120960
gagatttctt tttttttttt tttgagatgg agtcttgctc ttgccaccta ggctggagtg   121020
caatggcaca atctcagttc actgcaacct ccgcctccca ggttcaagcg attctcctgc   121080
ctcagcctct cgagtaggtg ggattacagg aacacaccac cttagcccga ctaattttg   121140 tattttagt agagacaggg ttcaccacgt tggccaggct ggtctcaaac tcctgacc    121198
```